(12) United States Patent
Chinnaiyan et al.

(10) Patent No.: US 9,658,231 B2
(45) Date of Patent: May 23, 2017

(54) USING PHAGE EPITOPES TO PROFILE THE IMMUNE RESPONSE

(71) Applicants: THE REGENTS OF THE UNIVERSITY OF MICHIGAN, Ann Arbor, MI (US); ARMUNE BIOSCIENCES, INC., Kalamazoo, MI (US)

(72) Inventors: Arul M. Chinnaiyan, Plymouth, MI (US); Xiaoju Wang, Ann Arbor, MI (US); Alex Tsodikov, Ann Arbor, MI (US); Jeanne Ohrnberger, Northville, MI (US)

(73) Assignees: The Regents of the University of Michigan, Ann Arbor, MI (US); Armune Biosciences, Inc., Kalamazoo, MI (US)

( * ) Notice: Subject to any disclaimer, the term of this patent is extended or adjusted under 35 U.S.C. 154(b) by 0 days.

(21) Appl. No.: 14/822,045

(22) Filed: Aug. 10, 2015

(65) Prior Publication Data

US 2016/0041174 A1 Feb. 11, 2016

Related U.S. Application Data

(63) Continuation of application No. 13/050,544, filed on Mar. 17, 2011.

(60) Provisional application No. 61/314,750, filed on Mar. 17, 2010.

(51) Int. Cl.
*G01N 33/574* (2006.01)
*C07K 16/00* (2006.01)

(52) U.S. Cl.
CPC ....... *G01N 33/57434* (2013.01); *C07K 16/00* (2013.01); *C07K 16/005* (2013.01); *G01N 33/57415* (2013.01); *G01N 33/57419* (2013.01); *G01N 33/57423* (2013.01); *G01N 33/57488* (2013.01); *G01N 2333/4703* (2013.01); *G01N 2333/4704* (2013.01); *G01N 2333/705* (2013.01); *G01N 2333/912* (2013.01)

(58) Field of Classification Search
None
See application file for complete search history.

(56) References Cited

U.S. PATENT DOCUMENTS

| 4,109,496 A | 8/1978 | Allemann et al. |
| 4,323,546 A | 4/1982 | Crockford et al. |
| 4,657,760 A | 4/1987 | Kung et al. |
| 4,873,191 A | 10/1989 | Wagner et al. |
| 4,968,103 A | 11/1990 | McNab et al. |
| 4,981,785 A | 1/1991 | Nayak |
| 5,034,506 A | 7/1991 | Summerton et al. |
| 5,206,344 A | 4/1993 | Katre et al. |
| 5,223,409 A | 6/1993 | Ladner et al. |
| 5,225,212 A | 7/1993 | Martin et al. |
| 5,283,317 A | 2/1994 | Saifer et al. |
| 5,358,691 A | 10/1994 | Clark et al. |
| 5,489,677 A | 2/1996 | Sanghvi et al. |
| 5,539,082 A | 7/1996 | Nielsen et al. |
| 5,599,677 A | 2/1997 | Dowell et al. |
| 5,602,240 A | 2/1997 | De Mesmaeker et al. |
| 5,614,396 A | 3/1997 | Bradley et al. |
| 5,631,169 A | 5/1997 | Lakowicz et al. |
| 5,672,480 A | 9/1997 | Dowell et al. |
| 5,674,486 A | 10/1997 | Sobol et al. |
| 5,714,331 A | 2/1998 | Buchardt et al. |
| 5,719,262 A | 2/1998 | Buchardt et al. |
| 5,824,544 A | 10/1998 | Armentano et al. |
| 5,830,730 A | 11/1998 | German et al. |
| 5,872,154 A | 2/1999 | Wilson et al. |
| 5,885,530 A | 3/1999 | Babson et al. |
| 5,885,808 A | 3/1999 | Spooner et al. |
| 5,904,920 A | 5/1999 | Dranoff et al. |
| 5,972,334 A | 10/1999 | Denney, Jr. |
| 5,981,225 A | 11/1999 | Kochanek et al. |
| 5,994,069 A | 11/1999 | Hall et al. |
| 5,994,106 A | 11/1999 | Kovesdi et al. |
| 5,994,128 A | 11/1999 | Fallaux et al. |
| 5,994,132 A | 11/1999 | Chamberlain et al. |
| 5,994,523 A | 11/1999 | Kawakami et al. |
| 6,001,557 A | 12/1999 | Wilson et al. |
| 6,019,978 A | 2/2000 | Ertl et al. |
| 6,033,908 A | 3/2000 | Bout et al. |
| 6,051,230 A | 4/2000 | Thorpe et al. |
| 6,080,912 A | 6/2000 | Bremel et al. |

(Continued)

FOREIGN PATENT DOCUMENTS

| EP | 1270724 A3 | 5/2003 |
| EP | 1074617 A3 | 4/2004 |
| EP | 1464709 A1 | 10/2004 |
| EP | 2130926 | 5/2016 |
| WO | 90/08832 A1 | 8/1990 |
| WO | 93/03367 A1 | 2/1993 |
| WO | 94/10300 A1 | 5/1994 |
| WO | 99/02685 A1 | 1/1999 |
| WO | 00/09675 A1 | 2/2000 |
| WO | 00/12738 A1 | 3/2000 |

(Continued)

OTHER PUBLICATIONS

Gingras et al. "Regulation of translation initiation by FRAP/mTOR." Genes & Development. vol. 15, pp. 807-826 (2001).

(Continued)

*Primary Examiner* — Christopher M Gross
(74) *Attorney, Agent, or Firm* — Casimir Jones, S.C.

(57) ABSTRACT

The present disclosure provides compositions and methods for using one or more polypeptide probes to profile an immune response. The polypeptide probe can be used to detect one or more antibodies from a sample. Furthermore, the present disclosure provides methods and compositions for characterizing a cancer based on the detection of one or more antibodies, such as autoantibodies.

29 Claims, 130 Drawing Sheets

(56) References Cited

U.S. PATENT DOCUMENTS

| | | | |
|---|---|---|---|
| 6,159,750 A | 12/2000 | Edmonds | |
| 6,180,357 B1 | 1/2001 | Young et al. | |
| 6,207,147 B1 | 3/2001 | Hiserodt et al. | |
| 6,506,559 B1 | 1/2003 | Fire et al. | |
| 6,573,361 B1 | 6/2003 | Bunkers et al. | |
| 6,610,508 B1 | 8/2003 | Hentze et al. | |
| 6,686,147 B1 | 2/2004 | Scanlan | |
| 6,783,961 B1 | 8/2004 | Edwards | |
| 6,913,241 B2 | 7/2005 | Bernarding | |
| 7,067,258 B2 | 6/2006 | Esser et al. | |
| 7,115,416 B1 | 10/2006 | Edwards | |
| 7,205,117 B1 | 4/2007 | Robertson et al. | |
| 7,214,498 B2 | 5/2007 | Nelson | |
| 7,368,527 B2 | 5/2008 | Fu | |
| 7,402,403 B1 | 7/2008 | Robertson et al. | |
| 7,541,150 B2 | 6/2009 | Miller et al. | |
| 7,597,890 B2 | 10/2009 | Chinnaiyan et al. | |
| 7,858,323 B2 | 12/2010 | Chinnaiyan et al. | |
| 8,574,848 B2 | 11/2013 | Robertson et al. | |
| 8,592,169 B2 | 11/2013 | Robertson et al. | |
| 8,617,547 B2 | 12/2013 | Chinnaiyan et al. | |
| 8,722,339 B2 | 5/2014 | Robertson et al. | |
| 9,267,133 B2 | 2/2016 | Chinnaiyan et al. | |
| 2003/0028981 A1 | 2/2003 | Chandler et al. | |
| 2003/0092009 A1 | 5/2003 | Palm | |
| 2003/0138860 A1 | 7/2003 | Robertson et al. | |
| 2003/0175736 A1 | 9/2003 | Chinnaiyan et al. | |
| 2004/0044181 A1 | 3/2004 | Tang et al. | |
| 2005/0032065 A1 | 2/2005 | Afar | |
| 2005/0147961 A1 | 7/2005 | Esser et al. | |
| 2006/0014138 A1 | 1/2006 | Ghosh | |
| 2006/0024692 A1 | 2/2006 | Nakamura et al. | |
| 2007/0037143 A1 | 2/2007 | Jost et al. | |
| 2007/0054353 A1 | 3/2007 | White et al. | |
| 2007/0082330 A1 | 4/2007 | Barrett et al. | |
| 2007/0269798 A1 | 11/2007 | Dower et al. | |
| 2008/0153113 A1 | 6/2008 | Robertson et al. | |
| 2008/0213791 A1 | 9/2008 | Freije et al. | |
| 2008/0213921 A1* | 9/2008 | Robertson | G01N 33/54393 436/536 |
| 2008/0280844 A1 | 11/2008 | Lessnick | |
| 2009/0246781 A1* | 10/2009 | Klem | G01N 33/57434 435/6.14 |
| 2010/0009382 A1 | 1/2010 | Chinnaiyan et al. | |
| 2011/0070652 A1 | 3/2011 | Chinnaiyan et al. | |
| 2011/0086061 A1 | 4/2011 | Robertson et al. | |
| 2011/0236903 A1* | 9/2011 | McClelland | C12Q 1/6886 435/6.14 |
| 2011/0237457 A1 | 9/2011 | Ohrnberger et al. | |
| 2013/0130355 A1 | 5/2013 | Ohrnberger et al. | |

FOREIGN PATENT DOCUMENTS

| | | |
|---|---|---|
| WO | 01/98537 A1 | 12/2001 |
| WO | 02018424 | 3/2002 |
| WO | 03010199 | 2/2003 |
| WO | 03064593 | 8/2003 |
| WO | 2005/123993 A2 | 12/2005 |
| WO | 2005123993 A2 | 12/2005 |
| WO | 2006100156 A2 | 9/2006 |
| WO | 2009/149166 A2 | 12/2009 |
| WO | 2009149166 A2 | 12/2009 |
| WO | 2011/120015 A2 | 9/2011 |

OTHER PUBLICATIONS

Morino et al. "Eukaryotic Translation Initiation Factor 4E (eIF4E) Binding Site and the Middle One-Third of eIF4GI Constitute the Core Domain for Cap-Dependent Translation, and the C-Terminal One-Third Functions as a Modulatory Region." Molecular and Cellular Biology. vol. 20, pp. 468-477 (2000).

Cromer et al. "Identification of genes associate with tumorigenesis and metastatic potential of hypopharyngeal cancer by microarray analysis." Oncogene. vol. 23, pp. 2484-2498 (2004).

Park et al. "Bmi-1 is required for maintenance of adult self-renewing haematopoietic stem cells." Nature. vol. 15, No. 423 (6937), pp. 302-305 (2003).

Brass et al. "Translation initiation factor eIF-4gamma is encoded by an amplified gene and induces an immune response in squamous cell lung carcinoma." Human Molecular Genetics. vol. 6, pp. 33-39 (1997).

Bauer et al. "Translation Initiation Factor eIF-4G Is Immunogenic, Overexposed, and Amplified in Patients with Squamous Cell Lung Carcinoma." Cancer. vol. 92, pp. 822-829 (2001).

Bauer, C. et al. "Overexpression of the Eukaryotic Translation Initiation Factor 4G (EIF4G-1) in Squamous Cell Lung Carcinoma." International Journal of Cancer. vol. 98, pp. 181-185 (2002).

Fukuchi-Shimogori et al. "Malignant Transformation by Overproduction of Translation Initiation Factor eIF4G." Cancer Research. vol. 57, pp. 5041-5044 (1997).

Mazumder et al. "Regulated Release of L13a from the 60S Ribosomal Subunit as a Mechanism of Transcript-Specific Translational Control." Cell. vol. 115, pp. 187-198 (2003).

Miura et al. "Laser Capture Microdissection and Microarray Expression Analysis of Lung Adenocarcinoma Reveals Tobacco Smoking- and Prognosis-related Molecular Profiles." Cancer Research. vol. 62, pp. 3244-3250 (2002).

Racz et al. "Expression Analysis of Genes at 3q26-q27 Involved in Frequent Amplification in Squamous Cell Lung Carcinoma." European Journal of Cancer. vol. 35, pp. 641-646 (1999).

Molofsky et al. "Bmi-1 dependence distinguishes neural stem cell self-renewal from progenitor proliferation." Nature. vol. 425, pp. 962-967 (2003).

Singh and Figg. "Upregulation of the Androgen Receptor During Prostate Cancer Progression." Cancer Biology and Therapy. vol. 3 pp. 284-285 (2004).

Taplin et al. "Androgen Receptor: A Key Molecule in the Progression of Prostate Cancer to Hormone Independence." Journal of Cellular Biochemistry. vol. 91, pp. 483-490 (2004).

Liao and Witte. "Autoimmune anti-androgen-receptor antibodies in human serum." Proceedings of the National Academy of Sciences USA. vol. 82, pp. 8345-8348 (1985).

Latulippe et al. "Comprehensive Gene Expression Analysis of Prostate Cancer Reveals Distinct Transcriptional Programs Associated with Metastatic Disease." Cancer Research. vol. 62, pp. 4499-4506 (2002).

Luo et al. "Gene Expression Analysis of Prostate Cancers." Molecular Carcinogenesis. vol. 33, pp. 25-35 (2002).

Luo et al. "Human Prostate Cancer and Benign Prostatic Hyperplasia: Molecular Dissection by Gene Expression Profiling." Cancer Research. vol. 61, pp. 4683-4688 (2001).

Singh et al. "Gene expression correlates of clinical prostate cancer behavior." Cancer Cell. vol. 1, pp. 203-209 (2002).

Welsh et al. "Analysis of Gene Expression Indentifies Candidate Markers and Pharmacological Targets in Prostate Cancer." Cancer Research. vol. 61, pp. 5974-5978 (2001).

Bolstad et al. "A comparison of normalization methods for high density oligonucleotide array data based on variance and bias." Bioinformatics. vol. 19, pp. 185-193 (2003).

Bo et al. "New Feature subset selection procedures for classification of expression profiles." Genome Biology. vol. 3, No. 4, research0017.1-0017.11 (2002).

Rhodes et al. "Large-scale meta-analysis of cancer microarray data identifies common transcriptional profiles of neoplastic transformation and progression." Proceedings of the National Academy of Sciences USA. vol. 101, No. 25, pp. 9309-9314 (2004).

Rhodes et al. "Oncomine: A Cancer Microarray Database and Integrated Data-Mining Platform." Neoplasia. vol. 6, No. 1, pp. 1-6 (2004).

Radmacher et al. "A Paradigm for Class Prediction Using Gene Expression Profiles." Journal of Computational Biology. vol. 9, No. 3, pp. 505-511 (2002).

(56) References Cited

OTHER PUBLICATIONS

Tukey et al. "Tightening the Clinical Trial." Controlled Clinical Trials. vol. 14, No. 4, pp. 266-285 (1993).

Kleijnen et al. "The hPLIC Proteins May Provide a Link between the Ubiquitination Machinery and the Proteasome." Molecular Cell. vol. 6. No. 2, pp. 409-419 (2000).

Mah et al. "Identification of Ubiquilin, a Novel Presenilin Interactor That Increases Presenilin Protein Accumulation." Journal of Cell Biology. vol. 151, No. 4, pp. 847-862 (2000).

Hiltunen et al. "Ubiquilin 1 Modulates Amyloid Precursor Protein Trafficking and Aβ Secretion." Journal of Biological Chemistry. vol. 281, No. 43, pp. 32240-32253 (2006).

Thomas et al. "Interaction between Presenilin 1 and Ubiquilin 1 as Detected by Fluorescence Lifetime Imaging Microscopy and a High-throughput Fluorescent Plate Reader." Journal of Biological Chemistry. vol. 281, No. 36, pp. 26400-26407 (2006).

Slifer et al. "The Ubiquilin 1 Gene and Alzheimer's Disease." New England Journal of Medicine. vol. 352, No. 26, pp. 2752-2753 (2005).

Garber et al. "Diversity of gene expression in adenocarcinoma of the lung." Proceedings of the National Academy of Sciences USA. vol. 98, No. 24, pp. 13784-13789 (2001).

Chen et al. "Protein profiles associated with survival in lung adenocarcinoma." Proceedings of the National Academy of Sciences USA. vol. 100, No. 23, pp. 13537-13542 (2003).

Zhong 2003 "Antibodies to HSP70 and HSP90 in serum in non-small cell lung cancer patients" Cancer Detection and Prevention, vol. 27, pp. 285-290.

Zhong 2004 "Identification of circulating antibodies to tumor-associated proteins for combined use as markers of non-small cell lung cancer" Proteomics, vol. 4, Apr. 4, 2004 pp. 1216-1225.

Koziol et al. "Recursive Partitioning as an Approach to Selection of Immune Markers for Tumor Diagnosis." Clinical Cancer Research. vol. 9, No. 14, pp. 5120-5126 (2003).

Rossi et al. "Review: The role of the ubiquitination-proteasome pathway in breast cancer: Use of mouse models for analyzing ubiquitination processes." Breast Cancer Research. vol. 5, No. 1, pp. 16-22 (2003).

Huebener et al. "AACR Special Conference in cancer research: ubiquitination in normal and cancer cells." Expert Opin. Biol. Ther. vol. 3, No. 1, pp. 187-192 (2003).

Abe et al., "Plasma Levels of Heat Shock Protein 70 inPatients with Prostate Cancer: A Potential Biomarker for Prostate Cancer" Clin Prostate Cancer, Jun. 2004; 3(1): 49-53.

Brass et al., Blood, "Role of Amplified Genes in the Production of Autoantibodies" vol. 93(7) (Apr. 1), 1999:2158-2166.

Sjöblom et al., "The consensus coding sequences of human breast and colorectal cancers." Science, (2006) 314 (5797):268-274.

Sivasubramaniam et al., Genes & Dev. (2008); 22(5):687-600.

Soulet et al., "Fibroblast growth factor-2 interacts with free ribosomal protein S19." Biochem. Biophys. Res. Commun. 2001, 289(2):591-596.

Zucchi et al., "Gene expression profiles of epithelial cells microscopically isolated from a breast-invasive ductal carcinoma and a nodal metastasis." Proc. Nat'l Acad. Sci. (2004); 101(52):18147-52.

Gu et al., "A novel fusion of RBM6 to CSF1R in acute megakaryoblastic leukemia." Blood (2007), 110(1):323-333.

Berx & Van Roy, "Involvement of the members of the cadherin superfamily in cancer." Cold Spring Harbor Perspectives in Biology 2009.

Burger et al., "Expression analysis of δ-catenin and prostate-specific membrane antigen: their potential as diagnostic markers for prostate cancer." Int. J. Cancer 2002, 100:228-237.

Ole et al., "A switch from E-cadherein to N-cadherin expression indicates ephithelial to mesenchymal transition and is of strong and independent importance for the progress of prostate cancer." Clin. Cancer Res. 2007, 7003-7011.

Rhodes et al., "Multiplex biomarker approach for determining risk of prostate-specific antigen-defined recurrenc of prostate cancer." Journal of the National Cancer Institute 2003, 95(9):661-668.

Fossa Alexander et al, "Serological Cloning of Cancer/Test is Antigens Expressed in Prostate Cancer Using CDNA Phage Surface Display," Cancer Immunology, Immunotherapy: CII, May 2004, vol. 53, pp. 431-438.

Soussi Thierry, "P53 Antibodies in the Sera of Patients With Various Types of Cancer: A Review," Cancer Research, (Apr. 2000) vol. 60, pp. 1777-1788.

Sreekumar A. et al, "Humoral Immune Response to Alpha-Methylacyl-Coa Racemase and Prostate Cancer," JNCI Cancer Spectrum (Jun. 2004) vol. 96, pp. 834-843.

Beer D. G. et al, "Gene-Expression Profiles Predict Survival of Patients With Lung Adenocarcinoma," Nature Medicine (Aug. 2002) vol. 8, pp. 816-824.

Wang X., et al "Prostate Cancer Detection by Epitomic Profiling of the Humoral Immune Response," Prostate Cancer Symposium (2005) XP002558315.

Canevari et al, "1975-1995 Revised Anti-Cancer Serological Respons: Biological Significance and Clinical Implications," Annals of Oncology (1996) vol. 7, pp. 227-232.

Karanikas et al, "Antibody and T Cell Responses of Patients With Adenocarcinoma Immunized With Mannan-MUC1 Fusion Protein," J. Clin Invest (1997) vol. 100, pp. 2783-2792.

Moingeon, "Strategies for Designing Vaccines Eliciting TH1 Responses in Humans," Journal of Biotechnology (2002) vol. 98, pp. 189-198.

Scanlan et al, "Characterization of Human Colon Cancer Antigens Recognized by Autologous Antibodies," Int. J. Cancer (1998) vol. 76, pp. 652-658.

Zisman et al, "Autoantibodies to Prostate Specific Antigen in Patients With Benign Prostatic Hyperlasia," Journal of Urology (19995) vol. 154, pp. 1052-1055.

Kawahara et al, "Use of Four Monoclonal Antibodies to Detect Tumor Markers," Cancer (1986) vol. 58, pp. 2008-2012.

Carney et al, "Potential Clinical Utility of Serum Her-2/NEU Oncoprotein Concentrations in Patients With Breast Cancer," Clin Chem 2003, 49(10) 1579-98.

Luderer et al, "Measurement of the Proportion of Free to Total Prostate-Specific Antigen Improves Diagnostic Perfomrance of Prostate-Specific Antigen in the Diagnostic Gray Zone of Total Prostate-Specific Antigen," Urology 1995, 46(2) 187-94.

Marley et al, Free and Complexed Prostate-Specific Antigen Serum Ratios to Predict Probability of Primary Prostate Cancer and Benign Prostatic Hyperplasia, Urology 1996, 48(6A Suppl) 16-22.

Nicolini et al, "Biomolecular Markers of Breast Cancer," Front Biosci 2006, 1; 11, 1818-43.

Van Cangh et al, Free to Total Prostate-Specific Antigen (PSA) Ratio Improves the Discrimination Between Prostate Cancer and Benign Prostatic Hyperplasia (BPH) in the Diagnostic Gray Zone of 1.8 Top 10NG/ML Total PSA, Urology, 1996 48(6A Suppl) 67-70.

CAS Entery 142: 2133341 (Database Entry) 2005.

Autoantibodies in Prostate Cancer (Letters to the Editor 2005 New England Journal of Medicine 353: 2815-2817).

Wang 2005 "Autoantibody signatures in prostate cancer" The New England Journal of Medicine, Sep. 22, 2005, vol. 353, pp. 1224-1235.

Somers, Veerle A., et al.; "A Panel of Candidate Tumor Antigens in Colorectal Cancer Revealed by the Serological 2 Selection of a Phage Displayed cDNA Expression Library"; The Journal of Immunology, Sep. 1, 2002; vol. 169 0 p. 2772-2780; Baltimore, MD.

Sioud, M., et al.; "Profiling the immune responses in patient sera with peptide and cDNA display libraries (Review)"; International Journal of Molecular Medicine, Jan. 1, 2000; vol. 2, No. 6 p. 123-128; Spandidos, Athens, GR.

Beghetto, Elisa, et al.; "Identification of a human immunodominant B-cell epitope within the GRA1 antigen of 4 Toxoplasma gondii by phage display of cDNA libraries"; International Journal of Parasitology, Dec. 1, 2001; vol. 31, No. 14 p. 1659-1668; Pergamon Press, GB.

(56) References Cited

OTHER PUBLICATIONS

Hansen, Mona H., et al.; "Antigen-Specific IgG Antibodies in State IV Long-Time Survival Breast Cancer Patients"; Molecular Medicine, Blackwell Science, Jan. 1, 2001; vol. 7, No. 4 p. 230-239; Cambridge, MA.

Sioud, Mouldy, et al.; "Profiling the immune response in patients with breast cancer by phage-displayed Cdna 6 libraries"; European Journal of Immunology, Mar. 1, 2001; Wiley-V C H Verlag GMBH & Co.; vol. 31, No. 3 p. 716-725; KGAA, DE.

Minenkova, Olga, et al.; "Identification of Tumor-Associated Antigens by Screening Phage-Displayed Human cDNA 1 Libraries With Sera From Tumor Patients"; Publication of the International Union Against Cancer; 106, p. 534-544 (2003); 2003 Wiley-Liss, Inc.

Chen Guoan et al, "Autoantibody profiles reveal uniguilin 1 as a humoral immune response target in lung adenocarcinoma," Research Article, Cancer Res. 2007; 67 (7) Apr. 1, 2007 p. 3461-3467 www.aacrjournals.org.

Erkanli, Al, et al.; "Application of Bayesian Modeling of Autologous Antibody Responses against Ovarian Tumor-3 Associates Antigens to Cancer Detection"; Research Article, Cancer Res 2006; 66: (3). Feb. 1, 2006; p. 1792-1798; www.aacrjournals.org.

Mintz, Paul J., et al.; "Fingerprinting the Circulating Repertoire of Antibodies from Cancer Patients"; Research Article,4 Published online Dec. 23, 2002; doi:1 0.1038/nbt 774; www.nature.com/naturebiotechnology; Jan. 2003 vol. 21 p. 57-63.

Vaarala, Markku H., et al.; "Several Genes Encoding Ribosomal Proteins are Over-Expressed in Prostate-Cancer 5 Cell Lines: Confirmation of L7a and L37 Over-Expression in Prostate-Cancer Tissue Samples"; Publication of the International Union Against Cancer; 78, p. 27-32 (1998); 1998 Wiley-Liss, Inc.

Gure, Ali O., et al.; "Human Lung Cancer Antigens Recognized by Autologous Antibodies: Definition of a Novel 6 cDNA Derived from the Tumor Suppressor Gene Locus on Chromosome 3p21.3"; Ludwig Institute for Cancer Research; Cancer Research 58, p. 1034-1041; Mar. 1, 1998.

Elek D "Microarray-Based Expression Profiling in Prostate Tumors" Center for Molecular Biology and Biotechnology and Department of Biology, Boca Raton, FL invivo 14: p. 173-182, 2000.

Tureci, Ozlem; "Serological Analysis of Human Tumor Antigens: Molecular Definition and Implications"; Molecular Medicine Today, Aug. 1997 p. 342-349; Elsevier Science Ltd.

Albertus Daniel L. "AZGP1 Antibody Predicts Survival and Histone Deacetylase Inhibitoes Increase Expression in Lung Adenocarcinoma," journal of Thoracic Oncology vol. 3 No. 11 p. 1236-1244, No. 2008.

Walker, Michael G., et al.; Prediction of Gene Function by Genome-Scale Expression Analysis: Prostate Cancer-1 Associated Genes; Genome Res. 19979: p. 1198-1203; Access the most recent version at doi: 10.11 01/gr.9.12.11 98; 1999 Cold Spring Harbor Laboratory Press ISSN1054-9803/99.

Mudenda B, "The Relationship Between Serum p53 Autoantibodies and Characteristics of Human Breast Cancer" Br. J. Cancer (1994) 69 p. 1115-1119; MacMillan Press Ltd. 1994.

Stockert, Elisabeth, et al.; "A Survey of the Humoral Immune Response of Cancer Patients to a Panel of Human Tumor Antigens"; J. Ep. Med. The Rockefeller University Press; 0022-1007/98/04/1349/06; vol. 187, No. 8 Apr. 20, 1998 p. 1349-1354; http://www.jem.org.

Old, Lloyd J., et al.; "New Paths in Human Cancer Serology"; Ludwig Institute for Cancer Research; J. Exp. Med. The Rockefeller University Press 0022-1007/98/04/1163/05; vol. 187, No. 8, Apr. 20, 1998 p. 1163-1167; http://www.jem.org.

Kuriyama, M., et al.; "Multipile Marker Evaluation in Human Prostate Cancer With the Use of Tissue-Specific Antigens"; JNCI, vol. 68, No. 1 Jan. 1982 p. 99-105.

Mercer Donald, "Use of Multiple Markers to Enhance Clinical Utility," Immunodiagnosis of Cancer, Immunology Series, 53, pp. 39-54, 1990.

Hale et al, "Zin a-2-Glycoprotein is Expressed by Malignant Prostatic Epithelium and May Serve as a Potential Serum Marker for Prostate Cancer" Clinical Cancer Research, Apr. 7, 2001,(4) 846-53.

Zhong, et al. "Efficient Identification and User of Tumor-Associated Antibodies as Markers of Non-small Cell Lung Cancer" Chest 2004, vol. 125, pp. 105-106.

Hufton 'Serological antigen selection of phage displayed colorectal tumour cDNA libraries' Biochemical Society Transactions vol. 26, 1998, p. S5.

Miller et al.: 'Antibody microarray profiling of human prostate cancer sera:Antibody screening and identification of potential biomarkers' Proteomics vol. 3, 2003, pp. 56-63.

Eisen "Cluster analysis and display of genome-wide expression patterns," 1998 vol. 95, pp. 14863-14868.

Li "Gene Assessment and Sample Classification for Gene Expression Data Using a Genetic Algorithm/k-nearest Neighbor Method," 2001, vol. 4, pp. 727-739.

Goloub "Molecular Classification of Cancer: Class Discovery and Class Prediction by Gene Expression Monitoring," Science, 1999, vol. 286 pp. 531-537.

Crescenzi "The main biological determinants of tumor line taxonomy elucidated by a principal component analysis of microarray data," 2001, vol. 507 pp. 114-118.

Denis and Green. "A novel, mitogen-activated nuclear kinase is related to a *Drosophila* developmental regulator." Genes & Development. vol. 10, pp. 261-271 (1996).

Denis et al. "Ring3 Kinase Transactivates Promoters of Cell Cycle Regulatory Genes through E2F." Cell Growth & Differentiation. vol. 11, pp. 471-424 (2000).

Kanno et al. "Selective Recognition of Acetylated Histones by Bromodomain Proteins Visualized in Living Cells." Molecular Cell. vol. 13, pp. 33-43 (2004).

Acession NM_015021 data, http://www.ncbi.nlm.nih.gov/nuccore/NM_015021, retrieved Dec. 18, 2011.

European office action dated Jun. 27, 2012 for EP Application No. 09006617.6.

International search report dated Jan. 2, 2012 for PCT/US2011/030091.

NCBI reference sequence for hypothetical protein XP_373908 (current status) http://www.ncbi.nlm.nih.gov/protein/XP_373908.5?report=girevhist. Retrieved Dec. 21, 2011.

NCBI reference sequence for hypothetical protein XP_373908 http://www.ncbi.nlm.nih.gov/protein/XP_373908.5?report=genpept. Retrieved Dec. 21, 2011.

Office action dated Jan. 5, 2009 for U.S. Appl. No. 11/145,861.
Office action dated Jan. 16, 2009 for U.S. Appl. No. 11/715,642.
Office action dated Jan. 18, 2012 for U.S. Appl. No. 12/556,831.
Office action dated Feb. 3, 2010 for U.S. Appl. No. 11/145,861.
Office action dated Jul. 8, 2008 for U.S. Appl. No. 11/715,642.
Office action dated Jul. 16, 2012 for U.S. Appl. No. 12/556,831.
Office action dated Aug. 19, 2009 for U.S. Appl. No. 11/145,861.

Stone, et al. Serologic analysis of ovarian tumor antigens reveals a bias toward antigens encoded on 17q. Int J Cancer Mar. 10, 2003;104(1):73-84.

European Search Report Dec. 18, 2009, Application No. 09006617.6, Filed Jun. 8, 2005, 6 pages.

Gravdal, et al. A switch from E-cadherin to N-cadherin expression indicates epithelial to mesenchymal transition and is of strong and independent importance for the progress of prostate cancer. Clin Cancer Res. Dec. 1, 2007;13(23):7003-11.

International Search Report dated Feb. 8, 2012 PCT/US2011/028845.

Abate-Shen et al. Molecular genetics of prostate cancer. Genes Dev. Oct. 1, 2000; 14(19): 2410-34.

Zuckermann et al. Discovery of nanomolar ligands for 7-transmembrane G-protein-coupled receptors from a diverse N-(substituted)glycine peptoid library. J Med Chem. Aug. 19, 1994; 37(17): 2678-85.

Bartel et al. Elimination of false positives that arise in using the two-hybrid system. Biotechniques. Jun. 1993; 14(6): 920-4.

(56) References Cited

OTHER PUBLICATIONS

Bradley et al. Formation of germ-line chimaeras from embryo-derived teratocarcinoma cell lines. Nature. May 17-23, 1984; 309(5965): 255-6.
Brinster et al. Factors affecting the efficiency of introducing foreign DNA into mice by microinjecting eggs. Proc Natl Acad Sci U S A. Jul. 1985; 82(13): 4438-42.
Brummelkamp et al. A system for stable expression of short interfering RNAs in mammalian cells. Science. Apr. 19, 2002; 296(5567): 550-3. Epub Mar. 21, 2002.
Caplen et al. Specific inhibition of gene expression by small double-stranded RNAs in invertebrate and vertebrate systems. Proc Natl Acad Sci U S A. Aug. 14, 2001; 98(17): 9742-7. Epub Jul. 31, 2001.
Carrell et al. A novel procedure for the synthesis of libraries containing small orgainic molecules. Angew. Chem. Int. Ed. Engl. 1994; 33: 2059-2061.
Carrell et al. A solution phase screening procedure for the isolation of active compounds from a library of molecules. Angew. Chem. Int. Ed. Engl. 1994; 33: 2061-2064.
Chamberlin et al. New RNA polymerase from *Escherichia coli* infected with bacteriophage T7. Nature. Oct. 17, 1970; 228(5268): 227-31.
Cho et al. An unnatural biopolymer. Science. Sep. 3, 1993; 261(5126): 1303-5.
Cull et al. Screening for receptor ligands using large libraries of peptides linked to the C terminus of the lac repressor. Proc Natl Acad Sci U S A. Mar. 1, 1992; 89(5): 1865-9.
Cwirla et al. Peptides on phage: a vast library of peptides for identifying ligands. Proc Natl Acad Sci U S A. Aug. 1990; 87(16): 6378-82.
Devlin et al. Random peptide libraries: a source of specific protein binding molecules. Science. Jul. 27, 1990; 249 (4967): 404-6.
Dewitt et al. "Diversomers": an approach to nonpeptide nonoligomeric chemical diversity. Proc Natl Acad Sci U S A. Aug. 1, 1993; 90(15): 6909-13.
Dhanasekaran et al. Delineation of prognostic biomarkers in prostate cancer. Nature. Aug. 23, 2001; 412(6849): 822-6.
Elbashir et al. Duplexes of 21-nucleotide RNAs mediate RNA interference in cultured mammalian cells. Nature. May 24, 2001; 411(6836): 494-8.
Elbashir et al. Functional anatomy of siRNAs for mediating efficient RNAi in *Drosophila melanogaster* embryo lysate. EMBO J. Dec. 3, 2001; 20(23): 6877-88.
Elbashir et al. RNA interference is mediated by 21- and 22-nucleotide RNAs. Genes Dev. Jan. 15, 2001; 15(2): 188-200.
Epstein et al. The pathological interpretation and significance of prostate needle biopsy findings: implications and current controversies. J Urol. Aug. 2001; 166(2): 402-10.
Erb et al. Recursive deconvolution of combinatorial chemical libraries. Proc Natl Acad Sci U S A. Nov. 22, 1994; 91(24): 11422-6.
Etzioni et al. Cancer surveillance series: interpreting trends in prostate cancer—part III: Quantifying the link between population prostate-specific antigen testing and recent declines in prostate cancer mortality. J Natl Cancer Inst. Jun. 16, 1999; 91(12): 1033-9.
Evans et al. Establishment in culture of pluripotential cells from mouse embryos. Nature. Jul. 9, 1981; 292(5819): 154-6.
Felici et al. Selection of antibody ligands from a large library of oligopeptides expressed on a multivalent exposition vector. J Mol Biol. Nov. 20, 1991; 222(2): 301-10.
Fodor et al. Multiplexed biochemical assays with biological chips. Nature. Aug. 5, 1993; 364(6437): 555-6.
Gallop et al. Applications of combinatorial technologies to drug discovery. 1. Background and peptide combinatorial libraries. J Med Chem. Apr. 29, 1994; 37(9): 1233-51.
Ghose et al. Preparation of antibody-linked cytotoxic agents. Methods Enzymol. 1983; 93: 280-333.
Golub et al. Molecular classification of cancer: class discovery and class prediction by gene expression monitoring. Science. Oct. 15, 1999; 286(5439): 531-7.

Graham et al. A new technique for the assay of infectivity of human adenovirus 5 DNA. Virology. Apr. 1973; 52(2): 456-67.
Griffin et al. Initial clinical study of indium-111-labeled clone 110 anticarcinoembryonic antigen antibody in patients with colorectal cancer. J Clin Oncol. Apr. 1991; 9(4): 631-40.
Grossler et al. Transgenesis by means of blastocyst-derived embryonic stem cell lines. Proc Natl Acad Sci U S A. Dec. 1986; 83(23): 9065-9.
Hage et al. Recent advances in chromatographic and electrophoretic methods for the study of drug-protein interactions. J Chromatogr B Biomed Sci Appl. Oct. 10, 1997;699(1-2):499-525.
Haskell et al. Efficient production of transgenic cattle by retroviral infection of early embryos. Mol Reprod Dev. Mar. 1995; 40(3): 386-90.
Heegaard NH. Capillary electrophoresis for the study of affinity interactions. J Mol Recognit. 1998 Winter; 11(1-6): 141-8.
Hnatowich et al. The preparation and labeling of DTPA-coupled albumin. Int J Appl Radiat Isot. May 1982; 33(5): 327-32.
Hogan et al. Manipulating the mouse embryo: a laboratory manual. vol. 34. Cold Spring Harbor NY: Cold spring harbor laboratory 1986.
Holen et al. Positional effects of short interfering RNAs targeting the human coagulation trigger Tissue Factor. Nucleic Acids Res. Apr. 15, 2002; 30(8): 1757-66.
Houghten et al. The use of synthetic peptide combinatorial libraries for the identification of bioactive peptides. Biotechniques. Sep. 1992; 13(3): 412-21.
International search report and written opinion dated Mar. 22, 2013 for PCT Application No. PCT/US2012/058100.
Iwabuchi et al. Use of the two-hybrid system to identify the domain of p53 involved in oligomerization. Oncogene. Jun. 1993; 8(6): 1693-6.
Jacobsen et al. Incidence of prostate cancer diagnosis in the eras before and after serum prostate-specific antigen testing. JAMA. Nov. 8, 1995; 274(18): 1445-9.
Jaenich R. Germ line integration and Mendelian transmission of the exogenous Moloney leukemia virus. Proc Natl Acad Sci U S A. Apr. 1976; 73(4): 1260-4.
Jaenich R. Transgenic animals. Science. Jun. 10, 1988; 240(4858): 1468-74.
Jahner et al. De novo methylation and expression of retroviral genomes during mouse embryogenesis. Nature. Aug. 12, 1982; 298(5875): 623-8.
Jahner et al. Insertion of the bacterial gpt gene into the germ line of mice by retroviral infection. Proc Natl Acad Sci U S A. Oct. 1985; 82(20): 6927-31.
Kacian et al. A replicating RNA molecule suitable for a detailed analysis of extracellular evolution and replication. Proc Natl Acad Sci U S A. Oct. 1972; 69(10): 3038-42.
Khaw et al. Myocardial infarct imaging of antibodies to canine cardiac myosin with indium-111-diethylenetriamine pentaacetic acid. Science. Jul. 11, 1980; 209(4453): 295-7.
Kohler et al. Continuous cultures of fused cells secreting antibody of predefined specificity. Nature. Aug. 7, 1975; 256(5517): 495-7.
Lam et al. A new type of synthetic peptide library for identifying ligand-binding activity. Nature. Nov. 7, 1991; 354(6348): 82-4.
Lauffer RB. Targeted relaxation enhancement agents for MRI. Magn Reson Med. Dec. 1991; 22(2): 339-42; discussion 343-6.
Maattanen, et al. European randomized study of prostate cancer screening: first-year results of the Finnish trial. Br J Cancer. Mar. 1999; 79(7-8): 1210-4.
Madura, et al. N-recognin/Ubc2 interactions in the N-end rule pathway. J Biol Chem. Jun. 5, 1993; 268(16): 12046-54.
Martin, et al. New access to 2'-O-alkylated ribonucleosides and properties of 2'-O-alkylated oligoribonucleotides. Helv. Chim. Acta. 1995; 78: 486.
McConnell, et al. The cytosensor microphysiometer: biological applications of silicon technology. Science. Sep. 25, 1992; 257(5078): 1906-12.
Nielsen, et al. Sequence-selective recognition of DNA by strand displacement with a thymine-substituted polyamide. Science. Dec. 6, 1991; 254(5037): 1497-500.
Office action dated Jan. 2, 2014 for U.S. Appl. No. 13/072,542.

(56) References Cited

OTHER PUBLICATIONS

Office action dated Mar. 21, 2013 for U.S. Appl. No. 13/072,542.
Office action dated May 16, 2014 for U.S. Appl. No. 12/914,465.
Office action dated Jul. 11, 2013 for U.S. Appl. No. 12/914,465.
Office action dated Nov. 7, 2012 for U.S. Appl. No. 12/556,831.
PCR Technology: Applications and Principles of DNA Amplification, H Erlich (ed). New York, Stockton Press, 1989.
Rivas, et al. New developments in the study of biomolecular associations via sedimentation equilibrium. Trends Biochem Sci. Aug. 1993; 18(8): 284-7.
Robertson, et al. Germ-line transmission of genes introduced into cultured pluripotential cells by retroviral vector. Nature. Oct. 2-8, 1986; 323(6087): 445-8.
Ruijter, et al. Molecular genetics and epidemiology of prostate carcinoma. Endocr Rev. Feb. 1999; 20(1): 22-45.
Sambrook, et al. Molecular cloning: A laboratory manual+ Cold Spring Harbor. 1989: 16.9-16.15.
Sambrook, et al. Molecular cloning: A laboratory manual+ Cold Spring Harbor. 1989: 7.39-7.52.
Sambrook, et al. Molecular cloning: A laboratory manual+ Cold Spring Harbor. 1989: 9.31-9.58.
Scheinberg, et al. Tumor imaging with radioactive metal chelates conjugated to monoclonal antibodies. Science. Mar. 19, 1982; 215(4539): 1511-3.
Schroder, et al. Evaluation of the digital rectal examination as a screening test for prostate cancer. Rotterdam section of the European Randomized Study of Screening for Prostate Cancer. J Natl Cancer Inst. Dec. 2, 1998; 90(23): 1817-23.
Scott, et al. Searching for peptide ligands with an epitope library. Science. Jul. 27, 1990; 249(4967): 386-90.
Sjolander, et al. Integrated fluid handling system for biomolecular interaction analysis. Anal Chem. Oct. 15, 1991; 63(20): 2338-45.
Stewart, et al. Expression of retroviral vectors in transgenic mice obtained by embryo infection. EMBO J. Feb. 1987; 6(2): 383-8.
Sumerdon, et al. An optimized antibody-chelator conjugate for imaging of carcinoembryonic antigen with indium-111. Int J Rad Appl Instrum B. 1990; 17(2): 247-54.
Szabo, et al. Surface plasmon resonance and its use in biomolecular interaction analysis (BIA). Curr Opin Struct Biol. Oct. 1995; 5(5): 699-705.
Thorpe, et al. Improved antitumor effects of immunotoxins prepared with deglycosylated ricin A-chain and hindered disulfide linkages. Cancer Res. Nov. 15, 1988; 48(22): 6396-403.
Tuschl, et al. Small interfering RNAs: a revolutionary tool for the analysis of gene function and gene therapy. Mol Interv. Jun. 2002; 2(3): 158-67.
Wergeland, et al. Monoclonal antibodies evoked by the free oligopeptide (Gly)5 reacting specifically with peptidoglycan from staphylococci. J Immunol Methods. Nov. 23, 1987;104(1-2):57-63.
Wong, et al. A rapid chemical method of labeling human plasma proteins with 99mTc-pertechnetate at pH 7.4. Int J Appl Radiat Isot. May 1978; 29(4-5): 251-3.
Wong, et al. Imaging endocarditis with Tc-99m-labeled antibody—an experimental study: concise communication. J Nucl Med. Mar. 1982; 23(3): 229-34.
Wu, et al. The ligation amplification reaction (LAR)—amplification of specific DNA sequences using sequential rounds of template-dependent ligation. Genomics. May 1989; 4(4): 560-9.
Zervos, et al. Mxi1, a protein that specifically interacts with Max to bind Myc-Max recognition sites. Cell. Jan. 29, 1993; 72(2): 223-32.
Extended European Search Report Dated May 30, 2016, EP Application 16156268.1, 7 pages.
Obata et al., "Identification of cancer antigens in breast cancer by the SEREX expression cloning method" Breast Cancer, Oct. 1999, vol. 6, Issue 4, pp. 305-311.
Qiu et al., "Development of Natural Protein Microarrays for Diagnosing Cancer Based on an Antibody Response to Tumor Antigens" Journal of Proteome Research, 2004, 3 (2), pp. 261-267.
Zhang Jian-Ying et al., "Enhancement of Antibody Detection in Cancer Using Panel of Recombinant Tumor-associated Antigens" Cancer Epidemiol Biomarkers Prev Feb. 12, 2003; 136-143.
Notice of allowance dated May 29, 2009 for U.S. Appl. No. 11/715,642.
Notice of allowance dated Aug. 23, 2013 for U.S. Appl. No. 12/556,831.
Notice of allowance dated Sep. 23, 2010 for U.S. Appl. No. 11/145,861.
Office action dated Jun. 2, 2015 for U.S. Appl. No. 13/050,544.

* cited by examiner

FIGURE 2

Homo sapiens DCHS1 gene for protocadherin-16 precursor, complete cds, without stop codon, AB384634.1

```
   1 gcgatcgcca tgcagaagga gctgggcatt gtgccttcct gccctggcat gaagagcccc
  61 aggccccacc tcctgctacc attgctgctg ctgctgctgc tgctgctggg ggctggggtg
 121 ccaggtgcct ggggtcaggc tgggagcctg gacttgcaga ttgatgagga gcagccagcg
 181 ggtacactga ttggcgacat cagtgcgggg cttccggcag gcacggcagc tcctctcatg
 241 tacttcatct ctgcccaaga gggcagcggc gtgggcacag acctggccat tgacgaacac
 301 agtggggtcg tccgtacagc ccgtgtcttg gaccgtgagc agcgggaccg ctaccgcttc
 361 actgcagtca ctcctgatgg tgccaccgta gaagttacag tgcgagtggc tgacatcaac
 421 gaccatgctc cagccttccc acaggctcgg gctgccctgc aggtacctga gcatacagct
 481 tttggcaccc gctacccact ggagcctgct cgtgatgcag atgctgggcg tctgggaacc
 541 cagggctatg cgctatctgg tgatggggct ggagagacct tccggctgga gacacgcccc
 601 ggtccagatg ggactccagt acctgagctg gtagttactg gggaactgga ccgagagaac
 661 cgctcacact atatgctaca gctggaggcc tatgatggtg gttcaccccc cggagggcc
 721 caggccctgc tggacgtgac actgctggac atcaatgacc atgccccgc tttcaatcag
 781 agccgctacc atgctgtggt gtctgagagc ctggcccctg gcagtcctgt cttgcaggtg
 841 ttcgcatctg atgccgatgc tggtgtcaat gggctgtga cttacgagat caaccggagg
 901 cagagcgagg gtgatggacc cttctccatc gacgcacaca cggggctgct gcagttagag
 961 cggccactgg actttgagca gcggcgggtc catgaactgg tggtgcaagc acgagatggt
1021 ggggctcacc ctgagctggg ctcggccttt gtgactgtgc atgtgcgaga tgccaatgac
1081 aatcagccct ccatgactgt catctttctc agtgcagatg gctcccccca agtgtctgag
1141 gccgccccac ctggacagct cgttgctcgc atctctgtgt cagacccaga tgatggtgac
1201 tttgcccatg tcaatgtgtc cctggaaggt ggagagggcc actttgccct aagcacccaa
1261 gacagcgtca tctatctggt gtgtgtggct cggcggctgg atcgagagga gagggatgcc
1321 tataacttga gggttacagc cacagactca ggctcacctc cactgcgggc tgaggctgcc
1381 tttgtgctgc acgtcactga tgtcaacgac aatgcacctg cctttgaccg ccagctctac
1441 cgacctgagc ccctgcctga ggttgcgctg cctggcagct ttgtagtgcg ggtgactgct
1501 cgggatcctg accaaggcac caatggtcag gtcacttata gcctagcccc tggcgcccac
1561 acccactggt tctccattga cccacacctca ggcattatca ctacggctgc ctcactgac
1621 tatgagttgg aacctcagcc acagctgatt gtggtggcca cagatggtgg cctgccccct
1681 ctagcctcct ctgccacagt tagcgtggcc ctgcaagatg tgaatgataa tgagccccaa
1741 ttccagagga cttttctacaa tgcctcactg cctgagggca cccagcctgg aacttgcttc
1801 ctgcaggtga cagccacaga cgcggatagt ggcccatttg gcctcctctc ctattccttg
1861 ggtgctggac ttgggtcctc cggatctccc ccattccgca ttgatgccca tagcggtgat
1921 gtgtgcacaa cccggaccct gaccgtgac cagggccct caagctttga cttcacagtg
1981 acagctgtgg atgggggagg cctcaagtcc atggtatatg tgaaggtgtt tctgtcagac
2041 gagaatgaca accctcctca gttttatcca cgggagtatg ctgccagtat aagtgcccag
2101 agtccaccag gcacagctgt gctgaggttg cgtgcccatg accctgacca gggatcccat
2161 gggcgactct cctaccatat cctggctggc aacagccccc cacttttttac cttggatgag
2221 caatcagggc tgttgacagt agcctggccc ttggccagac gggccaattc tgtggtgcag
2281 ctggagatcg gggctgagga cggaggtggc ctacaggcag aacccagtgc ccgagtggac
2341 atcagcattg tgcctggaac ccccacacca cccatatttg agcaactaca gtatgttttt
2401 tctgtgccag aggatgtggc accaggcacc agtgtgggca tagtccaggc acacaaccca
2461 ccaggtcgct tggcacctgt gacccttcc ctatcaggtg gggatccccg aggactcttc
2521 tccctagatg cggtatcagg actgttgcaa acacttcgcc ctctggaccg ggagctactg
2581 ggaccagtgt tggagctgga ggtgcgagca ggcagtggag tgcccccagc tttcgctgta
2641 gctcggtgc gtgtgctgct ggatgatgtg aatgacaact ccctgccctt tcctgcacct
2701 gaagacacgg tattgctacc accaaacact gccccaggga ctcccatcta tacactgcgg
2761 gctcttgacc ccgactcagg tgttaacagt cgagtcacct ttaccctgct tgctgggggt
2821 ggtggagcct tcaccgtgga ccccaccaca ggccatgtac ggcttatgag gcctctgggg
```

FIGURE 2 (cont.)

```
2881 ccctcaggag ggccagccca tgagctggag ctggaggccc gggatggggg ctccccacca
2941 cgcaccagcc actttcgact acgggtggtg gtacaggatg tgggaacccg tgggctggct
3001 ccccgattca acagccctac ctaccgtgtg gacctgccct caggcaccac tgctggaact
3061 caggtcctgc aagtgcaggc ccaagcacca gatggggggcc ctatcaccta tcaccttgca
3121 gcagagggag caagtagccc ctttggcctg gagccacaga gtgggtggct atgggtgcgg
3181 gcagcactag accgtgaggc ccaggaattg tacatactga aggtaatggc agtgtctggg
3241 tccaaagctg agttggggca gcagacaggc acagccaccg tgagggtcag catcctcaac
3301 cagaatgaac acagtccccg cttgtctgag gatcccacct tcctggctgt ggctgagaac
3361 cagccccag ggaccagcgt gggccgagtc tttgccactg accgagactc aggacccaat
3421 ggacgtctga cctacagcct gcaacagctg tctgaagaca gcaaggcctt ccgcatccac
3481 ccccagactg gagaagtgac cacactccaa accctggacc gtgagcagca gagcagctat
3541 cagctcctgg tgcaggtgca ggatggaggg agcccacccc gcagcaccac aggcactgtg
3601 catgttgcag tgcttgacct caacgacaac agccccacgt tcctgcaggc ttcaggagct
3661 gctggtgggg gcctccctat acaggtacca gaccgcgtgc ctccaggaac actggtgacg
3721 actctgcagg cgaaggatcc agatgagggg gagaatggga ccatcttgta cacgctaact
3781 ggtcctggct cagagctttt ctctctgcac cctcactcag gggagctgct cactgcagct
3841 cccctgatcc gagcagagcg gccccactat gtgctgacac tgagtgctca tgaccaaggc
3901 agccctcctc gaagtgccag cctccagctg ctggtgcagg tgcttccctc agctcgcttg
3961 gccgagccgc cccagatct cgcagagcgg gacccagccg caccagtgcc tgtcgtgctg
4021 acggtgacag cagctgaggg actgcggccc ggctctctgt tgggctcggt ggcagcgcca
4081 gagcccgcgg gtgtgggtgc actcacctac acactggtgg gcggtgccga tcccgagggc
4141 accttcgcgc tggatgcggc ctcagggcgc ttgtacctgg cgcggccct ggacttcgaa
4201 gctggcccgc cgtggcgcgc gctcacggta cgcgctgagg ggccgggagg cgcgggcgcg
4261 cggctgctgc gagtgcaggt gcaagtgcag gacgagaatg agcatgcgcc cgcctttgcg
4321 cgcgaccgc tggcgctggc gctgccagag aacccggagc ccggcgcagc gctgtacact
4381 ttccgcgcgt cggacgccga cggccccggc cccaatagcg acgtgcgcta ccgcctgctg
4441 cgccaggagc cgcccgtgcc ggcgcttcgc ctggacgcgc gcaccggggc gctcagcgct
4501 ccgcgcggcc tggaccgaga gaccactccc gcgctgctgc tgctggtgga agccaccgac
4561 cggcccgcca acgccagccg ccgtcgtgca gcgcgcgttt cagcgcgcgt cttcgtcacg
4621 gatgagaatg acaacgcgcg tgtcttcgcc tcgccgtcac gcgtgcgcct cccagaggac
4681 cagccgcctg ggcccgcggc cctgcacgtg gtagcccggg acccggatct gggcgaggct
4741 gcacgcgtgt cctatcggct ggcatctggc ggggacggcc acttccggct gcactcaagc
4801 actggagcgc tgtccgtggt gcggccgttg gaccgcgaac aacgagctga gcacgtactg
4861 acagtggtgg cctcagacca cggctccccg ccgcgctcgg ccacgcaggt cctgaccgtc
4921 agtgtcgctg acgtcaacga cgaggcgcct actttccagc agcaggagta cagcgtcctc
4981 ttgcgtgaga acaaccctcc tggcacatct ctgctcaccc tgcgagcaac cgaccccgac
5041 gtgggggcca acgggcaagt gactatgga ggcgtctcta gcgaaagctt ttctctggat
5101 cctgacactg gtgttctcac gactcttcgg gccctggatc gagaggaaca ggaggagatc
5161 aacctgacag tgtatgccca ggacagggc tcacctcctc agttaacgca tgtcactgtt
5221 cgagtggctg tggaggatga gaatgaccat gcaccaacct tgggagtgc ccatctctct
5281 ctggaggtgc ctgagggcca ggaccccag acccttacca tgcttcgggc ctctgatcca
5341 gatgtgggag ccaatggca gttgcagtac cgcatcctag atggggaccc atcaggagcc
5401 tttgtcctag accttgcttc tggagagttt ggcaccatgc ggccactaga cagagaagtg
5461 gagccagctt tccagctgag gatagaggcc cgggatggag gccagccagc tctcagtgcc
5521 acgctgcttt tgacagtgac agtgctggat gccaatgacc atgctccagc cttcctgtg
5581 cctgcctact cggtggaggt gccggaggat gtgcctgcag ggaccctgct gctgcagcta
5641 caggctcatg accctgatgc tggagctaat ggccatgtga cctactacct gggcgccggt
5701 acagcaggag ccttcctgct ggagcccagc tctggagaac tgcgcacagc tgcagccttg
5761 gacagagaac agtgtcccag ctacaccttt tctgtgagtg cagtggatgg tgcagctgct
5821 gggcccctaa gcaccacagt gtctgtcacc atcacggtgc gcgatgtcaa tgaccatgca
```

FIGURE 2 (cont.)

```
5881 cccaccttcc ccaccagtcc tctgcgccta cgtctgcccc gcccaggccc cagcttcagt
5941 accccaaccc tggctctggc cacactgaga gctgaagatc gtgatgctgg tgccaatgct
6001 tccattctgt accggctggc aggcacacca cctcctggca ctactgtgga ctcttacact
6061 ggtgaaatcc gcgtggcccg ctctcctgta gctctaggcc cccgagatcg tgtcctcttc
6121 attgtggcca ctgatcttgg ccgtccagct cgctctgcca ctggtgtgat cattgttgga
6181 ctgcagggg aagctgagcg tggaccccgc tttccccggg ctagcagtga ggctacgatt
6241 cgtgagaatg cgccccagg gactcctatt gtctccccca gggccgtcca tgcaggaggc
6301 acaaatggac ccatcaccta cagcattctc agtgggaatg agaaagggac attctccatc
6361 cagcctagta caggtgccat cacagttcgc tcagcagagg ggctagactt cgaggtgagt
6421 ccacggctgc gactggtgct gcaggcagag agtggaggag cctttgcctt cactgtgctg
6481 accctgaccc tgcaagatgc caacgacaat gctcccgtt tcctgcggcc ccattatgtg
6541 gccttcctc ctgagtcccg gcccttggag gggccctgc tgcaggtgga ggcggatgac
6601 ctggatcaag gctctggagg acagatttcc tacagtctgg ctgcatccca gccggcacgt
6661 ggattgttcc acgtagaccc aaccacaggc actatcacta ccacagccat cctggaccgt
6721 gagatctggg ctgaaacacg gttggtgctg atggccacag acagagggag cccagccctg
6781 gtgggctcag ctaccttgac ggtgatggtc atcgacacca atgacaatcg ccccaccatc
6841 ccccaaccct gggagctccg agtgtcagaa gatgcgttat tgggctcaga gattgcacag
6901 gtaacaggga atgatgtgga ctcaggaccc gtgctgtggt atgtgctaag cccatctggg
6961 ccccaggatc ccttcagtgt tggccgctat ggaggccgtg tctccctcac ggggcccctg
7021 gactttgagc agtgtgaccg ctaccagctg cagctgctgg cacatgatgg gcctcatgag
7081 ggccgtgcca acctcacagt gcttgtggag gatgtcaatg acaatgcacc tgccttctca
7141 cagagcctct accaggtaat gctgcttgag cacacacccc caggcagtgc cattctctcc
7201 gtctctgcca ctgatcggga ctcaggtgcc aacggtcaca tttcctacca cctggcttcc
7261 cctgccgatg gcttcagtgt tgaccccaac aatgggaccc tgttcacaat agtgggaaca
7321 gtggccttgg gccatgacgg gtcaggagca gtggatgtgg tgctggaagc acgagaccac
7381 ggggctccag gccgggcagc acgagccaca gtgcacgtgc agctgcagga ccagaacgac
7441 cacgccccga gcttcacatt gtcacactac cgtgtggctg tgactgaaga cctgccccct
7501 ggctccactc tgctcaccct ggaggctaca gatgctgatg gaagccgcag ccatgccgct
7561 gtggactaca gcatcatcag tggcaactgg ggccgagtct tccagctgga acccaggctg
7621 gctgaggctg gggagagtgc tggaccaggc ccccgggcac tgggctgcct ggtgttgctt
7681 gaacctctag actttgaaag cctgacacag tacaatctaa cagtggctgc agctgaccgt
7741 gggcagccac cccaaagctc agtcgtgcca gtcactgtca ctgtactaga tgtcaatgac
7801 aacccacctg tctttacccg agcatcctac cgtgtgacag tacctgagga cacacctgtt
7861 ggagctgagc tgctgcatgt agaggcctct gacgctgacc ctggccctca tggcctcgtg
7921 cgtttcactg tcagctcagg cgaccatca gggctctttg agctggatga gagctcaggc
7981 accttgcgac tggcccatgc cctggactgt gagacccagg ctcgacatca gcttgtagta
8041 caggctgctg accctgctgg tgcacacttt gctttggcac cagtgacaat tgaggtccag
8101 gatgtgaatg atcatggccc agccttccca ctgaacttac tcagcaccag cgtggccgag
8161 aatcagcctc caggcactct cgtgaccact ctgcatgcaa tcgacgggga tgctgggct
8221 tttgggaggc tccgttacag cctgttggag gctgggccag gacctgaggg ccgtgaggca
8281 tttgcactga acagctcaac aggggagttg cgtgcgcgag tgcccttgta ctatgagcac
8341 acagaaagct tccggctgct ggtggtgct gctgatgctg ggaatctctc agcctctgtc
8401 actgtgtcgg tgctagtgac tggagaggat gagtatgacc ctgtatttct ggcaccagct
8461 ttccacttcc aagtgcccga aggtgcccgg cgtggccaca gcttgggtca cgtgcaggcc
8521 acagatgagg atggggtgc cgatggcctg gttctgtatt cccttgccac ctcttccccc
8581 tattttggta ttaaccagac tacaggagcc ctgtacctgc gggtggacag tcgggcacca
8641 ggcagcggaa cagccacctc tgggggtggg ggccggaccc ggcgggaagc accacgggag
8701 ctgaggctgg aggtgatagc acgggggcct ctgcctggtt cccggagtgc cacagtgcct
8761 gtgaccgtgg atatcacccca caccgcactg gcctggcac ctgacctcaa cctgctatta
8821 gtaggggccg tggcagcctc cttgggagtt gtggtggtgc ttgcactggc agccctggtc
```

FIGURE 2 (cont.)

```
8881 ctaggacttg ttcgggcccg tagccgcaag gctgaggcag cccctggccc aatgtcacag
8941 gcagcacccc tagccagtga ctcactgcag aaactgggcc gggagccacc tagtccacca
9001 ccctctgagc acctctatca ccagactctt cccagctatg gtgggccagg agctggagga
9061 ccctaccccc gtggtggctc cttggaccct tcacattcaa gtggccgagg atcagcagag
9121 gctgcagagg atgatgagat ccgcatgatc aatgagttcc cccgtgtggc cagtgtggcc
9181 tcctctctgg ctgcccgtgg ccctgactca ggcatccagc aggatgcaga tggtctgagt
9241 gacacatcct gcgaaccacc tgcccctgac acctggtata agggccgaaa ggcagggctg
9301 ctgctgccag gtgcaggagc cactctctac agagaggagg ggcccccagc cactgccaca
9361 gccttcctgg ggggctgtgg cctgagccct gcacccactg gggactatgg cttcccagca
9421 gatggcaagc catgtgtggc aggtgcgctg acagccattg tggccggcga ggaggagctc
9481 cgtggcagct ataactggga ctacctgctg agctggtgcc ctcagttcca accactggcc
9541 agtgtcttca cagagatcgc tcggctcaag gatgaagctc ggccatgtcc cccagctccc
9601 cgtatcgacc caccacccct catcactgcc gtggcccacc caggagccaa gtctgtgccc
9661 cccaagccag caaacacagc tgcagcccgg gccatcttcc caccagcttc tcaccgctcc
9721 cccatcagcc atgaaggctc cctgtcctca gctgccatgt cccccagctt ctcaccctct
9781 ctgtctcctc tggctgctcg ctcacccgtt gtctcaccat ttggggtggc ccagggtccc
9841 tcagcctcag cactcagcgc agagtctggc ctggagccac ctgatgacac ggagctgcac
9901 atcgtttaaa c
```

FIGURE 3

Homo sapiens centrosomal protein 164kDa (CEP164), mRNA, NM_014956.4

```
   1 ttgcgcgctg caggggcaaca ccccggcgtc cctggaagct gggggagcgg gagaaataac
  61 tttatttgga ctgagagctg gagaatgaga ataggacctg agagtatatt gggctaagga
 121 ggagaggtgt ttgagcccag atgagtcatg gctggacgac ccctccgcat aggagatcag
 181 ctggttctgg aagaagatta tgatgagacc tacattccta gtgagcaaga aattcttgaa
 241 tttgcccggg agattggtat tgatcccatc aaggaaccag aactgatgtg gctggcgcga
 301 gagggcatcg tggccccact gcctggagag tggaaaccat gccaggacat cacaggtgac
 361 atttactatt tcaacttcgc caacgggcag tctatgtggg accatccatg tgacgaacac
 421 tatcggagct tggtgatcca agagcgggca aagctgtcaa cttctgggc cattaagaag
 481 aagaaaaaaa aaaaggaaaa gaaagacaag aaggacagag acccccccaa aagttcgctg
 541 gccttgggtt cctcattagc cccagttcat gttcctcttg ggggcctggc tcctttacga
 601 ggtcttgtgg ataccccacc ctctgctctt cgtggatctc aaagcgtgag cctggggagc
 661 tcagtggagt ctggacgtca gcttgaagaa ctcatgctgc cttcacaggg tctcaagacc
 721 tctgcttata caaagggtct cttgggctcc atatatgagg acaagactgc tctcagcctc
 781 ttgggtttag gagaagaaac caatgaggag gatgaggagg aaagtgacaa ccagagtgtc
 841 cacagctcaa gtgagcctct taggaaccta cacctggaca ttggggcact ggggggtgac
 901 tttgagtatg aggagtctct gagaacaagc cagccagagg agaagaagga tgtttctctg
 961 gattcagatg ctgccggtcc ccctactccc tgcaagccct ccagcccagg tgcagacagc
1021 agtctgagca gtgctgttgg caaagggcga cagggaagtg gagcaagacc tggtcttcca
1081 gaaaagagg aaaatgagaa gagtgaacct aagatttgca ggaatctggt gaccccaag
1141 gcagacccta caggcagtga gcctgccaaa gcctctgaaa aggaagcacc agaggacaca
1201 gtagatgcag gagaggaggg ttccaggagg gaagaggcac ccaaggagcc aaagaagaag
1261 gcttctgctc tggaagaggg cagttcagac gccagccaag aactggaaat tagtgaacac
1321 atgaaggaac cacagctctc agactccata gcttctgacc ccaagtcctt ccatggcctg
1381 gacttcggtt ttcgcagccg gatctcggag cacctgctgg atgttgatgt gctttcccca
1441 gtcctgggtg gagcttgtcg gcaggccag caaccactgg aatagaaga caaggatgac
1501 agccagtcca gccaagatga gctgcagagc aagcagtcca aaggcctgga ggagaggtta
1561 tctcctccac ttccacacga ggagcgggcc cagagtcccc ctcgcagcct ggccactgaa
1621 gaagagcctc cccagggccc cgaggggcag cccgagtgga aggaggcaga ggagcttggg
1681 gaggactctg cagccagcct cagcctgcag ctgtccctcc agaggagca ggccccaagc
1741 ccacctgctg cctgtgagaa gggcaaggag cagcattccc aggccgagga gctgggccct
1801 gggcaggaag aggcagagga tcctggaggag aaggtggcgg tcagccccac cccgccagtc
1861 tctccagagg tgcgatccac agagcctgtg gctcccccag agcagctctc agaggctgca
1921 ctaaaggcca tggaagaggc agtggcccaa gtactcgagc aagaccagag gcacctgctg
1981 gaatccaagc aagagaagat gcagcaactg cgggagaagc tgtgccaaga ggaggaagag
2041 gagatcctcc ggcttcacca gcagaaagag caatctctca gttccttgag ggagcggctg
2101 cagaaagcca ttgaggagga ggaggcccgg atgagagagg aggaaagcca gaggctatcc
2161 tggctccgag ctcaggtcca gtccagcaca caagcagatg aggaccaaat cagggctgag
2221 caagaggctt ccctgcagaa actgagagaa gagttggagt ctcaacagaa ggctgagagg
2281 gccagcttgg aacagaaaaa taggcaaatg ctggagcagc tcaaggaaga gatagaggct
2341 tcggagaaga gcgagcaggc tgccctgaat gctgcaaagg agaaggctct gcagcagctg
2401 agggagcagc tggaagggga gaggaaagaa gctgtggcaa cgctggagaa ggagcacagt
2461 gctgagctgg agcggctctg ctcctcattg gaggccaagc accgggaggt ggtctccagc
2521 ctccagaaga agatacagga agctcaacag aaagaggagg cccagctgca gaagtgcctt
2581 gggcaagtgg agcacagagt tcaccagaag tcttatcacg tggctgggta tgagcacgag
2641 ctcagcagtc cctgcgaga gaagcgccag gaagtggaag gggagcatga gaggaggttg
2701 gacaagatga aggaggagca ccagcaagtg atggctaagg ccagagagca gtatgaagct
2761 gaggagagga agcagcgggc tgagcttctg gggcacctga ccggagagct ggagcgcctg
2821 cagagggccc atgaacgaga actggagact gtgaggcagg agcaacacaa gcgtcttgag
```

FIGURE 3 (cont.)

```
2881 gacttgcggc gccggcacag ggagcaggaa aggaagctcc aggatttaga gttggacctt
2941 gaaaccagag ctaaagatgt caaggccaga ttggctctgc tggaggtcca ggaggagacc
3001 gcccggaggg agaagcagca gctgcttgat gtgcagaggc aggttgctct gaagagtgag
3061 gaagccacag ccacccatca gcagctggag gaggcacaga aggagcacac ccacctgttg
3121 cagtcaaacc agcagctccg agaaattctt gatgagctgc aggcccgcaa gctgaagctg
3181 gagtcccaag tggatctgct gcaggctcag agccagcaac tgcagaaaca cttcagcagc
3241 ctggaggctg aagctcaaaa gaagcagcac ctgttgagag aagtgacagt tgaggaaaat
3301 aatgcttccc cacattttga gccagatctc catattgagg acctgaggaa atcccttgga
3361 acaaaccaga ccaaagaggt gtcttcttct ctctcccaga gcaaggagga cttatacttg
3421 gacagcctgt cctcccacaa tgtctggcac ctcctctctg ctgaggggt agccctccgt
3481 agtgccaagg agttccttgt gcagcagaca cgctccatgc ggaggcggca gacagctctg
3541 aaagctgccc agcagcattg gcgccatgag ctggccagtg cgcaggaggt ggccaaagac
3601 ccaccaggca tcaaggccct ggaagatatg gcaagaacc tggagaagga gaccaggcac
3661 ctggatgaga tgaagtcggc catgcggaaa ggccacaacc tgctgaagaa gaaagaggag
3721 aagctgaatc agttggagtc ctctctttgg gaagaggcct cagatgaggg cactctggga
3781 ggatccccca ccaagaaggc agtaaccttc gacctcagtg acatggacag cctgagcagt
3841 gaaagttctg aatcttttc cccgcctcac cgtgagtggt ggcggcagca gaggatcgac
3901 tcaaccccga gtctcacctc ccgcaagatc cacgggctta gccactccct ccggcagatc
3961 agcagccagc tgagcagtgt cctcagcatc ctggacagcc tcaaccctca gtcgccgccg
4021 ccgctcctcg cctccatgcc agcccagctc cctcccggg accctaagag cacccccacc
4081 cccacctact atggctccct ggccaggttc tcagccttat catctgctac acccacgtcc
4141 acccaatggg cctgggattc agggcagggg cccaggctcc cctcctctgt ggctcaaacg
4201 gtggacgact tcctgttgga gaagtggcgc aagtattttc catctggcat cccgctgctc
4261 agcaacagcc ccacccgct ggagagcagg ctgggttaca tgtctgccag tgagcagctc
4321 cggctcctac agcactccca ttcgcaagtc cctgaggcgg gcagcaccac ctttcagggc
4381 ataattgagg ccaaccggag gtggctggaa cgtgtcaaga atgacccag gttacctctc
4441 ttctcgtcaa cacccaagcc aaaagctact ttgagcctcc tgcagctggg ccttgatgag
4501 cacaacagag tgaaggtgta tcgcttctga ggccctgagc aggggcttgg ggcagcccag
4561 cctctcctcc acccagacca agtgcctgag gagctgcctg ccttcttcca tctgagaaag
4621 caccctcctt ccccctttga cttgcaggag ccacagggga ccaggggtt gagtggaaca
4681 gtaaagccac acattctgtg actatataac ctatctcagg ctaaaatgtg tggactcgta
4741 cgagctcttg tcattgacat ggcaagctga tggcgtgcgg tggctgcggg gtatcagggc
4801 cgggagccct ttgggaggaa gggaggcgtt agaggagctg ccttcggagg ctcagggagt
4861 ccctttggag ctggttgttt ccttggccct gcagcgcact gctcggggct cccaaggagg
4921 ttgtgtgtat ggttcttaat tcatcaggac aaagacccc agcatgtgtg taccctggga
4981 cccgatttct ctgggccccac atctatctcc aatacctcag cctcagatca gacccttct
5041 tttttgtctt tcttctctta attttttaaat gcctcttttc ttgagcattc catctctctt
5101 tttgaccctc tcaggactgg gcttagctgt ccagacccct gccggagggt gctgggggct
5161 gtccctctgc aggcactgtg ttttcctcag gggctgtcct cagaacaccc ctcctgctcc
5221 ctggggctcc tcagggagcc atttcagctg gagtctcagg tctcaaaaac aacttctcca
5281 ggaggccaaa aaaagactgg gttggcttct ggtcctcatg atggcttta tcctcctggg
5341 acactttggg tatattcatg ggcattgttt ccatctgtct tttctacctg tgccaccct
5401 gccctgattc cacggctgcc tcaggcaggc aggcaaggag ctaggccggt gcccggccct
5461 ggcagcaagg ggtctttgtg cagttggaga tgctgccgtt gtggcagagc gtcctgcagc
5521 cccgcttcca tcagcaggct ctggggtggg ggctttgcag gggatgctct ctgatgtttg
5581 ttccgttgtt taaataaat gcacttattt ttgtttttt ttttgcaaaa aaaa
```

FIGURE 4

Homo sapiens kelch repeat and BTB (POZ) domain containing 6 (KBTBD6), mRNA

```
   1 cattgtcgcc cacgctgcag tagcggcttc tgcggctcca agccagcggg tcctgtgaag
  61 gcgagcagac gcggagaaag gacgcgggag tgagagaggg tgagtcagcc actgtctaaa
 121 cgataacggg aggcggctct gcggggtagg gttgaattca gtaaatgggc tcgtgctgct
 181 gtctcttcgg agacgctgct atcttagcgt cagcgaggga aggttgagga ggagccagag
 241 ccgggtcctg cagcgtttct cgccatcagc gcccgtcgcc atctccacca tgcagtcccg
 301 ggaagacgcc ccgcgctctc gccgcctagc cagtccccgt ggtgggaagc ggcccaagaa
 361 gattcacaaa cccacagttt cggccttttt cacgggtcca gaggaattaa aggacacggc
 421 ccattctgca gccctgctgg cacagctcaa gtccttctac gatgcgcggc tgctgtgtga
 481 tgtgaccatc gaggtggtga cgcctggcag cgggcctggc acgggtcgcc tgttcccctg
 541 caaccgcaat gtgctggccg cggcatgtcc ctacttcaag agcatgttca caggtggcat
 601 gtacgagagc cagcaggcca gcgtgaccat gcacgatgtg gacgccgagt ccttcgaggt
 661 gttggtcgac tactgctaca cgggtcgtgt gtctctcagt gaggccaacg tggagcgcct
 721 gtacgcggcc tccgacatgc tacagctgga atatgtgcgg gaagcctgtg cctccttctt
 781 agcccgacgt cttgacctga ccaactgcac cgccatcctc aagtttgcag atgcctttgg
 841 ccatcgcaag ctgcgatccc aggcccagtc ctatatagct cagaacttca agcaactcag
 901 ccacatgggt tcaattcggg aggagactct agcagatctg accctggccc agctgctggc
 961 tgtcctgcgc ttggatagtc tggacgtgga gagtgagcag acagtgtgcc atgtggcagt
1021 gcagtggctg gaggctgctc ccaaagagcg gggtcccagt gctgcagaag tcttcaagtg
1081 cgtgcgctgg atgcacttca ctgaagaaga tcaggactac ttagaagggc tgctgaccaa
1141 gcccatcgtg aagaagtact gcctggacgt tattgaaggg gccctgcaga tgcgctatgg
1201 tgacctgttg tacaagtctc tggtgccagt gccaaacagc agcagcagca gtagcagcag
1261 caactctctt gtatctgcag cagaaaatcc accccagaga ctgggtatgt gtgccaagga
1321 gatggtgatc ttctttggac accccagaga tccctttctc tgctgtgatc catactcggg
1381 ggacctttac aaagtgccgt cacccttgac ctgtctggct cacactagga ctgtcaccac
1441 tctagctgtc tgtatctctc ctgaccatga catctatcta gctgctcagc caggacaga
1501 cctctgggtg tataaaccag ctcagaatag ttggcagcaa cttgcagatc gcttgctgtg
1561 tcgtgagggc atggatgtgg catatctcaa tggctatatc tacattttgg gggggcgaga
1621 ccctattact ggagttaagt tgaaggaagt ggaatgctac aatgttaaga gaaaccagtg
1681 ggcattggtg gctccactgc cccattcttt tttatccttt gacctaatgg taattcgaga
1741 ctatctctat gctctcaaca gtaagcgcat gttctgttat gatcctagcc acaatatgtg
1801 gctgaagtgc gtttctctga agcgcaatga ctttcaggaa gcctgcgtct tcaatgagga
1861 gatctattgt atctgtgata tcccagtcat gaaggtctac aacccagtta gggcagaatg
1921 gaggcaaatg aataatattc ccttggtctc agagaccaac aactacagaa ttatcaagca
1981 tggcccaaaa ttgttgctca tcacctctcg caccccacag tggaaaaaga accgggtgac
2041 tgtgtatgaa tatgtatta gggagaccaa atggattaat ataggtacca cattaggcct
2101 cttgcagttt gattctaact ttttttgcct ctctgctcgt gtttatcctt cctgccttga
2161 acctggtcag agtttcctca ctgaagaaga agaaataacca agtgagtcta gcactgaatg
2221 ggacttaggt ggattcagtg agccagactc tgagtcagga agttcaagtt ctctttctga
2281 tgatgatttt tgggtgcgtg tagcgcctca gtgaaatgca caggatcaac agggtttgtt
2341 gtaactagat tgaaacacta agttgttttt actgttttgg aaaatatctt aaatatcctt
2401 tttgttccta aaggagagga aaagttgatt aacttctggt ttggtttaga aaaagtaatg
2461 tttgaaatac gaaggtaatt taatgttaca aatttttaaca ctcaaatcaa ccttttaata
2521 attttctgtg ctaagggtcc agtatttatt tgattattta gtatgtttat gtttcatgac
2581 actaatttag tcttttgata cattttacat tctgtttact gccacaagca ctgtggcaat
2641 aactttgaa ttttaatttt tataatagaa aaatgattag gaattgctag atagtgtttt
2701 gaaagcatat ctttttcttc agaacaatgt agacttccaa aatggttaac ctaagggtc
2761 tttacaaaat gtgttataag ttaaacataa tttgggaagt tttacttttg ttttcttcta
2821 tgaagaaaaa aatgcaggct gggcgcggtg gctcacgcct gtaatcctag cactttggga
2881 ggccgaggca ggtggatcac ctgaggtcag ttcaagacca gcctggccaa catggtgaaa
```

FIGURE 4 (cont.)

```
2941 ccccgtctct actaaaaata caaaaattag ctgggcgtgg tggcatgcgc ctgtaatccc
3001 agctacccag gaggctgagg caggagaatt gctgaaaccc gggagtcaga ggctgcagag
3061 agccgagact gggccactgc actccagcct ggatgacaga gtgagactcc gtctcaaaaa
3121 aaaaaaaaaa aaaaaaagga aaaaaaaaaa agaaaaaaaa ccatatgtgt attagggtga
3181 ctgagtggtg acttcattta taataataca gagaatagct ataagctcat tgacagtaaa
3241 aacaacaaac caggattcta ctgtttgaaa agaagtttcg ttttaatttt ggaatttaga
3301 atgtgtattt gcaaagtcac caattttcat ctaaaaggtt atattctagt tgtgtcacca
3361 aatcatcaaa aaaccttaaa aaagaagtaa cttgctttgt aggtttgtat tgttgatcta
3421 aacctgatac atgcttcatt taatcaggaa taatcctttt ttttctgctg gacatgtata
3481 aatttcactg gattgtataa attttatct attgccttaa acatttacat gattctcaat
3541 atgttttagc tgtacagttt tggtgttcat cttagaggat tcttcagcag aagtgatatt
3601 tctttactgt tttgtgaggt aatactgatt ttgaaaatat ataaagcta aaaacagtat
3661 ttcgttgata tcagtagtca ttgtgttaac tataaagtca agtgccagca aagaacttta
3721 aaactgtaaa gctgtgtata gaactgtttt gtgtagcatg gaaatattct gtcagctttt
3781 taaagtcact aaatgttctt gattatcagc ttgaaggtat ttttgtatta caagttgaca
3841 gttgctgggt gtagtggctc atgcctgtaa tcctagcaac tcggggctga ggtgggagga
3901 ttgcttcagc ccaggagttt gagaccagcc tgggcaacat agcaaaaccc catctctaca
3961 aaaataaaaa atatgtctgg gcatggtggc ccaagtctga gtcccagtta cttgggagga
4021 tcacttgaat gtaggatcac ttgagtctag gagttcgggg ctgcagctat catctgcagc
4081 tataatcata gctcactgca gctatgatca tgtctcagca ctccagcttt ggcaacagaa
4141 cgagatccca tctcttagaa aaacaaagtt gatagttaaa gaacataagt ggatgatggc
4201 atttgaggcc actagtgaaa gtatgttttc tctaaaatat ttctctaata gtgatataaa
4261 tggctatttt attatgatgt ttgtatgtgt tttgtatttc tctgtaaacc atgctccagt
4321 ctttgttttt ctgttaccat aatgtaagag aaggtcctgg aacagagact aaatcccacg
4381 aaactgacat tgttaaacac actaaaacag aagtacttac ctcttgaaga tttaatatat
4441 aatggttgac atgatacatg tacatgatga atgaccagat gcttatggtc tacattttcc
4501 tttatcctgt tagtattacc ttccttaatc tttgttcatt aacatgctaa ttcctcttca
4561 gtgtttattt tctagtgaca gaatgctaac atttcttaca ccctggcaga agggagagaa
4621 atgtgttttg gggtgggtaa ctaaattttt gagtgaaata tcataagatg agaatggaaa
4681 gagggagaca caaagagtta taacaaaaaa acaatggttt ttttagccat ttgactggct
4741 ctttaaaatag tctacaagac attcacgttt aacatcactt ttagtgaaat aaaatgtgcc
4801 atactagtat gtgcttcaaa agggcaaatg tgctttagtg ccctaaggct aaattttggt
4861 catttgacat cagagatgtt gtaagtattg cacttaatac gcacctattt ctcaatagtg
4921 ttattttttg gctagcattt tctttaccac tatcttgttg atagcttttt gttctctaag
4981 gttgaaacat gacagtgctt atctcaaaca gattacccat ctgcagaact aaggaaagca
5041 atttatgtat gaaagaaatt cttgaattcg tcattctcaa cctttgaatt aaagcttaga
5101 ctaaatagta atatatcgtg ggaaggattt tggttttgtg atatttctgt gaattaagga
5161 atagatgtta accattattt tgtagaaaag tgatttgtat gtggttaatt ataaataaaa
5221 ctggtacc
```

FIGURE 5

Homo sapiens ribosomal protein S19 (RPS19), mRNA, NM_001022.3

```
  1 gtactttcgc catcatagta ttctccacca ctgttccttc cagccacgaa cgacgcaaac
 61 gaagccaagt tcccccagct ccgaacagga gctctctatc ctctctctat tacactccgg
121 gagaaggaaa cgcgggagga aacccaggcc tccacgcgcg accccttggc cctcccctttt
181 acctctccac ccctcactag acaccctccc ctctaggcgg ggacgaactt tcgccctgag
241 agaggcggag cctcagcgtc taccctcgct ctcgcgagct ttcggaactc tcgcgagacc
301 ctacgcccga cttgtgcgcc cgggaaaccc cgtcgttccc tttcccctgg ctggcagcgc
361 ggaggccgca cgatgcctgg agttactgta aaagacgtga accagcagga gttcgtcaga
421 gctctggcag ccttcctcaa aaagtccggg aagctgaaag tccccgaatg ggtggatacc
481 gtcaagctgg ccaagcacaa agagcttgct ccctacgatg agaactggtt ctacacgcga
541 gctgcttcca cagcgcggca cctgtacctc cggggtggcg ctggggttgg ctccatgacc
601 aagatctatg ggggacgtca gagaaacggc gtcatgccca gccacttcag ccgaggctcc
661 aagagtgtgg cccgccgggt cctccaagcc ctggaggggc tgaaaatggt ggaaaaggac
721 caagatggcg gccgcaaact gacacctcag ggacaaagag atctggacag aatcgccgga
781 caggtggcag ctgccaacaa gaagcattag aacaaaccat gctgggttaa taaattgcct
841 cattcgtaaa aaaaaaaaaa aaaaaaaaa aa
```

FIGURE 6

Homo sapiens ribosomal protein L34 (RPL34), transcript variant 2, mRNA

```
  1 gtctgcaggt atggatgttg ttctcttttc cctgtcttta tttccttacc aatcggctgc
 61 catccgagga gctgaggaag cctagagctc tcagaagcag tcctttgagc tggtgtaggg
121 gcactcagaa tggtccagcg tttgacatac cgacgtaggc tttcctacaa tacagcctct
181 aacaaaacta ggctgtcccg aacccctggt aatagaattg tttaccttta taccaagaag
241 gttgggaaag caccaaaatc tgcatgtggt gtgtgcccag gcagacttcg aggggttcgt
301 gctgtaagac ctaaagttct tatgagattg tccaaaacaa agaaacatgt cagcagggcc
361 tatggtggtt ccatgtgtgc taaatgtgtt cgtgacagga tcaagcgtgc tttccttatc
421 gaggagcaga aaatcgttgt gaaagtgttg aaggcacaag cacagagtca gaaagctaaa
481 taaaaaaatg aaactttttt gagtaataaa aatgaaaaga cgctgtccaa tagaaaaagt
541 tggtgtgctg gagctacctc acctcagctt gagagagcca gttgtgtgca tctctttcca
601 gttttgcatc cagtgacgtc tgcttggcat cttgagattg ttatggtgag agtatttaca
661 cctcagcaaa tgctgcaaaa tcctgttttc ccccagagag ctggaggtta aatactacca
721 gcacatccct agatactact caagttacag tatatgatca ctaatatagt atgctcttgg
781 taccaggagc tctgatatat atctggtaca tgtttgataa tgacttgatt gttattataa
841 gtacttatta atacttcgat tctgtaaaga gtttagggtt tgattttata aaatccaaaa
901 tgagccttt  attgaatcca gttctctatg tgaccagttc tctgtatgaa tggaagggaa
961 aagaattaaa aatcttgcaa aggggaaaaa aaaaaaaaaa aaa
```

FIGURE 7

Homo sapiens HemK methyltransferase family member 1 (HEMK1), mRNA

```
   1 gcgtccgagg gagcgcgcga cgggccacgc acgtccgggc gtccagttcg gggcagcttc
  61 tccggctggt gggtgggtgg ggcagccttt caggcagggt ggcaaccaac tatatctgag
 121 gaccagagcc attttggggc accagagctc gtgacctctc catctccacc cagctgggtc
 181 cagggccac tctcagcact cacctcagca gctgacatca taaagcagac ttgggaacct
 241 ggaagcactc tggagaacct ttccctgaga catggagctt tggggccgaa tgctgtgggc
 301 cctcctgtct ggcccaggga ggaggggaag tacccggggc tgggccttca gctcatggca
 361 accccaacca cctctggctg ggttatccag tgccatagaa ctggtcagcc actggactgg
 421 ggtctttgag aagagggta tccctgaggc ccgggaatcc agtgagtaca tcgtggctca
 481 tgtccttgga gccaaaacat ttcagagcct gaggccggca ctttggaccc agcccttgac
 541 ctctcagcaa ctacagtgta tccgggagct gagtagccgt cgattgcaga ggatgccggt
 601 gcagtacatc cttggagagt gggacttcca ggggctcagc ctaaggatgg tgccccagt
 661 gtttattcct cggccagaaa cagaggaact ggttgagtgg gtgctggaag aggtggccca
 721 gaggtcccat gctgtgggat ccccaggcag cccctcatt ctggaggtgg gctgcggatc
 781 aggagccatc tccctcagcc tgctgagcca gctcccccag agccgagtca ttgctgtgga
 841 taagcgggaa gctgctatct ctctgaccca tgaagatgct cagaggcttc ggttgcagga
 901 caggatttgg atcatccacc tcgacatgac ctcagaaagg agctggacac acctgccctg
 961 gggccccatg gacctgattg tcagcaaccc tccctacgtc ttccaccagg acatggagca
1021 gctggccct gagatccgca gctatgaaga ccccgcggcc ctggatggtg gggaggaggg
1081 catggacatc attacccaca ttctggcctt ggcacccggg ctcctgaaag actctggtag
1141 tatcttctta gaagtggacc caaggcaccc ggagcttgtc agcagctggc ttcagagccg
1201 gcctgacctg tacttaatc ttgtggctgt gcgcagggac ttctgtggga ggccccggtt
1261 cctgcatatc cggaggtctg ggccatagca tggctgccct gtggatgcct tgtcagtgcc
1321 gccagcctga ccagagggga ggtggatggc actttccaga gcccaggttc ttatggcatt
1381 tcccagggtt ctgtgatttc cccatgctct gcatttctag gatatttcta ggacacctgg
1441 attggctcca tcacatcaga gtggctgagg gcagttgctc tgtgttggtg aaattgctgt
1501 gggggtatcg ggggatatgg ccagtaaagt attgagagac taacaaatgg tgacctaatg
1561 ttttgtccat gacttgcagg tccctgacc ccttactcc caggtagcac tggggcaagg
1621 gtttccttct gccccagcag ggctggccgt cagtcccctg cttggtagtg gtgtgggggt
1681 gcagtgtgga ggaaggcacg tgagtcctca ctcctggcct tggataccat gggtcctggc
1741 atagagcagc tcactcccag ggattgatta gtcctccact gccctgggtg catgcgtaca
1801 caattccctg gccaagcctg gctcgagcac aggaagctca tctgcgtttt ggctcaagga
1861 tgactgcctg ctttctggag gggagggtct ggaggtcttt gctgcacagt tcctgggtcg
1921 cacatccacg ttcatttaac tgaaggcttg agccagtgag gggtgtttcc tttttatccc
1981 catagctttt agctaaaaca tccctcccga gttgaccccc tggggtttca aataacccat
2041 gtgtccctgg ttggggctgg ggagagtgag aagctgagat actgggcaca gggttgtggc
2101 ctccacccca gctctggtct gtgcagactc atggccacca ggaggcctgc agatccagcc
2161 ttcctgtcaa cagcgacagg aaatctctag gttggtgagt gctggtgatg tgagcctaca
2221 tcaggggtgg tcctaagaaa catggcaaac caggctgtct cattccacta gactgcccc
2281 tgccaccctg gcacttccca gggcctggca gtatggtctg atgggcagta tggtccaata
2341 ggcagcatcc tctgctgcag ctgggagagc tgagttccag ggctgtgtcc tgcagtggga
2401 ccttgggcaa ctcctttccc tatgagaagc tggctcttct gagtccaggg ccaacgccaa
2461 ctggcaacct ctttactctt agtcaagtgg aatgtgcatg ctggcatctg aatgtccatt
2521 cgccaggcat ggagagcaag agaaggtatg tactgcctga ggtcacatga cagtgaccaa
2581 gtggagacag taagttagat ccctccctt ggggagccta tattgctgga gtcatacca
2641 gcctaagtgt tgccctgcac tatggctgga gacacattt ggtagaggtc acactgcagc
2701 tcccagtgcc ccagtgtcct gccctgtgcc cagcccagc tgcatggact ctgagctgcc
2761 cctggcttcc tttaaggagg ctgctccaga aggaacctgg gtggggaggg cgaagggggt
2821 gcacaaccag ggcaaggctc cccacttcct tagtccccca tgctcacaga cctttgcctg
2881 ctaaggtcct caccagtatt gcccttctg tctttctcct tgtgcccttt ggctcttgct
```

FIGURE 7 (cont.)

```
2941 gtcttcagca gcatctcagg gtagctgccc tgacctcgga gcagtctgtc gccccctac
3001 acctcagcca gtcctggctt ccctgatggt ctctccctcc tggcctcagg cccattcctg
3061 aggaagggcc ttggcgagct tgtggatgtt gcaccagaag agagtgcagt gttggagagt
3121 gacactgtcg gggcagctgg ggccacaagc aggagccggc ctcgggcaca actttctgcc
3181 cagaaaaatg tgcagcttga ctctgctgag gaaaaggtcc aagccaagag gactggcagg
3241 cggggcctca agcctgcagc cactggcttg attgggccct ggacgttgag cccagatgtt
3301 ggagccacac cagcctggat ttcaatccca gaatctgccc ctcaccagga tgtgaccttg
3361 ggcagatgac ttcacctcac tcagccttgg cttctaaggc tgagaaatgg gacttaatgc
3421 tttattttat aggatgcatg tgaggagccc atggaatgtg cctggcttgg cacattgtgg
3481 catttttcct tgccttcctc ggagggcaga cacagggagg aaggacccag tgccctcagg
3541 cgtccatctg atgcatggga ccaacataag gcaggcaggg atacaaggca gtctggaaag
3601 aagggaaggc aggagtttca gtcttgggct cttgactcct cactgttgtc tagagatgga
3661 gccagcaggc tggtagcctg gcagcctaca tctcccctca gcctctcctc actatggccc
3721 cagtgccttg aggcccaggc cagggcagcc agtggctcta gctcagggaa agccaggccc
3781 acctgcccta tcccctccct tgctcctgag gccaaagcca gagactcgaa cagcctcccc
3841 accaccacca gcatatgtca aggagcactt gcaggcagaa tgggaggagg acatggagct
3901 gatggagtcc aggctgtgca agcccctgag gtcttgagag atgtgcccac tgcccgtgca
3961 gcctccttca gccagagccc agagcataga caggagtgta ggagtccctg tttgatgtac
4021 tctgggagag taattctatc tcctcttctg atagttgggg aaactgaggc cttgtctcac
4081 agttggatgc ttttcccagt tgtcagtggg tttctccatg ggtctcatac agctgcctta
4141 ttgaaatagg ccccgaaccc cctaaatgca aaaaatactc tttttttgctc ctttacccccc
4201 acctggaccc tgggctattg gctgctccca atccttgccc caaacactta gctgctccc
4261 catgacttaa gtgtgttctc ttgtgtccta tggaatccag ttctgaagag gtgggggagg
4321 acaactgtgg gaaaagccct gggggcccct cccaaggccc catcagtgct ctgagtaggc
4381 tgtcatcaga acaaagggct ccactgctga caaggtttga gaactgctgg cttgaggtga
4441 gaacccctt aacctctgcg ggacagcatg tctttcccta tccaccttcg attcttttct
4501 cttttttttc ttcattggct ccttcttagt ggattctctt ctctactgcc ctgggcttca
4561 gcctttgtgc agtactctcg atgcctgaa cacacaccttt ccctttgccc aggcggtgca
4621 aacaatccac ttcttcaagc tccaacacaa atgctgcctc ctttaggatg cctgctctgt
4681 gctctccctg cctcccctag cccatacctc tgctggcacc ttctgtacca tgccttcaga
4741 aaccttctta tcccctcat ctctgggccc cctgtggat ctggcatacc caagttcagt
4801 aaatgtctat cagtaagctg atggtacatg catttttctag aatagagctg ggacttccca
4861 tgtggcccac atctgacctg gcagcccatg tattccggtc attagggatg ggaagccatg
4921 aggacctggc cttctgcccg acccaggcag ccattcaagt tgagcaatgg ccacttcgaa
4981 gactcaagtg cacctgatcc ctgcgcaaca gccacaccag gagaacaggc tgtccttggc
5041 ggcagtagga gcaggcgcca ggtttcctgg agctcttggc ttcagccagc ccccagccag
5101 agtcctggct aggacagtga cctgatctcc tcctcatgac cttctgccct ggacaagccc
5161 cctgaactgg atttgggact gtcaaagcaa ctctacccct gctctggtag gctgaacagt
5221 gaccccccaa aatggcagtg tcttaatcac ctaaaccta acatgtgact atattacctt
5281 cacatagcaa aatggacttt gcagatgtga ttaaggatct tgagatggaa ggagtatcct
5341 ggatttttca ggtaaactga gtataatcac aagggcctct gtaaaggagg caggagtgtc
5401 agagtgacgg aagaaaatgt atgtaacaat ggaagcagag gtcagagtga tgcaattgct
5461 ggaggaagag ccatgagccg aggaatgcag acagcctctt ctcctctggg gcctcaagaa
5521 gaatgcagtc ctgccaatac cttgatttta agccctgtga aactgatttc agattgctga
5581 cctccagaac agtaagatca taaatttgtg ttgttttcac atgtgtgaaa acacatgtgt
5641 gataatttgt tacagcagcc acgggaaacg aatatagatt gtggtgccca aattagagtg
5701 ctgctgtaac acacgcctac tgattgaagt ggctttggaa ttgcaacgtg gaaatgggca
5761 gaggctggaa gaattttgag agtcatgata aattgcctta accacctctc ttctgatagg
5821 tgatgtggcc aggggaactc ttcctcaacc ttcagaccta aa
```

FIGURE 8

Homo sapiens eukaryotic translation initiation factor 4 gamma, 1 (EIF4G1), transcript variant 1, mRNA

```
   1 tcctcgacgg ccgccgcccg cctggccttt tagggcctga ctcccgccct tcctggccta
  61 cactcctggg cggcggcagg cctagcttct ggcccagtgc gggttccccg gcggcaggcg
 121 tatcctgtgt gccctgggc caggcccgaa cccggtgtcc ccgggtgggg ggtggggacg
 181 ccacggccga agcagctagc tccgttcgtg atccgggagc ctggtgccag cgagacctgg
 241 aatttccggt ctggttggtc tggggccccg cggagccagg ttgataccct cacctcccaa
 301 ccccaggccc tcggatgccc agaacctgta ggccgcaccg tggacttgtt cttaatcgag
 361 ggggtgctgg ggggaccctg atgtggcacc aaatgaaatg aacaaagctc cacagtccac
 421 aggcccccca cccgcccat cccccggact cccacagcca gcgtttcccc cggggcagac
 481 agcgccggtg gtgttcagta cgccacaagc gacacaaatg aacacgcctt ctcagcccg
 541 ccagcacttc taccctagcc gggcccagcc ccgagcagt gcagcctccc gagtgcagag
 601 tgcagcccct gcccgccctg gcccagctgc ccatgtctac cctgctggat cccaagtaat
 661 gatgatccct tcccagatct cctacccagc ctcccagggg gcctactaca tccctggaca
 721 ggggcgttcc acatacgttg tcccgacaca gcagtaccct gtgcagccag gagcccagg
 781 cttctatcca ggtgcaagcc ctacagaatt tgggacctac gctggcgcct actatccagc
 841 ccaagggggt cagcagtttc ccactggcgt ggccccgcc ccagttttga tgaaccagcc
 901 accccagatt gctcccaaga gggagcgtaa gacgatccga attcgagatc caaaccaagg
 961 aggaaaggat atcacagagg agatcatgtc tggggcccgc actgcctcca cacccacccc
1021 tccccagacg ggaggcggtc tggagcctca agctaatggg gagacgcccc aggttgctgt
1081 cattgtccgg ccagatgacc ggtcacaggg agcaatcatt gctgaccggc cagggctgcc
1141 tggcccagag catagcccct cagaatccca gccttcgtcg ccttctccga ccccatcacc
1201 atcccagtc ttggaaccgg ggtctgagcc taatctcgca gtcctctcta ttcctgggga
1261 cactatgaca actatacaaa tgtctgtaga agaatcaacc cccatctccc gtgaaactgg
1321 ggagccatat cgcctctctc cagaacccac tcctctcgcc gaaccatac tggaagtaga
1381 agtgacactt agcaaaccgg ttccagaatc tgagttttct tccagtcctc tccaggctcc
1441 caccccttg gcatctcaca cagtggaaat tcatgagcct aatggcatgg tcccatctga
1501 agatctggaa ccagaggtgg agtcaagccc agagcttgct cctcccccag cttgcccctc
1561 cgaatcccct gtgcccattg ctccaactgc ccaacctgag gaactgctca acggagcccc
1621 ctcgccacca gctgtggact taagcccagt cagtgagcca gaggagcagg ccaaggaggt
1681 gacagcatca atggcgcccc ccaccatccc ctctgctact ccagctacgg ctccttcagc
1741 tacttcccca gctcaggagg aggaaatgga agaagaagaa gaagaggaag aaggagaagc
1801 aggagaagca ggagaagctg agagtgagaa aggaggagag gaactgctcc ccccagagag
1861 tacccctatt ccagccaact tgtctcagaa tttggaggca gcagcagcca ctcaagtggc
1921 agtatctgtg ccaaagagga gacggaaaat taaggagcta aataagaagg aggctgttgg
1981 agaccttctg gatgccttca aggaggcgaa cccggcagta ccagaggtgg aaaatcagcc
2041 tcctgcaggc agcaatccag gcccagagtc tgagggcagt ggtgtgcccc cacgtcctga
2101 ggaagcagat gagaccctgg actcaaagga agacaaaatt cacaatgctg agaacatcca
2161 gcccggggaa cagaagtatg aatataagtc agatcagtgg aagcctctaa acctagagga
2221 gaaaaaacgt tacgaccgtg agttcctgct tggttttcag ttcatctttg ccagtatgca
2281 gaagccagag ggattgccac atatcagtga cgtggtgctg gacaaggcca ataaaacacc
2341 actgcggcca ctggatccca ctagactaca aggcataaat tgtggcccag acttcactcc
2401 atcctttgcc aaccttggcc ggacaaccct tagcacccgt gggccccaa gggtggggcc
2461 aggtggggag ctgccccgtg ggccggctgg cctgggaccc cggcgctctc agcagggacc
2521 ccgaaaagaa ccacgcaaga tcattgccac agtgttaatg accgaagata taaaactgaa
2581 caaagcagag aaagcctgga aacccagcag caagcggacg gcggctgata aggatcgagg
2641 ggaagaagat gctgatggca gcaaaaccca ggacctattc cgcaggtgc gctccatcct
2701 gaataaactg acaccccaga tgttccagca gctgatgaag caagtgacgc agctggccat
2761 cgacaccgag gaacgcctca aagggggtcat tgacctcatt tttgagaagg ccatttcaga
2821 gcccaacttc tctgtggcct atgcaaacat gtgccgctgc ctcatggcgc tgaaagtgcc
2881 cactacggaa aagccaacag tgactgtgaa cttccgaaag ctgttgttga atcgatgtca
2941 gaaggagttt gagaaagaca aagatgatga tgaggttttt gagaagaagc aaaaagagat
```

FIGURE 8 (cont.)

```
3001 ggatgaagct gctacggcag aggaacgagg acgcctgaag gaagagctgg aagaggctcg
3061 ggacatagcc cggcggcgct ctttagggaa tatcaagttt attggagagt tgttcaaact
3121 gaagatgtta acagaggcaa taatgcatga ctgtgtggtc aaactgctta agaaccatga
3181 tgaagagtcc cttgagtgcc tttgtcgtct gctcaccacc atttggcaaag acctggactt
3241 tgaaaaagcc aagccccgaa tggatcagta tttcaaccag atggaaaaaa tcattaaaga
3301 aaagaagacg tcatcccgca tccgctttat gctgcaggac gtgctggatc tgcgagggag
3361 caattgggtg ccacgccgag gggatcaggg tcccaagacc attgaccaga tccataagga
3421 ggctgagatg gaagaacatc gagagcacat caaagtgcag cagctcatgg ccaagggcag
3481 tgacaagcgt cggggcggtc ctccaggccc tcccatcagc cgtggacttc cccttgtgga
3541 tgatggtggc tggaacacag ttcccatcag caaaggtagc cgcccccattg acacctcacg
3601 actcaccaag atcaccaagc ctggctccat cgattctaac aaccagctct ttgcacctgg
3661 agggcgactg agctggggca agggcagcag cggaggctca ggagccaagc cctcagacgc
3721 agcatcagaa gctgctcgcc cagctactag tactttgaat cgcttctcag cccttcaaca
3781 agcggtaccc acagaaagca cagataatag acgtgtggtg cagaggagta gcttgagccg
3841 agaacgaggc gagaaagctg gagaccgagg agaccgccta gagcggagtg aacggggagg
3901 ggaccgtggg gaccggcttg atcgtgcgcg gacacctgct accaagcgga gcttcagcaa
3961 ggaagtggag gagcggagta gagaacggcc ctcccagcct gagggggctgc gcaaggcagc
4021 tagcctcacg gaggatcggg accgtgggcg ggatgccgtg aagcgagaag ctgccctacc
4081 cccagtgagc ccctgaagg cggctctctc tgaggaggag ttagagaaga aatccaaggc
4141 tatcattgag gaatatctcc atctcaatga catgaaagag gcagtccagt gcgtgcagga
4201 gctggcctca ccctccttgc tcttcatctt tgtacggcat ggtgtcgagt ctacgctgga
4261 gcgcagtgcc attgctcgtg agcatatggg gcagctgctg caccagctgc tctgtgctgg
4321 gcatctgtct actgctcagt actaccaagg gttgtatgaa atcttggaat tggctgagga
4381 catggaaatt gacatccccc acgtgtggct ctaccctagcg gaactggtaa cacccattct
4441 gcaggaaggt ggggtgccca tgggggagct gttcagggag attacaaagc ctctgagacc
4501 gttgggcaaa gctgcttccc tgttgctgga gatcctgggc ctcctgtgca aaagcatggg
4561 tcctaaaaag gtggggacgc tgtggcgaga agccgggctt agctggaagg aatttctacc
4621 tgaaggccag gacattggtg cattcgtcgc tgaacagaag gtggagtata ccctgggaga
4681 ggagtcggaa gcccctggcc agagggcact ccccctccgag gagctgaaca ggcagctgga
4741 gaagctgctg aaggagggca gcagtaacca gcgggtgttc gactggatag aggccaacct
4801 gagtgagcag cagatagtat ccaacacgtt agttcgagcc ctcatgacgg ctgtctgcta
4861 ttctgcaatt atttttgaga ctcccctccg agtggacgtt gcagtgctga aagcgcgagc
4921 gaagctgctg cagaaatacc tgtgtgacga gcagaaggag ctacaggcgc tctacgccct
4981 ccaggccctt gtagtgacct tagaacagcc tcccaacctg ctgcggatgt tctttgacgc
5041 actgtatgac gaggacgtgg tgaaggagga tgccttctac agttgggaga gtagcaagga
5101 ccccgctgag cagcagggca agggtgtggc ccttaaatct gtcacagcct tcttcaagtg
5161 gctccgtgaa gcagaggagg agtctgacca caactgaggg ctggtggggc cggggacctg
5221 gagccccatg gacacacaga tggcccggct agccgcctgg actgcagggg ggcggcagca
5281 gcggcggtgg cagtgggtgc ctgtagtgtg atgtgtctga actaataaag tggctgaaga
5341 ggcaggatgg cttgggggctg cctgggcccc cctccaggat gccgccaggt gtccctctcc
5401 tccccctggg gcacagagat atattatata taaagtcttg aaatttggtg tgtcttgggg
5461 tggggagggg caccaacgcc tgcccctggg gtccttttt ttattttctg aaaatcactc
5521 tcgggactgc cgtcctcgct gctggggca tatgccccag cccctgtacc accctgctg
5581 ttgcctgggc aggggaagg ggggcacgg tgcctgtaat tattaaacat gaattcaatt
5641 aagctcaaaa aaaaaaaaaa aa
```

FIGURE 9

Homo sapiens BMI1 polycomb ring finger oncogene, mRNA (cDNA clone MGC:12685 IMAGE:4138748), complete cds

```
   1 cagcaactat gaaataatcg tagtatgaga ggcagagatc ggggcgagac aatggggatg
  61 tgggcgcggg agccccgttc cggcttagca gcacctccca gccccgcaga ataaaaccga
 121 tcgcgccccc tccgcgcgcg ccctcccccg agtgcggagc gggaggaggc ggcggcggcc
 181 gaggaggagg aggaggaggc cccggaggag gaggcgttgg aggtcgaggc ggaggcggag
 241 gaggaggagg ccgaggcgcc ggaggaggcc gaggcgccgg agcaggagga ggccggccgg
 301 aggcggcatg agacgagcgt ggcggccgcg gctgctcggg gccgcgctgg ttgcccattg
 361 acagcggcgt ctgcagctcg cttcaagatg gccgcttggc tcgcattcat tttctgctga
 421 acgactttta actttcattg tcttttccgc ccgcttcgat cgcctcgcgc cggctgctct
 481 ttccgggatt ttttatcaag cagaaatgca tcgaacaacg agaatcaaga tcactgagct
 541 aaatccccac ctgatgtgtg tgctttgtgg agggtacttc attgatgcca caaccataat
 601 agaatgtcta cattccttct gtaaaacgtg tattgttcgt tacctggaga ccagcaagta
 661 ttgtcctatt tgtgatgtcc aagttcacaa gaccagacca ctactgaata taaggtcaga
 721 taaaactctc caagatattg tatacaaatt agttccaggg cttttcaaaa atgaaatgaa
 781 gagaagaagg gattttatg cagctcatcc ttctgctgat gctgccaatg gctctaatga
 841 agatagagga gaggttgcag atgaagataa gagaattata actgatgatg agataataag
 901 cttatccatt gaattctttg accagaacag attggatcgg aaagtaaaca aagacaaaga
 961 gaaatctaag gaggaggtga atgataaaag atacttacga tgcccagcag caatgactgt
1021 gatgcactta agaaagtttc tcagaagtaa aatgacata cctaatactt tccagattga
1081 tgtcatgtat gaggaggaac ctttaaagga ttattataca ctaatggata ttgcctacat
1141 ttatacctgg agaaggaatg gtccacttcc attgaaatac agagttcgac ctacttgtaa
1201 aagaatgaag atcagtcacc agagagatgg actgacaaat gctggagaac tggaaagtga
1261 ctctgggagt gacaaggcca acagcccagc aggaggtatt ccctccacct cttcttgttt
1321 gcctagcccc agtactccag tgcagtctcc tcatccacag tttcctcaca tttccagtac
1381 tatgaatgga accagcaaca gccccagcgg taaccaccaa tcttcttttg ccaatagacc
1441 tcgaaaatca tcagtaaatg ggtcatcagc aacttcttct ggttgatacc tgagactgtt
1501 aaggaaaaaa attttaaacc cctgatttat atagatatct tcatgccatt acagctttct
1561 agatgctaat acatgtgact atcgtccaat ttgctttctt ttgtagtgac attaaatttg
1621 gctataaaag atggactaca tgtgatactc ctatggacgt taattgaaaa gaaagattgt
1681 tgttataaag aattggtttc ttggaaagca ggcaagactt tttctctgtg ttaggaaaga
1741 tgggaaatgg tttctgtaac cattgtttgg atttggaagt actctgcagt ggacataagc
1801 attgggccat agtttgttaa tctcaactaa cgcctacatt acattctcct tgatcgttct
1861 tgttattacg ctgtttgtg aacctgtaga aaacaagtgc tttttatctt gaaattcaac
1921 caacggaaag aatatgcata gaataatgca ttctatgtag ccatgtcact gtgaataacg
1981 atttcttgca tatttagcca tttttgattcc tgtttgattt atacttctct gttgctacgc
2041 aaaaccgatc aaagaaaagt gaacttcagt tttacaatct gtatgcctaa aagcgggtac
2101 taccgtttat tttactgact tgtttaaatg attcgctttt gtaagaatca gatggcatta
2161 tgcttgttgt acaatgccat attggtatat gacataacag gaaacagtat tgtatgatat
2221 atttataaat gctataaaga aatattgtgt ttcatgcatt cagaaatgat tgttaaaatt
2281 ctcccaactg gttcgacctt tgcagatacc cataacctat gttgagcctt gcttaccagc
2341 aaagaatatt tttaatgtgg atatctaatt ctaaagtctg ttccattaga agcaattggc
2401 acatctttct atactttata tactttctc cagtaataca tgtttacttt aaaaattgtt
2461 gcagtgaaga aaaacctta actgagaaat atggaaaccg tcttaatttt ccattggcta
2521 tgatggaatt aatattgtat tttaaaaatg catattgatc actataattc taaaacaatt
2581 ttttaaataa accagcaggt tgctaaaaga aggcatttta tctaaagtta ttttaatagg
2641 tggtatagca gtaattttaa atttaagagt tgcttttaca gttaacaatg gaatatgcct
2701 tctctgctat gtctgaaaat agaagctatt tattatgagc ttctacaggt attttttaaat
2761 agagcaagca tgttgaattt aaaatatgaa taccccacc caacaatttt cagtttattt
2821 tttgctttgg tcgaacttgg tgtgtgttca tcacccatca gttatttgtg agggtgttta
2881 ttctatatga atattgtttc atgtttgtat gggaaaattg tagctaaaca tttcattgtc
```

FIGURE 9 (cont.)

```
2941 cccagtctgc aaaagaagca caattctatt gctttgtctt gcttatagtc attaaatcat
3001 tacttttaca tatattgctg ttacttctgc tttctttaaa aatatagtaa aggatgtttt
3061 atgaagtcac aagatacata tatttttatt ttgacctaaa tttgtacagt cccattgtaa
3121 gtgttgtttc taattataga tgtaaaatga aatttcattt gtaattggaa aaaatccaat
3181 aaaaggata ttcatttaga aaaaaaaaaa aaaaaaaaaa aaaaaaaaaa aaaaaaaaaa
3241 aaaaaaaaaa a
```

FIGURE 10

Human DNA sequence from clone DAMA-147C13 on chromosome 6, complete sequence

```
   1 accatatcct cctacactct gagcaatctc acggggtaga ccgcaggtta acacctctca
  61 gactccttga aaaatagctg gtgacgggtc agtgcccaga gctcacctgc ctttcgccaa
 121 actctaaaca cccctgtgtg tttcccctac tatacccgtt tccctggggg caggtccctg
 181 cattatgaag ccactaggaa aatgagataa agctttccta cttttcttcc cctgaaaaga
 241 cagattttgt ttttattttt ttgagaatac caagtaagat tttatttttt atttatttta
 301 aattatttta acctttgttt taggttcaag ggtacacatg caggtttgtt atataggtaa
 361 attgtgtgtc atcgggattt ggcgtaaaaa tttatttcat cacccaggta ataagtatag
 421 tatctgatag gtagtgtttt gatcctctcc ctcctcccat cctccaccct caagtagggc
 481 ccagtgtcta ttattccctt ttttgtgtcc atgtgtactc aatgtttagc tcccacttat
 541 aaaagtgaga acatgcagta tttcattttc tgctcctgtg ttagtttgcc taggataaca
 601 gccccagct ccatccatga tgctgcaaaa gacgtgatct cgtccttttt tgtctgtgga
 661 gtattccatg tgtatatgt accacatttt ctttatacag tctactgttg gtgggcattt
 721 aggctgattc catgtctttg ctattatgaa tactgctgca gtgagcattc atgtgcatgt
 781 gtccttatgg tagaacaatg tatactcctt tgggtatatg cctaataatg ggattcctgg
 841 gacgaatggt agctctgttt taaggttctt gagaaattgc caaactgctt tcctcaatgg
 901 ctgaactaat ttatgttccc accagcagtg tataagcctt ccgttttctc tgcaacctct
 961 ccaacatttg ttattttttg actttttaat aatagccatt ctgactggtg tgagacggta
1021 tctcattatg attttgattt gcattttttct aatcattagt aatgttgaac attgtttcat
1081 atgcttcttg gtcacgtgtg tgtcttgaaa aggcagattt tatgtatttg cgtatttatt
1141 tttttcacag gttttttttt tgaaagtctc actctgtcgc ctaggctgga gtacagtggg
1201 ataatctcgg ctcactgcaa tcttcgcctc ctgggttcaa atgactctca tgcctcagcc
1261 acttgagtag ctggggttac agtcatgtgc caccactcct ggttagtttt tgtctttttt
1321 tttttttttgg tagagacagg gtttcatcat gttggccagg ctgttcttga actcctgacc
1381 tcaagtgatc cacccacctc agcctcctaa agtgctagga ttacaggcat gagccatcgt
1441 gcctggcctg aaaaagcaga ttttaaacgg caattcattc ttctatccca ttgtgaacta
1501 tacagttgat ggatttttcca tcactaactt gaaactctaa attggcttcc ttctgctccc
1561 cagtaggttt cagggctgcc tcttcacatc ttagtttctg agaactcttg gatttttatta
1621 aatagtgagc taaacaaaac aggattgtgg aaggggcccc ttgacaccac acttacctgc
1681 cctccctcaa agtccctgat ctcaggaaaa tctaacacct atgaagaaaa tggggataaa
1741 aaatgcatac aaagattatt accaaaaacg aaagattcgt tgtgtaacta attgagatta
1801 actgaagctc tgccatagct cccagccact gccccactc accttgctta tatactctaa
1861 ctctgctaac gaactgtcaa gtgtgttgga atgggcagaa tatggggtgg ggagtgcata
1921 atctgtagag cttctacaga tacagtgcta ggtaggtcct ttctataata tctcatctca
1981 tcttaaaaga cttgttggcc gggcatggtg gctcacgctt gtaatcccag cactttggga
2041 ggctgaggaa ggcatatcac ctgaggtcag gagtttgaga ccagcctggc aaacatggtg
2101 aaaccccgtc tctacaaaaa atacaaaaat tagctgggtg tggtggcgcg tgcctgtaat
2161 cccagctact ctggaggctg aggcaggaga atcgattgaa cctgggaggt ggaggttgca
2221 gtgagccgag atcgtgccac tgcactccag cctgggtgac agaatgagac tgtctcaaaa
2281 aaaaaaaaaa aaaaaaaaaa cttgttaatt gtcctcattt cccaggttgg aaaacaggtc
2341 caaagattca cacccaaggt ctaaaggctg taactcctct tcttatacag ctgttacaca
2401 tgcacgtgtg tacacacaca cacacataca cactctcttg agcatgccca cacactcact
2461 acatcttgga actgggatgg ctcaaataaa gggagttagt gaggcctccg ctgagaaaga
2521 gagaaagaga agagtcacaa tccataaccc aattcaccca agtcttatct ttcctgtcct
2581 cagagttcct tctgctctga gaaccaccgt cccttccact ttctcttttg acaagtttca
2641 aaactgaatt ttcccccaca cccccccaat acatttcccc ctcacattcc tccccatcct
2701 gcccaggtaa gctgttagcc taaccttata ggaaccaagt cctgggatcc ttttcaatgt
2761 ctacaaagcc tagccctggc aagggagcac tggctgtgtg gtcctgtgcc agcactgaac
2821 atggccctag ccagtaacag tgggggctgaa tgtagttccc tcttatgtct agatctctgc
2881 tccggcagtc aaaggagatg tgaaaccttc tgtgaggcca caacaggaaa tggtaggaga
2941 ggatttcact tctctattaa ttcaaacact gagggagctt tttagaataa agaaggacag
```

FIGURE 10 (cont.)

```
3001 aaaacccaga cacctgtgct cagcagtgtt ttccttcctc tcctcctccc aacccttcca
3061 tttttacaga tatagctctg tctttccacc tctagccaat tcaaaataac atttcagttg
3121 ctctgtccat tgttacttat ttgttaatta ttgatatagc accgggaccg aagaggtatg
3181 gagcccccaac caggttccca catgttgcct ttctttattt gcctctacac aaccacccaa
3241 agagtgagtc ctctcctttc ccattgcctc tgcccttagc ctgaccacca catgcctgca
3301 gtaaactagt cccagggttt gtgtgcaaag cattactggg aaaatacaga gtgagaagat
3361 atggattctg cccccatatc gctttgcttg tacgtcaatt ggggagtgag aacaaacact
3421 ttaaatagtt tatattaaag taagtaagca ataaggccag tggtcttaaa agagaagaga
3481 gaaatcacca tggacatggt agacagggag tactctcagt cgagagggcc tggaatgagc
3541 cttgaatact gggctggatt tgtgttggag aggaggaagg cagttggcat tgtaggtctg
3601 gtgtatagct ccacaagctt gacaatgctg tgaggtgcca tcagggagga ggtgtcctac
3661 gagagcctgg gttagctaaa acaaagacaa gctacaataa cgtcactggc actgcacgtt
3721 ggaggaagtc acaaatgtga tttcttgttt ttttctgaga gtatggccat aataataaat
3781 ctcttctagg cacttcctaa agttgctcca tgtcagttcg caggttcttg gggcagacgg
3841 ttttaactga agtctccatt ttataaacac aaaattgctc aaccagttaa tcacgcctca
3901 tagcataaga ccacattcgt gacttcagtg tcttttcaaa actacacaca cctacatcct
3961 gccaagatta tattacttgc ccaatctgtc caatccccac cccaccccctg ccatctaccc
4021 cttacctcac ctccgcccac acacacaccc tcctaccctg tcaggattca ctgctctaga
4081 ccctgacctt tggattatag tttctgtagt cagttcacca tccttccaac ctacagtcaa
4141 attatttgaa ctactaggga tagtctatct gatttgccac aactattttt cctttttaa
4201 tttttatttt tgccaccaca actattgaag aatgctatct tcatcttacc cacgagaaaa
4261 tggaggcaga gggaggttaa gtggttgccc agatttaccc agatactaag taataaaacc
4321 attacttgaa ctcaggattt attactttaa atcctgtatt gccaataatc aattgaaaa
4381 taactgaaaa ttgcctacta tttataataa caataaaaac catagcatat ttatgaatta
4441 acatatcaaa tataagaatt ttaagaaaaa agaaaacttt attgaagtgc acaaagacct
4501 gagaggtgta gagatatacc atattcatgg ataggccatg ctaacataat gacaacctct
4561 ccccacatct ctaacctaaa tgctacccca attaaagtaa cagtaggatt tcaggagaat
4621 ttaacaaact gattatagaa tgtacatgga aataaagtcc aagagtatct tagaatattt
4681 tgataaagaa aaggaaaata aattttttgg gaaggtggtg aaggaatgga gactagttct
4741 actaaatagt aacacatatt aaaaagccaa aataatcaaa caatatgata ctgattagta
4801 atgagagaaa agcaaattaa aacaacaaaa taccactcta cacccaccat gttgccaaca
4861 tttgaaagtc aaataattac aagcattagt gagcataaag ggaaatgtga actatcttgc
4921 tttgttgatg ggagtgtaaa ctgtttatga tccctgaatt atagaaatta taaactagtt
4981 gggcgaaaaa attaacatag gaaataaagc ggcatatccc aatccttagg ttgagtgctt
5041 taagtcttgg aagatttcaa taaagagaaa ttaggggcag gttcatggaa taagttgaac
5101 tggagttgga cctatggagt gggttaagac aggaacaaga tgagcagaat aaagaaagca
5161 ttcttgtgag aggaaagagc ctgggcaaat gccctaaacc aaaatcagat ataatacctc
5221 aaggaagagt gaggaaaaaa gatttattca agaatagcat tcctgctggg aatagtgagt
5281 aatatttttt attagaaaag gggcaccaga ctagagagga tactgagtgc ttctagagta
5341 cttaagtaac agtatcatag aaggtttcat cagagagcat ctaatctaag cccatcattt
5401 tacagatgaa gactttgagg cccagagagg ggaagtgact tgtctaaagt cacacagcat
5461 aataaagcac ttttaagtct tgcctgacag gaaatatcta gataagttgg aaaacagaga
5521 gacagagaaa ttaggaagaa ctagaaagca ccacatctag aattactaac atgagaataa
5581 aaagaaaaac atctaaaatg gagaaaatac aatacttgaa gctagtattg aggtatattt
5641 cagaaaagag aaagaagtct acgaggcaac taagttctcc tctgaagatc aagaccaata
5701 atgataaggt taggttattc agcacatttt ctatgtgcca aacactattt taagcattct
5761 gtaggtatta acttatttaa gcttcacagc atgaggatat gctgccttat ttcctatatt
5821 aacttttca ctcaactagt tcataatttc tgtaattcgg gcatcataaa cagtttacat
5881 tcccaccaac agaccaagat attacagttc acattttcct ttatcctcgc taatacttat
5941 ttgactttca aatgttggca acatggtggg tgtagagtgg taaggggggac accattgtta
6001 tcatcatcct tttacagaaa atgacaccaa agcacaagtt aagtaacttg cccaagggct
```

FIGURE 10 (cont.)

```
6061 cacagctaaa cgctgacagt tacgattgaa tccccagcag tcaggttcca gagcccatgc
6121 ttcttaaccg gtacacatga tgctgttaga aatgagatgg ttcagagaca gtgcaacttc
6181 tcttagggag aatttaatat tttcttttag attagactct agtacaatgc caagaacaga
6241 aactccctca ccaaataatt gccctctcaa ctttattgcc accctgtcat ccaaagcaac
6301 tcccagaccc taaggaatgc aagaaagaaa gcatatgcaa agcaatttac caccagtggt
6361 catgtgctgc caccttttcgt tatcttccca ggacagcacc tgtgcagttc tccttggaca
6421 gttcactcag gccaaggaac agattgtcag gaaagacatg tgaattcttt gcccttccag
6481 gctgttttca cttcatgtta ggggcttcat gatactgttt tcccagaact gacataactg
6541 attggtatag cacttgggag cttattcttc ccatccctga gcttctgttt ctcagttacg
6601 gtgagggttg aagggagtta tatgttcctc agggcagcct atacgagaca taaacattt
6661 cacaaacagt aaaatacaca acacacacac acacgcacaa aacacacaag cagcttcctt
6721 aaccattttg taagcagatt attagaaaat aactctgcct tcgtttctca catattttgc
6781 acaaaccgat agatggaaaa acatcatgta ccgccaagac cagggaataa gagctcagct
6841 ggcaaattag gggttttccc tatttccctc cctaacgagg tcaagctgtg ttcaggttaa
6901 ggcatgctga atttgaaacg acaacccact caagttgaga tatccagaaa caaataccat
6961 gagttaagaa agaagccaca ctgatataaa gaatgagat ttattgcctt gtgggggaa
7021 gggatgtggt tgtgataggc aggccactct gggatccctg ggatgcaagc ccagggacag
7081 cagagtcccc aggtgggaaa tctacacaca caccccaggg atgtcccaga gacttcttct
7141 accctaagag agatcctgg gcaggatgtg agaaatctga gcatcctctg tttggatggc
7201 cgaagctgct ggcatcaaac tctggtctgg aagaatcagt ctgggggaga gacaggggatg
7261 gaggaaaggc atcagggat ccatcctcct cctccttctc ctcctcctcc tccccacaa
7321 aggccttgct cgccctgcct gcaccacacc ctgcagaagt tgatctctcc ttgttcccaa
7381 atcatctcca agcacccttc ctacagcacc ccatgattcc tttttcact caaagcaatt
7441 cttgtgaccc ataactgtgt gtgtgtaact gggtcccaa ctgggaagat gtgcccccat
7501 ggtgctggat acaggccccc acacccaagg gcctgaggat cgctatatgt cccccatgc
7561 cacaaaataa tcctgacaca tgcacgcatg caccactgta tctggctccc acaggctcac
7621 ccgccccctc cagatgacat accacctgag caaggcttcc ggaagtagat gatgagaaca
7681 atgcccacga tgatgcccag cacacccagg cgccacacag cgccacacag cacattctcc
7741 agcagatctg agggcagtgc gttccgggggt actggaggaa atgagtggct cagcctgggg
7801 acctagttag ggagcctccc acccagggaa atgacgtggg tgtctgggat gacatgggag
7861 actgggatgg gcttagggta ggaatggact aaacaaggta ccagtggaga aagaagcctc
7921 ctcccatgga tctatccctt tttgcccccca aaaggaccag aattccaggg agaaagcctc
7981 accccaatag gcaattgctg tgtagcggtc aattctgtga gtcacaatgc aggagaaaat
8041 gtcagaaggt tctggtgtga agtttaagta agaaaggcc tggaagctga gtccatcgac
8101 agctgagaca aaagtaggcc caaatccttc cacagggacg gaatgatgct gccagttcac
8161 tgtcagcatg ggtgggaaga gattactgac aaaacagacc aaagtgttgg gcttgccaaa
8221 ctccagggc ttcagcgtga acacttcagc gataggaaac cctggtgggg ggattgaagt
8281 gtaggggaa aaagagacta gtttagatgg tatctctgtg tttggagggg ccatggcata
8341 tggaggggag ggcagagaag aacacagtgg gtcaggcttt gggagacaga gatgagcgag
8401 gagctgggct ctgaagggag gtcttcttcc aggcaaggac tgcagctaga cgtagaagca
8461 gagccagatc caggctactc tggacccctc caccatgact tccttcagca cttcctgtct
8521 agagctcaca ttgatgtcta accatgcact gtcttctcac taagacatag tcacgtcatc
8581 agatatttcc actcttccca tccatcttgc tgggcatagt agcacaagtg ttaatattca
8641 gtaggtatca gttggtacct gttgaattca tcacattcaa tacatagttc tgaatgccta
8701 ctacatgcta ggtacttcgg cccaccaaaa gaacacaggg tgcagaccaa ggctggtgga
8761 aaaattaagg tgatgaagag aaccagaaag tatttgagat ggggagctgg tatcaagggg
8821 aattattcag tgtacagatc aatgaggtta atgcagccct cctcccttca ctcccagaa
8881 aactcctgac ctctggacac cgggattttc ccatcaagtt ttggccctat ttgctggatc
8941 atccactcgc agaactcttt gtcaaataaa atggcaggag catctccctg ttcctgagcc
9001 cagtcagcaa attcgggcag gcgaggcacc cgagtgttct gggaaaagtc gaagaagaaa
9061 agctggtcct cgtcgtaggc ctcagagagt cccacactgg gactcccatc ctggcagtac
```

FIGURE 10 (cont.)

```
 9121 actgtgtgca ggaatgtgtg gttttgcagg tcatctggcc acattggagt aggagctgca
 9181 aaggacacag ggtgaggttc agggaggtgg gagccttctc ctccaactta aaaaacagca
 9241 aggtggggct aggcgcagtg gctcatgcct gtaatcccag cactttggga ggccaaggtg
 9301 ggtggatcat gaggtcagga gtttgagacc agcctggcca gcatggtgaa actccatctc
 9361 tactaaaaat acaaaaaagt agctgggcat gttggcatgc gcctgtagct actcgggagg
 9421 ctgagggagg agaattgctt gaaccaggga ggcagaggtt gccgggagct aagattaagc
 9481 cactgcactc cagcctgggt gacagagtga gactctgtct caaaacaaaa caacaaaaac
 9541 aagcaaggcc tgcttaagga gcgtgggctg aggtgagacc cttcctgtg tctgttattt
 9601 agactccccc tcccaagggg ggtgaagaac aaattatggc atctctccaa gcttcccctg
 9661 cctataaaaa ggccagttgg caaaagtaaa gagttctact ttctaaagtg acagattcag
 9721 gccaggcatg gtggctcatg cctgtaatcc cagcactttg ggaggctgag gcaggcagat
 9781 tgcttgagcc caggagttca agaccaacct gggcaacaca gcgagaccgt ctctacaaaa
 9841 aatcaaaaa cttagccagg tgtggtggca aacacctgtg gtctcagcta ctctggaggc
 9901 tgaggcagga ggattgcttg tgcctaggaa gttggggctg cagtgagcca tgattgtgcc
 9961 actggactcc agcccaggtg acagaatgag cccgtctcaa aaaatatata tataaaggcc
10021 gggcgcggtg gctcaagctt gtaatcccag cactttggga ggccaaggcg ggtggatcac
10081 ctgaggtcag gagtttgaga ccagcctggc aaacataatg aaacccatc tctactaaaa
10141 atacaaaaat cagctgggtg tggtggcatg cgcctgtaat cccagctact tgggaggctg
10201 aggcaggaga gtctcttgaa ccccagaggc aggggttgca gggagccgag atcacgtcac
10261 tgcactctag cctgggtgac agagcgagat gccgtgtcaa aaaaaataaa ttaaatcaaa
10321 taaaaaattt aaaaatgtat atatataaaa taaagtgaca gattcagagt cactgttcat
10381 tgtgtgtttg ggggctgcac aaagacacct agccaaagaa gcaagtgaaa gcctgcattc
10441 tgctcaccat gccatacatc ctggcatagg gctgtatcct cccaaagggg attcctttgt
10501 ctaattcata ccaggccact gtattgacta gagaaggcca tggatgggtt tctcactctt
10561 agaagggaaa gaggaggaat ggctacagcc tccccaagcc atagatggga ctgcctccca
10621 ctatccccag acacaaatgg taaattggaa aacctgtatc cagacatttc ttcagccact
10681 tcattggcac caagcgtctc tcaaaatgtc ttctgttcct taacctacca ggcctcccaa
10741 agacagcaat gggagaagtg accccataac tgcataaaat aatccctctt ctttgaagct
10801 cttggcagga atcgctcagc cagcaggaaa cctttaaccc aataccccaga aaaacagaca
10861 tttggaggaa gagggatctt ccagattatt cttccattct gccccatcct ctacagagaa
10921 ggaaactaag acacttttca agaatcacaa gataagttaa tgatagaaag cagagtagaa
10981 tcttgagtgg aggagtgaaa ataacattca ctttgttcaa atcccagctc taccactttc
11041 caatggtgtg aacttgcaca ataactctg agtctcattt tcttcatttg taaaatggag
11101 agaacaatct ccgcttcaag agattgtctt aaatggaaca tgcaaagcat cactgatatc
11161 gtttaccaac cacacatagc agctgtcttt ccccactccc ctgttgtttc cactgcctca
11221 taagacttcc caccactcac aaagcacagc gcttttcctc acaaagctga gtgggctccc
11281 taggttcagg atggaagtaa ataggagtac catcttacct tcagggacgg cccaggagtg
11341 gggtagcagc cacagaagtg gtaacatctg tagcagcgca gctccttggt tctgttcatg
11401 acccatacct tcttgccaca cagtaggtag gagctaccaa cccagccaac ccagcttccc
11461 caactccctc cccgagaggg tggccttaga tcatgttttg ccagatcatt tccaataggt
11521 gcccttgtca ttttgtctaa accaatcaga gaagcgtagg gtttaacatc atcagtcact
11581 ggggagacgc ctggggccag taacctcctg aagacttggc tgtttgacca ggcagagta
11641 tgcatgtaa ctgggctggg aagcccagtg gaggaatgtt gcttcctggt ggagttccct
11701 ctttggtttc aagctgtcag cctcagtctg taagcgacca gctggctctt cagagcagtg
11761 ccacctcctg gcagaatgct gcaatgggga accgcatctt ccccaagtaa accccagggg
11821 ctcttcggac cctgccttct cctccctcct ggctcttcct ctttctcaaa aaacttatt
11881 ctccttcagg cattagctct aattcatttg gcagacatat attgaaaata caagaaattc
11941 tgggtgttgg gcccagggct agaaatacaa agatgaatag gcatagtctg ccttcaaaga
12001 gcttagagtc tagtgctggg ggagggggcc aagggataat tacacaacaa tgtaatgtat
12061 tcaaataaga atgtgccaag tgttttggaa gtcgcagtaa ttttatgagg atgcggaata
12121 ggaggaacat aatcaggcag gctcctaaga cttgaaggaa aaacaatttg gccagcagaa
```

FIGURE 10 (cont.)

```
12181 catgaaggaa gagaaaaaca cgccagggca aagggtaggc agaagtacaa agatcacagg
12241 catccagagg tcctctttgg agaccctgtg tactagttga tatgaatgtt gtgaaggtcg
12301 cttgggtgtt cctgtataat aggaggtaat gggggtaga aggatgttgt gataagctac
12361 aaattcgggc aagggccaga tcacgtgggc cctgctacgc cacaaggagg agcttgcttt
12421 tacttagcag atgatagaga tattaaaact ggggaatgac aatcatttta gcattttgga
12481 aaaaatgttc tgattgatat ttcaaacaat gaactggagc ttttaaagaa ttgaggcaaa
12541 actgctgggc aagagtctat agcataccaa gatgaacagt tgcacatata cacaccactc
12601 ctgtagcaat acagcaataa tttaaatgac agataataag agcctgaatt aagtcataat
12661 tagaggaggc agaggagata gaatatcaag ataattagga agtagaatct aaagggtttg
12721 gctactgatt agctgtggga gtgggaaggt ggaggagtca aagatatctc agatttccag
12781 catgggtggc tgggtgggtg gtcagggatg gactgaattg aagcagaaaa gaatgccatg
12841 ggagcaggtt tacagagaga aagagcttga ttttgtacat gttgaatttg aaatgccagt
12901 ggaacagcca gctgaaactg catgggagcg cagtgaggcg tgtgggtatg gaccccaggt
12961 atggtctgaa gaccctgatt tgagagtcat cagcacaaat gtcgaagcag aggccatgaa
13021 taagatcacc caagtaaact gtgcagaagg agtgggaagt gaaacaagga caaaagcatg
13081 catgggctca aaccccaaac ctcataccag ttatccagga tccagtcagg agcatttaac
13141 tactttatgt gcttcagact gaaagaattt aatatagaga attggttaca aaggtgttaa
13201 aagggcaaga agtacaaaaa aaaaaaaaaa ggagagtcct agaaatgtac attttaaaaa
13261 aagattgcta tctggaaatc agaagctgcc atcatccctg agctggaatc tgtaaatcta
13321 ctcattgcct tgtgagagac actgtcatag tcagttccaa tctactagaa aggtgccacc
13381 tccttcaagg ctagaatcct tgagaaggta cttctgctca ggaggctgga gtcctgagtc
13441 tcccattctt cctgctgcta cagctacagc caatagctac cagctattgc cagccaccgc
13501 cactgtttag aggctgaagc aggatgcttc tcagtttctc ttgccttctg atctcccatc
13561 agtgcctcct actggcagaa tcaaaaagga agccagatgt ccaggaaggc tgggaaatac
13621 acacctggct gactcctaag ctaagcagtt caaaacacag tagaggaggg tgtgtgtgtc
13681 actgagacaa agataataac gagtacactg aaataccctg gtttgtaaga atctggtggc
13741 acgaggacca tccagagcac taagaaaaga ccaaggtaga agcagatcag agaaatttaa
13801 aagaggtgtg ccatgaagga gggcaaggtc agcattttta aatgctactc aaaagtcaag
13861 aaaggattga aaagtgtcct tagatttggt gattatgaga tggctgacaa atttattgag
13921 agcagtttca gtgttgtagt gggagtcaac tccagattgt ggtgggctga gaagtaagtg
13981 ggaggtgagg aagaaactgt cagtgtacat gcttcaagtt tgttagacaa aagaaagaga
14041 aagacagaag gggtggggga agaggcagtg agaaagctct aatgtggcaa tcaagtaatc
14101 tgagaaatta atatatgtga atattgtcca acagtgtttc tgaggctttc aaaattcata
14161 ccttccacct tttttttttt ttttttttaag acaaagtttc ccctgttgcc cagactggag
14221 tgcagtggct acttacaggt gcaatcataa ctcactccag tcttgaaccc ccgagttcaa
14281 gcgatcctcc cgcctcagta gctgggact ataggcacat gccactgtgc ctggcttcat
14341 atcctctttt gataaacaag taatagcagc agtaatagcc aaaaacaaaa acaactctat
14401 gacctcctag atattctgga acagcaatgt gtatatatgt gtgtgtgtct gtgtggtgga
14461 ggcagggtgc cagggaagga ctagggtttg gaaatcatgg taaccctcca gaaaacaaaa
14521 gaacatttcc cagtatccca acatttatgc actaacccat cagcggttct ggcagtgggg
14581 agattcaggc ccctggacag tagaaaagaa gtttatgaga ctaccagtgg ggagacatat
14641 gggacacagc cacctagagt cctaaaccag gggttagcaa acttttttctg taaagggcca
14701 gatggcaaat attttagaca ttgtgggcta tcagatctct gtcatgagta ctcaactgtg
14761 gcacgaaagc ctccatgcac aatatgtaaa tgaaggagag tggctgtgtt cctagtttcc
14821 tcctagcttt tcctcccact tcttgagcat ctccttctca gtctccttca tagactcctt
14881 cctttcagct actctttaaa tactggtgtt cctggagtt tttgtcctca accctctttt
14941 tatttatgga cactaaaatt caaatttcat gtaattttca tgtgtcacga aatattcttc
15001 atttgctttt ttttcccta accatttaaa aatgtgaaga ccattcttag ctttaggcc
15061 atttaaaaac aggtggtagg caagattgtg ctcacagccc atagtgtgct gaatgatgct
15121 ctacacgtgg tcagaattgg tacgaaagcc ccaaattaaa cccacccttc aaagaggaac
15181 ctcagtcccc ttattattgg attggcaatc agttaacaaa cactttgtgc cagttacacc
```

FIGURE 10 (cont.)

```
15241 agtctatttg gaaggagatc tggggaagaa caggagaaac tagactgggt ggaagggcat
15301 aggaataggt acagcagaca ctgcaatttc tctgggtgag aggaacaagg cagaggggtc
15361 caagttctcc atagggagca cagtgtagac aagaccaagg tgaggacaaa cataaccatc
15421 cctcaccaag actgtggtga ggggtggtta actccattct cccttctat aatctcagtt
15481 taaatggtaa caagttcaaa cacttataac tactcttccc tccatgtaat ccttccccac
15541 caggacctcc caactacctc catcataagt atctcaggaa tagtctctca tcagtttgga
15601 aagtaataat tgtgggcaag agatgagcaa ggcagccagt tctgctttgc agtagttcac
15661 tgtctacttt gtcattagct atgaatgcct ctgaaaataa tggcacagca ccggtaaatc
15721 caggaggctc tggctttcta acactcagct ctgccatccc tttctagcat ttaaaaatgg
15781 actctatttg gccaggcgca gtgattcacg cctgtaatcc cagcactttg ggaggccgag
15841 gggggtggat cacgaggtca ggagatcaag gccatcctgg ttaatggtaa aatcccatct
15901 ctactaaaaa tacaaaaaaa aaaaaaaatt agccaggcgt gatggcgggt gcctgtaatc
15961 caagctactc aggaggctga ggcaggagaa tcacttgaat tcgggaggtg gaggttgcag
16021 tgagctgaga tcgtgccatt gcactccagc ctgggtgaca gagcaagact ccatctcaaa
16081 aaataaataa ataaatatat aaaaaggact ctatttttt tcccctagca gagtcagatt
16141 tcttggaaaa gtcatgggca actgtggccc cgctcccatt cttaccattt aatctttaa
16201 ctctcaacaa tgcaattgtt caccaatact tttgtgttgc caaatcaaat gaactagtct
16261 ctgcaacatc tgacactgtt ggccataccc tatctcctaa attggtcaaa tttctggcat
16321 ccctgatggc actctctcct agtttccct cctactttc tggcgtcccc ttttcagtcc
16381 ctttgggact cctttcttc agcaacctt taagtattgg tgttccctgg agttttgtcc
16441 tcaaccttta ctcttcttag actatacact tgccctggat ggtcctctca tttactccca
16501 catgccttct gttaccaccc atttgctaat gtcttccaag cttacctctt cagctcagat
16561 cttgctctga gttccacact acccatatct gaaccacttc tggtcaaatc cacttggatg
16621 ctatgcaata gcagtttttt gttttgttt tttttttaaa tatggaacgc ttcatgaatt
16681 tgcatgttct taaactgtat tcttcacaat agcgttcctc aagaaataaa aaaagtaagt
16741 ttgatgatag caatcattta ttttgaatt tatttccaca tagacataat gcaacatcaa
16801 acacatttat ataatatttt ttattatgta acaatttatt atatttaata agtctattta
16861 ttgcaagcaa tagaaaccaa ttctggctaa cttacatttt aaaaatgagg atttattgga
16921 aagatactga tctaactcat gaaatgaaag taatagttga ataagctagc ctcaggtaga
16981 atagccacag ggaccttaga agcaggggtt gagttgccat taatatgctc acctgcaaag
17041 gcctcctgcc tctttatctt tcaagttttg ctttgctggg agagcctctc tcactggctc
17101 agcttgtatt aggtgtgtac cactggattc attggttgtg gccaggtaca gtattacctc
17161 tatggattag agctattcct agagaaggga gaatcatatg aaaagtaacc acctcaatac
17221 agctattttc aacatatggc atctcagaca attgtatgag atcatctgag gcataaacat
17281 aaggttaaat ctgtgtatta atgctcaaac agcatttcct aactactcag gtgacatatg
17341 tcatctgctt gatgatctct ggtcggtcac ttgtcttatc acatattcaa attacattta
17401 tcatgtgatt caatattgat ttattaattt aaaattatat attccacgaa tttcctttga
17461 atctctgact aaaaaggttt ttttaatttt actttgaaaa gctccaagca cacacagaag
17521 agaagaatct aataaactcc aatgtactct catgaatgtc aacaatttc aacatttaac
17581 attcttccat tcttgtttca tctattgttc tgcatttttt ggagtatttt aaacaaattc
17641 tgtcattaca tttcaccagt aaatactttt aggcatatct ataatagata ataacctttc
17701 ccttaacata actataatgc catcaccaca accaacaaaa ttaaaaatta cttaacttca
17761 tttgacccaa tctgttcatt tctcctagtt atctcaaaaa tgtgtaagag aatgaagttt
17821 taaatgaaaa gcagtgtctt ataattttca aaccgtgcca ttagtttaaa aaaattggtg
17881 agttttctat tttatgtttc ataagctatt gatggttcaa taatgaattc taattaggta
17941 ttccataggc aaataaagtt agcaattgtt actctgaatg tatctccatc tcaagattac
18001 aagagtacac tcatcacttt cccttcccaa tatattccaa ctcctctctt atatttaaga
18061 cttcagtgaa taacaagatg tccaccgag ctacaaatgt gggtcatcgt tgatgacccc
18121 atcttcctca aaccttccca ttcaattgtc ctaacaattc tacctttcta atagctcttg
18181 aatcttcctt tcttttcctt ccattcctac tggtccaggc cttcaatggt tggttttcac
18241 tgattattgc aactttcttt ataattggtc tctctctctc caatcttatt attttccaca
```

FIGURE 10 (cont.)

```
18301 gtgctgccag aaggatattt ttattatgct tagttgatca tattatactt ctgcatgaaa
18361 accttccatg attgttaatg atctactttc cttgtcatga cccataatga cctgaagtct
18421 acttacctac ttctatatgt cttttcaggt gaaatctcac tcctctcagg aagccttcct
18481 tgaacccaga gttgagatta atagcctctt cagtacgttt ccaaagcacc ctgtgttggc
18541 cattatcact gttttaattg tattattctc ttccatttat atgtctgttt catagtcacc
18601 tcatctctac tgcaaggtcc ttaggggagg gtgtactata tatatatata tctccaccaa
18661 gaggcccact aagtgacctt tcactcgatg aacaaatggg ctaccagtct ctgaaggtgc
18721 tgaactgaga atggaagagc cttcaggtat tagatgatga tggattgtcc cttctaacag
18781 atgtttcaaa ggtaaatctt atcaggttta tctataagcc attcttttt tttttttttt
18841 gagatggagt ttcactctgt tgccaaggct ggagtgcagt ggtacggtgt ccgctcactg
18901 caacctccac ctcccaggtt caagtgattc tcctgcctca gcctctggag tatctgggac
18961 tacgggcacg tgccaccata cccggctaat tttttttttt tttttttgta ttttagtag
19021 agatggggtt tcactgtgtt agccaggata atcttgatct cctgacctcg tgatccacct
19081 ggctcggcct ccctaagtgc tttgattaca ggcatgagca accacaccca gtctctatga
19141 gccattttac acctccacag ccttccctat atactctact acccttccaa ttccattcta
19201 ggcccttccc aagctccttg ccaactacca ttttcttcct actccctgcc acctcctgtt
19261 tcagagagca aacctagcca tccagctccc acatttactc ttatttctac ctcagtacat
19321 ttctccatac ccatattcat cctcccttt agtgacatta ctatgatgca gcaatcctta
19381 caactactct acaaggttat aatttattat cccattata taaacaagaa aactgggact
19441 cagaaaggtt catttattta gcaaatattt attggccacc ttctgtgtct agcagtatgc
19501 tctgtatcag atacctgcca tcatcacact taaagtctaa tgaaaataaa gagacattaa
19561 acaagaaaac atacaaattt ataaactaaa aggtccacac acacacacac acaaaatctc
19621 ttagaattga taaattcagt acagttgcag gatacaaaat tatcatataa aaattaatgg
19681 tgcttctgga tacaaacagt aaactagtgg gaaaagaaat caaagaaagt aatcccattt
19741 acaatagcta caacccctcc ccccaccaaa aaaacaaaat agaataccta gaataaacca
19801 aggaggtgaa agatctctac aaggaaaact atgagaccta gaggaaaaaa actgaagagg
19861 tcacaaaaaa atagaaagac atcctatgtc ttcggaagaa ttcgtatcgt gaaaatgact
19921 gtactaccaa aagcaatcta cagatttgtt gcaattccta tcaaaataca aagatattcc
19981 ttgcagaaac agaaaaaaca aacctaaaat taatatggaa ccacagaaaa cacaaatagt
20041 caaggtaatt ctgaacaaaa agaacaaagc tgtagacatc ataccaccca acttcaaaat
20101 atactacaaa gctacagtaa ctaaaagagc acggtactgg cataaaaaca gatacacaga
20161 ccaatagaac cgaataaagg acccagaaat aatagatcca catcttaaca gccaactgat
20221 tttcaacaaa ggtaccaaga tattcaatgg gaaaaggaca cactcttcat taaatggtgc
20281 tgggaacact gaataacaat atgcagaaaa atacaactac accccatct ctcatcaaat
20341 acaaaaatta aatcaaaatg gattaaaaac ttaaatgtaa gacctgaaac tataaaagtt
20401 actgtaagaa aatactgggg aaatgctcaa gactttgagc aaacattttt tggtttaaga
20461 cttcaaaagg agaggcaatg aaagcaaaaa tacacaaatg ggattacatc aagctaaaag
20521 gcttctgcca cagcaaagga aacaatcaac agagtgaaga gacaaccttc agaatgggaa
20581 aaaatatgtg caaactatcc atctgataag ggattaataa ccagaatata taaggaactc
20641 aaactcaaca gcaaaaatcc tccaaataat cccatttgaa aatgggcaaa tgatctgaat
20701 agacatttct caaaagacat caaaatggcc aacaggcata tgaaaaaatt ctcaacgtta
20761 ctaaccatca gggatatgca aatcaaaacc acaatgagat atcatctgaa tctaattaaa
20821 atggctatta tcaaaaagac acagataaga gatactggtg aggatgcaaa gaaagggaa
20881 tgctcatata ctgatggtag aaatgtaaat taacatagcc actatggaaa acagcataaa
20941 ggttcctcaa acaactaaaa atagatctac tagatgattc agcaatccca ctgctgggta
21001 tatatccaaa agaaggaaa tcagtgtatc aaagagatgt gtacatgccc atgtttattt
21061 cagcactacc cacagtagcc aagacatgga atcaatctaa gtgtctatca agtgactgga
21121 taaagaaaat gtggtgtata tatatacaat ggatactagt cagccataaa aaagaatgaa
21181 atcctgtcat ttccagcaac atggatggaa ctggaagtca ttatgttaat gaaataagtc
21241 agacacagaa aaaaaaatat cacgttctca taagtgggag ctaaaaaagt tgatcttatg
21301 gaggtagagg gtagaatgat ggttaccaga gactgggaaa gggaggggt ggaggggga
```

FIGURE 10 (cont.)

```
21361 tgaagagaga ttcattaatg gttacaaaaa tatagttaaa ttgaaggaat aaattctata
21421 gtgtttgata gcacagctgg gtgactacag ttaacattaa tttactgtat attccaaaat
21481 agctagtaga tttgaagtgc tcccaacaga aggaaataat aaatgtttga ggtgatggat
21541 atcctaatta tcctgatttg atcattacac atcgtatgca tgtatcaaaa tatcatatgt
21601 accccataaa tatgtacaat tattatgtat caataaaaaa taaaaaaaaa caattcagaa
21661 gtccataaac ttggatggaa taaaaaaaag tcaactttat tttcaaaaaa ctctcactga
21721 aatctaattt tatgaatgta gaaaataaat ctttgtagta ccagccagca gctgtaacac
21781 tgtcatcaat agaaaacacc atcaattaat attttcatat cacattatag ttgttacaga
21841 catcttaaaa tatcacttac aattatggga gctgttaaac ttgccaaaaa atcatgcttt
21901 ttaatgtatt agtaaagaaa cactgtattg tattaataca gaaacacata ctactagatc
21961 atcacacgtt tctttgaata tagtagtgtc cccacacag caccaaatgt gattatacag
22021 tttattccta tccatagata tacctatgat aaagtttaat ttataaattt gcacaggaag
22081 agattaacaa caaaatagga caattatatt gtaataaaag ttatgtgaat atggtccttc
22141 tgtctcatac acaaagtatc ttattgtact tattttcaga ccaggttgac cttgggtaac
22201 tgaaatcaca gaaattgaaa ctgcagttaa gggggggacca ctgtattttg ataactatag
22261 tttatatttt attttatgca tttacaaata ttatcagaca agatccaaag gcttcaccaa
22321 actgccaaaa aagctaatgg cacataaaaa gcttaaggag tcctgattta atcagtcatt
22381 caatgaacat gacatccttc ctggaaccat ctcctgttct agcttcctca cattatgttg
22441 ctctgcttct ccttgagatc ttccattggt tccacttcct attcttgctt cctgtatgaa
22501 gatgtaaccc aaagctcaat ccttcaccct aaattgtttt tataccccct cttttacaaa
22561 cctcagctac cttcgtggct gattcaaaca tcacctcaaa ggtgactctc aaatctgctt
22621 ttcctaatct ttttttctcta acttcaatct tggatcttaa actccctgct gtgcctagta
22681 aacagaataa tatgccaccc agagtcagct gggttcaaat cccagttctg ctacttacta
22741 aaggtgtgac attaggtaaa tattacctgc tatggtttga atctctcctc caaaactctt
22801 gttgaaaata attgccattt tgacagtttt aagaagtggg acctttaaga gttaattagg
22861 tcatgagggc tctgctctca tgaatggatt aatgctacta atgtaggtat gggttcccat
22921 ttaaaagggg acattctgag gccgggcaca gtggctcaca cctgtaatcc cagcactttg
22981 ggaggccgag gcaggtggat catgaggtca ggagatgag accatcctgg ctaacacggt
23041 gaaacccccgt ccctactaaa aatacaaaaa attagccagg cttggtggcg ggcacctgta
23101 gtcctagcta cttgggaggc tgaggcagga gaatggtgtg aacccgggag gaggagcttg
23161 cagtgagtca agattgcact actgcactcc agtctgggcg acagagcgag actccgcctc
23221 aaaacaaaca aacaaacaaa caaacaaagg gtacattctg gcctctattc tctctccatc
23281 tcatgtgctt gtttgccttt ctgccgtggg atgatgcagc acaaggctct caccagatgc
23341 caatgccatg ctcttggact tccaagcaac tggaactgag ccaaataaac tactgtttat
23401 aaattaccca gtctgtggta ttctgtgata gcatcagaaa acagactaag acgtcctttg
23461 cttctgttgt ttcatttgaa aactgagggt gataatatta gtattgactt tatagggtta
23521 taaggattaa aagagttact acatgtactc attgcagtac ctgacacatt ttaactactc
23581 aataaatgtt ttgtatcacc aatcacatct ccttccaacc ccgacatttt aatttgatgt
23641 ttattaacat ggacggtgcc agccactgga agacagagtt tctatctaac aacataattc
23701 tgatcaagtc attagtcaaa aaatttcagt ggttccccac tgattccaaa cttaacagca
23761 ctggaaacct tctataatgt gttctctaat ataaatttac ctcccatttt ctcttctcct
23821 gctctacttc ttgtagctta tgttctggcc agactggact agactactct ctgtgacaat
23881 aacctgtgct gttctatgtc tgtctttcct cacataattc taatgtctca ggtttgaagg
23941 caataatttt gtctatgatt attcccctat acatggcacc ccataaaaca tacacatttc
24001 aatcttacct aagtcacata cttacttaca catcaattca cctccatatt tgctcaattt
24061 gtgagaacct aatattggcc agatactgtg ctaggaccta gggatattaa aaaaaaaaaa
24121 aaagcaaagc aagaaaaaga atgcataatg gccctgctct caaaatcaag gtctagtact
24181 agagagaaac atgtaatcac ataaatgcca ttcactgtgg aaagtaaaat cataagggga
24241 agggacacca aagaatgagc agttagctca acttgaacag taacattaag cttttcagag
24301 atgttatttg ggcgtacata gattggggaa aagtctactc catatagaaa gtgcacatgt
24361 gtaaaacaca gaggcatgaa acaaaatgat gtgtctggga aacagttcaa tacagctgga
```

FIGURE 10 (cont.)

```
24421 atatagggcc caagaggaag tggttagaca tgaggctgga aagctaggca gactgttttg
24481 gcaaacatag gaatttggac tttatcacat agccaataag gaataacaca gagttttaaa
24541 aagagctatg gccagggcta tattttggaa agctctctcc tggcagtatt gtggcagagg
24601 cagagaggaa agtctaaagc agcactgtcc aacagaactt cttgtaatga ggccgcgcgc
24661 agtggctcac gcctgtaatc ccagcacttt gggaggctga ggcgggcgga tcacgaggtc
24721 aggaattcga gactaatttg gccaacatgg tgaaccccg tgtctactaa aaatacagac
24781 actagccggg tgtggtggca ggcgcctgta atcccagcta ctcgggaggc tgaggcagaa
24841 ttgcttgaac ccgggaggca gaggttgcag taagccaaga ctgcgccact gcactccatc
24901 ctaggccaca gagcaagact ccgtatcagg gaaagaaaaa acaacttct tgcaatgaca
24961 caaatgttca ataatctgtg ctttcccata tgacagccac tagtcacatg tggctattga
25021 gaacttaaaa tgtggctagt gtattgaggc actaaattta aaattgtatt aatttaaatc
25081 caaatagcca tgtgtctagc aaataattta ggagactgtt ggtatagctc aggtgataga
25141 attaggacag aagggtgagt tgatggatag ttaagaggca aaattatgag tctgtaaggg
25201 tgtgagaaaa ggaaatcaag aacaggctcc cagattacag actttgtggt taaacagcca
25261 ccattactca ggacaacaga agagaaagag caggtctaga gtgtatagtg atttcatcaa
25321 ttttgaacat actggtgtct gagagttatc ccagtgggaa tatttagtag aaagtttagc
25381 ttagagagct gtctgaacta aagattcaga cttcagaggc tttgagccat ggagtcagat
25441 tacctagaga agttgaacaa aattagaagc aaacaagaat cacagcaaat atcaacacat
25501 aaaaagggc taaggaagaa aaatctactg agactggaga ggaacagtta cacaaatagg
25561 aaaagaaaca agtgagagtg gtatagaagt caagggtaga gagaatgtca ggaaggaaac
25621 atgatcaaat gtcgaatgcc tcagaggtca aataaagtga gaactgtaaa gtgcttcctg
25681 actttgccag ttaggaggtt cttggtgaca tctgccagaa aagttttggt ggtagcagcc
25741 tgacagaggt agcttgaaga gtggggatgg ggaaagagaa tgtgaccaag aattgagata
25801 gtaaggataa tttcaatttc aggtcttggc tgtgcaagga agccgagaga catgagtctc
25861 taagagggca cgatattgag agggttgtta tctttctgtc agcgggaaa ccaagagaaa
25921 agtttaaaaa ggtcaaaagg gggagaaggg aagacagctt ccgggtaaca gagaaggttg
25981 accaggtcaa tagtaaagga tttcctcaaa ccgaagggag gacctctagt gaaatgagaa
26041 aggaatacac aattgaccca gtttgcaggt gggaaatggg aagccagttc tgcaaattgg
26101 cctttctgtt ctgtgaagtg ccatctgtcg gtgaggagag attagggtct gcagcgtgaa
26161 aatctggacc atactctggg taatcaaggg agaggttatc ggctaatgac aaattaaagg
26221 cttactttt agctggcaac tgaatcacca taacatttta tgttaccagt tccaaaattt
26281 tgggggaat tcactcaagc ttgggagagg agagatcata actttaagag tataagaggt
26341 ttaaacggtc cactacgaaa taaatagaga aggaaaagtt atcagctggt aaatatcgta
26401 gaaggtagag cggtccaggg actcacaggt ctcactaaag aaaagtctag cgtaggttca
26461 cggcacggag agattttaag gctgcctaag actaaagcca aatacgaagt ccacatctgc
26521 ggtccgcacc ttatctctcc gcgcggcagg cgcgacgagg gcgagaaact ccctctccag
26581 tggtcgcacc acacgacacc agggaagggg ccctctctc cagaccctca tatctccagg
26641 tccaggcccc attttcctcc gctgacagct cagcagcgtg cgcttccgct ggattcaggc
26701 caggaccagc gaagccgcac cttacacccca ccgaggagga aacaagcctg gccacccgag
26761 gctaccccgc taggccgcgg gtagtggggg aggggcgct gaggcaggag gtcagcaccc
26821 gggcgcgggc tcccgcccca cgaaatgcgc gcgctccaag ccccgccgcc ggagatgcgg
26881 ttccggtccg gacgcctgcg cactacggct ctccccgcag cctctggccc tccttccccc
26941 tcccccagtc agggcgcacc cttgcgcctg cgctgtgtgt gttcctggtc tgcggcagcc
27001 atgctgaact cgtatgagga ggcgagtggg gggacagag tccaggactg cgggatagga
27061 agctggggat atggacaagc agcagcgtta tagcgctctg ggtttcggga cataggcctg
27121 ggccatgcgg ccccccttggc cccttggcgc gaccccagg aacgttcgga aagctggtcc
27181 tcgtggctgg gggaaaggcg gggggtgggg gggaagcggg cacgtgaccc cggtcagcca
27241 atctgggtgc tgctgacgtg gccgcgcggc cccgatgctc tccccacccc cccagcccgt
27301 tcgggaaggg aggggctggg ggctacgccc cctcccccag cacggcttcg ttttctgggg
27361 ggggttgac accccggatt acatacccccg taccaagccg agggcaactt tggaggcccc
27421 ctggaaggct ttaggatcca ggtgagaagg ggcccttgtg gggcggagat gtcagtcaag
```

FIGURE 10 (cont.)

```
27481 tgcttaacca atggtgggga gtccgggagg gggattcttg gggttcagga aagaatcctg
27541 agagtgggaa gatttgtcct tcaaaccttt tacagccaat gggagcgtgg agggggggcg
27601 agcgggagag ggccatgggg ggggagggga atggccagcc tcatgcctcc gtacccattg
27661 gagggcaaag gggttagggg gcggtgtggc ccccctatt ccattcgtcc cctggggta
27721 cagcagccgg gagccaggtg agaagggatc catcggcggc cgagggaggg gtgacctggc
27781 ggtgggctga ggagtggtgg ctgtggcccc tacccgtgga tgtgaatgct ttaggagttg
27841 gccacccatg ttgtgaactg aggttgttcc caggcgccaa cttcctttct ccccagagcc
27901 tctggaggga gcattgctgt gcgccctttg tgtccgcggt aggggagctc cagtcgtcac
27961 accgcaggct ggaggttacg cttcgagtcg cttaccgaat ttgtgtgcat tcacgtggac
28021 acggcctgtg gggccttttg cccctgtagg gtctttactg agcacgtgtc tactccaggc
28081 tggggtgctt acaagctgaa agcttgaggt ctgcttagga acagaaacca ggcccaaggt
28141 gggtgctggc agtaggggt ctagacagca tggtctgaga tgcgagggag gctcgggacc
28201 tggaatgatt tcacagctcc caaggtttcg ggtttctcca gggtggcctc ttccatcgcc
28261 tccctcatcc cctccccag tcctgaacag ttctctcctt gtgtactgcg ggggagggaa
28321 cggaaaggag gaaagagtta ctttcccaaa ttactgagta gcagtagcct ccctggtgac
28381 tcatgtgggg gaaggagga tagaggatcg ggaggcagtg attttccgga atgcagggaa
28441 taaacgagag caatgtctgg ctgcccttt cctaaggcct agtatttct cagcctccta
28501 agttttact ccatggccgg ccccctgatg ggcctctgtc ctggcctgca gagccccggt
28561 ggagaaaagc agatttggga ggttgggccg ctaggggag gggaaaaggc ctctgcaaag
28621 ttgctgtgtc attgccctcc atgctgcagc cacccaaacg gggccgcttg tacttttggg
28681 ggccagggcc tgatccctgg ctggggaag gggactctgc tctcctgacg ctcattttcc
28741 cccgccctcc cggggtttgc cctactcggg gggtcagaag acaggagatt ggcggccatt
28801 ttagacgcag taaccgaggt tggagttgaa gggctactgc agaggaggga gggtggcgtg
28861 gttgcagctc aaggacctag gcccttacga gcccttcccg ggcgaggggg aatcttaccg
28921 tatatttgtt cacctacgtt gattatttt cccagatacg tacacaagtt tgttttctcc
28981 ctggtagcga agaaagggga aacggggaga gggacgcccc accaaagccc aggttttctc
29041 gggtggggga gatcctttca ctctcttgta aggggcggg gacggcccca gagatgctct
29101 ggagatcctg actctgggct ctggttgatt cacagagtct gcacccttat ttagataacc
29161 aagttaggag gaagacttaa gagtaagttg gggggagggg gcgaaactga gctcccaaaa
29221 tggctcctgc ccctcctcgg aggcggacgg ccggggggag gggaggaggg gaggagggg
29281 agggctagtc tgagccgcag ccgccgcctc ctccgctcgc cctcctcct ggcgctgacc
29341 gatggaccag ccgctccgtg gggaggactc cggaccctgg tggggggggg gggggttct
29401 ttcgcccccg tggcggaggg ccctgagag gcggatacgg tgtgcctt gggggtgatg
29461 tggcgtgtgg ggggaaaggt ccgagctcgc ctggagggg aggtttttc ccttaagtca
29521 tccctcccag gacttgcttt ttctgctctg agccggacgc cggaatggag tttgaggaag
29581 aggtgaggtg tgttgcattg tatagggtag atggatgcgt ttggagattt taatcccact
29641 tttaggggtc ccgaggattt ttcgaacgag cagaaatgta ttggtaactg taggtgtgag
29701 tgggagggga ttagaaaggt gcttggacgt gcaaatttgg gagacgtatt ttagcttttg
29761 tggtctttgg gactaaacag tagtaaataa tgttttgctc gtctttccat cgtttggctt
29821 gagggaggga gtggagtatt ataagactct ggcaacactg ttttagactg tggggcatgg
29881 gaacgttaga tcccctcatc gccgttctga agcccgtagc tgttcgccat agaggagcag
29941 gccgcggctt ctaagatggc gtcttttttcc tcgtttcaga ttcttcgctg ctgctgcctt
30001 accgccgaga accaccaccc gccaggcgtc ttgcggccac acccctggcg ggttcaggca
30061 ggctacgccc acgcgacccc tcccgttttcc ctgctttggc caatggagga gctacgaatg
30121 gcacgacctg ctcgagcttg gcagtctcca gttgggctgt gcatggaagc ttgggaagac
30181 tttgttggaa gggggaggcgg ggagagagtg ctggaggctc tggggcgatg gcttccgcac
30241 ctcttccaac caccctcttt ccctggagtc ggcgaccac agctcagcca attggcttgg
30301 agatctggcg ggttgccact tccctgtggg tctctgcggc actcttctgc ctggtgactg
30361 acaccttgga aatgaagttt atgacgtcat cgttgcggct ggccaataga aaaagctccc
30421 gcggagaggt gttccttccc cttcgactca gcttcttcac ccgcgtgagc gagcgcgcgc
30481 gcgcggaggg ggtggggaaa atctcaagca gggtggcgcg catgagcggc gaagctcctc
```

FIGURE 10 (cont.)

```
30541 ctccccgcct atatataaag ggctggcgcg gggctcggcg gcgccatttc gtgctggagt
30601 ggagcagcct ctagaacgag ctggaggatt ctgcctaccg atacagagcc ttcgagtcgt
30661 ccggggccgc cattacaatc cacctccatc cgcttggaaa tggccttcgt cccggcctat
30721 gactggtccc agcggcagt acagacccc tagaagcccc tggagctccc cttttcggg
30781 ccccgcccaa tcctcggagt ctgtccaccc cctctactcc gccctcaaga ggatttcaaa
30841 gatggaggcg gcggctccct aaaccactt tcgtgttcat ccgcctccat ccgagatcga
30901 aacgggacct cgtcggcccc gtaggggccc gacaagaaga gggaatccct gcagaccaac
30961 agcgggctat attgacgacg gtgtctgaga tcggggaccg tcttttgaag agtcagtccc
31021 tccttagttg cccgcctcag ctgaggccgc cgccatttc ttgctgtccg ccgtctgcag
31081 agcgcgccaa gctgcccgga gctctccgag aggccccaaa gagactgctt tcgtgccggc
31141 caggcagggg gtttgtcgcc tggaggccca agaggaacgg cctccccca acttagcggg
31201 ttatgctgga ccgggcggtg aggggaaccg aggccacccg gactttccgc ggctgagggc
31261 agcgccggtt ccttgcggtc aagatgctgc aaaacgtgac tccccacaat aagtacgttt
31321 ccgcgagccg cgtgtgggaa ggggatgttg cagggcggcg gcacaggggt gtgggcgcc
31381 gtgttgggag tactgagcgg ccccggcgcg ctgctgttgc ggcgcagctg tcgactcggt
31441 cgcgcggagg gaattgagcg acggtttgg aacggtggtg gcggctcggc tactgctcgt
31501 ggagggaat acaggttgtc aatttatacg ctattaatgc cgccgtggcc cagtcttaac
31561 cgagtcaggc agagctagtt tgacggtgga gtggagtgag gttgaacagc aggtttggcg
31621 tttggtgggt ctggtatcta gcggcggtct gttagccttt tagggggat tcacggacac
31681 ctctagcgcc ctgtagggtt gccatggtga cggagcgctt aagggactgg caacgggat
31741 tcccagagaa gggtaaaggg atcactctcc cgtgtgtgca ggttcctaat gcccagggca
31801 tgtcattaaa tcttttgctt tctttgggtg ggtggttgt gtgtggtgtt tgttggtgca
31861 gggattgttt tttcctaaca ttaaaagttt gattcagggc aggagggtag agctaaggtt
31921 cctagttcag ctctgcgatg taaacaatga gattcccata tgatgttta attcttaggt
31981 ggtaggaaag actgatcgga ggagcaccag agggactgta aatgaaccac tgttagcgtt
32041 tggtgtccgg agttggtgct acaggggaa ctggtagtgg aatcgtgttg tgtagtgggt
32101 gggtggaagg gggctatcac ttggtgacct tgactgtttt gtacggcttt ttgacttcct
32161 tggagtgagg agactctgat ttggtgcgaa taattttgag ggcctggaag ttacgggctg
32221 tgaagtctga caaattcttc cttgtctgaa tttgtttta agttgatatg gttcttcctc
32281 tgggtttcta gtctatgttc tgttgtggcg tgaactaccc agaccttgtg gaagatggt
32341 ctctctcttc tatctaggtg gattattctg tgtcttatca gcattttatg gaatttttta
32401 tagccataat ttgttctttt cctccttacc ggcgctcaac caccatggca accaccaaac
32461 ccctagtgag gaggaagctt ggggtttgag tttcttaact ccacccattt tgcttaatcc
32521 ccatcccat agggctgtag ttctgagatg tcgtgccttg tcagaaacaa tttgggagtt
32581 ttttaaaata tgaaaaagaa cagatagagc ctatcagact taagaaggtg ggatctagat
32641 agtatactaa aaatattaat aaaaggaagg cggggccagc aataaaagct ccacagattg
32701 tttggatatt gtttctgctt aagaagcact tggcataagc ttaaccacct cactagggcc
32761 agcacctgga ttcatcagac tattgtgcag atgcactttt tcctcatttg gacgatattg
32821 ccctaatttt gttcccatct ttacaggctc cctggggaag ggaatgcagg gttgctgggg
32881 ctgggcccag aagcagcagc accagggaaa aggattcgaa acccctctct cttgtatgag
32941 ggctttgaga gccccacaat ggcttcggtg cctgctttgc aacttacccc tgccaaccca
33001 ccacccccgg aggtgtccaa tccaaaaag ccaggacgag ttaccaacca gctgcaatac
33061 ctacacaagg tagtgatgaa ggctctgtgg aaacatcagt tcgcatggcc attccggcag
33121 cctgtggatg ctgtcaaact gggtctaccg gtgagtagag acattggagc cggggaggtg
33181 tgggatgagc aagaatgcgt gtgaatgggg gtggtctgcc tagtgtagat gctgcggcc
33241 ctagggagtt cccatttctc ccctgtaggg cagttagcta ccagatttct gggtatcttg
33301 gtcctttgt attgatccga ccgcttgctg taactatctt ggcatctttc cttgtgccct
33361 ccatgtgtcc ttccttaact tttgtgccct ggctccattt tacagattcc cacctcgggt
33421 tgggagagga ccacggtggc caaattctt agcttcttcc tttccctcat gcagcccatg
33481 gatagccagc cccagaggta atgtcacagg atgggaagtt tccagagtgg gtgggaggtg
33541 ggtggttaga gaaaggcagc aggggcctcc ctgtggatgt caagaatctt tttatttat
```

FIGURE 10 (cont.)

```
33601 ttatttattt tgtcccacag tttaattggg gccgcagttt aactgttcct ttgatgcata
33661 gggggtgtgt gtgtgtgtgt gtgtgtgtgt gagagtcggg gatcggtagt ctccctataa
33721 gcatttattt ttctgtggtt ctgacctaac atttctttat ttaggattat cacaaaatta
33781 taaaacagcc tatggacatg ggtactatta agaggagact tgaaaacaat tattattggg
33841 ctgcttcaga gtgtatgcaa gattttaata ccatgttcac caactgttac atttacaaca
33901 aggtgagttt ttctgtgtgt tcatttagta ggtggggaga aacagtaatt tctattattg
33961 ctggatatgt tgtctacata aagtttaaat cctttgctac tgaaggtgtt atccaggtag
34021 ggtagtcgga gtcttaaaaa cctgactcta gatggtacta ttgaacacag tgatgtgact
34081 tcagagctct agttgaaggt tatttagaac acttcatact tgggggtggt ggtcctgttt
34141 cttagaaatc accagagacc tgagtagacc agggatctgt tttcttgtca gctctcaagt
34201 tttttcttct ttcgaatttt gggagacagt taggagaaag tggaaattag tagtggcctg
34261 gagtagaaat tttctttaag atttgatgac aagatgactg gtgggggtat ggtaatggcc
34321 tagggcctga atgcctctga gaaagatggt gtgtatctat cttctgttgg catttttaa
34381 ctttctttat tgctgtctgt gttctcatag cccactgatg atattgtcct aatggcacaa
34441 acgctggaaa agatattcct acagaaggtt gcatcaatgc cacaagaaga acaagagctg
34501 gtagtgacca tccctaagaa cagccacaag aaggggggcca agttggcagg taggaagagt
34561 gggagttttg caaatggaca acttaaagat ggggaagaga atcaaactac acttttttcc
34621 tttttctag cgctccaggg cagtgttacc agtgcccatc aggtgcctgc cgtctcttct
34681 gtgtcacaca cagccctgta tactcctcca cctgagatac ctaccactgt cttcaacatt
34741 ccccacccat cagtcatttc ctctccactt ctcaagtcct tgcactctgc tggacccccg
34801 ctccttgctg ttactgcagc tcctccagcc cagcccttg ccaaggtatg atctgtggat
34861 ttcctctggg cagcagggag gcaagggtct taagtaaagt gggcttggag tgacaggttc
34921 cctatcttgt ttctttctgc agaaaaaagg cgtaaagcgg aaagcagata ctaccacccc
34981 tacacctaca gccatcttgg ctcctggttc tccagctagc cctcctggga gtcttgagcc
35041 taaggcagca cggcttcccc ctatgcgtag agagagtggt cgccccatca agcccccacg
35101 caaagacttg cctgactctc agcaacaaca ccagagctct aagaaaggaa agctttcaga
35161 acagttaaaa cattgcaatg gcattttgaa ggagttactc tctaagaagc atgctgccta
35221 tgcttggcct ttctataaac cagtggatgc ttctgcactt ggcctgcatg actaccatga
35281 catcattaag cacccccatgg acctcagcac tgtcaaggta cccactgcat ggggcagatg
35341 ggatgctcaa gcagtgatgg gagcctaggt gcaaaacaat aagtctcctt atgtgggcac
35401 acagcagtct ttggttcttg gcattttact tttataaaat aatagtggaa cagaaggtct
35461 ggtgttttga gaatttgtat ttcttggagt ttgaaacagt agggtggggt ttctttgtct
35521 tgagaaaaat actgtctata attaagtact aatgtggcag tgttgggtta aggaagttat
35581 agggtggaaa gacaggcata ggccacctct ctgtcactta gaaatgattt cttttttctag
35641 acataaatat ttcttcaacc cacccaaatt cctttgactt caaacttgaa ccccagggca
35701 cagatcctta aggtcatccc cactgtgctc tcaagagagg gctcttcttg tggtgtctgg
35761 ggttggcagg gaaaggtgag tcttcctgcc tgtgcagctt ctgatgctgc ctccttctgc
35821 agcggaagat ggagaaccgt gattaccggg atgcacagga gtttgctgct gatgtacggc
35881 ttatgttctc caactgctat aagtacaatc ccccagatca cgatgttgtg gcaatggcac
35941 gaaagctaca ggtgagtgga aaggttggag tttgaaaaat aaatggtatg gggagttatt
36001 ttgtcatgtg tgctgcatag cctcaacgtg agggtctcac tgttctgtac agttgtaaat
36061 tggagctata tcacttggtg gctgggtatg tagggcactg tttatcagca tagttttgag
36121 tttgtgcctc tttctaggat gtatttgagt tccgttatgc caagatgcca gatgaaccac
36181 tagaaccagg gcctttacca gtctctactg ccatgccccc tggcttggcc
```

FIGURE 11

Homo sapiens nucleolin (NCL), mRNA

```
   1 ctttcgcctc agtctcgagc tctcgctggc cttcgggtgt acgtgctccg ggatcttcag
  61 cacccgcggc cgccatcgcc gtcgcttggc ttcttctgga ctcatctgcg ccacttgtcc
 121 gcttcacact ccgccgccat catggtgaag ctcgcgaagg caggtaaaaa tcaaggtgac
 181 cccaagaaaa tggctcctcc tccaaaggag gtagaagaag atagtgaaga tgaggaaatg
 241 tcagaagatg aagaagatga tagcagtgga gaagaggtcg tcatacctca gaagaaaggc
 301 aagaaggctg ctgcaacctc agcaaagaag gtggtcgttt ccccaacaaa aaaggttgca
 361 gttgccacac cagccaagaa agcagctgtc actccaggca aaaaggcagc agcaacacct
 421 gccaagaaga cagttacacc agccaaagca gttaccacac ctggcaagaa gggagccaca
 481 ccaggcaaag cattggtagc aactcctggt aagaagggtg ctgccatccc agccaagggg
 541 gcaaagaatg caagaatgc caagaagaa gacagtgatg aagaggagga tgatgacagt
 601 gaggaggatg aggaggatga cgaggacgag gatgaggatg aagatgaaat tgaaccagca
 661 gcgatgaaag cagcagctgc tgcccctgcc tcagaggatg aggacgatga ggatgacgaa
 721 gatgatgagg atgacgatga cgatgacgaa gatgactctg aagaagaagc tatggagact
 781 acaccagcca aaggaaagaa agctgcaaaa gttgttcctg tgaaagccaa gaacgtggct
 841 gaggatgaag atgaagaaga ggatgatgag gacgaggatg acgacgacga cgaagatgat
 901 gaagatgatg atgatgaaga tgatgaggag gaggaagaag aggaggagga agagcctgtc
 961 aagaagcac ctggaaaacg aaagaaggaa atggccaaac agaaagcagc tcctgaagcc
1021 aagaaacaga agtggaagg cacagaaccg actacggctt tcaatctctt tgttggaaac
1081 ctaaacttta acaaatctgc tcctgaatta aaaactggta tcagcgatgt ttttgctaaa
1141 aatgatcttg ctgttgtgga tgtcagaatt ggtatgacta ggaaatttgg ttatgtggat
1201 tttgaatctg ctgaagacct ggagaaagcg ttggaactca ctggtttgaa agtctttggc
1261 aatgaaatta aactagagaa accaaaagga aagacagta agaaagagcg agatgcgaga
1321 acacttttgg ctaaaaatct cccttacaaa gtcactcagg atgaattgaa agaagtgttt
1381 gaagatgctg cggagatcag attagtcagc aaggatggga aaagtaaagg gattgcttat
1441 attgaattta agacagaagc tgatgcagag aaaaccttg aagaaaagca gggaacagag
1501 atcgatgggc gatctatttc cctgtactat actggagaga aaggtcaaaa tcaagactat
1561 agaggtggaa agaatagcac ttggagtggt gaatcaaaaa ctctggtttt aagcaacctc
1621 tcctacagtg caacagaaga aactcttcag gaagtatttg agaaagcaac ttttatcaaa
1681 gtacccccaga accaaaatgg caaatctaaa gggtatgcat ttatagagtt tgcttcattc
1741 gaagacgcta agaagcttt aaattcctgt aataaaaggg aaattgaggg cagagcaatc
1801 aggctggagt tgcaaggacc caggggatca cctaatgcca gaagccagcc atccaaaact
1861 ctgtttgtca aaggcctgtc tgaggatacc actgaagaga cattaaagga gtcatttgac
1921 ggctccgttc gggcaaggat agttactgac cgggaaactg ggtcctccaa agggtttggt
1981 tttgtagact tcaacagtga ggaggatgcc aaagctgcca aggaggccat ggaagacggt
2041 gaaattgatg gaaataaagt taccttggac tgggccaaac ctaagggtga aggtggcttc
2101 gggggtcgtg gtggaggcag aggcggcttt ggaggacgag gtggtggtag aggaggccga
2161 ggaggatttg gtggcagagg ccggggaggc tttggagggc gaggaggctt ccgaggaggc
2221 agaggaggag gaggtgacca caagccacaa ggaaagaaga cgaagtttga atagcttctg
2281 tccctctgct ttccctttc catttgaaag aaaggactct ggggttttta ctgttacctg
2341 atcaatgaca gagccttctg aggacattcc aagacagtat acagtcctgt ggtctccttg
2401 gaaatccgtc tagttaacat ttcaagggca ataccgtgtt ggttttgact ggatattcat
2461 ataaactttt taaagagttg agtgatagag ctaaccctta tctgtaagtt ttgaatttat
2521 attgtttcat cccatgtaca aaaccatttt ttcctacaaa tagtttgggt tttgttgttg
2581 tttcttttt ttgttttgtt tttgttttt ttttttttgc gttcgtgggg ttgtaaaaga
2641 aaagaaagca gaatgtttta tcatggtttt tgcttcagcg gctttaggac aaattaaaag
2701 tcaactctgg tgccagaaaa aaaaaaaaaa aa
```

FIGURE 12

Homo sapiens splicing factor, arginine/serine-rich 14 (SFRS14), transcript variant 1, mRNA

```
   1 ggcggcttgc gcctgcgcgg cgcggcgctg cggagaccgt tggttcattt gcatgtcccc
  61 gcctcgcgcg gcggcggcgg cgggtgagga gcctgaggcg gcggcggggg tggctccgcg
 121 cgcggtggtc tcgggggcaa aataacatgg cagccagacg aattacacag gagactttttg
 181 atgctgtatt acaagaaaaa gccaaacgat atcacatgga tgccagtggt gaggctgtaa
 241 gcgaaactct tcagtttaaa gctcaagatc tcttaagggc agtcccaaga tccagagcag
 301 agatgtatga tgacgtccac agcgatggca gatactccct cagtggatct gtagctcact
 361 ctagagatgc cggaagagaa ggcctgagaa gtgacgtatt tccagggcct tccttcagat
 421 caagcaaccc ttccatcagt gatgacagct actttcgcaa agaatgtggc cgggatctgg
 481 aattttctca ctctgattct cgggaccagg tcattggcca ccggaaattg gggcatttcc
 541 gttctcagga ctggaaattt gcgctccgtg gttcttggga acaagacttt ggccatccag
 601 tttctcaaga gtcctcttgg tcacaggagt atagttttgg tccctctgca gtttttggggg
 661 actttggatc ttccaggctg attgagaaag agtgtttgga gaaggagagt cgggattatg
 721 acgtggacca tcctggggag gctgactctg tgcttagggg cggcagtcaa gtccaggcca
 781 gaggtcgagc tctaaacatc gttgaccagg aaggttccct cctaggaaag ggggagactc
 841 agggcctgct cacagctaag gggggtgttg ggaaacttgt cacattgaga aatgtgagca
 901 caaaaaaat acccaccgtg aatcgtatta ctcccaaaac tcagggcact aaccaaatcc
 961 agaaaaacaa tccaagtcct gatgtgaccc tgggacaaa cccagggaca gaagatatcc
1021 agttccccat tcagaagatc cctctgggc tggatctgaa gaatcttcgg ctccccagaa
1081 gaaagatgag ctttgacatc atagataagt ctgatgtttt ttcaagatttt gggatagaaa
1141 taatcaaatg gcaggattc cacaccataa aagatgatat taaattttcc caacttttcc
1201 agactctctt tgaacttgaa acagaaacct gtgctaaaat gcttgcctca ttcaaatgtt
1261 ccttaaaacc agagcacaga gattttttgct tttttactat caaattttta aagcactctg
1321 ctttgaaaac acccagagtt gataatgagt ttttaaacat gcttttagac aaaggtgctg
1381 tgaagaccaa aaattgcttt tttgaaatca taagccttt tgacaagtac ataatgagac
1441 ttcaagaccg gcttctgaag agtgtcacac ctttgcttat ggcctgcaat gcctacgagc
1501 taagtgtcaa gatgaagacc ctcagtaacc ccctggactt ggctcttgcc ctagaaacca
1561 ccaactctct ctgccggaag tctttggccc ttttgggaca gacattttcc ttggcctctt
1621 ctttccggca ggagaaaatc ttagaagctg tcggcctgca agatatagct ccctcacctg
1681 ctgcgtttcc aaacttcgaa gactccactt tgtttgggcg agagtacata gaccacctga
1741 aggcctggct agtcagcagc ggatgtcccc tccaggttaa gaaagccgaa ccagagccga
1801 tgcgagagga ggagaaaatg attcctccta cgaaacctga aattcaggcc aaggctccaa
1861 gtagtctgag tgatgctgtc ccccagcgag cagatcacag ggtagtgggc accatcgacc
1921 agcttgtgaa acgtgtcatc gaaggcagcc tgtctcccaa agagagaact cttctcaaag
1981 aggaccctgc ttactggttt ttgtctgatg aaaatagtct ggagtataaa tattacaagc
2041 tgaagttggc agaaatgcag cggatgagcg agaacttgcg aggagccgac cagaagccga
2101 cctcagcaga ctgtgcagtg agggccatgc tgtactcccg ggctgtccgc aacctcaaga
2161 agaaactcct tccgtggcag cggcggggc tcctccgtgc tcaagggctc cggggctgga
2221 aggcgaggag agcgaccacc gggacccaga ccctcctatc ctcaggcacc aggctgaaac
2281 accacggccg gcaggctcca ggcctctcac aggcaaaacc atccctgcca gacagaaatg
2341 atgctgccaa ggactgcccg ccagacccag ttggaccttc tcctcaggac cccagcttag
2401 aagcctcagg cccatccccc aagccagcag gagtggacat ctctgaagca cctcagacct
2461 cttctccctg cccatctgct gacattgaca tgaagacaat ggagactgca gagaaactgg
2521 ctagatttgt tgctcaggtg ggaccagaga tcgaacaatt cagcatagaa aacagcaccg
2581 ataaccctga cctgtggttt ctacatgacc aaaatagttc tgctttcaaa ttctatcgaa
2641 agaaagtgtt tgaactatgt ccatcaattt gtttcacgtc atctccgcac aaccttcaca
2701 ctggtggtgg tgacaccacg ggttctcagg agagcccgt ggacctcatg gaaggggaag
2761 cagagtttga agacgagccc cctccgcggg aggctgagct ggagagccca gaggtgatgc
2821 ctgaggagga ggacgaggac gatgaggatg ggggagagga ggcccccgct cctggaggg
2881 cggcaagtc tgagggcagc accctgccg acggccttcc cggcgaggct gccgaggacg
2941 acctggctgg agcacctgcc ttgtcacagg cctcctcagg tacctgcttc cctcggaaga
```

FIGURE 12 (cont.)

```
3001 ggatcagcag caagtcattg aaggttggca tgattccagc tcccaagaga gtgtgtctca
3061 tccaggagcc aaaagtccat gaaccagttc gaattgccta tgacaggcct cggggtcgtc
3121 ccatgtccaa aaagaagaaa cccaaggact tggacttcgc ccagcagaag ctgaccgata
3181 agaacctggg cttccagatg ctgcagaaga tgggctggaa ggagggccat ggcctgggct
3241 ccctcggaaa gggcatcagg gagccggtca gcgtgggaac cccctcggaa ggggaagggt
3301 tgggtgctga cgggcaggag cacaaagaag acacattcga tgtgttccga cagaggatga
3361 tgcagatgta cagacacaag cgggccaaca aatagatcaa aaccactgat gtgaaagata
3421 agccttgaag cagcaattgc ccttaaaaca tcatccctgc cctggatcgg cctggagcca
3481 gtgcccaagt acggtttggt gtgtacatga aaacaaacgt ctctgcagtc tctgggcgg
3541 aggtttcgct ggcttttctt tctctcaaag aaaaaaacat gcaccatttt caatgtgctt
3601 ttgcctctcc tctctgttca catgctttta gcagcaagtc ccctccaaat ctgtcttggt
3661 tcccctttag aaggtggcgc tgcccccgaa aggcacctca gcctgtgagt gctgaggaac
3721 cagctcctct ggctgatttt ccagttggac tggccattgc tctccagaag tgctctgtta
3781 gcaaacgtga tgtggaaacg atcacagatg gtgttttctc gttgttcgcc agaatttata
3841 cgggggagac aaattcccgg taattaccaa gtctgcactc gggtaccaaa gctctgaagc
3901 tctctgaaca gttgccatac ttgagttgat gaatgtgtta ttcatggtgt ctcatctcat
3961 caatgcatct tgagagactt aatgaaattt tagcaacagt atagaatagc tctatcggt
4021 ggggagtaat cattaaacag atgaaatcgg ccccagattt acatgtctct ttagaatcca
4081 cagtgtaagc aaactacagt tacaaaggga tggggggttgt aaaccctctg agactctgca
4141 ctttttcgcac gtatggcatc gtcaagtgct gtcttattac agcctttgta aggagaggca
4201 ggctcctcct ggggtgggct ctgcagctgc tctatttcca ggcatgtgat cgcccccgct
4261 ctccagattc cccagcactc tgctgcgtgt aactccactc aattctccac tcatccttcc
4321 ttgtgaagca ggatcgttga agttttaagt atgggcaaaa atctggaaaa cttaggatcc
4381 ctctgacacc ccaggattag gggacacagc agtggctagg gcatcagcca cagaactgag
4441 cgggaaatgc cacttgtatt ggctgtaaag aaatcctgcc tttggccag gcacagtggc
4501 tcaagcctgt aatcccagca ctttaggagg ttgaggcgga tggatcacct gaggtcagga
4561 gtttgagacc agcctggcca acatggtgta acccgtctc tactaaaaat acaaaaaaat
4621 tagccaggcg tggtagcggg cacctgtaat cccagctact caggaggctg aggcaggaga
4681 atcacttgaa ccggggaggc agaggttgca gtgagctgag atcatgccac tccactccag
4741 cctgggcgac agagcaagac tccatctc
```

FIGURE 13

Homo sapiens cDNA clone IMAGE:40127577

```
  1 ctgcgagaat cgaggcactc gctggcgtac ccatgtatcg aaatgagttc acggcctggt
 61 accggcggat gtcggtggtc tacgggatcg gcacctggtc tgtgttgggc tcactgcttt
121 actatagccg gacaatggcg aagtcgtcag tagaccaaaa ggatggctca gcaagtgaag
181 tacccagtga actctctgaa cgcccaaaag gattttatgt ggaaacagtt gtcacatata
241 aagaagattt tgttccaaat acagaaaaga tcctcaacta ttggaaatca tggactggtg
301 gccctggtac agaaccatga ctggctgctg aattctgaaa accaggactt ggttcaacat
361 ttaaatttga tagttgccct gattcccatt ttggt
```

FIGURE 14

Homo sapiens chromosome 3 genomic contig, GRCh37 reference primary assembly, Region: 49917591..50054681

```
   1 cgcggcgctg ggtcggtggc ggaggctgag gagaaggagg agcgggccgt ggaggcttcg
  61 ccgcctaggt aagggcccgg gactggaggg gaggcgtgcc agagcctgcc agggaatagc
 121 cagcagacag gcccgctcta gacatcgcag gcccgcgcag cctgaaagct gtggcttcag
 181 tgtcgcgggg cggctgcggc ctcgctcggg aagaagacca agcaacggtg agatgaggga
 241 ggcgccgccc gtggcaggaa cgccccggaa ccgtcgcggg cctggggcgg ggcccggcgc
 301 ggcagtagat taccggtccc gccgcggagc ggccagctgt gaggctgggg ccggcgcgtg
 361 gttgcggctc tgtgctccta ctcttcggag ctgtaagcgg gctgttcttg cggttttcct
 421 gtttcagatc caattctgtg gcatcactag gaagggagct cttgtgctta gcacgtagcc
 481 tcgtcctcag acttggacag acacaaggga ggctccgctg gaccggaggg cacaagagct
 541 ccgagcccgg tcgtcgggc ggtagaacct ggaagcggga gagtggtctg gtgggttctg
 601 cgcccgttag gcaatgaagg agaaggatgt tttatcgtat tcacgcttta gattccatta
 661 gcggtgtaaa tagatgtttt tctctttatt ttagaattga cgttaggcga atgggttcaa
 721 ctttgggaat gccttttttt ttttttttttt tttgaaggaa gggccctgtt tcgtagggta
 781 cataaaccgt gagcgtaatt gtatttttg catattccag gtttgcttgt gaaggtcaga
 841 gtagccggat ttaagtgaag gagttcagta gacatgcaga catggtcacc tggttcattt
 901 tctgaaccct ggattgtgcc ctcggcttgc tagtttccac cttcctattg agaaatgcca
 961 ccagcgtgaa tgatttaaat atgtcaccat tactgaattt gtgaggtctc taacgagagg
1021 tgtcaagagc tggtgcgtga tggtaggact ggcagtgaag aaagtaacta aataatatgt
1081 taccattttg gtgaaacaca aagttgaat ttgaaccttg tctcagaaac tagcatctaa
1141 ctagatacct aacctgcagg acaggtccca ggtctctctg gatagttgta gcacctttcc
1201 ttatagaatt ctattaccag gccgagcctg gtgctcaca cctgtaatcc cagcactttg
1261 ggaggctgag gtggggagtt cgagaccagc ctgactaaca tggagaaacc gcgtctctac
1321 taaaagtaca aaattagccg ggcatggtgg cacatgcctg taatcccagc tacttgggag
1381 gctgaggcag gagaatcgct tgaacctggg aggcggaggt tgcggtgagc tgagattgct
1441 ccattgcact ccagcctggg ccacaagagt gaaactctgt ctcaaaaaaa aaaaaaaaaa
1501 aaaaaaaaaa aaacccgcaa aactcaacaa aaaccaacat agtagaggca gcgtttcgcc
1561 ttatgcccag ctaattttttt gtatttttttt agtagaggcg gagtttcgct atgttggcca
1621 ggctggtctt gaactactga cctcaggtga tccacctgcc ttggcctccc aaagtgctgg
1681 gattacaggc gtgagccacc gtgcccggcc ctgttatagt atttctaaaa caaattgtga
1741 gcctgggcaa catcgcaaaa ccctgtctct acaaaaaata caaaaaaaaa aaattagcca
1801 ggcgtggtgg catgctcctg ttagcccta actactcagga ggctgagatg gaaaaatcgc
1861 ttgagccggg gaggtagagg ttgtagtaag gggagatagt gccactgcac tccaacctgg
1921 gccacagaac aagactgtct caaaaaaaaa aaaatcaatt aaataaattg tggtaaatat
1981 atattttat gtatgtttat gtatatttta acaaaatttg ctctttaaac cattgttaag
2041 tatacaattc agccaggcac ggtggctcac gcctgtaatc ccagcacttt gggacgccga
2101 ggtgggcgga tcacgaggtc aggagatcga gaccatcctg gctaacacgg tgaaaccca
2161 tctctactaa aaatacaaaa aatgagccgt gcgtggtggt gggcgcctgt agtcccaggt
2221 actcaggagg ctgaggcagg agaatggtgt gaacccgaga ggcggagctt gcagtgagcc
2281 gagattgcgc cactgcactc cagcctgggc aacagagcga gactccgaga ctccatctca
2341 aaaaaaaaaa aaaaagtat acaattcaat ggtattaatt acattcacaa tgtagtacaa
2401 gcaataccac tatttctgaa actttagtat ctcaaacaga aactctgtaa ccagggaggg
2461 catggtggct cacgcctgta atcccagcac tttgggaggt caacgtgggc agatcacttg
2521 agttcaggag ttcaagaaca gcctggccaa catggtgaaa ccccgtatct actaaaaata
2581 caaaaattag ccatgcatgg tggcatgcat ctgtaacacc agctactaag gaggcagagg
2641 ttgcagtgag ctgaggtcat gccattgcac ttcagcctgg gctgcacagc cagactccat
2701 ctcaaaaaaa aagaaaaaaa gaaactgtaa ccattaacaa agttaacttc ccattcctc
2761 ctcttaatct ctaatctact ttgtgtctgt ctgtgagtgt gcttgttcta ggtactgcaa
2821 atactaaatg gaatcataca gtattgtcct tttttgtgtc tggtttattt cacttagtgt
2881 aatggtttca aggttgatcc atgttgtact gtgtatcaga atttcattcc tttttaaggc
```

FIGURE 14 (cont.)

```
2941 ttaatccgtt gtgtgtgtac actacatttt gtttattaat tcatttgtag cagacacttg
3001 ggttgcttct gccttttgac tattgtaaat aatgatgctg tgatcattgg tgtacaaata
3061 tctctttgag tccctgcttt gaattctttt gggtatatac ccagaaggga aattgctata
3121 tggtaattat tattattatt aattatttta tttatttttt tttgagacag ggtcttgctc
3181 tgttgcccag gctggagttc agtggcacag tcatggctca ctgcagcctc gaactcgagc
3241 tcaagcagtc atcccgcctc agcttcctga gtagctggga ctacaggcat gggctgccac
3301 aaccagctaa ttttttttgtt taattttat ttttgtgat gaagtcttgc cttgttgtct
3361 agggtggtct cgaactcctg agttcaagtg atcctcctgt cttggcctcc cgaagtgctg
3421 gcattacagg catgagccac cacatctggc cataatttt tttattttaa tttttttgtg
3481 gagacagggt ctccctatgt tgcctatgct ggtctcaaac tcctggcctc aagccatttt
3541 ccctccttgg cctctcaagg tactggtatt acaggcatga gccactgcac ccagttgata
3601 cttggttatt atatgtttag cttttttgagg acccaccata ctgttttcct caatggctgc
3661 atcgttttac attcccacca gtaatacaca agggttccaa ttttcccaca tcctccccaa
3721 cacttatttt ctgtttttcc tttttttgata aatttgtgtg tgtatatgtg gttttttatt
3781 tgtgtgtttt gatgatagcc accctaatgg gtgtgaagtg gtatctcgtt gtgttttctt
3841 ggttttttgct tgtttgtacc ttttttaccca ttttttaagtg tgctacttag tagtagtaag
3901 tacattcttc tttttgtgca accataataa aaatccagct tcagaactt tttcatcttc
3961 ccaaactgag tttctgtacc cattgaatag taactcccta ttctctcctc ccctgacaat
4021 caccattctg ctttctgtct ctatgaattt gactactcta ggtatctcat gtaagtggaa
4081 tcatataata tttgatcttt tgtgtatggc ttattttact tagcataata tcttcaggat
4141 tcatccatct tgtagtatgt atcagaattt tattccttt taaggctgag taatattcca
4201 ttatacatat ataccacatt ttgtttatcc atttatctat tgatggacat ttgggttgtt
4261 tccacctttt tgctcttgtg aatataatgg tgctatgaat atcagtgtac aaatatcttt
4321 tttttttttt tttttgtgag acagtatcgc tcttgtcacc caggctggag tgcagtggcg
4381 cgaccttggc tcactgcaac ctctgcctcc tgggttcaag gcattctcct gcctcagcct
4441 cccgagtagc tgggattaca gatgtgcgcc accatgccta gctaattttt ttatttttag
4501 tagagaagga gtttcgccat gttgggcagg ctggtcttga acttctgacc tcaggtgatc
4561 aacctgcctc ggcctcccaa agtggtggaa ttacaggtgt cagccaccgc gcccagccac
4621 aaatatcaag tcttttacttt catttctttt gggaatatat atactcagaa atggaatcga
4681 caattgacag agcaaatggt aattctatgt gtaatttttt tttaaatttt ttttttttgag
4741 acggattctt gctctgtcgc ccaggctgga gtgcagtggc gtgatctcgg ctcactccaa
4801 gctccgcctc ctgggttctt gccattctcc tgcctcagcc tcccgagtag ctgggactac
4861 agcatccgcc accacgcccg gctaattttt tgtattttta gtagagacgg ggtttcaccg
4921 tgttagccag gatagtctcc atctcctgac ctcatgatct gcccgccttg gcctcccaaa
4981 gtgctgggat tacaggcgtg agccaccgcg cccggccaat ttttttttt tttttttttta
5041 gacagggtct tgctctgttg tccaggctgg agtgcagtgg tgcagtcaca gttctctgca
5101 gccctgacct tctcagttca agctatcctc tcacctcacc ctcttaagta gctgagacta
5161 caggtgcatg ccaccatgcc taactaattt ttttattttt ttgtagctgt gggatttcgc
5221 taggttgccc aggctttatg tatcattttt tgaggaactg ccttactgtt ttccacactg
5281 gttgcaccat tttacattct gttagcagtg tacaaaggtt ttgttataga ctgaattgtg
5341 tcccctgaa aattcacgtg ttgaagccct aagcccagt gtgactgtat ttggaaatag
5401 gacctttaca gagaaattaa aaagttagaa gatatcataa ggggctgggc gcgggtggct
5461 catgcctgta atcccagcac tttgggaggc tgaggcaggc ggatcacaag gtcaggagat
5521 cgagaccatc ctggccaaca cggtgaaacc ccgtctctac taaaaataca aacattaac
5581 cgggcgtggc ggcatgcacc tgtagtccca gctgctgggg aggctggggc aggagaatgg
5641 cgtgaacccg ggaggcacag cttgcagtga gccaaaatcg cgccactgca ctccagcctg
5701 ggcgacagag cgagactcca tctcaaaaaa aaaaaaaaaa aaaaaaaag aagatataag
5761 gatgagacct taatccagca ggactgctgt cttcgtaaga aaaggactgg ataccaggag
5821 tgcgtgtaca gagagaaaaa gctgcatgag gacagaggta gaagggggct gcctgcaagc
5881 caaggagaga gacctcacct aaaacaaacc ttgctgacac cttgatcttg gactcccagc
5941 ctccagagct gtgagaataa tttctgtggc ttaagccttc cactccatgg tattttgtta
```

FIGURE 14 (cont.)

```
6001 tggcagtcct agcatactgt gtaatatagg tttcaattca gtttctctgc atcctccaca
6061 tcctggccaa cacttgttat tttctttctt tttttttttt ggagacagat tctcgctctg
6121 tcacgcaggc tggagtgcag tggcacaatc ttggctcact gcaacctcca cctcccgggt
6181 tcaagcgatt ctcctgcctc agcctcccga gtaactggga ttacaggcag ccgccaccgt
6241 gcccagctaa tttttgcatt ttagttgaga tggtgtttct ccatgttggc caggctggtc
6301 ttgaactcct gacgtcaggt gacccgccag ccttggcctc ccaaagtgtt gggattataa
6361 gcatgagcca ccgcgcctgg catttttctt tttttttgaga cagagtctca ctctgttgcc
6421 caggccggag tgaagtggca tgatctcggc tcactgcaac ctctgcctcc cagattgaag
6481 caattcttgt gcctcagcct cccgggtagc tgggattaca ggcgtgtgcc accacgcctg
6541 gctaattttt gtatttttagt agagacaggg tttcaccata ttagccaggc tggtcttgaa
6601 ctcctgacct caagtgatct gtccaccttg gcctcccaag gtgctgggat tacaggtgtg
6661 agccatctca cccggcctat tttctgtttc gttttttttt ttttcattag tagctatcct
6721 agtggatgtg aagtggtatc ttattgtggt ttctgatttg catttccctg atgataagtg
6781 atgttgagcg tctgttcatg ttcttattgg ctatttgcat attctctttt ggagaagtat
6841 ctattcatgt cttttgttga ccatttttaaa atggggtttt tcatcctggc taacacggtg
6901 aaaccctgtc tctactaaaa atacaaaaaa aaaaaaaaaa aaaaattagc cgggcgcagt
6961 ggcaggcgcc tgtagtccca gctactcggg aggctgaggc agaaggatgg tgtgaacctg
7021 ggaggcagag ctcgcagtga gcagagattg agccactgca ctccagcctg ggcgacagag
7081 cgagactccg tctcaaaaaa aaaaggggg ggggggggg ttttgagctg ggtgtgcagg
7141 tgcacacctg tattcccagc tgctcaggag gctgaggtag gtggatctct tgagcccagg
7201 tgtttgaggg tgcagtgagc tgtgattgca ccactggact ctaccctggg tgacagagtg
7261 gcccagtctc taaaaataaa ataaaattag gttttttgtct gtgttgttga gttttaggag
7321 tcctttatac actctagata ttaattcctt gtcagatatt tgacttacaa atattttctc
7381 tctgtggttg tctttatact ctgttgatag tgtcttttga tgcacagagg ttttcattt
7441 gatgaagtcc aatttatctt cttttttttaa aatctgtgcc tcatctgcaa atattaccaa
7501 tcgaaagtca tgaattttt cccctaagat tttatagttt tagcgcttac gtttgggtct
7561 ttgatccaat ttgagttaat ttttttatata tttttgttgt gtaagagtcc cactttattg
7621 ttatgcatgt ggatattcag ttttcggagt accattttcc atttgggaaa aagattgtac
7681 tttccccatt ggatggtctt gacacctttg ttgaaaatca gttgactaaa gttcaagact
7741 agccttgcca acatggcaat atcccgtctg tactaaaaat accacaatta gctgggcatg
7801 gtggtgcctg gctgtaatcc cagctactcg ggaggctgag gcaggagaat cgcttgaact
7861 gggaggtgga ggctgcagtg agctgagatt gcgccactgc cctccagcct gggcgacaga
7921 gcgagacatg agaatctgtc ttaaaaaaaa aagaaaattg accatatatg tgaggattta
7981 tttctggtct ctccattcag ttgattggtc tttatgtcta tctttatgtc cttactgcac
8041 tgttgtgatg gctgtagcta aatggtacac ttaaaaatgg ttaaaatagg ccaggcacgg
8101 tggctcacgc ctataatctt agcactttag gaggctgagg tgggcagatt gcctgtgctc
8161 aggggttcga gaccagccta ggcaacatag tgaaacccg attttactaa aatacaaaaa
8221 ttagctgggt gtggtgtgtg cctgtaattc cagctactca ggaggctaag gcacaagaat
8281 tgcttgaggc ctggtgctgt ggctcacgcc tgtaatccca gcactttggg aggccgaggc
8341 aggtcaagag atcgagacca tcctggccaa tgtcatgaaa cctagtctct actaaaaata
8401 caaaaaatta gctgggtgtg gtggcgcgca cctagtccca gctacttggg aggctgaggc
8461 aggaggatca cttgaaccca ggaggtggag gttgcagtga gccaagattg cgccactgca
8521 ctctagattg gcagcagagt gagactctgt ctcaaaaaag aaaaaaaaaa aaaagaattg
8581 cttgaaccca ggaggtagag gttgcagtga gctgagattg caccctgcac tccagcctgg
8641 gcaacagagt gagactattt acatacccaa tttttttttt tttttttttt tgggatggtg
8701 tcttgcactg tcgcccaggc tggagtgcag tggcgtgatc ttggctcact gcaacctctg
8761 cctcctgggt tcaagcaatt ctcctgcctc aggctctcaa gtagctgggt tacaggtacc
8821 tgccaccacg cctggctaat ttcttgtatt tttagtagag atggagtttc actatattgg
8881 ccaggctggt ctcaaatttc tgaccttgtg atccgctggc ctcagcctcc caaagtgctg
8941 ggactacagg tgtgagccac cacgcctggt catacccaaa tattttacca taattataca
9001 agaatttatt attttttattt ttttcttttt aaattcttta atcttcttca tttgttaatg
```

FIGURE 14 (cont.)

```
 9061 ctttgctgaa tcataaaaaa ttatgaaata aaaagaatag gtcttgttga ttcttctttt
 9121 tacttacctc cccctactta ccccctctta ctttatcaaa gaaaacactt catttgaaac
 9181 ttaacggaag tacattctcc cagagaggaa aatccttcag gacaacattt ttttttgttt
 9241 gcttgttttt tttgagacgg agtctcactc tgtccccgag gctggagtgc agtggtgtga
 9301 tcgcagctca ttgcaacctc tgcctcccgg gttcaagcga ttctcctgcc tcagcctccc
 9361 gagtagctgg gactacaggc gcctgtcacc atgccctgct aatttctgta ttttttagtag
 9421 aaacagttgg ccaggatggt ttcaatctta tgactttgtg atctgaccac tttggcctcc
 9481 caaagtgctg ggaatacagg cgtgagccac agtgctcagc caattttttg tattttttagt
 9541 ggagaaaagg tttcaccgtc tttgccagga tggtcttgat ctcctgacct cgtgatccgc
 9601 ccgcctccca aagtgctggg attacaggcc tgagctacca cgcccagcct ttttattttt
 9661 ttattttatt tattttattc tcagccttct gggtaactgg gactacaggt gtataccacc
 9721 acgctcagct aatttatgta ttttttagtag aaatgggggtt tcgccatatt ggccaggctg
 9781 gttttgaatt cctggtctca agtgatctgc ctgcctccgc ctccaaagt gctgagatta
 9841 caggcatgag ccactggccc agactacact taaaattttc aaatcgagat attttggggg
 9901 gcaagggtgc ttctagcagc cactaattcc agttcttgag tgcatattaa agttgctact
 9961 gtttaaaagc ttgtagttgg atccaggagg tgggtaggcg gtcagagtaa cccttgcttc
10021 ttggtgtctc cttgatgctc ttagctgaat gtcctgtgta gcccacaaca tttactttgg
10081 gaaaaaatta agagtgttta aagcaggatc aagctgctgc ataccacagc taaaactact
10141 agaataagac ccctggttct gtttcattgt ttttttggagc taaagtcatg attaagaagg
10201 atggcctggg atattggtac tgtgctgcta gaggtgcaat tcctggttct ttgcaagata
10261 gaccagagtg aaagcatttg ttaggaatgt ttttattaat caagagtgaa aggcaaggcc
10321 aggcgtggtg actcaggctt gtaatcccag cactttggga ggccaaggtg tgggatcatt
10381 tgaggtcagg agttcaagac cagcctggcc aacatggtga aaccccgtct ctactaaaaa
10441 tacaaaaatt ggctgggtgt ggtggtgcat gcctgtaatc ccagctactc gggagactga
10501 ggcaggagaa tcgcttgaat ccgggagacg gaggttgcag taagctgaga tcatgtcact
10561 gtggtacagt ctgggtgaca gagggagact gtttcaaaaa aaaaaaacag aaagaatgaa
10621 aggcaaaaca ttaaaaatag aattaccatg tgatctaaca attttacttc tggatatata
10681 tccaaaataa ttgaaaacaa agaaaaagaa aaacagagtc tcgatgagat atttgtaccc
10741 atgttcataa cagcgttatt cacattagct aaaatgtgga agcaacccaa ctattcattg
10801 atggatgaat agataaggaa aatgtggtat gtacatataa ctgaaaaatt attcagtgtt
10861 aggaaggaag gtaattctga catatgctac aacatggatg aaccttgagg atattatgct
10921 aagtgaaata agccagtcat gtaaaagaca aataccatat aatttcactt agacactttg
10981 agtagtgaaa atcatagaaa cagaaaatag ttgtcaggga tggtgtgagg gatgaatcag
11041 cagttactat ttcttttttgt ttgtttgttt tttgagatgg ggtcttgctc tgttgcccag
11101 gctggagtac agtggtgtga tcttggctca ctgcaacctc tgcctcccag gcacaagcca
11161 tcttcccacc tcagcgtcct cagtagctgg gactacagat gtgttccacc ttgtccggct
11221 gatttgtgtg tgtgtatatg tgtgtgtgtg tgtgagaca aggttttgcc atgttgccca
11281 ggctggtctc gaactcctga gctcaagcat caagcaatct accttttttca gctttccaaa
11341 gtgctggcat tacagacaag gccactgtg cctggccttt actatatttt atttttattta
11401 ttatttattt atttatttat ttatgtattt tgagatgaag tctcactctg ttgcccaggc
11461 tggagtgcag tggcacgatc ttggctcact gcatcctctg cctcccaagt tcaagtgatt
11521 ctcctgcctc agcctccagt tattattatt attattatta tttttttgtt gttctgtttt
11581 tttgaggtgg agtctcgccc tgtcgcccag gctggagtgc agtggcacaa actcggctca
11641 ctgcaacctc catctcccag gttcaagtga ttcttctgcc tcaacctccc aagtagctgg
11701 gaatacaggt gcccgccacc acgcctggct aattttttgta ttttttagtag agacgggggtt
11761 tcaccacatt ggtcaggctg gtcttgatct cctgatcttg tggtccacct gcctcggcct
11821 cccaaagtgc tgggattata ggtgtgagcc cccatgccct gccttgttat tattattatt
11881 tttattttt tgtctgagac ggagtcttgc tctgtcaccc aggctagaat gcagtggcac
11941 gatcttggct tagtacaacc tctgcctccc gagttcaagt gattctcctg cctcagcctc
12001 ccgagtatat aggactacag gtgtgtgcca ccatggctaa ttttttgtatt tttagtagag
12061 atgggggttttc accatgttgg tcaggatggt ctagatctct tgacctcgtg atctacccgc
```

FIGURE 14 (cont.)

```
12121 cttggcctcc caaagtgctg ggattacagg catgagccac tgcgcctggc cccagttttt
12181 gtatttttaa tagagacagg gttttggcat gttggccagg ctggtctcag actcctgacc
12241 tcaagtgatc tgcccacttc agccttctga agtgctggga ttaaagacat gagcactgtg
12301 cccagccact tttactatat tttaaattag gttacttatc ctttgttttt ttttttttt
12361 gagacgaagt tttgctcttg ttgcccaggc tggtgtgcaa tggtgcatct cgactcaacg
12421 caacctctgt ctcccggggtt caagtgattc tcctgcctca gcctcccgag tagctgggat
12481 tacaggcatg catcaccacg ccagctaatt ttgtattttt agtagagaca gggtttctcc
12541 atgttggtca ggctggtctc aaactcccga cctcaggtga tccacctgcc ttggcctccc
12601 aaagtgttgg gattacaggc gtgtgccact gctcctggct tattttcctt tttgttactg
12661 agttgaaatc atttttata tattttagat acaagtcact taccaaatat gtaatttgca
12721 caaattttct cccattctgt gggatgtctt ttcatttaaa ccaaaaaatt gtagagatgg
12781 gggttttgct gtgttgccca ggttggtctt gaactcctgg tcttaagtga tcctctgacc
12841 ttggcctcaa aaagtgctgc gattataggc atgagccaat gtgcgcagct tacctttctc
12901 tcttttcttt tttttgagg cagggtcttg ctctgttgcc caggctggag tgcagtggtg
12961 caatcatggc ttactgcagg ctgaaactcc catgctcaag tgatcctccc actttagcct
13021 cctaggtaac tgggacctta ggggcgtgcc atcacacctt gctaatttt ttttttttt
13081 gagatggagt cttgccctgt cgcccaggtt ggagtgcagt ggagcgatct tggctcactg
13141 caaattccac ctcccggatt caagtgattc tcctccctca gcctcctgag tagctgggac
13201 tacaggcgtg tgccaccacg cccagctaat ttttgtattc tgagtagaga cgggatttca
13261 ccacattggc caggctggtc tcgatctctt gacctcgtga tctgcccgcc ttggcctccc
13321 aaagtgctgg gattacaggg gtgagtgtga gccaccgaac ctggccttt tttttttt
13381 tgagaccgtc tctgtcaccc aggctggagt gcagtaacat gacacaatct ccgctcactg
13441 caacctctgc cttctgggtt caagtgatcc ttctgccaca gcctcctgag tagctgggat
13501 tgcaggcatg tgctaccacg cctggctaat ttttgtattt ttagtagaga cggggtttca
13561 ccatgttggc ctacctggtc ttgaattcct gacctcagat gatctgcccg catcagcctc
13621 ccaaagtgct ggggttacaa gcgtgagcca ccacgcctag ctggacctga ctaattaaaa
13681 aaaaaatttt gtaggctggg cagggtggct cacacctgta atcccagtac tttgagaggt
13741 ggaggcgggg taatcgcctg aatcaggagt ttgagaccag cccgggcaac ataacgaaac
13801 cctaggtcta ccagaaatac acaaaaaaat tagccgagca tggtagtgca catttgtagt
13861 cccagctact caggaggctg aggtgggagg atggctggag ccagggaagc agtggttaca
13921 gtgagccgag aatgtgccac tgcactcccg cttgggtgac agagtgagat aaggtctcag
13981 aaaaaaaaaa aaaatttata ggccgggcgc aatggctcac gcctgtaatc ccagcacttt
14041 gggaggacca ggcgggcgga tcacaaggtc aggagatcga gaccaccctg gccaacatgg
14101 tgaaaccccg tctccactaa aaaaatacaa aaattagctg ggcgtggtgg cacgtgcctg
14161 tagtcccagc tacttggcag gctgaggcag aagaattgct tgaaccctgg aggcggaggt
14221 tgcagtgagc cgagattgca ccattgcact ccagcctggg cgacagagcg agactccatc
14281 tcaaaaaaaa aaaaaaaaaa aatttgtgaa gacaaggtct caatatttgc caggatggt
14341 ctgaaacttc tgggctcaag ccatccttct gcctcagcct cccaaagtat tggaattaca
14401 ggtgtgagcc actgtgtctg gcctatttat agactcttaa ttctgtttcc ttggtctgta
14461 tgtctatact atgtcagtgc cacactgtct tgattactgt agctttgtgg tgagttttgg
14521 aattgggaag tgtcagtcct ctaactttgt tgtatatatt cttttctgtt ttgcacagat
14581 atcaggttac aaatattttg cacactttt tttttttg aaatggagtc ttactctgtc
14641 acccaggctg gagtgcagtg gcgcgatctc agcccactgc aagctccgcc tcccaggttc
14701 acaccattct cctgcctcag cctccccagc agctgggact gcaggcgcac actgccatgc
14761 ccagctaatt ttttgtatt ttaagtagag acagggtttc actgtgttag ccaggatggc
14821 ctcgatcctcc tgacctcgtg atccgcctgc ctaggcctcc caaagtgctg ggattacagg
14881 cgtgagccac cgcacccggc cttgcacatg ttttaaaac ttaatacata atagcttatc
14941 ctgtatcaat taacatagct actttattta ttcttagggc cgcatagtat tttttttct
15001 ttcttttttt tttttttttt tttttttgag actgagtctc gctctgttgc ccaggctgga
15061 gtgcagtggt gtgatcttgg cttaagcaac ctctgcctcc tgggatcaag cctcgggatc
15121 ctcctacctc aacctctgca gtatttggga ctacagacac ctgctaccac acccagttaa
```

FIGURE 14 (cont.)

```
15181 ttttcgtatt tttttgtaga gatagggtct ctattgatgt gcatttaggc tttataatat
15241 ttatatatat atttttttgaa acaaagtttt gctcttgttg cccaggctgg agtgcagtgg
15301 catgatcttg gctcactgca accttcgcct cccaggttca agtgattctc ctgccttaga
15361 ctcccgagta gctgggatta cagttttaa aaaatgtatc ctaggctggg cgcagtggct
15421 cacgcctgta atcccagccc tttgggaggc tgaggcgggt ggatcacctg aggtttggag
15481 tttgagacca gcctggccaa catggtgaaa cctcgtctgt actaaaaata caaaaattag
15541 ctgggtgtac tggcgggcac ctgtaatctc agcttcttgg gaggctgaga caggagaatc
15601 tcttgaactt gagaggcggt ggttgcagtg agccattgca ctccagcctg ggtgtcaagc
15661 aaaactctgt ctctctctct ctctgtgtct ctctctctct ctctgtgtgt gtgtgtgtgt
15721 gtgtgtgtat atgtatatat attctgccaa tattttgtga ttagagagtt taaagtattt
15781 acatttaaag taattactga taaggactt tgccattttg ctactacttt tatgtttagc
15841 tgatttttt tttttggta gtgaaaaaaa attttttt tttgagagca tgagactgtt
15901 gcctaggctt tggtgagcaa aatagtgcag tgccacaatc tcagctcact gcaactttgg
15961 gctcaagtga tcctcctgtc ccagtctcct gagtagctgg tagtataggt gtgccaccac
16021 catgcctggc taattttgt atttttgta gagatagggt tttgccatgt tgcccaggct
16081 ggtctcaaac tgggttcaaa caatctacct gccttagcct tccaaagtgt tgggattaca
16141 ggcattagcc actttctgcc ccctccccg cttttttt ttttttt ttttgagac
16201 ggagtttcac tcttgttgcc caggctggag tgcagtggca tgatttcagc tcactgcaac
16261 ctccgcctcc cgggttcagg cattttcctg cctctgcctc ccaagtagct gggattacag
16321 gcttgccacc atgcctggct aattttgtat tttaataga gatggggttt ctctatgttg
16381 gtcaggctgg tctcgaactc ctgacctcag gtgatcctcc tgccttggct tcccaaagtg
16441 ctgggattat aggcgtaagc catcacgcct ggcccacgct ttattttt attttattt
16501 tttattattt atttattttat tttttgagac ggagtttcgt tcttgttgcc caggctggag
16561 tgcaatggca taatctcagc tcaccgcagc ctccgcctcc tgggttcaag tgattctcct
16621 gcctcagcct cctgagtagc tgaatttaca ggcatgcgcc accatgccca gctaattttg
16681 tatttttagt agagacgggg tttctccatg ttggtcaggc tggtctcgaa ctccagacct
16741 caggtgatcc tcccgcctcg gcctcccaaa gtgctgggat tacaggcgta agccaccagg
16801 cctggcctgc ttttttaatt tttatttat tttttcttt taagagggag ggtcttgctg
16861 tgttgtccag attggagaac agtgatgaga tcatagctca ctgcagactt ggattcctgg
16921 actcaagcaa tcctcccgct tcattctttg caagtaactg gaagtgcaga catgtgccac
16981 ctgccttttt tgttttaa attttcata gagatggggt cttgctatat tgcctaggct
17041 ggtctcaaac tcctggcctc aagcaatcgg cttcctgaag tgctgggatt acagatgtta
17101 gccactggcc tgttgtgaaa atgttttgac tttcttctca tttctttct ttcttttt
17161 tttttttga agtagagaga gtctcactat atggccaatg gtggtttcaa accctgagc
17221 ccaaggaatc ctcctgcctc agcctcccag tgcttgtcgt gctaggacaa caagcatgag
17281 ccactgtgcc tagcccttc tcatttctt tttctttcta gtgcataagc aggcaaccctt
17341 attttcttat gtgtatattc taaagatatg ttctttgcag ttaccatggg aattacactt
17401 aacatctcac agttataatc taatttgaat ttatactaac ttaagttcca tagtatacaa
17461 atctctgttc ctatccagct cctttctctt ccctttctg ttaagtcatg gattacatct
17521 ttgtaaatcg tatctcagga acctagatta ataatttttt atgcatctgt cttttagatc
17581 acattgaaag tgaaaagtag gagttacaaa gcaaaattgc aataatgcta gttttttacag
17641 ttgccctgt atttgccttt accagagatc tttctttctt tttttttt ttgggatgga
17701 gtctcgctct ttcgcccagg ctggagtgca atggcgcaat ctcagctgac tgtaacctct
17761 gcctcccggg ttcaaaagat tttcttgcct caggctcctg agtagctggg actgtagttg
17821 tacgccacca cacgtggctg atttttgtat ttttagtaga gatggggttt tgccatgttg
17881 gccaggctgg tcttgaactc ctgacctcag gtgtgagcca ccgcacctgg ccgagatctt
17941 tatttcttca catggcttca cgtctagctt ttaaaaattc attctgggcc gggcgcagtg
18001 gctcacgcct gtaatcccga cactttggga ggctaaggcg ggcggatcac gaggtcagga
18061 gatcgagacc atcctggtta acacagtgaa accccgtctc tactaaaaac acaaaaggcc
18121 gggtgcggtg gctcacgcct gtaatcccag cactttggga ggctgaggtg ggtggatcac
18181 gaggtcagga gatcgagacc atcctggcta acatggtgaa accccgtctc cactaaaaat
```

FIGURE 14 (cont.)

```
18241 acaaaaaaca aaacaaaaca aaaaaaacta ttagctggca ttgcggtggg cacctgtagt
18301 cccagctact cgggaggctg aggcaggaga atggcgtcaa cccaggaggc ggagcttgca
18361 gtgagccaag atcacgccac tgcactccag cctgggagac agcaagactc tgtctcaaaa
18421 acaaaaaaca aaaaaccaca aaaattagcc gggcgtggtg gcgggcgcct gtagtcccag
18481 ttactcggga agctgaggca ggagaatggc atgaacccag gaggtggagc ttgcagtgag
18541 ccgagatcgc tcaactgcat tccagccttg gcaacagagc gagactccat ttcaaaaaaa
18601 aaaaaaattc attctgaaga attccttttt ttttttttt ttttgtaaaa atggagtctc
18661 actctgttgc cctggctgga gtgctgagtg ccatggcatg atctcagctc actgcaacca
18721 accccactc caagttgaag cgatactcc gcctcagcct cctgactagc tgggattagg
18781 ggtgcctgct actgcacctg gctaatttt gtattttag tagagacggg tttcaccatc
18841 ttggccaggc tggtgtcgaa ctcctgacct cgtgaccaac ccacttcggc ctcccaaagt
18901 gctgggatta caggcgtgag ccactgtgcc cggactgaag aattcccttt tagcatttct
18961 tacaaggtct gtatagtggt aatgagcctc cctcagcttt tgtttatctg agaatgtctt
19021 gatttttttc cttttttttt tttttttttg agatggagtc tcgctctgtc gcccaggctg
19081 gagtgcagtg gcgtgatctc agctcactgc aagctccgcc tcctgggttc acaccattct
19141 cctgcctcag cctcgtgagt agctgggact acaggtgccc gccaccacgc ctggctaatt
19201 tttttttttt ttttgtatt tttagtagag acggggtttc actgtgttag ccaggatggt
19261 ctcaatctcc tgaccttgtg atccgcccgc ctcggcctcc caaagtgctg ggattacagg
19321 tgtgagccgc ctcgcccggc caatgttttt ccctatttt tgaaagacag tgttgccatt
19381 tacagaattc ttggttggca atttatattt agggttttt ttttttttt tgagacagag
19441 tcttgctctg ttgcccaggc tggagtgcag tggtgtgacc tcggctcact gcaacctccg
19501 cctccagggt tcaagtcatt ctcctgcctc agcctcccaa gtagctggga ctacaggtgc
19561 ccgccactac gcctggctaa tttttgtat ttttagtaga cgggggtgt caccatgttg
19621 gccaggctgg tctcgaactc ctgacctcaa gtgatccaca cgcctcagcc tcccaaagtg
19681 cagggattac agacatgagc ccccacgccc ggcctaggtc ttgtatgatc atacattttg
19741 ccttggcatt catatggctt tctaaatttc accatataca tgttgctttg gaatgtccta
19801 atttgccaaa gagtttcacc tcaacttctg tgggcatcta tctgtaatct cttgccccaa
19861 gtgcctgtta gtctgtagtc tgctttgcag cttcattag caatacctgc tgctttctct
19921 gcctgagttt tgtattaggt tgaaatagaa acatgcacct tatgtctgtc cttcaaatac
19981 ccccgcagac agggtagaac agatatgtac gataatttgc aaataaggtc tgctttgctc
20041 tttgagggag ggagctggga attgggcttc tactgcttta agacaaaaaa cactgccatg
20101 ctggagaggg ggtagggcaa ggttgagtaa aacaccacag aactttcctt ctgtttgaa
20161 gatggctttt tcttcattgg atatttgctt gtaaacctt gactcttttc taaaactgtc
20221 aaatttggtt cagacagtta ctacttgttt ttctgatgtt tctatgaagg aatgagacct
20281 tgaaacttcc tagtctgcca ttttgatgac ctatgggctg tctttgtact ctcttgatag
20341 tgtcctttga tacacagaag tttttaattt tggtgaagtc cctttatcta ctttttcttt
20401 taaagttcct tgtgctgtag gggtcatatt taagaaatca ttgccaaatc caaggtcatg
20461 aagatttgcc tcttttcag tagctataac aaaggtcctg gaaataactt cttatcttga
20521 cttgagttac atgtctgtct tcaaagcaat gactgtggtg agggtaatag attattccga
20581 ttgctcatgc tggatggtgt ccgatcaggt ctgagacagt ggggttgata ctacagtgct
20641 gtttccaaaa aggaagggct agtgagcgct agaaaaatca gtaaatactt acttcatgta
20701 gtaaatgtga agcattcata gcacattgaa aagtttatgg tgcccagagt acctttttt
20761 tttttttttt ttgagacagc ctcactctgt ttcctgaact ggaatgcagt ggtgcgatct
20821 tggctcactg cagcctcaac ctcctgggtt caagcgatcc tcccccactt cagccttcca
20881 agaagctgag actacacata gtcatcatgc ctgactaatt tttgtatata tatttttaa
20941 gatggagtct cgctctgtca cccaggctgg agtgcagtgg catgatcttg gctgactgta
21001 gcctccgcct cccggtttca agcgtttctc ctgcctcagc ctcctgcata gctgggatta
21061 caggtgcctg ccaccacacc tggctaattt ttgtattttt agtagagatg agatttcacc
21121 atgttgccta ggctggtctc gaactcctga cctcaggtga tccacctgcc tagcctccca
21181 aagttctggt aattttgta ttttttgtag atggcatt ttgctatgtt gcccaggctg
21241 gtctcaaact ccttggctca agcggtctgc ctgccttggc ctcccaaagt gttgaggtta
```

FIGURE 14 (cont.)

```
21301 caggtatgag ccaccgtgcc cgaccccaga gtacacattt taattaaaaa cttattttc
21361 tggccgggca cggtggctca cgcctgtaat cccagcactt tgggaggccg aggtgggtgg
21421 atcacaatgt taggagttcg agaccagcct ggccaatatg gtgaaacccc atctctacta
21481 aaaatacaaa aattagccgg gcatggtgac gcgtgcctgt agtcccagct actcgggagg
21541 ctgaggcaga agaatcgctc gaaccgggga ggcagaggtt gtggtgggct gagatagtgc
21601 cactggactc cagcctgggc gacagagaga gattctgtct ttaaaaaaaa aaaaaaagta
21661 ttttttcttat tataaattta atatgtaagt gatgtaagtg tttgaaagtg acttccagct
21721 ggatgcggtg gctcatgcct gtaatcctag cactttggga ggccgaggcg ggcggactgc
21781 ttgagctcag gagtttgaga ccagcctggg taacacagtg aaaacccgtc tctactaaaa
21841 tacaaaaaaa ttagctgggc ggccggcgtg cgcctgtagt tctagctact tgggaggctg
21901 aggcaggaga attgcttgaa cccggaggtt gcagtgggct gagatcgtgc ctttgcactt
21961 cagcctgggc aacaaagcaa gactccatct cttaaaaaaa aaaaaaaaaa agaaggccgg
22021 gtgcagtggc tcacgcctgt aatctcacac tttgggaggc ctaggtgggc ggatcatgag
22081 gtcaggagat ctagaccaca gtaaaccccg tctctactaa aaatacaaaa aattagctag
22141 gcgtggtggc gggcgcctgt agtcctagct actcgggagg ctgaggcagg agaattgctt
22201 gaacccggag gttgcaatgg gctgagatca tgcctttgca ctccagcctg ggcgacagag
22261 cgagactcca tctcaaaaaa aaaaagaaa agaaagaaaa gaaagacctt caaaattatt
22321 gctgctgatg tggtccctca taaaccaagc agtgggaaac tggtttagct tttagttcac
22381 attctaaagt actaatttt gtggtttatt ttgtacaggt actgctataa ccagaatttg
22441 gtagaaaaag gatttacttg ttggggccct cttgataaaa agagatgtgg ggggattctc
22501 gacctgctaa cagaactgga ccttttcggt aagttctcaa atttgaatat tgaaattgcc
22561 agtattttaa ttataaatgt gtaacatttt cgcctactat aaatgaagat attttctctg
22621 tggagaaata gtttctgatt ttttaaaaat agaaatttgg ctgggcgcgg tggctcacgc
22681 ctgtaatccc agcactttgg gaggctgagg cgggcagatc atgaggtcag gagatcgaga
22741 ccatcctggc tatcacggtg aaaccccgtc tctactaaaa aatacaaaaa aaactagccg
22801 ggcgtggtgg cggctgcctg tagtcccagc tactcgggag gctgaagcag gagaatggtg
22861 tgaacctggg aggcggagct tgcagtgagc cgagatcgtg ccactgcact ccagcttggg
22921 cgacagagga agactctgtc tcaaaaacaa aaacaaaaaa aaaaaaagaa aaaaaaagaa
22981 aaatagaaac tcaatttgga aaataatttc gaaaatgatt gtgagcctga atacccagca
23041 tgccaaatgt tttgtcacat agcattttaa aattttattt atttgtttgt ttttgagac
23101 aagtctctct ctgtctccca ggctggagtg cagtggtgcg atcttgactt actgcaacat
23161 ccgcctcccg tgttcaagtg attctcctgc ctcagccttc tgagtagctg ggattacagg
23221 cgcgtgccac tatgcctggc taatttcatt attttaatat taaaaaatac ccaaatattt
23281 tatttctttt tgtctcttag cgaaggaata catatttggc tagtaaggaa agctagcaaa
23341 atttacataa atgtttataa aagttgtatt gagttcacta atttatgtct agaattcaga
23401 gctgtgcctt gtctgtggca tgttgacgca gtttgctaag ccacctctca attttagggg
23461 ttacttggta ccaagaagag tggagaaagt ggtagcattt agttgtaaat agattgtatt
23521 ttaaatttgt agggaattaa ttttttata gctagtatca tacacactgt attttaacta
23581 gtatttaaac attttttcgta ttgtgtttac aattaatgag atgctatatg aatgtgactt
23641 ttttggtttt acttggtaca tagcaaataa atctgacctt taaatgtatg cattcataag
23701 tattgttgct ccagttgaaa cttctattaa ctagtacatt ttccttttt tacctttttt
23761 caaaatggag tctcactctg ttgcccatgc tggagtgcag gggtatgatc tcagctcact
23821 gcagcctttg cctcctaggt tcaagtgatt ctcctccctt agcctcctga gtagctggga
23881 ctacaggtgt atgccaccat gcctggctaa ttattgtatt ttttttttta gtagagatgg
23941 cgtttcacca tgttggccag gctgatctca aactcctgac ctcaagtgat ccacctacct
24001 cagcctccca aagtgctggg actataagtg tgagccaccg cacctgccat ttggattggc
24061 aatctgcaag attttattac ttaaatgcaa cagatgttct cattcattgt tctgaagctt
24121 ggagttccaa tgaaaaattt aggtggagaa ctgagtttag aaaatccata taatgtttag
24181 taaaactagt atttcataaa tgctgaatga cagagattgg tctttaaatt aaaacaacag
24241 tgtgatgttg ggtatttttt ttcttttcaaa atactaagga ttagatcagt ggtcagcaaa
24301 ctacagctga tagcctgttt ttgtaaataa agttttactg gaaaacagcc actcttactc
```

FIGURE 14 (cont.)

```
24361 atttgcagat tgtgtatggc tgctttcatg ctatgatggc agagttgaat agttgtaaca
24421 gagattgtat aacccacaaa atccgatatg tttacgaact ggctcttcat ggaaaaagtt
24481 tcctgacctc tcatctagat caatggggtt gtacgttacc atttaaaaat atttaggttg
24541 taatctatcc tcttattact tgtatttatg ggtaactatt ttgtaagtaa ggctgtttcg
24601 tatagaatta acgtggttta ggtaagcatt cagaaatgtt aggttaattt agctttattg
24661 tctaacttft ttcaaattta gaacatttgt cttgactcg tttaaactta tttaaaatta
24721 tattttccca ccttaatttt agtttaaatg taagtcatta tatgctgttt tttaacatct
24781 ttgactagga gggagacagt ttttgggaac taatttgaac caaacagat ataggaaaat
24841 gattttgtta catttccttt gaacttttct tttaaaattt gtttttattt ggttgaaaat
24901 aattttcata actactgata ttttatatta gtagaatggt ttcttgattc gtctgtataa
24961 aatacaaatc taagaaccct gctacagtaa gttactctaa atctatttga tcttaattta
25021 gaagagtaag ataatcttta ggccatgttg gatgtgttct ggtcagaaaa catgtagatt
25081 tcatacctca gtcctcatcc catgagtgtc tgatgaagct taatcttcc tgcaagaaag
25141 acttgaatga ttttaaacat gagagacact gtatttagtg gtaacatctt aattttagtg
25201 ttaaattgta ttgcctaaga agaacatcta gggcgggcgt ggcggctcac gcctgtaatc
25261 ccagcacttt gggaggccga ggcgggtgga tcacgaggtc aggagatcaa gaccatcctg
25321 gctaacacgg tgaaaccccg cctctacaaa aaatacaaaa aaattagctg ggcgtggtag
25381 cgggcgcctg tagtcccagc cccttgggaa gctgaggcag gagaatggcg tgaacccggg
25441 aggcggagct tgcagtgagc caatatcgcg ccactgcact ccagcctggg cgacagagcg
25501 agactccgtc tcaaaaaaaa aaaaagaag aacatctaaa cttgctcctc ttatgatgaa
25561 ccacatagac ataactagtg ttaatggggg tcagtggaag tcatcatgtt ctgaaaatcc
25621 attaaatgta catcattcta gtgtttaggt taatgctgtt aaattcctgt tactttaaga
25681 aagggttggc cgggcatggt ggctcacgcc tgtaacccta accttgggga gacagagatg
25741 ggtggctcac ctgaggtcaa gagttcaaga ccagcctggg cagcatggta aaaccccatc
25801 tctgctaaaa ataaaaaaat tagctgggca tggtggcgca tgcctgtaat cccagctact
25861 ctggaggctg aggcatgaga attgcttgaa cccaggaggc agaggctgca gtgaaccgag
25921 atcatgccat tgcactccag cctgggcaac agagcagac tccgtctcaa aaaaaagaa
25981 aaagagaaag aaaaggtttg gcattgcaac tatttctctt gaactgagtg acccagaatc
26041 agttgtcctt tgaattttag tatagtagca tagtctgagc tcagaagggc cttatgatag
26101 acctgtatg ttctgggagg caagaattga gttggtatta atatcttaat gcttttgttt
26161 tactgctgaa taacagatga cccttcaggt cttttcatgt tttccttttt catgtctccc
26221 tgcctaggat cctaggtgcc taattgccta cttaaactag tttagggaat cttggactga
26281 agccaaaaca tgtaaaatgc cctgaaggtt aggcaaaggg aagaagttgg gtagtatgaa
26341 agattaggtc acatcttgtt tatctcttga gttctataaa ttgagaatgt aaatttaata
26401 ctatgtctat ttttaaaatg tattttattg ccatgaaaaa gtagcatgag acattggaat
26461 atggaatatc agcttcttca tttgggtcat ggggatcatg cttgaagacc taatgctctc
26521 tctaggtcta tctcagcatt gagcccctgg atgctgttgc gtggcttaga tgacttatac
26581 atgctttgtg gcatgattca tactaccttc taccttctgt gatacccttg ggtagttata
26641 ataggaccca ggttagagtg cttcttggtg gagccactgt agaactggga tttagatgca
26701 gccagggctg atgctcagct ggtgaacact gtgtgcttg ttcctactgg tgatttacaa
26761 ccagtgtttc ttcttttggg gcctgcatcc attttgattg ggtggtgtcc atgctgtatc
26821 tgtaataaaa tattttgaa tgttaccgct ggatgcagcg tgagaaagat acctcctgaa
26881 acttactgta agaaatttac agtgcattga ttttttctgat atataggaat cgtcatgttg
26941 accttggaat tcttaagttc cctggctgta ggaaatggaa attttttgtag tatgtcacca
27001 ttgttagctt atttggtatt gcggatttc cctgttgcag gactgggtga aagcttttttc
27061 tgcagcagtc atgttgaaaa ccttgtgttg actttcctcg tgttctgaaa tgggagcata
27121 aaagtttact ccgccacttc gtcttaaaat agcaaaactt tgctgttttc tgcagatcta
27181 ggaccttgtt acagaactct gccaaaaaaa aaatgtttac agaagaatgt gctgtgatta
27241 gagaagaata tgctggtgtg tagatttcaa actctctgga caatatgaat aacactgtct
27301 ttgttttctac agtgggagcc aagaagaaag gtttgctccc gggtggaaca gggattatcc
27361 tcctcctccc cttaagagtc atgctcaaga gagacactct ggcaactttc ctggcagaga
```

FIGURE 14 (cont.)

```
27421  ttcacttccc tttgatttcc agggcattc ggggcctcct tttgcaaatg tagaggagca
27481  ttctttcagc tatggagcta gagacggacc gcatggtgac tatcgaggag gggagggacc
27541  tggacatgat ttcagggggg gagattttc gtcttctgat tccagagca gagattcatc
27601  acagttggac ttcaggggta gggacataca ttctggggat tttcgggata gagaaggacc
27661  acctatggac tatagggggtg gagatggtac ttctatggat tatagaggta gggaggcacc
27721  tcatatgaac tacagagaca gggatgctca cgctgttgac ttcagaggta gggatgctcc
27781  tccatctgac ttcaggggcc ggggcactta tgatttagat tttagaggcc gggatggatc
27841  ccatgcagat tttaggggaa gggatttatc agatttggat tttagggcca gagaacagtc
27901  ccgttctgat tttaggaata gagatgtatc tgatttggac tttagagaca aagacggaac
27961  acaagtagac tttagaggcc gaggttcagg tactactgat ctagacttta gggacaggga
28021  tacgccacat tcagatttca gaggtagaca ccgatctagg actgatcagg attttagggg
28081  cagagagatg ggatcttgta tggaatttaa agatagggag atgccccctg tggatccaaa
28141  tattttggat tacattcagc cctctacaca agatagagaa cattctggta tgaatgtgaa
28201  caggagagaa gaatccacac atgaccatac gatagaaagg cctgcttttg gcattcagaa
28261  gggagaattt gagcattcag aaacaagaga aggagaaaca caaggtgtag cctttgaaca
28321  tgagtctcca gcagactttc agaacagcca aagtccagtt caagaccaag ataagtcaca
28381  gctttctgga cgtgaagagc agagttcaga tgctggtctg tttaaagaag aaggcggtct
28441  ggactttctt gggcggcaag acaccgatta cagaagcatg gagtaccgtg atgtggatca
28501  taggctgcca ggaagccaga tgtttggcta tggccagagc aagtcttttc cagagggcaa
28561  aactgcccga gatgcccaac gggaccttca ggtatgttga tgggggtggat tgctttttt
28621  tttttttttt ttttttttt tgagacggag tctcgctctg ttgcccagcc tggagtgcag
28681  tggtgcgatc tctgctcatg caagctccgc ctcctgggtt catgccattc tcctgcctca
28741  gcctcctgag tagctgggac tgactacagg cgccaccac cacgcctggt gtgagccacc
28801  gcgcccggcc tgcttttttt tttttttctt aaataagact tttgtgaagg atgacattta
28861  tttatttatt tatttattta ttttttgaaac ggagtcttgc tctgtcaccc aggctagagt
28921  gcagtgacat aatctcagct cactgcaacc tccgcctccc agggtcaagc aattttcctg
28981  cctcaacctc ctgagtagca gggattgcag gcatgtgcca ccatgcccag ttaattttg
29041  tatttttagt gcagatgggg tttcaccatg ttggccaggc tggtctcgaa ctcctgacct
29101  cgtgatccgc ccacctcggc ctcccaaagt gctggaatta caggcatgag ccaccgtgcc
29161  tggccagttt ttttttttt ttttcatttt attttattct ttgcataacc attagaaagc
29221  aaaatttgta ttcaggagtg gaatgtagga atgtaaatct ctagagaaaa ggtcctcagc
29281  tcagatcata tatatgtgtg tgtgtgtgta tatatatata tgaatatata tgtatatata
29341  tgaatatata tttatatata tatatttctt ttttcttta ttctttcttt cctgcttcac
29401  tttccatttg tgtatatatg tgtgtgtata tatgaaggaa ctatatatat atatatttga
29461  gacacggtct tgctctgtca ctcgggctga agtgcgtgg tgtaattatg gctccttgca
29521  gccttgacct cccaggctca agcgatcctc ccacctcagc cttctgagta gctggaacta
29581  cagatgtgcg ccagccacta tgcctggcta gtttttttttt tttcctttg agaatgagtc
29641  ttgctctgtc gctcaggctg aagtgcagtt gtgcgatctc agctcactgc aacctctacc
29701  tcctgggttc aaggggttcc cccgcctcag ccttccagga agctgggact acaggtatat
29761  ttcaccattc ctagttagtt gtgtttttt ttttctttt tgagatggag cctcaccgtg
29821  ttgcctaggc tggagtgcag tggcacgatc ttggctcaca gcaacctccg cctcccgtgt
29881  tcaagcagtc ttcctgcctc agcctcctga gtagttggga ctgtagttgt gcaccaccaa
29941  atctgactaa ttttgtatt tttgtagag atgaagttta ggcatgttac ctaggctggg
30001  ctggaacccc tgatctcaaa tgatccaccc ttctcagctt cccaaagagc tgggatttca
30061  ggcatgcacc accatgcctg gccagcaatt tttgtatttt tttgtagaca gaaggttgca
30121  acatatttcc caggctggtt tcaaattcct gggttcaagc agtcccccca ccttagcttc
30181  ccaaagtgct gggattacag caatgagcca ctgccctac ccttttgatg tgtgtttatt
30241  cattattttg ttttatgatg ctgatttaca tgccttggga taatttagtt tgaaagtata
30301  tgtctttggg agttgactct tgcaactctc gcttagttag acctgtgatt gtttagggat
30361  catttctta tttaaattca ttgagagaat acttaggagt ctccctagtt gtgaagagct
30421  gatattaatg ttgcaactat cctcttgcag ctaacgtaat taacttaaat gttaaacttc
```

FIGURE 14 (cont.)

```
30481 ttgaatatat gatttaagca aggagggtta tatttgtaat tttacaatga aggtattctc
30541 ttttaaagta gatttggctg ggtacagtgg cctatgcttg taatttcagt gctttaggag
30601 gctgaggtgg gaggatcact tgaggccagg aacttgagac cagtgtggtg caacctcagg
30661 agagaatgtg agggtgggga agaaaaataa ggccaggcac agtggctcat gcctgtaatc
30721 ccaacacttt gggaggcaaa ggtgggcaga tcatttgagg tcaggatttc aagaccagcc
30781 tggtcaacat ggtgaaaccc catctctact aaaaataaca aaaattaggc caggcgtggt
30841 ggttcttgcc tgtaatccca acactttggg aagctgaggc aggtggatca tttgaggtcg
30901 tgggtttgag accagcctga ccaacacgga gaaaccccat ttctactaaa aatacaaaat
30961 tagctgggcg tagtgatgca tgtgtgtaat cccagctact cgggaggctg aggcaggaga
31021 atcccttgaa cctgggaggc agaggttgcg gggaggcaga ggttgcacta ttacactcca
31081 gcctgggcag caagagcgaa actccatctg aaaaaaaaaa aaaaaacgaa aaccaaaacc
31141 agccaggtgt ggaggtgggc gcctgtaatc ccaactactt gggaggctga ggcaggagaa
31201 ttgcttgaac ctgggggcg gaggctgcag tgggctgaga ttgtgccact gcactccagc
31261 ctggcgaca gagcgacact ctgtctcaaa aaaaaaaga cattatctag tcatcttctc
31321 tcaccagagg tatgaagtac tgctagttta cagcccattc tccagctctc agaccaggga
31381 aattttcctt ttttttttgag acgggggtct cgctctgtca cccaggctgg agtgcagtgg
31441 cacaatcttg gctcactgaa acctctgcct cccaggttca agtgattctt ccgcctcagc
31501 ctcctgagta gctgggacca caggcgtgca cagcacagtt ggctaatttt tgtattttta
31561 gtagagacgg ttttaccatg ttggctaggc tgagaaaatt actgttttga gactatgtta
31621 gtgtgtcttt ctggttatta aagtcttact cagtcttgtc tctcgtaatg ttttgcttta
31681 ctttgaagac tctttcagtg agacttggtc ttagcacatt tacattctta tgatttgaag
31741 tcacattctg gcactcagaa caatagagaa aattgtaatt ttttatatct tcacgtgaca
31801 tgtcattatc attttttgatc ctgagtggct aaatttcatg ttgatttgtg ttttgtgcag
31861 taaagtatat ttgtgaaata attttttcatt ctcaatttaa ggatcaagat tataggaccg
31921 gcccaagtga ggagaaaccc agcaggctta ttcgattaag tggggtacct gaagatgcca
31981 caaaagaaga ggtaaggcat gtcttctctc ctgtttctct gtgtcaatta aaaattaaaa
32041 aaaccttta atttgaaaaa ttgtagattc acaagaaggt gcaaagaaat gcacagagaa
32101 gtcttgtgta ttttttttccc atcttccctc agtgttaata ttttgcacaa ctgtggtata
32161 gtatctaaac caggaaattg accctggtat aatacataaa gtttattcag atttcaccat
32221 ttatacatgc actcactgag gtgaggttaa aaaaaattat gacaaatgat tgctctcttt
32281 agacctgatc acatccttta gagcatatta tttctggagt atgtacataa ggatgcagtt
32341 tatttacaat agtaaaaact agaaactgcc taactgccct gtatcaaagg attggctgac
32401 taaattaagt ctgaacttat ggcagtgctc gctctgtgcc aggcattgtg tgatacttac
32461 aagcattagt tcatttaatt atcacatatt taatataatc actctaaata ttaagcatta
32521 ctgtatgtaa ttgttctaga tactgagtga cacagcagtg tatattatca agtcactgcc
32581 tccatggata atgaaaaagc aagcaaaagg attacacaat tttagtcagc aaataaatac
32641 tctgaagaaa actaaagtac aggcggggca tggtagctcg gcctgtaact cggagacaga
32701 gtcttgcttt gtcgcccagg ctggagtgtg tggcgcgacc ttggtgcact gcaacctcca
32761 cctcccagt tcaagcagtt ctcctgccgc agcctcccga gtagctggga ctacaggcac
32821 acaccaccac gcccagctaa ttttttgtact tttagtagag acggagtttc accacattgg
32881 tcaggctggt cttgaactcc tgacctcagg ttatctccct gcttctgcct cccaaagtac
32941 tgccattaca ggcatgagcc accaagccca gcccatttt gattttttg aggcagcgtc
33001 tcactttgtt gcccaggctg gagtgcagtg gcacaatcac ggctcactgc agcttctacc
33061 tcttgggctc aatcgatcct accacctcag cctcctgagt agctgggacc acgggcatgc
33121 atgctaatgg ggctgttttt tgtattgtgt agttagggag acatcactga ggaagaggca
33181 ttcgagccca ggcttgaatg ccgtgagaga acagtttata tgaatatggg gaaatgaact
33241 gcccaggcag ttcatgctga ggaagtgctg tggccctgga ctgtaatgaa cccagtacat
33301 cattttatat ttaacacatg agaaactgga cactaaaagg ttacacagca agtgagcaga
33361 gagcttggaa tgcacacagt atgatttcag agcttaagcc tttgaaggtt atgctcttct
33421 gcttttcttt tttttttttt tttttttgaga cagagtctca ctctgtcacc caggctggag
33481 tgcagtggcg cgatctcggc tcactgcaac ctctgccgcc agggttcaag agattctcct
```

FIGURE 14 (cont.)

```
33541 gcctcagcct cccaagtagc tgggattaca agcacctgcc actgcaccca gctgattttt
33601 gtattttag tagagatggg gtttcaccat cttggtcagg ctgatcttga actcctgacc
33661 tcaagtgatc cacccgcctc ggcctctcaa agtgctgaga ttacacgcat gagccaccgc
33721 gcccagcatt ttgtttgttt gtttgtttgt ttgttttga gacagagtct tgctctgtca
33781 cccaggctgg agtgcagtgg cacaatcttg ggtcactgca acctccgcct ctcgggttca
33841 aatggttctc ctgcctcagc ctcctgagta gctgggacta caggcatgtg ccaccacgcc
33901 cggctaagtt tttgtatttt tagtagagac ggggtttcac cgtgttagct aggatggtct
33961 cgatcccctg acgtcatgat ccgcctgtct cggcctccca aagtgctagg attacagatg
34021 tgagccaccg cttctggccc tgcttttcct atgtacctga gaattttaa atatttattt
34081 atttattttt gagacagggt actccagact ggagtgcaat ggcccaatca aggctcacta
34141 cagcctcaaa ctcctgggct caaactatcc tcccgagtag ctgggattat aggtgtgagc
34201 cagtactcct ggctaatttt tttttttttt ttgagatgga gtctcgctct gttgcccagg
34261 ctggaatgca gtggtgcgat cttggctcac tgcaagctcc ttctcccggg ttcacgccat
34321 tcttctgcct cagcctccca agtagctggg actacaggtg cccgccacca cgcctggcta
34381 atttcttgta ttttttagta gaaacgggt tttaccgtgt tagccaggat ggtctcaatc
34441 tcctgacctt gtgatctgcc cacctcggcc tcccaaagtg ctgggattac aggcgtgagc
34501 caccgtgccc ggccaatttt tttttttttt tttttttttt tttttaaag atagtgtctc
34561 gctctgttgc ccaggctgga gtgcagtgtc atgatctcag ctcactgcag cctcagcctt
34621 ccaggttcaa gtgattctcc tgcctcagcc ttccaagtag ctgggattac aggtgtgtgc
34681 caccacacca ggctaatttt tgtattttta gtagaaatgg ggtttcacca tgttagccag
34741 gctggtctcg aactcctgac ctcaggttat ccacccgcct tggattccca aagtgctggg
34801 attacatgtg tgagccacca cgcccggtct ctcctggcta attaagaatt tttttttttt
34861 ttttagagat agggtctcac tatgttgccc aggcttgtct caaacatgtg gctttaagca
34921 atcctctcac cttggcctcc caaagtgctg ggattatagg caggagccac tgcatcccac
34981 caattttga ataattatgt tctactcatt caatatgtga atgccttgag tgttcatagt
35041 ttaacttgc ttttccaaag taatcatggc tttaaattat gtatgataaa aactgttagg
35101 gaaaatctga tattcagtgt ttgattatga tttgtatcat ttgtataaat gccatatttt
35161 tgcagattct taatgctttt cggactcctg atggcatgcc tgtaaagaac ttgcagttga
35221 aggagtataa cacaggtgag tttcttgact tgcatatggc cttgggttag gaagggtctt
35281 tgtcagatct ctgcatcatg tgctacttaa aatttgtttc aagaaaccac aattaaaatt
35341 tccagaagcc tcccgttggt gcctccaaat aacaaccagc tttagtttta gctgtggttc
35401 tttgtggatg tttgtccaca catgggtgat gaggatgcat gttccagttc ttctgaatgc
35461 ctgtgatata tagagtgttg cagcaattgc cttgaatata ttatataa ttattaaact
35521 tgctatgcat gttcttcatg gtggtggaat gtttatgctt gagcctaata ggatttaata
35581 agcttgttgt atgtaaaatt ttacattcat tgcttcagta aaatttatga cttcccagag
35641 aaattgtaca aattagtggt ttaattttca gttttgcttt gagaatggag tcctgttaca
35701 gttattttgt tgaaatccat gaatagaccc agaagagctt ccctttgac atctgttctg
35761 tggtctgaat ggtagattaa acttttcaga atatcctcct agttgtattt cacagtacca
35821 atttcagtca tttccttta atcttactac agtaaaagta ggcaaaggtg aaatgccaag
35881 aactcaaggt ttttgaccaa tattttaga actatgtata ataagtt tatttattta
35941 aaaataaagg taatcttag gtgacctatt ttgcagaatt ttaaatggaa gggaatagag
36001 catgagtctt cacagaactt agaatttcag taattcagtt aaagacatct tcaagtaaga
36061 acatgtcata ttttgaggat ataatttact attagcagtt tatcatggga taaaaatttt
36121 gcattaacta gataacttct tcagaatgct tctgcagagg aaaattatcc acaaaataaa
36181 tttggtgct tgaaagaata tggtgttaag ttcagaaata atttgttctg taatttgaga
36241 acaagctcag aagtattatt tctcagagag ccaattattt atttgtttta aaaacatcaa
36301 ccctgaattt gtggaagcat gagtaagagt agatatta ttattcttgg tatctcactt
36361 atgttggtta tatttatttt ttgcatatgc cttatacatg cttctcttgg gaactcaagg
36421 tagaatttac aggctggaga tgcttttttaa ctctcaggat aataacctca gtctggtttc
36481 atgaactgtg ctttcattaa gtattgatat gtttaggaaa ggagatgtct taatatttaa
36541 atagcagttc aaactccagt ttctttagta ttcattgact ttctaattgt caaatttgtc
```

FIGURE 14 (cont.)

```
36601 aggacagtaa aaattgtatt aacatatagt gtctagagag gaagttctta aatttgccga
36661 ttgtggtagc tgttagaatt ggcagactga agacattgat acacatggga aatcattcag
36721 ggcagtgctt aaaaataaaa cgaaaaatac ctttcagcaa atacaatctt ttcttggcat
36781 tctgttaagt tgtgtttttt attttgttt tttagtgaaa gaattggatt gctagtttca
36841 tgttatttat attacatctc tatgtgacaa ataggatgaa cttttgacaa tatcagccag
36901 atcatgttac tcccatgtct aaaaccctct tagggccttc atcttcactt ggaagaaatt
36961 cccagcttct tcttttgtct tacaaaccca tgcgtgagct gacccttggc tgtttgatct
37021 cattcagtac tgccctccac ctaccctatt ttgctgtagc cacactgagc ttttctcttg
37081 tcttttgacca atacaaactt ctttctgtgt cagggtcttt gcactactct tctctctgat
37141 ctttacttgt cttctggggt ttagttcttg gcttcagttt cacgtctctg aggccttgtg
37201 tcactctcaa atctaaaatc atcgggcagt tgttttccat catatccttg tttggatcta
37261 tcactgattg gatatttcta tcactggtat ttttcagttg gatctatcac tgatctatca
37321 ctggtcactg attggattga atctgtcagt ggtattggat ctatcactga tattttctc
37381 cgtggttttg tgtatcttat ttctctcact agagaggaat gtcagcagga gccttattcc
37441 ttcttgtttc caccagtgct tgacactcgg taggttccct atatgcatgg aatagattat
37501 tatttatggt gtatgtgaag agcagctgtg atttccctc aggtgaggaa cataaaaggg
37561 tagtgtaggt ttcacagcag tgcagcttag gtcttacata tctgttgaag aatatgtctt
37621 ggaacaatca gatgttctaa gaactatagt gtttactgtt aaaagatcat atgtggtagt
37681 caggcatggt gttgcacacc tgtagtccta gctacttggg agtctgagat gggagaattt
37741 tttgagcctg agaatttgag atcagcctga gcaacatagc aagaccttgt ctcttaaaaa
37801 gaaaaagaaa aaaaatgtg aatcttagta gtaacagtga cttaaaaatt tttttttata
37861 agagaaaggg tcttactctg ttgcccaggt tggagtgcat tggtacgatc atagcttact
37921 gtaacctcaa accctcggc tcaagtgatc cttctgtctc aacctccaga gtatttggga
37981 ctacaggtgc gtaccaccat ggcaggctaa tttttaaact ttttgtagag gcgcggtctc
38041 actatgtttc ccaggctggt cttgaactcc tgggtcaag tgattctcct gcctcatcct
38101 cccacagtgc tgggattaca gatgtgaacc agtatgcaca gacaaaaagg tgacattcat
38161 aggtgaaaac tggtaataaa tattttaggc tgagtgatga cctgcagaga ccatgcagga
38221 tggatattgc tcataagagg ggaattgtgg agtacagtct gtcctgttag ttgatgtaat
38281 ggagggctga tctataacac aggagagaag attaacgcct cttcgttgac tctagtaatg
38341 tattagtgta attttttgtct cctctagagc tgtataagta cagggtcaca atttttatcta
38401 gaacctgtga ggttaaatga gcttatgaat ttttcaagtt atagaaatgt agtttacata
38461 gatcatatgg gaattatatc tcccagggga atgtgtactc agacataata cttacgctgc
38521 aaaattatta atattctcac taacaggagt aaataaagtc tcacagtata ggccaggatt
38581 tgcctcaaaa tgagtttgtt gaattttacc aaaaaacttg acatttatgg gattttggaa
38641 ttgtagataa gagattttgg acctatatat gttgtgtata tttgaatttt tcatttgcca
38701 tttacaaata cattataacc ccatgaattg taaattatct tgaattatat gattatttct
38761 ggaaaaagta ccaggagtaa aatgtctttt ggtgactaga caaactctag tatatatata
38821 aaatggaata cttctcagca atgaagaaga aactactcat gcacctaaca acatggatga
38881 atctcaatgg caatatgctg agtgaaagaa actagactca taaggatata tacactacca
38941 taaggaggaa tgaaatactg atgtatgcta caagttggat gaaccttgaa aacattataa
39001 aagaagccag acacaaaaga ccaaatattg tgcaattcag tttatatgaa atatctagag
39061 aaggcacacc cgtagagata gaaagcagat tggtggttgc caggggctaa gcgggaatgg
39121 ggaacgactc cctaatggtt atggtacttc ttttgggctg atagaagtgt tctggaacta
39181 ggtagtagtg atggttgcat gacattgtga atgtacttaa tgctcctgaa ttgtacactt
39241 taaaatgatg catttatttt gatgtgtatt tgcttacttt gttttttttt tttttttttg
39301 agatgaaatc ttgctcccgt tgtgtaggca ggagtgcagt ggcatgacct cggctcactg
39361 caacctccat ctcccgggtt caaacgattc tccttcctca gcctcccaag taactgggat
39421 tacaggtgtg tgccaccaca cctggctaat tttttgtatt tttagtagag acggggtttc
39481 gccatgttgg ccaggctggt cttgaactcc cgacctcagg ttatctacct gcctgggcct
39541 cccaaagagc tagcattaca ggagtgagcc actgtgccca gccagcttac aatttttaa
39601 aaaggctaca tactatatgt gtatgtgtga tttcacttat gtgacattct ggaagggaca
```

FIGURE 14 (cont.)

```
39661 aaattttagg gattggaaat agtggtggcc agggtattgg gggaggagtt aactataaag
39721 cggaagcatg agggaatttt tgggtataat ggaattgttc tatatcttga ttgtggtgat
39781 gatgtatcaa tgttaaattc cccgagttga taactactgt ggttatgtta gagaacatct
39841 ttttctttt cttttttttt ttaaacggag tctcgtttgg tcacccaagc tggagcgtaa
39901 tggcgcgatc tcagcttact gcaacctctg cctcctggat tcaagcaatt ctgcctgcct
39961 taacttcctg agtagctggg attacaggcg cctgcccta ctcctagcta attttgtat
40021 tttttttagt agcgacaggg ttgcgccatg ttgaccaggc tggtcttgaa caccctgacct
40081 caggtgatct gcccaccttg gcctcccaaa gtgctggaat tacagacgtg agccaccatg
40141 cccggctgag agtatcttta ttcttagaaa atacataatg aagttttag aagtaaagta
40201 ctgtgatgta tgcagctttc tctcatggtt tcgaaaataa tacttgctat aaatggagaa
40261 ggaaggaaga gagtattgat aaagtagatg gatcacaatg ttattaatag ttgaatctgg
40321 ggccacacgc ggtggctcac gcctgtaatc ccagcacttt ggaggccaa ggcaggtaga
40381 tcatctgagg tcaggagttt gagaccagcc tggccaacat ggcgaacgaa acctgtctac
40441 taaaaaatac aaaaattagc cgggcgtggt ggcgggtgcc tgtaatccca gctactcggg
40501 aggctaaggc aggagaatca cttgaactcg ggaggcggag gttgcagtga gccaagatca
40561 cgccattgca ctccagcctg ggcgacagag caagaattca tcttaaaaaa aaaaaaaaaa
40621 aaagttgaac ctgggtaaag catatatgaa tcttttccct gtactattat tattgcaatt
40681 tttttgtaac ttggaaatta tttccaataa aaagttgaaa aactgacaaa actgatttat
40741 tttatttat ttttattt tttgagacgg agtcttgcac tgtcaccagt gctggagtgc
40801 agtggcgcga tatcggctca ctgcaacctc cgcctcctgg gttcaagcga ttctcctgcc
40861 tcagccatcg gagtagctgg gattataggc gcctgccacc atgcccagct aatttttgt
40921 atttttagt agagacgggg tttcaccatg ttggccagcc tggtctcaaa ctgacctcat
40981 gattcgtcca cctctgcctc ccaaagtgct gggattacag gcatgagcca ctgcgtccgg
41041 cctatatttt atctttaaat gatcagcaga aaccttgtaa gctgaagact gcaatcaaca
41101 gcttatgtca agtaaactat agagcagtgg ttctcagagt ggatcctgga ccatcatcat
41161 ctctttaccc cttgggaact tgttggaatc caaattctta agccccatcc taaacctact
41221 gaatcagaaa ctctggggtg gggcccagta gcctgtgctt taagaagtc ctccagatat
41281 ttttaatgta ccctgaggac cactggcagt agataaagtg tttgtttaga ttctttattc
41341 tagaactttt gtatagttta aaagtgactt aataataagc aagtggacct tttgtaagta
41401 gacaaagcta atgcttatgt gctttaggag ccagtgctga tcacatgcct tgcctaccta
41461 atatcagttc tcctgctctg catagcagga gaaggagctg gagtagtgtt ggtactatct
41521 tatgactta gttatatgta actaaggaca tataacttag ttgtttttc tgtttatata
41581 tagtatactt cctccagaga tcttggaatg gttgtagatc ttctcattca cacagtgttt
41641 ctgtgacata tgaatgcagg cagaattgct tttgatttt aggtttgttt gcatactacg
41701 tagtatataa gcttgctgtg atatttttcc aaaagggatt tatatcattt aagcaaaaat
41761 gatacagctt ctggattatg tttcctaata aggctcaaac atagaaagta attatagtaa
41821 ctgaagtgct acagaattac tttagtactg gttattaac taatgtcaca aagttagagg
41881 attactaagg tggtgttagt aggaagaagc aatatcttgc tttagcccgt cagtgttcat
41941 gtggtgaatg gacagtctct gtattcttgg gaaggaaaat tcttcttgga aagtgagtat
42001 ttgcaatgac taggtcagtc acttggtctg ttgcctggca ttttgggtct actgaaagtg
42061 acgttgtagc aaaggccctg taccttctgc atttcttttc tttcttttt ttttttttt
42121 tttttttt tttggtagaa acaaggtctt gctttgttgc ccaggctgcc cttgacctcc
42181 tgtcaagcag tcctcccacc ttagcttcct gagtagctgg gactacaggc gtgtgccacc
42241 atgcctggtt aatgtaaatt tgtttggttt ttttgagaca gagtttcact cttgttgccc
42301 aggttggagt gcagtgacgt gatctcagct cactacagtc tctgcctcct gggttcaagc
42361 gattctcctg cctcagtctc ccaagtagct gggcttacag gcacccgcca ccacgcccag
42421 ctaattttt gtattttttt agtagagacg gggtttcatc atgttggcca ggctggtctt
42481 gaactcccga gctcaggtga tccacccacc tcggcctccc aaagtgctgg gattacaggt
42541 gtgagccacc gtgtctggcc tatttttaaa ttttttttga gacagagtct ctctcagtca
42601 cccaggctgg agtgcagtgg tgcaatctca gctcactgca gtctctgcct cctgagttca
42661 attctcctgc ctcagcctcc ctagtagctg ggattacagg cctgccatcg tgcccagcta
```

FIGURE 14 (cont.)

```
42721 attttgtat ttttagtaga gacagggttt caccatgttg gccaggctgg tttcaatctc
42781 ctgacttcaa gcaatccacc tgcctcggcc tcccaaagtg ctgggattac aggcatgaac
42841 caccacgcct ggcctaaatt ttttttttgt agagacaggg tctcacgctg ttgctcaggc
42901 tggtcttaca ctccaaggct caagcaatcc tcctgccttg gactcccaaa atgctgagat
42961 tacaagtgta agacactgag gccagctgcc ctttacattt cttaagggta acaggctcat
43021 gtcctttcat tattcacaat ttaaatattt tgagtcttta cttctgtgtc aatataacag
43081 aagtaacttc cttacgaaga aaattccaga gggaatcttt caatgtaggg atagaaatcc
43141 attgtgaaac tcgagaattg acactgatga tataaaacat gcacagtagc cgagtgtggt
43201 gatgtgtgcg tgtagtctta gctactcaac agtccgagac atgagctcag gagtttgtga
43261 ccagcatggg caatatagtg agactctgtc tcaaaaaaag gaaaaaaaaa agtgcatagt
43321 ttatggtatc ccaactggag gagctaaaga cagaatagct taacatcatt tagaaaaaaa
43381 attataattg aaaagtgcaa atacacattt tgcagtgttt ttggcattta caaaatatgt
43441 aaacactttt agtttcttag ggaaaagatg acgataggct gattgaaaaa tatcattttt
43501 acttgtcaca tctctaaaac agcagaagtt cttgttttta accaggagtc ctatcaggtt
43561 tgatacaacc ttcggggagg atgtggcagt tgaaatttaa ggaaacttag tttccttaag
43621 gtggctgagc ttaaaaaatc aaaatgttta ggaaggcagg agacactaat agggctgggc
43681 tagtcttgtg gaggcagtgg atggacgctt tggctggcct agggaagaat ctgtgattca
43741 gtgctgcagg gatcaggtga tcctggtgag agaggtcctg gaacaagggt taatttggtc
43801 attttggaa tgacctggga tttggcttat ttatttatt tttaaaattt cccgctgggc
43861 acagtggctc aaacctgtaa ttccagcact ttggaacgcc aaggccagtg gatcactcga
43921 gctcaggagt tcgagaccac cctgggcaac atggtgaaac tctatctctc caaaaaaat
43981 acaaaaaaaa ttagctggat gtggtggtgc atgcttgtag tcccagctac ttaggaggct
44041 aaagcaggaa gatcacttga gctagggagg tgaggtgga ggttgcagtg agccaagatc
44101 atgccactgc actccagcat gggcaacaga gagagacctt gtctcaaaaa aataaaatgg
44161 tgaatgtaaa ataaaatggt agctcacgcc tataatcctg gtactttggg aggccgagat
44221 gggtggatca cttgaggcca ggagttacag accagcctgg tcaatatggc aaaactccca
44281 tctctactaa aaatacaaaa actagctggg ctggtggtgt atgcctataa tcccagttac
44341 tcaggaggct gaggcagagg tcacagtgag ctgagatcac accactgcac tccaggctgg
44401 atgacagagt gagaccctgt ctaacgtgac atcacatcac atcacatcac atcacatcgc
44461 atcgcatcgc atcgcatcgc atcgcatcgc atcgcatcgc atcgcattgc atcacatcac
44521 atcacaacat aacataaatt tcaaggcag aaatcttgta gtcagcctta ctgtttgttg
44581 acaaggacac ggccctgagc actccagaat cggcagttga taaagccaag aagaaggata
44641 ctaattaaag aaattttcag attttgcatc ttctggcatc tcagctaaat agctctgagg
44701 aggaggatgc cacttaccag ttttgagaca caggcaggtt atattatttt cctgaaaacc
44761 atttagctga gatggaattt gcctctctga ggttggggaa ggtgtttgaa ctctgtttac
44821 agccctctgt cagttccact gccttgctga gttccctcac ccttctttag atagaattgc
44881 tgttggcttc tatagtcctc acttacctct tttgccaaat gctcaggtag ccttggctga
44941 gtcttccagg tttgataagg ctgtatgggg cttcctatgc cttttggtag ttagaagtca
45001 ctgaagaggt acttctgcta cagtgacaag aagaaaggg cattactcag cttgtatagt
45061 gcaaggctg cttgactccc agcttcagtc taggcagggg aatttattta tacaattacc
45121 ttaaatgagc accagataga ggccatctat aaaaactgtt tacaggattt aaaaatacgt
45181 tgacattggc ttcttccttt aactttctgc ttgcaacaga acatctgatg cgacctatgc
45241 tgctcactgt ttctaggtta cattctctac ccttgcagtg taaattaatt tttgcctggt
45301 tccatgtttc ttgcttaggt tatctcttag gtcttttgtc tgatttaaat ataagccttc
45361 ttaggactag atagtggtga tggttgcact actttgtcaa tataccactg aattgtatgt
45421 attcactctt ttaagaatga gtttatttt atttttattt ttattttgag atagagcctc
45481 actctgtcgc ccaggctgga gtgcagtggc gtgatctcag ctcactgcaa cctccacctc
45541 ccgggttcac gccattctcc tgcctcagcc tcccgagtag ctgggactac aggcgcctgc
45601 caccacgccc ggctaatttt ttgtattttt agcagagacg gggtttcact gtgttagcca
45661 ggatggtctc gatctcctga ccttgtgatc cgcccacctc ggcctcccaa agtgctgggt
45721 ttacaggcgt gagccaccat gcctggcctt aagaatgagt tgattgttct tagtctcagt
```

FIGURE 14 (cont.)

```
45781 tgagtacatt gtgttatgta tagaaaatgt tatattttca tttttaaaaa ttattattat
45841 tattttgaga tggggtctca ctttgtcacc caggctggag tgcagtggca cggtcttggt
45901 tcactggcaa cctccacctc ccaggtacaa gtgattcttc tgcatcagcc tcctgaatag
45961 cgggaattac aggcgcctgc caccaagcct aagtaatttt tgtattttt ttttttagta
46021 gagacggggt ttcaccatgt tagccaggct gatcttaaac tcctgacctc aagtgatcca
46081 ttcgtctcag actcccaaag tgctgggatt acagatgtga gccattgcgc ccagcccatt
46141 ttaaaaaatt aaactggcct ggtgcggtgg ctcacgcgtg tgatcccagc actttgggag
46201 gccgaggcaa gcggatcatg aggtcaggag attgagacca tcctggctaa catggtgaaa
46261 ccccatctgt actaaaaaat acaaaaaatt agccgggcat ggtggcgggc tcctgtagtc
46321 ccagctaatt gggaggctga gacaggagaa tggcatgaac ccgggaggca gagcttgcag
46381 tgagccgaga tagcgccaat gcactccagc ctgggcaaca gagcaagact ccgtctcaaa
46441 aaaaaaaaa aacaaaacaa aaaaaacca aaacattaaa ccatactctc taactgtgaa
46501 gaagttgtga tttattcttt agtgttacct gccattcttt ttgtctcttt ctctctcttc
46561 tcttctcctc tcttctcttc tcttcttctc cctcccttcc cctccctcc cctcccttc
46621 tcttttcttc tcttctcttt tcttttcttt cagagttttg ctctgttgcc caggatggag
46681 tgcattggca tgctcacggc tcactgcagt gtcaacctcc caggttcaag ctgtcctcct
46741 acctcaccct ccctagtagc tgggactata gacatgcacc accatgccta attattttgt
46801 attttttgta gagacgaggt tttgccatgt tgcccaggct ggtcttgaac tcctgagctc
46861 aagtgagcta cctgcctcag cctcccaaaa tgctgtgatt acaggtgtga gccttatttt
46921 attattttt tttgggacag agtctctctc tgtcctccag gctggagtgc agtggcacga
46981 tcttggctca ctgcaacctc tgcttctcgg gttcaagcaa ttctcctgcc tcagcctccc
47041 aagtagcctc ccaaagtgct gggattacag gcatgagcca ccatgccagg cctctgatgc
47101 atatatttt taaaaatagt attttccacc ttacagtgta tttaagagtt tgtaaatttc
47161 ctttttttgt ttcttttgg aacagtgttg ctctgttgcc caggctggag tgcagtgaca
47221 tgatcttggc tcattgcaac ctccacctcc cagattcaag tgattctcct gcctcagctt
47281 cccgagtagc tgggattaca ggtgcccgcc actacgccca gctaaatttt ttgtaatttt
47341 agtagagaca ggtttcacca tgttggccag gcaggtcttg atctcctgac ctcaagtgat
47401 ccgcccacct cgacctccca aagtcctggg attacggaca taagatactg tgcctggctg
47461 agtttgtaaa tttctttctt tcttttttct tttttttg agacagagtc ttactctgtc
47521 acctgggcta gaatgcaata atgcgatctc tgctcactgc aacctctgcc tcctgggttc
47581 aaacaattcc cctgcctcag cctcctgagt agctgggatt acagccgcct gccactatgc
47641 ccagctaatt tttgtatttt ttgtagagat gggttttgc cgtgtaggcc aggctggtct
47701 agaactcctg acttcaggtg atccacccac cttggcctcc caagcgtggg gattacaggt
47761 atgagccacc acgcccggtc atcaaagata atgttttaa tgatcaggag cactttgaga
47821 tgtttagaac aatctgaaac ctgatttcca agccatctca aaatatactt tggtaatcaa
47881 gacagggaaa tgatggtgtt atatcatttg tgggactcaa ctgattttgt tgagtattga
47941 ttttgctgtg ggattccttg ttctcttggt tgtgttgggc ctactgcttt ttaaaaagt
48001 attttgagac agggtcttac tctgttgctc aggctggagt gtagtggcgc agtctcttgt
48061 ctctgcaacc tcaatctcct gggctcaagg gatcctccca cctcagcctc ccaagtagct
48121 gggaccacag gtacccacca tcacacctgg ctaattttg tatttttgt agacatgggg
48181 gtcactgtct tgcccaggca ggtcttgaac tcctaagctc aaacaaccgt cctgccttgc
48241 cctcccaaat tgctggaatt acaggtgtga gccagtgcgc ctggccttct tttttttt
48301 taaccactat tttttagaac tagatttggc ctggaaagag aaaaagata ttcctcgact
48361 tgatctatat attttatggt tcattcattt gcttagagg tagaaggagc aggaaaagt
48421 acaacaaaac aaaatcttac ctttggtgtt taatttgaat gcccacagat gcttttgcat
48481 ttattagtag tgagttttca taattatcaa atatgtagta gaaaatctg gctgtgcatg
48541 gtggctaatg cctgtaaatc cctatatgct gggaggctga ggcaggtgga ttttctgagc
48601 tcaggagttc aagaccagcc tgggcaacat ggcaaaaccc catctctgcc aaaaataagc
48661 tgggtgtggt ggcacacgcc tgtggtacca ggtactccgg aggctgagct gagaagattg
48721 tggaggtttc agtgagccaa gattgcacca ctgcactcca acctgggtga cagagtgaga
48781 ctccatctca aaaaaagaa aaaaaatctc ccttgtccag gagctgtgtt gagtgggctg
```

FIGURE 14 (cont.)

```
48841 tggactagca ggaattcata gctctggtga aagatgacta gataatgtca ttttttttt
48901 aaaagtccct gaatgattgt gacagggtag gaaaatcatc acatagcaaa atcttcatta
48961 gattttccct aatgacttat caactgggtt tgtgcaccaa acgaaacaac ttcctgcctt
49021 tgtttgtctg aaagtcaaag aaaatattat tcaggtatat tatattgtac tccatgctac
49081 agaagtttct ggcagcaata taggttatat gccaatcggt taaataatat ttgtgggcca
49141 ggcccggtgg ctcatgcctg taatgccagc actttgggag gccgaggcgg gtggatcact
49201 tgaggtcagg agttcaagac cagccagggc aacatggtga aacccccatct ctactaataa
49261 aacaaaaatt agcctagtgt ggtggcacac gcctgtaatc ccagctactc aggaggctga
49321 ggtaggagaa tcgcttgaac ccggaaggtg gaggttgcag ctgagattgt gccattgcac
49381 tctagcctgg ggccacaaga gtgaaactgt ctcaaaataa ataaataaat aaataaaata
49441 ataataatat ttgtgtaagt acagggatat gtttcttcaa ctccaaagta tgagttaatg
49501 tgcatatgcc aactctagaa ataaagtatt aagtcaaaac tcccaagaaa atttccccaa
49561 aaagttgcta acagacgtta ttttatttta tttatttatt ttgatacaga gtctctccca
49621 ctgtcaccca ggctggagtg gtgcagtggc atcatctcga ttcactgtag cctccgcctc
49681 ccagattcaa gccattctcg tgcctcagcc tcccttgtag ctgggattac agttgcccac
49741 caccacgcct ggctgatttt tgtatttta gtagagatga ggtttcacca tgttggccac
49801 gctggtctcg aactcctgac ctcaagtgat ctgcccgcct tggcttccca aagtgctggg
49861 attacagttg tgagccactg cacctggcct ttaattttaa tttctaaaac tatggagtaa
49921 tactacattg agggaacaga attttctatt ccttcatttg tattattatt aaatacagtc
49981 atgcattgca taatgacagg aatacatttt gagaaatgga tcaagtgatt ttttcattgt
50041 gtaaacatca tagggtatat ttacacaaac tagatgttat agcctactat acagctaggc
50101 tatattgtat agcctgttac tcttcggcca caaaactgta cagtgtgtta ctgtattgaa
50161 caccataggc aattgagaca caacggcatt tgtgtatcta aatatagaaa aggtaatgca
50221 ttgtgccacc aaatcaacaa cagctatgat gtcactgggt gataggaatt tttcagtgcc
50281 attataatct tatggaacca ttgtttcata tgcatgcagt ttgctgttga tcaaaatgta
50341 gttaagcagc acatggctgt aattaaaaca ctattgtttg ttataataga aaataaaatt
50401 tttcttttta gcctctgtat taataaagag cactagaaag tactttgttt atcagataat
50461 gaatatgttt gacagatgta catacgtatt tatcaaatga atctttttt gtgggggaaa
50521 ccttaactaa gaataggcct gtgtttaaa atggctgcct ggaggacaag tgctataagg
50581 aaatttcagt ggtatttgct tgacctggca ttaagtgggg ggaaaaacaa gccccaggtg
50641 aattgataga tggatgtctg aacatgttca ggaatgatgt tttgaacaat gtttgcctcc
50701 tgtgtcatgt aggcagagag atgataaaag ttttttttccc ctcttgatac caggtaattc
50761 tgataccgac taccagaagt tagcttcaga ctccgcaggt tgaagggctt tgtcccataa
50821 gaccattctt acttcagaca ccaattgcaa tgatcagtta tcaggtccca aggttaccta
50881 cacttatgtc tgatttggct acaaaattgg aggttcccac agtctacccc ttcagatttg
50941 ataactttct aatatggctg caaaaaactc agagaaatac ttatgtttat cagttttta
51001 taaaggatac aattagccag atgaggagat agatagggca aagtccagga gggtcctgag
51061 tgttgagtgt aggagtctct gtcctgtgga atatgccacc gtcccagcat gtagatgtat
51121 tcaccaatca ggaagctctc tgagcccttt tgtgtagttg tttttatgga ggtctcatta
51181 tgtaggcagg attgattaaa tcattgacag tgggtgattt gctcaagccc ctctcccctc
51241 atcagaagtt ggtgggtggt actgaaagtt ctgaacttct ggtcaaggct ttgtctttct
51301 aggtagccct catcctgaag ctatctaggg gctttccaag agttgtctta ttagaacaaa
51361 gaacactcct atcacccta tcactcagga aattccaagg gttttaggag ctgtatgcca
51421 ggaacctggg acagaccaag tatctttctg tgataccaca gaatgggacc ccaaaagcca
51481 gctccagctg gtgtctagtg cctttagttg ggcactggat atcggttaca gggcataagt
51541 ggcccagtgg ggttgccgtt taacccatct ctgctgtatt aacctcatgt accttagctc
51601 atggctaggt cgtttcaagt ctcacctaat gtcagttgtt tcatccttct ctggatgcat
51661 gttcacttct ggaataggtg aatatctggg ccactatgtt tgctgtcatc ctgagcaaac
51721 ttccagctta gaaaccagct ttatggaatc atcccagagc ctttatttta ttttatttta
51781 ttttatttta tttatttatt tatttatttt ttgaggcaga gtcttgctct gtagcccagg
51841 ctgaaatgca gtggcaaagt catggctcac tgcagcttca acctcccagg ctcaagcaat
```

FIGURE 14 (cont.)

```
51901 ccttccgttt cagcctccca agtagctgag attacaggtg tgtaccacga cacctggctg
51961 atttaaaacc ttttgtagag atagtgtccc agtgtgtttg cccaggctgg tctcagactc
52021 ctggggttaa gcgatcctct tgcctcagcc tcccaaaatg ttgggattac gggcgtgagc
52081 cactgaactt ggtcccagag cctttagaa cagtgttgag ttgcccttta tttgcaccag
52141 ggctaaggca gtagaaaaaa aatgtttatg ggccatgttt ttcttcctag tcaaaataaa
52201 aatagccatg taatctatgg aggcagcaga tatgttgtta gtatacacta gaagtcagga
52261 aattcgtact gcctttcagc tgctaaagta ctgggacata tttgagaagc agtaatgcag
52321 aggcagctgt ctgatctttg atctctgata atgcttattt cattgcatcc ctgaaaccac
52381 cctgcaaagg atttatcatc tttgctgctt tgcatatgga atagcatagg cccagagaga
52441 cgtagcttga ctgcaatcac atggtgagtt agttgtagct tctgcaaatg tacagaacta
52501 agaagctact tttcttgtgt gttattctag tgatgatggt cattataatt gatgtacctg
52561 atattatgct aggtttaggg atacagaaat gaaagaagat cacagtccct catctgggac
52621 ctctgttttt ttggtgtcac ctctctgcat agacagttct gcagtattga tgctgctgtt
52681 ctggttgatc cttctgtcat gcctgcacca tcttttctgc cagactgaag tgttcttgct
52741 tggggaaaag cagatttgca aaggttctct ttttcctgat tgttgctttg cagattgagt
52801 atatttgttt gtttgttttt aagtgaacaa aagttgaatg agattgatta ctggctcttt
52861 aaagaataat tactccccct tttgacttat gtagcatctt gaggtgatct atgaccgttt
52921 gtacttgtca tgacttccat tagattaaac tctgggcaa agacgttgct cttcattgtg
52981 ctcatatgac accattactg ccagtggaat tgaaataaat tgagtaaggg cgagtgtttc
53041 ctaacaaatg ttatcctggg cctgaggaac catcatcaag atggagtggc cctgcgatta
53101 attttggact taaagcaaaa aacaaacaaa ttttttttctt taaataacca gttggcacag
53161 atacagaata aaataagata gatccacgtg tagtttttga aaatttaggt caggtggctc
53221 actcctataa tcccagcact ttgggaggcc aaggcgtgtg gataactcga ggttaggagt
53281 ttaagaccag tctggccatc atgatgaaac cccatctcta ctaaaagtac aaaaattagc
53341 tgggcatggt ggcgcatgcc tgtaaaccta gctactcagg aggctaaggc aggagaattg
53401 cttgaacctg gtaggcggta gttgcaatga gccagatttg cgccactgca ctccagcctg
53461 ggtgacagag tgagactctg tctcaaaaga aaaaaaatt taagaaataa tcatcagtgt
53521 atatcttcct tttttcattt ttctttaaaa aaaaaaacaa cccttgtatg catagctgaa
53581 ggagaaataa ttgaaagtgt ttataagatt tcaaggtgat gggctggaca cagttgctca
53641 tgcctaataa tctgcacgcc tgtaatccca gctattcggg agcctgaggc aggagaatca
53701 cttgaaccca ggaggcagag gttgcagtgg gccgagatag tgccattgca ctctagcctg
53761 ggcgacaaag gtgaaactcc atctcaaata aaaaaaaaga tttcaaggtg atgggtttca
53821 tgtggaccaa ttttatcctt ccctgatgat aatttgacat atgagtcaga tattttccta
53881 attttcgtaa ttcgagtggg attgtgtgtt tgtttgtttg ttttgagaca gggtctcact
53941 ctgttgttca ggctggagtg cagtaggcca gtcatggctc actgtagcct ggcttctca
54001 ggctcaagtg agcctcccac ctcagcctct taagtagctg ggactatagg tgcgtgctcc
54061 cacacctggc taattttttc tgttttttt tgtagagaca aggtctcatt atattgccga
54121 ggctgggact cctgagctca agtaatcctc ctaccttggt ctcctaaagt gctgggatta
54181 tatccacgag ccaccacacc cagcctcgca tgagatttta acagagcaaa gtacctgttg
54241 gaaatcttgc gcacaaagcc tcctttattc tgttattccc actgacagga attcagatac
54301 ctggatcaat tctgtttcgg ttttgctaaa atctctaact tgatatttta cttttctaaa
54361 aacctgtatt atcaatgaaa tggaattagg aaaacaggac ctatagaagt taagacctct
54421 tcaatctatt gatgtttcat ggtgcctttt atattcaaaa tgctttgttc tcacaaaaat
54481 aatacttttt gtttggagaa aaaggctgtg gggtgtgtgt gtgtgtgtgt gtgtgtgttt
54541 tcctctcaaa gatagcagta aaataaactc cttctgacaa aggcttctta aaagaaagga
54601 gaaaaaaaa ccttcctgct aattgtgttc tttaaaatcc tgattccccg ttttactttc
54661 tggatgtgta ttctgggctt tttcaatgtc aaccaatact ctcttgatgg gaaattcagc
54721 tggatttggg tatgttcatt gggttttcct agaacagttt gaagatccat ctcatttacc
54781 taaacaaata ttccttataa ttattatgaa aattgggcct gttatagact aataattgac
54841 ttaaaccata caggggttatg tttgtcagta tctcgtgagt cagcttttct aggggcagag
54901 attgaagagt tagttctgag attgaatact atttatcagg gttttgtttt gtgtaccta
```

FIGURE 14 (cont.)

```
54961 ttctcctgta accacctggt tggcttttat catagataca tttttgggaa acaggcaacc
55021 acatggttaa tgaagataga gaagacgtga aatttgttac ctttatagat tttttcccct
55081 tgccctgttc tcattcttct catttgccta aaaaaaaata taaggaggcc gggtgcggtg
55141 gctcacgcct gtaatcccag cactgaggca ggcagatcac ctgagctcag gagttcgaga
55201 ccagcctggc caacgtggcg aaactccgtc tctactgaaa atacaaaaat tagccgggcg
55261 tggtagtccc agctactgca ggtacctgag gcaggagaat tgcttgagcc tgagaggcag
55321 aggttgcaat gagccgagat tgtgtgccat tgcattccag cctgggtgac aaagcaagac
55381 tctgtctcaa aaaaaaaaaa aaaagtataa ggagtattca catttctatg agatctgtaa
55441 atttaggtta gaaaatttag ttaactgtgt tttgtaatag tcatataaat aagcacaaag
55501 accctccaga cttcttccca gcatgtgaca gtggaagaaa ggggtaataa agtagatttt
55561 tttgttactc tcattggtaa aaataagtct gtccatggga aggttaacac tgagtttacc
55621 atcttgatga ttccatatgg ttcctagcaa ttctaatctc aaagttggtt ggcagaatgt
55681 ttaggtcttt gggtagaata tcttctgtgc cttttctgtg aattgtaaaa ttacatttgg
55741 gaaataaaga aaaaaatccc tgattatccc actatagcaa tacaaccact gtaaacattt
55801 tggtatacag ttgtgttgca ttatatgcat tttctgattt ttgtatgtcc acctgtgctt
55861 atttgaactg tatcccctc cccacttccc acccctgtt ttctcactcc tggagtgagc
55921 atgggcagtg gggatgagac tcgcctgtgg cttcagtttg tctccttttc taagtttctc
55981 tgagtgggca ttcactgtgc tggctgtgat tctgttattt aaagcaatat attttcatac
56041 cttatggccc ttaaatgcaa gccaacctct tcatctggtg tcaaccaaag gaaaagtgat
56101 ctgttgcagc gctggaggaa aaactggcaa tgttggactt acctaaattg aaagatggta
56161 tgttgttctt caccttgggg tcttcaagta tgattttga cagtgcatgg tttttatctt
56221 acatgctgac ttttgtctct aacccttgag ttagatgcaa tttaattcca gcccttttc
56281 cctatataca ttttacataa ttatccataa gggtatattc attttaagg ctcttaaaat
56341 atactatatc aagtatcttt ccatattgct atacaatttt tgtagctgtc atttataata
56401 agacatttta gttttcgtct tttcagaaga attttgggag ctagtataat cagctcctta
56461 gaatgctttc taatttgcat actcaggtct actcacaata gttctgccat agatatttaa
56521 aatagaagca actgttatgc tgctaaattg aatatttctt aactaggctt atttcttaac
56581 aggggcatag atgtatgttt tcaggcatat gggaccctt ctgtaactag gcttctagag
56641 tttagaatta agattattta aattggtcta tgatcttatt gaagagtgag aggctagagt
56701 gtagtggtta aaaacatcaa cttgaatctg gactgcttgc atttaaagct cagtattggt
56761 acttacttgg ttactttgat cagtttacct atcctttctt tgccgccttc tacatggcta
56821 aaatcaggtt aataatattt acctcttaag atagtattgt gaatattaaa tcagtatata
56881 caaagtattt agaataaaat cttgaaccaa caagttttat gtaaatatta cttactttca
56941 taggctagtt tgctaattgc tgaaaatcct tatggcacaa ccatgagtct tgaacacaca
57001 gaataccttt ttttttttta acgttttagg cagtatagtt aaaccttaaa tttctgttct
57061 tgtttgatag ctaaagtttc agtcagaata aatttagtgt tgggcttgtg aatataatat
57121 taaatctgaa gtatgttgtc aacatatagt attgcagggt tgatgtctag aaatgctata
57181 ttagatgctc ataatgtttt ctgtatcttt tcttcccaa tgtctacttg tcctttagca
57241 aagtatgaac gttgtcatga atcttttctc tctgtccaca gattctgtgt gctcctctgg
57301 gccacagtag ttacttcttt aagcacagaa aggaaactta gggctttgcc agttttagta
57361 ttagttctct atgtttttca tccgggcagc tatggagagg gttgcttttcc acacacctgg
57421 gtactccatt gatatgttct gtagaggtaa tcaacacact agagagtaca cctgtttgtt
57481 ccatggctaa ccctttctga ttgtagacat gcatttgagt gtttgcagtg gatatttggt
57541 gctaacaggt gtcttagttc cttctgttat tctgtaatgt ttcccaagaa tattcagagc
57601 tgtttataaa atgcagagtg atttatgtat taggtgttca atgagtttga tcaagaagat
57661 tcacttgaaa ggaattaact aacaaagcag tttccattgt taataggata tgcatgctgt
57721 ttctctaaag tatttttatt tcttcaaaga gttattaagc agaggagact gattttgtgg
57781 taagtttgga ggggttagtt ttaatccacg ttggtcaaaa ctaaagtag attagaaaat
57841 ctatttctca tcctacagta gtgctgaggt ttctagtaga ttgttttttct tcttcctagt
57901 cattttctga aactcaaaac aagaatcaac ctataccatt gtaatgtttc acagttaact
57961 tggagtattt aacaagtcta aaatcaaagt ttattgttat tagtaaaaca ttttgaagcc
```

FIGURE 14 (cont.)

```
58021 attcatttca tgtgacaagg aatcttattt caccaaatgt ggtatgtttt taaacttata
58081 ctttctattg ttctagtttt gttgatcttt gatattgatg cagtgatatc agtttcctat
58141 tgttatatat actttgtggt caaaattatc ataggttttt gtgttttct ttgcctgagt
58201 tttgcttctc atctgaacat cacatcttt tcttgcggtt ccatttacac agtgtgattc
58261 ctagagatga gcttctttat cctctgaggc agtggaggaa gcatggaagc cacttgggga
58321 gcactgcatt gacaagtgta tttttgtagt cacatgctgg cagtgtcagg gaaattatag
58381 gactggttag attctagttc agcaacctat aaatcccagg acttccagt ctcgtgagtc
58441 atacaactct caggcctgtg ctgcaaatga cacttgctta ggagtaaggt gaagggtatt
58501 ttatagctct aatggtttgt acagttctta aacatgtatt gattgctaac aactgctgtc
58561 tttctcccag cttgccccac caccagtctt tgtgcataag cacaattttg gacatagtta
58621 tttgtactta tttatgcttt tacaccttct tccttttata aagattttag ctggtttatg
58681 acttgagttg aaacaaggaa aaaagagga gacctgaaat ggtctgtccc ctgccaacca
58741 gaagcctcct gtggtatcca aacagaatag ttgcctcagt ctgtcagcac ttctgtcttt
58801 gaaggtggtt tctgcttgaa aagtggtgac tattagcata gcctggggat aattgctttt
58861 ttttcttctc tcgggatacc tttttttttt tttttttcca gatactttct tgctcttgtc
58921 gactttgttt ttccagaaga tttagcctgt ggttaaaatg tttcgggtcc ccacgtgaac
58981 tctctgtggg attacccaat tctggggtac cttcaccaga tcaccagtgc taaagagggc
59041 aaaggatctt cttggttaat agaaaaggct gttttggaat gaatctcaaa gtccagaaac
59101 atcgagactt ttcttcaata ctttttcta tttggggtag caactttacc tagtgtaggg
59161 gagggagggg ttagttggga gggcttgtgt ttaaggggtt cagaaacagg ggatttaagt
59221 gtgtcttttg tgtttgcaag gcactaacac cactcccgtc tgtatttaaa tgctgtcccc
59281 aggttacgac tatggctatg tctgcgtgga gttttcactc ttggaagatg ccatcggatg
59341 catggaggcc aaccaggttg ctttatactt cggtcaaatg atgctggaag gatatatttt
59401 tttatatatg gggagggagg gtttcaaatg attttacttt ggaaaggtac aagaagtcta
59461 tctgtggagc atactgtatt ccaaccatcg gttgtgagga aaatctttaa aaaggctgga
59521 aagctttctc tacaaaactt aatgggcaca gagtgcattt taaaagctag agcccagttg
59581 cttttggact agattccaaa gacaatagtt ggaaaaaaaa aaaaaagaca catctggagt
59641 gtttcctttt ggagtgtgac tgagatggta atcctgatgc aaagaatgat ccttgattgt
59701 ctgtgacccc aaggatctgc ctagcacaga aattctaggt caatagttac acccagacct
59761 agggtgaaga cctctgatgg tgacttctgt ggcatcagat cctgcctgca ggggctactt
59821 ccaaaagaga gctatcaggg aagagagagg agtggattgt tggtgtctat tgcattcatc
59881 attgtttttt gccaattgga gttgcatact caagtccttg gctgcgtata gtcagagctg
59941 gtgaatcaga atctgtactc accttacgtt tgaactatct ggagttactc agcttgccac
60001 ctagattttt catctatgtc tttaatagaa ccctacctgg tagttttgag aggaattaat
60061 aaataggtag aatccttctt gttatggtgc ttccttgggg aaagttgttt tctttgggtt
60121 gtttcagttc ctccatctgt aaagtaggaa aagaaactta ggaatatagt ttgatgtgtt
60181 tttttttttct tttttttttt ttttaatgta cccactgcct atacttaaca gtgtgaatac
60241 agtgggccca gaatctttct ttctttcttt tttttttttt gagacggagt tttgctcttg
60301 ttgcccaggc tggattgcaa tggtgcgatc tcggctcact gctacctcca cctccctggt
60361 tcaagcgatt ctcctgtctc agcccctga gtagctggga ttacaggcat gcgccaccac
60421 gccggctaat tttgtatttt tagtagagat ggggtttctc catgttggtc aggctgctct
60481 cgaactccag acctcaggtg atctgcctgc ctcggcctcc caaagtcctg ggattacagg
60541 catgagccac cgtgcccagc caggcccaga atcttaaaag aaggctctgc cagagaagag
60601 tagttattag atgagaactc ttcttcttct gtagcctgat gctttgttca gctttgttta
60661 actcagtgtg gctcattata cgtacttttc tcttcttggc caagttctcc tcttatgggt
60721 atggagatga catgctctaa atgctttggg agcaagcact cattagagaa gacttttgat
60781 gtatccttat cttgttagta gtttaagctt gtcagatcct taaagaatga caggcttagg
60841 accatatccc ctagacttaa gaggattctc attgaccatt tgttcagtgt ccatcactga
60901 atcacttacc aaatacagtt gacactctgt atccacaggt tccacaccca tagattcaac
60961 caaatgctga ttggacatat tcaggaaaaa aatgcattaa cactgcaaca ataaaaaata
61021 atacaggcca ggagtggtgg cttactctgt aatcccaaca ttttgggagg cccgggtggg
```

FIGURE 14 (cont.)

```
61081  aggattgctt  gaggccagga  gtttgagacc  agcctgggca  acacagggag  accccatctc
61141  tacaaaaaat  aaaagtgaaa  aaattagcca  agtgtggtgg  ctatcaactt  gggaggctaa
61201  gatgagagga  ttacttgagt  ctggattgag  actgcagtga  gctgtgatca  ctctgctgca
61261  ctctagcctg  gggtgacaga  gtgagacccc  gtctcaaaaa  acaaaaaagt  acagttaact
61321  atttatatag  tctttattag  gtattagata  taagtaatct  agagatggtt  taaagtatgt
61381  tggaggatgt  gtgtaggttg  tatgcaaata  ccatgtgatt  ttatataagg  gacttgagca
61441  tcctgagatt  tttgtgtcct  tgtgggtcct  ggaaccaatc  ccctgtggac  accaagggac
61501  aactgtacta  accatgtgtc  agaaactgct  acatgccaat  tttggagaga  agaaaaaagc
61561  ttccaatctg  tgtgctttcg  gtggatccta  ttctgacagt  ctgtccaatt  ttgagaacac
61621  tcattaattc  ataagcagtg  aatgtgatta  agtcgttcgc  ctctgtgcta  aatactcaat
61681  gtaatagctg  atagctgagt  gctataaaga  aaatgaagca  gggtattggg  agaatgcatc
61741  atggtggcaa  ttttagaggg  gtggtcaggg  aaacttcttg  aggagtgaca  tacatttaag
61801  ttgtgactct  tggcgaataa  tgtatccaga  acacttacta  tagtacctag  cacttggtag
61861  catttgaatt  aatttgaaat  tcagtgtcct  tctttctctc  tcttaccctc  ctccacatgt
61921  caagtaattt  ccaattataa  attttgtgtg  tgtgtgtgag  acggagtcca  gccaggctgg
61981  agtgcagtgg  cgtaatcttg  gctcactgca  acctcgcca   cccgggttcc  agagatcctc
62041  ctgtctcagc  ctcccaggta  gctgggacta  cagatatgcg  ccaccatgct  tgggtaaatt
62101  tttttctttt  tttttttttt  ttgagatgga  gtctcgctct  gttgcccagg  ctggagtgcg
62161  gtggcacgat  ctcagctcat  tgcaacctct  acctcctggg  ttcaagtgat  tctcctgcct
62221  cagcctccca  aatagctggg  attacaggtg  cccgccacca  cacctggcta  attttttgtat
62281  ttttagtaga  gatggggttt  caccatgttt  gccaggctgg  tctggaactc  ctgacctcag
62341  gtgatccgac  tgccttggcc  tcccaaagtg  ctgggactgc  aggcgtgagc  caccatgtcc
62401  tgccaatttt  tgtattatta  gtagagatgg  ggtttcacta  tgttggccag  gctggtcttg
62461  aactgcagac  cttaggtgat  ctgcccacct  tggcctccca  aagtgctggg  atgacacgca
62521  cgagtcaccg  tgcctggcct  tcaattataa  ttataagaaa  ataaatttat  ttttatatct
62581  gaagtttaat  aaaactaatt  ctttaaggaa  atggatgtgg  attaaactcc  ttatgacata
62641  gtaaacaatc  ttatgagaga  cataagaatg  tgagggaaga  agtcctgtct  cctcagggtg
62701  aataaagtaa  atattttggg  aggctgaggc  gagcggatca  tgaggtcagg  agagcaagac
62761  catcctgacc  aacaaggtga  aaccccgtct  ctactaaaat  acaaaaaaat  tagccaggtg
62821  tggtggcgca  cgcctgtagt  cccagctact  tgggaggctg  gggcaggata  attgcttgaa
62881  cccaggaggt  ggaggttgca  gtgagccaag  attgcaccac  tgcactccag  cctgctgaca
62941  gagcaagact  ctgtctcaag  aaaacaataa  aattgaataa  ataaataaat  aaataaaata
63001  aatatttgtg  gaagataaaa  tgtgtttgta  ggccgggcac  tatggctcaa  gcttataatc
63061  ccaccacttt  gggagaccaa  ggctggagga  tcacttgagc  ccaggagttt  gaaatgagca
63121  tggggtaaat  agtgagaccc  tgtctaaatt  taaaaaaaaa  aaaaaaaaaa  aaaagtctt
63181  tgtctatcct  ttcccccagt  tttacttaca  gaccaaattg  gtatggattc  tgagtcacca
63241  cgatctgctt  ggcaactctt  agtagagcct  gagtgtgtgt  gtgcctctga  gaaggttact
63301  ccgaagtact  ttgagttttt  ttgtaactct  ttgctattcc  gactcttgat  gtgaaatgtc
63361  ttttatttat  cattggctgg  tacttgtagg  cctaggggat  ggaaataaag  gaattttctg
63421  ctagcttgct  ttgtcaaata  ttgttgggta  tgtgtgcctt  cgtgaagttg  ctcaagatga
63481  taaccaaggt  ccctctagcc  ttttcctggt  gcctagatca  agctgttaaa  cagtaggatg
63541  ctctgcagca  gtactgagct  ttgtggctgt  ggtgaccgat  cagggtatca  cttaggcagc
63601  agctgtctat  ctggagaaat  aatttccaac  aggtatgaag  gtatgaatct  gttagtctgt
63661  accatcacca  tttctgtcta  ggagaagggg  gcagccagca  agcactgtca  ggcagagcct
63721  ttcgttccac  ccttcctgca  aagtgtattt  ctagccctgt  catatgccct  tggctttctt
63781  tgttgtcaag  tctctgggag  attgagggta  catattattt  ccttctgctt  tgtgtgccct
63841  tgcactggga  cttggggagg  ggagtaagaa  gtattgtgtt  aaaatgttaa  tccctttcat
63901  tggttgccca  gttgtgagta  ctagccctct  cagactgttg  gcatttggta  tgcagggatt
63961  agcattttat  gttctcaagt  atgctggtgt  gatgcttatt  gtctattatt  tggccaaatt
64021  agtcactaaa  gtgcccttat  agaagataac  tctgggagag  gtatttattt  ctctgaaatt
64081  tttattctcc  ttcccccttt  cctttccttt  ccttttcctt  tttcttttttt  tctttccttt
```

FIGURE 14 (cont.)

```
64141 ttctcccctc ccccccctcc cctctcctct tattggagac aaggtctccc tctgtcacct
64201 acgctggagt gtagtggtac aatcatggct cactgcggcc tcgatctctt gtgccgaagt
64261 gatcctccca actcagttct ctttagtagc tggaactacc accaccacag ctggctattt
64321 tttttttttt tttttttgtag aggcagggtt ttgcaacatt ccccaggctg gtcttgaact
64381 cctggactca agcaatttac ctatctcggc ctcccaaagc actgggattc caggtgtgag
64441 ccactatgcc tggcctattt ttaaattttt atttttttga gacttagggt tctgttctgt
64501 tgctcaggct ggagtacagt ggtacgatga gagctcattg cagctttgaa ctcctgggct
64561 taagcaatcc tctcacctca gccttctgag tagctggact acaggcacct gccaccatgt
64621 tcggctaatt aaaaaaataa caaactctgt tcgtaaagat ggggtcttgc tgtgttgctc
64681 aggctgctct tgaactcctt gcctcaagtg agcctcccac ctggacctgc caaattgctg
64741 ggattataag catgagccac tgcgcccagc cttactcacc tttttgtatg acactatcag
64801 tctttctaaa gtgcaaagaa aaagggttct gttatcatct gatgtgaaaa ttcctttaaa
64861 cattgacttt ttctggtgtg aggaatgaaa gctgtggaat acgtgaagtt ttatgaaata
64921 gtgttttttt gtgtgtgtgt caacaaaatt aagagagttt gggttattga agatacaaga
64981 gtgttttttga aggtatatat aggaaaccaa atctcaaatg tggtctgtcc ttgtgattaa
65041 aattagagca ataggaagc caggtgtgat ggctcacacc tgtaattcca gcacttttgc
65101 aggctgtgac aggaggatca cttgagccca ggagttgagt ccagcctggg taacatagca
65161 agacctcatc tctacaaaac attgttaaaa attagctggg tgtagtggca catgcctatt
65221 gtcccagcta tttggaaggc taaagtggga ggattgcttg agcctgggag gtcaaagcta
65281 cagtgagccg tgattgtgcc actgcactgc aacctgggcg acagagagat cctgcctcaa
65341 aaaaaaaaaa aaaagcaaca gagaaagctt atgtttttag tgatgagaat gctatttgtg
65401 aggccatgat ggaaaaatt gaagaaccta gtttgttgga aacttaaatt ggtagtaaag
65461 acataatact atctgaaaca ctttagtact taaattgtgt gcattccaag caacaaaacc
65521 aataatctgt aggttgaagg ttgtagtgtt acctaaacaa ctatcacccc aaaaacactt
65581 cattgaggag tatccagcat cctagccaga gctcaactgt ataacttatg gctggaatca
65641 tgccattctt gctggaaact tcaatttcag tacttttttcc ttatcacccct cagaagggta
65701 gtagtagaaa catggggaac tgcattctaa aatgagtgta taggttcata acctagctag
65761 aaaaaaaaat taaaacaatt aatgagtaca aaccaagggt tattgaagag tctcgctctc
65821 aagagagttg gggtattcaa gaaaattgaa agtgagttta aggatcgatg acttgattac
65881 acattttggc tatttatcca ctgattgaga cttttttttt tgagatggag tctcactggt
65941 tcgcccagc tgtagcgcag gggtgcgatt tatccactga ttgagactttt tttttttttt
66001 tttttcagat ggagtctcgc tgtgtcgccc aggctgtagc acagaggtgc tcactgcaac
66061 ctccgcctcc tgggttcaag tgattctcct gccttagcct cccgagtaac tgggattaca
66121 agcatgtgcc accacgcctg gctaattttt gtatttttcag tagaaatggg gtttcaccat
66181 gttggccagg ctggtcttga actcctcacc tcaggtgatc cgcccgcctc ggcctcccag
66241 agtgctggga ttacacatgt gagccactgt gcccagccca gtgattgaga ctcgactgga
66301 catgaagcag tataatgtag cagtataaca tagtattctg gaagcagact accgggggtt
66361 gcatttcggc tccatcactt tctaaggtgt acttgaacaa gtggcttaac ctctctgtgt
66421 tttaacgtac tctcacacac atctagggat taaataagtt aatgcatgta aggtgattag
66481 aactggggct ggtggccggg tgcggtggct catgcctgta atcctagcaa gttgggaggc
66541 caagacgggc ggatcacgag gtcaggagat ggagaccatc ctggctaaca tggtgaaacc
66601 ccgtctctac taaaaataca aaaaattag ctgggcgtgg tggcgggcgc ctgtagtccc
66661 agctacttgg gaggctgagg caggagaatg gcgtgaactg ggaggcggag cttgcagtga
66721 gccgagatcg caccactgca ctccagcctg ggcgacagag tgagactcca tctcaaaaaa
66781 aaaaaaaaag aactgggget ggcacaaagt gaatgttgag tgcatctttg ttgttttcac
66841 acaacttctc atctgaaaca aagtcttaag ttacagcagc tctggtcttg gcttaatgga
66901 gtatatggca aaaagaggat ttggtggcag tgcctaggag gatttttttt tttcccatca
66961 acaatacttc tcatttagcc tgttgattga tacgattat cagggactc cttccagctt
67021 ccctagttgg agtttttttt ttttttttc cttttttgag acagggtctc attctgtctc
67081 ctaggctgga gtgcagtggt gcgatctcgg ctcactgcaa cctccgtttt tgggctcaa
67141 gccactctca tgcctcagcc tcccaagtag ctgtggctac agacacgtgc ctggctaatt
```

FIGURE 14 (cont.)

```
67201 ttgtattttt gtagagacgg ggttttgcca tattgcccag gctgatctcg aactcctgag
67261 gtcaaagcga tctgcctacc tcagcctccc aaagtgctgg attacaggag tgagctacca
67321 tgtccggccc ttagtaggag tttctgctgc cttagccttc aagagagaat cttaaatttt
67381 ctttttttt tttgagacag agtctggctc tgtcgcccag gttggagtgc ggtggcgtga
67441 tctcggctca ctgcatgctc cgcctcccgg gttcacacca ttctctcgcc tcagcctcct
67501 gagtagctgg gactacaggc gcctgccacc acacccggct aattttttg tatttttagt
67561 agagacgggg tttcaccatg ttagccagga tggtctcgat ctcctgacct cgtgatccac
67621 ccgcctcggc ctcccaaagt gctgggatta caggcgtgag ccacctctcc cggccataag
67681 aatcttaaat tttctaaaga gaaagagcag gagacagaca gtaccacatg gagtatgttt
67741 aggccatgta ggaaatctag cctgtggctt taaaaccgta agttctaaat tagctgggta
67801 tggtggtgca cacctgtagt cctagctact ctggaggctg aggtaggagg atcacttgtg
67861 cccaggagtt caaggttgca gtgagctgtg atggtgtcac cgcactccag cctgggcaac
67921 agaatgagat gctgtctctc aaagcaaaac accctaagct ctgataacca gcccattatt
67981 tgccacatct caggctcttt aattatgaga ggtgctctaa acgactcatt ttaattctct
68041 cgaatttgaa aaataaacat ttatcatttg gcagttttaa gggaaccttc tgatatgtgt
68101 cctacaatgg gtttataatt attttgtca caaatcatgg tttatttcta tggattaaag
68161 tagtttagtt cttaatttgt tctaaattgg aaatatacct atatgtttta acctcgtgct
68221 tcagtgttgt cacatctcat tagttcaggg gtcgtacaaa ggcatagttc agttagccat
68281 cttgattata actttggttt atgaccttat gtatgttcag atggtatagg gttcgtagca
68341 cagaaagatt tagaattcca gcttcattac ctcctggctc ttttgtaact tttttttttt
68401 tttttttt ttttgagac ggatcttgct ctgttgtcca agctggagtg cagtggtgtg
68461 atctgggctc aatgcaacct ccacctcccg ggttaaagcg attctcctgc cttggcctcc
68521 cgagtagctg ggattacggg catacaccac cacgcccagc taatgtttat tttagtagag
68581 atggggtttc accatgttgg ccaggctgga cttgaactcc tgacctcagg tgatccaccc
68641 accttggcct ttcaaagtgt tgggattata ggcgtgagcc accgtgcctg gcctctcttt
68701 tgtaacttct gaacctcagt tttctcatct gtaaaatgag aggatgatca taataccacc
68761 catagtgcag ttgtgaggtt agagtatgta gtatatgtaa agtgatcagc atgataactg
68821 gcatgtggta agtgctctgt agtaaagggt gattcataac actggactct gcttggttgt
68881 accaacttct catttccct ggctccttat ccacctcttg ggattcagag ttggctgaaa
68941 gtggcaggca gtgctgcttt gggtggcagc ttgattttag acagccagtt cacatagtgc
69001 ttttgttcag gacctctcgg gatttctaga cagacagcaa gagagttggg ctaacacctg
69061 tcatgaagtg tctaaggaat gagtgcacaa gcattcaggc atgtgagggc agaagaccat
69121 gaccatacct gccttcctac agtaaacagc ctgttgtttc tgcaggtagc attgcaggta
69181 gttcttttat cagaaaattc ttgtaggctg caggtgacat tgagtgttat taggtatctt
69241 cttcattcaa gttgaacttg gaggttacag tatatcttta tgtcccccctc tccacaggtg
69301 tttaagtgtt gtcattcatc ctctagtgca tagattatgt gtgcacattt cttgttaagg
69361 atattgatga actgatagtt tatctagaat aatgttttatt ttatattta ttttattgag
69421 acagggtctt gctctatcac ccaagctgga gtgcagcggc atgatcatgg ctcactgcag
69481 cctcaacctc ctgggttcaa gccatcctcc ctacctcagc cttctgaata gttgggacta
69541 caggtgtgcg ccaccacacc tggctaattt tgagggggta gaggggaggt acagatgaga
69601 tctcactgtg ttgtccaggc tggccttttg ctcctggact caagcagtcc tgcctcagac
69661 tcacaaagtt ctggaattac agatgtgagc cactgtaccc agcctagaat aattattatt
69721 tattttatt tttatttatt tatttttga gacagagttt tgctcttgtt acccaggctg
69781 gagtgcgatg gcacagtctt ggctcactgc aacctctgcc tcccgggttc cagtgattct
69841 cctgcctcag cctcccatgt agctggaatt acaggcacac caccacacct ggctaatttt
69901 tgtattttta gtagagacag ggtttcacca tgttggccag gctgctctcg aactcctgac
69961 ctcaggcaat ccaccgtctc ggcctcccca aagtgctggg attacaggcg tgagtgatgg
70021 cacccagcca gaataattag ttttaatctc acagggtgag atttgtgagg ttaattttgt
70081 atattaatga tgtatatatt accaaaatct gtggtcaagt gaaatttgtg cttaatcttt
70141 gcaaatgcta tttccaaagg aaaatatgta ggagaaaagg tggtgtatca caggatgtag
70201 agtagtggtt actgggcaca agggtggccg ggagtcggg gggtggcagg agaggataga
```

FIGURE 14 (cont.)

```
70261 gaatgataac tgattgatac agggtctctt ttttgggatg aggaaaatat tttagaatta
70321 aatagtgagg atggttgacc aagcttgtgc atgtactaaa agccattaaa ttgtatatac
70381 tttaaaacag tggattttat ggtatgtgaa ttttatctca attttaaaaa aagtctttaa
70441 atgtagtatg aaactttttt taaggccagg cagggtggct cacacctgta atcccagcac
70501 tttgggaggc tgaggcgggc agatcacctg aggtcaggag ttctagacta gcctggccaa
70561 catgatgaaa ccctgtctct accaaaaata cgaaaattag cccagcatgg tggtgtgttc
70621 ctgtagtccc agctactcgg gaggctgagg caggagaatt gcttgaactc aggaggcaga
70681 ggttgcagtg agctgagatt gtaccactgc actccagcct gggcgacaga gcaagactgt
70741 ctcaaaaaaa aaaaaaaaaa aaaaaagtt tttttagggt tccagcacaa tgggaatgag
70801 tccagatcta aaataaagta cagattcatt taccaccctc caccctaccc caaccccca
70861 aaaagattgt ctatcagttt gtcaggaagt tagagtaaaa tggtcttaaa atgcatcaag
70921 agggctgggc acagtggctg atgcctgtag tttcagctac tcaggaggct gagataggag
70981 gatcacttga gcccaggaat tcgagtgagc catgattaga tcactgcact ctagcctgaa
71041 tgacagagca ataccttgtc tcttaaaaaa aaaaaggcat gaagaatttt tttgctaatg
71101 gtatctactt accacagagg aacatttaag ctaaacatct gaaagattat ggatggagtt
71161 ggtaacaggc tccatttgaa ctggttatgt agtttatgct cagtaaggtt gaacggactt
71221 tctgctttga gttattcaca gttaaaaata aaggactatt ttgaagtaga ccgaaaatga
71281 aaataacatt aagaaatcct tggactaatt tttaggggag attcctgtaa tcggatggtt
71341 tgtagttgtc aatgtagacc tttcctggtt tcctgaaatt gctaatcaaa gctcaaagcc
71401 atgggaaaag actggattgc agctagaatg tgtgctctcc acatatgtct ttcttagagg
71461 cctctttcaa gcagcattga cactatggct atcatctttg accctcttag tatacagaga
71521 gttgtaggtt ttctttttt aaggggaaa acattattga cataaattat atatcataaa
71581 agtcactcat tttaactgta caattcaatg atttttagt aaatttacca agttgtaaca
71641 tttattatta taattagttt tacaacattt ttctttctt tctttttttt ttttctttt
71701 tctttttttc tgggacacag gatcttgctc tgttgcccaa gctgagtgca gtggcatgac
71761 catggctcac tgcagcctcc acctcccggg ctcaagcaat tctcccacct caacctcctg
71821 agtagctgga actataagtt ggaaccatcg tgcccagcta atttttatt ttttgtagag
71881 agaaggtctt gctatattgt ccaggttggt cttgaacttc taaactcaag caatccttcc
71941 tgcctcacct tcccaaagtg ctgggattac aggtgtgaac catcatgcct ggtctagaac
72001 attttcatta cctcaatcgg atccccgttt ggggatacat ttacatttt aattttttaa
72061 ttttttatttt ttttagagac gaggtctcaa tctattgcca aggtggtctt gaactcctgg
72121 tttcaagtga tcctcccacc ttggtttccc gaagtgctgg gattacaggc atgaaccacc
72181 atgcccagtc cattccaatt ttttttttct ttttttttga gatagagcct cactctgtcg
72241 cccaggctgg agtgcagtgg cgtgatctca gctcactgca acctccacct cccgggttca
72301 cgccattctc ctgcctcagc ctcccgagta gctgggacta caggtgcctg ccaccacgcc
72361 cggctaagtt tttgtatttg tagtagagac ggggtttcac cgtgttagcc aggatggtct
72421 caatctcctg accctgtgat ccgcccgtct cagcctccca aagtgctgag attacaggcg
72481 tgagccaccg tgcctggccc attccaattt tttacaaaag tgatttcaga cttataaaaa
72541 agctgcaaaa attcctgtgt tcttttcacc tagattctac cttttttttt tttttttttt
72601 ttgaggcgga gttttgctct tgtttcccag gctggagtgc aatggcgcaa tctcggctca
72661 ccacaacctc cccgtcccgg gttcaagcaa ttctcctgcc tcagcctccc aagtaattgg
72721 gattacagcc atgcgccacc acgcctggct aatttttatat ttttagtgg agaccaggtt
72781 cctccatgtt ggtcaggctg gtattgaact cccgacctca ggtgatctga ccacctgggc
72841 ctcctaaagt gctgggatta caggcgtgag ccacgtgcc aggcccaccc agattcttct
72901 tagcacattt gaatgcagat ttttgaatag ttatgatcta ttctcattga aaagggaca
72961 tcatttgact tgacctccca ccagactctt cctttgaggt tggatggagg tgcttaatgg
73021 atgctgtgga tggtgtgtga atttccattg ggttgagtgg atgatgtatg tggaaggcga
73081 ttgggattta ctttgtcggt gtctccaaga ggtcccccac tgggctttgt caggtgctgg
73141 ggttggaggt caagaagtag ggcaacatct aaagcttcta ctcctgggca ctgtgaggtt
73201 tttataggtc ttttaaaaaa aacagtgaat aggccgaacg cggtggctca cacctgtaat
73261 cccagcactt tcagaggccg agggaggcgg atcacgaggt caagagatca agaccatcct
```

FIGURE 14 (cont.)

```
73321 ggcctcgtgg tgaaacccca tctctactaa aaatacaaaa attagctggg catggtggca
73381 catgtctgta gtcccagcta ctcgggaggc tggagcagga taatcgcttg aaccctggag
73441 gtggaggttg cagtgagccc agatttcacc actgcactcc agcctggcga cagcgaggct
73501 ctgtctcaaa aatatgttct tccatgagac agcgggcatt tggatgcctg atacaaaaag
73561 aggagggact atgtgctagt cagctttaga ctgagaagca gcagcaacca tggcaaaggg
73621 gaagcaaact ttcctgagtg gccttaataa tgttattcgt caggcagtgg ctcttaaaca
73681 ggggcttcaa gcagtgattt ttgacatgct cttctcctcc ccaaccactg gacatttggc
73741 aatgtctgga gacatttttg gttgtcacca ctgggagagg gtgctactgg tatctagtga
73801 atagagccag ggatgctgct aaacatccta cagtgcaaag ggcagctctc cacacaaaga
73861 atcatctggc ccaaaaatct ctattgctga ggttgaaaaa tactggtgta aggagacaag
73921 agttgtggtt agtcagaaag gatgacctgg cttgccgtgg attgtcttat aataatcagt
73981 tatctctttc cttgccttat tcctggtccc aacagagtga ggattggcaa ggggggtttgg
74041 gaatatagtg ggaatgctgt gtagtgagag tgcaggcacg gcactccaga ctaccagtca
74101 cgagcttagc ctgtgtcctt ggggtaggag ctgtagaata agacctattt tgatatgtgg
74161 accagaataa gttctttaaa taatcaaagg taataaacat tcttaaaata tactatcact
74221 aaggtagtct gtcatccagc agaatgaggg agtagtcaga agattacaca tatttggcag
74281 caattactag aaaaaacaaa caagttgaga gttttcaaaa tagatgttac ttcatatttc
74341 agatagtttt ccagggaata ttgaaaatgc aagtgcagat tttcacatcc ttctttatac
74401 tgattaaaac atttgaatct attggatcat cttttcatta ggctttactt cacagggcca
74461 tctactggat cctgtatgct gatatagtta aggggactga cctcaaagta aaagatgcat
74521 atattttatc ttaatacaat atcactttgc tgtgaagggg agctgctgtg tatatagaat
74581 gctgtgtaat agtgattggg ctgttgggaa tcacattgga aatatcagta agcaactcat
74641 tttaactttt gttaacacag ttaagtgctg agcacctctt gtgtttgaag ctctgtgcta
74701 ggtaatatgt gttcattaat gaatgaaaaa acaatacaaa aattagccag gcatggtggc
74761 gtacacctgc agtcccagct actcaggagg ctgaggcaca agaattgctt gaacccagaa
74821 ggtggaggtt gcggtgagcc gagatcacgc cactgtactc cagcctggcc aacagagtga
74881 gactgtctca aaaaaaaaaa aaaaaaaaaa aaaagttttt tattttttaaa ttttttgttt
74941 tatttctttt ttacttttttt ttcttttgag acagagtcac gctctgtcac ccaagctgga
75001 gtgcagtagc accatcttgg ctcactgcaa ccccccgcct gccaggttca agtggttgtc
75061 ctgcttcagc ctcccaagta gctgggacta caggtaccca ccaccacgcc cggctaattt
75121 ttgtattttt agcagaggcg gggtttcacc atattggcca ggctggtctc aaactcctga
75181 ccttatggtc tgcccgcctc agcctcccaa agtgctggga ttacaagcat gagccactgt
75241 gcctggcaaa attttatttt tattattatt attattttttt tttttttttt tgagatggag
75301 cctcgctctg ttgcccaggc tggagtgcag tggcgcgatc tcggatcact gcaagctccg
75361 cctcctgggt tcatgccatt ctcctgcctc agcctcctga gtagctggga ctacaggcgc
75421 gtgccaccac gcccggctaa ttttttgaat ttttttagta gaggcggggt ttaccatgt
75481 tagccaggat ggtctccatc tctgacctc gtgatccacc tgcctcagcc tcccaaagtg
75541 ctgggattac aggcgtgagc caccgctccc ggccaatttt tatttttattt ttaattgata
75601 attgtacatg tttatggagt acccatgtta tgatacatgt gcacattgta gaataatttt
75661 taattgataa ttgtatacgt ttatggagta cccacgttat gatacatgtg tacattgtag
75721 aatgattgaa tcagactagt taacatatcc atcacctcat gtagttattt ctttgtagtg
75781 agaacattta aaatctcttt tagcaatttt gaaatagata caatacattg ttattaacta
75841 tagtcaccat gctgtgcaat agataactaa aacttcttcc tcctgtctga ctgaaacttt
75901 atactctttg actaacattc tcccgttctc ctccaccgc cttctccacc cacggcctct
75961 ggtaaaccac cattctgctc tctacttctg tctgaatatt tgattttttt agattgcaca
76021 tgtgagatca tgcagtattt gtctttctgt acctagttta taatacactt agctaagtgt
76081 ccttcatgtt tttccacatg tcgcaaatgg cagaatttcc ttcttttta aggccaaata
76141 gtatttcatt gtgcttacat accacatttt cattatccat tcattcattg atgggcaatg
76201 gatgaatgga tatcatggct attgtgaata gtactgcagt gaacatggga atgcaggtat
76261 ctctcagaca taatgatttc agtttcattg gatatatact gtacccaaaa gtgggactgc
76321 tagatcatat ggtgattctc gttttagttt ttttttttttt aagaacctcc atacagtttc
```

FIGURE 14 (cont.)

```
76381 caaaatatct gtactaattt acattcccac agtgtaaagg gttccctttt ctccatatcc
76441 tcactaacac ttgttaccgt tcatctttt tatagtaacc atgctaacaa gtatgaggtg
76501 acatctcatt atggttttgt ttgtttgttt gagacagtgt cttgctgcat cacacaggct
76561 ggagttcagt ggcgtgatcc cagctcattt gcagccttaa cttcctgcac tcaagcagtc
76621 ctcccacctc agcctcccag gtagctggtg tgtcaccatg cctagcgttt ttttttttt
76681 tttttgaga cagagtctcg ctgtgttgcc caggctggag tgcagtggta tgacctcggc
76741 ttactgcaat ctctgcctcc cgggttcaag taattctcat gcctcagcct cctgagtagt
76801 tgagattaca ggcatgtgcc accacaccca gttaactttt gtatttttag tagagatgag
76861 gtttcattat gttgtccggg ctggtcttga actcctaggc tcaagtgatc ctcccacctt
76921 ggtttctgaa agtgctggga ttaccagcat gaaccactat gcccagctcc ttatggtttt
76981 aatttgtaat tctctgataa ttattgatgt tgaacatttt gtcatatatt ttttggcaat
77041 tttttttctt cttttaaaaa ttttgttttt agccataagg ccaggaatgc acgtatgtct
77101 tctttcaaga aatgtctggg ctggcacag tgctcacgc ctgtaatccc aacactttgg
77161 gaggccgagg cgggtggatc acgaggtcag gagatcgaga ccatcctggc taacatggtg
77221 aaacccgtt tctactaaaa atacaaaaaa attagctggg tgtggtggtg ggcgcctgaa
77281 gtcccagcta tgtgggaggc tgaggcagga gaatggcgtg aacccaggag gtggagcgtg
77341 cagtgagcca agatcgcgcc actgcactcc agcctgggcg acagagcaag actctgtctc
77401 aaaaaaaaaa aaagaaaaaa gaaaaaaaaa tgtctattca ggtcctttgc ccatttttta
77461 atagggttat ttgttttcat tattgagtag tttgagttct ttgtacattt tggatattag
77521 ccctttatca gatgaagat ttgtaagtat tttctctcaa tctgtgcatt gtttcttcac
77581 tttgttaatt gtttccttgc tttgcagaag cttttagtt tgacgcaatt ccatttgtct
77641 gttttgctt ttgttgcctg gcctttgggg gtcatgcaca agaaatcatt gcctagacca
77701 gtgttgtgga gctttccaac tatagtttct tctagtagtt ttacaatttc tgttcttaca
77761 tgaagctatg aacagttcct gtatagttat ccctgccacc cttctcccaa cattacatac
77821 acagcctccc caactatcag catcctgcac tgtagtgtat atgttacaat cagtgaagca
77881 acattgatac atcattatca agggttcact ctgggtgttg taccttctat gggtttccac
77941 aaatgtatgt catatatcca ccattatagt atcatacaga atagtttcat tgccctagaa
78001 accctctttt ctccacctgt ttgttctttc ctcttgcaaa cccctgcaac cactgaactt
78061 tttattgtcc gtgtagtttt gcctttgca gaattttata tagttggaat tggacaatat
78121 gtagcctttt cagattggct tctttcattt agtagtacat ttctctatgt agtctcattc
78181 ctctatgtct ttttgtggtt tgatagctca tttcttttta gcactgaata atatcccatt
78241 gtatggatat atcacagttt attcattcac ctactaaatg acattttggt tgcttccatg
78301 ttttgacagt tacgaataaa gctgcaataa atatccatat gcatgttttt gtacggacat
78361 acgttttcaa ctagttttggg taaatacaag gggcatgatt actggatcgt atggtaggag
78421 tgtgtttttt tttttttttt tttttttttt ttttgacacg gagccttgct ctgtcaccag
78481 ctggagtgca gtggtgcgat ctcggttcat tgcaacctct gcctcccagg ttcaagtgat
78541 tcttctgcct cagcctccca agtagctggg actacaggtg catgaccatg cccagctaat
78601 tttttgtatt tttagtagag acagggtttc aacatgttgg ccaggatggt cttgatcttg
78661 tgacctcgtg attcgtccac ctcggcctcc caaagtgttg ggattacagg cgtaagccac
78721 tgcacccagc ctgtagagta tgtttaattt tgtaagaaac tgtcaaacag ttttttccaaa
78781 gtagcgatta caatttgcat tgctaccagc aatgaattag agttctgttg ctctgtatcc
78841 ttgccagcat ttggatggta gccattttta ttttatttta tttattttt tttttgaga
78901 caaggtcttg ctctttcacc caggctggag tacagttgga cgatctcagc tcactgcagc
78961 ctccgcctcc caggttcaag ttattctcct gcctcagcgt tctgcatagc tgggattaca
79021 ggcacgcacc accacaccca gctaattttt gtatttttag tttcaccatg ttggctaaga
79081 tggtcttgaa ctcctgacct taggtgatct gcccgcctt ggcctcctga attgctggga
79141 ttacaggcat gagccaccat gcctggcctc ctttgggtat ttctattgga cagtcatgtc
79201 attcatgaat aaagacaatt ttatttcttc ctttctaatc catataccttt tatgtcctt
79261 ttcttggctt attgcactag ctaggatttc tagtacaatg ctgaaggag ctgtctttct
79321 cttcttttct ctcctttcct tgccttttcc ttttcttctt tttctttctt ttcttcctat
79381 agagataggg tctcgctatg ttgccaaaac tggtctccag ctcttgggcc caggtgatcc
```

FIGURE 14 (cont.)

```
79441 tcccacctca gcctcccaaa gtgctgggat tacaggtgtg agccaccaca cctagctgaa
79501 aaggagctgt tgagaataca tccttgtctt gttcctgatg ttagtgggaa gaaagcatct
79561 agtctctcac cataagtgtg atgttagcta taggtttatc aagttgagga ggttcccctc
79621 tgttcctagt ttgctgagag gtttttttttt ttaaatcatg aaaggggatt ggattttttgt
79681 caaatgattt ttctgcatct attggtatgt tcatgttaat ttcttcttca gcatgtcgat
79741 gtgatggatt acattaattg atttttttttt ttttttttag atgcagggtc tcactctgtt
79801 gcccaggcta gagtgcagtg gcacaatcac agctcactat aacctcaagt tcctcagctc
79861 aagcaacttt cccatctcag ctttccaagt agctaggact acaggcacat accaccatac
79921 ccatctagtt ttttaaaaca ttatttgtaa agatgaagtc tctctatttt gtccaggctg
79981 gtctggaact cctgggcggg ctcaagcagt cttcaccttg gcctcccaat ttgtttggat
80041 tacaggtgtg agccactatg cccagcctca ttttttgttat tagtaatttg tatcttcttt
80101 cttttttttct tagactggtt aaatgtttat caattttatt gatcttttca aagaaccaac
80161 ttttggtttc actgatttat ctctattgat ttactgtttt caatttcatt gacttcagct
80221 ctaattttta ttattttctt ctgcttactt ttgatttaat ttgctctttt actggtttcc
80281 taaagtggaa gctcagatta ttgattttct ctcttttaat atatgcattc
80341 agtgctataa atttccctct cagcactgct ttttgtgtat cgcacaaatt ttgataagtt
80401 gtgttttttca ttatcgttta cagttgtgtg ttaatcccca tacagttaat gatggggata
80461 aattctgaga aatgcactct taggcaattt tgtctttgtg caaataccat ggagtgtaca
80521 tacacaaacc taaatggtat agcctgctac ccacctaggc tatatcattt agcctattgc
80581 tccttaactg caaacctgta caacttgtta ccatattgta tatgataggc agttgtgaca
80641 cagtagtatc taaagataga aacggtacag tgaaaataca gtatttcagt attttgggac
80701 caccatcata tatgcaagcc cattgttgac tgagatgtca ttatacagca tctgaccata
80761 attcggaata ttttttaaatt cctcttgaga tttcttcttt agcttgtgtg ttatttagaa
80821 gtatgttttt aaatctccat atactttggg attttttacaa ctatattact gttactgact
80881 tctagtttaa ttctattgtg atctgagagc atatattatt ttttctgtca ttttaaactg
80941 gaaaaggtat gttttatggc ccataatgtg ctgcgtgagc ttgaagagaa tatgtagttc
81001 gctgttgctg gatgaaatag tctacaaatg ttgattagat tgctgctgtt attttgatgc
81061 gtatccttcc agatttttct atgcatgtat catctatctg tgtatctatc tgtaggatag
81121 gagagtcttg tacaaatggt tttataactc tttaacttca aatattgtgg acttacttcc
81181 ttgtcattaa atacatttaa ggctgggtgc agtggctcat acctgtaatc ctagcacttt
81241 gggaggccga aacaggcaga tcacctgagg tcaggagttt gagaccagcc tagccaacat
81301 gttgaaaccc cgtctctact aaaaatacaa aaattagctg ggtgtggtgg cacacgcctg
81361 taatcccagc tgctcaagag gctgaggcac gaaaatcggt tgaaccaag gaggcggagg
81421 ttgcggtgaa ccaagattgc gccagtgcac tccagcctgg gtgacagagc aaaactttgt
81481 ctctaaataa ataaatcaac aaataaaata catacctatg tacatacata cattttaaga
81541 atcatttga tatattcatc tccatactga ggaatttaag tgcttttttt ttttttttttt
81601 tttttttttt tttgagacag agtctcactt tgttgcccag gctggagtgt ggcggcacga
81661 tcttggctca ctgcaacctc tctacctcct gggttcagga aattctcctg cctagccggg
81721 tgagatttcc tctttagctt gtgtgttatt tagaagcatg ttttttgtacc tatcgtagct
81781 tctctagaga agggaggtag gagaatcgct tgagcccggg aggtcaaggc tgcagtgact
81841 gacccatgac catgccactg cactgtagcc tgggtgacag agtgagcccc tgtctcaaaa
81901 aggaaaaaaa agaaatcagc atattttatg acttaataaa tgtattcaaa ttccatccag
81961 atatttccta atttattatt ttactaacag tgtttgagag cacttgtctc ccctgccttc
82021 caaccagtgt caagtgtatt ttaacaaaat acttgtattg ggtagtagta catggttggt
82081 tgttactctc taatcgcctg ttgtgtttga aatatttaat aattttttta atgttgctag
82141 tgtagtgaag aagataatga tttagttttt cttctttctt ttttttttttt gagatggagt
82201 ttcaccttg ttgcccaggc tagagtgcaa tggtgcgatc tcagctcacc aaaacctctg
82261 cctcccggt tcaagtgatt ctcctgcctc agcttccga gtagctggga ttataggctc
82321 atgtcaccac gcctggctaa ttttgtattt ttagtagaga cagggtttct ccatgttggt
82381 caggctggtc gcgaactccc gatcttaggt gatctgccta ctttggcctc ccaaagtgct
82441 gggattacag gcgtgagcca ccgcacctga caaatgatgt agttttctc ccttaggtta
```

FIGURE 14 (cont.)

```
82501 ttagtaggca gaatagtttt acatttgatt attagttatt catatttctt ttgtgacttg
82561 ttggttctta atatatctat tcagccaaaa atgaaaaata ggatatctta gcctgtctag
82621 tcttaaggta aatatatgtg ggatataagg gagtttgggg gctgggcgca gtgactcaca
82681 cctgtaatcc cagcacgttg ggaagctgag gtgggctgat cacttgagcc caggagttca
82741 agaccagcct gggcaatgta gcaaaacccc atctctacca aaagtacaaa aattagccag
82801 gtacagtggc acatacctgt attcccagct actagggagg ctgagatgga aggatagctt
82861 gagcccaaga ggttgaggct gcagtgagct ataagcatgc cccactacat tccagcctgg
82921 gtgacagagc gagaccctgt ctcaaaaaaa agatttttt gaaaagttga aaatgagtat
82981 attcgctgaa tacgagatga gttttcccaa gaatttatcc ctcagaatct ttcacgttct
83041 tcctcctcct tctcctcctc ctgctttctt cttcttcttt cttcttttc tgtttcttct
83101 tcttgctttt ataaagtctt agctcctgtg gagttttctc tcagttactt cttatttatt
83161 tatttgagac agagtttcac tcttgttgcc caggctggag tacagtggcg cgatctcggc
83221 tgactgcaac ctccgcctcc tgggttcaag ctattctcct gttcagcat cccaagtagc
83281 tgggattaca ggtgcctgcc accacacctg actaatttct gttacttctt ttgagccaca
83341 aagtatttga aaaagatgca ttaagtagtg accgcagtcc gtgctagtat tgggtgctta
83401 cagaggtcta gtagaatacc gtgttttaaa aggaggtgaa tttaataatt gctgtgatta
83461 ctctggcatt atacgctcac aaataaaatg tttggtgatt ttttttttt tttttttgg
83521 agacagattc ttgctctgtc acccaggctg tgcaatgatg tgatctcagc ttactgcaac
83581 ctccgagttc aagtgattct cgtgcctcag cctctcgagt agctgggatt acaggcaccc
83641 gccatcatgc ctggctaatt tttgtatttt tgtagagatg gggtttcacc atgttggcca
83701 ggctggtctt gaactcctga cttcaggtga tccacccatc tcagcctccc aaagtgctgg
83761 gattacaggt gtgagccact gctcccagcc gggtgtgata ttttaataa aacaagtatt
83821 caaattcact tacaggacca atgaaagaat cgtttgtcgt aatttttatgc caaagggtac
83881 ttgtggctta agataaactt cccataatga cattatccac agattcaaaa agtagtttat
83941 cttaaacaac ttctgtgaca ttttaaaatg atgtggctta gaaaattgct aggttatcta
84001 aaatggctct attgatgatg taaatgtagc acatgaagag cttgaataaa atagactttt
84061 gaagtgtgca aatggaaaga acagtccttc taaataatta tttccctcc cttttattga
84121 cgtatacata cagaaaagat atcatgtcgt aagtgtattg cttagtgaat tactccaaag
84181 ttggatatac ctggttaacc accacctgaa tgaaaaaaac agaacactgc ttcatatgga
84241 gaagcccctc ctgcccctcc tggtcattgt ccttttcatc cctcccacag gtagtcactg
84301 agttctaata ccacagagtc ttttgacttt cttttgagcc ttatgtaatt agaatcacaa
84361 aagatgtatt cttttgcctg acttttatac ttagtattgt ttttgaaatt catcttgtgt
84421 gtaactgcga tttgttcatt tcattgcctt agtgaattat tccaaagttg gatatacctg
84481 gttaaccacc acccgaatga aaaaaacagt ttttggccgg gcacgatggc tcacgcctgt
84541 tatcccagca ctttgggagg ctgaagcgtg cagattacga ggtcaggaga tcaagaccat
84601 cctggctaac acggtgaaac cccgtctcta ctaaaaatac aaaaaattag ctgggcgtgg
84661 tgacgggccc ctgtagtccc agctactcag gaggctgagg caggacacct gtaatcccag
84721 ctacttgaga tgctgaaaca ggagagtggc gtgaacttgg gagatggagc ttgcagtgag
84781 ccgagattgc gccactgcac tccagcctgg gcgacagagc aagactccgt ctcaaaaaac
84841 aaaaacaaa aacaagaaa acagttttcc agtctaagaa tgtattacaa tttattcaaa
84901 ttccactcta gatggactgt gggttttttt tttttcccca tttggagcta tggcaaatga
84961 tgttttttca aagttgttat ttctcagcca ggcgcggtgg ctcacgcctg taatcccagt
85021 actttgggag actgaggtgg gcagatcacc tgaggtcaga agcaagacca gcctggctaa
85081 catggcgaaa ccccgtcttt tctaaaaata caaaaattag ccaggtgtgg tgatgggcac
85141 ctgtaatccc agctacacag gaggctgagg caggataatc acttgaaccc aggaggtaga
85201 ggttgcagtg agctgagatc acaccactgc actccagcct gggtgacaga gcgagactct
85261 atctcaaaaa agaaaacaaa acaccacgga attgttattt ctcttggcga ataggtagat
85321 gcacttattc ctgttaatat atacctacct gtgaatgtgc tgttggatt tctatgtat
85381 cttctgtctg ccacctagaa atttaacctt ttatatatat acaactttaa ttttttttt
85441 tttttttta agagacaggg tgtcactatg ttgcccaggc tggttgggaa ctcctggcct
85501 taagccgtcc tcctgcttca gtctcccaaa gtgttgggaa tataggcgtg agccactgtg
```

FIGURE 14 (cont.)

```
85561 ccccactgtt caagtttttca ttgattgctg cctacatata gttgttcaac agctattgat
85621 tccccctgct ctgtatatat gtctcctagt gtaggtatca gggttacagc agtaattaag
85681 accacattat ttcattttat catttaaata tataagacta attgataaat taagtataga
85741 actttgacca acatggtgaa accccatctc tactagaaat acaaaaatta gctgggtgtg
85801 gtggcagacg cctgtaatcc cagctactca ggaggccgag gcagaactgc ttggagatgg
85861 aggttgcagt gaaccaatat cagaccacta tactccagct tggatgacag agggagactt
85921 tgtctctttt ttttttttctt ttttttttgag acggaatctc gccgtcttcc aggctggagt
85981 gcagtggcac gatctcggct cactgcagcc tccgcctccc gggttcaagc gattcttcta
86041 cctcagcctt ccgagtagct gggattacag gcacccacca ccatgcccgg ctaattttg
86101 tattttagt agacagggtt tcaccatgtt ggccaggctg gtctcaaacc cctgacctca
86161 agggatcaac ctgctttggt ctcccaaagt gctaggatta taggcgtgag ccactgtgcc
86221 cggcccttt ttttttttt ggagacagaa tttcgcccag ttgccagact ggagtgcagt
86281 ggcacgatct cagctcactg caacctctgc ttcatgggtt caagccattt tcctgcctca
86341 gcctcccaaa tagctgggac tacaggcatg caccaccacg tctggctaat ttttgtatt
86401 tttagtaaag ccagagtccc aaagtgctgg gactaggcag gcgtgaacca ccacgcctgg
86461 ccaagactct gtctctcaaa aaaaaaaaaa agaaaaaaaa atataggact ttgggaggcc
86521 gaggcaggca gatcacctga ggtcaaaagt ttgagaccag cctgactaac atggtgaatc
86581 cccatatcta ccaaaaaata caaaaattag gcaggtgtgg tggcgtgcac ctgtagtccc
86641 agctattggg gaagccgagg tgggagattg tacctgggag gcagtgagca gagatcgcac
86701 cactgcactc cagcctgggt gacagagtga gaccttgtct caccaaaaaa aaaaaaaaaa
86761 aaaaaatagc ataggtaggc atttgatgat ttgatgattt cattcgcatc cctaaaagtt
86821 tatttgttcc tgggtcgtca gatagcttt tgccatctt cctgttgaga aaattgatgt
86881 acccttctgg agtcctccaa ttttccatta taatatggta agtgggagct agagctttgg
86941 gtaagaattg ggatgtgata aggaggatga gttttgcagt ggtgtgcatg gttaggagga
87001 gaaaagctg gaggcagagt gttcacttag aggcttgggg taggaggggt aggtttaagt
87061 ggtgctcatc tgggccagaa tagggcaaaa agggaagaat gaaataacca gatgtctttg
87121 ctttgtcagt agtcttgcag ccctgaaagc ttttttttgtt gtgttatatt tgttgtaatt
87181 gaggtataat ccacataaca taaaacttac ctctttcaag tgtacaattt agtagttttt
87241 agtatattca taaaattgtg caactatcac cactgatacc agaacatttc tgggaacaaa
87301 aagaaactat atatccatta agagtcactc tccatttcct cctacttcct tctctaccc
87361 cagtcatctg ctagtcggct ttctgtctct atagatttgc ctgctctgga tatttcatat
87421 aaatggaatc ataccata tggtcttttg tgactggctt cttttactta gcctaatgtt
87481 tttaaggttc atccatgtta tatgaatcag tacttaaatc atttataggg ttgaataata
87541 ttccatcata tggatatacc acattgtctt tatctgctca ttaattggta gacatttagg
87601 ttgtttccac ttttgtttat tatgaataat actattcaca ttcatgtaca aggttttgtg
87661 tggacacatt ttcagttctc ttcgatatat accaaagagc cacaatgcta aaacttccag
87721 cttttttacca gctatcccca gatgcgtagc ctagtaagcc ccatgttgga gtggtgtagt
87781 gttgaaaaca tggcatactc atacattaga taaccaggtt tcaattctgg tttgaagcc
87841 tttgatatt tgcattaccc atttgaattc tctcttgggc tgtgtttggt ttggggttt
87901 gtacttgttt ttttttttttt aactagatgt tttgaggcac ttggtactgt ggacatgtgt
87961 cagtcttaaa tatttgggtt ttgagcatat caagggcttg gtttgcagtt gacagttgaa
88021 tagcagtctt cttccttcca ttccttacag attctcctgt tcagagtcaa ccattgaata
88081 gcatatttat tgtttctgcc tgtgtgtctg ttagtgctca tatggtctag ttcctgagtt
88141 aagaagtata gggtagtggt catctttttt ctttgacttg attcctgcgt actgtgaatg
88201 cagagcaatg caggatatgt tgggttttct acaaacagag catcagccca gagacatgtt
88261 tgcatttgtt tctgtcaggt ttcctggctc aactggcacc ctttaaggcc agaaacgtt
88321 agtttaggca cttttcctag taaatactt cttgtggctc ttcctgtgta cttggaataa
88381 aggaggcatt ccattgttag acatgcttgg gtagttcagg gtaatcttag agtcatgaga
88441 gatatgatat aaaggaataa ctagctaaac cagaaaaaat gcctgggtaa tgactagcaa
88501 ataggtggtc aacagatgtc ctcattagat tgaaaggtcc atgaaagcag ggactatttc
88561 ttttctttac tgcttaaaaa ggttagaact ggacctggca acatatgatg agctaaataa
```

FIGURE 14 (cont.)

```
88621 atacatattt gtgaattggg ttaacacata ttgcataaag tggttttggc tctgttttat
88681 tcttcataag ccctagtgat ctttttaatt tctgtaaaat gtggtcttga cccccccaac
88741 ccaagtgacc tccttatttg ctaggctctg atatttctgt taggtttcta ctgtattttc
88801 tgagatagca attagtagat actatttctc ctttgatgga gctagccata tattcttgtt
88861 tgttcatttt agctttcaaa tttctgtctg attcttgttc ttttactctg gaatgtagtg
88921 aatggaatga cttggaaggt acaaggtagg tcagtttagg ttgtctaggg ccttgcattt
88981 aaaagtttaa tttgatgaca tggtggatta caagaatgta acagtatcaa aatgatacta
89041 tcttcttgtg gtggtatgta gacttaaaaa gagaaactgc agagaaaagg gtcccttagg
89101 atgtagagca gcagttgata tgtgagaagt tgatgccttg cattagggat taggagtaga
89161 tgtggaagga agagatcagg tttgaaagag tttaaacaaa gaatctctag gatttgataa
89221 cactggatat cagaggggaa ggtacaagag agagggcaga atcaaaggcc actcagaggt
89281 taaaggaatc ataccggttt ggcatggtgg ctcacgcctg tcatcccagc actttgggag
89341 gctgaggcgg gcagatcacg aggtcaggag ttcgagacca gcctagccaa tatggcgaaa
89401 ccccgtctct actaaaaata caaaaattag ctgggcgtgg tggcgtgtac ctgtaggccc
89461 agctactcag gagactgagg cagaagaatc acttgaaccc aggaggcaga ggttgcagtg
89521 agccgagatc gtgccactgc actccagcca gggcgacaga gcgagactct gtctcaaaaa
89581 ataataataa taataaataa ataaaggagt aattccaaca cttgggaggc cgaggcagga
89641 ggattgcttg agcccaggag ttcaagacca gcctgggcaa catagtaaaa cctcatcgct
89701 ataaaaattt tttaaaaaga aatttagcca ggcatggtgg tgtgcccctg tagttcccat
89761 tactagagag gttgaggtgg aaggatctct tgaacccaag aggtcgagag tacagtgagc
89821 catgatgcac cagggcactc cagcatgggc aacagagtga gactttggga ggccatggca
89881 gaaggattgc ttgagcccag gagttcgaga ccagcctggg caatgtagtg ggaccttgtc
89941 tctataaaaa ttttacaaat atatataaaa gctgggcatg ggggcacgtg cctgtagtcc
90001 cagtgactgg tgggtgggggc ggggtgagg tgggagaatc acttgggccc aggaagtcga
90061 gattgcagtg agccatgatc atgccactgc tctctagcct gggtgacaga gtgagactct
90121 ttttgtctta aaaaaaaaaa aaaaaaaaa aaaaatggt tgtaccttga acagatacaa
90181 agcatgtaga agaggaaagc atttgggagg gagaataatt ggttggatac attaagtgtc
90241 aagtgacagt aggacctcta gaaatacaca aacagagctc cacaggtttt ttcattgtca
90301 tttcttatac cttttgttcc actacctact ttttttcctac aactttctgt ttattttata
90361 gtttatgaat tttaagcaaa atacttcctt ctgcctctta ccagtaattt tcaaaagcgt
90421 ctgtattggt taggattaga tttggctggg aatgacagaa aactaaaaat aaaagcagtt
90481 taaacaagtt tatttctctc taatgcaaat gaagtttgag ctgtccaggc tttcttatgg
90541 tggtttggtc atgatcaggg acccaggttc tttcaaccat gtagccccat cttaacatgt
90601 gatttctatc ttattgttca agatggctat ttgagtgtca gttatcagtt ttatttagca
90661 accaatggga aggaagggg atgaaaatgg gccctgtctt taaggatact tcctggacat
90721 agtgagtaga aggatggtta ccagagtatg ggaagggtag ttagggggct ggggggaagg
90781 tgggaatggt aaagggtat aaaaaaggta gaatgagtaa gaccatcaga gaaatgcaaa
90841 tcaaaaccac aatgatatag gtggctcacg cctatatgta tctcacacca gttagaatag
90901 tgatcagtaa aaagccagga acaacaggt gctggagagg atgtggagaa acaggaacac
90961 ttttacactg ttggtgggac tgtaaactag ttcagccatt gtggaagaca gtgtggcgat
91021 tcctcaagga tctagaacta gaaataccat ttgacccagc catcccatta ctgggtatat
91081 acccaaagga ttataaatca tgctgctata aagacacatg cacatgtatg tttattgcgg
91141 cactattcac aatagcaaag acttggaacc aatccaaatg tccatcaatg atagactgga
91201 ttaagaaaat gtggcacata tacaccatgg aatactatgc agcaataaaa aaggatgagt
91261 tcatgtcctt tgtagggaca tggatgaagc tgtaaaccat cattctgagc aaactatcta
91321 agggcagaaa accggacacc acatgttctc acttatacgt gggaattgaa caatgagaac
91381 acttggacac agagcgggga acatcacaca ctgggcctg tcgtggggtg ggggagggggg
91441 gagtgatagc attaggagat atacttaatg taaatgacga gttaatgggt gcagcacacc
91501 aacatggcac atgtatacat gtgtaacaaa cctgcacatt gtgcaccatg taccctagaa
91561 cttaaagtat aaaaaaaaag acctactatt tgataccaca ataggtgag tatagtcaat
91621 aatgacttaa ttgtacattt taaaataaca taaaagaaa aaataaaat aatgcagagt
```

FIGURE 14 (cont.)

```
91681 ataatttgat tggttgtaac tcaaaagata aatgcatgag gggatggata ctctattccc
91741 catgatatgc ttatttcaca ttgcatgcct gtatcaaaac atctcctgta ctccataaat
91801 aaatacacct actatgtatc cacaaaaatt tcttaaaaaa ggatactttt gagcgtttca
91861 agcattactt ctagttatgt tcagttgatc agaatttagt catagccaca cttcagcttc
91921 aaggagggct gcagaacgtc tttattttag gcagctatgt gcccagttaa aaagcagatt
91981 ttctcccaag gtaaagagag cagataggca ttaggagact actagtagtc ttttaatttt
92041 ccaggccggg cacggtggct cacacctgta atcccagcac tttgggaggt cgaggcaggc
92101 ggatcatgag atcaagagat gggagaccatc ctggccaaca tggtgaaacc ccatctctac
92161 taaaaaaaat acaaaaatta gctgggcgtg gtggtgcgtg cctgtagtcc aagctactca
92221 ggaggctgag gcaggagaat tggttgaacc caggaggtgg aggttgcagt gagcgaaggt
92281 cgtgccattg cgctccagcc tggcaacagg gcgagactcc atctcaaaaa aaaaaaaaaa
92341 aaagcaggga tttgctccca aggtaagaga gcaaatagac attgggagac tattagtagt
92401 ctcttaattt cccagaatga gaaccagatt cttccggtt acagaactcg tttctccaaa
92461 cattaattat tcttataata attttaaaaa atactaaata tataattatc accagccaaa
92521 tgcttctttt aagaaataga gacaggggggc cgggcacggt ggctcacgcc tataatccca
92581 gcactttggg aggccgaggc aggtggatca cctaaggtca gagttcgaga ctagcctggc
92641 caacatgggg aaaccctgtc tctactaaaa atacaaaatt agccgggcat ggtggtgcat
92701 gcctgtaatt ccagctattc gggaggctga ggcaggagaa ccgcttgaaa caaggaggca
92761 gaggttgcag tgagccgaga tcgtgccatt gcactccaac ctgggcaaca agagcaaaac
92821 tccatctcaa aaaaaaaga aaagaaata gagaagagac agggaagcca agctcatgcc
92881 tgtaatcaca gcacttcggg aggccaaggt gggcagatca cctgaggtca ggagtttgag
92941 accagcctgg ccaacatgga gaacccagt ctctactaaa aatacaaaaa ttagctgggc
93001 atggtggtgc ataccggtaa tcccagctac tcaggaggct cagacaggag aagtgcttga
93061 acccggggagg cagaggttgc agtgagccaa gactgtgcca ctgcactcca gcctgggtga
93121 cagagtgaga ctctgtctcg aaaagaaaaa aaagaaaaag agacggggcc tcacatatgt
93181 acagtggtat gatccgtagt tcactataat cttgagctcc tgaaacctga tgctttaaaa
93241 caaaacagta caaaactact aaatttataa ttaaatatat aaataaaata taataaaaat
93301 gttcacttct gttttttatat tctttaaaat gacccatagg ctggtgatta gtaactaaag
93361 catatgctgt ggaacatcca gcactgatgt aagtatatga agtttgaatg ccaggtcagt
93421 agattcagaa gctaagttac tgtatggtaa agaccatgtt ttgcctgagc agctttggat
93481 atggtttttt ctttttttttc tttttttgag atggagtctc gctctgtcac caggtggagt
93541 gcagtggcgt aatctcagct cactgcaagc tctgcctccc aggttcaagt aattctgcct
93601 cagcctcccg agtagctggg gctacaggtg cataccacca cgcccagcta attttgtat
93661 ttttagtaga gatggggttt taccatgtag gccaggatgg tctcaatctc ccgacctcgt
93721 gatcccctg ccttggcctc ccaaagtggt aggattacag gactgagcca cagcacttgg
93781 ccggatatag ttttttctatg tgtgttttttc ctaaaccttta ttatacataa acatacaagg
93841 acagagatca aatgcccct gtctagaaac accatttctg ccaggcccat cttaataaga
93901 ctatgtcttc tttttatttg tttctatact tcctttttttt ttttttttttt tctgagacag
93961 ggtttcactc ttgttgccac cacactcagc taattttgt gtttttagta gagacaaggt
94021 ttcatcatgt tagccaggct ggtctggaac tcctgacctg aagtgatccc cccacctcgg
94081 catcccgaag tgctgggatt acaagcgtga gccatcagcc tcagcctaga cttcttagtg
94141 tggtgtttca ttttcttttc tctggttccc atccagcttt gttcattgta catgctcacg
94201 gtgcacttta tatgacctgt tggcatattt tctcactctc ttttgtctc tcttcacttc
94261 cagcagtgtt aaataactct ttccattctg cagttttcct gataagaatt tcagatggtg
94321 gtgccaggt gcggtggctc acgcctgtaa tcccagcact tgggaggcc aaggcggcag
94381 atcacttgag gtcaggagtt tgagaccagc ctggccaaca tggcgaaacc ccatctctac
94441 taaaaataca aaagctagcc gggtgtagta gcgcatgctt gtaatcccag ctactaggga
94501 ggctgagtca ggagaattgc ttgaacccgg gaggcggaag ttgcagtgag ccgagatcac
94561 aacactgcac tccagcctgg gcgacagagc gagactccgt ctcaaaaaa aaaggcaatg
94621 aataattgga caaggaacca aaactttat tctgaaaaga gaaattcca gtctatagca
94681 agggcagttt tccttctaag gaacagtact gatatatcat ggctaaagaa gcaggctcag
```

FIGURE 14 (cont.)

```
94741 cttctttgtc cctttcacta atttgctatg gcttctaaca taggctagga aaagaaaaaa
94801 atctgtttct ctttctcctc tcctctcctc tcctcttccc tctcctctcc tctcctctca
94861 tcttccctcc cctcccctcc cctctcctcc cctactcccc tctcctcccc tcccctctct
94921 ttatctgtct atctgctaag ggcagcaaat ctgtatccat acaggtctgc agcaacttca
94981 attcttgcct cctcagaaga aacaatttga ctgagggtca taaggcagaa ggagagacca
95041 aggcaagttt tacaacagga gagagtttat ttaaaagctt tagaacagga atgaaaggaa
95101 ggaaagtaca cttggaagag ggccaagcag gtgacctgaa agacaagtgc accaacacat
95161 agcctttcaa caggatagag agcagttaaa actgccctgg aaaagccaga cttacaggct
95221 actctgtata atagaaactt caggacaggg tgcggtggct cacacctgta atctcagcac
95281 tttgggaggc cgaggtgggc ggatacgagg tcagaagat cgagaccatc ctggctaata
95341 cggtgaaacc ccgtctctac taaaaataca aaaattagc cgggcatggt ggcgggtgcc
95401 tgtagtccca gctacttggg aggctgaggc aggagaatgg tgtgaacctg ggaagcggag
95461 cttgcagtga gctgagatca tgccattgca ctccagcctg gtcgacagag ccagactccg
95521 tctcaaaaaa aaataaataa aaagaaact tcagcatgct tcctaatact gttcaaaggt
95581 ctccctttt atgattttat ttaaaaaaat tttttttttt tgagacagag tctcactctg
95641 ttgcccaggc tggaacgcag tggcgtgatt tcggctcact gcaacctccc ctcccaggtt
95701 caagcaattc tcgtgcctca gcctcctgag tagctgggat tacaggtgcc caccaccatg
95761 tctggctaat ttttttgtat ttttaataga gacagggttt caccatcttg gccaggctag
95821 tcttgaactc cacaccttgt gatccaccca ccttggcctc ccaaagtgct gggattacag
95881 acgtgagcca ctgcgcccag ctcattttt atattttgg tacagaccag gtttcactat
95941 attggccagg ctgttctcaa actcctgacc tcagttgatt cgcccacctc agctcccaaa
96001 gtgctgggat tacaggcatg agccactgcg cccagcaggg tctcccttt taaacgtatt
96061 ttcttttat agcctacaaa ctacaagaga tgccttttaa taaactggat ggtatgtctt
96121 aacgtctgat ggagtttaaa ggcatccaag ggttacgtct gtgatagatt gccaaggcat
96181 acaggtctga tcaggagagt ttcttgatga ctagctatgg gctatgcctt tgtagcacat
96241 gatcccaact ccagcaggga tatagttagt gacatgctgg ctttgtcttc tccctaactc
96301 ctgattact acaaatttct tcttcgtgca ggaatcattc cctcactcta tacatatctg
96361 ctgttaaaaa aaaaaagtt aagatattat agccattata ttgtagcagc catgatatta
96421 tagctcagta aatgctgctt tccaaatatt ggctaattta accatagcat gtcttcaatg
96481 ttagaagcca gccctcattt ttatcaaggg ctgaagtttg ataattcttt gtgttatttg
96541 cttgtgaaaa taagtagaac aaaaaggatt agggacctaa ccttgtatcc catgtatccc
96601 agtgaaccctt ttctgactta aagcttcctt tcttttttt tgggagatggg agtcttgctc
96661 tgtcgcgagg ctagagtgca gtggcgcgat cttggctcac tgcagcctcc gcctcctggg
96721 ttcaagtgat tctcctgcct cagcctccca agtaattggg actacaggct catgccacca
96781 tgcccagcta atttttttt taattttag tagagacggg gcttcaccat gttggccagt
96841 atggtctcga tctcttgacc tcgtgatcca tccaccttgg cctcccaaaa agcttccatt
96901 cttagtcttg gtacttctaa gtggcattgg gtcaatagct ttctgcctaa gaagagaatt
96961 ggctgggcat gatggctaac acctgtaatt ccagcccttt ggaggctgt ggcaggagga
97021 tcatttgagc ccaggagttc aagaccagcc ggggcatcat aggaagaccc catgtctgca
97081 taaaataaaa taaattagcc agacttggtg acatgcacgt attgtcccag cttgtcagga
97141 agctgaggtg ggatgattgc ttgagctcag gagatcaagg ctacaatgag ctatgatcat
97201 acaacaccag tgcactctag cctgagtgac agagcaagac cctgtctcaa aaaagcagg
97261 ggggcatagt cacctcccta aaatattagt tgaacagtat gtattcagaa gtccagaggc
97321 tctgtatttt attaatattt tcaaggcact atttctgcag aaatcaagtc agcaagactc
97381 tttgaggacg ttacaggcag aggggctaaa gataccttg aggaagctca agtacttggg
97441 tgggaggtga tagataaagg gtcagtagaa ataatgtctc tttttatttt ttttcccatt
97501 aaaaaatttt gttttaatag caatggagat ggggtctcac tgtgttccct gagctggtct
97561 ggtctcgagc tcctgggttc aagcagttct cccaccttga ccttctaaag tgtagggatt
97621 atagacatga gccaccatgc gtggcaaatt tcttttcttt cctttttttt tttttttttt
97681 tgagacagag ttttgctctt gttgcccagg ctggagtgtg gtggcacgat cttggttcac
97741 tgcaccctcc acctcccagg ttcaggtgat tctcttgcct cagcctcctg agtagctggg
```

FIGURE 14 (cont.)

```
97801 attacaggcg cccgccacca tgcccgggta attttttgtat ttttagtaga gatgggattt
97861 caccatgttg gccaggctgg tcttgaactc ctgacctcag gtgatccacc cgcctcagcc
97921 tcccaaagtg ctgggattac aggtgtgagc caccgctgcc ggttccaatg tctcttttgg
97981 atggtggatc ctgaagaata gctgctggtt ctttggggat gcctggggaa tactgtgcag
98041 gctttgtgat gggctcagca gtgaggcctg tacagtatct taggtcttgt gggcctcagt
98101 ctgctctctt ggctgttctc taccacctcc tgccattaag tttttaagaa aaaggaatag
98161 ttttattata ttctttggta aacaaagcaa attaagaagc tttatatttt ccacatttat
98221 ttaccaaact ccctatttgt ttttctctat agtgattcag tttagagacc tattcaatga
98281 agcatgcctt gatgttgaat ttagagtcta cttttttccag aagaaaagag ccagggagct
98341 ccaatagtag tcatctcaga atataaaagt gttatagaaa tgatgtaaat caggccgggt
98401 acaggggctc acgcctgtaa tcccagcact ttgggaggcc gaggcgggcg gatcatgagg
98461 tccggagatc gagaacatcc tggctaacag ggtgaaaccc cgtctctact aaaaatacaa
98521 aaaaaatcag ccaggtgtgg tggccggcac ctgtagtccc aactactcag gaggctgaga
98581 caggagaatg gcgtgaaccc aggaggaaga gcttgcagtg agccgagatc gcgccactgc
98641 actccagcct aggcaacaga gcaagactcc gtccccaaaa aagaagaaa aagaagaaaa
98701 gaaatgatgt aaatcagctg cccttcactc tgtgttgagg tggggatgt ccctaattgc
98761 agtaggagag agcctctctt ttatctggga ctaaaagccc ttgccctaca tacctcataa
98821 ttattttagg gttaactgat tcaattgtca gaaaagaaca agctgtatct tgtttctgta
98881 catattctac tttgtgagta tttttatttc attgctatgt gattggaatc aactcaggaa
98941 agaggaaaaa aataagatag aggttataga attctgaatt ctgaagggaa ttctgagaat
99001 tatcagtaaa atatgtcaaa atgtgatatt ttacttccac caagaattag gccatatctt
99061 tgtgtgaaaa taaattatta ttattttattt atttatttg agatggagtc tcgctctttt
99121 cacccaggct ggagtgcaat cacacaatct cggctcgctg caacctccac ctcccaggtt
99181 caagcgatgc tcctgcctca gcctcccgag tagctgggat tagaagcgcc cattaccaca
99241 cccagctaat tttgtacttg tagtagagac agggtttcac catgttggcc aggctggtct
99301 cgaactcctg acctcaggtg atccaccccc cccccccca cccttggtct cccaaagtgc
99361 tgggattaca ggcatgggcc accgcaccca gcatacggaa ataaattatt aaccagagaa
99421 attttgacta aggtttttat aaatgttagg tgaaccattg ctctaaaaga tacaaaatta
99481 taacaagctg aaaagttttt taaaaatctg cattttagtg gttcagtttt tcagttgttc
99541 tgagtgctaa tagttggagt ttataaattg taagaagcaa tctacggaga ttctgtgatg
99601 aaggaatttg ttgaatgccc tgtctgcctc acagtctcag tctttatgat agagtcttgt
99661 cttctcacaa ggagagaaaa gatttgaggc tcttttgatt acttacttac ttgcttattt
99721 atatattttg cctctttgtt tttgccgcaa atacaaatgt aatggaacct tagaatagga
99781 gagacgtgtg gatccctgg taggcactgt tcttttctatg ttcctggagc caagttcatg
99841 gaattacctc caagactacg gatccctggt tttctttcat catgatagga ggcatttct
99901 agaacctgaa tcttacttta aaatgcatgt aagacctgca aggagtggta gtgaagtggg
99961 tggaatatat tcttagcacc agacaccttt aaaatattta agttctcggc cgggtgccct
100021 ggctcacgcc tgtaatccca cactttgggg aggccgaggt gggcagctca cgaggtcagg
100081 agaccgagac catcctggct aacacggtga aaccccatct ctactaaaaa tacaaaaaat
100141 tagccaggcg tggtgatggg tgcctgtagt cccagctact cgggaggctg aggcaggaaa
100201 attgcatgaa cccgggaggc agagcttgca gtgagctgag atcgcaccac tgcactccag
100261 cctgggtgac agagcaaggc tccttctcaa aaaaaaaaaa aaaaaaaaaa aaaaatatat
100321 atatatatat atatatatac acacacacac acacacacac gtgtgtatat atatacacac
100381 acacatgcat atatatatac acacacatgt atatctatag atatatacat atatatgtgt
100441 atatttacat tttcttatgt cagggtctgg cttggagtgt attgtgttcc cagagcagaa
100501 ttcttttttt ttttttttgag attgggtctt actttgtcac ccaggctgga atgcaatggc
100561 gtgagcttgg ctcactgcag cctcgacctc acaggttcaa gcaaccctcc cacctcagcc
100621 cctggagtag ttaggataac aggcgcacac taccatttg tattttttgt agaggcgggg
100681 ttttatcaca ttgcccaggc tggtctcgaa ctcctgagct caagcaatcc acctgccttg
100741 acctccccaa atgctggggt tacaggcgtg agccactgtg cccagccgca gagttcatct
100801 tgagaccctg acttctgcca gctctgatcc tagtgggtgg ggctctgggg ctcagtgaaa
```

FIGURE 14 (cont.)

```
100861 cagtcagccg ttttgcttca gagaacacaa ataagatttt ggcttgatgc tggttgttgc
100921 tggcgtcata tagtctaaaa cgtttgctgt caagaacatt ttagtaaaag ttttttgttgt
100981 gctttcatct agtcaagaaa agataggaag tggcagctga cagggcagtg tcttcatgcc
101041 cctcaacctt acattggaca ctgaagtagg attgtgtttt cactggaagt cccagtgggg
101101 ccttatctcc tggatgctca aagtgcagct cagatcctgt tgggtaaaaa gtctagtcaa
101161 aatggaggac atggagaagg ccaacaggca gagctataga gctgacatag ggcattcttt
101221 gtacttccct tagccactgt actttctttc ttcctccatc tcctccttcc ctcttctatc
101281 tcattttggt ttggcctttg ggaatagtgg gtttttaaaaa atatttgaac tataacatat
101341 ccttgtacca taaagaatga gcctgactgc tttacaaagg atttctataa aaagtaatct
101401 tttatactaa gagaaatgac acatctgttt taaacctgtt acttttcttc cccgggcttt
101461 gctctttctg caggtccgtt tgacatggtt cttgaaactc ctggtagcag ccatttacta
101521 gtagcactct ttatcttaga cacagcacct aaagcaattg taggtgtttt aagaacagaa
101581 agcccatctt aagcagacca gtttgaggga ttggcagtgc tgtcaagaaa caagggcttt
101641 gtggcagtct ctctaaaaac tccctatgag tccatttctt gcaaacttct ttagactcta
101701 ctgtatcttt tcatcagaag ctacctcttt gatgtgggaa gtgtcatgaa tggactgact
101761 ctctggaatt taaaaacaaa gacaatatgg caaaagaaa acctgacttt tagtactgta
101821 tgtgttgcta attagctctg tattcttggg cagactactc catgtatccc agccatccat
101881 atgccctatt tgtaaggatc taatgagatg atattgtgaa gaatgccttt gtaaactgta
101941 aattgctttg tgaataaaga tactatctct gataaacagt accagttctc agccaccaat
102001 aacctgatac tcccatactg tgtttggaag aaacacaaaa caatgaagag taattgtgac
102061 ttttcaatgt gagttgtatt cacaaagctc atatacttttt tccctgcctt ttgatactgt
102121 ttatcgctttt ctgtgttgta atgggaagat cacacagcaa tcattttctc agtacaaagt
102181 ataactacaa ctgagcttgc attgaagatc tttaacaaag atgcaaagct gctgtccaga
102241 aatgttttct ttccattttc tcttgtacct cccagtattt taagaatcct tgaggctggg
102301 caccataact cacgcctgta atctcaacac tttgggaagc tgaggcagga ggatcacttg
102361 ggcccaggag tttgagacca gcctgggcaa catagtgaga cccccatctc tacaaaaaaa
102421 tttaaaaatt agctgggcat ggtggtgtgc acctgtggtc tcagctactt agggaggctg
102481 aggtaggagg attgcttgag cctgggaggt caaggctgca gtcagtcatg attgcaccac
102541 tgtgctctat ctagcctcca acctgggcaa cagaagcgag accctgtctt ttttttaaaa
102601 aaaaaagact atccttgatg attggttttg agccaacgga atgggagcat atggtagagt
102661 ttcaacactc tgaccctagt ccttctgaca ggcagtcaca aaatgagatc atgaagtctc
102721 taagagcagc tgatgaaaaa ggaaatggga atgtagatgt tcaatcagca gccctccaga
102781 cccagagttt gctcctctgt ggtgtctcta ggtggagaat aaggacttga tttgccattc
102841 tggagtgcaa atatctagct ttttgcagct tcatattaag atttcttgaa atgtacttag
102901 taatatccat gtgtgacttt gccaagtgat ggctttgggc tggaaaggat tttagcaggt
102961 tttagtctaa tttaagccta atctaacact gctgagaaag gaggagatgt ctttggtttt
103021 actttctaat atatggtacc tcttagccgg gtgcagtggc tcatgcctgt aatcccagca
103081 cttcgggagg ccgaggcagg cgatcacttt aggccaggag ttcaagacca gcctggccaa
103141 catggtgaaa ccccatctct actaaaaata caaaaattat cccggtgtag tggcgcacac
103201 ctgtaatccc agctacttgg gaggcagaaa caggagaatc gcttgaacct gggaggcaga
103261 ggttgcagtg tgccaagatc atgccactgc atgccactcc agcctgggca acagagcaag
103321 accctgtctc aaaaaaaaaa aagagagatc tatctctctt cttttttatat acatatacat
103381 atacatacat acatacatat atgtatgtac acacatatat atatatggcc cctcttttt
103441 tatttgagtc ggaatctggc tctcttgcca ggctagagtg cagtggcatg atcttggctc
103501 actgcaacct ctgacttcct ggttcaaacg gttctcctgc ctcagcctcc cgagtagctg
103561 ggattacaag catgtgccac cacacccagc tcacttttgt attttttagta gagacgggat
103621 ttcaccatgt tggcagggat ggtcttgatc tcctgacctt gtgatcctcc cacctcagcc
103681 tcccaaagtg ctgggattac aggcatgggc caccgtgccc agccttttt tttttttttt
103741 taaagagacg gagtctcact ctgtcaccca ggctggagtg cagtggcgtg atcttggctc
103801 agtgcaacct ccacctcccg ggttctagca attctgcctc agtcttccga ctggctggga
103861 ctgcaggtgt atatcaccgc aaccagctaa ttttttgtat tttagtagag acagggtttc
```

FIGURE 14 (cont.)

```
103921 actgtgttgc ccaggctggt ctcgaactga gctcaggcag tccacccgcc tcggcctccc
103981 aaagtgctag gattacaggc gtgagccacc gtgcctggcc tatatggtac ctctttagga
104041 gccagacctg gttaatcaga cacatggctt tcatgactcc tttgcttgag tagcttaata
104101 actcaataaa tcaaaagatg aataaatatt ctaatgtgtg aagatactct aatagataat
104161 aggcaattaa gaatggacat ccacggctgg gcgctggggc tcatgcctgt aatcccagca
104221 ctttgggagg ctgaggcggg tggatcatga ggtcaggagg tagagcccat cctggccaac
104281 atggtgaaac cccatctctg ctaaaataca agctactcga gaggccgagg caggagaatt
104341 gctcgaactt gggaggcgga ggttgcagtg agccaaaatc gcatcactgc actccagcct
104401 ggcgacagag cgagactccg tctcaaaaaa aaaaaaaaag aatggcatc tactgaaggt
104461 gattgcatca tcctacccat tcattaatct aactccctac aggatacttt cctaggagac
104521 actgacaggt ctgttttctg aaatccagag aaaggcagca atggggaggg gtgcagtgta
104581 tgtatgtcat acctgtgctt ggtatatctg agttgcctgt gtatgatagc agctgggaa
104641 tcaaatcata gataaattgt tctcatacag gtttgtccta tgactaccta ttcttattaa
104701 acaattggct atattgaccc ttttggttt tggaaaaata ataataattt ttttaagaga
104761 gaaaaagaaa caattggcta cccttcaaca gtgatgttaa aaccatttca cattctttag
104821 cagtggtcac tgtcctatgt ctaactatgt gcaggttgag aaaaaggact gcccgagtta
104881 tagatgattc tgtgagaata agaaatcatt gcttttgtaa cacatgaggt aaaagtaatc
104941 tcaaagttga catgctgatg gggactcctg gcaaggggag ttccctgccc tcaacaaaag
105001 gtcatccaca gctactggaa catttttgtt gtctgagaag tataaagtgc cttagaaata
105061 cctgaatcca ttaatgcctc cagttggtga aatcagaatt tgcaggtgac tgaaattgac
105121 agtagtgcct tgttcttact cactgttcaa atgacaaccc acatgtttta tggattgggt
105181 atacagatgt atgctctaac agcagtatct ccctccagag ccactgtgta ccaagcacca
105241 ggtcctccag ggatagttgg ctctattcag tctttgattc attcaacaag agcttactaa
105301 gctccttttt ggtaccagat actctttgtt gctgaaaata aataaaagc cagcaagatt
105361 aagtagactg tgagatctgg accagtaatt tgacaacaca aagtactgtc gtaaagatac
105421 agtttctgat gtgtagtgac cattccgtat gaaagcttag tctttcagga gattaaaatg
105481 ggtggtggaa tattcctacc tagcaagcaa gcaaggtgaa atgagtggct gtttgactcc
105541 cacctgctga tgctggtctt ttttggttcc tagggcttat aatgatcaac atttcttgag
105601 ccctcactat attctatgct aagctcttta catgtatgaa tttacttaat cttcacaacc
105661 accctaagaa ataggtactg ttgtccttac tttacagatg aggaaatgga agcacaaaga
105721 agtaaggac cttgctgaag gtcatggagt agaggcagga ttcaaattta gggaactcag
105781 cctacagtcc atgctcttaa agatgttata tcctgtctct gggcttagaa ggggttcatc
105841 ttaggccgga cacagtggct cacgtctgta atcccagcac tttgggaggc caaagcgggc
105901 agatcacgag gtcaggagtt cgagaccagc ctgaccaaca tagtgaaacc ccatctctac
105961 taaaaataca aaattagcc aggcatggtg gtgtgcgcct gtagtcccag ctactcggga
106021 ggctgaggca ggagaattgc ttgaacctgg gaggcggagg ttgtggtgag ccgagatcgt
106081 gccactgtac ttgagagtga gtgacagagc aagactctgt ctcaaaaaaa aaaaaagac
106141 ggccaggcgc agtggcttac gcctgtaatc ccagcacttt ggaggccga ggtgggcgga
106201 ttacctaagg ttgggaattc gagaccagcc tgaccaacgt ggagaaaccc cgtctctact
106261 aaaaatacaa aattagccaa gcgtggtggc atatatctat aatcccagct actcgggagg
106321 ctgaggcagg agactcgctt gaacctggga ggcggaggtt gcagtgagcc gagatcacgc
106381 catagcactc cagcctgggc aacaagagcg aaactctgtc tcagggaaaa aaaaaaaaa
106441 aaaaggaggg ggcgcttcat cttgactaac ttcctgcatt ggtggagctt gatagagtgg
106501 tccttcccag atccttccct gcatacagag cctgtctctt ttctgattgg tccctaaggc
106561 cagattacct gtccctaata ctgagcagaa gctggtgaat gaaacaggag atccctcagt
106621 caaaacaaaa ggaaaaagaa aaatgaaaca ggagatccct tctctacagc ccagatgtaa
106681 gtccagctgt gcccttcacc acctgggtga ccccacctct gtgaacatag gtcctcatct
106741 gtaaagtgta gataatgtta tttcatcgga tcatttaggg gattaaataa gataatgtac
106801 ttcgtggttt ctggctctta gtaagtgctt aataaatgtt agcgattttt attatcattg
106861 tccttagcct tgagaacaag ccagggaata gtgtctcaga ccagatgcta agacctaggt
106921 agatgggcaa ttttccttgg ttttgacaag acaataattt tatcctgtgt atttctcttg
```

FIGURE 14 (cont.)

```
106981 acttttttga tgtgaaaagc agagaggtaa agcattattt gacagatgta tggattcaag
107041 caagaaactg aggtccaatt gcaaagaaat ggcttgtata actcagagcc ctgtctgagg
107101 aaacacagag gaccctagag ggcggagaat gaacacagcg caggggctag ttccagagtc
107161 gcattctcgg ttagttcact ttcaagtgtg ggtgagggtc ccttgtcagt aggcagagaa
107221 ttttttttccc ctgcaccaac acatacctgc tgcctagtgt ttattaaaca aactttatt
107281 ttaatgtgaa atagaattca tgacttgtcc aaaatggaga ggcaagggag ctctttaaca
107341 ggcttgttga gcccttttc ccacctgttc ctgtgccaga cttttcccaaa ggcttacttg
107401 ccaatggttg ctcctcagat ctcagggcta gctcactcta taggctccaa gccagagtga
107461 taccgccgcc gccgctgttg ctcccaccag ccaatcagtt tcctgctgta aggatgtaac
107521 ttgctgtgaa gctttcacct tcctccttc ttcctgtctt caatgttgta tgtctttgtc
107581 ctggtgcttt tgccatacag ccagtgtttc aaagaaaatt ttcaggcact aaagttatag
107641 cccttactac cttccaagg agatgtgaga tagctgtgga aaagaagagg gctcctctgc
107701 ctctgtgcag aaggaacagt ttacttcttg atagtgtgct agctcctgag ctaggtgggg
107761 gacttgctgg gattcaagag agtgcattac ctgacctctg gacaagtaga ctgggcatag
107821 cctgcccaag gacagcaccc taacctgcag gaaccaaggc cgaagactga tttcaccttc
107881 tcgtactccc cttttcctaag ctaaagcttg ctctgtaaca ctgccccagg tctgtggctt
107941 aaaacagcca tttcctttca ccagtgaatt aagctcactc tttataaaat gtttcagctt
108001 ggggattgga aaggctctct gtgcctttct gtctctgtct gtttctccaa gggttgatgt
108061 tgatggcttc tgtctttgtc tttacaggga actctaatga tccaggacaa agaagttacc
108121 ctggagtatg tatcaagcct ggattttttgg tactgcaaac gagtaagtac caagaatccc
108181 tttctttaga agtaagtatc tggaataaca gctcctccat atctctagga aggctgcctg
108241 ctaacatgca ttcccaagga caaagctctt cttcctcagg tcacttcagt tgaacaggag
108301 gaggtcaaga caaggtcatt cataatttct ccttcccagc tgctacatgt ggccatagag
108361 agttctggac ctgcaattgg agacactttc ccaaggacat gtgccattat ttctatcagt
108421 tataaaaata acagttcctt gacatataat atcttctcac ctctcctggg ggtggtcata
108481 aaggaattct tggttggaaa agtaggtttg gagagactag ttcttttggga gtcgtacatt
108541 ttttggatat tcttgggttt ccaagggtat agaacttcag acaccatggc attttacctc
108601 tattaaactc catattctct tagagtggga tatttaaaat tttaggctat actcttttt
108661 tttgaaacgg aatctcattc tgttgcccag gctagagtgc aatggcgtga tttccactca
108721 ctacaacctc tggctcctgg gttccagtga ttctgctgcc tcagcctccc gagtagctgg
108781 gattacaggc acttgccacc tcacctgcct gattttttgta tttttagtag agatggggtt
108841 tcaccatgtt ggccaggctg gtcttgaact ccgacctcaa gtgatccacc tgcctcagcc
108901 tcccaaagtg ctgggattat aggcatgagc caccgcgctg gcctgtttat ttatttattt
108961 atttatttttg agacagagtc ttgctctgtc gccaggctg gagtgcagtg gcgcgatctc
109021 agctcactac aacctctgcc accgggttc aaacgattct cctgccccag cctcccgagt
109081 agctaggatt acagttgtgt gccaccatgc tcagctaatt tttttgtagt ttttagtaga
109141 gatgggggttt caccatcttg gccaggctgg tcttgaactc ctgacctcat tatccaccca
109201 cctcggcctc ccaaagtatt gagattacag gcttgagcca cggcacccag ccggctatac
109261 tctttaaagg tccagtttga ttgcagtgag catgaaaata taatttgttt tcattgctac
109321 tacttagtat caaaaataat tatgaaaaat atataaagtt tctgagcccc gacacactaa
109381 aaatgttaca gtacttgaaa aaatttagta aagactttag cttgacattt gttagtctcg
109441 gtagaattga cattgtgtta gtctcggtag aatacaactt gaagagctat gattgttatt
109501 agccaaagta ctcatatttc atggatatac tcccttatgg tgtcatttta ggaagatatt
109561 tcgtttcctt ttattgagat aaaatacatg taacattaca tttgccattt taaccatttt
109621 gaagcattaa ttcagtgaca ttaagtacct tcacaatgtt gtgcagctat caacactact
109681 tcctagaact tctttttttt tttttttaa ataagagatg ggatctcact atgttgccca
109741 ggctggtctc acagtccctg gctcaagtca tcctctcacc tcaacctccc aaatagctgg
109801 gactataggt gccatcatgt ccaggttagt tccagaaatt ttttttttct gtctttttt
109861 tgagacagga tctcactctt gtttctcaag ctggagtaca gtgatgtgat catggctcac
109921 tgtacccttg acctcctgtg ctcaagcgat cctctcacct tggcctcccg aagttctggg
109981 attacaggtg tgagctgcca tatctagcct cagatctttt ttaaaccctc aaaaggaaac
```

FIGURE 14 (cont.)

```
110041 ctcttatcat taatcagtaa cttcccactt cttcttcccc cagtccccag aaaccattaa
110101 tcttttttct atctccatgg atttgcctat tccggatatt tcatataaat ggaatcaaaa
110161 tatgtaaact tttctgttgg cctttcacct agcatgtttt cagagttcat gtatgttgca
110221 gtatttatca gtacctcatt tcttttttgtg gctaaataat atgaatatat cacattttgt
110281 tcatccattc ctcaattgat ggacatttgg gttgtttcta ccctgactttt ggtgaataat
110341 agaacctttg tgtgctagtt tttgtttgaa cagctgtttt cagttatttg ggggtatgta
110401 tccaggagtg gaattgctga gtcatatggt aattttatat ttaactcttt gaggaaccat
110461 caaactgtat ttcttttatt ttattagcaa acctttttcat agaccacagc tgtaccattt
110521 tatattccag caatatgtaa gggcttcatt tctccacctg cttgccaaca tttgttcttt
110581 tcccttttatt tgataatagc catcctaatg ggtatgaaat aatatctcat tgtggttttg
110641 atttgcatttt tcctaatgac tttgagggtt tttttttcatg tgtttgttgg ccatttgtat
110701 acctcctttg gagaaatgtt caaccaagtc ctctgccctt tggaattgat ttgcatgtat
110761 ttttgttgtt gagttataag agtactttat attttctgga tattaatccc ttatcagata
110821 tatgatttat aaatattttc tatgtgttat ctttcacttt cttgagagta tcctttctaa
110881 agaaaaaaaa agagagagag agagataagg tgtggctcat ggctgtaatc ccaacactttt
110941 gggaggctaa agtgggcaga tcacttgagc ccaggagttc gagaccagcc tgggcaacat
111001 ggcaaaaccc catctctaca aaaaatacaa aatttaactg ggtgtggtgg tgcatgccta
111061 tgatcgcggc tactaagcag gctgaggtgg gaggatcacc tgagcccagg aggtcgaggc
111121 atcagtgagc tatgatagtg ccactgtact tcagtactcc atcctgggtg acagagcaag
111181 accttgtctc aaaattttt ttagctgggt gtggtggctc acgcctataa tcccagcact
111241 ttgggaggcc gaggcaggcg gatcatctga ggtcgggagt tggagatcag cctgaccaac
111301 atggagaaac cccatctcta ttaaaaatac aaagttagct gggcatggtg gcacatgcct
111361 gtaatcccag ctacttggga ggccgaggca ggagaatcac ttgaacctgg gaggcagagg
111421 ttgcggtgag ctgaaattgc actattgcac tccagcctgg acatcaagag tgaaactcca
111481 tctcaaaaac aaaaagaaa aattttaagt ttattatgta cctattaaaa ttttttttgta
111541 attaaaacaa atgctaatgg cggtattatt cataatagcc aaaaaatgga ataaccaaa
111601 atgtccattg gctgatggat ggatgaacaa gttggcatat ccatacaatg aaatgctatt
111661 tgacaatgaa aaggaatgaa gtactgatgc atgttacaac ctagatgaac cttgaaaata
111721 ctatgccaga cacagaagac catacattgc acaattccat gtccctaggg gtaagaatgg
111781 gggaggtaac tccactagat ttcttttggg gtgatgaaaa tgtttcagaa ttagattatg
111841 gtgatggttg cactatacat ttactaaaaa tcattgaatt gtacacataa aataggtaaa
111901 ctttatgggg tttgtttttg tttttaagag agagtcttgg tttgtcaccc aggctggatt
111961 gcagtggcac aatctcggct cacgacaacc tccacctccc aggttcaagt gattctcgtg
112021 cctcagcctc ccaagtagct gggattacag gcgtgtgcca ccatccccag ctaattttttg
112081 tatttttaat agagatgagg tttctccatg ttggctaggc tggtcttgaa ctcctggccc
112141 gaaatgatcc aacttcctcg gcctcccaaa gtactgggat tactggcatg agccatcatg
112201 ccaggcctgt tttatgctat ttaaattata cctactaagg ttaggatcct aactgccact
112261 cactaactga agtgtcacat actttattcg ttggcatgta tatactcagt tgtcccagca
112321 ccatttgttg aagagactat tcttttccca ttggcactttt ccccattgtt agaaatcagt
112381 tgaccataat ctataggttt attcctagat tctcagttttt attctgttga tctatatgtt
112441 tacaaatagc accagttacc acagcagctc tcctgtagta acaactctcc aatcccagta
112501 gcttaaaaca gcaagcatat tcttcactca cattacatgt cagggactat gggttgtttg
112561 ctacagttct gttccacgtg gcttctcatc ccaggaccca ggcggaagaa acagtctcaa
112621 tatgggcag tgtccctctg gctaagggag agagaggttc attcacgcaa gcagtggctc
112681 ctaaggcttc tcttagacct agtgtaggtc atgttcactc atgtttttatt ggtgaaagca
112741 aggaaggcac atggccaagg ctgacaatgg agagaggaag tatactcacc ctgtgggaag
112801 gcataacagc catttggcag tgggcagggg tgtgtgtgtg tgtgtgtgtg tgtgtgtgtg
112861 tgtgtgtgtg tgtgtgtgtt tataatctgt ttatagggaa gggaacaatg aaataactga
112921 ctgtagtgat cttcctcaag tgagttaacc tctctaggcc tcagtttcct catctacaaa
112981 atgaggagat aagagtaccc atttcatgaa gtttattggg gttgtcagga tcaataagtg
113041 atgacatata cagtaggcca aatacatggt atgtactatt taagaattag ccggctgggc
```

FIGURE 14 (cont.)

```
113101 gcagtgactc acacctataa tcccagcaat ttgggaggcc gaggcgggca gatcacctga
113161 ggtcgggagt tcgagaccag cctgaccaac atgagaaac cctgcctcta ctaaaaatac
113221 aaaattagcc aggtgtagtg gcacatgcct gtaatcccgg ctactcggga ggctgaggca
113281 ggagaatcgc ttgaacccgg gaggtggagg ttgtggtaag ccgagatcat gccgttgcac
113341 tccagcctgg gcaacaagag tgaaactccg tctcaaaaga aaaaaaaaa aagaattagc
113401 cactgctact attgttattg ttttctcctc aactccatct ggcagacctt tactcgccct
113461 ataaggccct cctcaaatac catcctcttt atagttctta ctcttttatt tcctgccaac
113521 caagtttctg cccccatggc atttggaagc tcagtggcaa aagttcaggg atttcggggt
113581 tgggcagtgt gcttgacttt ttgttcacat gttcagacaa aaataattac attcacatta
113641 aaaatgtctc ttaccttatt ctgggctagt gaatgttccc tttcaatgtc ttttagatag
113701 ctgccagaga cactatctgt atctcttcct cctaccttgt acctcattat cagtgtttga
113761 gaaaggagtt gataactgaa ttctcagttc tagccaaatg tgaatgggga tctcatagtc
113821 agttcaggcc caagttttgg gtgcagactg taaatggctt tgggacaata atattctata
113881 aaccatgtaa cagtagtttt ctaggcatat ttcctatagg aatctttatc cagggcaaag
113941 gcatttgggc tgcaccaaag tcccagatgc cttgttataa ggtagctctc aaacagtagc
114001 tcatcagatc ccatctgcca gctctaatca gtggggaata tcagattctt ttttttaagct
114061 ttgaggggat ctgggatatg gcttgtttct ttcatttttg ggggtttca ctttgttaga
114121 tatacataag atttttaaaa atgttttcag tcaaattgat ttccttcttc cttacagtgt
114181 aaggcaaaca ttggtgggca ccgatcttcc tgttcattct gcaagaaccc aagagaaggt
114241 gagtggcgaa agtggtagca gttttttatct cgtgcattga gcaaaacaaa tttcatgttt
114301 tccttggctt tgaagaatta tcatccctaa atccaagttg atctacaaac cttttttttt
114361 ttttttgaga tggagtctcg ctgtgttgcc caggctggag tgcagtggca ccatcttggc
114421 tcactgcaac ctccagctcc caggttcaag cgattcccct gccctagcct cctgattagc
114481 tgggattcca ggcatgtgcc accacgccct gtagcccggc taatttttt gtattttag
114541 tagagacggg gtttcaccat gttggtcagg ctggccttga actcctgacc ttgtgacccg
114601 acccaccttg gcctcccata gtgctgggat tacaggtgtg aatcactgca caaggcctgc
114661 aaaccttat ttatttattt attttgaga cagagtctcg tactcacca ggctggagtg
114721 cagtggcgca atctcggatc actgcaagct ccgcctccca ggttcacgct gttctcctgc
114781 ctcagcctct ctagtagctg ggactatagg cgcccaccac catgcccagc taattatttg
114841 tattttagta gagacggagt ttcaccgtgt tagccaggat ggtctcgatc tcctgacctc
114901 gtgatctgtc tgcctcagcc tcccaaagtg ctgcgattac aggcgtgaac caccacgacc
114961 ggcccaaacc tttcaaaagt gcaatttgag ctaggcatgg tggctaacgc ttgtaatccc
115021 agcacttttgg gaggccaagg caggtggatc acctggtgtc aggagttcaa gaccagcctg
115081 accaacatgc cgaaaccctg tctctactaa aattacaaaa attagccaca ggtgtggtgg
115141 cacatgcttg gaatcccagc tccttgggag gctgagacac tagaatcgct tgaacccagg
115201 agtcagaggt tgcagtgagc tgagatctcg ccactgcact ccagcctagg caacagagtg
115261 agaaaaaaaa aattgcagtt tggtgcccaa cttaacgtaa cctgttagta aatgatttca
115321 gatcttattt tcaccagagg aaagagatag ggttgtgggc tcctaggcta aagtggctaa
115381 gtgggcagct gagcagaggt cagtatattg ttatttggaa tacatttaag gattaaggat
115441 gttaggttga aaaagagtct ttatgacatc agtctgtgtg gcaaaccttt ctcccactcc
115501 tacttctttg aagttattgg gaatcatttg ctctattgtt ttctcttta cattctgtaa
115561 gcatttcagg atttttcaaga gaaaacatt tgttaaaata acagtaaaaa cataaatagg
115621 agaaataat caggatgtgg ggaacatttt attatttag aggaataaaa ctaccagctt
115681 ctcaagcact tatctttaat gtaaatttct ttagagaaat ttcaggtagg caacttcgaa
115741 gagtcagaca catgcatcca taacaacagt cctgtagtca tcccttaagg aaagcacag
115801 catgaccata aaatatagtt cagtgcaggg attcaggtag ccttctgttt gttgcaaggt
115861 tagagtttaa tgtgcctaca aggagtttct taggtgggct tttgtcctct tgtggagatt
115921 ttactctggt gaagactgaa aggcaggtgt tctgaaaatc tttaggggaa ggctgtgtat
115981 gttctagaaa ccaaaccaaa atgtgggaag gaggatgaac aactgagatt tttgcttgtt
116041 aggtcacttc aggttaggca aagttgtgtt ttttccccc cacaagaaac actttttttc
116101 aaagctattc cagcaaatga atagatagtt ttttgttttt tttcttttt tttttgagac
```

FIGURE 14 (cont.)

```
116161 ggagtcttgc tctgtcaccc aggctgaagt gcagtggcgc aatctcggct cactgcaagc
116221 tctgcctccc aggttcacgc cattctcctg cctcagcctc ccaagtagct gggattacag
116281 gcacccgcca ccgtgccagc taatttttt gtattttcag tagagacagg gtttcactgt
116341 gttagccagg atggtctcga tctcctgacc tcgtgatctg cccgcctcag tctcccaatg
116401 tgctgggatt acaggcgtga gccaccgctc ccggccatga atagatagtg tatgaaaacc
116461 actgggcacc ataccactaa gatgagacag ctttaatctg gaaacctgtc actgctatta
116521 tgtaatctct atattgctct catataatac ctcttttga gccacatgga ttccagtgaa
116581 ccctccaaga atgaattagt tacaagaatg tgcccctaat tataaaacaa actataaaga
116641 caaattatcc tgctgtagta ggacatttga aataaatcat ttatattttg aaggacgtct
116701 gcccattatg tttatttgca tataaaggag ctacgtgcag atagggtctg ttcctagctt
116761 cactggagga gggcctgtgg tcttacagga tatgagtagc tgtttgagca ctgtaacact
116821 ggaagaagca aggcttctag atgtgtgttt gggatatgtg tttctactaa accttaagta
116881 agggccatat cttcggtaat tttgtcccca gatgtgttgt tatcattgat tatgatagtc
116941 aggttcaagg tgtcatgaag gatttgttat atttaaatgt ttagtaggtg atatagagat
117001 ttcataagat tacatttttt aaatgcttgg atagtttctt ctgtgaacta tttcatgtcc
117061 tgtctcagct tcacttaaaa tattttgtca ggaactgtca gaggactttt tattagatat
117121 ttctgagata atattaaaag cattccaggc cgggcgtgtt tgctcacacc tgtaatccca
117181 gcactctggg aggccgaggc aagtggatca cctgaggtca ggagttcgag accagcctgg
117241 ccaacatggt gaaaccctgt ttctactaaa aatacaaaaa attacctggg cgtggtggtg
117301 ggcacctgtg atcccagcta ctctgaaggc tgaggcagga gaatcgcttg aacccgggag
117361 gcagaggttg cagtgagcca agatcatgcc attgcacttc agctgggcaa caagagcaaa
117421 actccgtctc aaaaaaaaaa aaaaaaaaa aaggcattcc agtatgagta tttgctggca
117481 ggtaaggaga aattacagta gcagtgtttt ttcttttttt ttttttttga taaagctttc
117541 tagagattct ctttgtttct gttccactag tgacagaggc caagcaagaa ttaataacct
117601 accctcagcc tcagaaaaca tccataccag caccattgga aaaacagccc aaccagcccc
117661 taagaccagc tgataaggaa cctgaaccca ggaagaggga agaaggccaa gagtcacgct
117721 taggacatca aaagagagaa gcagaaaggt atctgcctcc ttctcgaagg gaagggccaa
117781 cttttccgaag agaccgagag agggagtcat ggtctggaga gacacgccag gatggagaga
117841 gcaaaagtaa gtagtttgtc agggcacata ccagactgtg atcatcacaa tggagcatag
117901 atggccaatg ttatgtccgg gagctatctg cttccagta ccctgagaga tctgtgcatg
117961 acctgatgac agaggccatt gctgtctgtg gaccttcctg tactgcttaa aggaatctat
118021 gcccttcaaa tagtaaattg ctatatgaat gcagtaaggc atgattttag atttctaagt
118081 attggtgaag aaaagtatgc agtatttatt tgtttagcat ttttttacag aaccagcctt
118141 gctagtagca tctatagtaa aaaatgacag tcagattctt gggacttcaa aaatttatct
118201 ttctctccct tgtgttgccc ttctcccatt tatggttgat tcagctatca tgctaaagcg
118261 tatctatcgt tccacaccac ctgaggtgat agtggaagtg ctggagccct atgtccgcct
118321 tactactgcc aacgtccgta tcatcaagaa cagaacaggc cctatggggc atacctatgg
118381 ctttattgac ctcgactccc atgcggtgag tttcctccac cttggattgg cctagagaca
118441 gatggctaaa gaaccttcaa gaaggtttga ctgggggccg ggcctggtgg cttacgcctg
118501 taatcccagc actttgggag gccgaggtgg gtggatcacg aggtcaggaa atcaagacca
118561 tcctggctaa cacggtgaaa ccctgtctct actaaaaat acagaaaaat tagctgggcg
118621 tggtggcagg cgcctgtagt cgcagctact cgggaggctg aggcaggaga atggcgtgaa
118681 ctccggaggc ggagcttgca gtgagccgag atcgcgccac tgcacttcag cctgggtgac
118741 agagcgagac tctgtctcaa aaaaaaaaaa aaaaaatttg agggacttct tgatcatttg
118801 aattcttgtg tgctacctga tatcataatc cctcttgctc tctcctttgg gtttattgtt
118861 cattcaggtc aggtgacagc cctcaaaagt taggatcccg tctggttttc taggttcatt
118921 tttttcttgt gtcatttact gtttccaact tactcgcttg tgaagaatct gagtactgaa
118981 tccttcatga ttttagtgaa ctttctgatt tattttgtcc agccacagat ggttttatat
119041 ttgatgataa acatttcct cttttcctc aaagtattta tagattcctg tggcttaaat
119101 ttttagttgc ggggccttt tctatggaag taaggtgaag ataatgaaag tcattggtat
119161 ttcttagatt tttcatgctc aaaagtcaca agggactttg taaactgaat ctgattgatg
```

FIGURE 14 (cont.)

```
119221 ataattgcaa cctaaaagaa gaggatttga atttctgaag tttatgccag aactgacatc
119281 tattctgatt cctgttccaa tcagtccttc attaaaagtt gcctgtttct gccagtatgc
119341 tcttactgtt aaaattttga cagaatataa tgtagtaaat ttatcctctg agaaggaaaa
119401 tccacgttca cttctctttc aaggagaat ttttctgtct ttgggttctg gcattttctg
119461 tctctgggtt caagtgtgtc tggttctata ggaagctctt cgtgtggtga agatcttaca
119521 gaaccttgat ccgccattta gcattgatgg gaagatggta gctgtaaacc tggccactgg
119581 aaaacgaagg taaggcagaa gggtgaggat ctcttgtgct gcccccactt gtgtttttga
119641 gaggaaactc cttttcctgg ctggaaaaac agtaaagcat gatgttttcc taacatggac
119701 tgcttcagat aggtgtttat tacagtttct ttctgaagcc tgacttgtcc tgactctcga
119761 attgttttct ttcttgaata atactaggta cttttgtcct ttccctttg actgtctggt
119821 atctttgggt cccaaatggc ctggcgtggt agcacatatc tctattccaa gctactaaag
119881 aggctgaggc gagatgggga gcgggttaca tgagcccagg agttctaggc catagtgtgc
119941 aatgaagatg cctgtgaata accactgtac tctaccctgg gcaacacagc aagaccctat
120001 ctcttaacaa aaaaatgatg gtacagtttt ggatgtgcag acacatgtca atacattctt
120061 gcccccttgca atcctaggaa aatgctgtcc tggcttttcc ttccctgac cttgtgcata
120121 tttccatagc actgggaaat ctaatttctc tttcctcctt cactcatctt gacccaggag
120181 tggtaacttg gaaatggcca tgtcagagaa acaggcttac caatatgggg catatcttgc
120241 tctagcaccc tccacttaat ggctgttttg ctccaccact tggctttgta agagtcttac
120301 tgctcattgg gcaggcgtgg tggctcacgc ctgtaatctc agcacctggg gaggccagg
120361 cgggcagatc atgaggtcag gagattgaga tcatcctggc taacacggta aaacccgtc
120421 tctactaaaa atacaaaaaa aaaaaaatta gctgggcgtg gtggtgggca cctgtagtcc
120481 cagctacttg ggaggctgag gcaggagaat ggtgtgaacc caggaggcgg agcttgcagt
120541 gagctgagat cacgccaccg cactccagcc tgggcgacag agcaagactc cgtctcaaaa
120601 aaaaaaaaa aaaaaaaag agtcttactg ctcattcttt caggagtgtc tggaccaccc
120661 aacctgcttg ctgtctaggt tggttccttt ccctgcaaaa tgaggaacag aggatttctc
120721 gataggaact gtaggattaa gtactcgtca aatgccactt ggtagcagcc ttaagaattg
120781 ttgtgttatc tgttgcagaa atgattctgg ggaccattct gaccacatgc attactatca
120841 ggtaggctgt aacaggtggg gagtgctcta ttaaaatcct caggtgacta taagggtgat
120901 cttgaattt ctttagtggg tgactgttaa ggtgaatgac cattggatag ttctgtaatt
120961 ttaacttgcc tttctgtgat agggtaaaaa atatttccga gataggaggg gaggtggcag
121021 aaattcagac tggtcttcag atacaaatcg acaaggacaa cagtgtaagt aacctttgtt
121081 ttatttctgt tgctcttttt tgcttgactt gctactcatt acttgacatc tgtgtgatca
121141 cagttggcaa gatacactgt tgactgaggg tgctcatcca gagagaggca tctgtagatg
121201 cacctatttg tgttggtcac cctaattctt gggttcttga tgagtctcca gtaagggctt
121261 cattggacag agactaacat tggctctgat cttgttacct ttagcatcat ctgactgcta
121321 catatatgat tctgctactg gctactatta tgaccccttg gcaggaactt attatgaccc
121381 caatacccag gtgagtttgg ggctttttt tttttttt tttttttacc tctgtcaatg
121441 attctttga gaaagcacc cataatttgc tacttgagga ttttattccc tggattctct
121501 ggatgctcat tgcatgaaaa gtggaaagt ttagatctat ggaaacagaa ctgttgccta
121561 tatggaaaat cagtgccttg tggcaataca ggtaagaaca gtgttgctct tgaaaaagtg
121621 gacagtgggt ggtctgaatg tgtcctggtc cctggagtgg gttttagat tgatgtggac
121681 tcttcttaga cttgtaagta aaaagttgt ttcttcccct aaaagggaac tgtgcgcctt
121741 agacctggaa ttgctgggaa actgaaacat tctgtagact tacttgttc caactgtatc
121801 gcagcaagaa gtctatgtgc cccaggatcc tggattacct gaggaagaag agatcaagga
121861 aaaaaaccc accagtcaag gaaagtcaag tagcaagaag gaaatgtcta aaagagatgg
121921 caaggagaaa aaagacagag gagtgacgag ggtaagagga attgttaatt tgctgtcttt
121981 tgccacatag ttattaaaat gttggaggta cgaacagagg atatctatgt ttgcaagtgt
122041 aaagtaactt taaaaatact ctgtcagccg gcgtggtgg ctaacgcctg taatcccagc
122101 actttgggag gccaaggcgg gcggatcatg aggtcaggag atcgagacca tcctggccaa
122161 catggtgaaa ccctgtctc tactaaaaat acaaaaatta gctgcgtgtg gtggtacacg
122221 cctgtagtcc cagctactca ggaggctgag gcaggagaat tgcttgaacc ctggaggcag
```

FIGURE 14 (cont.)

```
122281 aggttgcagt gagccgagat cgcgccacta cactccagcc tggcaacaga gcaagactct
122341 gtatcaaaaa aaaaaaaaaa acctctgtta atgagtattt ttacctggtg taggcaattc
122401 cctcacctct tatatcccaa ctctctcttt tacaaatggg aaaactatgg atggtagaac
122461 aaagtggccc agctcaaatc ccaacacctc agctccatac attttcactt ttctacattc
122521 ctttttagt gtttgacttt atacacattt ctctagttgt aattatagca ggagatactg
122581 tttagtcact ttttatccta agtattttt ccatgtttct atatactcta ttatttttaa
122641 tgcccacatg gtaaaaattc acgtataac tgtaccttca ttttcttcat ctctcctaca
122701 ttatttgtct tctctttcta atcttttctt tttccttttt tttttttttt ttctgagaca
122761 aagtcttcct ctgtctccca ggttggagtg cagtggcatg atcatagctc acttctacgt
122821 caaacccatg ggcttaagca gtcctcccac ctcagcctcc caagtagcgg ggactacagg
122881 catgagccac catgaccagc taattttgc tttttgtag agacaggatc ttgctagatt
122941 gaccaggctg atctcgaact tctggcctca agtaagcttc ctgtctcagt ctcccaaagt
123001 gcttcagtta caggcaagac ccaccttgct cgcctctttc taatcttata ctgtcataat
123061 atataacatt tagcatttg ttcttcttt taaattactc cctatgacac attttcagaa
123121 tcagagatga tgaacatttt tacatctaat acaaaatcaa attattaggc agggtgcagt
123181 ggctcacacc tgtaatccca gcacgttggg aggccaagac aggtggatgc ctgagtttag
123241 gagtttgaca ccagcaacat ggtgaaactc catctctacc aaaaatacaa aaaaaattag
123301 cctactgtgg tgatgcatgc ctgtagtcca agctacttgg gagactgagt taagaggatc
123361 gcttgagccc aggagattgc agtgagctgt gattgcgcca ctgcactcca gcatggacaa
123421 cagagccaga cttgtctcaa aaaaaaaaaa aaagaaaat ctgccgggca tggtggctca
123481 tgcctgtaat cccagcactt tgagaggcca aggcaggcgg attactttag gtcaggagtt
123541 tgagaccgcc tagccaatat ggtgaaaccc ccatctctac taaaaagaca aaaattagct
123601 ggacgtggtg gcgcaagcct gtagtccag ctactcagga ggctgaggca ggagaatctc
123661 ttgaacctga gaggcagagg ttgcagtgag ccaagatcac acctaccttg atatcagtta
123721 tgcattagtg aaaatggatg aatttgcttg tgattcaatt cataacacct tttttccct
123781 tttttttctt ttgagacgga gccgctctgt cgcccaggct ggagtgcagt ggcgtgatct
123841 atctcggctc actgcaacct ccgccttcca ggctcaaggg attctcctgc ctcagcctcc
123901 tgagtagctg ggatatcagg cgctgccaca acgcccagct aattttgta ttttagtag
123961 agacgcggtt tcaccatgtt ggtcaagctg gtctcgaact cctgaccttg tgatccgccc
124021 acctcagcct accaaagtgc tgggattaca ggcatgagcc actgcgccca gccttttttt
124081 ccccttctaa cactgttagt tgtttagaga tacagaaaag aggagagaga gtgtgtgtgt
124141 gtgtttaaaa acttagagtc atactgattt aatatttgga ctctgcttca gccacttaat
124201 ctgtcaaact atattcccaa tcatttgtaa aattaagata gtaaagctta cataggagga
124261 tcatagtaaa gtctgaagaa gacaatgttt atatatacat gcctcatctg gtctgacata
124321 cagtaatcat gcaatatata ctaacgtttt attttatttt attttatttt ttgagacaga
124381 gtctctctct gtcacccagg ctggaatgga gtggcacgat ctcggctcac tgcaacctct
124441 gcctcccagg ttccagcagt tcttctacct cagcctccca agtagctggg attacaggcc
124501 aaaaccacca cacccagcta atttttgtat ttttactaga gacggggttt caccatgttg
124561 gccaggctgg agcacagtgg cacaatcttg gctcactgca agctccgcct ctcgggttca
124621 ttctcctgcc tcagcctccc tactaactgg gactacaggt gcccgccacc acgcccagct
124681 aattttttgt attttagta gagatggagt ttcactgcat tagccagggt ggtctcgatc
124741 tcctgacgtt gtgatccacc tgccttgacc tcccagagtg ctgggattat aggcgtgagc
124801 caccgcaccc agcccagcct ttatcagtta ttatgagtga atatcatgtg agagttacct
124861 ctggtttgat cagtttcagg aaaatgccag tgaagggaag gccctgcag aagacgtctt
124921 taagaagccc ctgcctccta ctgtgaagaa ggaagagagt cccctccag taagaccaac
124981 attgatcccc tggacctagg gctggggctg gggatggttc cgagtagaag aggaagcgca
125041 aaggctgatg ccttcctctg gtgttggtct tttacctcac tatgtctccc gaataaggat
125101 tcccatttct tttgagtaca agcatgagat aaagttttct gtctgctaat gggggtatta
125161 ctggagaacc agaggcagtt atctggactc tttctctctg ccctgtgcca ttcttaccag
125221 acgagatgcc tagccctttt tatcatcttg ttcttgtcag ttctctaaat caccaaggaa
125281 acccgtttc tcagcctcaa tctttcctgc cttttggcat cacacaagaa tctcttagat
```

FIGURE 14 (cont.)

```
125341 atggagtgca tgcgtggtca tttttttata gtttctgcct gttcagagtg aatgatgcta
125401 atattggtgc ccatttttta gatgccttca agcagtagtc tcaacctaat caccagtgat
125461 tctgattgaa tgcaggtata taacaatagt gaccatgcat tatttattta ttttgagtga
125521 tcatagacca atgattatgc atcattattt aacagttctt ataaggtacc cttttcctgc
125581 tccgcattat taattcagct cattgtgcca tctgtcttaa ccatgctttg cctttacctt
125641 acatgtgagc tggatctgtc tacccaagtg cctattaatg cagttgcttt tagtttactt
125701 cctaaatcct ctttgctaga gtcttaatga aagtcatctt ttcttccctc catgagttac
125761 agtaatttgg aggtatttat ctcttcctct ttgtaatttg taacctttta ctattttcta
125821 tgtttatttt cctttctctt cctctcctc acattctgtt gctagagtca cttctaaagg
125881 aatctttctt gtttattctt aatgaacaag gagcaaagcc aagctctggc catgttgctt
125941 tcatctggga aatgagcagc atggctagtg agtttatttt gaacccaatt caatgaaatg
126001 agatgcccat atcagaatat caaaaaaaat ggaccccaaa atataggttg aatttggtat
126061 tgatccctgg ccttctcctt ccagcctaaa gtggtaaacc cactgatcgg cctcttgggt
126121 gaatatggag gagacagtga ctatgaggag gaagaagagg aggaacagac ccctccccca
126181 cagccccgca cagcacagcc ccagaagcga gaggagcaaa ccaagaagga gaatgaagaa
126241 gacaaactca ctgactggaa taaactggct tgtctgcttt gcagaaggca gtttcccaat
126301 aaagaagttc tgatcaaaca ccagcagctg tcagacctgc acaaggtatt aggggaagga
126361 gctatgccct ttcaaactgt tgactcttgg ccgggctttg tggctcatgc ctgtaatcct
126421 agcactttgg gaggccgagg cgggtggatt gcctgggctc agaagtacaa gaccagtctg
126481 ggcaacatgg tgaaacccccc tttgtactaa aatacaaaaa attagccagg tgtggtgttg
126541 tgtgcctgta gtcccagcca ctcgggaggc tgaggcagga gaattgctag aacctgggag
126601 gcagaggttg cagtgagccg agatcgtgcc actgcactcc agcctgggta acagagcaag
126661 actccatctc ttaaaaaaca aaacaaaaca aaactgttga ctcatattat tgatggggat
126721 tatggggaat aaaaaagatt atttaggccg ggcctagtgg tttacacctg taatcccagc
126781 actttgggag gccaaggcac ctagtagat cacttgagat caggagtttg agaccagctt
126841 ggccaacatg tgaaactgt ctctactaaa aatacaaaaa ttacctggat gtggtggcgc
126901 atgcctgtaa tcccaactac ttgggaggt gaggcaggag aatcgcttga acctgggagg
126961 caaaggttgc agtgaaccga gatcacacca ctgcactcca gcctgggtga cagaccaaga
127021 ctctatctca aaaaaaaaa aaaaaaaaa aaaagccgc agcagcttat acaatccttc
127081 ctcagtgtat atcagcccca gttcctatca ttaaaacagt ccaattcaag aatgaattgc
127141 tctggattaa ggttatgcct accctcaaag aacttccatg tataggccga agccaagcat
127201 tatgactgtg gctagggtgc caaatatgga ggatgggtag gaagagaaag ggttgtggaa
127261 taggacatta cttgctgggt ttctcatctt agctgtgtca ttaacgttac agttggacct
127321 cagataagcc ccтттттcттc tttggtcctt gtaacttcat ctgattctat ccagctctga
127381 cagtgtgcag ttttcaccat aggtgagtca aattctgcca tttcttcatg tagtgaatat
127441 tgttatgagc cacagcacaa catctatact tgggatgtta aaccgacata cattggtctt
127501 cccctgtagt attcccattt atatgaactg accaaggatc caaaтттaтgg acaaataaag
127561 tccctaaatg gactcacatt ctcagagcaa ттттgтттcac accccttctc tagtagatgt
127621 tgcaagagca ggtgatggaa ctagattcag actttctctg aatacagagc тcaaagттттт
127681 atttagctaa aagctgagaa gttctgcttt tggtaatagg tacactactt тттcccagcca
127741 tctctgtgga ggctttgcaa agataggact ctgaaaagct cctgataatc cctggaacag
127801 actacctccc atgtccttt tg acctgaaagтт gtgagttgtc agactgacac attgaaattt
127861 cacccatctg atgtaaatac taataaatgg cтaaagaggат aaaaagtaat cgtcaggaaa
127921 gaggagccaa aggtctggtg aattcacaaa ctgaactggt cataggacag tggaaagtag
127981 actgtagtac ttttcctttc ttaaggtcg tctgctacaa agaaccacca ttcatgtaa
128041 gagctgcttt ggactcctta agtttcatac atatgtctga gggcttgtgt agtagagcca
128101 tgcgtgagga atttgcaact ctcagagcag тcтcтттggaa cctgggggct cctttccatg
128161 ттттcтcтggg ggctgaaaga gtgactcatg tctgggaatg gtatgtatgg cagagtatgt
128221 gggcatttgg ttttcttcac tggtgtgccc acatcctctg tcccatgatt ttcaacttag
128281 ataaagagat agatatttgt ttcccacatc ttggagataa gtaaaatgat attcctctta
128341 tgccatacca cataactaat ctgcatgaca agaccagtta gggattgttg gttgcaggat
```

FIGURE 14 (cont.)

```
128401  acagtgatca tttagtagat ctgatcaatc aaaagagcta caatccaaaa gcaactattg
128461  ggaaaggcct agaagcatct ctaggaccat tgtttcttag acctatactc atagaattgc
128521  ctctcttctc agcaaaacct ggaaatccac cggaagataa aacagtctga gcaggagcta
128581  gcctatctgg aaaggagaga acgagaggta aactttggtg acctattact cccttgacct
128641  cagctctttt tgctttctga tatagacttc ataggctgtg ctgatccctc cttataagaa
128701  gatggagaac aaaagcagcc tcaaaagata gtgcatacat ttgccaaatt atataataca
128761  atcaaaatag gtgcttttta ttatttgtaa gtttatactt caatgaagtt gatatctttt
128821  ttaaaaggtg gtgttagggt ctctaggtag ataacactcc tctttcctgc ttagcttttta
128881  aattagttga gttaatgaac aagtgttgaa tagcgctgct gaaatagcat cttttactat
128941  taaaggctaa gctggaggaa gtagcttagt gtcagagtca aatggacttg ctacctcaac
129001  cacacagtta gggtgaatta cccagtcata ggcttcactg gcctctctca tgatggttaa
129061  gaacccacct atgggtcagg cacggtggct cacgcctata atcccagtac tttgggaggc
129121  tgagacgggc ggatcacttg agctcacaag tttgaaacca gcctgggcga catggcgaaa
129181  tcctatctct acaaaaaata taaaaattag gtggacatgg ggtgtgtgcc tgtagtccca
129241  gctacttgag aggctgaggg aggatcgcat gagctgggag gcagaggttg cagtgagctg
129301  agtttgtgcc actgcgctcc agcctgggtc atagagccag accttgtctc aaaaaaaaaa
129361  aaaaaaaagg aagccacctg tggagagcca ggcacagtgg cacatgcatg taatcccagc
129421  agtttaggag gctgaggtgg gagaattgct tgagcccaag agttccaggc tgcagtgagc
129481  tatgatcaca gccctgtact ccagcctggg tcacagagta agtccctgtc tcaaaaccaa
129541  acaaaagaat ccacctatgg aggactgtta gagatagtga attcacaaac tgaactggcc
129601  ataggacagt ggaaagtaga ttgtagtatt tttcctttcc ttagagttgt ctactacaaa
129661  gaaccacctc tccatgtaag agctgctttg gactccttaa gttttatatt atatgcccga
129721  gggcttgtat agtggagggc ttgtgtactt tcccctgctt ctcagaaggg gaaaagacag
129781  cggaaccaag cgtgccaact tattctttcc aaatgtttaa gttaggaagt cactgctttc
129841  tctagaagaa cgtgtaaagg agtgagagat tccaggagtt accaagtgag ctactttcac
129901  tttaaaagaa ataacaaggc cgggtgcggt ggctcacacc tgtaatccca gcactttggg
129961  aggccgaggc tggtggatca tgaggtcagg agttcgagac tagcctgact aacatagtga
130021  aacccccgtct ctactaaaaa tagaaaaatt agctgggcat tgtggcactc acctgtagtc
130081  ccagctactt gggaggctga ggcaggagaa tcgcttgaac ctgggaggcg gaggttgcag
130141  tgagctgaga tcacgccagt gtactccagc ctgggcaaca gagtgagact ctgtctcaag
130201  aaaaaaataa taataataac agcaatgggg tagaatttcc ccactcccca attccctcag
130261  gtggcaatct caggtctgct cttctgctta ccaacaggga aagtttaaag gaagaggaaa
130321  tgatcgcagg gaaagctcc agtcttttga ctctccagaa aggaaacgga ttaagtactc
130381  cagggaaact gacaggtaag ccaggaactc ttcattcagc ctaggcctca agcctaatga
130441  taaaaccacc tcctccttca actgtactgc tgttttctgt ctcagggaga tgatattatg
130501  agtagattct gtctgaactg ctaaaacatg aggtctatgc cagccttttt actatctgtc
130561  tttatacggg gagtgtacat ggaaggttgg ctggcagctt cgccttccca aagccagggc
130621  tggagtagcc atgatcggga acccttctg tcttcatcag taatactgca ccctctttac
130681  gggcctgata agaatgtcac actcttgggc ttttctcta gggaacctcc attctcacac
130741  ataggtgcta aataaatggt tggctgctga tggagatgta tgatatctag cttcctatac
130801  ttgttttcag tcagctagtt cccaagttgt aagcccagag ttatatagaa tttgttgata
130861  acccactgtt tacaggtgtc aagtgcaaga aatactcagg tggacaagac atagattatc
130921  cttgactgaa cacagaatag acaagactta ggtgatggtg cgtctcatag ggcagacaca
130981  gaaatcagtg gggaagggaa gggcatttca ggaatttca tataccaggg atataagagc
131041  ttatgatgtg tttgaggagt tgcaaatagt ttgatggtcc tgaacactgc aggtatattg
131101  ttgagtgaca gtagataagc ctggtccaaa agatgcaggc cagttcatga agtttaaaca
131161  ccttgaacac cttgctaagg ctttatctta aaggcagtgg acggtcatgg aataatttta
131221  agcagggtat tgacttagct ttgcattttg gagagattac taatcatgtg gaagatgagt
131281  ttgtagagag actaatgcat tatgcaaatt ctatagtaat tcaagtgaaa gatcatgatt
131341  gcctgagtga aggtgatgag tctagaaagg agagtggcct ataatcccaa cacagagagg
131401  ctgaggaagg aggatctctt gagcctagga gttccaggcc agcctaggca acatagggag
```

FIGURE 14 (cont.)

```
131461  aagggagacc ctgcctctat ttaaaaaaag aaaagaaaag gagtgtggct tagagagagg
131521  tgtcagatct gccagtcttt gtgatcacct ggggaaaggg agaagtcact gatggtgttc
131581  aggtctctgg tctctggata gctaggagga gaagggacag taaagtcctt gaaaaggaaa
131641  aatgggggcc aggcgtggtg gcttacgcct gtaatcccag cactttggga ggccgaggcg
131701  ggtggatcac aaggtcagga gttcgagacc agcctggcca agatggtgaa accccttctc
131761  tactaaaaat ataacaatta gctgggcgct gtggcaggcg cctgtaatcc cagctactca
131821  ggaggctggg gcagaagaat cgctcaaacc tgggaggcag aggttgcagt gagctgagat
131881  catgccactg cactctagcc tgggtgacag agcaagactc tgtctcaaaa aaaaaaaaa
131941  aaaaaaaga aaggaaagg aaaatgggg ccaggtgtgg tggctcacac ctgtaatccc
132001  agcactttgg gaggctgagg caggtggatc acttaaggtc aggagttcga gaccagcctg
132061  gccaacatgg tgaaaccctg tctctaccaa aaatataaaa aaattagcca ggcgtggtgg
132121  tgggtacctg taatcccagc tactcgggag actggggcag gagaatcgct tgaacatggg
132181  aggtggaggt tgcagtgagc caagattgca ccactgtact ctagcctggg taatagagcg
132241  agactccaaa tcaaaaaaaa aaagaaaag aaagaaaag gaaagtggg taacaagtgg
132301  atgcatgagc agaaggaaag ggagataatt gacagagcaa ggcccttgag gaggctggac
132361  aggttttggg gctctggcat tccagcttat ttgatccaac ccacaataag agaagtattt
132421  ttgtatcatg gcccaataat aaagtgtgtg tgtgcacaac tgaaaaagtt ttcatctaaa
132481  atactttctt accaggtaca gtgaaccctg atatttttat tcaagtctag tctctcttca
132541  tttttatgag ttgttacagt gggaccattt agtgtgacat tccattgggt cattctctgc
132601  aatttgaaat acagtggatt aggactaggt gaaggagtca gccatcagga ggaaggacac
132661  cttggccttg agtcttctgg gacaaggctt aggtggggtg cggaaagaga cccttcttta
132721  ttctcagcac cctttatacc acattctcct ggctcttctc ctttccagtc accttttctg
132781  ctcctcttcc ttttctggat aaatccaggt gttctctagg actcttctct cagtgcttct
132841  ttggtcttgc tgctctaccc tcttgacctg ggctttctaa ggtacccatg gcctcaacca
132901  ccaccacagt ctaacaagtc caaatctcct gtattattat ttcagagtag cagcatcata
132961  gcatcactgt ctacatggtc tgatccatcc tcctccttta tcccctgtgt ccaattagtg
133021  accaaatccc taattaagtc ttgccccctg tcttagtctg ttttatgata ccataactga
133081  ataccacaga ctgggtaatt tataatgaac agaaatttat ttggctcatg cttctggagg
133141  ctgggaggtc caagattgag gagctgcatc tggtgagggc cttcttgctg tgtcacctca
133201  tggtggaaag taaaagaaca agagagctta ggcaaaagag ggggttggga gaaagaaacc
133261  agactaatca ttttatcagg agaacccact cctgcaataa cagcattaat ccatttgtga
133321  gggcagagct ctcatgacct aatcacttcc tgaagtttca cctctcaata ctgttgcatt
133381  ggggattatg tttccaacat atgtactttg agggacacat ttaaaccaca gcatctccca
133441  ttctattcca cctccacact ggactcctac tcccagtctt tgctcccact gttcttcagt
133501  ccattctcta ccctgccacc aaaatgactt ttgtaaagag aaatctactc ttataacttg
133561  tcttttttaca aaccgtatac cttgcctaca gggaggcctg agctccaact tttgccagaa
133621  ggatgaggtt cagagacatg atttagctta ataagttcaa ggttttttac agtctgaccc
133681  catgcagcct ttttttttttt tccttttgtt ttgagacagt ctcattctgt cgcccaggct
133741  ggagtgcaat ggcacgatct tggctcactg caacctccgc ctcccaggtt caagcgattc
133801  tcctgcctca gcctcccag tagctgggac tatgggctaa tgtttgtatt tttagtagag
133861  aggggtttca cctgttggtc agggtggtct cgaactcctg acctcaggtg atccacccgc
133921  cttggcctcc caaagtgctg ggattacagg cgtgagtcac tgcacccggc caccaagcag
133981  ccttaccttt gtcagtttct actactactc tcttggacaa attgtctttt gtgtctcctt
134041  gcttgtgtcc tccttttctc ttacacaaac tccttatttc gagatccaat tcagatgtat
134101  cttcctgttg aaattcctgt cattttggt gatgcccctt cagagttttc gttccttcta
134161  ctgcatttct tttttttttt tgaaacagag tttcactctt gttgcccagg ctggagtgca
134221  atggcgcgat atcagctaac cacaacctcc acctcctggg ttcaagcgat tctcctgcct
134281  cagcctcccg agtagctagg attacaggca tgcgccacca cacccggcta attttgtatt
134341  tttagtagag acagggtttc tccatgttgg tcaggctggt cacgaactcc caacctcagg
134401  tgatctgccc acctcagcct cccaaagtga ttccttctac tgtatttcta tagcagacat
134461  ctactgttgc tacatccatg gttgagctct cttcaatgtt ctataagcat ctcttgacat
134521  aatgtttgag acctttcttg tgaacagggc catatcttag tagtctgtgt acccagcaac
134581  aaaacatagc tatcaggcac tcagaggtac tgttaaatat acttacttaa taagaggcag
```

FIGURE 14 (cont.)

```
134641 atatgaatca agaggacaga gattttatat taggcttata agcaggtctt catcaaaatg
134701 atggtgtcag gttgggcatg gtggctcatg cctgtaatcc agcactttgg gaggccaagg
134761 catgcggatt acctgaggtc aggagtttga gagcagcctg gccaacacag tgaaactctg
134821 tctctactga aaaaaaaaaa aattaaaaat tagccaggtg tggtggcggg cacctgcaat
134881 cccagctaat cgggaggctg aggcaggaga atcgcctgaa cccaggaggc agaggttgca
134941 gtaagctgag ttcgagccat tgcactccag cctgggcaaa aagagtgaaa ctccgtctca
135001 aaaaaaaaaa aaaaggaagt gatggtgtct gcttcttttg cagtgatcgt aaacttgttg
135061 ataaagaaga tatcgacact agcagcaaag gaggctgtgt ccaacaggct actggctgga
135121 ggaaagggac aggcctggga tatggccatc ctggattggc ttcatcagag gaggtaaaat
135181 ggtttccatc ttttgggggg tgacatgaac ctggaatgta attaactttc actttctggc
135241 ctagagtgat gtctttgcca ttttgctggg cttttctctac tgctgggata ggacatgaga
135301 gttgaacact ttagccttga atactgggtt atagcttggc aggctgggcc ctttgcagtt
135361 tggagttagg aagagaagga aggagttgga atggatttca tcatacttt acatggagta
135421 aatagtagag cagtatctga ggcagtttga gactgaagaa tcatttgggc aaaagaacca
135481 gggaatcagc aatgaaaggt acagaggcat ctctgagagg gactgtcagc ggaagtcttt
135541 ggtggctaaa atttaaggag catgttgttc tggttcccat gaaggacttt gcccctcata
135601 tttcaagagc ctctagaaaa ggtgataaga ggaaacatta cccattttgt gttggcttgc
135661 ttctcctctg aaaatgccaa ccataagaga ttggcttatt tctctcctac cgagtttctc
135721 atatctctgg tattaaagcc tgtatcttgc aatcatagca tcaccaccca ccttaattca
135781 tcttgggtat ttgtttaata atgaaagatt cttttctttt tttttttttg agacagagtc
135841 ttgctctgtc gcccaggctg gaatgcagtg gtgcgatctc agctcactgc aacctcctcc
135901 tcccaggttc aagcaattct cccaccccaa cctcctgagt agctgggatt acaggtgcat
135961 accaccatac ccagctaatt tttgtgtttt tagtagagac agagttttgc catgttggcc
136021 aggctggtct cgaactcctg gcctcaagtg atccgcccac ctcagcctcc caaagtgttg
136081 ggattacagg cgtgagccac tgtgcccggc caaaagattc tttaaaaaaa ttatcctgcc
136141 agggtccggg cgcagtggct tatgcttgta atcccagcac tttgggaggc cgaggtgggt
136201 ggatcacaag gtcaggagtt cgagaccagc ctgaccaata tgatgaaacc cctgtctcta
136261 ctaaaaatac aaaaattagc tgggtggcag tggcgcgcgcc tgtaatcaca gctactcagg
136321 aggctgaggc agaagaatcg cttgtaccgg ggaggcagag gttgcagtga gccaagatct
136381 tgatcgtgcc actgcactcc agcctgggtg acagagcgag actctgtctc aaaaaaaaaa
136441 ttattctgcc aggtgtggtg gctcacatct gtaatcccaa cactttggga ggccaaggtg
136501 ggcggatcac ttgaggccag gagttcgaga ccagcctggc caacatggcg aaaccctgtc
136561 tctactaaaa atacaaaaat tagccgggcg tggtggcagg cgcctgtagt cccagctact
136621 cagaggctga ggcacaagaa ttgcttgaac cggggaggca gacttgcagt gagcccagat
136681 cgcaccactg cactctagcc cgggcgacag agcatgactc catctaaaaa aaaaaaaaaa
136741 attatcctat atactgcttc ttactagtcc agaaatgcct gtggtcaaag accagcgctg
136801 aggctaatta atctataggg cccacttcat agtttgtctt tgttttacag gctgaaggcc
136861 ggatgagggg ccccagtgtt ggagcctcag gaagaaccag caaaagacag tcaacgaga
136921 cttaccgaga tgctgttcga agagtcatgt ttgctcgata taaagaactc gattaagaaa
136981 ggagacaagt tccatgggat acaacctccc tcttgttttg tttgtctctc cttttctttt
137041 gttactgttc ttgctgctag aactttttta aataaacttt ttttcaatgt g
```

FIGURE 15

Homo sapiens breast cancer metastasis-suppressor 1-like (BRMS1L), mRNA

```
   1 ggggaggagc caaggggcg agcaagctcg gtggctgggt gggttggggc gttccgcgcg
  61 cccttcattg aagcggcggt ggccggctg ggcgccggta gtggaaagcg acggcgcggc
 121 tggaaaatgc cagtccattc ccgagggat aagaaggaga ccaaccatca cgatgagatg
 181 gaggtggact acgccgaaaa tgagggagc agctccgagg acgaggacac tgagagctcg
 241 tcggtctccg aggatggaga tagctcagaa atggatgatg aagactgtga aagaagaaga
 301 atggaatgtt tggatgaaat gtccaatctt gaaaacagt ttaccgatct caaagatcaa
 361 ctttataaag aacgattaag tcaggtggat gcaaaactac aagaagtcat agctggaaaa
 421 gcaccagaat acttggaacc gctggcaact ttacaggaaa atatgcaaat tcgtacaaag
 481 gtagcaggaa tctatagaga gctctgctta gaatctgtaa agaacaaata tgaatgtgaa
 541 attcaagctt ctcgccagca ttgtgagagc gaaaagctgt tgctatatga tacagtccag
 601 agtgaactag aggagaagat aagaaggctt gaagaggata ggcacagcat tgatattacc
 661 tcagagctgt ggaatgatga gcttcagtca agaaaaaaga ggaaggatcc tttcagtcct
 721 gacaaaaaga agccagttgt tgtttcaggt ccatatatag tttatatgct acaagatctt
 781 gatattcttg aagactggac aacaattagg aaggcaatgg ctacattggg gccacacaga
 841 gtgaaaacgg aaccacctgt gaaactggaa aaacatctgc acagtgctag atctgaagag
 901 ggaagactat attatgatgg tgaatggtat atacgtggac aaacaatatg tattgataaa
 961 aaagatgaat gtcctacaag tgctgtaatt acaacaatta accatgatga agtttggttt
1021 aagaggcctg atggaagcaa atctaagctt tacatttcac agctacagaa aggaaaatat
1081 tcaattaaac attcataatc atgatttaag tgttatctaa atttaccta ttagtgttac
1141 caaatgtaag tgccatgaga gtaaaaaaat gtattcaata acttaatatt ctcactgaat
1201 catgagagaa tgtgtatttg taggtagtac tctaaataga tctcattgat atgttattaa
1261 aagaaacagt aataaaaatt ttatcacgat ccttacgttg atttgcctct taggtccgat
1321 gaccaataga tattctgtat atggtagggg tttctttcta aacattttc tttggtttta
1381 aaaaaagtta tgcaaatttg tcttatcttt agtaaactat gactacattt atctgcaatt
1441 tttaaaattt tccatatctt tgtcattcat tgtgtgttg taaataaggc cgatagaatg
1501 tttcctataa atggtttgta ctagtacatt agtgttaaac cagaactgaa atttaaacat
1561 atatatatat gaggatgtat atatggcatc atcagcttat ttagaactga tggccatacc
1621 ttacaatctt gttttaccca aaattaagct attggggttg aaagctaaaa ggagcacttt
1681 tgtagaatag caacttttct tttcctcttt cttgattgta tggtggggtg gtgacctatt
1741 tttacaaatt atacctaatg agtaaaatta gtgtaaagtg ataacatgct tctacctgta
1801 tttctagtga cccctttagcg gcaggtattt atacctggta tttatgatgc agtatataag
1861 tggtgaacaa taactgacag tattgtgctt gctgtacatg tctggtcttt tgaaacagat
1921 tttagtaagc attttccaga ggtaaaactg tgtccttatt ctaattttat tcctagggca
1981 aagtagacag ggattatttc cttgaatcta tttccaaatt aatattttt tctttggtat
2041 ttctacactt taaggccatt tggtgcaatt tagaaagtgt tggcctccct tccgctagcc
2101 acattcaaaa ttaacttcca aaacctcagg aacagtacaa agaattgaaa ccctcaatat
2161 ggcagcacag ccggctgtag tgtatattta gggtacacca aatcaggtat tcctggtggt
2221 cttgtgcact ttaatttctg ttacaatgag ttaagaggat gaggaagaaa tctacttatt
2281 aacacttact gcagaaatgt ctgcattatt ccgtttgttt tcttattatt ttacctctcc
2341 aaacatcttc ctgtgcagat cactacttca tagttgccaa attttaaaac acttaactgc
2401 tgaaattcag tgtcagcaaa gtgatattac gttgttctgt ttctaattaa ccttagcaaa
2461 tgtacataat gtcaaaaccc aatagtattt gacagtactt atgtatacaa tgtttgataa
2521 gcatttttaa taagatttgt atttttaaat ttagtatata ataaaagat gtgtttcagt
2581 gtgaaaaaaa aaaaaaaaa aaaa
```

FIGURE 16

```
Homo sapiens NK3 homeobox 1 (NKX3-1), mRNA.
   1 gcggtgcggg ccgggcgggt gcattcaggc caaggcgggg ccgccgggat gctcagggtt
  61 ccggagccgc ggcccgggga ggcgaaagcg gaggggccg cgccgccgac cccgtccaag
 121 ccgctcacgt ccttcctcat ccaggacatc ctgcgggacg gcgcgcagcg gcaaggcggc
 181 cgcacgagca gccagagaca gcgcgacccg gagccggagc cagagccaga gccagaggga
 241 ggacgcagcc gcgccggggc gcagaacgac cagctgagca ccgggccccg cgccgcgccg
 301 gaggaggccg agacgctggc agagaccgag ccagaaaggc acttggggtc ttatctgttg
 361 gactctgaaa acacttcagg cgcccttcca aggcttcccc aaaccctaa gcagccgcag
 421 aagcgctccc gagctgcctt ctcccacact caggtgatcg agttggagag gaagttcagc
 481 catcagaagt acctgtcggc cctgaacgg gccacctgg ccaagaacct caagctcacg
 541 gagacccaag tgaagatatg gttccagaac agacgctata agactaagcg aaagcagctc
 601 tcctcggagc tgggagactt ggagaagcac tcctctttgc cggccctgaa agaggaggcc
 661 ttctcccggg cctccctggt ctccgtgtat aacagctatc cttactaccc atacctgtac
 721 tgcgtgggca gctggagccc agctttttgg taatgccagc tcaggtgaca accattatga
 781 tcaaaaactg ccttccccag ggtgtctcta tgaaaagcac aaggggccaa ggtcagggag
 841 caagaggtgt gcacaccaaa gctattggag atttgcgtgg aaatctcaga ttcttcactg
 901 gtgagacaat gaaacaacag agacagtgaa agttttaata cctaagtcat tcctccagtg
 961 catactgtag gtcattttt ttgcttctgg ctacctgttt gaaggggaga gagggaaaat
1021 caagtggtat tttccagcac tttgtatgat tttggatgag ttgtacaccc aaggattctg
1081 ttctgcaact ccatcctcct gtgtcactga atatcaactc tgaaagagca aacctaacag
1141 gagaaaggac aaccaggatg aggatgtcac caactgaatt aaacttaagt ccagaagcct
1201 cctgttggcc ttggaatatg gccaaggctc tctctgtccc tgtaaaagag aggggcaaat
1261 agagagtctc caagagaacg ccctcatgct cagcacatat ttgcatggga gggggagatg
1321 ggtgggagga gatgaaaata tcagcttttc ttattccttt ttattccttt taaaatggta
1381 tgccaactta agtatttaca gggtggccca aatagaacaa gatgcactcg ctgtgatttt
1441 aagacaagct gtataaacag aactccactg caagagggggg ggccgggcca ggagaatctc
1501 cgcttgtcca agacaggggc ctaaggaggg tctccacact gctgctaggg gctgttgcat
1561 tttttatta gtagaaagtg gaaaggcctc ttctcaactt tttccttg ggctggagaa
1621 tttagaatca gaagtttcct ggagtttca ggctatcata tatactgtat cctgaaaggc
1681 aacataattc ttccttccct ccttttaaaa ttttgtgttc cttttttgcag caattactca
1741 ctaaagggct tcatttagt ccagattttt agtctggctg cacctaactt atgcctcgct
1801 tatttagccc gagatctggt cttttttttt ttttttttt ttttttttcc gtctccccaa
1861 agctttatct gtcttgactt tttaaaaaag tttggggggca gattctgaat tggctaaaag
1921 acatgcattt ttaaaactag caactcttat ttctttcctt taaaaataca tagcattaaa
1981 tcccaaatcc tatttaaaga cctgacagct tgagaaggtc actactgcat ttataggacc
2041 ttctggtggt tctgctgtta cgtttgaagt ctgacaatcc ttgagaatct ttgcatgcag
2101 aggaggtaag aggtattgga ttttcacaga ggaagaacac agcgcagaat gaagggccag
2161 gcttactgag ctgtccagtg gagggctcat gggtgggaca tggaaaagaa ggcagcctag
2221 gccctgggga gcccagtcca ctgagcaagc aagggactga gtgagccttt tgcaggaaaa
2281 ggctaagaaa aaggaaaacc attctaaaac acaacaagaa actgtccaaa tgctttggga
2341 actgtgttta ttgcctataa tgggtcccca aaatgggtaa cctagacttc agagagaatg
2401 agcagagagc aaaggagaaa tctggctgtc cttccatttt cattctgtta tctcaggtga
2461 gctggtagag gggagacatt agaaaaaaat gaaacaacaa aacaattact aatgaggtac
2521 gctgaggcct gggagtctct tgactccact acttaattcc gtttagtgag aaacctttca
2581 atttctttt attagaaggg ccagcttact gttggtggca aaattgccaa cataagttaa
2641 tagaaagttg gccaatttca ccccatttc tgtggtttgg gctccacatt gcaatgttca
2701 atgccacgtg ctgctgacac cgaccggagt actagccagc acaaaaggca gggtagcctg
2761 aattgctttc tgctctttac atttcttta aataagcat ttagtgctca gtccctactg
2821 agtactcttt ctctcccctc ctctgaattt aattctttca acttgcaatt tgcaaggatt
2881 acacatttca ctgtgatgta tattgtgttg caaaaaaaaa aaaaagtgt ctttgtttaa
2941 aattacttgg tttgtgaatc catcttgctt tttccccatt ggaactagtc attaacccat
3001 ctctgaactg gtagaaaaac atctgaagag ctagtctatc agcatctgac aggtgaattg
3061 gatggttctc agaaccattt cacccagaca gcctgttct atcctgttta ataaattagt
3121 ttgggttctc tacatgcata acaaaccctg ctccaatctg tcacataaaa gtctgtgact
```

FIGURE 16 (cont.)

```
3181 tgaagtttag tcagcacccc caccaaactt tatttttcta tgtgtttttt gcaacatatg
3241 agtgttttga aaataaagta cccatgtctt tattagattt a
```

FIGURE 17

Homo sapiens ribosomal protein SA (RPSA), transcript variant 1, mRNA.

```
   1 cgcctgtctt ttccgtgcta cctgcagagg ggtccatacg gcgttgttct ggattcccgt
  61 cgtaacttaa agggaaattt tcacaatgtc cggagccctt gatgtcctgc aaatgaagga
 121 ggaggatgtc cttaagttcc ttgcagcagg aacccactta ggtggcacca atcttgactt
 181 ccagatggaa cagtacatct ataaaaggaa aagtgatggc atctatatca taaatctcaa
 241 gaggacctgg gagaagcttc tgctggcagc tcgtgcaatt gttgccattg aaaaccctgc
 301 tgatgtcagt gttatatcct ccaggaatac tggccagagg gctgtgctga agtttgctgc
 361 tgccactgga gccactccaa ttgctggccg cttcactcct ggaaccttca ctaaccagat
 421 ccaggcagcc ttccgggagc cacggcttct tgtggttact gaccccaggg ctgaccacca
 481 gcctctcacg gaggcatctt atgttaacct acctaccatt gcgctgtgta acacagattc
 541 tcctctgcgc tatgtggaca ttgccatccc atgcaacaac aagggagctc actcagtggg
 601 tttgatgtgg tggatgctgg ctcgggaagt tctgcgcatg cgtggcacca tttcccgtga
 661 acacccatgg gaggtcatgc ctgatctgta cttctacaga gatcctgaag agattgaaaa
 721 agaagagcag gctgctgctg agaaggcagt gaccaaggag gaatttcagg gtgaatggac
 781 tgctcccgct cctgagttca ctgctactca gcctgaggtt gcagactggt ctgaaggtgt
 841 acaggtgccc tctgtgccta ttcagcaatt ccctactgaa gactggagcg ctcagcctgc
 901 cacggaagac tggtctgcag ctcccactgc tcaggccact gaatgggtag gagcaaccac
 961 tgactggtct taagctgttc ttgcataggc tcttaagcag catggaaaaa tggttgatgg
1021 aaaataaaca tcagtttcta aaagttgtct tcatttagtt tgcttttttac tccagatcag
1081 aatacctggg attgcatatc aaagcataat aataaataca tgtctcgaca tgagttgtac
1141 ttctaaaaaa aaaaa
```

FIGURE 18

Homo sapiens cytochrome c oxidase subunit Va (COX5A), nuclear gene encoding
mitochondrial protein, mRNA.

```
  1 gcccacgcgc cagagtcgca gtgggcgggc ctacgtgctc cgcccgctgt gagcctgtcc
 61 ggcccccgcc cgctccggag caacccgcga gcttacaccg gcttctctct gtcctcagcc
121 cgcgcgccgc catcgccgtc atgctgggcg ccgctctccg ccgctgcgct gtggccgcaa
181 ccacccgggc cgaccctcga ggcctcctgc actccgcccg gaccccggc cccgccgtgg
241 ctatccagtc agttcgctgc tattcccatg ggtcacagga gacagatgag gagtttgatg
301 ctcgctgggt aacatacttc aacaagccag atatagatgc ctgggaattg cgtaaaggga
361 taaacacact tgttacctat gatatggttc cagagcccaa aatcattgat gctgctttgc
421 gggcatgcag acggttaaat gattttgcta gtacagttcg tatcctagag gttgttaagg
481 acaaagcagg acctcataag gaaatctacc cctatgtcat ccaggaactt agaccaactt
541 taaatgaact gggaatctcc actccgagg aactgggcct tgacaaagtg taaaccgcat
601 ggatgggctt ccccaaggat ttattgacat tgctacttga gtgtgaacag ttacctggaa
661 atactgatga taacatatta ccttatttga acaagttttc ctttattgag taccaagcca
721 tgtaatggta acttggactt taataaaagg gaaatgagtt tgaactgaaa aaaaaaaaaa
781 aaaa
```

FIGURE 19

Homo sapiens family with sequence similarity 53, member B (FAM53B), mRNA.

```
   1 cgccgccgcc gcacgccgcc tgcctcctgc acgccgccgc cgcgcctagc gcccgggccc
  61 gcgacaccgc ccgctaagcg ccgggccgag ttcacgcagc cgcggtctgg cggctccgcg
 121 gcggcggcgg gtgcgggcgg cctggccggt gccggttaaa gggacgagtt gcaaacactt
 181 caggaagtga caagtcgatt tcctcctccc cgggagtcgc tcgtacaaag cgctcggcgc
 241 cggcaggcga gcgtgcgcgc ggcggacgcg cggcgggcac cccggacgac ttggcgagcg
 301 ctggcggtga cggcgcgggg tccgcgcccg gagcgccccg ccgcgcacag gagttgacca
 361 catttggcca tttcccagaa gggcccacc ccaagggtga gtggccaatg gggagctgtt
 421 tctgctgaca tcaattcccc aggaggtact caccccaagt ctgcccaagt gaagatggct
 481 gatacccacc ctgggatgga gcccagcgcc tgaggcccct atcatggtga tggtcctaag
 541 tgaaagcctc agcacccggg gagctgactc cattgcatgt gggaccttca gccgtgaact
 601 gcacacgcca aagaagatga gtcaaggacc tacacttttc tcttgtggaa ttatggaaaa
 661 tgacagatgg cgagacctgg acaggaaatg ccctcttcag attgaccaac cgagcaccag
 721 catctgggaa tgcctgcctg aaaaggacag ctcactatgg caccgggagg cagtgaccgc
 781 ctgcgctgtg accagtctga tcaaagacct cagcatcagc gaccacaacg gaaccccctc
 841 agcaccccct agcaagcgcc agtgccgctc actgtccttc tccgatgaga tgtccagttg
 901 ccggacatca tggaggccct tgggctccaa agtctggact cccgtggaaa agagacgctg
 961 ctacagcggg ggcagcgtcc agcgctattc caacggcttc agcaccatgc agaggagttc
1021 cagcttcagc ctcccttccc gggccaacgt gctctcctca ccctgcgacc aggcaggact
1081 ccaccaccga tttgagggc agccctgcca aggggtgcca ggctcagccc cgtgtggaca
1141 ggcaggtgac acctggagcc ctgacctgca ccccgtggga ggaggccggc tggacctgca
1201 gcggtccctc tcttgctcac atgagcagtt ttcctttgtg gaatactgtc ctccctcagc
1261 caacagcaca cctgcctcaa caccagagct ggcgagacgc tccagcggcc tttcccgcag
1321 ccgctcccag ccgtgtgtcc ttaacgacaa gaaggtcggt gttaaaaggc ggcgccctga
1381 agaagtgcaa gagcagaggc cttctctaga ccttgccaag atggcacaga actgtcagac
1441 cttcagcagc ctcagctgcc tgagcgcagg gacagaggac tgcggtcccc agagcccctt
1501 cgcccgccac gtcagcaaca ccagggcctg gaccgccctg ctctcagcct ccggcccagg
1561 gggcaggacc cccgctggga ccccggtccc tgagcctctt ccccttcct tcgacgacca
1621 cctcgcctgc caggaggacc tgtcctgtga ggagtcagac agctgcgccc tggacgagga
1681 ttgtggcagg agagcggagc cggctgcagc ctggcgggac cgcggggccc ctgggaacag
1741 cctctgctcc ctggacggcg agtttggacat tgagcagata gagaagaact gaggggggtgt
1801 gggcccaggc agggctgggg tgtgctggca tcgacagccc ccactctggg cactaggtgg
1861 gcccttgaag gggagcccaa ctcgtgggcc tgatgaaagc ttcctgagtg gtgtcgggtc
1921 ccagagaggg agcccacctg ctgcctgggg gagagcctgg cctgccgcg tcatacagcg
1981 ggtgtgtcag cctctcaccg gctccccgag cgtggcagcc accaggtcca cagaactact
2041 gcagcccaga ggacagcttt gaagtttgcg tcttttctgc ctctttccct gtgggatgtt
2101 gggcagtctc tgttgtcccc ggcagagctg ggcaccgctc tgtatccccc tggtggtggg
2161 ggctgtcagg gagggcctgg ggtgggggcc aggggccatc tgctatgtca gggcccttct
2221 tggcctcact caggttcact tctggggagt cggccccgca gcttctttca ctcagtttta
2281 ctccgtgcct tctctcccag gtctccctgc ttcaggcttg gaaggttcg ggagatgctt
2341 ccttctgtaa caccagaacc atttggcctt aattccaatg tgagagacag aatccctggg
2401 gtgctggact ggccctccag agggtaagcc atgtccggag tctcgggccc aaggaacgat
2461 ttggagggtg cttgttaggg cctccgtgt tgggtagaaa tttggtggat ctgttggctg
2521 aaaagacgga cttgcttgcc tctcctacag catggagagg ctgaccccat ggctctgcca
2581 ccgttggggc agggttagca gatggcagcc cttctctgtg gctgacaggt cactgagtga
2641 taagcatggt tggttccggt gagtgtaggg atggcacgat accagggcag cctcttgaaa
2701 acggcctcgg gagacgggag ctgcgagcag gtgggcagat gagggcccta tgcgcactca
2761 ggggtgaagg gcgtccgctg gccactctgc aggggcccct gcaggattcc aggcacctcc
2821 cgtttgtcct tgaggactgc tggctgtaac cagggcacat cacccacctc aagacaagcc
2881 cacgcccttg tcagcttagg gggagcccag tcctgagggc tgcatctctg ttgtaggccc
2941 agccaccggc acaaagctgg attcatgctc cctgcccta ccccaccctg gctcctcacc
3001 ctggggcatc cgaggagcct agccccctga gggtttgctc tcctctcaag gtttgtagct
3061 cctctccggc tgccttgcag acaccaccac atgggctctg ctctatggga atctggcttt
```

FIGURE 19 (cont.)

```
3121 tagcgaatgt ggcgtcttct gcaaacaata gcaattgggc tggcttagga gcaagtggct
3181 cattttccca taaggctaaa aataactggt gcgctccctt gtgttggctg acacgcgcgt
3241 tcaaagcact tttgtagtca ctttgctttt gctcgtcttc atggacgagt gaacgcctcg
3301 cttctgcagg ttgagtccag atgcttctca ccttctttct cctcaagaaa gatgctttt
3361 gggaaacgtt gtttaaatct tatttttta ctacatcaaa aggatggtgg ttcaagttcc
3421 caatatgtgg gtggcacttc ttaaaaatca gctttaagga gctggcagaa agccccagc
3481 cccacagccc tgagagatgg tgttgctagc tcaggtggct gacacatggg gtatgccggg
3541 cactgggcag gtcccagagc cggggaacca gctcacctct ggttgctgta gctcctgccg
3601 gaggcatgtc tacttgtgat cccggacagc cgaacccaag agctggtggc tctgagcaga
3661 cagagacatc ttggcctgtc cctgcctggg ggtcatggag accatgtctt cttagagcaa
3721 atgtggaggc ggccagggca gttgttgggt gaatgtggag agcacatggc catgtcttgc
3781 ccccggagta ccactgggcg tgggggtcc tggcaccaca tgcccggtgt ggccgagggc
3841 acacagcctc tatagcaggc cttcctgtgg aaggcagagg cagtgaggga ggtggacgt
3901 gccagctgag gctgaggcat gcagcagccc ccagctacct ttgcttaggg ctggggtggg
3961 aggcacatgg tgacaggtat atgtcgtggg actggggtgt gggtgacctg ccctcaaacc
4021 ttgcctgcca cctccccatt caggcctggt ggcaggaagg gacaagctgt ggagctggct
4081 gagtcacagc cacctcccca cctccccgca agctggtccc atcgaccagc aagcccagcc
4141 ccagggcgct tagggagaaa tgacccagcc tcctcagacc ccgcctgcct gtcctgtgcc
4201 caccacgcag cagtcagggg agaaaatggt ggctatccct tctgcttaga gaaagaaatg
4261 gcctttagct ggtttcatgt ttgtgttttg actggaggga gtagacccta tctataaggt
4321 gccaccccat catccaagct gccacactgc ccggagcagc ctgttcctgc actccaccct
4381 gctggcccca ggacttctga tctcagtcct ctgggaggga ggttcgccta ggaggtgccc
4441 cccacattgg tgtccccatg ggcagcaggc agacagctca cccccaccag catgatggcc
4501 ccagctgggg gcagtggcag gagccttact tttgtcacag ccttgcccac aaaccctgcc
4561 tctgaggga gactgaggaa gggcagagcc agaagcaagc cgtgccaggc catctgcctg
4621 ctcatggggt cctaaagcgc gggctaagcc tgcaggaaag ccggggcggt ggggggggct
4681 tagtgccaca tgcaccccac tcattccaaa gccaccaaac tgccaggggc tgccgtccac
4741 ccgtggggcc caggggctgg ggccacagcc ttgccatttt cgttgccata ccctcttgcc
4801 ttactcgcgg tggaggccgg atttgcacgg gcagacgtgc acctgggccc gtggggagct
4861 tgttctgacc agacgtacag attttcattc tcagaaagcc ttacttttca accaaatttt
4921 tgtagccagt tttgtgaatt tgtacactga aagaaaattt aaataaaggg gaagtccaca
4981 ttaaaaagaa aacaaaacaa accctaacta acttccaaat gggtctcctg gtgcggggc
5041 gtgagtggcc gtgccctggg tgtgctgcct gtctgagcaa gcttccctag ctgtggaacc
5101 ccgggcccc tgctgcggc tctgccttgg tgtcatgcct gctgcacccc cgtttccact
5161 gacgtgccgt ctgtggctat gggggtggtc actggaatga cggtcactcc agacgtcagc
5221 cggcagggat gcagcaggct ggccgcgcac cggggctcgg gcaccctctg gccccacact
5281 ggcaatgatg ccacaccttg ccatgtccac gctgttggtc aaaccctct gtcatgcctc
5341 tttaaagaga aaagaagaga aagattttt tttttttaa tggcagaccg aagtggagat
5401 cttgtagcct agataggata gtctgacctt ctagcatagt ctttttggca aatgatttgt
5461 gttttcagtg tgtggggaag ctgtcctggg ggctgggcg acagatagca cataggctgt
5521 ttctggggct gcagggcttt ccctgagctg gatgttgtgg gtgttgccgt gcttcaggaa
5581 gtgtggcgac cagaaagcgt agacccgggg cccagggtct gcccgcccct gcagcctggc
5641 ctccccgcac aggctgtggc ttgcactcca gccgctctag tctctcagga atttgcttgt
5701 tacttgtact gtgtaaataa agcttcctgg ttcaataccc
```

FIGURE 20

Homo sapiens genomic DNA, chromosome 11 clone: CTD-2579L12, NTs 149521-151500.

```
149521 gcaatggaca agtcttggtt aaatgtgctt tggaggaact tcctgaaatg gggaagagga
149581 tcatctgaaa atgagataga gatccacatc tgatttgtaa ttttgaacct aatagtttat
149641 tatttatatt tgagagtatc ctaaatctgc tattagcagc caaaaatgaa tacaagaaag
149701 tacaatcgtt atttaaaaga agcaagttat agttgacaaa gattaaaatg ttaaaagttg
149761 tttgaagttt aggcaactga caataacaga acaacttatt aataacagta atgaagttaa
149821 aaattataga gcatttgcta taacctaagt atgtccgttt aaacttcacc actttcttag
149881 attaggaagc tgaccttcag ataagtaaaa ttatatcgga aaggtcctct taattcacag
149941 tgccaaatcc agattttccc tgacttcccc aaatgccact tataagataa tttaattatt
150001 attcatcccc tgatgactgc aggaaaacct ctgtgggtaa gtagagataa atgtgaagag
150061 cagaagcaaa gaaaagagct agcagtagtg aatgttgaac ttcatgtgct aattggtgtg
150121 tgtccatttc tgatacagcc actttgagac aagggctata tcatccatga attggatctt
150181 aatgtccatt gctgtatttt tacttctcta gttttaaga aatttaggct gtggttcaca
150241 ttgtgtattc gaaagataga atacctcgct aactagacaa acaaaagctt tgttctaaaa
150301 atgtactttc cttaaagcag aagtaacctg cagagaagca ggatgcctga agagagatgg
150361 atctctgctt actgtgtctt tagaacagaa atagtggttt tcaacttcac aactctgcat
150421 tgagccctcc tttcacatct tccctgtatc attgcagaat tgatctgaat aattctcatt
150481 ttatcttaga caatttttg tgtggcttga aaaataaat ttgcaataga ggtgaaatgg
150541 aaaaaattat ccttcatttc ctactccaaa ctgaggataa acaattattc ttggaaattc
150601 caccatagaa ttgaattcat tgtacgtgtg aattgcacct tttaagcttt taaatgatgt
150661 ggcatttta tttagcagca ttccaaaagg gaccacgaaa taatgagct ccctggtttt
150721 gcagcatttt ataattccaa tatgaaagtt ttagcattat tactaactga agaatcagaa
150781 aggaaattca tagactatca cttctgggtt ttcaagtatt tttaatccat gcaactcttc
150841 ctccaaactt tttcttcaac ttctcatgag aaagtcagca tataagttc ttaaaagctg
150901 tgctcccctg accgaaatgg agatgagtac catggtggga gaatgcatct ttccccctcg
150961 agagtcctct agcacctgcg gtggtctctg gaagaactca gcagaactcc caagtgccaa
151021 ggaacacata ttacagaaca acggactgca gaaattcaga tagatgaaaa ctatagatca
151081 ttctaggtac tttgttccca gacttataat actcccaata gcttctctaa tgtatgatca
151141 agtggctgtc tgctgtaata ttttcagagc tataatgttt atatctaacc tcttatattt
151201 atgtccaaat cagctggtat attttggctt attctgagca gtagctgcta gatctatctt
151261 gtggtacaca ttaagcctat tccttcttcc acagttcttc ttgacattat gctacttaaa
151321 aagtcatccc ttatcaaaat caaatttcat tatttagtt atatcacatc caatatttaa
151381 ttgtgtaaac cactctttac tctagctatt cgtcctcaga attgcttctg ttataaatgc
151441 tcttttgaa cagacttcct agagtagaag agaaagctcc agatatgatc tgatgggggt
```

FIGURE 21

Homo sapiens mitogen-activated protein kinase kinase kinase 9(MAP3K9), mRNA.

```
   1 atggagccct ccagagcgct tctcggctgc ctagcgagcg ccgccgctgc cgccccgccg
  61 ggggaggatg gagcaggggc cggggccgag gaggaggagg aggaggagga ggaggcggcg
 121 gcggcggtgg gccccgggga gctgggctgc gacgcgccgc tgccctactg gacggccgtg
 181 ttcgagtacg aggcggcggg cgaggacgag ctgaccctgc ggctgggcga cgtggtggag
 241 gtgctgtcca aggactcgca ggtgtccggc gacgagggct ggtggaccgg gcagctgaac
 301 cagcgggtgg gcatcttccc cagcaactac gtgaccccgc gcagcgcctt ctccagccgc
 361 tgccagcccg gcggcgagga ccccagttgc tacccgccca ttcagttgtt agaaattgat
 421 tttgcggagc tcaccttgga agagattatt ggcatcgggg gctttgggaa ggtctatcgt
 481 gctttctgga taggggatga ggttgctgtg aaagcagctc gccacgaccc tgatgaggac
 541 atcagccaga ccatagaaa tgttcgccaa gaggccaagc tcttcgccat gctgaagcac
 601 cccaacatca ttgccctaag aggggtatgt ctgaaggagc caacctctg cttggtcatg
 661 gagtttgctc gtggaggacc tttgaataga gtgttatctg ggaaaaggat tccccagac
 721 atcctggtga attgggctgt gcagattgcc agagggatga actacttaca tgatgaggca
 781 attgttccca tcatccaccg cgaccttaag tccagcaaca tattgatcct ccagaaggtg
 841 gagaatggag acctgagcaa caagattctg aagatcactg attttggcct ggctcgggaa
 901 tggcaccgaa ccaccaagat gagtgcggca gggacgtatg cttggatggc acccgaagtc
 961 atccgggcct ccatgttttc caaggcagt gatgtgtgga gctatgggt gctactttgg
1021 gagttgctga ctggtgaggt gcccttcga ggcattgatg cttagcagt cgcttatgga
1081 gtggccatga acaaactcgc ccttcctatt ccttctacgt gcccagaacc ttttgccaaa
1141 ctcatggaag actgctggaa tcctgatccc cactcacgac catctttcac gaatatcctg
1201 gaccagctaa ccaccataga ggagtctggt ttctttgaaa tgcccaagga ctccttccac
1261 tgcctgcagg acaactggaa acacgagatt caggagatgt tgaccaact cagggccaaa
1321 gaaaaggaac ttcgcacctg ggaggaggag ctgacgcggg ctgcactgca gcagaagaac
1381 caggaggaac tgctgcggcg tcgggagcag gagctggccg agcgggagat tgacatcctg
1441 gaacgggagc tcaacatcat catccaccag ctgtgccagg agaagccccg ggtgaagaaa
1501 cgcaagggca agttcaggaa gagccggctg aagctcaagg atggcaaccg catcagcctc
1561 ccttctgatt tccagcacaa gttcacggtg caggcctccc ctaccatgga taaaaggaag
1621 agtcttatca acagccgctc cagtcctcct gcaagcccca ccatcattcc tcgccttcga
1681 gccatccagt tgacaccagg tgaaagcagc aaaacctggg gcaggagctc agtcgtccca
1741 aaggaggaag gggaggagga ggagaagagg gccccaaaga gaagggacg gacgtggggg
1801 ccagggacgc ttggtcagaa ggagcttgcc tcgggagatg aaggatcccc tcagagacgt
1861 gagaaagcta atggtttaag taccccatca gaatctccac atttccactt gggcctcaag
1921 tccctggtag atggatataa gcagtggtcg tccagtgccc ccaacctggt gaagggccca
1981 aggagtagcc cggccctgcc agggttcacc agccttatgg agatggcctt gctggcagcc
2041 agttgggtgg tgcccatcga cattgaagag gatgaggaca gtgaaggccc agggagtgga
2101 gagagtcgcc tacagcattc acccagccag tcctacctct gtatcccatt ccctcgtgga
2161 gaggatggcg atggccctc cagtgatgga atccatgagg agcccacccc agtcaactcg
2221 gccacgagta cccctcagct gacgccaacc aacagcctca gcggggcgg tgcccaccac
2281 cgccgctgcg aggtggctct gctcggctgt ggggctgttc tggcagccac aggcctaggg
2341 tttgacttgc tggaagctgg caagtgccag ctgcttcccc tggaggagcc tgagccacca
2401 gcccgggagg agaagaaaag acgggagggt cttttcaga ggtccagccg tcctcgtcgg
2461 agcaccagcc ccccatcccg aaagctttc aagaaggagg agcccatgct gttgctagga
2521 gacccctctg cctccctgac gctgctctcc ctctcctcca tctccgagtg caactccaca
2581 cgctccctgc tgcgctccga cagcgatgaa attgtcgtgt atgagatgcc agtcagccca
2641 gtcgaggccc ctcccctgag tccatgtacc cacaaccccc tggtcaatgt ccgagtagag
2701 cgcttcaaac gagatcctaa ccaatctctg actccaccc atgtcaccct caccaccccc
2761 tcgcagccca gcagtcaccg gcggactcct tctgatgggg cccttaagcc agagactctc
2821 ctagccagca ggagcccctc cagcaatggg ttgagcccca gtcctggagc aggaatgttg
2881 aaaaccccca gtcccagccg agacccaggt gaattccccc gtctccctga ccccaatgtg
2941 gtcttccccc caaccccaag gcgctggaac actcagcagg actctacctt ggagagaccc
3001 aagactctgg agtttctgcc tcggccgcgt ccttctgcca accggcaacg gctggaccct
3061 tggtggtttg tgtcccccag ccatgcccgc agcacctccc cagccaacag ctccagcaca
```

FIGURE 21 (cont.)

```
3121 gagacgccca gcaacctgga ctcctgcttt gctagcagta gcagcactgt agaggagcgg
3181 cctggacttc cagccctgct cccgttccag gcagggccgc tgcccccgac tgagcggacg
3241 ctcctggacc tggatgcaga ggggcagagt caggacagca ccgtgccgct gtgcagagcg
3301 gaactgaaca cacacaggcc tgcccctat  gagatccagc aggagttctg gtcttagcac
3361 gaaaaggatt ggggcgggca aggggacag  ccagcggaga tgaggggagc tggcgggcac
3421 agcccttct  cagggttgga cccctgaga  tccagccta  cttcttgcac tgataatgca
3481 ctttgaagat ggaagggatg gaaacagggc cacttcagag ggtctcctgc cctgcagggc
3541 ctttctaccc gtgtccactg gaggggctgt ggccatcagc tctggctgtg taggggagga
3601 aggggtgcat gcatgtcccc caccctccac agtcttcctt gcctttagag tgaccctgca
3661 gagtcactca gccaaatctg tctgctgctc cctctcctca gccagttggg tgtgcgcaga
3721 gctgtcatag ggtcccttg  tcagcccga  gttcagcttc ccaaacacca gtgttggata
3781 ttctgtgatt gattttggtc ctcctccgct gtcccccaac acccaggaat gggaatctgg
3841 cttggttcga gataggagct tttctgtgtc ctaagccctt tcatgctagc aggaagactg
3901 aaagcaaggt ggcccagtgt ggggtcatag ggcttgatag acctggcact gcctatctgc
3961 acttccaggt gccccaccta tttatctgag cccacaggtg gaaaggggaa ctgcctcagt
4021 gagaacgggg ggacggggat gttaggaaaa atacagtaaa gttgcaatga agaggttcat
4081 gaagtatgtc cttgttcttt ttggaaactc tcggcaaagg gcaaaccagc aagtattgag
4141 ggtacccatc tagctacttg gggtcaggac ctcgtcagac caggttcgga tacaatcatc
4201 tgctcatccc aggaatagtt tcttggggga ctcactcact ggtgccagtt ctaagtcaga
4261 gacaaaattc cactgtctgt tccttttgct gtctgaactt tatgtgttac tcccttcctt
4321 tggtcttcac tctaatccct ggagtttgtg ggcttttggt tatgtttggt tagtagatat
4381 caccgcaatg ccctagaaca gctatgaagc agaataccat atggccacct ggacattggg
4441 acttgggaat tcactctcaa ctgggccatc catgttgtga tgcccttgaa gtaaaatgga
4501 gccagcagga gtaccttctg taaatgcatg tggcaaagtg ctatttatag ggtgcccagg
4561 gagccgctga tgtacaataa ccttgaggtc ccccatactg aaaactgacc aaggcctgtg
4621 cacaggtagc ccctcatgct gggctctgga ccatgagctg agtaggaagg atagcagagg
4681 ccaaccctga ccttcctgga agttgtttcc ttaacttgaa tgttgagctt cctctaaagc
4741 tttctcgtgt atgtcttctc catgccacta ctctgaggcc tcctgtgtta tgtgtgaaca
4801 gttgtcttta tgtgggaatg acgacttgat tgggagtaga gtctcaaggt cattccctc
4861 ttccctcaag actctctgaa tgctgctcca ctgtcttttg tcttggaggt cactcagcag
4921 gttccttgca tttgctgcct ggatgtgcag ctggcaacag tgatgaattg gtcactgctc
4981 tttctctata actggatag  atgtcctgcc ttggggtcac taaaggggtg accttgttcc
5041 ttgctttatg agcccattag cactttggtt caaggggccc accaagtctt ggacgggaag
5101 gcgctactgg ttttattgcc caaggttttg ttattgcttc tcttctgtgt ccttctcttt
5161 gttcagtgaa gccaatatgt aagatactgt ttttgtcccc attccctac  tcctgagcta
5221 ggaggaaaaa atgtgaatct taccagcagt tccagccaac caagtgattc ttcttcattc
5281 ttgatgggga gaagtacata caaagtttgt tctgacaggg cgcggtggct cacgcctgta
5341 atcccagcgc tttgggaggc agaggcaggt ggatcacctg aggtcgggag ttcgagacca
5401 gcctgaccaa catggagata tcctgtctct actaaaaata caaaaaatt  agccaggcat
5461 ggtggcacgt gcctgtaatc ccagctactc gcaaggctga ggcaggagaa tcgcttgaac
5521 ctggggaggcg gaggttgcag tgagccaaga ttgcgccatt gcactccagc ctgggcaaca
5581 agagagaaac tctgtctcaa aa
```

FIGURE 22

PREDICTED: Homo sapiens hypothetical LOC643783, transcript variant 2 (LOC643783), partial miscRNA.

```
  1 ccgggccccg ccgcgccgcc tccttcccag ctcgcccgcc caggcctggc ctcctgcttt
 61 tccatttgat tccctgcctc tttctattcg gactggaatg ccgggccagg ctccggggcg
121 cgccgctgcg gcagccgcac ctcgcaggtc ccccggccga ccccgacgcg gaagcggcgg
181 ccctcctcgc cgtcggggag ccagggagcc ggggacgatc agtcacataa ggcttagagg
241 atcaaggatc ctgcccagat gacttaccga aatgttacag attaagttgg tgtggtaacc
301 tgggctgagc actctgggag aggaagagaa gagagaagac aggaaacaac tgaactatga
361 ccaatcccag cacggaggcc cagaaaactt taagatttga gtattaatgt ctcaaggtca
421 ggagcaacct caaggctaaa actcagatct caggactcaa tttcacagaa gttccactat
481 aaaggcaata atctaaagct ttaaatgata tgaaaatttt gtaataagag ttcagtattt
541 ctgccaacat tggcgcatgg attgcaaagt tcacaggatt gaaaacacca tcgacataat
601 ggaaattgaa cagcatctga ttactgagtg ctatatcagc aagttaaaag gatcttttgc
661 atacctttta atggtatata tcctaaaact gaagtgttca atatagacat ccagattgaa
721 actcaggcag tgaattacat acacaacaaa tcagttgaac atggcagagc ttgtcagact
781 tatgaaagat taaatacatt ttacatttcc acaagtgtgg tatt
```

FIGURE 23

Human prostate specific antigen gene, complete cds.

```
   1 gaattccaca ttgtttgctg cacgttggat tttgaaatgc tagggaactt tgggagactc
  61 atatttctgg gctagaggat ctgtggacca caagatcttt ttatgatgac agtagcaatg
 121 tatctgtgga gctggattct gggttgggag tgcaaggaaa agaatgtact aaatgccaag
 181 acatctattt caggagcatg aggaataaaa gttctagttt ctggtctcag agtggtgcag
 241 ggatcaggga gtctcacaat ctcctgagtg ctggtgtctt agggcacact gggtcttgga
 301 gtgcaaagga tctaggcacg tgaggctttg tatgaagaat cggggatcgt acccacccc
 361 tgtttctgtt tcatcctggg catgtctcct ctgcctttgt ccctagatg aagtctccat
 421 gagctacaag ggcctggtgc atccaggtg atctagtaat tgcagaacag caagtgctag
 481 ctctccctcc ccttccacag ctctgggtgt gggaggggt tgtccagcct ccagcagcat
 541 ggggagggcc ttggtcagcc tctggtgcc agcagggcag gggcggagtc ctggggaatg
 601 aaggttttat agggctcctg gggaggctc cccagcccca agcttaccac ctgcacccgg
 661 agagctgtgt caccatgtgg gtcccggttg tcttcctcac cctgtccgtg acgtggattg
 721 gtgagagggg ccatggttgg gggatgcag gagggagc cagccctgac tgtcaagctg
 781 aggctctttc cccccaacc cagcacccca gcccagacag ggagctggc tcttttctgt
 841 ctctcccagc cccacttcaa gcccataccc cagcccctc catattgcaa cagtcctcac
 901 tcccacacca ggtcccgct ccctcccact taccccagaa ctttctcccc attgcccagc
 961 cagctccctg ctcccagctg ctttactaaa ggggaagttc ctgggcatct ccgtgtttct
1021 ctttgtgggg ctcaaaacct ccaaggacct ctctcaatgc cattggttcc ttggaccgta
1081 tcactggtcc atctcctgag cccctcaatc ctatacagt ctactgactt ttcccattca
1141 gctgtgagtg tccaaccta tcccagagac cttgatgctt ggcctccaa tcttgcccta
1201 ggatacccag atgccaacca gacacctcct tcttcctagc caggctatct ggcctgagac
1261 aacaaatggg tccctcagtc tggcaatggg actctgagaa ctcctcattc cctgactctt
1321 agcccagac tcttcattca gtgcccaca ttttccttag gaaaaacatg agcatcccca
1381 gccacaactg ccagctctct gattcccaa atctgcatcc ttttcaaaac ctaaaaacaa
1441 aaagaaaaac aaataaaaca aaaccaactc agaccagaac tgttttctca acctgggact
1501 tcctaaactt tccaaaacct tcctcttcca gcaactgaac ctggccataa ggcacttatc
1561 cctggttcct agcacccctt atccctcag aatccacaac ttgtaccaag tttcccttct
1621 cccagtccaa gaccccaaat caccacaaag gacccaatcc ccagactcaa gatatggtct
1681 gggcgctgtc ttgtgtctcc taccctgatc cctgggttca actctgctcc cagagcatga
1741 agcctctcca ccagcaccag ccaccaacct gcaaacctag ggaagattga cagaattccc
1801 agcctttccc agctccccct gcccatgtcc caggactccc agccttggtt ctctgccccc
1861 gtgtcttttc aaacccacat cctaaatcca tctcctatcc gagtccccca gttccccctg
1921 tcaaccctga ttccctgat ctagcacccc ctctgcaggc gctgcgcccc tcatcctgtc
1981 tcggattgtg ggaggctggg agtgcgagaa gcattcccaa ccctggcagg tgcttgtggc
2041 ctctcgtggc agggcagtct gcggcggtgt tctggtgcac cccagtgggg tcctcacagc
2101 tgcccactgc atcaggaagt gagtaggggc ctggggtctg gggagcaggt gtctgtgtcc
2161 cagaggaata acagctggc atttttcccca ggataacctc taaggccagc cttgggactg
2221 ggggagagag ggaaagttct ggttcaggtc acatggggag gcagggttgg ggctggacca
2281 ccctccccat ggctgcctgg gtctccatct gtgtccctct atgtctcttt gtgtcgcttt
2341 cattatgtct cttggtaact ggcttcggtt gtgtctctcc gtgtgactat tttgttctct
2401 ctctccctct cttctctgtc ttcagtctcc atatctcccc ctctctctgt ccttctctgg
2461 tccctctcta gccagtgtgt ctcaccctgt atctctctgc caggctctgt ctctcggtct
2521 ctgtctcacc tgtgccttct ccctactgaa cacacgcacg ggatgggcct gggggaccc
2581 tgagaaaagg aaggcttttg gctgggcgcg gtggctcaca cctgtaatcc cagcactttg
2641 ggaggccaag gcaggtagat cacctgaggt caggagttcg agaccagcct ggccaactgg
2701 tgaaacccca tctctactaa aaatacaaaa aattagccag gcgtggtggc gcatgcctgt
2761 agtcccagct actcaggagg ctgagggagg agaattgctt gaacctggga ggttgaggtt
2821 gcagtgagcc gagaccgtgc cactgcactc cagcctgggt gacagagtga gactccgcct
2881 caaaaaaaaa aaaaaaaaa aaaaaaaaa agaaaagaaa agaaagaaa aggaatcttt
2941 tatccctgat gtgtgtgggt atgagggtat gagagggccc ctctcactcc attccttctc
3001 caggacatcc ctccactctt gggagacaca gagaagggct ggttccagct ggagctggga
3061 ggggcaattg agggaggagg aaggagaagg gggaaggaaa acagggtatg ggggaaagga
```

FIGURE 23 (cont.)

```
3121 ccctggggag cgaagtggag gatacaacct tgggcctgca ggccaggcta cctacccact
3181 tggaacccca cgccaaagcc gcatctacag ctgagccact ctgaggcctc cctcccccgg
3241 cggtccccac tcagctccaa agtctctctc cctttttctct cccacacttt atcatccccc
3301 ggattcctct ctacttggtt ctcattcttc ctttgacttc ctgcttccct ttctcattca
3361 tctgtttctc actttctgcc tggttttgtt cttctctctc tcttttctctg gcccatgtct
3421 gtttctctat gtttctgtct tttcttttctc atcctgtgta ttttcggctc accttgtttg
3481 tcactgttct ccctctgcc ctttcattct ctctgtcctt ttaccctctt ccttttttccc
3541 ttggtttctc tcagtttctg tatctgccct tcaccctctc acactgctgt ttcccaactc
3601 gttgtctgta tttttggcct gaactgtgtc ttccccaacc ctgtgttttt ctcactgttt
3661 cttttctct tttggagcct cctccttgct cctctgtccc ttctctcttt ccttatcatc
3721 ctcgctcctc attcctgcgt ctgcttcctc cccagcaaaa gcgtgatctt gctgggtcgg
3781 cacagcctgt ttcatcctga agacacaggc caggtatttc aggtcagcca cagcttccca
3841 cacccgctct acgatatgag cctcctgaag aatcgattcc tcaggccagg tgatgactcc
3901 agccacgacc tcatgctgct ccgcctgtca gagcctgccg agctcacgga tgctgtgaag
3961 gtcatggacc tgcccaccca ggagccagca ctggggacca cctgctacgc ctcaggctgg
4021 ggcagcattg aaccagagga gtgtacgcct gggccagatg gtgcagccgg gagccagat
4081 gcctgggtct gagggaggag gggacaggac tcctgggtct gagggaggag ggccaaggaa
4141 ccaggtgggg tccagcccac aacagtgttt ttgcctggcc cgtagtcttg accccaaaga
4201 aacttcagtg tgtggacctc catgttattt ccaatgacgt gtgtgcgcaa gttcaccctc
4261 agaaggtgac caagttcatg ctgtgtgctg gacgctggac aggggcaaa agcacctgct
4321 cggtgagtca tccctactcc caagatcttg aggggaaagg tgagtgggga ccttaattct
4381 gggctgggt ctagaagcca acaaggcgtc tgcctccct gctcccagc tgtagccatg
4441 ccacctcccc gtgtctcatc tcattccctc cttccctctt ctttgactcc ctcaaggcaa
4501 taggttattc ttacagcaca actcatctgt tcctgcgttc agcacacggt tactaggcac
4561 ctgctatgca cccagcactg ccctagagcc tgggacatag cagtgaacag acagagagca
4621 gcccctccct tctgtagccc ccaagccagt gaggggcaca ggcaggaaca gggaccacaa
4681 cacagaaaag ctggagggtg tcaggaggtg atcaggctct cggggaggga gaagggtgg
4741 ggagtgtgac tgggaggaga catcctgcag aaggtgggag tgagcaaaca cctgccgcag
4801 gggaggggag ggcctgcgg cacctggggg agcagaggga acagcatctg gccaggcctg
4861 ggaggagggg cctagagggc gtcaggagca gagaggaggt tgcctggctg gagtgaagga
4921 tcggggcagg gtgcgagagg gaagaaagga cccctcctgc agggcctcac ctgggccaca
4981 ggaggacact gctttttcctc tgaggagtca ggaactgtgg atggtgctgg acagaagcag
5041 gacagggcct ggctcaggtg tccagaggct gccgctggcc tccctatggg atcagactgc
5101 agggagggag ggcagcaggg atgtggaggg agtgatgatg gggctgacct gggggtggct
5161 ccaggcattg tccccacctg ggcccttacc cagcctccct cacaggctcc tggccctcag
5221 tctctccct ccactccatt ctccacctac ccacagtggg tcattctgat caccgaactg
5281 accatgccag ccctgccgat ggtcctccat ggctccctag tgccctggag aggaggtgtc
5341 tagtcagaga gtagtcctgg aaggtggcct ctgtgaggag ccacggggac agcatcctgc
5401 agatggtcct ggcccttgtc ccaccgacct gtctacaagg actgtcctcg tggaccctcc
5461 cctctgcaca ggagctggac cctgaagtcc cttccctacc ggccaggact ggagcccta
5521 cccctctgtt ggaatccctg cccaccttct tctggaagtc ggctctggag acatttctct
5581 cttcttccaa agctgggaac tgctatctgt tatctgcctg tccaggtctg aaagatagga
5641 ttgcccaggc agaaactggg actgacctat ctcactctct ccctgctttt acccttaggg
5701 tgattctggg ggcccacttg tctgtaatgg tgtgcttcaa ggtatcacgt catggggcag
5761 tgaaccatgt gccctgcccg aaaggccttc cctgtacacc aaggtggtgc attaccggaa
5821 gtggatcaag gacaccatcg tggccaaccc ctgagcaccc ctatcaactc cctattgtag
5881 taaacttgga accttggaaa tgaccaggcc aagactcaag cctcccagt tctactgacc
5941 tttgtcctta ggtgtgaggt ccagggttgc taggaaaaga aatcagcaga cacaggtgta
6001 gaccagagtg tttcttaaat ggtgtaattt tgtcctctct gtgtcctggg gaatactggc
6061 catgcctgga gacatatcac tcaatttctc tgaggacaca gataggatgg ggtgtctgtg
6121 ttatttgtgg gatacagaga tgaaagaggg gtgggatcca cactgagaga gtggagagtg
6181 acatgtgctg gacactgtcc atgaagcact gagcagaagc tggaggcaca acgcaccaga
6241 cactcacagc aaggatggag ctgaaaacat aacccactct gtcctgagg cactgggaag
6301 cctagagaag gctgtgagcc aaggagggag ggtcttcctt tggcatggga tggggatgaa
```

FIGURE 23 (cont.)

```
6361 gtaaggagag ggactggacc ccctggaagc tgattcacta tgggggagg tgtattgaag
6421 tcctccagac aaccctcaga tttgatgatt tcctagtaga actcacagaa ataaagagct
6481 cttatactgt ggtttattct ggtttgttac attgacagga gacacactga aatcagcaaa
6541 ggaaacaggc atctaagtgg ggatgtgaag aaaacaggga aaatctttca gttgttttct
6601 cccagtgggg tgttgtggac agcacttaaa tcacacagaa gtgatgtgtg accttgtgta
6661 tgaagtattt ccaactaagg aagctcacct gagccttagt gtccagagtt cttattgggg
6721 gtctgtagga taggcatggg gtactggaat agctgacctt aacttctcag acctgaggtt
6781 cccaagagtt caagcagata cagcatggcc tagagcctca gatgtacaaa aacaggcatt
6841 catcatgaat cgcactgtta gcatgaatca tctggcacgg cccaaggccc caggtatacc
6901 aaggcacttg ggccgaatgt tccaagggat taaatgtcat ctcccaggag ttattcaagg
6961 gtgagccctg tacttggaac gttcaggctt tgagcagtgc agggctgctg agtcaacctt
7021 ttactgtaca gggggtgag ggaaagggag aagatgagga aaccgcctag ggatctggtt
7081 ctgtcttgtg gccgagtgga ccatggggct atcccaagaa ggaggaattc
```

FIGURE 24

Homo sapiens histone cluster 2, H2aa4 (HIST2H2AA4), mRNA.

```
  1 cgactttccc gatcgccagg caggagtttc tctcggtgac tactatcgct gtcatgtctg
 61 gtcgtggcaa gcaaggaggc aaggcccgcg ccaaggccaa gtcgcgctcg tcccgcgctg
121 gccttcagtt cccggtaggg cgagtgcatc gcttgctgcg caaaggcaac tacgcggagc
181 gagtgggggc cggcgcgccc gtctacatgg ctgcggtcct cgagtatctg accgccgaga
241 tcctggagct ggcgggcaac gcggctcggg acaacaagaa gacgcgcatc atccctcgtc
301 acctccagct ggccatccgc aacgacgagg aactgaacaa gctgctgggc aaagtcacca
361 tcgcccaggg cggcgtcttg cctaacatcc aggccgtact gctccctaag aagacggaga
421 gtcaccacaa ggcaaagggc aagtgaggct gacgtccggc ccaagtgggc ccagcccggc
481 ccgcgtctcg aagggcacc tgtgaactca aaaggctctt ttcagagcca ccca
```

FIGURE 25

Homo sapiens ubiquitin-conjugating enzyme E2I (UBC9 homolog, yeast)(UBE2I), transcript variant 2, mRNA.

```
   1 gggtcctcgg agctgctctg gctgcgcgcg gagcgggctc cggagggaag tcccgagaca
  61 aagggaagcg ccgccgccgc cgccccgctc ggtcctccac ctgtccgcta cgctcgccgg
 121 ggctgcggcc gcccgaggct gccctgagga tctgtgtttg gtgaaaagga gccaaattca
 181 cctgcagggc aggcggctct agcagcttca gaagcctggt gccctggcga cactggacct
 241 gccttggctt ctttgatccc aaccccaccc ccgatttctg ctctgctgac tggggaagtc
 301 atcgtgccac ccagaacctg agtgcgggcc tctcagagct ccttcgtccg tgggtctgcc
 361 ggggactggg ccttgtctcc ctaacgagtg ccagggactt tgaacatgtc ggggatcgcc
 421 ctcagcagac tcgcccagga gaggaaagca tggaggaaag accacccatt tggtttcgtg
 481 gctgtcccaa caaaaaatcc cgatggcacg atgaacctca tgaactggga gtgcgccatt
 541 ccaggaaaga aagggactcc gtgggaagga ggcttgttta aactacggat gcttttcaaa
 601 gatgattatc catcttcgcc accaaaatgt aaattcgaac caccattatt tcacccgaat
 661 gtgtacccct cggggacagt gtgcctgtcc atcttagagg aggacaagga ctggaggcca
 721 gccatcacaa tcaaacagat cctattagga atacaggaac ttctaaatga accaaatatc
 781 caagacccag ctcaagcaga ggcctacacg atttactgcc aaaacagagt ggagtacgag
 841 aaaagggtcc gagcacaagc caagaagttt gcgccctcat aagcagcgac cttgtggcat
 901 cgtcaaaagg aagggattgg tttggcaaga acttgtttac aacattttg caaatctaaa
 961 gttgctccat acaatgacta gtcacctggg ggggttgggc gggcgccatc ttccattgcc
1021 gccgcgggtg tgcggtctcg attcgctgaa ttgcccgttt ccatacaggg tctcttcctt
1081 cggtcttttg tatttttgat tgttatgtaa aactcgcttt tatttaata ttgatgtcag
1141 tatttcaact gctgtaaaat tataaacttt tatacttggg taagtccccc aggggcgagt
1201 tcctcgctct gggatgcagg catgcttctc accgtgcaga gctgcacttg gcctcagctg
1261 gctgtatgga aatgcaccct ccctcctgcc gctcctctct agaaccttct agaacctggg
1321 ctgtgctgct tttgagcctc agacccagg tcagcatctc ggttctgcgc cacttccttt
1381 gtgtttatat ggcgttttgt ctgtgttgct gtttagagta aataaactgt ttatataaag
1441 gttttggttg cattattatc attgaaagtg agaggagg
```

FIGURE 26

Homo sapiens TIMP metallopeptidase inhibitor 2 (TIMP2), mRNA.

```
   1 cgcagcaaac acatccgtag aaggcagcgc ggccgccgag aaccgcagcg ccgctcgccc
  61 gccgccccc accccgccgc cccgcccggc gaattgcgcc ccgcgccccct cccctcgcgc
 121 ccccgagaca aagaggagag aaagtttgcg cggccgagcg gggcaggtga ggagggtgag
 181 ccgcgcggga ggggcccgcc tcggccccgg ctcagccccc gcccgcgccc ccagcccgcc
 241 gccgcgagca gcgcccggac ccccagccgg cggcccccgc ccgcccagcc ccccggcccg
 301 ccatgggcgc cgcggcccgc accctgcgc tggcgctcgg cctcctgctg ctggcgacgc
 361 tgcttcgccc ggccgacgcc tgcagctgct ccccggtgca cccgcaacag gcgttttgca
 421 atgcagatgt agtgatcagg gccaaagcgg tcagtgagaa ggaagtggac tctgaaacg
 481 acatttatgg caaccctatc aagaggatcc agtatgagat caagcagata aagatgttca
 541 aagggcctga gaaggatata gagtttatct acacggcccc ctcctcggca gtgtgtgggg
 601 tctcgctgga cgttggagga aagaaggaat atctcattgc aggaaaggcc gagggggacg
 661 gcaagatgca catcaccctc tgtgacttca tcgtgccctg ggacacctg agcaccaccc
 721 agaagaagag cctgaaccac aggtaccaga tgggctgcga gtgcaagatc acgcgctgcc
 781 ccatgatccc gtgctacatc tcctccccgg acgagtgcct ctggatggac tgggtcacag
 841 agaagaacat caacgggcac caggccaagt tcttcgcctg catcaagaga agtgacggct
 901 cctgtgcgtg gtaccgcggc gcggcgcccc caagcagga gtttctcgac atcgaggacc
 961 cataagcagg cctccaacgc ccctgtggcc aactgcaaaa aaagcctcca agggtttcga
1021 ctggtccagc tctgacatcc cttcctggaa acagcatgaa taaaacactc atcccatggg
1081 tccaaattaa tatgattctg ctccccccctt ctccttttag acatggttgt gggtctggag
1141 ggagacgtgg gtccaaggtc ctcatcccat cctccctctg ccaggcacta tgtgtctggg
1201 gcttcgatcc ttgggtgcag gcagggctgg gacacgcggc ttccctccca gtccctgcct
1261 tggcaccgtc acagatgcca agcaggcagc acttagggat ctcccagctg ggttagggca
1321 gggcctggaa atgtgcattt tgcagaaact tttgagggtc gttgcaagac tgtgtagcag
1381 gcctaccagg tcccttcat cttgagaggg acatggccct tgttttctgc agcttccacg
1441 cctctgcact ccctgcccct ggcaagtgct cccatcgccc cggtgccac catgagctcc
1501 cagcacctga ctcccccccac atccaaggc agcctggaac cagtggctag ttcttgaagg
1561 agccccatca atcctattaa tcctcagaat tccagtggga gcctccctct gagccttgta
1621 gaaatgggag cgagaaaccc cagctgagct gcgttccagc ctcagctgag tcttttttggt
1681 ctgcacccac ccccccaccc cccccccccc gcccacatgc tccccagctt gcaggaggaa
1741 tcggtgaggt cctgtcctga ggctgctgtc cggggccggt ggctgccctc aaggtccctt
1801 ccctagctgc tgcggttgcc attgcttctt gcctgttctg gcatcaggca cctggattga
1861 gttgcacagc tttgctttat ccgggcttgt gtgcagggcc cggctgggct ccccatctgc
1921 acatcctgag gacagaaaaa gctgggtctt gctgtgccct cccaggctta gtgttccctc
1981 cctcaaagac tgacagccat cgttctgcac ggggctttct gcatgtgacg ccagctaagc
2041 atagtaagaa gtccagccta ggaagggaag gattttggag gtaggtggct ttggtgacac
2101 actcacttct ttctcagcct ccaggacact atggcctgtt taagagaca tcttattttt
2161 ctaaaggtga attctcagat gataggtgaa cctgagttgc agatatacca acttctgctt
2221 gtatttctta aatgacaaag attacctagc taagaaactt cctagggaac tagggaacct
2281 atgtgttccc tcagtgtggt ttcctgaagc cagtgatatg ggggttagga taggaagaac
2341 tttctcggta atgataagga gaatctcttg tttcctccca cctgtgttgt aaagataaac
2401 tgacgatata caggcacatt atgtaaacat acacacgcaa tgaaaccgaa gcttggcggc
2461 ctgggcgtgg tcttgcaaaa tgcttccaaa gccaccttag cctgttctat tcagcggcaa
2521 ccccaaagca cctgttaaga ctcctgaccc ccaagtggca tgcagccccc atgcccaccg
2581 ggacctggtc agcacagatc ttgatgactt cccttttctag ggcagactgg gagggtatcc
2641 aggaatcggc ccctgcccca cgggcgtttt catgctgtac agtgacctaa agttggtaag
2701 atgtcataat ggaccagtcc atgtgatttc agtatataca actccaccag accctccaa
2761 cccatataac accccacccc tgttcgcttc ctgtatggtg atatcatatg taacatttac
2821 tcctgtttct gctgattgtt tttttaatgt tttggtttgt ttttgacatc agctgtaatc
2881 attcctgtgc tgtgtttttt attacccttg gtaggtatta gacttgcact tttttaaaaa
2941 aaggtttctg catcgtggaa gcatttgacc cagagtggaa cgcgtggcct atgcaggtgg
3001 attccttcag gtctttcctt tggttctttg agcatctttg ctttcattcg tctcccgtct
3061 ttggttctcc agttcaaatt attgcaaagt aaaggatctt tgagtaggtt cggtctgaaa
```

FIGURE 26 (cont.)

```
3121 ggtgtggcct ttatatttga tccacacacg ttggtctttt aaccgtgctg agcagaaaac
3181 aaaacaggtt aagaagagcc gggtggcagc tgacagagga agccgctcaa ataccttcac
3241 aataaatagt ggcaatatat atatagttta agaaggctct ccatttggca tcgtttaatt
3301 tatatgttat gttctaagca cagctctctt ctcctatttt catcctgcaa gcaactcaaa
3361 atatttaaaa taaagtttac attgtagtta ttttcaaatc tttgcttgat aagtattaag
3421 aaatattgga cttgctgccg taatttaaag ctctgttgat tttgtttccg tttggatttt
3481 tgggggaggg gagcactgtg tttatgctgg aatatgaagt ctgagacctt ccggtgctgg
3541 gaacacacaa gagttgttga aagttgacaa gcagactgcg catgtctctg atgctttgta
3601 tcattcttga gcaatcgctc ggtccgtgga caataaacag tattatcaaa gagaaaaaaa
3661 aaaaaaaaa
```

FIGURE 27

Homo sapiens WD repeat domain 77 (WDR77), mRNA.

```
   1 cgtccagttt gagtctaggt tggagttgga accgtggaga tgcggaagga aaccccaccc
  61 cccctagtgc ccccggcggc ccgggagtgg aatcttcccc caaatgcgcc cgcctgcatg
 121 gaacggcagt tggaggctgc gcggtaccgg tccgatgggg cgcttctcct cggggcctcc
 181 agcctgagtg ggcgctgctg ggccggctcc ctctggcttt ttaaggaccc ctgtgccgcc
 241 cccaacgaag gcttctgctc cgccggagtc caaacggagg ctggagtggc tgacctcact
 301 tgggttgggg agagaggtat tctagtggcc tccgattcag gtgctgttga attgtgggaa
 361 ctagatgaga atgagacact tattgtcagc aagttctgca agtatgagca tgatgacatt
 421 gtgtctacag tcagtgtctt gagctctggc acacaagctg tcagtggtag caaagacatc
 481 tgcatcaagg tttgggacct tgctcagcag gtggtactga gttcataccg agctcatgct
 541 gctcaggtca cttgtgttgc tgcctctcct cacaaggact ctgtgtttct ttcatgcagc
 601 gaggacaata gaattttact ctgggatacc cgctgtccca agccagcatc acagattggc
 661 tgcagtgcgc ctggctacct tcctacctcg ctggcttggc atcctcagca aagtgaagtc
 721 tttgtctttg gtgatgagaa tgggacagtc tcccttgtgg acaccaagag tacaagctgt
 781 gtcctgagct cagctgtaca ctcccagtgt gtcactgggc tggtgttctc cccacacagt
 841 gttcccttcc tggcctctct cagtgaagac tgctcacttg ctgtgctgga ctcaagcctt
 901 tctgagttgt ttagaagcca agcccacaga gactttgtga gagatgcgac ttggtccccg
 961 ctcaatcact ccctgcttac cacagtgggc tgggaccatc aggtcgtcca ccacgttgtg
1021 cccacagaac ctctcccagc ccctggacct gcaagtgtta ctgagtagat tggatttaag
1081 acaaaaagca agtcccccat gagtgtccac ttctttgccc tgccctctca gcttgtgaga
1141 caacacagga gccttctata gtatgttgat atgctagatc tgtgccgtta ataggcatcg
1201 tctctcagcc tgagggaggc tggattctgg gttcctgtag tcacagggag gaaaagcttt
1261 cttaaaaatg gacatgtatg tgcgtgtgag tgtgtgtgta gatttatagt ttttggtagt
1321 ggcaggaata aaaaaaatcc atcctacatc ttccctaagc actgcctctc tctcacccccc
1381 caaaacaagt tgacgaaagg gtttttatgta gctgtctatg aggaattggc cgtgtctggg
1441 tgggttatgg gatgtgggca tccctggggtt cttggaagca gctcttatgc tactcataga
1501 gatgggattg actttatttt tttatagtgc ttaattcacc attatgagaa atgcttccag
1561 tcacaaaaat gcagcccagc tcactctgag gaagaagcag gacttggtac ggttttacac
1621 aactccttac cattaaactg aatcagaaat ccatttctg gctgaataaa aagtttggct
1681 tgcctgtgta atgcccactc ccttccccct ggctccctag tgatgggaca tatatgagag
1741 agaagtgttt ttctatcata gacaccatag gggaaagttt ggggatgaag gagagcttaa
1801 aggtgtttca attaagttag aaaactgaca caggctgttg agaattcttt gccacttttc
1861 ccaccccaaa acagcatggg gcctgacatc ttctgccctg gtccccttc tcttgatgtg
1921 gaaagtctga atgcagtatt tatagactc taaggtttta aaatccagta tcaagaagaa
1981 aatcagaaat actggttggt gaaataaaga gtttaggcat tgttggcctg tcttttttga
2041 agcatgtgtg ttatgtgtag ttagatatat ttcacttatg tgagtcatca tggtgttggt
2101 cttgtagccc attattttc ctgtgcttcc ccagcttccc aaagtagcta gttagaactt
2161 aaggtaaata tttattcttg ggttggtgga gtggatattg ccagttagga gtcatggatc
2221 aattactgat tatattgaaa gtaaatataa tcaattatgt acttttgagc tttgcaggtt
2281 caatttaggt aaaaatcaca ttatgaaact gggaaagtct gaaggaatat gggcaaaata
2341 tttctcagta aagcttccat gcttcaccct tgacatgatt acccttgagt aaaacatggg
2401 aatttgtaaa aaaaaaaaaa aaaaaaa
```

FIGURE 28

Human DNA sequence from clone RP1-20N2 on chromosome 6q24 Contains the gene for a novel protein similar to yeast and bacterial cytosine deaminase, NTs 48121-50100.

```
48121 ttcgattttg gtgctgtgaa aagaatagaa aagaaaaaga aaatgaagag gtaagctcat
48181 agcagattct ctttgtatgg atttaaggga aggacattat ccacaacaga aaactgacca
48241 tttggatttt cttgtttgta gaaggtcttt aacatttcca ctgcttcctc agcccgatat
48301 ccagggatac actgatggaa tgagaaagtt gagaataaac ataggcctat gaaaatgtgt
48361 gctgtatccc ataaaaacaa catatatata catgattatg taaacagatt tcagatgtta
48421 ataaactttg gggatattag taacatggt aaggaggtac acttccaaaa gatgtttgat
48481 atatcatctt tttcattact cccaatcaac tgttattagg catcactccc aatcaactgt
48541 tattcatcca ttaactatta tagaagttac cagctttgtg atcttgggtt aggcacttaa
48601 actctccatg cctfatttat acaatgctgg caataatagc acttacttca ggggatttg
48661 tgaggattaa gtgagataat acctgttaaa taccaggcac atcataagtg ctcattaagc
48721 attagttatt tttatctgct cctatttact agtggtccat taagcattcc atgctataga
48781 gctagggttg gcaaattata cttggtggac caaatctgtt ccatagctga gaactgtgag
48841 ctaagaatgg ttttttatc ttaaaagctt tgttaaagaa aaaaaaagac taggtgacag
48901 agatgtaagc ggctcacaaa gggtgaaata tttactagtt aacccttgc agaaaaagtt
48961 tatcaaccct tgctacagag gatttaaaa aataaaatac agcttgttct atctttagca
49021 tctaactggg gaaaagaaat cataacatgt gaaagaataa ataagaaatt gtgctaacag
49081 taaggagtgt tatatgaaat attacctgaa gaacatgaaa cttgaacttg ccttagagat
49141 agagaatatt taaagaggct aagcagagca tttcagggaa agggcaagaa gaagcctggg
49201 ttgtgtgtga ggaaatcagc tgacagagga ggagactatt aaggaagcat aaggaaagaa
49261 agacaaaaaa ttggggtaaa aatatgtacg gctttgaaag cttgtcagaa gagtttggac
49321 ttaaaaccaa gcacccttct gaagtgcatg aagtgacaca atgagcatct ggaaggaagg
49381 agccagaaag cataggcaca gaggacagga ggaccagcta ctgtgagatg ctgttcagaa
49441 cgaacctccc attctcctgt gtcttcagtc tgcccttgcc tgggcctccg acacctgcat
49501 aaaccttcgc cataacaaat aaccttccat ccaccctgtc ccgtcaaagg ctgacaccct
49561 gctcctgcct tcactcctca gtggcctcat cttcactggc ttgagttccc agcacttcac
49621 tgagtctgcc ctctcagaaa tccccaggtc cctactgacc aaaacacttg cctcctttca
49681 gattcctcaa ctctgcagtc ctggaggcaa ctggccacac ctgctctgtc tgaccgctct
49741 tgcctccctt ggcttctcag catttttacca tcctaaccac tgccagccag tcccgtcaca
49801 gctgcccct gcttcctgct gtgttaagtg ctggagctcc ccagaggtcc ccctccactc
49861 cactcgcaca ctcagagccc tctcctctta cgtgggatga gagcagtggt tctcaaccat
49921 tgctgctcag gagaaccagt tggaactctc tggaaacaca gcactgttgg ccccctgcct
49981 tctgattcag atggtctggg gcagggactg agcagagtca ggcacagaag cctccaggtg
50041 attctaacgg gcagtccggg atgagaactg ctgagttaca ggcctcgaag gaaactgcac
```

FIGURE 29

Homo sapiens lamin A/C, mRNA (cDNA clone MGC:23638 IMAGE:4863480), complete cds.

```
   1 gagcgccgca cctacaccag ccaacccaga tcccgaggtc cgacagcgcc cggcccagat
  61 ccccacgcct gccaggagca agccgagagc cagccggccg gcgcactccg actccgagca
 121 gtctctgtcc ttcgacccga gccccgcgcc ctttccggga cccctgcccc gcgggcagcg
 181 ctgccaacct gccggccatg gagacccgt cccagcggcg cgccacccgc agcggggcgc
 241 aggccagctc cactccgctg tcgcccaccc gcatcacccg gctgcaggag aaggaggacc
 301 tgcaggagct caatgatcgc ttggcggtct acatcgaccg tgtgcgctcg ctggaaacgg
 361 agaacgcagg gctgcgcctt cgcatcaccg agtctgaaga ggtggtcagc cgcgaggtgt
 421 ccggcatcaa ggccgcctac gaggccgagc tcggggatgc ccgcaagacc cttgactcag
 481 tagccaagga gcgcgcccgc ctgcagctgg agctgagcaa agtgcgtgag gagtttaagg
 541 agctgaaagc gcgcaatacc aagaaggagg gtgacctgat agctgctcag gctcggctga
 601 aggacctgga ggctctgctg aactccaagg aggccgcact gagcactgct ctcagtgaga
 661 agcgcacgct ggaggcgag ctgcatgatc tgcggggcca ggtggccaag cttgaggcag
 721 ccctaggtga ggccaagaag caacttcagg atgagatgct gcggcgggtg gatgctgaga
 781 acaggctgca gaccatgaag gaggaactgg acttccagaa gaacatctac agtgaggagc
 841 tgcgtgagac caagcgccgt catgagacc gactggtgga gattgacaat gggaagcagc
 901 gtgagtttga gagccggctg gcggatgcgc tgcaggaact gcgggcccag catgaggacc
 961 aggtggagca gtataagaag gagctggaga agacttattc tgccaagctg gacaatgcca
1021 ggcagtctgc tgagaggaac agcaacctgg tggggctgc ccacgaggag ctgcagcagt
1081 cgcgcatccg catcgacagc ctctctgccc agctcagcca gctccagaag cagctggcag
1141 ccaaggaggc gaagcttcga gacctggagg actcactggc ccgtgagcgg gacaccagcc
1201 ggcggctgct ggcggaaaag gagcgggaga tggccgagat gcgggcaagg atgcagcagc
1261 agctggacga gtaccaggag cttctggaca tcaagctggc cctggacatg gagatccacg
1321 cctaccgcaa gctcttggag ggcgaggagg agaggctacg cctgtccccc agccctacct
1381 cgcagcgcag ccgtggccgt gcttcctctc actcatccca gacacagggt ggggcagcg
1441 tcaccaaaaa gcgcaaactg gagtccactg agagccgcag cagcttctca cagcacgcac
1501 gcactagcgg gcgcgtggcc gtgaggagg tggatgagga gggcaagttt gtccggctgc
1561 gcaacaagtc caatgaggac cagtccatgg caattggca gatcaagcgc cagaatggag
1621 atgatccctt gctgacttac cggttccac caaagttcac cctgaaggct gggcaggtgg
1681 tgacgatctg ggctgcagga gctggggcca cccacagccc cctaccgac ctggtgtgga
1741 aggcacagaa cacctgggc tgcgggaaca gctgcgtac ggctctcatc aactccactg
1801 gggaagaagt ggccatgcgc aagctggtgc gctcagtgac tgtggttgag gacgacgagg
1861 atgaggatgg agatgacctg ctccatcacc accacggctc ccactgcagc agctcgggcg
1921 accccgctga gtacaacctg cgctcgcgca ccgtgctgtg cgggacctgc gggcagcctg
1981 ccgacaaggc atctgccagc ggctcaggag cccaggtggg cggaccatc tcctctggct
2041 cttctgcctc cagtgtcacg gtcactcgca gctaccgcag tgtgggggcg agtggggtg
2101 gcagcttcgg ggacaatctg gtcacccgct cctacctcct gggcaactcc agccccgaa
2161 cccagagccc cagaactgc agcatcatgt aatctgggac ctgccaggca ggggtggggg
2221 tggaggcttc ctgcgtcctc ctcacctcat gcccacccc tgcctgcac gtcatgggag
2281 ggggcttgaa gccaaagaaa ataaccctt tggttttttt cttctgtatt tttttttcta
2341 agagaagtta ttttctacag tggttttata ctgaaggaaa aacacaagca aaaaaaaaaa
2401 aaaaaaa
```

FIGURE 30

Homo sapiens mRNA for Lsm3 protein.

```
  1 gcgcagggtt tgaaacatgg cggacgacgt agaccagcaa caaactacca acactgtaga
 61 ggagcccctg gatcttatca ggctcagcct agatgagcga atttatgtga aaatgagaaa
121 tgaccgagag cttcgaggca gattacatgc ttatgatcaa catttaaata tgatcttggg
181 agatgtggaa gaaactgtga ctactataga aattgatgaa gaaacatatg aagagatata
241 taaatcaacg aaacggaata ttccaatgct ctttgtccgg ggagatggcg ttgtcctggt
301 tgcccctcca ctgagagttg gctgaaacaa agaatttgtc ctgtatggaa aacgggagac
361 tttgtacagt ggcctctcta aaagtacaaa acattcataa gagaaacctg catacatttt
421 gatattaaga aataattccg gggattcttc cactcctgaa atgagttgat ttgcagataa
481 ctcacaactt cttaagctaa atggtatttt cattttctc aagctctcca ataaatatga
541 ccaccaagaa aaaaaaaaa aaaaaa
```

FIGURE 31

Homo sapiens chromosome 19 clone CTB-25B13, NTs 20521-22500.

```
20521 tttaagggtg tacaagctct aattgttttt ttttttttt tgagatggag tttcactctg
20581 tagcccaggc tggagtgcag tggcgcaatc gcggctcact gcaagctccg cctcctgggt
20641 tcacaccatt ctcctgcctc agtctcccga gtagctggga ctacaggcgc tcgccaccac
20701 gcccggctaa ttttttttgta tttttagtag agacggggtt tcaccatgtt agccagggtg
20761 gtctcgatct cctgaccttg tgatccgcct gcctcggcct cccaaagtgc tgggattaca
20821 ggcgtgagtg actgcgccca gcctcacagg ctctaattct tgactaattt tcctgtacac
20881 gtcacttgta attgaaaagc tgagtgtaag atcagccgac acacccagag ttttatttta
20941 ttttatttat ttatttatgg ttttttttg agatggagtc tcactctgtc gcccaggcta
21001 gagtgcagtg gcgccatctc ggcttactgc aagctccacc tcctgggttc acgccattct
21061 cctacctcag tctcctgagt agctgggact acaggcgccc accaccacgc ctggctaatt
21121 tttttgtatt tttagtagag acagggtttc accgtgttag gcaggatggt ctcgatctcc
21181 tgacctcgtg attcgcccgc ctcggcctcc caaagcgctg ggattagaag cgtgagccac
21241 cgcgcccgga ctattttatt tattttttg agatggagtt tcacttttgt tgcccaggat
21301 tgagtgcagt gccccgatct tggctcacta caacctctgc ctcctggtt caagcgactc
21361 tcctgcctca gtgtcctgag tagctgggat tacaggcgtc tgccaccacg cccggctaat
21421 tttgtatttt tagtagagaa caggtttcac tatgttggtc aggctggtct tgaactcctg
21481 acctcagcgc atccagaatt ttagacgggg cccccagggt gaggtcttgg caccctccag
21541 tagagaagaa gggacatggg ccatacgtgg ggtgtccttt ctgggagcct tgcgtccctt
21601 acctgcctag ccagggattg cacctcacag cacgcagcca gcaggaacgg caccgtgatc
21661 tgatttcacc tgcgggccct gggccctggg ggtgtttgac aattggggca tatcacagtg
21721 tgagctagtc ccgtctcggg ggttggagg ctccacgtgg ccgtggtaca ggagcaggca
21781 gttccatcct ctggcctgga tcaggctctg cacacggagg cctgtgggcc agatgactga
21841 caggagggga gttgggtgga acctcggcct gcctgatatc cagcaacaga gggcaaggc
21901 ggcagcacct ccagcatgac agtcccttcc aagcacgtca ggatgctccc ttgcctgtgc
21961 tggcagcttc ctaaacatgg ggactgggca tggtggcagg ttttttgtcct tctgaaagag
22021 caattttgct gtgaggttac ttgctccttg agttcttgtc tgaggcccac ctggcggctg
22081 ctccgtgagg aacgaggtgg ccctgctgca gctcagcatc ccgccacgct cccaggagtg
22141 tgtgtttcct gggggagcg gcccgggacc gtggctctgt ggtccattct gtggatgtcc
22201 acaaggcctg ggcgttctgt gggtttgggt ggcagtcccg tctgggcagc tcctgctggg
22261 ctgggtgtgg gtctcctgct ggtctgcccc cagctgcaca acgtgtcttg tgccttgccc
22321 tcttgtacct ctgcaggttt tggctacggg cctccacctc caccgccaga tcagtttgcc
22381 cctccggggg ttcctcctcc accagccact cccggggcag cacctctggc tttcccaccg
22441 cctccgtctc aggctgcccc ggacatgagc aagcccccga cagctcagcc agacttcccc
```

FIGURE 32

Homo sapiens ADAM metallopeptidase domain 9 (ADAM9), transcript variant 2, non-coding RNA.

```
   1 cggcagggtt ggaaaatgat ggaagaggcg gaggtggagg cgaccgagtg ctgagaggaa
  61 cctgcggaat cggccgagat ggggtctggc gcgcgctttc cctcggggac ccttcgtgtc
 121 cggtggttgc tgttgcttgg cctggtgggc ccagtcctcg gtgcggcgcg gccaggcttt
 181 caacagacct cacatctttc ttcttatgaa attataactc cttggagatt aactagagaa
 241 agaagagaag cccctaggcc ctattcaaaa caagtatctt atgttattca ggctgaagga
 301 aaagagcata ttattcactt ggaaggaac aaagaccttt tgcctgaaga ttttgtggtt
 361 tatacttaca acaaggaagg gactttaatc actgaccatc ccaatataca gaatcattgt
 421 cattatcggg gctatgtgga gggagttcat aattcatcca ttgctcttag cgactgtttt
 481 ggactcagag gattgctgca tttagagaat gcgagttatg ggattgaacc cctgcagaac
 541 agctctcatt ttgagcacat catttatcga atggatgatg tctacaaaga gcctctgaaa
 601 tgtggagttt ccaacaagga tatagagaaa gaaactgcaa aggatgaaga ggaagagcct
 661 cccagcatga ctcagctact tcgaagaaga agagctgtct tgccacagac ccggtatgtg
 721 gagctgttca ttgtcgtaga caaggaaagg tatgacatga tgggaagaaa tcagactgct
 781 gtgagagaag agatgattct cctggcaaac tacttggata gtatgtatat tatgttaaat
 841 attcgaattg tgctagttgg actgagatt tggaccaatg gaaacctgat caacatagtt
 901 gggggtgctg gtgatgtgct ggggaacttc gtgcagtggc gggaaaagtt tcttatcaca
 961 cgtcggagac atgacagtgc acagctagtt ctaaagaaag gttttggtgg aactgcagga
1021 atggcatttg tgggaacagt gtgttcaagg agccacgcag gcgggattaa tgtgtttgga
1081 caaatcactg tggagacatt tgcttccatt gttgctcatg aattgggtca taatcttgga
1141 atgaatcacg atgatggag agattgttcc tgtggagcaa agagctgcat catgaattca
1201 ggagcatcgg gttccagaaa ctttagcagt tgcagtgcag aggactttga gaagttaact
1261 ttaaataaag gaggaaactg ccttcttaat attccaaagc ctgatgaagc ctatagtgct
1321 ccctcctgtg gtaataagtt ggtggacgct ggggaagagt gtgactgtgg tactccaaag
1381 gaatgtgaat tggacccttg ctgcgaagga agtacctgta agcttaaatc atttgctgag
1441 tgtgcatatg gtgactgttg taaagactgt cggttccttc caggaggtac tttatgccga
1501 ggaaaaacca gtgagtgtga tgttccagag tactgcaatg gttcttctca gttctgtcag
1561 ccagatgttt ttattcagaa tggatatcct tgccagaata caaagccta ttgctacaac
1621 ggcatgtgcc agtattatga tgctcaatgt caagtcatct ttggctcaaa agccaaggct
1681 gcccccaaag attgtttcat tgaagtgaat tctaaaggtg acagatttgg caattgtggt
1741 ttctctggca atgaatacaa gaagtgtgcc actgggaatg ctttgtgtgg aaagcttcag
1801 tgtgagaatg tacaagagat acctgtattt ggaattgtgc ctgctattat tcaaacgcct
1861 agtcaggca ccaaatgttg gggtgtggat ttccagctag gatcagatgt tccagatcct
1921 gggatggtta acgaaggcac aaaatggt gctggaaaga tctgtagaaa cttccagtgt
1981 gtagatgctt ctgttctgaa ttatgactgt gatgttcaga aaagtgtca tggacatggg
2041 aaatgaatac tgcattgagg gacggacttc tggtcttctt cttcctaatt gttcccctta
2101 ttgtctgtgc tattttatc ttcatcaaga gggatcaact gtggagaagc tacttcagaa
2161 agaagagatc acaaacatat gagtcagatg gcaaaaatca agcaaaccct tctagacagc
2221 cggggagtgt tcctcgacat gtttctccag tgacacctcc cagagaagtt cctatatatg
2281 caaacagatt tgcagtacca acctatgcag ccaagcaacc tcagcagttc ccatcaaggc
2341 cacctccacc acaaccgaaa gtatcatctc agggaaactt aattcctgcc cgtcctgctc
2401 ctgcacctcc tttatatagt tccctcactt gattttttta accttctttt tgcaaatgtc
2461 ttcagggaac tgagctaata cttttttttt ttcttgatgt tttcttgaaa agcctttctg
2521 ttgcaactat gaatgaaaac aaaacaccac aaaacagact tcactaacac agaaaaacag
2581 aaactgagtg tgagagttgt gaaatacaag gaatgcagt aaagccaggg aatttacaat
2641 aacatttccg tttccatcat tgaataagtc ttattcagtc atcggtgagg ttaatgcact
2701 aatcatggat ttttgaaca tgttattgca gtgattctca aattaactgt attggtgtaa
2761 gattttgtc attaagtgtt taagtgttat tctgaatttt ctacctagt tatcattaat
2821 gtagttcctc attgaacatg tgataatcta atacctgtga aaactgacta atcagctgcc
2881 aataatatct aatattttc atcatgcacg aattaataat catcatactc tagaatcttg
2941 tctgtcactc actacatgaa taagcaaata ttgtcttcaa aagaatgcac aagaaccaca
3001 attaagatgt catattattt tgaaagtaca aaatatacta aagagtgtg tgtgtattca
```

FIGURE 32 (cont.)

```
3061 cgcagttact cgcttccatt tttatgacct ttcaactata ggtaataact cttagagaaa
3121 ttaatttaat attagaattt ctattatgaa tcatgtgaaa gcatgacatt cgttcacaat
3181 agcactattt taaataaatt ataagcttta aggtacgaag tatttaatag atctaatcaa
3241 atatgttgat tcatggctat aataaagcag gagcaattat aaaatcttca atcaattgaa
3301 cttttacaaa accacttgag aatttcatga gcactttaaa atctgaactt tcaaagcttg
3361 ctattaaatc atttagaatg tttacattta ctaaggtgtg ctgggtcatg taaaatatta
3421 gacactaata ttttcataga aattaggctg gagaagaag gaagaaatgg ttttcttaaa
3481 tacctacaaa aaagttactg tggtatctat gagttatcat cttagctgtg ttaaaaatga
3541 attttacta tggcagatat ggtatggatc gtaaaatttt aagcactaaa aatttttca
3601 taacctttca taataaagtt taataatagg tttattaact gaatttcatt agtttttaa
3661 aagtgttttt ggtttgtgta tatatacata tacaaataca acatttacaa taaataaaat
3721 acttgaaatt ctcttttgtg tctcctagta gcttcctact caactattta taatctcatt
3781 aattaaaaag ttataattt agataaaaat tctagtcaaa tttttacaga tattatctca
3841 ctaattttca gacttttgcc aaagtgtgca caatggcttt ttgttaataa agaacagatt
3901 agttttgaag aaggcaaaaa tttcagtttt ctgaagacag catgttattt taacaatcaa
3961 gtatacatat taaaaattgt gagcaatctc aaaaaaaaaa aaaaa
```

FIGURE 33

Homo sapiens alpha-2-glycoprotein 1, zinc-binding (AZGP1), mRNA.

```
   1 ccattggcct gtagattcac ctcccctggg cagggcccca ggacccagga taatatctgt
  61 gcctcctgcc cagaaccctc caagcagaca caatggtaag aatggtgcct gtcctgctgt
 121 ctctgctgct gcttctgggt cctgctgtcc cccaggagaa ccaagatggt cgttactctc
 181 tgacctatat ctacactggg ctgtccaagc atgttgaaga cgtccccgcg tttcaggccc
 241 ttggctcact caatgacctc cagttcttta gatacaacag taaagacagg aagtctcagc
 301 ccatgggact ctggagacag gtggaaggaa tggaggattg gaagcaggac agccaacttc
 361 agaaggccag ggaggacatc tttatggaga ccctgaaaga catcgtggag tattacaacg
 421 acagtaacgg gtctcacgta ttgcagggaa ggtttggttg tgagatcgag aataacagaa
 481 gcagcggagc attctggaaa tattactatg atggaaagga ctacattgaa ttcaacaaag
 541 aaatcccagc ctgggtcccc ttcgacccag cagcccagat aaccaagcag aagtgggagg
 601 cagaaccagt ctacgtgcag cgggccaagg cttacctgga ggaggagtgc cctgcgactc
 661 tgcggaaata cctgaaatac agcaaaaata tcctggaccg gcaagatcct ccctctgtgg
 721 tggtcaccag ccaccaggcc ccaggagaaa agaagaaact gaagtgcctg gcctacgact
 781 tctacccagg gaaaattgat gtgcactgga ctcgggccgg cgaggtgcag gagcctgagt
 841 tacggggaga tgttcttcac aatggaaatg gcacttacca gtcctgggtg gtggtggcag
 901 tgcccccgca ggacacagcc ccctactcct gccacgtgca gcacagcagc ctggcccagc
 961 ccctcgtggt gccctgggag gccagctagg aagcaagggt tggaggcaat gtgggatctc
1021 agacccagta gctgcccttc ctgcctgatg tgggagctga accacagaaa tcacagtcaa
1081 tggatccaca aggcctgagg agcagtgtgg ggggacagac aggaggtgga tttggagacc
1141 gaagactggg atgcctgtct tgagtagact tggacccaaa aaatcatctc accttgagcc
1201 caccccacc ccattgtcta atctgtagaa gctaataaat aatcatccct ccttgcctag
1261 cataaaaaaa aaaaaaaa
```

FIGURE 34

Homo sapiens desmocollin 3 (DSC3), RefSeqGene on chromosome 18. NTs 46261-48240.

```
46261 tcatttcaaa atttaggagt taatttatat ttttaattga atcagatttc ataggcatag
46321 atattgtctg tcaatattca tatgtttata tagtggtaat ttattaaact tcttaatcca
46381 gatgtattat tttagttatc tttttccac tctagtgtca tagtttaaac ttgttctttg
46441 atgttgagta tttattataa caatagtttt ttttgcctgc actctacaat gtatatttcc
46501 agatataatt tgtttatgta acttgttgac catttataat ggggaaaaaa gcttgctaaa
46561 agttctcaag atagctagga aaatatcaat gagatatatc taaaagaaag ggagagggt
46621 ttggaagatt actgccactc tctttcctta tatatttctt aggacttctg aggtgctttt
46681 atgcttcttg ttttgtgtaa agtatatata tatatatata tatatacaca cacacaaagt
46741 atatataaac acaaagtata tatatacaca cacatataca caaagtatat atatatacac
46801 acaaagtata tatatatgta cacaaaatat atatatatac acaaaagtac ttacaaggca
46861 tgttcttacc tcaaaagat gccaacttat ttatgagaaa tagatcctac tttatggaaa
46921 agcaaaatag gaacatgaca ataaccaat atgataaagc actgtcagag ttcaaaaaca
46981 cctatgatac ctaaatgtac tcatgtagtt tggatcaacc agaaaggctg gtgacaagag
47041 gtacagctta cttggtaact taaagaataa gaagggtttg aaagtgaaga gacggtgaga
47101 atagctaaag aagaggaaaa cagcatagcc tacaagacag gagatgataa agtttagggg
47161 ctatttagca aataataaat aaattgattt agaatagaag aaatcatgtg ttggaaaaga
47221 ggcttgaaac aagttcggtg ttagagaaga gaatattaag aaacaagtgg gagataggac
47281 ttctaaatgc tgcactaagt atttcggatt tattctcatg gtaaaggaga gccagccaag
47341 gcttttctac aggagagagg tataatcaag cagcgtgaag ctgagtcagt aggggatca
47401 gtgagaatag gaagacatca gggttgggga agatgaaagc ttagtttaag catgagttaa
47461 ttctaccagg atgatggtaa ttgttatatt aagataggga tgaataagaa atatttcaaa
47521 ggtataaagg ataagcttgt tgactgactg aacttaagga acaaagtaaa aagcagagtc
47581 aaagtggcag aggctatagc cagggacaac gactacatat ccagccttt ctatgtctcg
47641 gggtgaagat gcctttctta ttcactattt ctctcttcaa ctcctccaca ccaccatgca
47701 aaatcatagc ccatctatgc ttgacgtgcc tacatgtaga aacctgtgat gatctctcca
47761 gcgagaaagc aggtttaatc ccttgacagt ccttgactca tagtaagttc ttattttatt
47821 tttaagaccg gcatggatga cttttactta atatctgttc tttgccattt aatgctagag
47881 ctgatgatat tgagtggcca tttcacaata tgtacctgtt ctgtgttagg aacacttcta
47941 aaaggggctt ggaattatta atttatacaa aaacataaaa tttcatcttg aatctataaa
48001 cttgctttaa tacaatgagt aaaagtgatc atttagctt tggatctgaa tttcacttga
48061 aggcatgcac atggattag gagttgggtg aataatcagg actggaaaag taaacctaga
48121 aattattgac atggataaag agttgttgat accctgtgag aaggaacttt gggaaatgtg
48181 gatggaggag gacagaaagg agcagagaat aaaagtatga aagctagccc tgtaggctca
```

FIGURE 35

Homo sapiens PERP, TP53 apoptosis effector (PERP), mRNA.

```
   1 ctctgagtca ccggaatcta ggtggggccg cccggagcgg cgtcctcggg agccgcctcc
  61 ccgcggcctc ttcgcttttg tggcggcgcc cgcgctcgca ggccactctc tgctgtcgcc
 121 cgtcccgcgc gctcctccga cccgctccgc tccgctccgc tcggccccgc gccgcccgtc
 181 aacatgatcc gctgcggcct ggcctgcgag cgctgccgct ggatcctgcc cctgctccta
 241 ctcagcgcca tcgccttcga catcatcgcg ctgccggcc gcggctggtt gcagtctagc
 301 gaccacggcc agacgtcctc gctgtggtgg aaatgctccc aagagggcgg cggcagcggg
 361 tcctacgagg agggctgtca gagcctcatg gagtacgcgt ggggtagagc agcggctgcc
 421 atgctcttct gtggcttcat catcctggtg atctgtttca tcctctcctt cttcgccctc
 481 tgtggacccc agatgcttgt cttcctgaga gtgattggag gtctccttgc cttggctgct
 541 gtgttccaga tcatctccct ggtaatttac cccgtgaagt acacccagac cttcacccttt
 601 catgccaacc ctgctgtcac ttacatctat aactgggcct acggctttgg gtgggcagcc
 661 acgattatcc tgattggctg tgccttcttc ttctgctgcc tccccaacta cgaagatgac
 721 cttctgggca atgccaagcc caggtacttc tacacatctg cctaacttgg gaatgaatgt
 781 gggagaaaat cgctgctgct gagatggact ccagaagaag aaactgtttc tccaggcgac
 841 tttgaaccca ttttttggca gtgttcatat tattaaacta gtcaaaaatg ctaaaataat
 901 ttgggagaaa atattttta agtagtgtta tagtttcatg tttatctttt attatgtttt
 961 gtgaagttgt gtcttttcac taattaccta tactatgcca atatttcctt atatctatcc
1021 ataacattta tactacattt gtaagagaat atgcacgtga aacttaacac tttataaggt
1081 aaaaatgagg tttccaagat ttaataatct gatcaagttc ttgttatttc caaatagaat
1141 ggactcggtc tgttaagggc taaggagaag aggaagataa ggttaaaagt tgttaatgac
1201 caaacattct aaaagaaatg caaaaaaaaa gtttattttc aagccttcga actatttaag
1261 gaaagcaaaa tcatttccta aatgcatatc atttgtgaga atttctcatt aatatcctga
1321 atcattcatt ttagctaagg cttcatgttg actcgatatg tcatctagga aagtactatt
1381 tcatggtcca aacctgttgc catagttggt aaggctttcc tttaagtgtg aaatatttag
1441 atgaaatttt ctcttttaaa gttctttata gggttagggt gtgggaaaat gctatattaa
1501 taaatctgta gtgtttttgtg tttatatgtt cagaaccaga gtagactgga ttgaaagatg
1561 gactgggtct aatttatcat gactgataga tctggttaag ttgtgtagta aagcattagg
1621 agggtcattc ttgtcacaaa agtgccacta aaacagcctc aggagaataa atgacttgct
1681 tttctaaatc tcaggtttat ctgggctcta tcatatagac aggcttctga tagtttgcaa
1741 ctgtaagcag aaacctacat atagttaaaa tcctggtctt tcttggtaaa cagattttaa
1801 atgtctgata taaacatgc cacaggagaa ttcggggatt tgagtttctc tgaatagcat
1861 atatatgatg catcggatag gtcattatga ttttttacca tttcgactta cataatgaaa
1921 accaattcat tttaaatatc agattattat tttgtaagtt gtggaaaaag ctaattgtag
1981 ttttcattat gaagttttcc caataaacca ggtattctaa acttgtttcc agtttgtagt
2041 ttttccattt ttcaaatctg gggaaaggaa ttaaaaaaaa aatgggtaat aagaacatgg
2101 gatataatga aaagtggttt ttgtttgttt ttttgtttga agttttaagg gccttgctca
2161 ttttaggtgt ccaaaaccaa ttttttgagtg gagattaatg aattctaata gtctattccc
2221 tgaactttc ctcaatgaac aatacccta g acacacatta aacaatttct ctgcagtgct
2281 atcaaccaga ggaaatgga ctaagagatt tctggcaggt tcagacaccc gggggacatg
2341 tgtgcagtgt agctgaagcc tcctccttgt gctggggtcc ccttccattc aggtggtggg
2401 gtagcagtct ctctattttc ccctgccct ccttcccatt ttatcatttg ttatttttt
2461 tcccaccata agtcatatgt tacttccact atggtgtatg tcattgtgag gatgggtgca
2521 gagaggctgg gtgggagaac ggaaatatat ctccctaggg ctactgttgg ccagctagtc
2581 cttggcagtg aattttctta tgcttttcaa aatgcgaggt gaatgtttct catagagaaa
2641 tgtaatctgg gtgattatac caaaattgaa aagaaaaacc cacacaacta tgccgtggct
2701 ggtgagaat ttgaagtggt cattaaaaat gttaaaaatc ccatctttta aagtgatacc
2761 acagctcatt caagaagata ctggatatct agagattaag aaacgtggtc tcctgttaaa
2821 catgaaaatg actccgttta taagcttctc taccacatgc acttgtcttt gcatgatttc
2881 ccatccagcc ttcttcccct cctcaatcac acaatacctt aacggcgcac atttaggaaa
2941 aatgcaacct cctgggacca acgagcctga tataatgaa ccatgtcaac ctaaagtatt
3001 tatgacaaag ataaactctt attttgcaga aatggtctgc ttccttcagc cttgttctag
3061 tatagagatc tgccattcct tgttgatcca gattcaccaa gacagatacc tttatgtcat
```

FIGURE 35 (cont.)

```
3121 aacagaaggg aagttccaga ggattctgga gagtaatgaa gaattgggct gagaaaccac
3181 ctgaaggcta acagtgcatt gcatgagatt tcccacagta aagctgaggt gcttttggt
3241 tcagtaatta aatattgagt tcccaccctt taaataagca gttctaggtt cctaagcaat
3301 tatttcactc tgtaagtagc cagacatgct aagtggcact tactgctgat tgtaacaaag
3361 aagtaatata tcaaggtctt tccatgttca cacaaggtag cttgtgtgta ataacttagc
3421 ttcaaaacca tagactgcag aactcacaag ttcaacagcc tttccttttt taaggaaatg
3481 aaaacaatgg aaaatatagt catcataact taattcggtt tattttttt ttctgtaaac
3541 tccccctgaa agacattcct attaatacag taaatgtgaa cactgacttg tttttataag
3601 cacatctgaa agggcatatt tgagtctcat cccaactttg gtccttgcta tctgtgcagg
3661 cttgggcagg tcatctccct gctggtctca atatcctcac ctgtaaaatg attgtaaatg
3721 atcccctac cttcaagatt ctctgattga tagaatttt tctttaatta aaaaattta
3781 aatattcctt gagttggaag cactgatcaa taagtggatt gcttagggag gttggaacga
3841 atagattcag tcccaacttc ctcttttaaa ttccctcttc ctcactcttc ctgcaacact
3901 tatttttaca gttgagtttt aaaaataagt aatatataaa ataatttctg tagtgtggtt
3961 tcagatttaa aaattcctgc agacaggctg ggcttgcaac cccatcagtc gatggtcaga
4021 gccctttgct ttttgagacc atttttaggt gagcttggct tgcctggata cagtgtgcag
4081 tgcattcttc ctgaattttg caattctggt atctgggtgt attttctagg tgtgtcaggg
4141 tgagtgtaat ccacctaggg tgtggaaaaa gccaagaaag ggaaattaaa agaggttcct
4201 atccagtcat gttaatgatc ttccacttgt actatcctgt gcttcgttgt taacctcgaa
4261 aacatacttt gttggctgca aaataaaca aagggaaact caaaaaaaaa aaaaaaaa
```

FIGURE 36

Homo sapiens 3 BAC RP11-783D3 (Roswell Park Cancer Institute Human BAC Library)
NTs 178621-180600.

```
178621 ggcaccgtgg gagtttgcag ctctggttgc tccaagagca caaatattaa tgtagcacag
178681 atattaatat tattaattag cacagacatt aatgtagtca cagaaagaaa aagagatgaa
178741 aaagagacag gttcttcact gcatgagagg ctccgtttgg gatctctcag aaatgtggaa
178801 gcagaggcta cagcacaagc ctgggttatt gctagtagca agacagaaaa taaggcttgg
178861 gtaagctgta gttatagtta caatggaaat gactggccca agagagtgct acagattaca
178921 tagcagctac taagaaaaag gacaggcaga aggggtaggc aagacatgtt ctctggctgt
178981 tgcagccacc aaaaagccag gatacaaagg cagggagtta tctgaactgc cttcctggag
179041 ggtcatgcat ttaggatccg actcattgac tcttttcctt aattttgctc tgtacatttc
179101 tctaagaggg ctaaccagtg tcaaggtttg ataatatctg aaatggtatt ctggtgccaa
179161 agtatcatct cacaaattat ttagaaattg caaagagaaa atatatttta taatccagat
179221 atctggcagt taaccacatg accaaattta gcatcactaa cagtaggaca actagatatt
179281 atatacctct tgctgtgata tactatgaag tacacatcat caactatgaa gtattatttt
179341 tttttctttt gagatagggt catgctctgt cgcccaattt agagtgcagc gatgcaatca
179401 tagctcactg cagctttgac ctcccagtct caagtgatcc tcccacctca gcctccctag
179461 tagctgggac tacagatgtg ttccaccaca cctggctaat ttttatatat tttttgtagt
179521 gatggggttt caccatgttg cacaggctgg tcttgaactc ctgggcttaa gcaatctgcc
179581 tgaaagttct gggattatag gcatgagcca ctgtgtccag actatgaagt attcttgcca
179641 aaactgatca acctaaatct aatcaagctt ctgggccaga actgtccaat agcaatgtaa
179701 tgtcagctac atgtaattta aaattttcta gttgccacca aaagcacaga aaagaaaaaa
179761 tagataaatt gtgctacatc aagattaaat acttctttgc atcaaaggac ataatcaaca
179821 cagagaaaag gcaaaccact gaatgggaga aaatatttgc aaattgatat tcataatatg
179881 taaagaatct ttacaactca acacccacaa aataaaaaaa aagattaaaa aatggggaaa
179941 ggacttgaat agacatttct ccaaagaaga tgtacaactt gccaataagc acaagaaaag
180001 actaattatg agggaaatgc aaattaaaac cacaatgaga tcaaacacat tatgttggct
180061 atcataaaaa gaaagtgcca ggcgcaatga tcacagctac tcaacaggct gggtggaaga
180121 atcccttgag accaggagtt agaggctgca gtgtgttatg atcatgcctg tgaatagcca
180181 ctgcactcca acataggtaa catgcaagc cccatccata aaataaaata aaataaaata
180241 aaataaaggc aacaaaaaat aacaagtatt ggtaaggatg tggagaaatt ggaaccctcg
180301 tgcattgctg gtgggtgtgt aaaaaggtat ggctgctgtg aaaaatggga tggctattct
180361 tcaaaaaatt aaccacagaa ttactatatg atccagcaat cccacttctg catacacatc
180421 caaaagaagt ggactcaagg actcagacag atatttgtac cccctgttc atagcagcat
180481 tatttacaat agccaaaaag tagaagcaac cacagattca tcaatgtatg aatggataaa
180541 caaaatgtgg catatacaca tagtgggata tcattcagct ttaaaaggg aggaaattct
```

FIGURE 37

Homo sapiens cytochrome c oxidase subunit Va (COX5A), nuclear gene encoding mitochondrial protein, mRNA.

```
  1 gcccacgcgc cagagtcgca gtgggcgggc ctacgtgctc cgcccgctgt gagcctgtcc
 61 ggcccccgcc cgctccggag caacccgcga gcttacaccg gcttctctct gtcctcagcc
121 cgcgcgccgc catcgccgtc atgctgggcg ccgctctccg ccgctgcgct gtggccgcaa
181 ccacccgggc cgaccctcga ggcctcctgc actccgcccg gaccccggc cccgccgtgg
241 ctatccagtc agttcgctgc tattcccatg ggtcacagga gacagatgag gagtttgatg
301 ctcgctgggt aacatacttc aacaagccag atatagatgc ctgggaattg cgtaaaggga
361 taaacacact tgttacctat gatatggttc cagagcccaa aatcattgat gctgctttgc
421 gggcatgcag acggttaaat gattttgcta gtacagttcg tatcctagag gttgttaagg
481 acaaagcagg acctcataag gaaatctacc cctatgtcat ccaggaactt agaccaactt
541 taaatgaact gggaatctcc actccggagg aactgggcct tgacaaagtg taaaccgcat
601 ggatgggctt ccccaaggat ttattgacat tgctacttga gtgtgaacag ttacctggaa
661 atactgatga taacatatta ccttatttga acaagttttc ctttattgag taccaagcca
721 tgtaatggta acttggactt taataaaagg gaaatgagtt tgaactgaaa aaaaaaaaaa
781 aaaa
```

FIGURE 38

Homo sapiens isolate PD047 mitochondrion, NTs 4801-6780.

```
4801 ttcacttctg agtcccagag gttacccaag gcacccctct gacatccggc ctgcttcttc
4861 tcacatgaca aaaactagcc cccatctcaa tcatatacca aatctctccc tcactaaacg
4921 taagccttct cctcactctc tcaatcttat ccatcatagc aggcagttga ggtggattaa
4981 accaaaccca gctacgcaaa atcttagcat actcctcaat tacccacata ggatgaataa
5041 tagcagttct accgtacaac cctaacataa ccattcttaa tttaactatt tatattatcc
5101 taactactac cgcattccta ctactcaact taaactccag caccacgacc ctactactat
5161 ctcgcacctg aaacaagcta acatgactaa cacccttaat tccatccacc ctcctctccc
5221 taggaggcct gcccccgcta accggctttt tgcccaaatg ggccattatc gaagaattca
5281 caaaaaacaa tagcctcatc atccccacca tcatagccac catcaccctc cttaacctct
5341 acttctacct acgcctaatc tactccacct caatcacact actccccata tctaacaacg
5401 taaaaataaa atgacagttt gaacatacaa aacccacccc attcctcccc acactcatca
5461 cccttaccac gctactccta cctatctccc cttttatact aataatctta tagaaattta
5521 ggttaaatac agaccaagag ccttcaaagc cctcagcaag ttgcaatact taatttctgt
5581 aacagctaag gactgcaaaa ccccactctg catcaactga acgcaaatca gccactttaa
5641 ttaagctaag cccttactag accaatggga cttaaaccca caaacactta gttaacagct
5701 aagcacccta atcaactggc ttcaatctac ttctcccgcc gccgggaaaa aaggcgggag
5761 aagccccggc aggtttgaag ctgcttcttc gaatttgcaa ttcaatatga aaatcacctc
5821 ggagctggta aaaagaggcc tagcccctgt ctttagattt acagtccaat gcttcactca
5881 gccattttac ctcaccccca ctgatgttcg ccgaccgttg actattctct acaaaccaca
5941 aagacattgg aacactatac ctattattcg gcgcatgagc tggagtccta ggcacagctc
6001 taagcctcct tattcgagcc gagctgggcc agccaggcaa ccttctaggt aacgaccaca
6061 tctacaacgt tatcgtcaca gcccatgcat ttgtaataat cttcttcata gtaataccca
6121 tcataatcgg aggctttggc aactgactag ttcccctaat aatcggtgcc cccgatatgg
6181 cgtttccccg cataaacaac ataagcttct gactcttacc tccctctctc ctactcctgc
6241 tcgcatctgc tatagtggag gccggagcag gaacaggttg aacagtctac cctcccttag
6301 cagggaacta ctcccaccct ggagcctccg tagacctaac catcttctcc ttacacctag
6361 caggtgtctc ctctatctta ggggccatca atttcatcac aacaattatc aatataaaac
6421 cccctgccat aacccaatac caaacgcccc tcttcgtctg atccgtccta atcacagcag
6481 tcctacttct cctatctctc ccagtcctag ctgctggcat cactatacta ctaacagacc
6541 gcaacctcaa caccaccttc ttcgaccccg ccggaggagg agaccccatt ctataccaac
6601 acctattctg atttttcggt caccctgaag tttatattct tatcctacca ggcttcggaa
6661 taatctccca tattgtaact tactactccg gaaaaaaga accatttgga tacataggta
6721 tggtctgagc tatgatatca attggcttcc tagggtttat cgtgtgagca caccatatat
```

FIGURE 39

```
Homo sapiens myosin, heavy chain 9, non-muscle (MYH9), mRNA.

1 gagggcgggg cggaaggcg gcgaggagcc gagctgggtg cggtgaggcg cgcagatcac
  61 cgcggttcct gggcagggca cggaaggcta agcaaggctg acctgctgca gctcccgcct
 121 cgtgcgctcg ccccacccgg ccgccgcccg agcgctcgag aaagtcctct cgggagaagc
 181 agcgcctgtt cccggggcag atccaggttc aggtcctggc tataagtcac catggcacag
 241 caagctgccg ataagtatct ctatgtggat aaaaacttca tcaacaatcc gctggcccag
 301 gccgactggg ctgccaagaa gctggtatgg gtgccttccg acaagagtgg ctttgagcca
 361 gccagcctca aggaggaggt gggcgaagag gccatcgtgg agctggtgga gaatgggaag
 421 aaggtgaagg tgaacaagga tgacatccag aagatgaacc cgcccaagtt ctccaaggtg
 481 gaggacatgg cagagctcac gtgcctcaac gaagcctcgg tgctgcacaa cctcaaggag
 541 cgttactact cagggctcat ctacacctat tcaggcctgt tctgtgtggt catcaatcct
 601 tacaagaacc tgcccatcta ctctgaagag attgtggaaa tgtacaaggg caagaagagg
 661 cacgagatgc cccctcacat ctatgccatc acagacaccg cctacaggag tatgatgcaa
 721 gaccgagaag atcaatccat cttgtgcact ggtgaatctg gagctggcaa gacggagaac
 781 accaagaagg tcatccagta tctggcgtac gtggcgtcct cgcacaagag caagaaggac
 841 cagggcgagc tggagcggca gctgctgcag gccaacccca tcctggaggc cttcggnaac
 901 gccaagaccg tgaagaatga caactcctcc cgcttcggca aattcattcg catcaacttt
 961 gatgtcaatg gctacattgt tggagccaac attgagactt atcttttgga gaaatctcgt
1021 gctatccgcc aagccaagga agaacggacc ttccacatct tctattatct cctgtctggg
1081 gctggagagc acctgaagac cgatctcctg ttggagccgt acaacaaata ccgcttcctg
1141 tccaatggac acgtcaccat ccccgggcag caggacaagg acatgttcca ggagaccatg
1201 gaggccatga ggattatggg catcccagaa gaggagcaaa tgggcctgct gcgggtcatc
1261 tcaggggttc ttcagctcgg caacatcgtc ttcaagaagg agcggaacac tgaccaggcg
1321 tccatgcccg acaacacagc tgcccaaaag gtgtcccatc tcttgggtat caatgtgacc
1381 gatttcacca gaggaatcct caccccgcgc atcaaggtgg gacgggatta cgtccagaag
1441 gcgcagacta aagagcaggc tgactttgcc atcgaggcct tggccaaggc gacctatgag
1501 cggatgttcc gctggctggt gctgcgcatc aacaaggctc tggacaagac caagaggcag
1561 ggcgcctcct catcgggat cctggacatt gccggcttcg agatctttga tctgaactcg
1621 tttgagcagc tgtgcatcaa ttacaccaat gagaagctgc agcagctctt caaccacacc
1681 atgttcatcc tggagcagga ggagtaccag cgcgagggca tcgagtggaa cttcatcgac
1741 tttggcctcg acctgcagcc ctgcatcgac ctcattgaga agccagcagg cccccggggc
1801 attctggccc tgctggacga ggagtgctgg ttccccaaag ccaccgacaa gagcttcgtg
1861 gagaaggtga tgcaggagca gggcacccac cccaagttcc agaagcccaa gcagctgaag
1921 gacaaagctg atttctgcat tatccactat gccggcaagg tggattacaa agctgacgag
1981 tggctgatga agaacatgga tccctgaat gacaacatcg ccacactgct ccaccagtcc
2041 tctgacaagt ttgtctcgga gctgtggaag gatgtggacc gcatcatcgg cctggaccag
2101 gtggccggca tgtcggagac cgcactgccc ggggccttca agacgcggaa gggcatgttc
2161 cgcactgtgg ggcagcttta caaggagcag ctggccaagc tgatggctac gctgaggaac
2221 acgaacccca ctttgtccg ctgcatcatc cccaaccacg agaagaaggc cggcaagctg
2281 gacccgcatc tcgtgctgga ccagctgcgc tgcaacggtg ttctcgaggg catccgtatc
2341 tgccgccagg gcttccccaa cagggtggtc ttccaggagt ttcggcagag atatgagatc
2401 ctgactccaa actccattcc caagggttc atggacggga agcaggcgtg cgtgctcatg
2461 ataaaagccc tggagctcga cagcaatctg taccgcattg gccagagcaa agtcttcttc
2521 cgtgccggtg tgctgcccca cctgagcgga gagcgagacc tgaagatcac cgacgtcatc
2581 ataggttcc aggcctgctg caggggctac ctggccagga aagcatttgc caagcggcag
2641 cagcagctta ccgccatgaa ggtcctccag cggaactgcg ctgcctacct gaagctgcgg
2701 aactggcagt ggtggcggct cttcaccaag gtcaagccgc tgctgcaggt gagccggcag
2761 gaggaggaga tgatggccaa ggaggaggag ctggtgaagg tcagagagaa gcagctggct
2821 gcggagaaca ggctcacgga gatggagacg ctgcagtctc agctcatggc agagaaattg
2881 cagctgcagg agcagctcca ggcagaaacc gagctgtgtg ccgaggctga ggagctccgg
2941 gcccgcctga ccgccaagaa gcaggaatta gaagagatct gccatgacct agaggccagg
3001 gtggaggagg aggaggagcg ctgccagcac ctgcaggcgg agaagaagaa gatgcagcag
3061 aacatccagg agcttgagga gcagctggag gaggaggagg cgcccggca gaagctgcag
```

FIGURE 39 (cont.)

```
3121 ctggagaagg tgaccaccga ggcgaagctg aaaaagctgg aggaggagca gatcatcctg
3181 gaggaccaga actgcaagct ggccaaggaa aagaaactgc tggaagacag aatagctgag
3241 ttcaccacca acctcacaga agaggaggag aaatctaaga gcctcgccaa gctcaagaac
3301 aagcatgagg caatgatcac tgacttggaa gagcgcctcc gcagggagga gaagcagcga
3361 caggagctgg agaagacccg ccggaagctg gagggagact ccacagacct cagcgaccag
3421 atcgccgagc tccaggccca gatcgcggag ctcaagatgc agctggccaa gaaagaggag
3481 gagctccagg ccgccctggc cagagtggaa gaggaagctg cccagaagaa catggccctc
3541 aagaagatcc gggagctgga atctcagatc tctgaactcc aggaagacct ggagtctgag
3601 cgtgcttcca ggaataaagc tgagaagcag aaacgggacc ttggggaaga gctagaggct
3661 ctgaaaacag agttggagga cacgctggat tccacagctg cccagcagga gctcaggtca
3721 aaacgtgagc aggaggtgaa catcctgaag aagaccctgg aggaggaggc caagacccac
3781 gaggcccaga tccaggagat gaggcagaag cactcacagg ccgtggagga gctggcggag
3841 cagctggagc agacgaagcg ggtgaaagca aacctcgaga aggcaaagca gactctggag
3901 aacgagcggg gggagctggc caacgaggtg aaggtgctgc tgcagggcaa aggggactcg
3961 gagcacaagc gcaagaaagt ggaggcgcag ctgcaggagc tgcaggtcaa gttcaacgag
4021 ggagagcgcg tgcgcacaga gctggccgac aaggtcacca agctgcaggt ggagctggac
4081 aacgtgaccg ggcttctcag ccagtccgac agcaagtcca gcaagctcac caaggacttc
4141 tccgcgctgg agtcccagct gcaggacact caggagctgc tgcaggagga gaaccggcag
4201 aagctgagcc tgagcaccaa gctcaagcag gtggaggacg agaagaattc cttccgggag
4261 cagctggagg aggaggagga ggccaagcac aacctggaga agcagatcgc caccctccat
4321 gcccaggtgg ccgacatgaa aaagaagatg gaggacagtg tggggtgcct ggaaactgct
4381 gaggaggtga agaggaagct ccagaaggac ctggagggcc tgagccagcg gcacgaggag
4441 aaggtggccg cctacgacaa gctggagaag accaagacgc ggctgcagca ggagctggac
4501 gacctgctgg tggacctgga ccaccagcgc cagagcgcgt gcaacctgga gaagaagcag
4561 aagaagtttg accagctcct ggcggaggag aagaccatct ctgccaagta tgcgaggag
4621 cgcgaccggg ctgaggcgga ggcccgagag aaggagacca aggctctgtc gctggcccgg
4681 gccctggagg aagccatgga gcagaaggcg gagccgagc ggctcaacaa gcagttccgc
4741 acggagatgg aggaccttat gagctccaag gatgatgtgg gcaagagtgt ccacgagctg
4801 gagaagtcca agcgggccct agagcagcag gtggaggaga tgaagacgca gctggaagag
4861 ctggaggacg agctgcaggc caccgaagat gccaagctgc ggttggaggt caacctgcag
4921 gccatgaagg cccagttcga gcgggacctg cagggccggg acgagcagag cgaggagaag
4981 aagaagcagc tggtcagaca ggtgcgggag atggaggcag agctggagga cgagaggaag
5041 cagcgctcga tggcagtggc cgcccggaag aagctggaga tggacctgaa ggacctggag
5101 gcgcacatcg actcggccaa caagaaccgg gacgaagcca tcaaacagct gcggaagctg
5161 caggcccaga tgaaggactg catgcgcgag ctggatgaca cccgcgcctc tcgtgaggag
5221 atcctggccc aggccaaaga gaacgagaag aagctgaaga gcatggaggc cgagatgatc
5281 cagttgcagg aggaactggc agccgcggag cgtgccaagc gccaggccca gcaggagcgg
5341 gatgagctgg ctgacgagat cgccaacgac aaggccaaag gagccctggc gttagaggag
5401 aagcggcgtc tggaggcccg catcgcccag ctggaggagg agctggagga ggagcagggc
5461 aacacggagc tgatcaacga ccggctgaag aaggccaacc tgcagatcga ccagatcaac
5521 accgacctga acctggagcg cagccacgcc cagaagaacg agaatgctcg gcagcagctg
5581 gaacgccaga acaaggagct taaggtcaag ctgcaggaga tggaggcac tgtcaagtcc
5641 aagtacaagg cctccatcac cgccctcgag gccaagattg cacagctgga ggagcagctg
5701 gacaacgaga ccaaggagcg ccaggcagcc tgcaaacagg tgcgtcggac cgagaagaag
5761 ctgaaggatg tgctgctgca ggtggatgac gagcggagga acgccgagca gtacaaggac
5821 caggccgaca aggcatctac ccgcctgaag cagctcaagc ggcagctgga ggaggccgaa
5881 gaggaggccc agcgggccaa cgcctcccgc cggaaactgc agcgcgagct ggaggacgcc
5941 actgagacgg ccgatgccat gaaccgcgaa gtcagctccc taaagaacaa gctcaggcgc
6001 ggggacctgc cgtttgtcgt gccccgccga atgggccgga aggcgccgg ggatggctcc
6061 gacgaagagg tagatggcaa agcggatggg gctgaggcca aacctgccga ataagcctct
6121 tctcctgcag cctgagatgg atggacagac agacaccaca gcctcccctt cccagacccc
6181 gcagcacgcc tctccccacc ttcttgggac tgctgtgaac atgcctcctc ctgccctccg
6241 ccccgtcccc ccatcccgtt tccctccagg tgttgttgag ggcatttggc ttcctctgct
```

FIGURE 39 (cont.)

```
6301 gcatcccctt ccagctccct cccctgctca gaatctgata ccaaagagac agggcccggg
6361 cccaggcaga gagcgaccag caggctcctc agccctctct tgccaaaaag cacaagatgt
6421 tgaggcgagc agggcaggcc cccggggagg ggccagagtt ttctatgaat ctatttttct
6481 tcagactgag gccttttggt agtcggagcc cccgcagtcg tcagcctccc tgacgtctgc
6541 caccagcgcc cccactcctc ctcctttctt tgctgtttgc aatcacacgt ggtgacctca
6601 cacacctctg cccttgggc ctcccactcc catggctctg ggcggtccag aaggagcagg
6661 ccctgggcct ccacctctgt gcagggcaca gaaggctggg gtgggggag gagtggattc
6721 ctccccaccc tgtcccaggc agcgccactg tccgctgtct ccctcctgat tctaaaatgt
6781 ctcaagtgca atgcccctc ccctccttta ccgaggacag cctgcctctg ccacagcaag
6841 gctgtcgggg tcaagctgga aaggccagca gccttccagt ggcttctccc aacactcttg
6901 gggaccaaat atatttaatg gttaagggac ttgtcccaag tctgacagcc agagcgttag
6961 aggggccagc ggccctccca ggcgatcttg tgtctactct aggactgggc ccgagggtgg
7021 tttacctgca ccgttgactc agtatagttt aaaaatctgc cacctgcaca ggtattttg
7081 aaagcaaaat aaggttttct tttttcccct ttcttgtaat aaatgataaa attccgagtc
7141 tttctcactg cctttgttta gaagagagta gctcgtcctc actggtctac actggttgcc
7201 gaatttactt gtattcctaa ctgttttgta tatgctgcat tgagacttac ggcaagaagg
7261 cattttttt ttttaaagga aacaaactct caaatcatga agtgatataa aagctgcata
7321 tgcctacaaa gctctgaatt caggtcccag ttgctgtcac aaaggagtga gtgaaactcc
7381 caccctaccc ccttttttat ataataaaag tgccttagca tgtgttgcag ctgtcaccac
7441 tacagtaagc tggtttacag atgttttcca ctgagcatca caataaagag aaccatgtgc
7501 tacga
```

FIGURE 40

Homo sapiens asparagine synthetase domain containing 1 (ASNSD1), mRNA.

```
   1 gctattggta agactcgcgg gaaaagaaag ggtgagcgcg gctggaagcg cgcatgcgct
  61 gtggctaatg ccgtaggctc cttcagggct gagccatccc gcgtgtcttg cgctcggtgg
 121 aaatgcccag ccgagggacg cgaccagagg acagctctgt gctgatcccc accgacaatt
 181 cgaccccaca caaggaggat ctaagcagca agattaaaga acaaaaaatt gtggtggatg
 241 aactttctaa ccttaagaag aataggaaag tatataggca acaacagaac agcaatatat
 301 tctttcttgc agaccgaaca gaaatgctgt ctgagagcaa gaatatattg gatgaactga
 361 aaaagaata ccaagaaata gaaaacttag acaagaccaa aatcaagaaa tagtcaacct
 421 gatttcacat aacaatgtgt ggcatttgtt gttctgtaaa cttttctgct gagcatttca
 481 gtcaagattt aaaagaggac ttactatata atcttaaaca gcggggaccc aatagtagta
 541 aacaattgtt aaagtctgat gttaactacc agtgtttatt ttctgctcac gtcctacact
 601 tgaggggtgt tttgactacc cagcctgtgg aagatgaaag aggcaatgtg tttctatgga
 661 atggagaaat ttttagtgga ataaaggttg aagctgaaga gaatgacact caaattttgt
 721 ttaattatct ttcctcctgt aagaatgaat ctgagatttt gtcactcttc tcagaagtac
 781 aaggtccctg gtcatttata tattatcaag catctagtca ttatttatgg tttggtaggg
 841 attttttgg tcgccgtagc ttgctttggc attttagtaa tttgggcaag agtttctgcc
 901 tctcttcagt tggcacccaa acatctggat tggcaaatca gtggcaagaa gttccagcat
 961 ctggactttt cagaattgat cttaagtcta ctgtcatttc cagatgcatt attttacaac
1021 tgtatccttg gaaatatatt tctagggaga atattattga agaaaatgtt aatagcctga
1081 gtcaaatttc agcagactta ccagcatttg tatcagtggt agcaaatgaa gccaaactgt
1141 atcttgaaaa acctgttgtt cctttaaata tgatgttgcc acaagctgca ttggagactc
1201 attgcagtaa tatttccaat gtgccaccta caagagagat acttcaagtc tttcttactg
1261 atgtacacat gaaggaagta attcagcagt tcattgatgt cctgagtgta gcagtcaaga
1321 aacgtgtctt gtgtttacct agggatgaaa acctgacagc aaatgaagtt ttgaaaacgt
1381 gtgataggaa agcaaatgtt gcaatcctgt tttctggggg cattgattcc atggttattg
1441 caacccttgc tgaccgtcat attcctttag atgaaccaat tgatcttctt aatgtagctt
1501 tcatagctga agaaaagacc atgccaacta cctttaacag agaagggaat aaacagaaaa
1561 ataaatgtga aataccttca gaagaattct ctaaagatgt tgctgctgct gctgctgaca
1621 gtcctaataa acatgtcagt gtaccagatc gaatcacagg aagggcggga ctaaaggaac
1681 tacaagctgt tagcccttcc cgaatttgga attttgttga aattaatgtt tctatggaag
1741 aactgcagaa attaagaaga actcgaatat gtcacttaat tcggccattg gatacagttt
1801 tggatgatag cattggctgt gcagtctggt ttgcttctag aggaattggt tggttagtgg
1861 cccaggaagg agtgaaatcc tatcagagca atgcaaaggt agttctcact ggaattggtg
1921 cagatgagca acttgcaggt tattctcgtc atcgtgtccg ctttcagtcg catgggctgg
1981 aaggattgaa taaggaaata atgatggaac tgggtcgaat ttcttctaga aatcttggtc
2041 gtgatgacag agttattggt gatcatggaa aagaagcaag atttcctttc ctggatgaaa
2101 atgttgtctc ctttctaaat tctctgccga tttgggaaaa agcaaacttg actttacccc
2161 gaggaattgg tgaaaaatta cttttacgcc ttgcagctgt ggaacttggt cttacagcct
2221 ctgctcttct gcccaaacgg gccatgcagt ttggatcaag aattgcaaaa atggaaaaaa
2281 ttaatgaaaa ggcatctgat aaatgtggac ggctccaaat catgtcctta gaaaatcttt
2341 ctattgaaaa ggagactaaa ttgtaatgtg attcacaatg taacaatata aaaataagtt
2401 tttatataat tatataaaag taagatactc tgctgcttta ctattgtata atatagtagt
2461 tttaaagttc aaaaaaaaaa aaaaaaa
```

FIGURE 41

Homo sapiens cathepsin F (CTSF), mRNA.

```
   1 ggaggactca ggccccgctg gccgcgggct cggtacccgg tgggtcggtg gagcgtctgt
  61 tgggtccggg ccgccggctt cgcctcgcc atggcgccct ggctgcagct cctgtcgctg
 121 ctggggctgc tcccgggcgc agtggccgcc cccgcccagc cccgagccgc cagctttcag
 181 gcctggggc cgccgtcccc ggagctgctg gcgcccaccc gcttcgcgct ggagatgttc
 241 aaccgcggcc gggctgcggg gacgcgggcc gtgctgggcc ttgtgcgcgg ccgcgtccgc
 301 cgggcgggtc aggggtcgct gtactccctg gaggccaccc tggaggagcc accctgcaac
 361 gacccatgg tgtgccggct ccccgtgtcc aagaaaaccc tgctctgcag cttccaagtc
 421 ctggatgagc tcggaagaca cgtgctgctg cggaaggact gtggcccagt ggacaccaag
 481 gttccaggtg ctggggagcc caagtcagcc ttcactcagg gctcagccat gatttcttct
 541 ctgtcccaaa accatccaga caacagaaac gagactttca gctcagtcat ttccctgttg
 601 aatgaggatc ccctgtccca ggacttgcct gtgaagatgg cttcaatctt caagaacttt
 661 gtcattacct ataaccggac atatgagtca aaggaagaag cccggtggcg cctgtccgtc
 721 tttgtcaata acatggtgcg agcacagaag atccaggccc tggaccgtgg cacagctcag
 781 tatggagtca ccaagttcag tgatctcaca gaggaggagt tccgcactat ctacctgaat
 841 actctcctga ggaaagagcc tggcaacaag atgaagcaag ccaagtctgt gggtgacctc
 901 gccccacctg aatgggactg gaggagtaag ggggctgtca caaagtcaa agaccagggc
 961 atgtgtggct cctgctgggc cttctcagtc acaggcaatg tggagggcca gtggtttctc
1021 aaccagggga ccctgctctc cctctctgaa caggagctct tggactgtga caagatggac
1081 aaggcctgca tgggcggctt gccctccaat gcctactcgg ccataaagaa tttgggaggg
1141 ctggagacag aggatgacta cagctaccag ggtcacatgc agtcctgcaa cttctcagca
1201 gagaaggcca aggtctacat caatgactcc gtggagctga ccagaacga gcagaagctg
1261 gcagcctggc tggccaagag aggcccaatc tccgtggcca tcaatgcctt tggcatgcag
1321 ttttaccgcc acgggatctc ccgccctctc cggcccctct gcagcccttg gctcattgac
1381 catgcggtgt tgcttgtggg ctacggcaac cgctctgacg ttcccttttg ggccatcaag
1441 aacagctggg gcactgactg gggtgagaag ggttactact acttgcatcg tgggtccggg
1501 gcctgtggcg tgaacaccat ggccagctcg gcggtggtgg actgaagagg ggcccccagc
1561 tcgggacctg gtgctgatca gagtggctgc tgccccagcc tgacatgtgt ccaggcccct
1621 ccccgggagg tacagctggc agagggaaag gcactgggta cctcagggtg agcagagggc
1681 actgggctgg ggcacagccc ctgcttccct gcacccatt cccaccctga agttctgcac
1741 ctgcaccttt gttgaattgt ggtagcttag gaggatgtcg gggtgaaggg tggtatcttg
1801 gcagttgaag ctggggcaag aactctgggc ttgggtaatg agcaggaaga aaattttctg
1861 atcttaagcc cagctctgtt ctgccccgc tttcctctgt ttgatactat aaattttctg
1921 gttcccttgg atttagggat agtgtccctc tccatgtcca ggaaacttgt aaccacccct
1981 ttctaacagc aataaagagg tgtccttgtc ccgaaaaaaa aaaaaaaaaa aa
```

FIGURE 42
Homo sapiens genomic DNA, chromosome 11q clone:RP11-822I2, NTs 157801-159780.

```
157801 ttgagtaata gaaaataaat ctgggtcact tttttgtagc tgtaaatcca gccttagtaa
157861 tcctgacctc cattaacata gctagtattt caaattccac tgtaacagtt gctctgactc
157921 tttgggggct gggaggcaat ccaagtagcc agagaagcaa ttgtttcaca tgcttcaatc
157981 ctgccactcc agaaaaaata taaggggac tagggcaaaa gaaaatctct tatttgtttt
158041 ccatttctca tttctcgtat ctttattgct tctctctcat ccttaacctg tatctccctt
158101 cagctgatgc ctgattacct tctaccatgt tcaacattat gatcagtcac ctactatgtg
158161 ccaggaagtg tgcagtgtgt gaggatacca gaccctacct actgggagct tacagtctag
158221 ctcaacaggc acatcattaa ataagcaatt gcagcaatta tattaagtgc tgggccaagg
158281 gaggtaccag aagtcataag aatccctcct ctgagggat agaagtgaag acttcagagg
158341 ggaagtaatg attctggatg tgtaggactc agccaggtga agtgtaaaag taaggatgga
158401 ggagagtgtt ctaaaagagg gaacaacata atcaaagttc tggacaggag agagatttga
158461 catatttgag gaagtgaaaa ttttatctag aaacttgcaa tgagtaagta aacaccaggt
158521 caagaggaac tgagagattg gcagacaatg gaaaaccatt gaaaaggatt aaactgggaa
158581 gtgatatgtt ctcttttgca tttaaaaaga tcaccaatgg ggatatggag aatggtctgg
158641 ataggtctta agactagagc caggaagaca tgttagaagg ctatcaattg accctaaaga
158701 cactgcttca atcccttga tgacagtgag tttgctttcc ccagagatag cttattggac
158761 ctcaggactg ctgtgagaaa cagaaaatgc tcctttacgt gttgcctgaa gttaggctca
158821 ccgatttggg gcatgttcta attctaccag ctaggaacac acagaatcgc ttgtcaaaca
158881 ttctgagtca gatatgtcct ccctatgtct tttctgagaa aggcatacag aaaattcccag
158941 ctaaacatca ccagttccct catttgttcc tcagatgata tggtccattc aagttttgta
159001 atcatcatgg gggtagatgg agggtcccag tcctcacaac cattctggta atttactctt
159061 gaatttactg gttcacatgt atctatttg tagtgtggct cctgaaactg aaaaacctac
159121 cccaggtatt ctgtgaacag acagagtaga gagtctgtca ctgcccacgg agagatgatt
159181 aggcttccgg gaaaaggtga gaacactggc aaagttccgg aaggaggaac aatatccctt
159241 cttcccttct tcatgagtcg taccatccct tacttttggc tggtcacata accacccaaa
159301 ataagggcta cattttccag ccactctagc agctagggt gacagagtga ctaagattta
159361 cctggaagta tcgtgtgtga cttctgggaa gggtccttaa agagaggggt agtcctggct
159421 gggtgcggtg gctcacgtct gtaatcccag cactttggga ggccgaggca ggcggatcac
159481 aaggtcagga gttcaagacc agcctggcca agatgctgaa accccatctc taataaaaat
159541 acaaaaaaat tagccgggca tgctggcggg cgcctgtaat cccagctact taggaggctg
159601 agatggagaa ttgcttgaac ttgggaggca gagtttgcag tgggccaaaa tggcgccact
159661 gcactccagc ctgggcaaca gagcaagcct ccgtctcaaa aaaaaaaaa aaaaaaaaa
159721 aagagagggg tagtccttgt tgctgttgct gcaggtattt tctccttctt cccagctgga
```

FIGURE 43

Homo sapiens casein kinase 2, alpha prime polypeptide (CSNK2A2), mRNA.

```
   1 gcggccgccc gccgccgcgc tcctcctcct cctcctccag cgcccggcgg cccgctgcct
  61 cctccgcccg acgccccgcg tcccccgccg cgccgccgcc gccaccctct gcgccccgcg
 121 ccgcccccg gtcccgcccg ccatgcccgg cccggccgcg ggcagcaggg cccgggtcta
 181 cgccgaggtg aacagtctga ggagccgcga gtactgggac tacgaggctc acgtcccgag
 241 ctggggtaat caagatgatt accaactggt tcgaaaactt ggtcggggaa aatatagtga
 301 agtatttgag gccattaata tcaccaacaa tgagagagtg gttgtaaaaa tcctgaagcc
 361 agtgaagaaa aagaagataa aacgagaggt taagattctg gagaaccttc gtggtggaac
 421 aaatatcatt aagctgattg acactgtaaa ggaccccgtg tcaaagacac cagctttggt
 481 atttgaatat atcaataata cagattttaa gcaactctac cagatcctga cagactttga
 541 tatccggttt tatatgtatg aactacttaa agctctggat tactgccaca gcaagggaat
 601 catgcacagg gatgtgaaac ctcacaatgt catgatagat caccaacaga aaaagctgcg
 661 actgatagat tggggtctgg cagaattcta tcatcctgct caggagtaca atgttcgtgt
 721 agcctcaagg tacttcaagg gaccagagct cctcgtggac tatcagatgt atgattatag
 781 cttggacatg tggagtttgg gctgtatgtt agcaagcatg atctttcgaa gggaaccatt
 841 cttccatgga caggacaact atgaccagct tgttcgcatt gccaaggttc tgggtacaga
 901 agaactgtat gggtatctga agaagtatca catagaccta gatccacact tcaacgatat
 961 cctgggacaa cattcacgga aacgctggga aaactttatc catagtgaga acagacacct
1021 tgtcagccct gaggccctag atcttctgga caaacttctg cgatacgacc atcaacagag
1081 actgactgcc aaagaggcca tggagcaccc atacttctac cctgtggtga aggagcagtc
1141 ccagccttgt gcagacaatg ctgtgctttc cagtggtctc acggcagcac gatgaagact
1201 ggaaagcgac gggtctgttg cggttctccc acttttccat aagcagaaca agaaccaaat
1261 caaacgtctt aacgcgtata gagagatcac gttccgtgag cagacacaaa acggtggcag
1321 gtttggcgag cacgaactag accaagcgaa gggcagccca ccaccgtata tcaaacctca
1381 cttccgaatg taaaaggctc acttgccttt ggcttcctgt tgacttcttc ccgacccaga
1441 aagcatgggg aatgtgaagg gtatgcagaa tgttgttggt tactgttgct ccccgagccc
1501 ctcaactcgt cccgtggccg cctgttttc cagcaaacca cgctaactag ctgaccacag
1561 actccacagt gggggacgg gcgcagtatg tggcatggcg gcagttacat attattattt
1621 taaaagtata tattattgaa taaaaggttt taaagaaaa aaaaaaaaa aaaa
```

FIGURE 44

Homo sapiens aurora kinase A interacting protein 1 (AURKAIP1), transcript variant 1, mRNA.

```
   1 cccgcacccc ctgggattgt gggaaatgta gtttttttgcc tccgtaaggg accaggcgga
  61 gctgaggaac cgcgcgagga ctgggaccgt gattccacta accggaaacc gtcgcctttc
 121 gggcccggcg gggcctgagc caatgcagaa tcgggggccg cgaggacgcc agcgggcgct
 181 gtgcgtagga accgccgggt ggccgctgcc gatcggggcc gacttgggga cggaccggaa
 241 gtgcccgagg gcggccgcag aacggtcaat ttgagccgcg tcgagctccc ctgggacctg
 301 tggccgccgc ccacagacca tgctcctggg gcgcctgact cccagctgt tgagggccgt
 361 tccttgggca ggcggccgcc cgccttggcc cgtctctgga gtgctgggca gccgggtctg
 421 cgggcccctt tacagcacat cgccggccgg cccaggtagg gcggcctctc tccctcgcaa
 481 gggggcccag ctggagctgg aggagatgct ggtccccagg aagatgtccg tcagcccccct
 541 ggagagctgg ctcacggccc gctgcttcct gcccagactg gataccggga ccgcagggac
 601 tgtggctcca ccgcaatcct accagtgtcc gcccagccag ataggggaag gggccgagca
 661 ggggatgaa ggcgtcgcgg atgcgcctca aattcagtgc aaaaacgtgc tgaagatccg
 721 ccggcggaag atgaaccacc acaagtaccg gaagctggtg aagaagacgc ggttcctgcg
 781 gaggaaggtc caggagggac gcctgagacg caagcagatc aagttcgaga aagacctgag
 841 gcgcatctgg ctgaaggcgg gctaaagga agcccccgaa ggctggcaga cccccaagat
 901 ctacctgcgg ggcaaatgag tctggcgccg cccttcccgc ccgttgctgc tgtgatccgt
 961 agtaataaat tctcagagga ctcagccttt aaaaaaaaaa aaaaaaaaaa aaaaaaaaaa
1021 aaaaaaaaaa aa
```

FIGURE 45
Homo sapiens BAC clone RP11-327O17 from 4, NTs 107401-109380.

```
107401 aagaaataag cttattcaag acctgtagga ccaattttag caagaatcct gctaaatcaa
107461 tttatgattt ccccccgct ccacacctt gaaatctgat caccttgat atatagctcc
107521 tcatctccca cctttgatct gtaagtcctt ggcctgcctt tagcaagagt cctattaggt
107581 cgggttagca agaatccccc tacacttgat gtctcctctt aataattttc ccctcttagt
107641 gaattttcct ctcccctcac actctgccca ttggctataa atttccagct gtctttgctg
107701 tattcagaat agagccctat ctctgcctcc tactgtaata ctctaatgca atatagtctt
107761 caataaagct ttacttacca tctcaaccag catcagaata attttccctt taacatatcc
107821 aagcttggtc agaattaggg tgtacctaca cctacctgca ctattaatac tccgcacagc
107881 agggagaaag gaactaccta ccaggtgtca tgggcatgga aggatgtgag gaacgctagc
107941 actggccaaa tacagtggcc tcacaagcca tcttcacctt caggaaaatg aatattgagc
108001 tgccacagac actctgctgc cctcttaatt taccattacc atgaatctac aggatgctct
108061 gttccaaaca cccagtacat tcttatacat cttgtcctga tagatgcctg tgaggtaggc
108121 agggctgaga attatgaatt gttgtctatc aggctgaagt gactttccaa aaattgaagt
108181 tgacagcaat aaggtcaaga atcagctctg tgctgttttg acggagtgag tcattgcctc
108241 cttgaatctg gcacatacca gccaactgtc aaggtttgtt cttccacatg gtctaactgc
108301 taaatacaaa gtatactagg tttgtcagct tagggcatgt ttgcttccac tctgaaaaca
108361 tttcagctgc cctaatatat tgctataaag aattctctta ttattactgt cttcctcctc
108421 atatttagct ctgtcttcca tcacttcaaa agaagcattt gtagcttccc catcctcttt
108481 ctttctagtt gactttgaag actatctata taagtatttc tggcataaaa ctgacaggta
108541 aatgacttca aagctaattt ccgcccccc ccacccttg cccttttca gtctcaagat
108601 accatgtcag tcctctattc actctcaaaa atgatggctt aactgcacag tgccgttctg
108661 ggtcaattct taaatatact agaatatact agacatatct ggctcattta agtcattctt
108721 caccaatctt tcttcttatt tacctccttc ctcaacttgg aaattttgcc ttttcacaat
108781 atgtggatag ccatttctgc caagattgtg ccgacaagac tggttataaa tctacctact
108841 ttgtaaaagg ggaatatttt tgtaaccatt gcatatctct attaaaacat gaaagaaaca
108901 ctgaaggcca agtgttcaag tgacacgcag gaaaaaaaaa agctgatatt cagaaagcca
108961 agcatacaga gaaataatga gaggttaatg aagtgagttc tgaatcacaa gtgctgttca
109021 gaaaacaaaa aaagacatct gtgaaggctg accttggaac tagtcactgt tattcagtcc
109081 atatgtatgt atgttttat taaataact gttcaaagtt aactttcatc caagttaact
109141 tctgaagaaa taaaaaggca tcacgttaag gtttcaaaaa tttaaccatt ctacctttag
109201 caatggttag tccaccttat tttcacacat ttccatctta atgaaagcaa gtacattaaa
109261 ggatactcag aatagctgca aggcatacca caagatgtac cacaagatta gaaatttctt
109321 taaaagtaat taagatcggc cgagtgcagt ggctgactcc agcaatccca gcattttggg
```

FIGURE 46

Homo sapiens ADP-ribosylation factor 6 (ARF6), mRNA.

```
   1 ggtcggcctc tgctgcgcct gcgtggtcgg gaggggaagt gaggcggttt cctcggcgcc
  61 ttttccggca gcggcggcgg cagaactggg aggaggagtt ggaggccgga gggagcccgc
 121 gctcggggcg gcggctggag gcagcgcacc gagttcccgc gaggatccat gacctgacgg
 181 ggccccggag ccgcgcctgc tctcggtgt cctgggtcgg tggggagccc agtgctcgca
 241 ggccggcggg ccgggccgag ggctgcagtc tccctcgcgg tgagaggaag gcggaggagc
 301 gggaaccgcg gcggcgctcg cgcggcgcct gcgggggaa gggcagttcc gggccgggcc
 361 gcgcctcagc agggcggcgg ctcccagcgc agtctcaggg cccggtggc ggcggcgact
 421 ggagaaatca agttgtgcgg tcggtgatgc ccgagtgagc ggggggcctg ggcctctgcc
 481 cttaggaggc aactcccacg caggccgcaa aggcgctctc gcggccgaga ggcttcgttt
 541 cggtttcgcg gcggcggcgg cgttgttggc tgaggggacc cgggacacct gaatgcccc
 601 ggccccggct cctccgacgc gatggggaag gtgctatcca aaatcttcgg gaacaaggaa
 661 atgcggatcc tcatgttggg cctggacgcg gccggcaaga caacaatcct gtacaagttg
 721 aagctgggcc agtcggtgac caccattccc actgtgggtt tcaacgtgga cggtgact
 781 tacaaaaatg tcaagttcaa cgtatgggat gtgggcggcc aggacaagat ccggccgctc
 841 tggcggcatt actacactgg gacccaaggt ctcatcttcg tagtggactg cgccgaccgc
 901 gaccgcatcg atgaggctcg ccaggagctg caccgcatta tcaatgaccg ggagatgagg
 961 gacgcccataa tcctcatctt cgccaacaag caggacctgc ccgatgccat gaaacccac
1021 gagatccagg agaaactggg cctgacccgg attcgggaca ggaactggta tgtgcagccc
1081 tcctgtgcca cctcagggga cggactctat gagggggctca catggttaac ctctaactac
1141 aaatcttaat gagcattctc cacccatccc ctggaaggag agaaatcaaa aacccattca
1201 taggattatc gccaccatca cctctttcaa ttgccacttt ctcttctttt gaatttgaac
1261 tctggagtta ctgttctaca gtttggcggg gacggggctt gggggttttc tcttttgttt
1321 gtttcccttt cttttttcctt tttttttttt tttttttttt gttggctttg cgttaggatg
1381 ctctgatctg acatttgaca tgaacacaaa gttgctagat gctcttgttg acttccagca
1441 gatgggatgg gggaaacaca gcagttcttg gtaaagtcct ttgtaataat agtttgattt
1501 ttttatttcg agagaatctt tcatttttcct atgtatgctt ttttccttt tgcccagtt
1561 tccttatcac ttgctgtaga tggcttattt tgcattcatg cagactatgt tgcaagtctg
1621 tttcatctag taaactgaaa attattgctt aatcaaactg ccgtttgtct tttatattta
1681 aggccttccc cccccttcct tatgagttct aacttagtaa tttcaaatgt gaccttttat
1741 atctaagacc agtatagtaa acttagccca cagtggcaaa taatgagtaa tattgtaata
1801 tgttccagtt gcacctcagt atgttaaaca ggtaatgtaa gaagttctct gaaatgtcag
1861 caagtaagtt ctgaaacaca tcatgcatga gtaggaataa aacccaagtt ccccataacg
1921 tagataactt aatgctgcat aaaaatatga aagtgtaacc catgaaggac actttttctt
1981 tccactgcaa agttagccac tttgctgttt ttcctctttt ttaaactttg aaaatagact
2041 ctttccagaa attggagcaa taatggtgtt accacacaca gattaaataa tttgtagata
2101 ttttaagtga cttttgggca aaactggaat gtatacttt accttgtttc aaacacctaa
2161 gaccagtaat ttaaaaatta ctaaaaggtt tactttgttc attaataaaa catttaacaa
2221 ttcaaattat atgcaccttt tacctagttg aaaaaaatac acattcctgt tttcacatta
2281 tagcaactga ttaagctgaa gctgtaagtc attttttata gatgagtgat ccgcatctcc
2341 atcaattaga acactggaaa agatgtttta taaaagaggt atttaatttt gtttgtagga
2401 ttaactcatg caaataataa aaaagatatc ctgttggttc aatagtacac tgtctccttt
2461 aaggaaggaa gcgtgatgaa tgaatgatgt gtagacttga gggatgacta ttaaagggga
2521 cgtaggatga agagaaagaa cctacagatg acaatgaatg taaacttatt tttcttcatg
2581 tgtaagcagt gtgctcgctg gtgatatcca gatcctaaca agattacttg gttagctggt
2641 taggaccagt aactggattg cgaccactat gataatattt tgaaccaaat gttaatgctt
2701 gatgcagaat tgtaaagcag catctggttc ctatatagcc ttaaggatta attttagtga
2761 tcctcaagga attaaatagg gaatttcaga aatgtagact gcaaaggcag tatacaggaa
2821 aaggtggagt gggttttgtt tatgagggtg tctgaaaact aaaattgagc gggatatcat
2881 ggtatagttg gacagtattg gtccttcaca ctttggccat attgtataat ggagcttta
2941 ccaaagatgt atgagaagtg taagactata aaaaaatgaa ctattcaaag taaaactctt
3001 aacaaacatt ttacttaaag cagatgcaaa agggtattct catgtaggct cctgttggtg
3061 cagagggatt tttttgattt caggatacaa ctaaagtacg aagttctcag tttcacttta
```

FIGURE 46 (cont.)

```
3121 gtagaaagag ctctagaaat gaggctgata aacacatcta agaacactgg ttgctttcta
3181 aaatttccaa agctccacca taaatgtaat ttttagtgtt tcaaatgatt gcattttaaa
3241 gtatataaat atgggttatc caatatcaat gctatagtaa catcctgaaa caaaacaagc
3301 acaaaggtat aaatgcctaa actggaggaa acttgaaacc ctcatgttaa atcttaaatg
3361 tagtatttct aacttgtgaa gacagattgg taggcagcca ttttttgtg tcttaaaata
3421 actgggggca tagttaaaat tttatacatc aagtgattgc tattattgaa tgttgcaggt
3481 gagatgtggt tattttagt ttatttgaaa tgtttgactg gaaagggggg aggggaagc
3541 aaatatttga aatttggaaa accctaaacc ttttggtaag aaattgtaat tttcacttaa
3601 aattttcttt aaggatataa gaggtttata attgatgtag ttaaattgaa caataaccat
3661 tggtgactgg agcaggtaat tatagcctgc agaaaaaatt atctaagaat tttaaaaata
3721 agatcctgaa gttgtttaat tgcatccatt tctgtattta tgtgaattta taaactgcag
3781 taagttttga atgaggttaa tcttgtttaa tataagtaaa tgagtctgta gactgtgatc
3841 tccccaaact aaaaagtaca gtacttggaa ttgtgttctt tatggttgta gtgttggtaa
3901 agcactaata tgcagaaaat aaaggaatta cacagtgca
```

FIGURE 47

Human DNA sequence from clone RP1-278O22 on chromosome 20 Contains two novel genes, NTs 26161-26140.

```
26161 ttgtcactag aaggaggaag gaatgctgtg tggcaaggaa aggaattaat gtccacttga
26221 gatggatttg agaaggatgt ctgcaagcag aaataaaggg ttaaagggtg cttacattaa
26281 aaattttgat agctactgct ctcaaaattg tatcgcgatt tatattccca gtgccaacag
26341 tgtttgaaga gtctggctct ccagagcctg tagacactgg atattgtcag tgttttaaat
26401 ttcagcagat ctgatatcta aaaatggtat ctcactgttc taaactgttc tagtatggtg
26461 ttctacgtga acacccttc atgtgtttag ctggcctttg catttctttt ttttttttt
26521 tgaactgcct atgcatatct tttggtcaaa attcaattga attgcccttt tttattgtta
26581 gagctgctac aaacattact gaaaaggcaa ctcagttgtg tgtgtgtgta tgcacacaca
26641 tatatattta taatacatat gttacttagg gtttgtacca gctctatgag ctccttgagg
26701 gtggcacctt gctgtaatac agcctgacac ctaatacgaa gtagaaatca gtgattattt
26761 atcacgcaaa taaagaaaca aataagtgaa cgaatgaatg agtcaatagt gttgactgcc
26821 ttgtattgtc ctaggcccaa gagacagtga aatatccctg ttcttgtata cttttctgta
26881 agtttctgga agtttctctg taaagcatct cagtaagctt ttctataggc tgtgagaaac
26941 gcatgagtca ggctaatagg aggcatataa ttttgaattg cttttcagaa atggccttca
27001 tattcctta cactcactca tcctgttgat aagagcagat ggcctactgc atgtgactca
27061 gactcaaaca cacacctccg ctcccttgaa gtgccagccc tggagctttg ttgaggctcg
27121 catctgccac gggagtcagc tagtacgttg cccagttcaa catccatcca ggatttcata
27181 ggaacttgag aatcattgtt tttggcttga atcctgggtt tgaggtttct tcgtgtagga
27241 atctgaaaaa aggatttgga aacgttgttg tctctaatcc caaagtatgt atctgggagg
27301 ctgccttcgc catcacccac ctaataactc aggctcccgg ggccatttcg ctcaagtgca
27361 ttcattcctt tggtagaatc aaaagaaact gatccaggtg acagagtacc tgggttctaa
27421 tcccagtttt gatgagcaag ttatttaccc cttacagccc catttttcct attctaaaat
27481 gatatggttg caactgacga tctccaagtc tccgtccaac tcaacaattc agagtggaat
27541 tctgaattct gctctgccac caacagcatg tcctcggagc tttgcctatt actcatgaga
27601 atgtcaacgt ctgggtaaat agatattttg gggtcagctc taaaaaaccc agaagtacgt
27661 attgtatgtt gattttggca cacggacaag cctgaacagg gctgtgtcaa gccttttacc
27721 atgatagctg ccggaagaaa ggccaggcga agcagtctgg gtgagctgct tggaatgaag
27781 aggaccagcc cacatcccat ggcacagatg accttcagga gaagtggagg ggagcagcta
27841 atgtaaagaa atcattagca tctgtgttgg aaatggctta tgacactgtc tcaaagccac
27901 gttctcagac aacagggaaa gctgtaaata gatgcacaca gttatccaag catagcagag
27961 taaaactaaa ggaaagccaa attaaacagg ctcaaccaaa gttttgagtg aaagtgttga
28021 atattgctca tgccttcaga acgggaagct ctgtttagaa tactcacaat ggtgggtcct
28081 cttgaggtga ctacaggctg gtaggtcggt tctatcctcc ccctaggagc catctcagca
```

FIGURE 48

Homo sapiens isolate PD047 mitochondrion, NTs 2041-4020.

```
2041 gttcaacttt aaatttgccc acagaaccct ctaaatcccc ttgtaaattt aactgttagt
2101 ccaaagagga acagctcttt ggacactagg aaaaaacctt gtagagagag taaaaaattt
2161 aacacccata gtaggcctaa aagcagccac caattaagaa agcgttcaag ctcaacaccc
2221 actacctaaa aaatcccaaa catataactg aactcctcac acccaattgg accaatctat
2281 caccctatag aagaactaat gttagtataa gtaacatgaa acattctcc tccgcataag
2341 cctgcgtcag attaaaacac tgaactgaca attaacagcc caatatctac aatcaaccaa
2401 caagtcatta ttaccctcac tgtcaaccca acacaggcat gctcataagg aaaggttaaa
2461 aaaagtaaaa ggaactcggc aaatcttacc ccgcctgttt accaaaaaca tcacctctag
2521 catcaccagt attagaggca ccgcctgccc agtgacacat gtttaacggc cgcggtaccc
2581 taaccgtgca aaggtagcat aatcacttgt tccttaaata gggacctgta tgaatggctc
2641 cacgagggtt cagctgtctc ttactttaa ccagtgaaat tgacctgccc gtgaagaggc
2701 gggcatgaca cagcaagacg agaagaccct atggagcttt aatttattaa tgcaaacagt
2761 acctaacaaa cccacaggtc ctaaactacc aaacctgcat taaaaatttc ggttggggcg
2821 acctcggagc agaacccaac ctccgagcag tacatgctaa gacttcacca gtcaaagcga
2881 actactatac tcaattgatc caataacttg accaacggaa caagttaccc tagggataac
2941 agcgcaatcc tattctagag tccatatcaa caatagggtt tacgacctcg atgttggatc
3001 aggacatccc gatggtgcag ccgctattaa aggttcgttt gttcaacgat taaagtccta
3061 cgtgatctga gttcagaccg gagtaatcca ggtcggtttc tatctacttc aaattcctcc
3121 ctgtacgaaa ggacaagaga ataaggcct acttcacaaa gcgccttccc ccgtaaatga
3181 tatcatctca acttagtatt atacccacac ccacccaaga acagggtttg ttaagatggc
3241 agagcccggt aatcgcataa aacttaaaac tttacagtca gaggttcaat tcctcttctt
3301 aacaacatac ccatggccaa cctcctactc ctcattgtac ccattctaat cgcaatggca
3361 ttcctaatgc ttaccgaacg aaaaattcta ggctatatac aactacgcaa aggccccaac
3421 gttgtaggcc cctacgggct actacaaccc ttcgctgacg ccataaaact cttcaccaaa
3481 gagcccctaa aacccgccac atctaccatc accctctaca tcaccgcccc gaccttagct
3541 ctcaccatcg ctcttctact atgaaccccc ctccccatac caacccct ggtcaacctc
3601 aacctaggcc tcctatttat tctagccacc tctagcctag ccgtttactc aatcctctga
3661 tcagggtgag catcaaactc aaactacgcc ctgatcggcg cactgcgagc agtagcccaa
3721 acaatctcat atgaagtcac cctagccatc attctactat caacattact aataagtggc
3781 tcctttaacc tctccaccct tatcacaaca caagaacacc tctgattact cctgccatca
3841 tgacccttgg ccataatatg atttatctcc acactagcag agaccaaccg aaccccttc
3901 gaccttgccg aaggggagtc cgaactagtc tcaggcttca acatcgaata cgccgcaggc
3961 cccttcgccc tattcttcat agccgaatac acaaacatta ttataataaa caccctcacc
```

FIGURE 49

Human DNA sequence from clone RP1-278O22 on chromosome 20 Contains two novel genes, NTs 25321-27300.

```
25321 ctggagaatc ccttgaaccc aggaggagga ggttgcagtg agcgatcctg ccacggcact
25381 ccagcagggg tgacaagaat gaaactctat ttcaaaataa agaaaaaaaa gaaaaaaaaa
25441 gaaaacccaa cctcaactag cttaagcaaa agcaaattta tgtggtgaaa gggtggatct
25501 ggttttagaa tcagttacca agggctcaag aagtgtcaca gggactgatc cccccacccc
25561 cccgtccccc atgtcgtgtc attctccagg tcttttccttt tcattgccag gagctccagg
25621 tttctaccct cagaactcca aggccattgg aaaacagagg gcagttttct tagttgccca
25681 aggaaatgtt cccaaattgt atcaaaagcc cacctctagg ttaattattg tggctggagg
25741 atgtaatcca ttcataggtc agggctggcc aggtgtagtg gctcatgcct gtaatcccag
25801 cactttggga gactgagatg ggtgggtcac ttgaggtcag aagttcgaga ccagcctggc
25861 caacaggatg aaaccccgtc tctactaaaa atacaaaaat tagccaggca tggtggcggg
25921 cgcctgtaat cccagctgct cgggaggctg aggcaggaga atggattgaa cccaggaggt
25981 ggaggttgca gtgagcagag atcacgccac tgcactcaag cccaggcaac gaagcgagac
26041 tccttctcaa aaaaaaaaaa agagagaaac ataggctagg actaggcata tgccatgcct
26101 tgtgacataa actggacatg gggaagggga gtgattcccc agtgttagtt agccttgctc
26161 ttgtcactag aaggaggaag gaatgctgtg tggcaaggaa aggaattaat gtccacttga
26221 gatggatttg agaaggatgt ctgcaagcag aaataaaggg ttaaaggggtg cttacattaa
26281 aaattttgat agctactgct ctcaaaattg tatcgcgatt tatattccca gtgccaacag
26341 tgtttgaaga gtctggctct ccagagcctg tagacactgg atattgtcag tgttttaaat
26401 ttcagcagat ctgatatcta aaaatggtat ctcactgttc taaactgttc tagtatggtg
26461 ttctacgtga acacccttc atgtgtttag ctggcctttg catttctttt ttttttttt
26521 tgaactgcct atgcatatct tttggtcaaa attcaattga attgcccttt tttattgtta
26581 gagctgctac aaacattact gaaaaggcaa ctcagttgtg tgtgtgtgta tgcacacaca
26641 tatatattta taatacatat gttacttagg gtttgtacca gctctatgag ctccttgagg
26701 gtggcacctt gctgtaatac agcctgacac ctaatacgaa gtagaaatca gtgattattt
26761 atcacgcaaa taaagaaaca aataagtgaa cgaatgaatg agtcaatagt gttgactgcc
26821 ttgtattgtc ctaggcccaa gagacagtga aatatccctg ttcttgtata cttttctgta
26881 agtttctgga agtttctctg taaagcatct cagtaagctt ttctataggc tgtgagaaac
26941 gcatgagtca ggctaatagg aggcatataa ttttgaattg cttttcagaa atggccttca
27001 tattcctta cactcactca tcctgttgat aagagcagat ggcctactgc atgtgactca
27061 gactcaaaca cacacctccg ctcccttgaa gtgccagccc tggagctttg ttgaggctcg
27121 catctgccac gggagtcagc tagtacgttg cccagttcaa catccatcca ggatttcata
27181 ggaacttgag aatcattgtt tttggcttga atcctgggtt tgaggtttct tcgtgtagga
27241 atctgaaaaa aggatttgga aacgttgttg tctctaatcc caaagtatgt atctgggagg
```

FIGURE 50

Human DNA sequence from clone RP3-523G1 on chromosome 6p22.3-24.1, NTs 34621-36600.

```
34621 attcatctgt gttattggga aatgatgtga acttaatttc tctttccctt ctaaaacttt
34681 gcttactgaa tggaaatgtt cctgagatct gtttatttgg ttctatattt atgtacctcc
34741 cttttaaaat agagaataca tgttaatgtt tctttgatga ctcagtgtgt attatcggta
34801 acagtccatt catgatgttg ccataccaca cagcataatt ttctatctgc ttctgattga
34861 ttcttcattc tcccttgatc tcagtttgtc atttaataca tctaagtttt tcactcaaca
34921 aatcaaatac tgatggagaa tctgctatac accaggcact gtgctgctag gagctgagga
34981 ttgaacgggg agaaacagga agctccctgc tctcatagtg cttcttagtt ggggagaaaa
35041 gacattcatg atataatcac ataaatacct atttttatat gtaaaaaatg ttgtcaaaga
35101 aaagaacggg gtgatgggaa cagttggaag aggtgtaaaa actccagaga agctgtggct
35161 cctagaaaga aggtaggttt taggactaga atggtgatag tgggccggaa gagagagagt
35221 gcattcgaaa gacactgagg agattgcatc agtaggactt ggtgacacat tagatgcaga
35281 ggaagaggga cagaaatgct tcaaggagga cttttaggca tctgtcttgg gtaactagat
35341 gatgccaatg gctgagatgg ggaattcttg ggtagatgag gtttggtggg atggtgattg
35401 ttataacttt gactttgaac gtgctgagtt caggtgacat tgtgataccc caaggaggt
35461 gcagagtagg tagctggaga cacaggcccg aagatgatga gaggtctggc ctagaaacat
35521 ggatgcagga gtcatggatc catcaaggca ctgtgagttt ggatgagatc atctagcaga
35581 acacttaagt ggagaagcaa agtggtctag agactaagcc atgaggaact ccaacactta
35641 gaggcgtaga aagcaggtag aaagggaaca cctgaagact taggaaggag gggccagaaa
35701 gggatgatgg cacccgaaga cagtggtgtt caggaagcca agggaggaag gtatttagac
35761 aggagggga gagcagaatt ggcaaagctg tggagaaagt gagatgagaa ctcctattaa
35821 aaacacacaa ctggtccaat gacatgggat ggcatggaaa tcactgatga ccaagcagga
35881 gacaggggtg gaccgcaggg gaaaagagc aagctgaagc cagctaagga atgtcctcgg
35941 gccatctcct agcggaggcg gtagagccgt ggttgaaggt acaggaagtg gactgttagg
36001 gcccaggttc cccttaacca tgagacctga agcaagttac tttatttctc tagggctcaa
36061 ttttctcacc tgtaaaacaa gagtaacagt gctcacctac taggttgctg tgaggttctt
36121 tttcttttc tttttttttt ggagacagag tctcactctg tcacccaggc tggagtgcag
36181 tggtgcaatc ttggctcact gcaatctcca cctcccgggt tccagctatt ctcctgcctt
36241 agcctcctga gtggctggga ctacaggcgc ctgccaccac aactggctaa ttttgtatt
36301 tttagtagag atggggtttc accacgttgg ccagcctgga ctcaaactcc tgacctcagg
36361 tgatctgcct gcttcagcct cccaaagtgc tgggattaca ggcgtgagcc accacacctg
36421 gccttctgtg aggttcttaa catgtaagcc acttagccca gtggctgact catagtagtt
36481 gctgaataaa tgctaatttt atattaacac cctcataacc cattaaatca atatttattg
36541 agcatccatc tgccaggcac tgtactagat gctgacaaag acacccccaa caacaaataa
```

FIGURE 51

Homo sapiens mitogen-activated protein kinase kinase kinase 5(MAP3K5),
RefSeqGene on chromosome 6. NTs 222121-224100.

```
222121 tgagcctagg agtttgagat caccccaggc agtgtggcaa aaccgcatct ctacatgaaa
222181 aatacaaaaa taagtcaggc atggcagcat gtgcctgtgg tcctggctac tagggaggct
222241 gaggtgagag gatcaattga gcccaggagg tcaaggccac agtgagctga gattgcacca
222301 ctgcactctg gcctggggga cagagtgaga ccctgtctca aaaaaaaaaa aaaaaaatag
222361 tattgtatca atgttaattt cctggttttg ataatagtgc caaaggtata taaactgtta
222421 aggcaagagc aagtggctga aggctataca ggaactctct gcactatttt tgcaacttct
222481 ctgttatcct aaaattattt caaaataaaa agttaaaaaa aaagtgttta ggccgggcgc
222541 ggtggctcac gcctataatc ccagcacttt gggaggccga ggcgggcgga tcacgaggtc
222601 aggagatcaa gaccatcctg gctaacacag tgaaacccca tctctactaa agatacaaaa
222661 aattagccgg gcgaggtagc gggcgcctgt agtcccagct acgtgggagg ctgaggcagg
222721 agaatggcat gaacccagg gggtggagcc tgcagtgagc cgagatcgtg ccactgcact
222781 ccagcctggg tgaagagcg agactccttc tcaaaaaaaa aaaaaaaaaa aaaaagtgtt
222841 taatctttt tccaaaagga gcacacagaa cagagagtac agtacaagtc ccttaagaat
222901 ttgttttttc tcagactatt ttctcacttg tcatcaagaa tcagcccttta gattattggc
222961 agcattagtc ctctagtaca gtctgcttgt gggtgaccag atggagtaat gctgagcaca
223021 gagactatga tggccgtgct aaggtaagag tattgataat gtaagcatac ttcctctatc
223081 aacaataatt gttaacagct gcttcaagca cttgatatta ccactagttg ttaactgaat
223141 caagcatgtg ctccaagttc acattaatgt gaattgaaca gcattgtgta cgtacgagga
223201 gcttcatgca agtgttatac actgcactca caagtattat gatcttacta agcattagaa
223261 atactctgtg ttaaagaagc ttggtctagg ccaagcgtgg tggctcatgc ctataatctc
223321 agcactttgg gaggccaagg caggcagatc acatgaggcc aggaatttga gaccagcctg
223381 gccaacatgg tgaaacccca tctctactaa aaatacaaat attagccagg tatgatggcg
223441 catgcctata atcctaacta ctcaggaggc cgaagcagaa gaatcacttg aacctgggag
223501 gcggaggttg cagtgagcca agatcatgcc actgcactcc agcctgggtg acagagtgag
223561 actctgtctc aaaaaaaaaa aaagaaaga aagaaaaag aaacttggtc tagttatttt
223621 ccttcctctg gggaagtaac catttgggtg ggaatagttt tgttgttgat cccatcttgc
223681 tggtttggaa acaatgcact ggctccactt ttccactcat gggctttaag gcccccttga
223741 gtcccagtct ttctcctgac acatggctgt ctcctgacag tcccctctgc tttacattgt
223801 tctcagaggg tcctgggcca tcgtttgagc ttcattcttt caaatacact tccctctttc
223861 tctatcaagc caaggctccc ctcccccaga actctgcata ggcccttcag cctccatgaa
223921 tcccttagtg agtgagtaaa ctaccactgg attcagtcac tgcaaatgta ctttatttac
223981 cccttagcac tcttactaca tgtatgtgtt agggttcttc aaagaaacag aaccaatagg
224041 atacatagag atatataaga gaagatttat aatgggaatt ggctcatgtg attatggagg
```

FIGURE 52

Homo sapiens RAS p21 protein activator (GTPase activating protein) 1, mRNA (cDNA clone IMAGE:4733187), partial cds.

```
   1 agaatacgag gaggaagagg tggccatacc gttgaccgct cctccaacta accagtaagt
  61 taagactgct gttcaggaat ttgggaagct ggccccagaa aagaagtgga aatgaagggg
 121 tggtatcacg gaaaacttga cagaacgata gcagaagaac gcctcaggca ggcagggaag
 181 tctggcagtt atcttataag agagagtgat cggaggccag ggtcctttgt actttcattt
 241 cttagccaga tgaatgttgt caaccatttt aggattattg ctatgtgtgg agattactac
 301 attggtggaa gacgttttc ttcactgtca gacctaatag gttattacag tcatgtttct
 361 tgtttgctta aaggagaaaa attactttac ccagttgcac caccagagcc agtagaagat
 421 agaaggcgtg tacgagctat tctaccttac acaaaagtac cagacactga tgaaataagt
 481 ttcttaaaag gagatatgtt cattgttcat aatgaattag aagatggatg gatgtgggtt
 541 acaaatttaa gaacagatga acaaggcctt attgttgaag acctagtaga agaggtgggc
 601 cgggaagaag atccacatga aggaaaaata tggttccatg ggaagatttc caaacaggaa
 661 gcttataatt tactaatgac agttggtcaa gtctgcagtt ttcttgtgag gccctcagat
 721 aatactcctg gcgattattc actttatttc cggaccaatg aaaatattca gcgatttaaa
 781 atatgtccaa cgccaaacaa tcagtttatg atggggaggcc ggtattataa cagcattggg
 841 gacatcatag atcactatcg aaaagaacag attgttgaag gatattatct taaggaacct
 901 gtaccaatgc aggatcaaga acaagtactc aatgacacag tggatggcaa ggaaatctat
 961 aataccatcc gtcgtaaaac aaaggatgcc ttttataaaa acattgttaa gaaaggttat
1021 cttctgaaag aggccaaaaa aaaaaaaaaa aaaaaaaaaa aaa
```

FIGURE 53

Homo sapiens heat shock 90kDa protein 1 beta (HSPCB) mRNA, complete cds.

```
   1 agctctctcg agtcactccg gcgcagtgtt gggactgtct gggtatcgga aagcaagcct
  61 acgttgctca ctattacgta taatccttt cttttcaaga tttttatttt agatgcctga
 121 ggaagtgcac catggagagg aggaggtgga gacttttgcc tttcaggcag aaattgccca
 181 actcatgtcc ctcatcatca ataccttcta ttccaacaag gagattttcc ttcgggagtt
 241 gatctctaat gcttctgatg ccttggacaa gattcgctat gagagcctga cagacccttc
 301 gaagttggac agtggtaaag agctgaaaat tgacatcatc cccaaccctc aggaacgtac
 361 cctgactttg gtagacacag gcattggcat gaccaaagct gatctcataa ataatttggg
 421 aaccattgcc aagtctggta ctaaagcatt catggaggct cttcaggctg gtgcagacat
 481 ctccatgatt gggcagtttg gtgttggctt ttattctgcc tacttggtgg cagagaaagt
 541 ggttgtgatc acaaagcaca acgatgatga acagtatgct tgggagtctt ctgctggagg
 601 ttccttcact gtgcgtgctg accatggtga gcccattggc aggggtacca aagtgatcct
 661 ccatcttaaa gaagatcaga cagagtacct agaagagagg cgggtcaaag aagtagtgaa
 721 gaagcattct cagttcatag gctatccat caccctttat ttggagaagg aacgagagaa
 781 ggaaattagt gatgatgagg cagaggaaga gaaggtgag aagaagagg aagataaaga
 841 tgatgaagaa aaacccaaga tcgaagatgt gggttcagat gaggaggatg acagcggtaa
 901 ggataagaag aagaaaacta agaagatcaa agagaaatac attgatcagg aagaactaaa
 961 caagaccaag cctatttgga ccagaaaccc tgatgacatc acccaagagg agtatggaga
1021 attctacaag agcctcacta atgactggga agaccacttg gcagtcaagc acttttctgt
1081 agaaggtcag ttggaattca ggcattgct atttattcct cgtcgggctc cctttgacct
1141 ttttgagaac aagaagaaaa agaacaacat caaactctat gtccgccgtg tgttcatcat
1201 ggacagctgt gatgagttga taccagagta tctcaatttt atccgtggtg tggttgactc
1261 tgaggatctg cccctgaaca tctcccgaga aatgctccag cagagcaaaa tcttgaaagt
1321 cattcgcaaa aacattgtta agaagtgcct tgagctcttc tctgagctgg cagaagacaa
1381 ggagaattac aagaaattct atgaggcatt ctctaaaaat ctcaagcttg gaatccacga
1441 agactccact aaccgccgcc gcctgtctga gctgctgcgc tatcatacct cccagtctgg
1501 agatgagatg acatctctgt cagagtatgt ttctcgcatg aaggagacac agaagtccat
1561 ctattacatc actggtgaga gcaaagagca ggtggccaac tcagcttttg tggagcgagt
1621 gcggaaacgg ggcttcgagg tggtatatat gaccgagccc attgacgagt actgtgtgca
1681 gcagctcaag gaatttgatg ggaagagcct ggtctcagtt accaaggagg gtctggagct
1741 gcctgaggat gaggaggaga agaagaagat ggaagagagc aaggcaaagt ttgagaacct
1801 ctgcaagctc atgaaagaaa tcttagataa gaaggttgag aaggtgacaa tctccaatag
1861 acttgtgtct tcaccttgct gcattgtgac cagcacctac ggctggacag ccaatatgga
1921 gcggatcatg aaagcccagg cacttcggga caactccacc atgggctata tgatggccaa
1981 aaagcacctg gagatcaacc ctgaccaccc cattgtggag acgctgcggc agaaggctga
2041 ggccgacaag aatgataagg cagttaagga cctggtggtg ctgctgtttg aaaccgccct
2101 gctatcttct ggcttttccc ttgaggatcc ccagacccac tccaaccgca tctatcgcat
2161 gatcaagcta ggtctaggta ttgatgaaga tgaagtggca gcagaggaac ccaatgctgc
2221 agttcctgat gagatccccc ctctcgaggg cgatgaggat gcgtctcgca tggaagaagt
2281 cgattaggtt aggagttcat agttggaaaa cttgtgccct tgtatagtgt ccccatgggc
2341 tcccactgca gcctcgagtg cccctgtccc acctggctcc ccctgctggt gtctagtgtt
2401 ttttccctc tcctgtccctt gtgttgaagg cagtaaacta agggtgtcaa gccccattcc
2461 ctctctactc ttgacagcag gattggatgt tgtgtattgt ggtttatttt attttcttca
2521 ttttgttctg aaattaaagt atgcaaaata aagaatatgc cgttttata cgaaaaaaaa
2581 aaaaaaaaaa aaaaaaaa
```

FIGURE 54

Homo sapiens ribosomal protein S6 (RPS6), mRNA.

```
  1 cctcttttcc gtggcgcctc ggaggcgttc agctgcttca agatgaagct gaacatctcc
 61 ttcccagcca ctggctgcca gaaactcatt gaagtggacg atgaacgcaa acttcgtact
121 ttctatgaga agcgtatggc cacagaagtt gctgctgacg ctctgggtga agaatggaag
181 ggttatgtgg tccgaatcag tggtgggaac gacaaacaag gtttccccat gaagcagggt
241 gtcttgaccc atggccgtgt ccgcctgcta ctgagtaagg ggcattcctg ttacagacca
301 aggagaactg gagaaagaaa gagaaaatca gttcgtggtt gcattgtgga tgcaaatctg
361 agcgttctca acttggttat tgtaaaaaaa ggagagaagg atattcctgg actgactgat
421 actacagtgc ctcgccgcct gggccccaaa agagctagca gaatccgcaa acttttcaat
481 ctctctaaag aagatgatgt ccgccagtat gttgtaagaa agcccttaaa taaagaaggt
541 aagaaaccta ggaccaaagc acccaagatt cagcgtcttg ttactccacg tgtcctgcag
601 cacaaacggc ggcgtattgc tctgaagaag cagcgtacca agaaaaataa agaagaggct
661 gcagaatatg ctaaactttt ggccaagaga atgaaggagg ctaaggagaa gcgccaggaa
721 caaattgcga agagacgcag acttttcctct ctgcgagctt ctacttctaa gtctgaatcc
781 agtcagaaat aagattttt gagtaacaaa taaataagat cagactctg
```

FIGURE 55

Homo sapiens 3 BAC RP13-61613 (Roswell Park Cancer Institute Human BAC Library)
NTs 22921-24900.

```
22921 ttgatcttcc tgcctcagcc ttccaagtag ctgggactta aaggcgtgag ccaccacacc
22981 tgactaattt tcgtattttt tgtagagatg gggtttcgcc atgttgcccg ggctgttctc
23041 gaactcctga gctcaagcaa tctgcccacc tcagcctccc aaagcgctgg gattacaggc
23101 atgagccacc atcccagcca aaactataaa acttttagaa aagaacatag aagaaaatct
23161 ttgggtcctg ggggcaaaga gctctgagac ttgacatcaa aagcatgccg cataatagga
23221 aaatactaga ctttatttag gggttaagag tttagactct ggactctctc agccttggtt
23281 tcactagtta gctctatcac taactacatt gggcattgaa aattcctctg ttgtcccacg
23341 tggtgcatgg atgattgtag acgaggacac tgagatcctg aaggcagaag taatttctct
23401 aagcaacgtt gttggttggt ggcagagtct gggttacaac ccctggtttc ctgattccga
23461 gtccaagtga aatactttg cccctgcagt agaccctgct acagaggata aaaaggcacg
23521 tcataggcta ggagaaaaat tttgcctacc acatatgtaa ccaaggacta gcagctagga
23581 catctgaaga attctcaaca ttcaacgggg tagaagaatg aacgattcaa tagaatatgg
23641 gcaaaagaca tgaagaggca ttttaccaaa catagggtgc tatggtccga atgtttgcat
23701 tctcctcaaa ttcctgtgtt gaaatcctaa cccccaaggt attggtatta ggaggcaggg
23761 gccctgggaa gtgattaggt cataaaggtg gagtcctcat ggatgggatt agtgtcttta
23821 taaaagagac ctttgccatg tgaggttaca gtgagaagac atctgtctat gaagaaagtg
23881 ggccctcacc aaacacagtc tgctggcact ttgcacttca actccccagc ttccagaact
23941 gtaaggaata taagtctgtt gttggtaagc cacccggtct atgatatttt gttatagcag
24001 cccaaacaga ctaagacagg tgacaaataa acatgaaaag atgttcaaca tcattagcca
24061 ttagggaaat gcagattaaa accacagcga aatatcatga tacagttttc agcatggcta
24121 aactagaaaa tagtgacacc accaaatgcc gacaaggctg tggggaaact gggttgttca
24181 gcactgcca ctgggctgt agcgtactat agccactttc ataaacagtt tgtcagtttc
24241 ttaaaaaact aaacctgcaa ctaccatatg acccagcaat tacacccctg ggcacctacc
24301 caagagaaat gaaaactcaa cgtttgcgca aaaacctgtg taggaatgtt caagcagctt
24361 tattcataat atgcccaaac aggaaacaac tcagctgtcc ttcagtaggt aaatagttaa
24421 gcaaattgtc atacccctgt gtcatggagc actacctagc aataacaagg agcaaattat
24481 tgatacataa caatctggat gaatctccag agaattatgt tgaatgaaaa aagccagccc
24541 ctgaaggata catactgtat gatgccattt acataacatt cttgaaattc taaaattaca
24601 gagatgggga acagatttgt ggttaaagat ggagccgggt gggaagaaag taggtgtggc
24661 tataaacggg taacatgaag gatccttgtg gtgatggaaa tttctgtatt tttattgtat
24721 ccgtgtcagt atcctggttg tgatatggta atacagtttt gcaagatact acccttaggg
24781 gaaatgaggt aagacctggc atctctctgt attatttctt aattgcatgt gaatctacaa
24841 ttatttcaaa ataaaagta tgattgaagt aactctcagg aagcttagcc tactgtggat
```

USING PHAGE EPITOPES TO PROFILE THE IMMUNE RESPONSE

CROSS-REFERENCE

This application is a continuation of U.S. application Ser. No. 13/050,544, filed Mar. 17, 2011, which claims the benefit of U.S. provisional application Ser. No. 61/314,750, filed Mar. 17, 2010, which is incorporated herein by reference in its entirety.

BACKGROUND

It is desirable to improve cancer detection, prognostic prediction, monitoring, and therapeutic decisions. For example, when cancer is identified at the earliest stages, the probability of cure is very high and therefore diagnostic screening tests that can detect these early stages are crucial.

One example in which early detection can be beneficial is prostate cancer (PCA). PCA is a leading cause of male cancer-related death, second only to lung cancer (Abate-Shen and Shen, *Genes Dev* 14:2410 (2000); Ruijter et al., *Endocr Rev,* 20:22 (1999)). Prostate cancer is typically diagnosed with a digital rectal exam and/or prostate specific antigen (PSA) screening. An elevated serum PSA level can indicate the presence of PCA. PSA is used as a marker for prostate cancer because it is secreted only by prostate cells. A healthy prostate will produce a stable amount—typically below 4 nanograms per milliliter (ng/ml), or a PSA reading of "4" or less—whereas cancer cells produce escalating amounts that correspond with the severity of the cancer. A level between 4 and 10 ng/ml may raise a doctor's suspicion that a patient has prostate cancer, while amounts above 50 ng/ml may show that the tumor has spread elsewhere in the body.

The advent of prostate specific antigen (PSA) screening has led to earlier detection of PCA and significantly reduced PCA-associated fatalities. However, a major limitation of the serum PSA test is a lack of prostate cancer sensitivity and specificity, especially in the intermediate range of PSA detection (4-10 ng/ml). Elevated serum PSA levels are often detected in patients with non-malignant conditions such as benign prostatic hyperplasia (BPH) and prostatitis, and provide little information about the aggressiveness of the cancer detected. Coincident with increased serum PSA testing, there has been a dramatic increase in the number of prostate needle biopsies performed (Jacobsen et al., *JAMA* 274:1445 (1995)). This has resulted in a surge of equivocal prostate needle biopsies (Epstein and Potter *J. Urol.,* 166: 402 (2001)).

Thus, development of biomarkers to detect cancer, with improved sensitivity and specificity is advantageous.

SUMMARY

Provided herein are methods and compositions for screening for, or characterizing, a cancer in a subject. In one embodiment, an antibody profiling panel comprising: a plurality of polypeptide probes, wherein at least one of the polypeptide probes comprises a full-length or fragment of a protein encoded by a gene listed in Tables 1, 2, 3, or 4; and each of the probes in the plurality of polypeptide probes is capable of being specifically bound by an antibody, is disclosed herein. In another embodiment, an antibody profiling panel comprising: a plurality of polypeptide probes, wherein at least one of the polypeptide probes comprises a sequence listed in Tables 1, 2, 3, or 4 or a sequence encoded by a sequence listed in Tables 1, 2, 3, or 4; and each of the probes in the plurality of polypeptide probes is capable of being specifically bound by an antibody, is disclosed herein. In one embodiment the subject is a human. In one embodiment the antibody is an autoantibody. In another embodiment the antibody is a human autoantibody. In one embodiment the presence of a human autoantibody that binds to a polypeptide probe is indicative of cancer (e.g. an expression level for one or more autoantibodies is indicative of the presence, absence, or stage of the cancer). In another embodiment the quantity or level of a human autoantibody that binds to a polypeptide probe is indicative of cancer. In one embodiment the cancer is a prostate, lung, breast or colon cancer.

In one embodiment, the polypeptide probe comprises a polypeptide sequence selected from SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, the polypeptide probe comprises a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof.

In yet another embodiment, the polypeptide probe comprises the full-length or a fragment of a protein that is encoded by DCHS1 (SEQ ID NO: 29), Centrosomal Protein (CEP 164) (SEQ ID NO: 30), KBTBD6 (SEQ ID NO: 31), RPS19 (SEQ ID NO: 32), RPL34 (SEQ ID NO: 33), Hemk1 (SEQ ID NO: 34), eIF4G1 (SEQ ID NO: 35), BMI1 (SEQ ID NO: 36), BRD2 (SEQ ID NO: 37), RP3-323M22 (Nucleolin) (SEQ ID NO: 38), SFRS14 (SEQ ID NO: 39), LOC388789 (SEQ ID NO: 40), RNA binding motif protein 6 (genomic DNA sequence) (SEQ ID NO: 41), BRMSL1 (SEQ ID NO: 42), NKX3-1 (SEQ ID NO: 43), RPSA (SEQ ID NO: 44), Cytochrome C Oxidase 5 subunit (SEQ ID NO: 45), FAM53B (SEQ ID NO: 46), a fragment of the UTR region of chromosome 11 (*Homo sapiens* genomic DNA, chromosome 11 clone: CTD-2579L12, NTs 149521-151500) (SEQ ID NO: 47), MAPKKK9 (SEQ ID NO: 48) cDNA clone XR_113641.1 (*Homo sapiens* hypothetical LOC643783, transcript variant 2 (LOC643783), partial miscRNA) (SEQ ID NO: 49), PSA (SEQ ID NO: 50), H2aa4 (SEQ ID NO: 51). UBE2I (SEQ ID NO: 52), TIMP2 (SEQ ID NO: 53), WDR77 (SEQ ID NO: 54), a fragment of Deaminase Domain Cont 1 (Human DNA sequence from clone RP1-20N2 on chromosome 6q24 Contains the gene for a novel protein similar to yeast and bacterial cytosine deaminase, NTs 48121-50100) (SEQ ID NO: 55), Lamin A/C (SEQ ID NO: 85), Lsm3 (SEQ ID NO: 86), a fragment of cDNA clone Chromosome 19, which encompasses the nucleic acid sequence for DAZ associated protein (*Homo sapiens* chromosome 19 clone CTB-25B13, NTs 20521-22500) (SEQ ID NO: 87), ADAM metallopetidase domain 9 (SEQ ID NO: 88), AZGP1 (SEQ ID NO: 89), Desmocolin 3 (SEQ ID NO: 90), PERP (SEQ ID NO: 91), Chromosome 3 UTR region ropporin/RhoEGF (*Homo sapiens* 3 BAC RP11-783D3 (Roswell Park Cancer Institute Human BAC Library) NTs 178621-180600) (SEQ ID NO: 92), Cox5a (SEQ ID NO: 93), a Mitochondrion sequence (*Homo sapiens* isolate PD047 mitochondrion, NTs 4801-6780) (SEQ ID NO: 94), MYH9 (SEQ ID NO: 95), ASND1 (SEQ ID NO: 96), Cathepsin F (SEQ ID NO: 97), Mastermind-like 2 (*Homo sapiens* genomic DNA, chromosome 11q clone:

RP11-82212, NTs 157801-159780) (SEQ ID NO: 98), CSNK2A2 (SEQ ID NO: 99), AURKAIP1 (SEQ ID NO: 100), a fragment of Chromosome 4 (*Homo sapiens* BAC clone RP11-327O17 from 4, NTs 107401-109380) (SEQ ID NO: 101), ARF6 (SEQ ID NO: 102), JAG1 (Human DNA sequence from clone RP1-278O22 on chromosome 20 Contains two novel genes, NTs 26161-26140) (SEQ ID NO: 103), a Mitochondrion sequence (*Homo sapiens* isolate PD047 mitochondrion, NTs 2041-4020) (SEQ ID NO: 104), a fragment of Chromosome 20 (Human DNA sequence from clone RP1-278O22 on chromosome 20 Contains two novel genes, NTs 25321-27300) (SEQ ID NO:105), a fragment of Chromosome 6 UTR region (Human DNA sequence from clone RP3-523G1 on chromosome 6p22.3-24.1, NTs 34621-36600) (SEQ ID NO: 106), a fragment of MAPKKK5 (SEQ ID NO: 107), RASA1 (SEQ ID NO: 108), Hsp90b (SEQ ID NO: 109), ribosomal protein S6 (RPS6) (SEQ ID NO: 110), or a fragment of *Homo sapiens* chromosome 3 (*Homo sapiens* 3 BAC RP13-616I3 (Roswell Park Cancer Institute Human BAC Library) NTs 22921-24900) (SEQ ID NO: 111).

In one embodiment, the antibody profiling panel comprises a plurality of polypeptide probes, wherein at least one of the polypeptide probes comprises a full-length or fragment of a protein listed in Table 1, or a polypeptide sequence selected from SEQ ID NO: 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, or 141, and each of said probes in said plurality of polypeptide probes is capable of being specifically bound by an antibody. In one embodiment, one or more of the polypeptide probes can comprise SEQ ID NO: 1, 2, 3, 4, 5, 6, or 7. In another embodiment, one or more of the polypeptide probes can comprise a polypeptide encoded by SEQ ID NO: 15, 16, 17, 18, 19, 20, or 21. In one embodiment, the antibody profiling panel can further comprise a full-length or fragment of a protein listed in Tables 2, 3, or 4. In another embodiment, the antibody profiling panel, one of the polypeptide probes can comprise SEQ ID NO: 8, 9, 10, 11, 12, 13, or 14. In another embodiment, one or more of the polypeptide probes can comprise a polypeptide encoded by SEQ ID NO: 22, 23, 24, 25, 26, 27, or 28. In one embodiment the antibody is an autoantibody. In another embodiment the antibody is a human autoantibody. In one embodiment the presence of a human autoantibody that binds to a polypeptide probe is indicative of cancer (e.g. an expression level for one or more autoantibodies is indicative of the presence, absence, or stage of the cancer). In another embodiment the quantity or level of a human autoantibody that binds to a polypeptide probe is indicative of cancer. In one embodiment the cancer is a prostate, lung, breast or colon cancer.

In one embodiment, the plurality of probes comprise a polypeptide probe comprising a full-length or fragment of a protein encoded by CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789. In one embodiment, the polypeptide probe comprises SEQ ID NO: 2, 5, 9, 11, 14, 56, 57, 58, 59, 60, 61, 62, 63, 64, 65, 66, 67, 68, 69, or a fragment thereof. In another embodiment, the polypeptide probe comprises a polypeptide sequence encoded by SEQ ID NO: 16, 19, 70, 72, 73, 74, 76, 77, 78, 79, 80, 81, 82, 83, 84, or a fragment thereof.

In one embodiment, the plurality of probes comprise a polypeptide probe comprising a full-length or fragment of a protein encoded by CEP164, RPL34, BRMSL1, NKX31, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain. In one embodiment, the plurality of probes comprise a polypeptide probe comprising a polypeptide sequence selected from SEQ ID NOs. 2, 5, 56, 57, 58, 59, 61, 62, 63, 64, 65, 66, 67, 68, or 69. In one embodiment, the plurality of probes comprises a polypeptide probe comprising a polypeptide sequence encoded by SEQ ID NO: 16, 19, 70, 72, 73, 74, 76, 77, 78, 79, 80, 81, 82, 83, or 84.

In one embodiment, the plurality of probes comprise a polypeptide probe comprising a full-length or fragment of a protein encoded by FAM53B, 5'UTR BMI1, RP3-323M22, or LOC388789. In one embodiment, the plurality of probes comprise a polypeptide probe comprising a polypeptide sequence selected from SEQ ID NO: 9, 11, 14, or 60. In one embodiment, the plurality of probes comprises a polypeptide probe comprising a polypeptide sequence encoded by SEQ ID NO: 23, 25, 28, 71, or 75.

In another embodiment, an antibody profiling panel comprising: a plurality of polypeptide probes, wherein at least one of the polypeptide probes comprises a full-length or fragment of a protein that is DCHS1, CEP164, KBTBD6, RPS19, RPL34, RNA binding protein 6, or Hemk1; and each of the probes in the plurality of polypeptide probes is capable of being specifically bound by an antibody, is disclosed herein. In another embodiment, the plurality of probes further comprise a polypeptide probe comprising a full-length or fragment of a protein encoded by eIF4G1, 5'UTR BMI1, BRD2, RP3-323M22, SFRS14, or LOC388789. In one embodiment, the polypeptide probe comprises a sequence listed in Table 1 or 2, such as SEQ ID NO: 1, 2, 3, 4, 5, 6, 7, 8, 9, 10, 11, 12, 13, 14, or a fragment thereof. In one embodiment the antibody is an autoantibody. In another embodiment the antibody is a human autoantibody. In one embodiment the presence of a human autoantibody that binds to a polypeptide probe is indicative of cancer (e.g. an expression level for one or more autoantibodies is indicative of the presence, absence, or stage of the cancer). In another embodiment the quantity or level of a human autoantibody that binds to a polypeptide probe is indicative of cancer. In one embodiment the cancer is a prostate, lung, breast or colon cancer.

In another embodiment, one or more of the probes is displayed by a phage. In one embodiment, the one or more probes is attached to a substrate, such as attached via a phage. In another embodiment, the substrate is an array. In yet another embodiment, the panel comprises at least 2, 3, 4, 5, 6, 7, 8, 9, or 10 different probes. In one embodiment, the panel characterizes a cancer, such as prostate cancer, with at least 80% sensitivity and specificity. In another embodiment, the panel screens for a cancer, such as prostate cancer, with at least 80% sensitivity and specificity.

Also provided herein is a method of characterizing or screening a subject for a cancer, such as prostate cancer, lung cancer, breast cancer or colon cancer. In one embodiment, the method comprises detecting in a sample obtained from a subject a presence or level of one or more antibodies to one or more polypeptide probes comprising a full-length or a fragment of a protein encoded by DCHS1, CEP164, KBTBD6, RPS19, RPL34, SFRS14, RNA binding protein 6, or Hemk1; and characterizing or identifying, the prostate cancer based on a presence or level of the one or more antibodies. In one embodiment, the method further comprises detecting a presence, absence or level of one or more antibodies to one or more polypeptide probe comprising a full-length or a fragment of a protein encoded by eIF4G1, 5'UTR BMI1, BRD2, RP3-323M22, SFRS14, or LOC388789. In one embodiment the antibody is an autoantibody. In another embodiment the antibody is a human autoantibody.

In another embodiment, the method comprises detecting in a sample obtained from a subject a presence or level of one or more antibodies to one or more polypeptide probes comprising a full-length or a fragment of a protein encoded by CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain; and characterizing the prostate cancer based on a presence or level of the one or more antibodies. In one embodiment, the method further comprises detecting a presence, absence or level of one or more antibodies to one or more polypeptide probe comprising a full-length or a fragment of a protein encoded by FAM53B, 5'UTR BMI1, RP3-323M22, or LOC388789. In one embodiment the subject is a human. In one embodiment the antibody is an autoantibody. In another embodiment the antibody is a human autoantibody. In one embodiment the presence of a human autoantibody that binds to a polypeptide probe is indicative of cancer (e.g. an expression level for one or more autoantibodies is indicative of the presence, absence, or stage of the cancer). In another embodiment the quantity or level of a human autoantibody that binds to a polypeptide probe is indicative of cancer. In one embodiment the cancer is a prostate, lung, breast or colon cancer.

Also provided herein is a method of obtaining a biopsy, wherein a determination of whether a biopsy should be obtained is based on detecting an expression level for an antibody. In one embodiment, a subject suspected of having cancer based on an expression level of an antibody is recommended to have a biopsy obtained. In another embodiment, a biological sample is obtained from a subject with a PSA level of greater than about 2.5 ng/ml, and the sample is contacted with one or more probes for an antibody, and based on the expression level of an antibody, a biopsy is obtained or recommended for the subject. In one embodiment, the subject has a PSA level between about 2.5 ng/mL and about 10 ng/mL. In one embodiment the subject is a human. In one embodiment the antibody is an autoantibody. In another embodiment the antibody is a human autoantibody.

In one embodiment, the method further comprises contacting a biological sample obtained from the subject with one or more probes for a second antibody when the biopsy provides a positive result for a cancer, such as prostate cancer, and based on the expression level of the second antibody, a prognosis or theranosis is provided. In one embodiment the subject is a human. In one embodiment the second antibody is an autoantibody. In another embodiment the second antibody is a human autoantibody.

Also provided herein is a method of characterizing, identifying, or screening for a cancer in a subject. In one embodiment, the method comprises detecting an expression level for one or more antibodies, wherein the expression level of the one or more antibodies is indicative of the presence, absence, or stage of the cancer. In another embodiment, the indication is whether the cancer is aggressive or indolent. In one embodiment, the method of identifying a cancer as aggressive or indolent comprises: obtaining a positive biopsy result for cancer from the subject; contacting a biological sample obtained from the subject with one or more probes for an antibody; detecting an expression level for the antibody; and characterizing or identifying the cancer as aggressive or indolent based on the expression level of the antibody. In one embodiment the subject is a human. In one embodiment the antibody is an autoantibody. In another embodiment the antibody is a human autoantibody. In one embodiment the presence of a human autoantibody that binds to a polypeptide probe is indicative of cancer (e.g. an expression level for one or more autoantibodies is indicative of the presence, absence, or stage of the cancer). In another embodiment the quantity or level of a human autoantibody that binds to a polypeptide probe is indicative of cancer. In one embodiment the cancer is a prostate, lung, breast or colon cancer.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 2 lists the nucleic acid sequence for DCHS1 (SEQ ID NO: 29).

FIG. 3 lists the nucleic acid sequence for Centrosomal Protein (CEP 164) (SEQ ID NO: 30).

FIG. 4 lists the nucleic acid sequence for KBTBD6 (SEQ ID NO: 31).

FIG. 5 lists the nucleic acid sequence for RPS19 (SEQ ID NO: 32).

FIG. 6 lists the nucleic acid sequence for RPL34 (SEQ ID NO: 33).

FIG. 7 lists the nucleic acid sequence for Hemk1 (SEQ ID NO: 34).

FIG. 8 lists the nucleic acid sequence for eIF4G1 (SEQ ID NO: 35).

FIG. 9 lists the nucleic acid sequence for BMI1 (SEQ ID NO: 36).

FIG. 10 lists the nucleic acid sequence for BRD2 (SEQ ID NO: 37).

FIG. 11 lists the nucleic acid sequence for RP3-323M22 (Nucleolin) (SEQ ID NO: 38).

FIG. 12 lists the nucleic acid sequence for SFRS14 (SEQ ID NO: 39).

FIG. 13 lists the nucleic acid sequence for LOC388789 (SEQ ID NO: 40).

FIG. 14 lists the nucleic acid sequence for RNA binding motif protein 6 (genomic DNA sequence) (SEQ ID NO: 41).

FIG. 15 lists the nucleic acid sequence for BRMSL1 (SEQ ID NO: 42).

FIG. 16 lists the nucleic acid sequence for NKX3-1 (SEQ ID NO: 43).

FIG. 17 lists the nucleic acid sequence for RPSA (SEQ ID NO: 44).

FIG. 18 lists the nucleic acid sequence for Cytochrome C Oxidase 5 subunit (SEQ ID NO: 45).

FIG. 19 lists the nucleic acid sequence for FAM53B (SEQ ID NO: 46).

FIG. 20 lists the nucleic acid sequence for a fragment of the UTR region of chromosome 11 (*Homo sapiens* genomic DNA, chromosome 11 clone: CTD-2579L12, NTs 149521-151500) (SEQ ID NO: 47).

FIG. 21 lists the nucleic acid sequence for MAPKKK9 (SEQ ID NO: 48).

FIG. 22 lists the nucleic acid sequence for cDNA clone XR_113641.1 (*Homo sapiens* hypothetical LOC643783, transcript variant 2 (LOC643783), partial miscRNA) (SEQ ID NO: 49).

FIG. 23 lists the nucleic acid sequence for PSA (SEQ ID NO: 50).

FIG. 24 lists the nucleic acid sequence for H2aa4 (SEQ ID NO: 51).

FIG. 25 lists the nucleic acid sequence for UBE2I (SEQ ID NO: 52).

FIG. 26 lists the nucleic acid sequence for TIMP2 (SEQ ID NO: 53).

FIG. 27 lists the nucleic acid sequence for WDR77 (SEQ ID NO: 54).

FIG. 28 lists the nucleic acid sequence for a fragment of Deaminase Domain Cont 1 (Human DNA sequence from clone RP1-20N2 on chromosome 6q24 Contains the gene for a novel protein similar to yeast and bacterial cytosine deaminase, NTs 48121-50100) (SEQ ID NO: 55).

FIG. 29 lists the nucleic acid sequence for Lamin A/C (SEQ ID NO: 85).

FIG. 30 lists the nucleic acid sequence Lsm3 (SEQ ID NO: 86).

FIG. 31 lists the nucleic acid sequence for a fragment of cDNA clone Chromosome 19, which encompasses the nucleic acid sequence for DAZ associated protein (*Homo sapiens* chromosome 19 clone CTB-25B13, NTs 20521-22500) (SEQ ID NO: 87).

FIG. 32 lists the nucleic acid sequence for ADAM metallopetidase domain 9 (SEQ ID NO: 88).

FIG. 33 lists the nucleic acid sequence for AZGP1 (SEQ ID NO: 89).

FIG. 34 lists the nucleic acid sequence for Desmocolin 3 (SEQ ID NO: 90).

FIG. 35 lists the nucleic acid sequence for PERP (SEQ ID NO: 91).

FIG. 36 lists the nucleic acid sequence for Chromosome 3 UTR region ropporin/RhoEGF (*Homo sapiens* 3 BAC RP11-783D3 (Roswell Park Cancer Institute Human BAC Library) NTs 178621-180600) (SEQ ID NO: 92).

FIG. 37 lists the nucleic acid sequence for Cox5a (SEQ ID NO: 93).

FIG. 38 lists the nucleic acid sequence for a Mitochondrion sequence (*Homo sapiens* isolate PD047 mitochondrion, NTs 4801-6780) (SEQ ID NO: 94).

FIG. 39 lists the nucleic acid sequence for MYH9 (SEQ ID NO: 95).

FIG. 40 lists the nucleic acid sequence for ASND1 (SEQ ID NO: 96).

FIG. 41 lists the nucleic acid sequence for Cathepsin F (SEQ ID NO: 97).

FIG. 42 lists the nucleic acid sequence for Mastermind-like 2 (*Homo sapiens* genomic DNA, chromosome 11q clone:RP11-82212, NTs 157801-159780) (SEQ ID NO: 98).

FIG. 43 lists the nucleic acid sequence for CSNK2A2 (SEQ ID NO: 99).

FIG. 44 lists the nucleic acid sequence for AURKAIP1 (SEQ ID NO: 100).

FIG. 45 lists the nucleic acid sequence for a fragment of Chromosome 4 (*Homo sapiens* BAC clone RP11-327O17 from 4, NTs 107401-109380) (SEQ ID NO: 101).

FIG. 46 lists the nucleic acid sequence for ARF6 (SEQ ID NO: 102).

FIG. 47 lists the nucleic acid sequence for JAG1 (Human DNA sequence from clone RP1-278O22 on chromosome 20 Contains two novel genes, NTs 26161-26140) (SEQ ID NO: 103).

FIG. 48 lists the nucleic acid sequence for a Mitochondrion sequence (*Homo sapiens* isolate PD047 mitochondrion, NTs 2041-4020) (SEQ ID NO: 104).

FIG. 49 lists the nucleic acid sequence for a fragment of Chromosome 20 (Human DNA sequence from clone RP1-278O22 on chromosome 20 Contains two novel genes, NTs 25321-27300) (SEQ ID NO:105).

FIG. 50 lists the nucleic acid sequence for a fragment of Chromosome 6 UTR region (Human DNA sequence from clone RP3-523G1 on chromosome 6p22.3-24.1, NTs 34621-36600) (SEQ ID NO: 106).

FIG. 51 lists the nucleic acid sequence for a fragment of MAPKKK5 (SEQ ID NO: 107).

FIG. 52 lists the nucleic acid sequence for RASA1 (SEQ ID NO: 108).

FIG. 53 lists the nucleic acid sequence for Hsp90b (SEQ ID NO: 109).

FIG. 54 lists the nucleic acid sequence for ribosomal protein S6 (RPS6) (SEQ ID NO: 110).

FIG. 55 lists the nucleic acid sequence for a fragment of *Homo sapiens* chromosome 3 (*Homo sapiens* 3 BAC RP13-616I3 (Roswell Park Cancer Institute Human BAC Library) NTs 22921-24900) (SEQ ID NO: 111).

DETAILED DESCRIPTION

Figure 1:
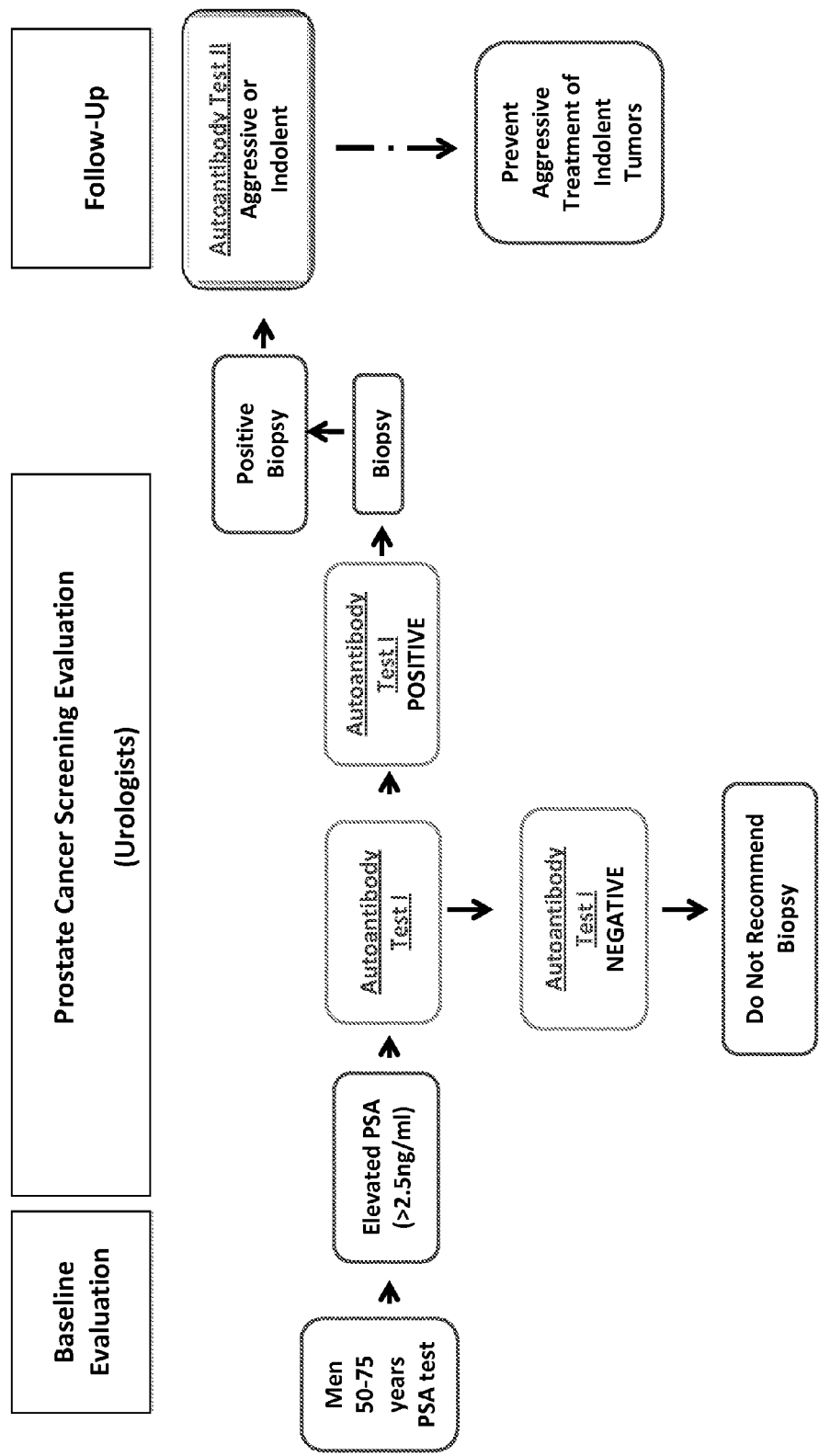
FIG. 1 is a schematic depicting detecting in a sample from a subject with PSA levels greater than 2.5 ng/mL the expression of one or more autoantibodies ("Autoantibody Test I"). If the result of the Autoantibody Test I is negative, a biopsy is not recommended to be obtained from the subject for further analysis. If result of the Autoantibody Test II is positive, then a biopsy is obtained. If the biopsy is positive for prostate cancer, expression of one or more autoantibodies is detected from a sample from the subject to characterize the cancer as aggressive or indolent, and a prognosis or theranosis provided.

The compositions and methods of the present disclosure relate to compositions and methods for characterizing a cancer or screening for a cancer. Provided herein are tests which can be used to analyze a presence or absence of an antibody from a subject, such as a subject being tested or screened for a cancer. In one embodiment, an antibody is an autoantibody. In another embodiment, the test comprises a single antigen, thus detecting only an antibody that binds to that antigen. In another embodiment, a panel of antigens is constructed such that the panel tests for a presence of one or more antibodies which specifically bind to two or more antigens derived from proteins associated with a specific cancer, such as lung cancer, prostate cancer, or ovarian cancer. By detecting an antibody to a protein associated with a disease state, the compositions and methods provided herein allow for the characterization of a cancer.

A cancer is characterized for a subject using a composition or method disclosed herein. In one embodiment, a subject is an individual or patient. In one embodiment, a subject is a human. In another embodiment, a subject is a cancer patient. In one embodiment, a subject exhibits no symptom of cancer, such as no symptoms of prostate cancer. In another embodiment, a subject has no detectable symptom of cancer, such as no detectable symptoms for prostate cancer. In yet another embodiment, a subject exhibits a symptom of cancer, such as a symptom for prostate cancer. In one embodiment, a subject is a human. In another embodiment, a subject is an individual. In yet another embodiment, a subject is a patient, such as a cancer patient.

Characterizing a cancer, or screening for a cancer, can include detecting the cancer (including pre-symptomatic early stage detecting), determining the prognosis, diagnosis, or theranosis of the cancer, or determining the stage or progression of the cancer. In one embodiment, a prognosis is predicting or giving a likelihood of outcome of a disease or condition, such as an extent of malignancy of a cancer, a likelihood of survival, or expected life expectancy, such as in an individual with prostate cancer. In another embodiment, a prognosis is a prediction or likelihood analysis of cancer progression, cancer recurrence, or metastatic spread or relapse.

In one embodiment, the diagnosis is prediction or likelihood an individual or subject has a disease or condition, such as prostate cancer. In one embodiment, the individual is an asymptomatic individual. In another embodiment, the individual is a symptomatic individual.

In one embodiment, a theranosis is a therapy selected based on an outcome of determining a binding of one or more antibodies from a sample from a subject to an antigen or polypeptide probe as described herein. In one embodiment, a theranosis is identifying an appropriate treatment or treatment efficacy for a cancer. In one embodiment, a theranosis is modifying a treatment. In another embodiment, a theranosis is selecting a treatment regimen. In yet another embodiment, a theranosis is discontinuing or not selecting a particular treatment regimen. In one embodiment a treatment regimen or therapeutic agent is selected based on the presence or absence of an autoantibody that binds to polypeptide probes described herein. In one embodiment the autoantibody is a human aautoantibody. In one embodiment a treatment regimen or therapeutic agent is excluded based on the presence or absence of an autoantibody that binds to polypeptide probes described herein. In one embodiment the autoantibody is a human aautoantibody.

In yet another embodiment, characterizing or screening for a cancer is detecting the cancer, such as pre-symptomatic early stage detecting. In one embodiment, characterizing a cancer is determining the stage or progression of the cancer, such as early-stage, late-stage or advanced stage of cancer. Characterizing or screening for a cancer can also be determining the likelihood or possibility an individual has a cancer. Characterizing or screening for a cancer can also be identification of a cancer, such as determining whether expression of one or more antibodies is indicative of the cancer.

In one embodiment, an antigen panel is used to detect a presence of one or more antibodies to one or more proteins, antigens, mimotopes, or epitopes. In one embodiment, one or more polypeptide probes described herein is a protein or fragment thereof. In another embodiment, one or more polypeptide probes described herein comprises an antigen, mimotope, or epitope. A "mimotope" can mimic the epitope of a protein or peptide. In one embodiment, the mimotope is structurally similar to an antigen or epitope of an expressed protein, but is unrelated or weakly related at the protein sequence level.

In one embodiment, the antigen panel comprises one or more polypeptide probes comprising a polypeptide sequence selected from SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, the antigen panel comprises one or more polypeptide probes comprising a sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the polypeptide probe comprises the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In one embodiment, the antigen panel comprises one or more polypeptide probes derived from one or more proteins encoded by one or more genes selected from: CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789. In one embodiment, detection of one or more antibodies is used to detect a presence of prostate cancer in a subject.

In one embodiment, the antigen panel comprises one or more polypeptide probes derived from one or more proteins encoded by one or more genes selected from: DCHS1, CEP164, KBTBD6, RPS19, RPL34, RNA binding protein 6, Hemk1, eIF4G1, 5'UTR BMI1, BRD2, RP3-323M22, SFRS14, and LOC388789. In one embodiment, detection of one or more antibodies is used to detect a presence of prostate cancer in a subject.

A cancer can also be characterized by determining a presence or absence, or level, of one or more antibodies in a sample. In one embodiment, a sample is obtained from a subject. The subject can be a mammal, including, but not limited to, humans, non-human primates, rodents, and the like. In another embodiment, a sample is a biological fluid. The biological fluid can be, but not limited to, peripheral blood, sera, or plasma. The sample can be ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, female ejaculate, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, or bronchopulmonary aspirates.

In one embodiment, the level, presence, or absence of an antibody can be determined by detecting the binding of one or more antibodies to a polypeptide probe. In one embodiment, an antibody is an autoantibody. An autoantibody refers to an antibody produced by a host (with or without immunization) and directed to a host antigen (such as a tumor antigen). Tumor-associated antigens recognized by humoral effectors of the immune system are an attractive target for diagnostic and therapeutic approaches to human cancer.

The binding of an antibody with a polypeptide probe can be specific, such that the interaction of the autoantibody with the polypeptide probe is dependent upon a presence of a particular structure (i.e., the antigenic determinant or epitope) of the polypeptide probe. Antigenic determinates or epitopes can comprise amino acids in linear or non-linear sequence in a polypeptide probe and can also comprise one or more amino acids which are in proximity to each other via protein folding (e.g., conformational epitopes). Thus, a single polypeptide or protein can potentially be bound by multiple antibodies which recognize different epitopes. In some instances, known epitopes of a particular polypeptide can be used as a probe to detect for a presence, absence or level of autoantibodies which bind a particular epitope The polypeptide probe can be an antigen identified through serologic identification of antigens, for example by recombinant expression cloning (SEREX), such as described by Kim et al., *Biotech. Lett.* (2004); 26: 585-588. Generally, in this method, an antigen can be identified by screening expression cDNA libraries from human solid tumors with sera of autologous patients. This type of screening of a cDNA expression library by conventional methods typically requires the preparation of a large number of membrane filters blotted with bacteriophage plaques that are then searched with a specific probe. In the case of the SEREX experiments, the screening is performed using sera from cancer patients, which can be in very limited quantities.

A polypeptide probe for detecting an antibody can also be identified by phage-display technology, which can be based on the insertion of foreign nucleotide sequences into genes encoding for various capsid proteins of T7 phage, resulting in a heterogeneous mixture of phages, each displaying the different peptide sequence encoded by a corresponding insert. A physical link between a displayed fusion protein and DNA encoded for it make this phage target selectable. The phage target can express or display a polypeptide probe, which can be used to detect antibodies that are produced by a subject, or autoantibodies, which can then be used to detect or characterize a cancer. The polypeptide probe can be displayed by a phage and used to detect an antibody from a sample obtained from a subject. In one embodiment, an antibody is an autoantibody.

Polypeptide Probes

Provided herein is a composition and method for detecting one or more antibodies in a sample using one or more polypeptide probes. Polypeptide is used in its broadest sense and can include a sequence of subunit amino acids, amino acid analogs, or peptidomimetics. The subunits can be linked by peptide bonds. The polypeptides can be naturally occurring, processed forms of naturally occurring polypeptides (such as by enzymatic digestion), chemically synthesized or recombinantly expressed. The polypeptides for use in the methods of the present invention can be chemically synthesized using standard techniques. The polypeptides can comprise D-amino acids (which are resistant to L-amino acid-specific proteases), a combination of D- and L-amino acids, β amino acids, or various other designer or non-naturally occurring amino acids (e.g., β-methyl amino acids, Cα-methyl amino acids, and Nα-methyl amino acids, etc.) to convey special properties. Synthetic amino acids can include ornithine for lysine, and norleucine for leucine or isoleucine. In addition, the polypeptides can have peptidomimetic bonds, such as ester bonds, to prepare polypeptides with novel properties. For example, a polypeptide can be generated that incorporates a reduced peptide bond, i.e., $R_1$—$CH_2$—NH—$R_2$, where $R_1$ and $R_2$ are amino acid residues or sequences. A reduced peptide bond can be introduced as a dipeptide subunit. Such a polypeptide can be resistant to protease activity, and can possess an extended half-life in vivo. A polypeptide can also include a peptoid (N-substituted glycines), in which the one or more side chains are appended to nitrogen atoms along the molecule's backbone, rather than to the α-carbons, as in amino acids. Polypeptide and peptide are intended to be used interchangeably throughout this application, i.e. where the term peptide is used, it can also include polypeptide and where the term polypeptides is used, it can also include peptide.

In one embodiment, a polypeptide probe can be a fragment or portion of a larger protein. A fragment can range in size from two amino acid residues to the entire amino acid sequence minus one amino acid. In one embodiment, a polypeptide probe is a fragment of an untranslated region (UTR) of a protein, such as a fragment that is encoded by a nucleic sequence that is a UTR region of a gene, such as the 5' or 3' UTR of a gene.

The fragment can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids in size. In one embodiment, the fragment is less than about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids in size. A polypeptide probe useful in the compositions and methods herein, regardless of size, is capable of specific interaction with an antibody, such as an autoantibody.

In one embodiment, a polypeptide probe can be a fragment of a protein encoded by a gene, or a region upstream or downstream of a coding sequence, such as a UTR region, of a gene listed in Table 1, Table 2, Table 3 or Table 4. In one embodiment, the polypeptide probe comprises a polypeptide sequence selected from SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, the polypeptide probe comprises a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the polypeptide probe comprises the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In one embodiment, a polypeptide probe is a fragment of a protein encoded by a gene, or a fragment encoded by a sequence of a UTR region of a gene.

In one embodiment, the gene can be CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain. In another embodiment, the gene is FAM53B, 5'UTR BMI1, RP3-323M22, or LOC388789.

In another embodiment, a polypeptide probe comprises SEQ ID NO: 2, 5, 9, 11, 14, 56, 57, 58, 59, 60, 61, 62, 63, 64, 65, 66, 67, 68, 69, or a fragment thereof. In another embodiment, a polypeptide probe comprises a polypeptide encoded by SEQ ID NO: 16, 19, 23, 25, 28, 70, 71, 72, 73, 74, 75, 76, 77, 78, 79, 80, 81, 82, 83, 84, or a fragment thereof.

In one embodiment, the gene can be DCHS1, CEP164, KBTBD6, RPS19, RPL34, RNA binding protein 6, or Hemk1. In another embodiment, the gene is eIF4G1, 5'UTR BMI1, BRD2, RP3-323M22, SFRS14, or LOC388789. A polypeptide probe can comprise a peptide sequence, or fragment thereof, such as those listed in Tables 1, 2, 3 or 4.

In one embodiment, a polypeptide probe comprises SEQ ID NO: 1, 2, 3, 4, 5, 6, 7, 8, 9, 10, 11, 12, 13, 14, or a fragment thereof. In another embodiment, a polypeptide probe comprises a polypeptide encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof.

TABLE 1

| Clone ID | Gene | NCBI Designation | Gene Sequence | Peptide Sequence | Clone DNA Sequence (Encoding Peptide Sequence) |
|---|---|---|---|---|---|
| 2E11 | DCHS1 (protocadherin-16 precursor) | AB384634.1 | FIG. 2 (SEQ ID NO: 29) | PQTTAPRRAR PRRS (SEQ ID NO: 1) | AGCTTTCGCTAGAGACGCCTCCATA AGTCACTTGCCCGTTGGCCCCCACG ATCGGGGTCGGTTGCTCGCAGGGC TGAGCAGAGATGTGCCAGGAGGGT TGTTCTCACGCAAGAGGACGCTGT ACTCCTGCTGCTGGAAAGTAGGCG CCTCGTCGTTGACGTCAGCGACACT GACGGTCAGGACCTGCGTGGCCGA GCGCGGCGGGGAGCCGTGGTCTGA GG (SEQ ID NO: 15) |
| 1B4A | Centrosomal Protein (CEP 164) (Minus strand) | NM_014956.4 | FIG. 3 (SEQ ID NO: 30) | PVSSSGSYSTP IRKSLRRAAPP FRA (SEQ ID NO: 2) | TGGAGGAGAGGCTGGGCTGCCCCA AGCCCCTGCTCAGGGCCTCAGAAG CCATACACCTTCACTCTGATTGTGC TCATCAAGGCCCAGCATGCAGGAG GCTCAAAGTAGCTTTTGGCTTGGGT GTTGACGAGAAGAGAGGTAACCTG GGGTCATTCTTGACACGTTCCAGCC ACCTCCGGTTGGCCTCAATTATGCC CTGAAAGGTGGTGCTGCCCGCCTC AGGGACTTGCGAATGGGAGTGCTG TAGGAGCCGGAGCTGCTCACTGG (SEQ ID NO: 16) |
| 37A8 | KBTBD6 | NM_152903.4 | FIG. 4 (SEQ ID NO: 31) | SSFSPLN (SEQ ID NO: 3) | GAATTCGTCATTCTCACCTTTGAAT TAAAGCTTAGACTAAATAGTAATA TATCGTGGGAAGGATTTTGGTTTTG TGATATTTCTGTGAATTAAGGAATA GATGTTAACCATTATTTTGTAGAAA AGTGATTTGTATGTGGTTAATTATA AATAAAACTGGTACCAGAA (SEQ ID NO: 17) |
| 4H10 | RPS19 | NM_001022.3 | FIG. 5 (SEQ ID NO: 32) | AARRPHDAW SYCKRREPAG VXQSSGSLPQ KVREAESPRM GGYRQAGQA QRACSLR (SEQ ID NO: 4) | TTTATTAACCCAGCATGGTTTGTTC TAATGCTTCTTGTTGGCAGCTGCCA CCTGTCCGGCGATTCTGTCCAGATC TCTTTGTCCCTGAGGTGTCAGTTTG CGGCCGCCATCTTGGTCCTTTTCCA CCATTTTCAGCCCCTCCAGGGCTTG GAGGACCCGGCGGGCCACACTCTT GGAGCCTCGGCTGAAGTGGCTGGG CATGACGCCGTTTCTCTGACGTCCC CCATAGATCTTGGTCATGGAGCCA ACCCCAGCGCCACCCCGGAGGTAC AGGTGCCGCGCTGTGNAAGCAGCT CGCGTGTAGAACCAGTTCTCATCGT AGGGAGCAAGCTCTTTGTGCTTGGC CAGCTTGACGGTATCCACCCATTCG GGGACTTTCAGCTTCCCGGACTTTT TGAGGAAGGCTGCCAGAGCTCTGA CNAACTCCTGCTGGTTCACGTCTTT TACAGTAACTCCAGGCATCGTGCG GCCTCCGCGCTGC (SEQ ID NO: 18) |
| 3D10 | RPL34 | NM_033625.2 | FIG. 6 (SEQ ID NO: 33) | QARLFIFITQK SFIFLFSFLTLC LCLQHFHNDF LLLDKESTLD PVTNTFSTHG TKTLLLTSLFL (SEQ ID NO: 5) | TTCTCGAGTGCGGCCGCAGCTTGGG TATGGAGACATATCATATAAGTAA TGCTAGGGTCNGTGGTAGGAAGTT TTTTCATAGGAGGTGTATGAGTTGG TCGTAGCGGAATCGGGGGTATGCT GTTCGAATTCATAAGAACAGGGAG GTTAGAAGTAGGGTCTTGGTTCCAT GTGTGCTAAATGTGTTCGTGACAGG ATCAAGCGTGCTTTCCTTATCGAGG AGCAGAAATCGTTGTGAAAGTGT TGAAGGCACAAGCACAGAGTCAGA AAGCTAAATAAAAAAAATGAAACTT TTTTGAGTAATAAAAATGAAAAGA CGCGCTTGA (SEQ ID NO: 19) |

TABLE 1-continued

| Clone ID | Gene | NCBI Designation | Gene Sequence | Peptide Sequence | Clone DNA Sequence (Encoding Peptide Sequence) |
|---|---|---|---|---|---|
| 40A3 | RNA binding protein 6 (Minus strand) | NT_022517.18 | FIG. 14 (SEQ ID NO: 41) | LRGITKNDRN FNRKIHLNWISK (SEQ ID NO: 6) | CTCTGAGGGGCATCACCAAAAATG ACAGGAATTTCAACAGGAAGATAC ATCTGAATTGGATCTCGAAATAAG GAGTTTGTGTAAGAGAAAAGGAGG ACACAAGCAAGGAGACACAAAAG ACAATTTGTCCAAGAGAGTAGTAG TAGAAACTGACAAAGGTAAGGCTG CTTGGTGGCCGGGTGCAGTGACTC ACGCCTGTAATCCCAGCACTTTGGG AGGCCAAGGCGGGTGGATCACCTG AGGTCAGGAGTTCGAGACCACCCT GACCAACAGGTGAAACCCCTCTCT ACTAAAAATACAAACATTAGCCCA TAGTCCCAGCTACTGGGGAGGCTG AGGCAGGAGAATCGCTTGAACCTG GGAGGCGGAGGTTGCAGTGAGCCA AGATCGTGCCATTGCACTCCAGCCT GGGCGACAGAATGAGACTGTCTCA AAACAAAAGGAAAAAAAAAA (SEQ ID NO: 20) |
| 25C4 | Hemk1 (minus strand) | NM_016173.3 | FIG. 7 (SEQ ID NO: 34) | RGCCAGIRCT (SEQ ID NO: 7) | CACTTCTTCAAGCTCCAACACAAAT GCTGCCTCCTTTAGGATGCCTGCTC TGTGCTCTCCCTGCCTCCCCTAGCC CATACCTCTGCTGGCACCTTCTGTA CCATGCCTTCAGAAACCTTCTTATC CCCCTCATCTCTGGGGCCCCCTGTG GATCTGGCATACCCAAGTTCAGTA AATGTCTATCAGTAAGCTGATGGTA CATGCATTTTCTAGAATAGAGCTGG GACTTCCCATGTGGCCCACATCTGA CCTGGCAGCCCATGTATTCCGGTCA TTAGGGATGGGAAGCCATGAGGAC CTGGCCTTCTGCCCGACCCAGGCAG CCATTCAAGTTGAGCAATGGCCACT TCGAAGACTCAAGTGCACCTGATC CCTGCGCAACAGCCAC (SEQ ID NO: 21) |

TABLE 2

| CloneGene | NCBI Designation | Gene Sequence | Peptide Sequence | Clone DNA Sequence (Encoding Peptide Sequence) |
|---|---|---|---|---|
| 24E1 eIF4G1 | NM_182917.3 | FIG. 8 (SEQ ID NO: 35) | IRDPNQGG KDITEEIMS GARTASTP TPPQTGGG LEPQANGE TPQVAVIV RPDDRSQG AIIADRPGL PGPEHSPSE SQPSSPSPT PSPSPVLEP GSEPNLAV LSIPGDTM TTIQMSVEE (SEQ ID NO: 8) | TTCTTCTACAGACATTTGTATAGT TGTCATAGTGTCCCCAGGAATAG AGAGGACTGCGAGATTAGGCTCA GACCCCGGTTCCAAGACTGGGGA TGGTGATGGGGTCGGAGAAGGCG ACGAAGGCTGGGATTCTGAAGGG CTATGCTCTGGGCCAGGCAGCCC TGGCCGGTCAGCAATGATTGCTC CCTGTGACCGGTCATCTGGCCGG ACAATGACAGCAACCTGGGGCGT CTCCCCATTAGCTTGAGGCTCCAG ACCGCCTCCCGTCTGGGGAGGGG TGGGTGTGGAGGCAGTGCGGGCC CCAGACATGATCTCCTCTGTGATA TCCTTTCCTCCTTGGTTTGGATCT CGAATTCGGATC (SEQ ID NO: 22) |
| 3C4 5'-UTR BMI1 | BC011652.2 | FIG. 9 (SEQ ID NO: 36) | GGGRGAG GGRGAGA GGGRPEAA (SEQ ID NO: 9) | ATCACAAATAGGACAATACTTGC TGGTCTCCAGGTAACGAACAATA CACGTTTTACAGAAGGAATGTAG ACATTCTATTATGGTTGTGGCATC AATGAAGTACCCTCCACAAAGCA CACACATCAGGTGGGGATTTAGC TCAGTGATCTTGATTCTCGTTGTT CGATGCATTTCTGCTTGATAAAAA ATCCCGAAAGAGCAGCCGGCGC GAGGCGATCGAAGCGGGCGGAA AAGACAATGAAAGTTAAAAGTCG TTCAGCAGAAAATGAATGCGAGC |

TABLE 2-continued

| CloneGene | NCBI Designation | Gene Sequence | Peptide Sequence | Clone DNA Sequence (Encoding Peptide Sequence) |
|---|---|---|---|---|
| | | | | CAAGCGGCCATCTTGAAGCGAGC TGCAGACGCCGCTGTCAATGGGC AACCAGCGCGGCCCCGAGCAGCC GCGGCCGCCACGCTCGTCTCATG CCGCCTCCGGCCGGCCTCCTCCTG CTCCGGCGCCTCGGCCTCCTCCGG CGCCTCGGCCTCCTCCTCCTCCGC CTCCGCCTCGACCTCCAACGCCTC CTCCTCCGGGGCCTCCTCCTCCTC CTCCTCGGC (SEQ ID NO: 23) |
| 8A6 | BRD2 | BX908719.9 | FIG. 10, (SEQ ID NO: 37) | ESRPMSYD EKRQLSLDI NKLPGEKL GRVVHIIQ AREPSLRD SNPEEIEID FETLKPSTL RELERYVL SCLRKKPR KPYSTYEM RFISWF (SEQ ID NO: 10) | TGTAGGGCTTCCGGGGTTTCTTAC GTAGGCAGGAAAGGACATAGCGC TCAAGCTCTCTAAGTGTGGATGG CTTGAGTGTTTCAAAATCAATCTC AATCTCTTCTGGGTTTGAATCACG TAAAGAGGGCTCCCTGGCTTGGA TTATATGCACAACTCGGCCCAGCT TCTCCCCAGGTAATTTGTTGATGT CCAGGCTCAGCTGCCGCTTCTCAT CGTAACTCATGGGCCTGCTCTC (SEQ ID NO: 24) |
| 15F1 | RP3-323M22 (Nucleolin) | NM_005381.2 | FIG. 11 (SEQ ID NO: 38) | LVSILLTKTIY (SEQ ID NO: 11) | TTACTGTTACCTGATCAATGACAG AGCCTTCTGAGGACATTCCAAGA CAGTATACAGTCCTGTGGTCTCCT TGGAAATCCGTCTAGTTAACATTT CAAGGGCAATACCGTGTTGGTTTT GACTGGATATTCATATAAACTTTT TAAAGAGTTGAGTGATAGAGCTA ACCCTTATCTGTAAGTTTTGAATT TATATTGTTTCATCCCATGTACAA AACCATTTTTTCCTACAAATAGTT TGGGTTTTGTTGTTGTTCTTTTTT TTGTTTTGTTTTTGTTTTTTTTTTT TTGCGTTCGTGGGGTTGTAAAAG AAAAGAAAGCAGAATGTTTTATC ATGGTTTTTGCTTCAGCGGCTTTA GGACAAATTAAAAG (SEQ ID NO: 25) |
| 6E2 | SFRS14 | NM_001017392.3 | FIG. 12 (SEQ ID NO: 39) | KAECFKNL IVKKQKSL CSGFKEHL NEASILAQ VSVSSSKR VWKSWEN LISSFMVW NPAHLIISIP NLEKTSDL SMMSKLA AALE (SEQ ID NO: 12) | AAGCAGAGTGCTTTAAAAATTTG ATAGTAAAAAAGCAAAAATCTCT GTGCTCTGGTTTTAAGGAACATTT GAATGAGGCAAGCATTTTAGCAC AGGTTTCTGTTTCAAGTTCAAAGA GAGTCTGGAAAAGTTGGGAAAAT TTAATATCATCTTTTATGGTGTGG AATCCTGCCCATTTGATTATTTCT ATCCCAAATCTTGAAAAACATC AGACTTATCTATGATGTCAAAGCT (SEQ ID NO: 26) |
| 12B2 | 5'-UTR BMI1 | BC011652.2 | FIG. 9 (SEQ ID NO: 36) | QRSGRDNG DVGAGAPF RLSSTSQPR RIKPIAPPP RAPSPEXG AGGGGGG RGGGGGP GGGGVGG RGGGGGG GGRGAGG GRGAGAG GGRPEAA (SEQ ID NO: 13) | AAGCTTATTATCTCATCATCAGTT ATAATTCTCTTATCTTCATCTGCA ACCTCTCCTCTATCTTCATTAGAG CCATTGGCAGCATCAGCAGAAGG ATGAGCTGCATAAAAATCCCTTCT TCTCTTCATTTCATTTTTGAAAAG CCCTGGAACTAATTTGTATACAAT ATCTTGGAGAGTTTTATCTGACCT TATATTCAGTAGTGGTCTGGTCTT GTGAACTTGGACATCACAAATAG GACAATACTTGCTGGTCTCCAGGT AACGAACAATACACGTTTTACAG AAGGAATGTAGACATTCTATTAT GGTTGTGGCATCAATGAAGTACC CTCCACAAAGCACACACATCAGG NGGGGATTTAGCTCAGTGATCTT GATTCTCGTTGTTCGATGCATTTC TGCTTGATAAAAAATCCCGGAAA GAGCAGCCGGCGCGAGGCGATCG AAGCGGGCGGAAAAGACAATGA AAGTTAAAAGTCGTTCAGCAGAA |

TABLE 2-continued

| CloneGene | NCBI Designation | Gene Sequence | Peptide Sequence | Clone DNA Sequence (Encoding Peptide Sequence) |
|---|---|---|---|---|
| | | | | AATGAATGCGAGCCAAGCGGCCA TCTTGAAGCGAGCTGCAGACGCC GCTGTCAATGGNCAACCAGCGCG GCCCCGAGCAGCCGCGGCCGCCA CGCTCGTCTCATGCCGCCTCCGGC CGGCCTCCTCCTGCTCCGGCGCCT CGGCCTCCTCCGGCGCCTCGGCCT CCTCCTCCTCCGCCTCCGCCTCGA CCTCCAACGCCTCCTCCTCCGCTT GAATTCGGATCCCCGAGCATCAC ACCTGACTGGAATACGAACAGCT CCACATNCNGT (SEQ ID NO: 27) |
| 21D10 Homo sapiens hypothetical LOC388789 (LOC388789) | BC150559.1 | FIG. 13 (SEQ ID NO: 40) | PASASILAG VPMYRNEF TAWYRRM SVVYGIGT WSVLGSLL YYSRTMA KSSVDQKD GSASEVPS ELSERPSLR PHSSN (SEQ ID NO: 14) | TTGGGCGTTCAGAGAGTTCACTG GGTACTTCACTTGCTGAGCCATCC TTTTGGTCTACTGACGACTTCGCC ATTGTCCGGCTATAGTAAAGCAG TGAGCCCAACACAGACCAGGTGC CGATCCCGTAGACCACCGACATC CGCCGGTACCAGGCCGTGAACTC ATTTCGATACATGGGTACGCCAG CGAG (SEQ ID NO: 28) |

TABLE 3

| Gene Clone | NCBI Designation | Gene Sequence | Peptide Sequence | Clone DNA Sequence (Encoding Peptide Seqence) |
|---|---|---|---|---|
| 8E10 BRMSL1 | NM_032352.3 | FIG. 15 (SEQ ID NO: 42) | APRTRTLR ARRSPRME IAQKWMM KTVKEEEW NVWMKCPI LKNSLPIS KINFIKND (SEQ ID NO: 56) | TCGTCGAGGCTCCTGCTCCTGTGA CTCTCGAGCAGCCAGAGGCTCCT ACCTCTATCGAGTCTTTACCTACT ACTTCTGACACTTTCTTCTTCTTA CCTTACAAACCTACTTTACAGGTT AGAACTTTTTGTCAAATGGCTAG AGTTTCTAGTTGAAATATTTCTTG CTAATTCAGTCCACCTACGTTTTG ATGTTCTTCAGTATCGACCTTTTC GTGGTCTTATGAACCTTGGCGACC GTTGAAATGTCCTTTTATACGTTT AAGCATGTTTCCATCGTCCTTAGA TATCTCTCGAGACGAATCTTAGAC ATTTCTTGTTTATACTTACACTTT AAGTTCGAA (SEQ ID NO: 70) |
| 1D10 5'-UTR-BMI1 | NM_005180.5 | FIG. 9 (SEQ ID No: 36) | GGRGGGG GGGGRGA GGGRGAG AGGGRPEAA (SEQ ID NO: 172) | GGAGGTCGAGGCGGAGGCGGAG GAGGAGGAGGCCGAGGCGCCGG AGGAGGCCGAGGCGCCGGAGCA GGAGGAGGCCGGCCGGAGGCGG CATGAGACGAGCGTGGCGGCCGC GGCTGCTCGGGGCCGCGCTGGTT GNCCATTGACAGCGGCGTCTGCA GCTCGCTTCAAGATGGCCGCTTG GCTCGCATTCATTTTCTGCTGAAC GACTTTTAACTTTCATTGTCTTTTC CGCCCGCTTCGATCGCCTCGCGCC GGCTGCTCTTTCCGGGATTTTTTA TCAAGCAGAAATGCATCGAACAA CGAGAATCAAGATCACTGAGCTA AATCCCCNCCTGATGTGTGTGCTT TGTGGAGGGTACTTCATTGATGCC ACAACCATAATAGAATGTCTACA TTCCTTCTGTAAAACGTGTATTGT TCGTTACCTGGAGACCAGCAAGT ATTGTCCTATTTGTGATGTCCAAG TTCACAAGACCAGACCACTACTG AATATAAGGTCAGATAAAACTCT CCAAGATATTGTATACAAATTAG TTCCAGGGCTTTTCAAAAATGAA ATGAAGAGAAGAAGGGATTTTTA TGCAGCTCATCCTTCTGCTGATGC TGCCAATGGCTCTAATGAAGATA |

TABLE 3-continued

| Gene Clone | NCBI Designation | Gene Sequence | Peptide Sequence | Clone DNA Sequence (Encoding Peptide Seqence) |
|---|---|---|---|---|
| | | | | GAGGAGGACGGTTGCAGATGAAG ATAAGAGAATTATAANCTGATGA TGAGATAATAAGGCTTGCGGCCG CACTCGAGAAACAGT (SEQ ID NO: 71) |
| 1H2 | NKX3-1 | NM_0067167.3 | FIG. 16 (SEQ ID NO: 43) | GTNQRREG KSSGIFQHFV (SEQ ID NO: 57) | GGAGAGAGGGAAAATCAAGTGGT ATTTTCCAGCACTTTGTATGATTT TGGATGAGTTGTACACCCAAGGA TTCTGTTCTGCAACTCCATCCTCC TGTGTCACTGAATATCAACTCTGA AAGAGCAA (SEQ ID NO: 72) |
| 4H9 | RPSA | NM_002295.4 | FIG. 17 (SEQ ID NO: 44) | GKWCHAC AELPEPAST TSNPLSELP CCCMGWQ CPHSAEEN LCYTAQW (SEQ ID NO: 58) | CGGGAAATGGTGCCACGCATGCG CAGAACTTCCCGAGCCAGCATCC ACCACATCAAACCCACTGAGTGA GCTCCCTTGTTGTTGCATGGGATG GCAATGTCCACATAGCGCAGAGG AGAATCTGTGTTACACAGCGCAA TGGTAGGTAGGTTAACATAAGAT GCCTCCGTGAGAGGCTGGTGGTC AGCCCTGGGGTCAGTAACCACAA GAAGCCGTGGCTCCCGGAAGGCT GCCTGGATCTGGTTAGTGAAGGT TCCAGGAGTGAAGCGGCCAGCAA TTGGAGTGGCTCCAGTGGCAGCA GCAAACTTCAGCACAGCCCTCTG GCCAGTATTCCTGGAGGATATAA CACTGACATCAGCAGGGTTTTCA ATGGCAACAATTGCACGAGCTGC CAGCAGAAGCTT (SEQ ID NO: 73) |
| 5B1 | Cytochrome C Oxidase 5 Subunit | NM_004255.3 | FIG. 18 (SEQ ID NO: 45) | INTLVTYD MVPEPKIID AALRACRR LNDFASTV RILEVVKD KAGPHKEI YPYVIQEL RPTLNELGI STPEELGL DKV (SEQ ID NO: 59) | GATAAACACACTTGTTACCTATG ATATGGTTCCAGAGCCCAAAATC ATTGATGCTGCTTTGCGGGCATGC AGACGGTTAAATGATTTTGCTAGT ACAGTTCGTATCCTAGAGGTTGTT AAGGACAAAGCAGGACCTCATAA GGAAATCTACCCCTATGTCATCCA GGAACTTAGACCAACTTTAAATG AACTGGGAATCTCCACTCCGGAG GAACTGGGCCTTGA CAAAGTGTAAACCGCATGGATGG GCTTCCCCAAGGATTTATTGACAT TGCTACTTGAGTGTGAACAGTTAC CTGGAAATACTGATGATAACATA TTACCTTATTTGAACAAGTTTTCC TTTATTGAGTACCAAGCCATGTAA TGGTAACTTGGACTTTAATAAAA GGGAAATGAGTTTGAACTGAAA (SEQ ID NO: 74) |
| 17B8 | FAM53B | NM_014661.3 | FIG. 19 (SEQ ID NO: 46) | EVHIKKKT KQTLTNFQ MGLLVRG REWPCPGC AACLSKLP (SEQ ID NO: 60) | GGGAAGTCCACATTAAAAAGAAA ACAAAACAAACCCTAACTAACTT CCAAATGGGTCTTCCTGGTGCGGG GGCGTGAGTGGCCGTGCCCTGGG TGTGCTGCCTGTCTGAGCAAGCTT CCCTAGCTGTGGAACCCCGGGCC CCCTGCTGCGGGCTCTGCCTTGGT GTCATGCCTGCTGCACCCCCGTTT CCACTGACGTGCCGTCTGTGGCTA TGGGGGTGGTCACTGGAATGACG GTCACTCCAGACGTCAGCCGGCA GGGATGCAGCAGGCTGGCCGCGC A (SEQ ID NO: 75) |
| 3C11 | UTR- Region Chromosome 11 | AP003173.4 | FIG. 20 (SEQ ID NO: 47) | DHSMVEFP RIIVYPQFG VGNEG (SEQ ID NO: 61) | ATTCTATGGTGGAATTTCCAAGA ATAATTGTTTATCCTCAGTTTGGA GTAGGAAATGAAGGATAATTTTT TCCATTTCACCTCTATTGCAAATT TATTTTTTCAAGCCACACAAAA ATTGTCTAAGATAAAATGAGAAT TATTCAGATCAATTCTGCAATGAT ACAGGGAAGATGTGAAAGGAGG GCTCAATGCAGAGTTGTGAAGTT GAAACCACTATTTCTGTTCTAAA |

TABLE 3-continued

| Gene Clone | NCBI Designation | Gene Sequence | Peptide Sequence | Clone DNA Sequence (Encoding Peptide Seqence) |
|---|---|---|---|---|
| | | | | GACACAGTAAGCAGAGATCCATC TCTCTTCAGGCATCCTGCTTCTCT GCAGGTTACTTCTGCTTTAAGGAA AGTACATTTTTAGAACAAAGCTT (SEQ ID NO: 76) |
| 3F6 | MAPKKK9 | NM_033141.2 | FIG. 21 (SEQ ID NO: 48) | SSGSGESRL QHSPSQSY LCIPFPRGE DGDGPSSD GIHEEPTPV NSATSTPQ LTPTNSLK RGGAHHR RCEVALLG CGAVLAAT GLGFDLLE AGKCQLLP LEEPEPPAR EEKKRREG LFQRSSRPR RSTSPPSRK LFKKEEHQ ACGRTRVT S (SEQ ID NO: 62) | TCAAGCGGGAGTGGAGAGAGTCG CCTACAGCATTCACCCAGCCAGT CCTACCTCTGTATCCCAT TCCCTCGTGGAGAGGATGGCGAT GGCCCCTCCAGTGATGGAATCCA TGAGGAGCCCACCCCAGTCAACT CGGCCACGAGT ACCCCTCAGCTGACGCCAACCAA CAGCCTCAAGCGGGGCGGTGCCC ACCACCGCCGCTGCGAGGTGGCT CTGCTCGGCTG TGGGGCTGTTCTGGCAGCCACAG GCCTAGGGTTTGACTTGCTGGAA GCTGGCAAGTGCCAGCTGCTTCC CCTGGAGGAGC CTGAGCCACCAGCCCGGGAGGAG AAGAAAAGACGGGAGGGTCTTTT TCAGAGGTCCAGCCGTCCTCGTC GGAGCACCAGC CCCCCATCCCGAAAGCTTTTCAAG AAGGAGGAGCACCAAGCTTGCGG CCGCACTCGAGTAACTAGTTAAC CCCTTGGGGC CTCTAAACGGGTCTTGAGGGGGT TANCTNGTTACTCGNTGCGGCC GCNNGCTTGGTGCTCNNCNTTN (SEQ ID NO: 77) |
| 21H4 | cDNA clone | XR_113641.1 | FIG. 22 (SEQ ID NO: 49) | QKLCQAKE KGMCMKK LRMLWEC QKLYSLGF* (SEQ ID NO: 63) | ATCCCAGCACGGAGGCCCAGAAA ACTTTAAGATTTGAGTATTAATGT CTCAAGGTCAGGAGCAACCTCAA GGCTAAAACTCAGATCTCAGGAC TCAATTTCACAGAAGTTCCACTAT AAAGGCAATAATCTAAAGCTTTA AATGTATATGAAAATTTTGTAATA AGAGTTCAGTATTCTGCCAACAT TGGCGCATGGATTGCAAAGTTCA CAGGATTGAAAACACCATCGACA TAATGGAAATTGAACAGCATCTG ATTACTGAGTGCTATATCAGCAA GTTAAAAGGATCTTTTGCATACCT TTTAATGGTATATATCCTAAAACT GAAGTGTTCAATATAGACATCCA GATTGAAA (SEQ ID NO: 78) |
| 4C4 | PSA | M27274.1 | FIG. 23 (SEQ ID NO: 50) | S E G R T V T N K V S R K Y T G (SEQ ID NO: 64) | TGTGTGGGTATGAGGGTATGAGA GGGCCCCTCTCACTCCATTCCTTC TCCAGGACATCCCTCCACTCTTGG GAGACACAGAGAAGGGCTGGTTC CAGCTGGAGCTGGGAGGGGCAAT TGAGGGAGGAGGAAGGAGAAGG GGGAAGGAAAACAGGGTATGGG GGAAAGGACCCTGGGGAGCGAA GTGGAGGATACAACCTTGGGCCT GCAGGCCAGGCTACCTACCCACT TGGAAACCCACGCCAAAGCCGCA TCTACAGCTGAGCCACTCTGAGG CCTCCCCTCCCCGGCGGTCCCCAC TCAGCTCCAAAGTCTCTCTCCCTT TTCTCTCCCACACTCTATCATCCC CCGGATTCCTCTCTACTTGGTTCT CATTCTTCCTTTGACTTCCTGATC CTGTGTATTTTCGGCTCACCTTGA TTTGTCACTGTTCTCCCCTC (SEQ ID NO: 79) |

TABLE 3-continued

| Gene Clone | NCBI Designation | Gene Sequence | Peptide Sequence | Clone DNA Sequence (Encoding Peptide Seqence) |
|---|---|---|---|---|
| 5A1 H2aa4 | NM_001040874.1 | FIG. 24 (SEQ ID NO: 51) | QRGSGQQE DAHHPSSP PAGHPQRR GTEQAAGQ SHHRPGRR LA (SEQ ID NO: 65) | ACGCGGCTCGGGGACAACAAGAA GACGCGCATCATCCCTCGTCACCT CCAGCTGGCCATCCGCAACGACG AGGAACTGAACAAGCTGCTGGGC AAAGTCACCATCGCCCAGGGCGG CGTCTTGCCTAACATCCAGGCCGT ACTGCTCCCTAAGAAGACGGAGA GTCACCACAAGGCAAAGGGCAAG TGAGGCTGACGTCCGGCCCAAGT GGGCCCAGCCCGGCCCGCGTCTC GAAG (SEQ ID NO: 80) |
| 1B4 UBE2I | NM_194259.1 | FIG. 25 (SEQ ID NO: 52) | ILYPETLLK LLISLRRFW AEMMEFSR YTIMSSEN RDNLTSSFP N* (SEQ ID NO: 66) | TGTGGCATCGTCAAAAGGAAGGG ATTGGTTTGGCAAGAACTTGTTTA CAACATTTTTGCAAATCTAAAGTT GCTCCATACAATGACTAGTCACCT GGGGGGGTTGGGCGGGCGCCATC TTCCATTGCCGCCGCGGGTGTGCG GTCTCGATTCGCTGAATTGCCCGT TTCCATACAGGGTCTCTTCCTTCG GTCTTTTGTATTTTGATTGTTATG TAAAACTCGCTTTTATTTTAATAT TGATGTCAGTATTTCAACTGCTGT AAAATTATAAACTTTTATACTTGG GTAAGTCCCCCAGGGGCGAGTTC CTCGCTCTGGGATGCAGGCATGC TTCTCACCGTGCAGAGCTGCACTT GGCCTCAGCTGGCTGTATGGAAA (SEQ ID NO: 81) |
| 18D3 TIMP2 | NM_003255.4 | FIG. 26 (SEQ ID NO: 53) | CSKHSSLL LFSSCKQL KIFKIKFTL (SEQ ID NO: 67) | ATGTTCTAAGCACAGCTCTCTTCT CCTATTTTCATCCTGCAAGCAACT CAAAATATTTAAAATAAAGTTTA CATTGTAGTTATTTTCAAATCTTT GCTTGATAAGTATTAAGAAATAT TGGACTTGCTGCCGTAATTTAAAG CTCTGTTGATTTTGTTTCCGTTTG GATTTTTGGGGGAGGGGAGCACT GTGTTTATGCTGGAATATGAAGTC TGAGACCTTCGGTGCTGGGAACA CACAAGAGTTGTTGAAAGTTGAC AAGCAGACTGCGCATGTCTCTGA TGCTTTGTATCATTCTTGAGCAAT CGCTCGGTCCGTGGACAATAAAC AGTATTATCAAAGAGAAAAAAAA (SEQ ID NO: 82) |
| 2B10 WDR77 | NM_024102.2 | FIG. 27 (SEQ ID NO: 54) | NSLPLFPPQ NSMGPDIF CPGPLSL DVESLNAV FIDF* (SEQ ID NO: 68) | GCCACTTTTCCCACCCCAAAACA GCATGGGGCCTGACATCTTCTGCC CTGGTCCCCTTTCTCTTGATGTGG AAAGTCTGAATGCAGTATTTATA GACTTCTAAGGTTTTAAAATCCAG TATCAAGAAGAAAATCAGAAATA CTGGTTGGTGAAATAAAGAGTTT AGGCATTGTTGGCCTGTCTTTTTT GAAGCATGTGTGTTATGTGTAGTT AGATATATTTCACTTATGTGAGTC ATCATGGTGTTGGTCTTGTAGCCC ATTATTTTCCTGTGCTTCCCCAG CTTCCCAAAGTAGCTAGTTAGAA CTTAAGGTAAATATTTATTCTTGG GTTGGTGGAGTGGATATTGCCAG TTAGGAGTCATGGATCAATTACT GATTATATTGAAAGTAAATATAA TCAATTATGTACTTTTGAGCTTTG CAGGTTCAATTTAGGTAAAAATC ACATTATGAAACTGGGAAAGTCT GAAGGAATATGGGCAAAATATTT CTCAGTAAAGCTT (SEQ ID NO: 83) |

TABLE 3-continued

| Gene | Clone | NCBI Designation | Gene Sequence | Peptide Sequence | Clone DNA Sequence (Encoding Peptide Seqence) |
|---|---|---|---|---|---|
| 5F4 | Deaminase Domain Cont 1 | AL031320.1 | FIG. 28 (SEQ ID NO: 55) | VSGSQRVK YLLVNPLQ KKFINPCY RGF (SEQ ID NO: 69) | GAGATGTAAGCGGCTCACAAAGG GTGAAATATTTACTAGTTAACCCC CTTGCAGAAAAAGTTATCAACCC TTGCTACAGAGGATTTTAAAAAA TAAAATACAGCTTGTTCTATCTTT AGCATCTAACTGGGGAAAAGAAT CATAACATGTGAAAGAATAAATA AGAAATTGTGCTAACAGTAAGGA GTGTTATATGAAATATTACCTGAA GAACATGAAACTTGAACTTGCTA GAGATAGAGAATATTTAAGAGG CTAAGCAGAGCATTTCAGGGAAA GGGCAAGAAGAAGCCTGGGTTGT GTGTGAGGAAATCAGCTGACAGA GGAGGAGACTATTAAGGAAGCAT AAGGAAAGAAAGACAAAAAATT GGGGTAAAAATATGTACGGCTTT GAAAGCTT (SEQ ID NO: 84) |

TABLE 4

| Clone | Gene | NCBI Designation | Gene Sequence | Peptide Sequence | Clone DNA Sequence (Encoding Peptide Sequence) |
|---|---|---|---|---|---|
| 1G7 | Lamin A/C | BC014507.1 | FIG. 29 (SEQ ID NO: 85) | SCGPSMRTRWS SIRRSWRRLILPS WTMPGSLLRGT ATWWGLPTRSC SSRASASTASLP SSASSRSSWQPR RRSLRPHSS (SEQ ID NO: 112) | AAGCTTCGCCTCCTTGGCTGCCAG CTGCTTCTGGAGCTGGCTGAGCTG GGCAGAGAGGCTGTCGATGCGGA TGCGCGACTGCTGCAGCTCCTCGT GGGCAGCCCCCACCAGGTTGCTG TTCCTCTCAGCAGACTGCCTGGCA TTGTCCAGCTTGGCAGAATAAGTC TTCTCCAGCTCCTTCTTATACTGC TCCACCTGGTCCTCATGCTGGGCC CGCAG (SEQ ID NO: 142) |
| 1B10 | Lsm3 | AJ238095.1 | FIG. 30 (SEQ ID NO: 86) | MRNDRAASRQIT (SEQ ID NO: 113) | AATGAGAAATGACCGAGCAGCTT CGAGGCAGATTACATGACTTATG ATCTACATTTAAATATGATCTTGG GAGATGTGGAAGAAACTGTGACT ACTATAGAAATTGATGAAGAAAC ATATGAAGAGATATATAAATCAA CGAAACGGAATATTCCAATGCTC TTTGTCCGGGGAGATGGCGTTGTC CTGGTTGCCCCTCCACTGAGAGTT GGCTGAAACAAAGAATTTGTCCT GTATGGAAAACGGGAGACTTTGT ACAGTGGCCCTCTCTAAAAGTACA AAACATTCATAAGAGAAACCTGC ATACATTTTGATATTAAGAAATAA TTCCGGGGATTCTCCACTCCTGAA ATGAGTTGATTTGCAGATAACTCT ACAACTTCTTAAGCTAAATGGTAT TTTCATTTTTCTCAAGCTCTCCAA TAAATATGACCACCAA (SEQ ID NO: 143) |
| 2D7 | cDNA clone Chromo 19 | AC027307.5 | FIG. 31 (SEQ ID NO: 87) | LAHRPPCAEPDP GQRMELPAPVP RPRGASKPRDG TSSHCDMPNCQ HPQGPGPAGEIR SRCRSCWLRAV RCNPWLGR (SEQ ID NO: 114) | GGAGTTTCACTTTTGTTGCCCAGG ATTGAGTGCAGTGCCCCGATCTTG GCTCACTACAACCTCTGCCTCCTG GGTTCAAGCGACTCTCCTGCCTCA GTGTCCTGAGTAGCTGGGATTAC AGGCGTCTGCCACCACGCCCGGC TAATTTTGTATTTTTAGTAGAGAA CAGGTTTCACTATGTTGGTCAGGC TGGTCTTGAACTCCTGACCTCAGC GCATCCAGAATTTTAGACGGGGC CCCCAGGGTGAGGTCTTGGCACC CTCCAGTAGAGAAGAAGGGACAT GGGCCATACGTGGGGTGTCCTTTC TGGGAGCCTTGCGTCCCTTACCTG CCTAGCCAGGGATTGCACCTCAC AGCACGCAGCCAGCAGGAACGGC ACCGTGATCTGATTTCACCTGCGG GCCCTGGGCCCTGGGGGTGTTGA |

TABLE 4-continued

| CloneGene | NCBI Designation | Gene Sequence | Peptide Sequence | Clone DNA Sequence (Encoding Peptide Sequence) |
|---|---|---|---|---|
| | | | | CAATTGGGCATATCACAGTGTGA GCTAGTCCCGTCTCGGGGTTTGGA GGCTCCACGTGGCCGTGGTACAG GAGCAGGCAGTTCCATCCTCTGG CCTGGATCAGGCTCTGCACACGG AGGCCTGTGGGCCAG (SEQ ID NO: 144) |
| 1H3 | ADAM metallo-peptidase domain 9 | NR_027878.1 | FIG. 32 (SEQ ID NO: 88) | NSGASGSRNFSS CSAEDFEK (SEQ ID NO: 115) | TCGGCATAAAGTACCTCCTGGAA GGAACCGACAGTCTTTACAACAG TCACCATATGCACACTCAGCAAA TGATTTAAGCTTACAGGTACTTCC TTCGCAGCAAGGGTCCAATTCAC ATTCCTTTGGAGTACCACAGTCA ACTCTTCCCCAGCGTCCACCAACT TATTACCACAGGAGGGAGCACTA TAGGCTTCATCAGGCTTTGGAATA TTAAGAAGGCAGTTTCCTCCTTTA TTTAAAGTTACTTCTCAAAGTCCT CTGCACTGCAACTGCTAAAGTTTC TGGAACCCGATGCTCCTGAATTC (SEQ ID NO: 145) |
| 3F5 | alpha-2 glyco-protein1 (AZGP1) | NM_001185.3 | FIG. 33 (SEQ ID NO: 89) | SSVPPQDTAPYS CHVQHSSLAQPL VVPWEAS (SEQ ID NO: 116) | TCAAGCGTGCCCCCGCAGGACAC AGCCCCCTACTCCTGCCACGTGCA GCACAGCAGCCTGGC CCAGCCCCTCGTGGTGCCCTGGG AGGCCAGCTAGGAAGCAAGGGTT GGAGGCAATGTGGGATCTCAGAC CCAGTAGCTGCCCTTCCTGCCTGA TGTGGGAGCTGAACCACAGAAAT CACAGTCAATGGATCCACAAGGC CTGAGGAGCAGTGTGGGGGGACA GACAGGAGGTGGATTTGGAGACC GAAGACTGGGATGCCTGTCTTGA GTAGACTTGGACCCAAAAAATCA TCTCACCTTGAGCCCACCCCCACC CCATTGTCTAATCTGTAGAAGCCG GAAGCTTGCGGCCGCACTCGAGT AACTAGTTAACCCCTTGGGGCCTC TAAACGGGTCTTGAGGGGTTANC TNGTTNCTCGNGTGCGGCCGCNN GCTTCCGGCTTCTNCNGNTTNGNC NNTG N (SEQ ID NO: 146) |
| 5F3 | Hemk1 (minus strand) | NM_016173.3 | FIG. 7 (SEQ ID NO: 34) | VAVAQGSGALE SSKWPLLNLNG CLGRAEGQVLM ASHP (SEQ ID NO: 117) | GTGGCTGTTGCGCAGGGATCAGG TGCACTTGAGTCTTCGAAGTGGCC ATTGCTCAACTTGAATGGCTGCCT GGGTCGGGCAGAAGGCCAGGTCC TCATGGCTTCCCATCCCTAATGAC CGGAATACATGGGCTGCCAGGTC AGATGTGGGCCACATGGGAAGTC CCAGCTCTATTCTAGAAAATGCAT GTACCATCAGCTTACTGATAGAC ATTTACTGAACTTGGGTATGCCAG ATCCACAGGGGCCCCAGAGATG AGGGGGATAAGAAGGTTTCTGAA GGCATGGTACAGAAGGTGCCAGC AGAGGTATGGGCTAGGGGAGGCA GGGAGAGCACAGAGCAGGCATCC TAAAGGAGGCAGCATTTGTGTTG GAGCTTGAAGAAGTG (SEQ ID NO: 147) |
| 5F8 | Desmo-collin 3 | NG_016782.1 | FIG. 34 (SEQ ID NO: 90) | SAFRGYLANNK (SEQ ID NO: 118) | TAAGCTTTCATCTTCCCCAACCCT GATGTCTTCCTATTCTCACTGATC CCCTACTGACTCAGCTTCACGCT TCTTGATTATACCTCTCTCCTGTA GAAAAGCCTTGGCTGGCTCTCCTT TAGGATGAGAATAAATCCGAAAT CCTTAGTGTAGCATTTAGAAGTCC TATCTCCCACTTGTTTCTTAATATT CTCTTCTCTAACACCGAACTTGTT TCAAGCCTCTTTTCCAACACATGA |

TABLE 4-continued

| CloneGene | NCBI Designation | Gene Sequence | Peptide Sequence | Clone DNA Sequence (Encoding Peptide Sequence) |
|---|---|---|---|---|
| | | | | TTTCTTCTATTCTAAATCAATTTAT TTATTATTTGCTAAATAGCCCCTA AAC (SEQ ID NO: 148) |
| 1G12 DAZ Associated protein | AC027307.5 (this is for a chromosome 19 clone, not the specified gene) | FIG. 31 (SEQ ID NO: 87) | SLAHRPPCAEPD PGQRMELPAPV PRPRGASKPPRRD (SEQ ID NO: 119) | GGCTAATTTTGTATTTTTAGTAGA GAACAGGTTTCACTATGTTGGTCA GGCTGGTCTTGAACTCCTGACCTC AGCGCATCCAGAATTTTAGACGG GGCCCCCAGGGTGAGGTCTTGGC ACCCTCCAGTAGAGAAGAAGGGA CATGGGCCATACGTGGGGTGTCC TTTCTGGGAGCCTTGCGTCCCTTA CCTGCCTAGCCAGGGATTGCACCT CACAGCACGCAGCCAGCAGGAAC GGCACCGTGATCTGATTTCACCTG CGGGCCCTGGGCCCTGGGGGTGT TTGACAATTGGGGCATATCACAG TGTGAGCTAGTCCCGTCTCGGGG GTTTGGAGGCTCCACGTGGCCGT GGTACAGGAGCAGGCAGTTCCAT CCTCTGGCCTGGATCAGGCTCTGC ACACGGAGGCCTGTGGGCCAG (SEQ ID NO: 149) |
| 1G5 RPL34 (Minus strand) | NM_033625.2 | FIG. 6 (SEQ ID NO: 33) | LFIFITQKSFIFLF SFLTLCLCLQHF HNDFLLLDKEST LDPVTNTFSTHGT (SEQ ID NO: 120) | GTCTTTTCATTTTTATTACTCAAA AAAGTTTCATTTTTTTATTTAGCTT TCTGACTCTGTGCTTGTGCCTTCA ACACTTTCACAACGATTTTCTGCT CCTCGATAAGGAAAGCACGCTTG ATCCTGTCACGAACACATTTAGCA CACATGGAACCAA (SEQ ID NO: 150) |
| 3C9 PERP (Minus strand) | NM_022121.4 | FIG. 35 (SEQ ID NO: 91) | PYQIYQVMIN (SEQ ID NO: 121) | CTTACCAGATCTATCAGGTCATGA TAAATTAGACCCAGTCCATCTTTC AATCCAGTCTACTCTGGTTCTGAA CATATAAACACAAAACACTACAG ATTTATTAATATAGCATTTTCCCA CACCCTAACCCTATAAAGAACTTT AAAAGAGAAAATTTCATCTAAAT ATTTCACACTTAAAGGAAAGCCTT ACCAACTATGGCAACAGGTTTGG ACCATGAAATAGTACTTTCCTAGA TGACATATCGAGTCAACATGAAG CCTTAGCTGAAATGAATGATTCA GGATATTAATGAGAAATTCTCAC AAATGATATGCATTTAGGAAATG ATTTTGCTTTCCTTAAATAGTTCG AAGGCTTGAAAATAAACTTTTTTT TTGCATTTCTTTTAAAAGTT (SEQ ID NO: 151) |
| 3D11 Chromosome 3 UTR region ropporin/ RhoEGF | AC117381.5 (Homo sapiens 3 BAC RP11-783D3) | FIG. 36 (SEQ ID NO: 92) | VSTFLSRVGRVS LLNFLPF (SEQ ID NO: 122) | GTTTCCACATTCTTGTCAAGGGTT GGTAGGGTCAGTCTTTTAAATTTC TTGCCATTTTAGTGACTGTGCATT GGTATTTCATTGTGGTTTATTTGC ATGATGACTAATGCTCAACACCA ACTAATCATGTTGAGTATTTTTAA TGTGCTTATTTGCCACTCATATAT CTTCTTTGATGAAGTGTCTCTTCA AATATTTTGCCCATTTAAAAACTG TATTGATTCTTATTATTGAATTGC AATAATTCTTTCTATCCGGATATA TATCCTTTGCCAGATATGTGTATT ACAAATGTTTTCTCCTAGCCTTCC ACCTCAGCCTCCCAAGTAGCTGG GAATGCAGGTGTGCACCACCACT CCAGGGTTTTTGTTGTTGTTGTT GTTGTTTTTCTGTAGAGACAGGGT CTTGCCATGCTGCCGAGGCTGCTC TCAAACTCCTGGGATCAAGAAAT CCTCCTGCCTCGGCCTCCCAAAGT GCTGACATTACAAGCATGAGCCA CTGTGCCTGGCTAACTTTTCATCT TTTAAAGTAGTGTCTTGCAAAGA ACAACATTTTAATGAAGTCCATTT |

TABLE 4-continued

| CloneGene | NCBI Designation | Gene Sequence | Peptide Sequence | Clone DNA Sequence (Encoding Peptide Sequence) |
|---|---|---|---|---|
| | | | | ATCAACTTTTTGATTCATTGTCCA TGCTTTTTGCATAATAAGAAATCT TTGCCTGCCTCAAAATTGCAAAGC TT (SEQ ID NO: 152) |
| 3E4 | Cox5a | NM_004255.3 | FIG. 37 (SEQ ID NO: 93) | NTLVTYDMVPE PKIIDAALRACR RLNDFASTVRIL EVVKDKAGPHK EIYPYVIQELRPT LNELGISTPEELG LDKV (SEQ ID NO: 123) | AACACACTTGTTACCTATGATATG GTTCCAGAGCCCAAAATCATTGA TGCTGCTTTGCGGGCATGCAGAC GGTTAAATGATTTTGCTAGTACAG TTCGTATCCTAGAGGTTGTTAAGG ACAAAGCAGGACCTCATAAGGAA ATCTACCCCTATGTCATCCAGGAA CTTAGACCAACTTTAAATGAACTG GGAATCTCCACTCCGGAGGAACT GGGCCTTGACAAAGTGTAACCGC ATAATAAAGGGAAATGAGTTTG AACTG (SEQ ID NO: 153) |
| 4B11 | Mito- chondrion sequence | HQ113226.2 | FIG. 38 (SEQ ID NO: 94) | PPSHHIPNLSLTK RKPSPHSLNLIH HSRQLRWIKPNP ATQNLSILLNYP HRMNNSSSTVQP (SEQ ID NO: 124) | GCCCCCATCTCATCATATACCAAA TCTCCCCTCACTAAACGTAAGCC TTCCTCACTCTCTCAATCTTATC CATCATAGCAGGCAGTTGAGGTG GATTAAACCAAACCCAGCTACGC AAAATCTTAGCATACTCCTCAATT ACCCACATAGGATGAATAATAGC AGTTCTACCGTACAACCCTAACAT AACCATTCTTAATTTAACTATTTA TATTATCCTAACTACTACCGCA (SEQ ID NO: 154) |
| 4B3 | MYH9 (Minus strand) | NM_002473.4 | FIG. 39 (SEQ ID NO: 95) | SAGSCSSA (SEQ ID NO: 125) | GGGTTCGTGTTCCTCAGCGTAGCC ATCAGGCTTGGCCAGCTGCTCCTT GTAAAGCTGCCCCACAGTGCGGA ACATGCCCTTCCGCGTCTTGAAGG CCCCGGGCAGTGCGGTCTCCGAC ATGCCGGCCACCTGGTCCAGGCC GATGATGCGGTCCACATCCTTCCA CAGCTCCGAGACAAACTTGTCAG AGGACTGGTGGAGCAGTGTGGCG ATGTTGTCATTCAGGGGATCCATG TTCTTCATCAGCCACTCGTCAGCT TTGTAATCCACCTTGCCGGCATAG TGGATAATGCAGAAATCAGCTTT GTCCTTCAGCTGCTTGGGCTTCTG GA (SEQ ID NO: 155) |
| 4D10 | ASND1 | NM_019048.2 | FIG. 40 (SEQ ID NO: 96) | KLLFALQLWNL VLQPLLFCPNGP CSLDQELQKWK KLMKRHLINVD GSKSCP (SEQ ID NO: 126) | AAATTACTTTTCGCCTTGCAGCTG TGGAACTTGGTCTTACAGCCTCTG CTCTTCTGCCCAAACGGGCCATGC AGTTTGGATCAAGAATTGCAAAA ATGGAAAAAATTAATGAAAAGGC ATCTGATAAATGTGGACGGCTCC AAATCATGTCCTTAGAAAATCTTT CTATTGAAAAGGAGACTAAATTG TAATGTGATTCACAATGTAACAAT ATAAAAATAAGTTTTTATATAATT ATATAAAAGTAAGATACTCTGCT GCTTTACTATTGTATAATAT (SEQ ID NO: 156) |
| 4D9 | Cathepsin F | NM_003793.3 | FIG. 41 (SEQ ID NO: 97) | EDDYSYQGHMQ SCNFSAEKAKV YINDSVELSQNE QKLAAWLAKRG PISVAINAFGMQ FYRHGISRPLRP LCSPWLIDHAVL LVGYGNRSDVP FWAIKNSWGTD WGEKGYYYLHR GSGACGVNTMA SSAVVD (SEQ ID NO: 127) | CAGAGGATGACTACAGCTACCAG GGTCACATGCAGTCCTGCAACTTC TCAGCAGAGAAGGCCAAGGTCTA CATCAATGACTCCGTGGAGCTGA GCCAGAACGAGCAGAAGCTGGCA GCCTGGCTGGCCAAGAGAGGCCC AATCTCCGTGGCCATCAATGCCTT TGGCATGCAGTTTTACCGCCACGG GATCTCCCGCCCTCTCCGGCCCT CTGCAGCCCTTGGCTCATTGACCA TGCGGTGTTGCTTGTGGGCTACGG CAACCGCTCTGACGTTCCCTTTTG GGCCATCAAGAACAGCTGGGGCA CTGACTGGGGTGAGAAGGGTTAC |

TABLE 4-continued

| CloneGene | NCBI Designation | Gene Sequence | Peptide Sequence | Clone DNA Sequence (Encoding Peptide Sequence) |
|---|---|---|---|---|
| | | | | TACTACTTGCATCGCGGGTCCGGG GCCTGTGGCGTGAACACCATGGC CAGCTCGGCGGTGGTGGACTGAA GAGGGGCCCCCAGCTCGGGACCT GGTGCTGATCAGAGTGGCTGCTG CCCCAGCCTGACATGTGTCCAGG CCCCTCCCCGGGAGGTACAGCTG GCAGAGGGAAAGGCACTGGTACC TCAGGGTGAGCAGAGGGCACTGG GCTGGGGCACAGCCCCTGCTTCCC TGCACCCCATTCCCACCCTGAAGT TCTGCACCTGCACCTTTGTTGAAT TGTGGTAGCTTAGGAGGATGTCA GGGTGAAGGGTGGTATCTTGGCA GTTGAAGCTGGGGCAAGAACTCT GGGCTTGGGTAATGAGCAGGAAG AAAATTTTCTGATCTTAAGCCCAG CTGTGTTCTGCCCCCGCTTTCCTC TGTTTGATACTATAAATTTTCTGG TTCCCTTGGATTTAGGGATAGTGT CCCCCTCCATGTCCAGGAAACTTG TAACCACCCTTTTCTAACAGCAAT AAAGAGGGTCCTTGTCCCGAAAA AAAAAAAA (SEQ ID NO: 157) |
| 4F1 | Mastermind-like 2 | AP000779.4 (*Homo sapiens* genomic DNA, Chromosome 11q) | FIG. 42 (SEQ ID NO: 98) | GTNQRQTMENH (SEQ ID NO: 128) | GGCAGACAATGGAAAACCATTGA AAAGGATTAAACTGGGAAGTGAT ATGTTCTCTTTTGCATTTAAAAAG ATCACCAATGGGGATATGGAGAA TGGTCTGGATAGGTCTTAAGACTA GAGCCAGGAAGACATGTTAGAAG GCTATCAATTGACCCTAAAGACA CTGCTTCAATCCCTTTGATGACAG TGAGTTTGCTTTCCCCAGAGATAG CTTATTGGACCTCAGGACTGCTGT GAGAAACAGAAAATGCTCCTTTA CGTGTTGCCTGAAGTTAGGCTCAC CGATTTGGGGCATGTTCTAATTCT ACCAGCTAGGAACACACAGAATC GCTTGTCAAACATTCTGAGTCAGA TATGTCCTCCCTATGTCTTTTCTG AGAAAGGCATACAGAAATTCCCA GCTAAACATCACCAGTTCCCTCAT TGTTCCTCAGATGATATGGTCCA TTCAAGTTTTGTAATCATCATGGG GGTAGATGGAGGGTCCCAGTCCT CACAACCATTCTGGTAATTTACTC TTGAATTTACTGGTTCACATGTAT CTATTTTGTAGTGTGGCTCAGAAA (SEQ ID NO: 158) |
| 5D11 | CSNK2A2 | NM_001896.2 | FIG. 43 (SEQ ID NO: 99) | SSCSEYNVRVAS RYFKGPELLVD YQMYDYSLDM WSLGCMLASMI FRREPFFHGQDN YDQLVRIAKVL GTEELYGYLKK YHIDLDPHFNDI LGQHSRKRWEN LSIVRTDTLSAL RP (SEQ ID NO: 129) | TCATCCTGCTCGGAGTACAATGTT CGTGTAGCCTCAAGGTACTTCAA GGGACCAGAGCTCCTCGTGGACT ATCAGATGTATGATTATAGCTTGG ACATGTGGAGTTTGGGCTGTATGT TAGCAAGCATGATCTTTCGAAGG GAACCATTCTTCCATGGACAGGA CAACTATGACCAGCTTGTTCGCAT TGCCAAGGTTCTGGGTACAGAAG AACTGTATGGGTATCTGAAGAAG TATCACATAGACCTAGATCCACA CTTCAACGATATCCTGGGACAAC ATTCACGGAAACGCTGGGAAAAC TTATCCATAGTGAGAACAGACAC CTTGTCAGCCCTGAGGCCCTAGAT CTTCTGGACAAACTTCTGCGATAC GACCATCAACAGAGACTGACTGC CAAAGAGGCCATGGAGCACCCAT ACTTCTACCCTGTGGTGAAGGAG CAGTCCCAGCCTTGTCAGACAA TGCTGTGCTTTCCAGTGGTCTCAC GGCAGCACGATGAAGACTGGAAA GCGACGGGT (SEQ ID NO: 159) |

TABLE 4-continued

| CloneGene | NCBI Designation | Gene Sequence | Peptide Sequence | Clone DNA Sequence (Encoding Peptide Sequence) |
|---|---|---|---|---|
| 7A9 | AURKAIP1 | NM_001127230.1; NM_001127229.1; NM_0017900.2 (transcript variants) | FIG. 44 (SEQ ID NO: 100) | AARLGPSLECW AAGSAGPFTAH RRPAQVGRPLSL ARGPSWSWRRC WSPGRCPSAPW RAGSRPAASCPD WIPGPQGLWLH RNPTSVRPAR (SEQ ID NO: 130) | CGGCCGCCCGCCTTGGCCCGTCTC TGGAGTGCTGGGCAGCCGGGTCT GCGGGCCCCTTTACAGCACATCG CCCGGCCGGCCCAGGTAGGGCGGC CTCTCTCCCTCGCAAGGGGCCCA GCTGGAGCTGGAGGAGATGCTGG TCCCCAGGAAGATGTCCGTCAGC CCCCTGGAGAGCTGGCTCACGGC CCGCTGCTTCCTGCCCAGACTGGA TACCGGGACCGCAGGGACTGTGG CTCCACCGCAATCCTACCAGTGTC CGCCCAGCCAGATAGGGGAAGGG GCCGAGCAGGGGATGAAGGCGT CGCGGATGCGCCTCAAATTCAGT GCAAAAACGTGCTGAAGATCCGC CGGCGGAAGATGAA (SEQ ID NO: 160) |
| 3C1 | Chromosome 4 | AC096741.3 (Homo sapiens BAC clone RP11-327017) | FIG. 45 (SEQ ID NO: 101) | GKERENIRTNT (SEQ ID NO: 131) | GGCAGGGAAGGGAGAACATTAGG ACAAATACCTAATGCACGCCAGG CCCTANTAATCGTAGATGATGGG TTGATGGGTGTAGCAAACCACCA TGGCACATGTATATCTATGTAACA AACCTGCACATTCTGTACATGTAT CCCAGAACTTCAAGTAAAATTTTA AAAAATTCAAAAAAAGTAATAGG AAAAGGGGAAACATCCACGTGAG CAGTCCAGTTTCCCAATCTGGAAC TTGGAGCTGTTCACCTGGTGGGTG TTTGTGACTATTCAGACACAGACA ACAAAGGCTACTCCAGATTGAAG TGCACTGCTTACTTTCAGTGACCT CATAGAACTACTCAACATTGTTTT TGGTGATTCCTGTGCTATGGTTTG AATGGCTCCGCTCCAAAACTCAG GTGTTGCCAATGNGATGGTATTA AGAAGTAGGGCATTTAAAAAACA ACAACAGGCCTGGCGCGGTGGCC CACGCCTGTAATCCCAGCACTTTG GGAGGCTAAGGCGGGCGGATCAC CGGAGGTCAGGAATTCAAAACCA GCCTGGCCAACATGGCGAAACCC TGTCTCTACTAAAAATACAAAAA TTAGCCAGGCATGGTTGCGGGCG CCTGTAATCCCGGCTACTCGGGA GGCTGAGGCAGGGGAATCCTTGA ACCCGGGA (SEQ ID NO: 161) |
| 3C3 | ARF6 | NM_001663.3 | FIG. 46 (SEQ ID NO: 102) | PKCRLQRQYTG KGGVGFVYEGV (SEQ ID NO: 132) | GAAATGTAGACTGCAAAGGCAGT ATACAGGAAAAGGTGGAGTGGGT TTGTTTATGAGGGTGTCTGAAAA CTAAAATTGAGCGGGATATCATG GTATAGTTGGACAGTATTGGTCCT TCACACTTTGGCCATATTGTATAA TGGAGCTTTTACCAAAGATGTATG AGAAGTGTAAGACTATAAAAAAA TGAACTATTCAAAGTAAAACTCTT AACAAACATTTTACTTAAAGCAG ATGCAAAAGGGTATTCTCATGTA GGCTCCTGTTGGTGCAGAGGGAT TTTTTTGATTTCAGGATACAACTA AAGTACGAAGTTCTCAGTTTCACT TTAGTAGAAAGAGCTCTAGAAAT GAGGCTGATAAACACATCTAAGA ACACTGGTTGCTTTCTAAAATTTC CAAAGCTCCACCATAAATGTAAT TTTTAGTGTTTCAAATGATTGCAT TTTAAAGTATATAAATATGGGTTA TCCAATATCAATGCTATAGTAACA TCCTGAAACAAAACAAGCACAAA GGTATAAATGCCTAAACTGGAGG AAGCTTG (SEQ ID NO: 162) |

TABLE 4-continued

| CloneGene | NCBI Designation | Gene Sequence | Peptide Sequence | Clone DNA Sequence (Encoding Peptide Sequence) |
|---|---|---|---|---|
| 3D1 | 3' UTR region JAG1 | AL135937.22 (Human DNA sequence from clone RP1-278O22 on chromosome 20) | FIG. 47 (SEQ ID NO: 103) | QTQTHTSAPLKC QPWSFVEARICH GSQLVRCPVQH PSRIS (SEQ ID NO: 133) | CTCAGACTCAAACACACACCTCC GCTCCCTTGAAGTGCCAGCCCTGG AGCTTTGTTGAGGCTCGCATCTGC CACGGGAGTCAGCTAGTACGTTG CCCAGTTCAACATCCATCCAGGAT TTCATAGGAACTTGAGAATCATTG TTTTTGGCTTGAATCCTGGGTTTG AGGTTTCTTCGTGTAGGAATCTGA AAAAAGGATTTGGAAACGTTGTT GTCTCTAATCCCAAAGTATGTATC TGGGAGGCTGCCTTCGCCATCACC CACCTAATAACTCAGG (SEQ ID NO: 163) |
| 5A5 | Mito-chondrion sequence | HQ113226.2 | FIG. 48 (SEQ ID NO: 104) | PRLHQXKANYI YSIDPIT (SEQ ID NO: 134) | AGACTTCACCAGTCAAAGCGAAC TACATATACTCAATTGATCCAATA ACTTGACCAACGGAACAAGTTAC CCTAGGGATAACAGCGCAATCCT ATTCTAGAGTCCATATCAACAATA GGGTTTACGACCTCGATGTTGGAT CAGGACATCCCGATGGTGCAGCC GCTATTAAAGGTTCGTTTGTTCAA CGATTAAAGTCCTACGTGATCTGA GTTCAGACCGGAGTAATCCAGGT CGGTTTCTATCTACTTCAAATTCC TCCCTGTACGAAAGGACAAGAGA AATAAGGCCTACTTCACAAAGCG CCTTCCCCCGTAAATGATATCATC TCAAGCTT (SEQ ID NO: 164) |
| 3E1 | Chromo-some 20 | AL135937.22 | FIG. 49 (SEQ ID NO: 105) | P Q T T A P R R A R P R R S (SEQ ID NO: 135) | CTCGCTCAAACACACACCTCCGCT CCCTTGAAGTGCCAGCCCTGGAG CTTTGTTGAGGCTCGCATCTGCCA CGGGAGTCAGCTAGTACGTTGCC CAGTTCAACATCCATCCAGGATTT CATAGGAACTTGAGAATCATTGTT TTTGGCTTGAATCCTGGGTTTGAG GTTCTTCGTGTAGGAATCTGAAA AAAGGATTTGGAAACGTTGTTGT CTCTAATCCCAAAGTATGTATCTG GGAGGCTGCCTTCGCCATCACCC ACCTAATAACTCAGGC (SEQ ID NO: 165) |
| 5A9 | Chromo-some 6 clone UTR region (Minus strand) | AL034375.23 | FIG. 50 (SEQ ID NO: 106) | G T I S I V C C W G C L C Q H L V Q C L A D G C S I N I D L M G Y E G V N I K L A F I Q Q L L (SEQ ID NO: 136) | ATTGTTTGTTGTTGGGGGTGTCTT TGTCAGCATCTAGTACAGTGCCTG GCAGATGGATGCTCAATAAATAT TGATTTAATGGGTTATGAGGGTGT TAATATAAAATTAGCATTTATTCA GCAACTACTATGAGTCAGCCACT GGGCTAAGTGGCTTACATGTTAA GAACCTCACAGAAGCCAGGTGTG GTGGCTCACGCCTGTAATCCCAGC ACTTTGGGAGGCTGAAGCGGGCA GATCACCTGAGGTCAGGAGTTTG AGTCCAGGCTGGCCAACGTGGTG AAACCCCATCTCTACTAAAAATA CAAAAATTAGCCAGTTGTGGTGG CAGGCGCCTGTAGTCCCAGCCAC TCAGGAGGCTAAGGCAGGAGAAT AGCTGGAACCCGGGAGGTGGAGA TTGCAGTGAGCCAAGATTGCACC ACTGCACTCCAGCCTGGGTGACA GAGTGAGACTCTGTCTCCAAAAA AAAAAGAAAAAGAAAAAGAACC TCCAGCAACCTAGTAGGTGAGCC CGGTTACTCTTGTTTTACAGGTGA GAAAATTGAGCCCTAGAGAAATA AAGTAACTTGCTTCAGGTCTCATG GTTAAGGGGAACCTGGGCCCTAA CAGTCCACTTCCTGTACCTTCAAC CACGGTTCTACCGCCTCCGCTAGG AAATGGCCCGAGGACATTCCTTA GCTGGCTTCAGCTTGCTCTTTTTC CCCTGCGGTCCACCCCTG (SEQ ID NO: 166) |

TABLE 4-continued

| CloneGene | NCBI Designation | Gene Sequence | Peptide Sequence | Clone DNA Sequence (Encoding Peptide Sequence) |
|---|---|---|---|---|
| 5H2 MAPKKK5 | NG_011965.1 | FIG. 51 (SEQ ID NO: 107) | G M S H H A W P R P S F F N T E Y F (SEQ ID NO: 137) | AGAGGGAGTATAGGGCTGTGCAC AGAGACTATGATGGCCGTGCTAA GGTAAGAGTATTGATAATGTAAG CATACTTCCTCTATCAACAATAAT TGTTAACAGCTGCTTCAAGCACTT GATATTACCACTAGTTGTTAACTG AATCAAGCATGTGCTCCAAGTTC ACATTAATGTGAATTGAACAGCA TTGTGTACGTACGAGGAGCTTCAT GCAAGTGTTATACACTGCACTCAC AAGTATTATGATCTTACTAAGCAT TAGAAATACTCTGTGTTAAAGAA GCTTGGTCTAGGCCAAGCGTGGT GGCTCATGCCT (SEQ ID NO: 167) |
| 1H5 RAS p21 Protein activator (RASA1) | BC020761.1 | FIG. 52 (SEQ ID NO: 108) | D R R P G S F V L S F L S Q Met N V V T H F R I I A Met C G D Y Y I G G R R F S S L S D L I G Y Y S H V S C L L K G E K L L Y P V A P P E P V E D R R R V R A I L P Y T K V P D T D E I S F L K G D Met F I V H N E L E D G W Met W V T N L R T D E Q G L I V E D L V E E V G R E E D P H E G K I W F H G K I S K Q E A (SEQ ID NO: 138) | GATCGGAGGCCAGGGTCCTTTGT ACTTTCATTTCTTAGCCAGATGAA TGTTGTCACCCATTTTAGGATTAT TGCTATGTGTGGAGATTACTACAT TGGTGGAAGACGTTTTTCTTCACT GTCAGACCTAATAGGTTATTACA GTCATGTTTCTTGTTTGCTTAAAG GAGAAAAATTACTTTACCCAGTT GCACCACCAGAGCCAGTAGAAGA TAGAAGGCGTGTACGAGCTATTC TACCTTACACAAAAGTACCAGAC ACTGATGAAATAAGTTTCTTAAA AGGAGATATGTTCATTGTTCATAA TGAATTAGAAGATGGATGGATGT GGGTTACAAATTTAAGAACAGAT GAACAAGGCCTTATTGTTGAAGA CCTAGTAGAAGAGGTGGGCCGGG AAGAAGATCCACATGAAGGAAAA ATATGGTTCCATGGGAAGATTTCC AAACAGGAAGCTT (SEQ ID NO: 168) |
| 18H9 Hsp90b | Ay359878.1 | FIG. 53 (SEQ ID NO: 109) | YFAYLISEQNEE NKINHNTQHPIL LSRVREGMGLD TLSLLPSTQGQE REKNTRHQQGE PGGTGALEAAV GAHGDTIQGHK FSNYELLT (SEQ ID NO: 139) | TGAAGTGG CAGCAGAGGAACC CA ATGCTGCAGTTCCTGATGAGATCC CCCCTCTCGAGGGCGATGAGGAT GCGTCTCGCATGGAAGAAGTCGA TTAGGTTAGGAGTTCATAGTTGGA AAACTTGTGCCCTTGTATAGTGTC CCCATGGGCTCCCACTGCAGCCTC GAGTGCCCCTGTCCCACCTGGCTC CCCTGCTGGTGTCTAGTGTTTTT TTCCCTCTCCTGTCCTTGTGTTGA AGGCAGTAAACTAAGGGTGTCAA GCCCCATTCCCTCTCTCACTCTTG ACAGCAGGATTGGATGTTGTGTA TTGTGGTTTATTTTATTTTCTTCAT TTTGTTCTGAAATTAAGTATGCAA AATAA (SEQ ID NO: 169) |
| 4D7 ribosomal protein S6 (RPS6) | NM_001010.2 | FIG. 54 (SEQ ID NO: 110) | C I V D A N L S V L N L V I V K K G E K D I P G L T D T T V P R R L G P K R A S R I R K L F N L S K E D D V R Q Y V V R K P L N K E G K K P R T K A P K I Q R L V T P R V L Q H K R R R I A L K K Q R T K K N K E E A A E Y A K L L A K R Met K E A K E K R Q E Q I A K R | GTTGCATTGTGGATGCAAATCTGA GCGTTCTCAACTTGGTTATTGTAA AAAAAGGAGAGAAGGATATTCCT GGACTGACTGATACTACAGTGCC TCGCCGCCTGGGCCCCAAAAGAG CTAGCAGAATCCGCAAACTTTTCA ATCTCTAAAGAAGATGATGTCC GCCAGTATGTTGTAAGAAAGCCC TTAAATAAAGAAGGTAAGAAACC TAGGACCAAAGCACCCAAGATTC AGCGTCTTGTTACTCCACGTGTCC TGCAGCACAAACGGCGGCGTATT GCTCTGAAGAAGCAGCGTACCAA GAAAAATAAAGAAGAGGCTGCAG AATATGCTAAACTTTTGGCCAAG AGAATGAAGGAGGCTAAGGAGA AGCGCCAGGAACAAATTGCGAAG AGACGCAGACTTTCCTCTCTGCGA GCTTCTACTTCTAAGTCTGAATCC |

TABLE 4-continued

| CloneGene | NCBI Designation | Gene Sequence | Peptide Sequence | Clone DNA Sequence (Encoding Peptide Sequence) |
|---|---|---|---|---|
| | | | R R L S S L R A S T S K S E S S Q K (SEQ ID NO: 140) | AGTCAGAAATAAGATTTTTTGAGT AACAAATAAATAAGATCAGA (SEQ ID NO: 170) |
| 36C4 | Homo sapiens chromo- some 3 genomic contig | AC128709 (Homo sapiens 3 BAC RP13- 616I3) | FIG. 55 (SEQ ID NO: 111) L I C I S L M A N D V E H L F M F I C H L S (SEQ ID NO: 141) | CCTGGGCAGTGATTAGGTCATAA AGGTGGAGTCCTCATGGATGGA TTAGTGTCTTTATAAAAGAGACCT TTGCCATGTGAGGTTACAGTGAG AAGACATCTGTCTATGAAGAAAG TGGGCCCTCACCAAACACAGTCT GCTGGCACTTTGCACTTCAACTCC CCAGCTTCCAGAACTGTAAGGAA TATAAGTCTGTTGTTGGTAAGCCA CCCGGTCTATGATATTTTGTTATA GCAGCCCAAACAGACTAAGACAG GTGACAAATAAACATGAAAAGAT GTTCAACATCATTAGCCATTAGGG AAATGCAGATTAAAA (SEQ ID NO: 171) |

An antibody, such as an autoantibody, to one or more of a protein, or a fragment of a protein, encoded by a gene such as listed in Tables 1, 2, 3 or 4, or a polypeptide encoded by a UTR sequence of a gene such as one listed in Tables 1, 2, 3 or 4, can be detected according to one or more methods described herein and used to characterize a cancer, such as prostate cancer. Many of the proteins may have a role in various cancers, including prostate cancer. For example, the human DCHS1 protein (protocadherin-16 precursor) is believed to be a calcium-dependent cell adhesion protein found in the cell membrane of fibroblast cells. Without being bound by theory, DCHS1 is a cadherin, a class of type-1 transmembrane proteins. Cadherins typically play important roles in cellular adhesion, for example, by binding cells expressing similar cadherins to each other. Structurally, DCHS1 is thought to contain 27 cadherin repeats (extracellular calcium ion-binding domains). DCHS1 expression has been associated with certain cancers, potentially playing a role in tumor adherence (see, e.g., Sjöblom, et. al. Science, (2006) 314:268-274).

Another of the proteins, CEP164 is believed to be a centrosomal protein which binds chromatin and plays a role in the DNA damage-activated signaling cascade. It is known to interact with ataxia telangiectasia mutated (ATM) and ATM/Rad3-related (ATR) kinases which phosphorylate CEP164 upon replication stress, ultraviolet radiation (UV), and ionizing radiation (IR). CEP164 also plays a role in cell cycle regulation, specifically at the G2/M checkpoint and in nuclear division (see, e.g., Sivasubramaniam et al., Genes & Dev. (2008); 22(5):687-600). As CEP 164 plays a role in genome stabilization, misregulation or mutation of this gene and/or protein can play a role in certain cancers.

In a further example, the human KBTBD6 (kelch repeat and BTB (POZ) domain containing 6) is a protein expressed in a wide variety of normal tissues. Its expression and/or misregulation has also been noted in multiple cancer types, including prostate, ovarian, kidney and lung tumors. The function of the protein is not currently known, however, the presence of the kelch repeat and BTB domain suggest that the protein is involved in protein-protein interactions and actin filament organization.

Certain ribosomal proteins, such as RPS19 and RPL34 have also been associated with certain cancers. RPS19 (ribosomal protein S19) encodes a ribosomal protein that is a component of the 40S subunit. Located in the cytoplasm as part of the ribosomal complex, mutations in this gene are associated with Diamond-Blackfan anemia, suggesting a non-ribosomal function for the protein in erythropoietic differentiation. RPS19 protein is also known to interact with fibroblast growth factor-2 (see, e.g., Soulet et al., Biochem. Biophys. Res. Commun. (2001); 289:591-596). Increased expression of RPS19 has been associated with some cancers, but the role of RPS19 in cancer development is unknown. RPL34 (60S Ribosomal protein L34) is a ribosomal protein that is a component of the 60S subunit and is located in the cytoplasm. Expression of the gene encoding the RPL34 protein is known to be regulated by c-MYC and has been shown to have increased expression in primary invasive and metastatic breast cancer cells and colorectal cancer cells (see, e.g., Zucchi et al., Proc. Nat'l Acad. Sci., (2004); 101:18147-18152; Sjöblom, et. al. Science, (2006) 314:268-274).

Certain nucleic acid-binding proteins, such as RMB6 and HEMK1 have also been associated with certain cancers when misregulated and/or mutated. RBM6 (RNA binding protein 6) is a cytosolic protein that binds to poly-G homopolymers in vitro, but its function in vivo is not currently known. The protein thought to be phosphorylated (potentially by ATM or ATR) in its active form. The gene encoding the protein, without being bound by theory, is located in a portion of the genome, modifications of which are associated with cancerous transformation, such as lung carcinomas. Additionally, translocations of the gene which result in aberrant fusion proteins have been reported to be associated with cancer cells (see, e.g., Gu et al., Blood, (2007); 110:323-333). The human HEMK1 (HEMK methyltransferase family protein 1) protein is an S-adenosylmethionine-dependent methyltransferase and is also thought to bind nucleic acids. HEMK1 is considered a tumor-suppressor, misregulation of which is associated with various cancers, including prostate cancer, pancreatic cancer and liver cancer (see, e.g., U.S. Pat. App. Pub. No. 2008/0213791).

Thus one or more polypeptide probes, such as a fragment of a protein encoded by a gene, or a polypeptide encoded by a sequence of a UTR region of a gene, such as a gene listed in Tables 1, 2, 3 or 4, can be used to detect one or more antibodies, such as autoantibodies, from a sample from a subject. In one embodiment, the polypeptide probe comprises a polypeptide sequence selected from SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, the polypeptide probe comprises a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the polypeptide probe comprises the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In one embodiment, a polypeptide probe is a fragment of a protein encoded by CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain, or may be a polypeptide encoded by a UTR sequence of the gene, such as the 5' or 3' UTR sequence of CEP164, RPL34, BRMSL1, NKX3-1, RPSA, Cytochrome C oxidase 5 Subunit, UTR-region of chromosome 11, MAP-KKK9, cDNA clone XR_113641.1, PSA, H2aa4, UBE2I, TIMP2, WDR77, or Deaminase Domain. In one embodiment, a polypeptide probe can be a fragment of a protein encoded by FAM53B, 5'UTR BMI1, RP3-323M22, or LOC388789. In one embodiment, a polypeptide probe comprises a peptide sequence, or fragment thereof, such as those listed in Tables 1, 2, 3, and 4. The polypeptide probe can comprise SEQ ID NO: 2, 5, 9, 11, 14, 56, 57, 58, 59, 60, 61, 62, 63, 64, 65, 66, 67, 68, 69, or a fragment thereof, or a fragment thereof. In another embodiment, the polypeptide probe comprises a polypeptide encoded by SEQ ID NO: 16, 19, 23, 25, 28, 70, 71, 72, 73, 74, 75, 76, 77, 78, 79, 80, 81, 82, 83, 84, or a fragment thereof.

In another embodiment, a polypeptide probe is a fragment of a protein encoded by DCHS1, CEP164, KBTBD6, RPS19, RPL34, RNA binding protein 6, or Hemk1, or may be a polypeptide encoded by a UTR sequence of the gene, such as the 5' or 3' UTR sequence of DCHS1, CEP164, KBTBD6, RPS19, RPL34, RNA binding protein 6, or Hemk1. In one embodiment, a polypeptide probe can be a fragment of a protein encoded by eIF4G1, 5'UTR BMI1, BRD2, RP3-323M22, SFRS14, or LOC388789. In one embodiment, a polypeptide probe comprises a peptide sequence, or fragment thereof, such as those listed in Tables 1 and 2. The polypeptide probe can comprise SEQ ID NO: 1, 2, 3, 4, 5, 6, 7, 8, 9, 10, 11, 12, 13 or 14, or a fragment thereof. In another embodiment, the polypeptide probe comprises a polypeptide encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof.

Antibody Profiling Panel

Also provided herein is an antibody profiling panel. A panel as provided herein can be used to analyze one or more antibodies to a plurality of polypeptide probes, such as one or more autoantibodies. A panel allows for the simultaneous analysis of multiple antibodies, such as autoantibodies, to a plurality of polypeptide probes correlating with carcinogenesis and/or metastasis. For example, a panel can include markers identified as correlating with cancerous tissue, metastatic cancer, localized cancer that is likely to metastasize, pre-cancerous tissue that is likely to become cancerous, and pre-cancerous tissue that is not likely to become cancerous. Depending on the subject, panels may be analyzed alone or in combination in order to provide the best possible diagnosis and/or prognosis.

In one embodiment, an antibody profiling panel can comprise a plurality of polypeptide probes, wherein one or more of the probes is capable of binding an antibody. In another embodiment an antibody profiling panel can comprise a plurality of probes, wherein one or more of the probes is capable of binding an antibody that targets a foreign antigen. In another embodiment an antibody profiling panel can comprise a plurality of probes, wherein each of the probes is capable of binding an autoantibody.

In one embodiment, an antibody profiling panel comprises 2-100 probes, 50-200 probes, 100-500 probes 200-750 probes, 200-1000 probes, 2-5,000 probes or 2-10,000 probes. In one embodiment, an antibody profiling panel comprises at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 polypeptide probes. In another embodiment, an antibody profiling panel comprises at least about 50, 100, 150, 200, 250, 500, 750, 1000, 5000, 10,000, 15,000, 20,000, 25,000, 30,000, 40,000, 50,000, 60,000, 70,000, 75,000, or 100,000 polypeptide probes. In one embodiment, the probes are polypeptide probes. In another embodiment, the probes are molecules that mimic an epitope bound by a particular antibody.

An antibody profiling panel can comprise at least 2, 3, 4, 5, 6, 7, 8, 9, 10, 11, 12, 13, or 14 polypeptide probes, wherein the polypeptide probes are a fragment of a protein encoded by a gene, or a fragment encoded by a sequence of a UTR region of a gene, such as genes listed in Tables 1, 2, 3, or 4. In one embodiment, the polypeptide probe comprises a polypeptide sequence selected from SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, the polypeptide probe comprises a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the polypeptide probe comprises the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In one embodiment, an antibody profiling panel comprises a plurality of polypeptide probes, wherein at least a subset of the polypeptide probes is a fragment of a protein encoded by a gene, or a fragment encoded by a sequence of a UTR region of a gene, wherein the gene is CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain. In one embodiment, the polypeptide probe can comprise a fragment of a protein encoded by a gene, or a fragment encoded by a sequence of a UTR region of a gene, wherein the gene is FAM53B, 5'UTR BMI1, RP3-323M22, or LOC388789.

In another embodiment, an antibody profiling panel comprises a plurality of polypeptide probes, wherein at least a subset of the polypeptide probes is a fragment of a protein encoded by a gene, or a fragment encoded by a sequence of a UTR region of a gene, wherein the gene is DCHS1, CEP164, KBTBD6, RPS19, RPL34, RNA binding protein 6, or Hemk1. In one embodiment, the polypeptide probe can comprise a fragment of a protein encoded by a gene, or a fragment encoded by a sequence of a UTR region of a gene, wherein the gene is eIF4G1, 5'UTR BMI1, BRD2, RP3-323M22, SFRS14, or LOC388789.

In one embodiment, an antibody profiling panel comprises a plurality of polypeptide probes, wherein at least a subset of the polypeptide probes is a peptide sequence, or fragment thereof, as listed in Tables 1, 2, 3, or 4. In one embodiment, an antibody profiling panel comprises a plurality of polypeptide probes, wherein at least a subset of the polypeptide probes comprises a polypeptide sequence selected from SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, an antibody profiling panel comprises a plurality of polypeptide probes, wherein at least a subset of the polypeptide probes comprises a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the polypeptide probe comprises the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In another embodiment, an antibody profiling panel comprises a plurality of polypeptide probes, wherein at least a subset of the polypeptide probes comprises SEQ ID NO: 2, 5, 9, 11, 14, 56, 57, 58, 59, 60, 61, 62, 63, 64, 65, 66, 67, 68, 69, or a fragment thereof, or a fragment thereof. In another embodiment, an antibody profiling panel comprises a plurality of polypeptide probes, wherein at least a subset of the polypeptide probes is encoded by SEQ ID NO: 16, 19, 23, 25, 28, 70, 71, 72, 73, 74, 75, 76, 77, 78, 79, 80, 81, 82, 83, 84, or a fragment thereof.

In one embodiment, an antibody profiling panel comprises a plurality of polypeptide probes, wherein at least a subset of the polypeptide probes comprises SEQ ID NO: 1, 2, 3, 4, 5, 6, 7, 8, 9, 10, 11, 12, 13 or 14, or a fragment thereof. In another embodiment, an antibody profiling panel comprises a plurality of polypeptide probes, wherein at least a subset of the polypeptide probes is encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof.

In one embodiment, an antibody profiling panel can also comprise one or more polypeptide probes of the protein PSA, or fragment of PSA, in combination with one or more of the polypeptide probes discussed herein.

In one embodiment, an antibody profiling panel can comprise polypeptide probes including a full-length protein or fragment of PSA and one or more polypeptide probes comprising SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, an antibody profiling panel can comprise polypeptide probes including a full-length protein or fragment of PSA and one or more polypeptide probes comprising a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the polypeptide probe comprises the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In another embodiment, an antibody profiling panel can comprise polypeptide probes including a full-length protein or fragment of PSA and a full-length protein encoded by a gene, fragment of a protein encoded by a gene, or a fragment encoded by a sequence of a UTR region of a gene, wherein the gene is CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, or Deaminase Domain. In yet another embodiment, an antibody profiling panel can comprise a plurality of polypeptide probes, wherein the probes include a full-length protein or fragment of PSA and a full-length protein encoded by a gene, fragment of a protein encoded by a gene, or a fragment encoded by a sequence of a UTR region of a gene, wherein the gene is FAM53B, 5'UTR BMI1, RP3-323M22, or LOC388789.

In another embodiment, an antibody profiling panel can comprise polypeptide probes including a full-length protein or fragment of PSA and a full-length protein encoded by a gene, fragment of a protein encoded by a gene, or a fragment encoded by a sequence of a UTR region of a gene, wherein the gene is DCHS1, CEP164, KBTBD6, RPS19, RPL34, RNA binding protein 6, or Hemk1. In yet another embodiment, an antibody profiling panel can comprise a plurality of polypeptide probes, wherein the probes include a full-length protein or fragment of PSA and a full-length protein encoded by a gene, fragment of a protein encoded by a gene, or a fragment encoded by a sequence of a UTR region of a gene, wherein the gene is eIF4G1, 5'UTR BMI1, BRD2, RP3-323M22, SFRS14, or LOC388789.

In another embodiment, an autoantibody profiling panel can comprise a plurality of polypeptide probes, wherein the probes includes a full-length protein or fragment of PSA and one or probes comprising a peptide sequence, or fragment thereof, as listed in Tables 1, 2, 3 and 4. In one embodiment, an autoantibody profiling panel can comprise a plurality of polypeptide probes, wherein the probes includes a full-length protein or fragment of PSA and one or more probes comprising SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, an autoantibody profiling panel can comprise a plurality of polypeptide probes, wherein the probes includes a full-length protein or fragment of PSA and one or more probes comprising a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, an autoantibody profiling panel can comprise a plurality of polypeptide probes, wherein the probes includes a full-length protein or fragment of PSA and one or more probes comprising the full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In another embodiment, an autoantibody profiling panel can comprise a plurality of polypeptide probes, wherein the probes includes a full-length protein or fragment of PSA and one or more probes comprising SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, or a fragment thereof.

In another embodiment, an autoantibody profiling panel can comprise a plurality of polypeptide probes, wherein the probes includes a full-length protein or fragment of PSA and one or more probes comprising SEQ ID NO: 2, 5, 9, 11, 14, 56, 57, 58, 59, 60, 61, 62, 63, 64, 65, 66, 67, 68, 69, or a fragment thereof, or a fragment thereof; or a polypeptide sequence encoded by a sequence selected from SEQ ID NOs. 16, 19, 23, 25, 28, 70, 71, 72, 73, 74, 75, 76, 77, 78, 79, 80, 81, 82, 83, 84, or a fragment thereof.

In one embodiment, a PSA polypeptide probe can be combined with any two or more of the polypeptide probes described herein, such as a polypeptide probe derived from a protein encoded by a gene, fragment of a protein encoded by a gene, or a fragment encoded by a sequence of a UTR region of a gene, wherein the gene is CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789.

In another embodiment, a PSA polypeptide probe can be combined with any two or more of the polypeptide probes described herein, such as a polypeptide probe derived from a protein encoded by a gene, fragment of a protein encoded by a gene, or a fragment encoded by a sequence of a UTR region of a gene, wherein the gene is DCHS1, CEP164, KBTBD6, RPS19, RPL34, RNA binding protein 6, Hemk1, eIF4G1, 5'UTR BMI1, BRD2, RP3-323M22, SFRS14, or LOC388789.

In yet another embodiment, a PSA polypeptide probe can be combined with at least 3, 4, 5, 6, 7, 8, 9, 10, 11, 12, 13 or 14 of polypeptide probes disclosed herein, such as listed in Tables 1, 2, 3, and 4. In one embodiment, a polypeptide probe comprises SEQ ID NO: 2, 5, 9, 11, 14, 56, 57, 58, 59, 60, 61, 62, 63, 64, 65, 66, 67, 68, 69, or a fragment thereof, or a fragment thereof. In one embodiment, a polypeptide probe comprises SEQ ID NO: 1, 2, 3, 4, 5, 6, 7, 8, 9, 10, 11, 12, 13 or 14, or a fragment thereof. In another embodiment, a polypeptide probe comprises SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof.

In another embodiment, a polypeptide probe comprises a polypeptide encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof. In another embodiment, a polypeptide probe comprises a polypeptide encoded by SEQ ID NO: 16, 19, 23, 25, 28, 70, 71, 72, 73, 74, 75, 76, 77, 78, 79, 80, 81, 82, 83, 84, or a fragment thereof. In yet another embodiment a polypeptide probe comprises a polypeptide encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof.

In one embodiment, a polypeptide probe disclosed herein is attached to a substrate (e.g., glass slide chip or nanowell chip). A polypeptide probe can be directly or indirectly attached to the substrate. In one embodiment, a polypeptide probe is attached to a substrate via a phage. The substrate can be any physically separable solid to which a polypeptide probe can be directly or indirectly attached including, but not limited to, surfaces provided by microarrays and wells, particles such as beads, columns, optical fibers, wipes, glass and modified or functionalized glass, quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polypropylene, polyethylene, polybutylene, polyurethanes, TEFLON™, etc.), polysaccharides, nylon or nitrocellulose, resins, silica or silica-based materials including silicon and modified silicon, carbon, metals, inorganic glasses, plastics, ceramics, conducting polymers (including polymers such as polypyrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers.

The polypeptide probe can bound to a planar surface or to a particle, such as a bead or microsphere. In one embodiment, the polypeptide probe is attached to a bead. The bead can be a polystyrene, brominated polystyrene, polyacrylic acid, polyacrylonitrile, polyacrylamide, polyacrolein, polydimethylsiloxane, polybutadiene, polyisoprene, polyurethane, polyvinyl acetate, polyvinylchloride, polyvinylpyridine, polyvinylbenzylchloride, polyvinyltoluene, polyvinylidene chloride, polydivinylbenzene, polyglycidylmethacrylate, polymethylmethacrylate, or copolymers, blends, composites, or combination thereof. The bead can have a diameter of between about 1 nm-1000 μm, 1 nm-500 μm, 5 nm-500 μm, or 10 nm-100 μm. In one embodiment, the bead has a diameter of between about 10 nm and 100 μm. In yet another embodiment, the bead has a diameter of less than about 1000 μm, 500 μm, 400 μm, 300 μm, 200 μm, or 100 μm.

In one embodiment, the bead is labeled or stained with more than one dye, such as at least 2, 3, 4, 5, 6, 7, 8, 9, or 10 different dyes. In one embodiment, the bead is labeled or stained with two dyes. In another embodiment, the two dyes are hydrophobic. In another embodiment, the two dyes are fluorescent dyes, such as squaric acid-based dyes. In yet another embodiment, the squaric acid-based dyes are selected from cyclobutenedione derivatives, symmetrical and unsymmetrical squaraines, substituted cephalosporin compounds, fluorinated squaraine compositions, alkylalkoxy squaraines, or squarylium compounds. In another embodiment, the squaric acid-based dyes are selected from a red fluorescent dye and an orange fluorescent dye, such as the red fluorescent dye comprising 1,3-bis(1,3-dihydro-1,3,3-trimethyl-2H-indol-2-ylidene)methyl]-2,4-dihydro xycyclobutenediylium, bis(inner salt) and the orange fluorescent dye comprising 2-(3,5-dimethylpyrrol-2-yl)-4-(3,5-dimethyl-2H-pyrrol-2-ylidene)-3-hydroxy-2-cyclobuten-1-one.

In one embodiment, the substrate is coated using passive or chemically-derivatized coatings with any number of materials, including polymers, such as dextrans, acrylamides, gelatins or agarose. Such coatings can facilitate the use of the array with a biological sample.

Cancer Screening

A presence of an immune response to a specific protein expressed in cancerous cells can be indicative of a presence of cancer. Accordingly, the present invention provides a method (e.g., diagnostic or screening method) for detecting a presence of an antibody, such as an autoantibody, to a tumor or tumor-associated antigen. In one embodiment, the presence of an antibody in cancerous but not cancerous cells is indicative of the presence of cancer. In one embodiment, the antibody is an antibody to a tumor antigen.

A method or composition disclosed herein can find utility in the diagnosis, screening, or characterization of a cancer. In one embodiment, a presence of an antibody, such as an autoantibody, to a specific protein can be indicative of a cancer. In another embodiment, detection of an antibody in a sample, such as an autoantibody, can be indicative of a specific stage or sub-type of the same cancer. The information obtained by detecting an antibody as described herein can be used to determine a prognosis or theranosis, wherein an appropriate course of treatment can be determined. In another embodiment, a subject with a specific antibody or stage of cancer can respond differently to a given treatment than individuals lacking the antibody. The information obtained from a method disclosed herein can thus provide for the personalization of diagnosis and treatment.

In one embodiment, a cancer is characterized by detecting the level or presence or absence of an antibody, such as an autoantibody, in a sample. The cancer can be, but is not limited to, breast cancer, ovarian cancer, lung cancer, colon cancer, hyperplastic polyp, adenoma, colorectal cancer, high grade dysplasia, low grade dysplasia, prostatic hyperplasia, prostate cancer, melanoma, pancreatic cancer, brain cancer (such as a glioblastoma), hematological malignancy, hepatocellular carcinoma, cervical cancer, endometrial cancer, head and neck cancer, esophageal cancer, gastrointestinal stromal tumor (GIST), renal cell carcinoma (RCC) or gastric cancer. The colorectal cancer can be CRC Dukes B or Dukes C-D. The hematological malignancy can be B-Cell Chronic Lymphocytic Leukemia, B-Cell Lymphoma-DLBCL, B-Cell Lymphoma-DLBCL-germinal center-like, B-Cell Lymphoma-DLBCL-activated B-cell-like, and Burkitt's lymphoma. The cancer can also be a premalignant condition, such as Barrett's Esophagus.

In one embodiment, a method for screening or characterizing a prostate cancer is provided. In one embodiment, the method can comprise detecting in a sample obtained from a subject a presence and/or level of one or more autoantibodies to one or more polypeptide probes comprising a polypeptide probe is a fragment of a protein encoded by a gene, or a fragment encoded by a sequence of a UTR region of a gene, wherein the gene is CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789. A polypeptide probe can also comprise a polypeptide sequence, or a fragment thereof, selected from Table 1, 2, 3 and 4, such as a polypeptide probe comprising polypeptide probe comprises SEQ ID NO: 1, 2, 3, 4, 5, 6, 7, 8, 9, 10, 11, 12, 13 or 14, or a fragment thereof, or a polypeptide probe comprising a polypeptide encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof. A polypeptide probe can also comprise SEQ ID NO: 12, 5, 9, 11, 14, 56, 57, 58, 59, 60, 61, 62, 63, 64, 65, 66, 67, 68, 69, or a fragment thereof, or a fragment thereof, or a polypeptide encoded by SEQ ID NO: 16, 19, 23, 25, 28, 70, 71, 72, 73, 74, 75, 76, 77, 78, 79, 80, 81, 82, 83, 84, or a fragment thereof.

In one embodiment, the method can comprise detecting in a sample obtained from a subject a presence and/or level of one or more autoantibodies to one or more polypeptide probes comprising a polypeptide probe is a fragment of a protein encoded by a gene, or a fragment encoded by a sequence of a UTR region of a gene, wherein the gene is DCHS1, CEP164, KBTBD6, RPS19, RPL34, SFRS14, RNA binding protein 6, Hemk1, eIF4G1, 5'UTR BMI1, BRD2, RP3-323M22, SFRS14, or LOC388789. A polypeptide probe can also comprise a polypeptide sequence, or a fragment thereof, selected from Table 1 or Table 2, such as a polypeptide probe comprising SEQ ID NO: 1, 2, 3, 4, 5, 6, 7, 8, 9, 10, 11, 12, 13 or 14, or a fragment thereof, or a polypeptide probe encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof.

In yet another embodiment, the method can comprise detecting in a sample obtained from a subject a presence and/or level of one or more autoantibodies to one or more polypeptide probes comprising SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof, or a fragment thereof; or polypeptide probe encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof; or polypeptide probe comprising full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

Depending on the results, a cancer (or absence of cancer) can be characterized. For example, in a sample from a subject a presence or level of DCHS1, CEP164 and/or RPS19 autoantibodies is detected, indicating a presence of prostate cancer in the subject. Alternately, a method further comprises detecting a presence or level of one or more autoantibodies to one or more polypeptide probe comprising a fragment of eIF4G1, 5'UTR BMI1, BRD2, RP3-323M22, SFRS14, or LOC388789. The fragment of a protein encoded by eIF4G1, 5'UTR BMI1, BRD2, RP3-323M22, SFRS14, or LOC388789 can comprise a polypeptide sequence selected from Table 2.

A method disclosed herein can comprise detecting a plurality of antibodies, such as through the detection of binding of one or more antibodies that bind to a plurality of polypeptide probes. In one embodiment, the antibodies are autoantibodies. In another embodiment, the antibodies are antibodies to foreign antigens. In one embodiment, the method comprises detecting in a sample one or more antibodies that binds to a panel of polypeptide probes, wherein the panel comprises 2-100 probes, 50-200 probes, 100-500 probes 200-750 probes, 200-1000 probes, 2-5,000 probes or 2-10,000 probes. In another embodiment, the panel of polypeptide probes comprises at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 polypeptide probes. In another embodiment, the panel comprises at least about 50, 100, 150, 200, 250, 500, 750, 1000, 5000, 10,000, 15,000, 20,000, 25,000, 30,000, 40,000, 50,000, 60,000, 70,000, 75,000, or 100,000 polypeptide probes. In one embodiment, the panels comprises a plurality of polypeptide probes, wherein a subset of the probes comprise fragments of the same full-length protein, such that autoantibodies to different epitopes bind to the different probes and indicate a presence of an immune response, or antibody, to the full-length protein.

A panel comprising multiple polypeptide probes allow for the simultaneous analysis of multiple markers correlating with carcinogenesis and/or metastasis. In one embodiment, a panel includes markers identified as correlating with cancerous tissue, metastatic cancer, localized cancer that is likely to metastasize, pre-cancerous tissue that is likely to become cancerous, pre-cancerous tissue that is not likely to become cancerous, or any combination thereof. Depending on the subject, a panel can be analyzed alone or in combination in order to provide a diagnosis, prognosis, or theranosis. One or more markers for inclusion on a panel can be selected by screening for their diagnostic, prognostic, or theranostic value.

Any of the proteins listed in Tables 1, 2, 3 or 4, or proteins encoded by the genes listed in Tables 1, 2, 3 or 4, in any combination, can be utilized to detect a presence of an antibody, such as an autoantibody, in a subject. In one embodiment, the protein is encoded SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In one embodiment, detection of an autoantibody to a protein encoded by a gene, a fragment encoded by a sequence of a UTR region of a gene, or fragment of a protein encoded by a gene, wherein the gene is CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789, or any combination thereof, is indicative of a presence of prostate cancer in a subject. In another embodiment, any combination of two or more proteins (e.g., cancer markers) or fragments thereof is used to detect one or more autoantibodies (e.g., a panel consisting of one or more full-length or fragments of the polypeptides listed in Tables 1, 2, 3, and/or 4).

In another embodiment, detection of an autoantibody to a protein encoded by a gene, a fragment encoded by a sequence of a UTR region of a gene, or fragment of a protein encoded by a gene, wherein the gene is CEP164, KBTBD6, RPS19, RPL34, RNA binding protein 6, Hemk1, eIF4G1, 5'UTR BMI1, BRD2, RP3-323M22, SFRS14, LOC388789, or any combination thereof, is indicative of a presence of prostate cancer in a subject. In another embodiment, any combination of two or more proteins (e.g., cancer markers) or fragments thereof is used to detect one or more autoantibodies (e.g., a panel consisting of one or more full-length or fragments of the polypeptides listed in Tables 1 and 2).

In one embodiment, the method comprises detecting one or more antibodies that bind to at least 1, 2, 3, 4, 5, 6, 7, 8, 9, 10, 11, 12, 13, or 14 polypeptide probes, wherein the polypeptide probes are full-length or fragments of proteins encoded by the genes listed in Tables 1, 2, 3, and/or 4, or polypeptides encoded by the UTR sequence of the gene. In one embodiment, the antibody profiling panel comprises a plurality of polypeptide probes, wherein one or more polypeptide probes is a protein or fragment of a protein encoded by CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789, or any combination thereof. In another embodiment, the antibody profiling panel comprises a plurality of polypeptide probes, wherein one or more polypeptide probes is a protein or fragment of a protein encoded by DCHS1, CEP164, KBTBD6, RPS19, RPL34, RNA binding protein 6, Hemk1, eIF4G1, 5'UTR BMI1, BRD2, RP3-323M22, SFRS14, LOC388789, or any combination thereof.

The cancer can be characterized with increased accuracy, such as with increased specificity, sensitivity, or both. The sensitivity can be determined by: (number of true positives)/(number of true positives+number of false negatives), whereas the specificity can be determined by: (number of true negatives)/(number of true negatives+number of false positives).

In one embodiment, the cancer can be characterized (e.g., detected, prognosed, etc.) with at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% sensitivity. In another embodiment, the cancer can be characterized (e.g., detected, prognosed, etc.) with at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100% specificity.

Specificity or sensitivity of detection can be altered by altering the polypeptide probe make-up of a panel. In one embodiment, sensitivity of a diagnostic, prognostic, or theranosstic assay (e.g., an antibody detection assay, such as an autoantibody detection assay) can be increased by increasing the number of probes, increasing the diversity of probes (e.g, utilizing probes comprising distinct epitopes from the same and/or different markers), or tailoring the probes to a particular subject or cancer to be diagnosed/prognosed. Furthermore, the confidence level for determining the specificity, sensitivity, or both, may be with at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% confidence.

A method and system disclosed herein can also comprise detecting a plurality of antibodies, such as through the detection of antibodies binding to a plurality of polypeptide probes, and characterizing or screening for a cancer with increased or greater specificity as compared to a characterization based on detection of antibodies that bind to less than the plurality of polypeptide probes. In one embodiment, the antibodies are autoantibodies. In another embodiment, the antibodies are to foreign antigens.

Two or more polypeptide probes can be used to diagnose a particular cancer. For example, a cancer can be diagnosed by measuring the binding of autoantibodies to two polypeptide probe. The number of polypeptide useful for diagnosing a cancer includes, but is not limited to, 2, 3, 4, 5, 6, 7, 8, 9, 10, 11, 12, 13, 14, 15, 16, 17, 18, 19, and 20 polypeptide probes. In another embodiment, prostate cancer is diagnosed with 5 or more polypeptide probes. In one embodiment, prostate cancer is diagnosed with 5 polypeptide probes, which provides a diagnosis that has a higher sensitivity as compared to using less than the 5 polypeptide probes. In another embodiment, prostate cancer is diagnosed with 10 or more polypeptide probes. In another embodiment, a prostate cancer is diagnosed with 10 polypeptide probes, which provides a diagnosis that has a higher specificity as compared to using less than the 10 polypeptide probes.

Antibody Detection

The level, presence or absence of an antibody can be determined by detecting the binding of one or more autoantibodies to a polypeptide probe. Detection of an antibody can be either quantitative or qualitative. For quantitative assays, the amount of antibody detected can be compared to a control or reference to determine whether an antibody is overexpressed or underexpressed in a sample. For example, the control or reference can be a normal sample or a sample from a known disease state, such as a cancer sample.

Antibody binding to a polypeptide probe can be detected by techniques known in the art, such as, but not limited to, radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays. Any of the assays used can be quantitative or qualitative, as desired.

Detection of an antibody bound to a polypeptide probe can be detected using labeling technology. For example, one or more antibodies in a sample collected from a subject to be tested can be directly labeled (e.g., with a fluorescent or radioactive label) and exposed to a polypeptide probe or probe panel. Detection of a signal from the interaction can be achieved using methodology appropriate to the type of label used (e.g., fluorescent microscopy can be used to detect binding of a fluorescently labeled autoantibody to a polypeptide probe). In one embodiment, an autoantibody is detected by detecting binding of a labeled secondary antibody or other antibody-binding reagent which specifically binds to the antibody bound to the polypeptide probe (e.g., a "sandwich immunoassay"). Many methods are known in the art for detecting binding in an immunoassay and are within the scope of the present invention. In one embodiment, the immunoassay described in U.S. Pat. Nos. 5,599,677, 5,672,480, or both, each of which is herein incorporated by reference, is used.

In one embodiment, automation is utilized to detect binding of one or more autoantibodies to a polypeptide probe or probe panels. Methods for the automation of immunoassays include those described in U.S. Pat. Nos. 5,885,530, 4,981,785, 6,159,750, and 5,358,691, each of which is herein incorporated by reference. Analysis and/or presentation of results can also be automated. In one embodiment, a computer with software that analyzes raw data and generates a prognosis, diagnosis, or theranosis based on the level, presence or absence of antibody binding to one or more polypeptide probes is used. A computer-based analysis program can be used to translate the raw data generated by the detection assay (e.g., a presence, absence, or amount of antibody binding to one or more polypeptide probes) into data of predictive value for a clinician. The clinician can access the predictive data using any suitable means. In one embodiment, the data is transmitted over a network. In another embodiment, the data is accessible by a clinician.

Any method capable of receiving, processing, and transmitting the information to and from a laboratory conducting the assay, medical personnel, and a subject can be used. In one embodiment, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. In one embodiment, the sample comprises a tissue or other biological sample and the subject visits a medical center to have the sample obtained and sent to the profiling center. In another embodiment, a subject collects the sample themself (e.g., a buccal swab) and directly sends it to a profiling center. In another embodiment, the sample comprises previously determined biological information. The information can be directly sent to the profiling service by the subject (e.g., an information card containing the information may be scanned by a computer and the data transmitted to a computer of the profiling center using an electronic communication system). Upon being received by the profiling service, a sample can be processed and a profile produced (i.e., antibody level, presence or absence of antibody). A profile generated can be specific for the diagnostic, prognostic, or theranostic information desired for a subject. In one embodiment, a sample from a subject is analyzed for a presence or expression level of one or more antibodies to one or more proteins encoded by a gene, fragment of one or more proteins encoded by a gene, or fragment encoded by a UTR region of a gene, wherein the gene is CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789. In one embodiment, the antibodies are autoantibodies. In another embodiment, a sample from a subject is analyzed for a presence or expression level of one or more antibodies to one or more proteins encoded by a gene, fragment of one or more proteins encoded by a gene, or fragment encoded by a UTR region of a gene, wherein the gene is DCHS1, CEP164, KBTBD6, RPS19, RPL34, RNA binding protein 6, Hemk1, eIF4G1, BMI1, BRD2, RP3-323M22, SFRS14, or LOC388789. In one embodiment, the antibodies are autoantibodies.

Profile data can be prepared in a format suitable for interpretation by a treating clinician. In one embodiment, rather than providing raw expression data, the prepared format represents a diagnosis, screening or risk assessment (e.g., likelihood of metastasis or PSA failure or the development of high prostate specific antigen levels in a patient following prostate cancer therapy (e.g., surgery)) for the subject, along with recommendations for particular treatment options. The data can be displayed to the clinician by any suitable method. In one embodiment, the profiling service generates a report that is printed for the clinician (e.g., at the point of care). In another embodiment, the report is displayed to the clinician on a computer monitor.

In one embodiment, the information is first analyzed at the point of care or at a regional facility. The raw data is then sent to a central processing facility for further analysis. In one embodiment, further analysis comprises converting the raw data to information useful for a clinician or subject, such as a patient. The central processing facility can provide the advantage of privacy (all data is stored in a central facility with uniform security protocols), speed, and uniformity of data analysis. The central processing facility can also control the fate of the data following treatment of a subject. In one embodiment, using an electronic communication system, the central facility provides data to the clinician, the subject, researchers, or any other individual. In one embodiment, a subject is able to directly access the data using the electronic communication system. In another embodiment, a subject chooses further intervention or counseling based on the result. In one embodiment, the data is used for research use. The data can be used to further optimize the inclusion or elimination of markers as useful indicators of a particular condition or stage of disease.

Antibody Test

The detection of one or more antibodies from a sample, such as described herein, can be used in conjunction with one or more other tests used for detecting or screening for cancer. The antibody detection can be used prior to, concurrent with, or subsequent to one or more other tests. In one embodiment, a genetic test for a mutation or expression level of one or more genes can be used in conjunction with determining the antibody profile of a subject.

Antibody detection can provide a non-invasive, inexpensive means for detecting or screening for a cancer. Thus, in one embodiment, the detection of a level, presence or absence of one or more antibodies can be used to determine whether a second sample or additional analysis of a sample from a subject is to be performed. In one embodiment, after detecting an expression level of one or more antibodies of sample obtained from subject to one or more polypeptide probes comprising a fragment of a protein encoded by, or a polypeptide encoded by a UTR sequence of, CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789, a biopsy can be recommended for the subject. In another embodiment, after detecting an expression level of one or more antibodies of sample obtained from subject to one or more polypeptide probes comprising a fragment of a protein encoded by, or a polypeptide encoded by a UTR sequence of, DCHS1, CEP164, KBTBD6, RPS19, RPL34, SFRS14, RNA binding protein 6, Hemk1, eIF4G1, 5'UTR BMI1, BRD2, RP3-323M22, SFRS14, or LOC388789, a biopsy can be recommended for the subject.

In another embodiment, an expression level for one or more antibodies from a subject can be detected, and based on the expression level of the one or more antibodies, the subject can be identified as suspected of having cancer. In one embodiment, the subject is characterized as having a high probability or likelihood of having cancer. Based on the detection or expression level of the one or more antibodies, a recommendation that a biopsy be obtained can be made for the subject. In another embodiment, if there is a lack of detection or expression of the one or more antibodies, further analysis is not recommended and a biopsy not be obtained. (see for example, FIG. 1, "Autoantibody Test I")

In another embodiment, prior to detecting one or more antibodies from a subject, the subject is suspected of having cancer. The subject can have had a genetic test for a mutation or gene expression analysis, image analysis (such as magnetic resonance imaging (MRI), positron emission tomography (PET) scan, computerized tomography (CT) scan, nuclear magnetic resonance (NMR)), or biopsy, and have inconclusive or uncertain results. Thus, prior to further analysis and treatment for a suspected cancer, the subject can seek further verification of their likelihood of having a cancer, or their diagnosis, prognosis, or theranosis of a cancer.

In one embodiment, an antibody profiling panel described herein can be used in conjunction with a separate test which determines a presence or level of PSA (e.g., a serum PSA test). In one embodiment, the panels is utilized to diagnose or prognose a presence of a cancer (e.g., prostate cancer) in a subject. In one embodiment, a subject is suspected of having prostate cancer based on their PSA level, age, or both. A subject can be male and over 30, 35, 40, 45, 50, 55, 60, 65, 70 or 75 years of age. In another embodiment, the subject is between 30-80, 40-75, 45-75, or 50-75 years of age. In another embodiment, the subject had a PSA blood test, digital rectal exam, or both. In yet another embodiment, the subject may have a PSA level of at least about 1.0, 1.5, 2.0, 2.5, or 4.0 ng/ml. The subject can have a PSA level of between about 1.0-15 ng/ml, 2.0-15 ng/ml, or 2.5-10 ng/ml.

In one embodiment, a biological sample from a subject, such as a subject with a PSA level greater than about 2.5 ng/ml, is contacted with one or more probes for an antibody, such as one or more probes for an autoantibody. Based on the expression level of the antibody, a biopsy for the subject can be recommended (see for example FIG. 1, "Autoantibody Test I"). The antibody test can comprise detecting one or more antibodies in a sample that bind to a polypeptide probe as described herein. In another embodiment, the antibody test is an autoantibody test.

In one embodiment, the antibody binds a polypeptide probe comprising SEQ ID NO: 1, 2, 3, 4, 5, 6, 7, 8, 9, 10, 11, 12, 13, 14, 56, 57, 58, 59, 60, 61, 62, 63, 64, 65, 66, 67, 68, 69, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, or a fragment thereof. In another embodiment, the antibody binds a polypeptide probe comprising a polypeptide sequence encoded by SEQ ID NO: 15, 16, 17, 18, 19, 20, 21, 22, 23, 24, 25, 26, 27, 28, 70, 71, 72, 73, 74, 75, 76, 77, 78, 79, 80, 81, 82, 83, 84, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, or a fragment thereof. In yet another embodiment, the antibody binds a polypeptide probe comprising full-length or a fragment of a protein that is encoded by SEQ ID NO: 29, 30, 31, 32, 33, 34, 35, 36, 37, 38, 39, 40, 41, 42, 43, 44, 45, 46, 47, 48, 49, 51, 52, 53, 54, 55, 85, 86, 87, 88, 89, 90, 91, 92, 93, 94, 95, 96, 97, 98, 99, 100, 101, 102, 103, 104, 105, 106, 107, 108, 109, 110, 111, or a fragment thereof.

In one embodiment, the antibody binds a polypeptide probe comprising a full-length or fragment of a protein encoded by, or a polypeptide encoded by a CEP164, RPL34, BRMSL1, NKX3-1, RPSA, Cytochrome C oxidase 5 Subunit, UTR-region of chromosome 11, MAPKKK9, cDNA clone XR_113641.1, PSA, H2aa4, UBE2I, TIMP2, WDR77, Deaminase Domain, FAM53B, 5'UTR BMI1, RP3-323M22, or LOC388789. In one embodiment, a polypeptide probe comprises SEQ ID NO: 2, 5, 9, 11, 14, 56, 57, 58, 59, 60, 61, 62, 63, 64, 65, 66, 67, 68, 69, or a fragment thereof, or a fragment thereof. In another embodiment, a polypeptide probe comprises a polypeptide encoded by SEQ ID NO: 16, 19, 23, 25, 28, 70, 71, 72, 73, 74, 75, 76, 77, 78, 79, 80, 81, 82, 83, 84, or a fragment thereof.

In another embodiment, the antibody binds a polypeptide probe comprising a full-length or fragment of a protein encoded by, or a polypeptide encoded by a UTR of, DCHS1, CEP164, KBTBD6, RPS19, RPL34, RNA binding protein 6, Hemk1, eIF4G1, 5'UTR BMI1, BRD2, RP3-323M22, SFRS14, or LOC388789. In one embodiment, a polypeptide probe comprises SEQ ID NO: 1, 2, 3, 4, 5, 6, 7, 8, 9, 10, 11, 12, 13, 14, or a fragment thereof. In another embodiment, a polypeptide probe comprises a polypeptide encoded by SEQ ID NO: 15, 16, 17, 18, 19, 20, 21, 22, 23, 24, 25, 26, 27, 28, 29, 30, 31, 32, 33, 34, 35, 36, 37, 38, 39, 40, 41, or a fragment thereof.

If a biopsy is recommended and the biopsy is positive for a cancer such as prostate cancer, a biological sample obtained from the subject can be contacted with one or more probes for an antibody, which can be the same or different, as those used in deciding whether to obtain a biopsy. Based on the expression level of antibodies in the sample, a prognosis for the cancer can be provided. (see for example, FIG. 1, "Autoantibody Test II")

Thus, in one embodiment, a method of characterizing or screening for a cancer from a subject with a positive biopsy result is provided. In another embodiment, the subject has not yet provided a sample for detecting one or more antibodies. In yet another embodiment, the subject has provided an initial sample for detecting one or more antibodies and detection of the one or more antibodies is used in deciding whether a biopsy is obtained. Furthermore, in one embodiment, detection of one or more antibodies is used for a diagnosis, prognosis or theranosis of a cancer, such as prostate cancer. In one embodiment, the method comprises detecting an expression level for one or more antibodies, wherein the expression level of the one or more antibodies is indicative of the presence, absence, or stage of the cancer. In another embodiment, the indication is whether the cancer is aggressive or indolent.

In one embodiment, a cancer is classified based on the detection of one or more antibodies to one or more polypeptide probes disclosed herein. In one embodiment, the cancer is classified as aggressive or malignant. In another embodiment, the cancer is classified as indolent or benign. Furthermore, after classification, detection of one or more antibodies from a sample from the subject can be used to select a treatment or therapeutic for the cancer.

The present disclosure is not limited to the embodiments described above, but is capable of modification within the scope of the appended claims. Those skilled in the art will recognize, or be able to ascertain using no more than routine experimentation, many equivalents of the specific embodiments of the present disclosure described herein.

EXAMPLES

Example 1

Probe Selection

Construction of T7 Phage Display Prostate Cancer cDNA Library mRNA was isolated from total RNA following Novogen's Straight A's mRNA isolation protocol. OrientExpression cDNA synthesis and cloning system were used for the construction of T7 phage prostate cancer cDNA libraries.

To eliminate the 3' bias inherent in oilgo(dT)-primed libraries, two libraries were constructed using directional oligo(dT) primer and random primer in parallel. After amplification, these two libraries were combined in same amount of titer.

Enrichment of Cancer Specific T7 Phage Library.

Protein A/G agarose beads (Pierce Biotechnology, Rockford, Ill.) were used to purify IgGs from the serum of prostate cancer patients. To enhance the selection of epitopes binding to IgGs specifically associated with prostate cancer, a dual procedure was performed.

First, a pre-clearing step was used to remove nonspecific clones by pre-absorbing the phage epitope libraries onto purified IgGs from normal serum pool from 10 control men. Next, the pre-cleared phage libraries were selected onto the pool of IgGs purified from the serum of 6 localized prostate cancer patients. In essence protein-A/G agarose beads provide a purification of the serum of IgGs. Fifty μl protein-A/G agarose beads were placed into 1.5 ml eppendorf tube and washed two times with 1× PBS. Washed beads were blocked with 4% nonfat milk at 4° C. for 1 hr. The beads were then incubated at 4° C. with 15 μl of pooled control sera at 1:30 dilution with 4% nonfat milk. After at least 2 hrs of incubation, the beads were washed three times with 1× PBS and then incubated with phage library (~1010 phage particles) at 4° C. for at least 2 hrs. The mixture was centrifuged at 3000 rpm for 2 min. The beads with unspecifically bounded phage particles were discarded and the supernatant was collected for further immunoscreening.

Fifty μl fresh protein-A/G agarose beads were washed and blocked as same as above. The beads were then incubated at 4° C. for 3 hrs with 500 ml of PBS containing 15 ml patient sera pool at a 1:30 dilution. This amount of serum provides a three-fold molar excess of IgG to calculated number of protein-A/G binding capacity. The beads were washed three times with 1× PBS and then incubated with phage library supernatant from above allowed to react with the antibodies on the beads at 4° C. overnight. The mixture was centrifuged at 3000 rpm for 2 min and supernatant was discarded. The beads were then washed three times with 1× PBS.

To elute the bound phage 100 ml 1% SDS was used to strongly break up the antibody-antigen reaction without disrupting the T7 phage particles. The mixture of phage and elution buffer was incubated at room temperature for 10 min. The bound phages were removed from the beads by centrifugation at 8000 rpm for 8 min. Eluted phages were transferred to 10 ml BLT 5403 bacterial cells with OD600=0.6~0.8 for amplification. Four or five cycles of affinity selections and biopanning were carried out with amplification of phage particles after each biopanning.

High Throughput Epitope Detection Using Phage Microarrays.

Random phage colonies were picked up and amplified in 96-well plates. Fresh phage lysates were spotted onto on FAST™ nitrocellulose coated glass slides (Schleicher & Schuell, Keene, N.H.). Extra T7 empty phage spots were spotted in quadruplicate as negative reference for normalizing the signal value from different slides. The arrays were dried overnight at room temperature. Before processing with serum, the arrays were rinsed briefly in a 4% nonfat milk/PBS with 0.1% tween-20 to remove unbound phage, then transferred immediately to 4% nonfat milk/PBS as a blocking solution for 1 hr at room temperature. Without allowing the array to dry, 2 ml of PBS containing human serum and T7-tag antibody (Novagen) at a dilution of 1:500 and 1:5000 respectively was applied to the surface in a screw-top slide hybridization tube.

The arrays were incubated at room temperature for 1 hour, and then washed gently three times in PBS/0.1% Tween-20 solution 10 min each. All washes were performed at room temperature. After washing, the arrays were incubated with 2 ml of PBS containing Cy3-labeled goat anti-mouse antibody and Cy5-labeled goat anti-human antibody (Jackson ImmunoResearch) at a dilution of 1:5,000 for both for 1 hr in the dark. Three washes were performed using PBS/0.1% Tween-20 solution with 10 min each. The arrays were then dried using a stream of compressed air and scanned using 532 nm and 635 nm lasers (Axon Laboratories).

Building Predictor and Validation of Biomarker Profile.

The arrays were quantified using GenePix software (Axon Laboratories). Raw ratios of each array were subtracted by median of ratios of the negative control spots with the observation that the signal for negative T7 empty phage on each chip correlates very well with the signal intensity for whole array. Then Z-transformation was applied to clones so that the mean of each clone is zero across arrays and the standard deviation is 1. Due to the fact a presence of antibodies specific to cancer was tested, epitopes with high reactivity in controls and low reactivity in patients were not expected. A GA/KNN algorithm, a machine learning language, was employed to calibrate the system. Briefly, the data set was randomly separated into a training set and a test set. In the training set, genetic algorithm (GA) was used to select optimized solutions (a subset of clones here) which had good fitness. The fitness was assessed by its ability to classify the training samples using the k-nearest neighbor (KNN) analysis (k=3 here). The fitness score was defined as the number of correctly classified training samples divided by the total number of training samples. The fitness score was specified to be equal or greater than 0.95. After getting 4000 optimized solutions, clones were ranked by their frequency in the solutions and top genes were used to predict the test samples. This cycle of sample partition, solution searching, clone ranking and test sample prediction was repeated 10 times and high-ranked clones were selected as optimized classifier.

What is claimed is:

1. A method for screening for prostate cancer, the method comprising:
   (a) contacting a biological fluid sample obtained from the subject with an antibody profiling panel comprising a plurality of polypeptide probes comprising a polypeptide or epitope fragment of:
      (i) amino acid sequence SEQ ID NO: 13 or an amino acid sequence encoded by nucleic acid sequence SEQ ID NO: 27,
      (ii) amino acid sequence SEQ ID NO: 132 or an amino acid sequence encoded by nucleic acid sequence SEQ ID NO: 162,
      (iii) amino acid sequence SEQ ID NO: 2 or an amino acid sequence encoded by nucleic acid sequence SEQ ID NO: 16,
      (iv) amino acid sequence SEQ ID NO: 141 or an amino acid sequence encoded by nucleic acid sequence SEQ ID NO: 171,
      (v) amino acid sequence SEQ ID NO: 129 or an amino acid sequence encoded by nucleic acid sequence SEQ ID NO: 159,
      (vi) amino acid sequence SEQ ID NO: 118 or an amino acid sequence encoded by nucleic acid sequence SEQ ID NO: 148,
      (vii) amino acid sequence SEQ ID NO: 122 or an amino acid sequence encoded by nucleic acid sequence SEQ ID NO: 152, and
      (viii) amino acid sequence SEQ ID NO: 130 or an amino acid sequence encoded by nucleic acid sequence SEQ ID NO: 160,
   wherein each of the probes in the plurality of polypeptide probes is attached to a substrate and is capable of being specifically bound by an autoantibody from a sample obtained from a subject; and
   (b) detecting a level of a bound antibody, wherein the bound antibody is bound to one of the probes in the plurality of polypeptide probes in the panel, and wherein the level is indicative of the presence or absence of prostate cancer.

2. A method of screening for prostate cancer in a subject, wherein the subject exhibits a symptom of prostate cancer, the method comprising:
   (a) obtaining a first biological fluid sample from the subject;
   (b) contacting the first biological fluid sample obtained from the subject with a first panel comprising at least two polypeptide probes comprising a polypeptide or epitope fragment of:
      (i) amino acid sequence SEQ ID NO: 132 or an amino acid sequence encoded by nucleic acid sequence SEQ ID NO: 162, and
      (ii) amino acid sequence SEQ ID NO: 130 or an amino acid sequence encoded by nucleic acid sequence SEQ ID NO: 160; and
   (c) detecting a level of autoantibodies bound to the polypeptide probes, wherein the level of the autoantibodies bound to the polypeptide probes are analyzed in combination to detect the presence of prostate cancer in the subject with a sensitivity of at least 80%.

3. The method of claim 2, further comprising confirming the detection of the presence of prostate cancer by obtaining a prostate tissue biopsy and analyzing the prostate tissue biopsy for the presence of prostate cancer.

4. The method of claim 2, further comprising selecting a treatment for prostate cancer based on the detection of the level of the autoantibodies.

5. The method of claim 2, wherein the symptom of prostate cancer is a PSA level that is from about 2.5 ng/mL to about 10 ng/mL.

6. The method of claim 3, further comprising:
   (d) contacting a second biological fluid sample obtained from the subject with a second panel comprising one or more polypeptide probes for an autoantibody when the prostate tissue biopsy provides a positive result for cancer;

(e) detecting a level for the second autoantibody; and (f) providing a prognosis or theranosis based on the level of the autoantibody.

7. The method of claim 2, wherein the first panel further comprises a polypeptide probe comprising a polypeptide or epitope fragment of:
   (i) amino acid sequence SEQ ID NO: 13 or an amino acid sequence encoded by nucleic acid sequence SEQ ID NO: 27,
   (ii) amino acid sequence SEQ ID NO: 2 or an amino acid sequence encoded by nucleic acid sequence SEQ ID NO: 16,
   (iii) amino acid sequence SEQ ID NO: 141 or an amino acid sequence encoded by nucleic acid sequence SEQ ID NO: 171,
   (iv) amino acid sequence SEQ ID NO: 129 or an amino acid sequence encoded by nucleic acid sequence SEQ ID NO: 159,
   (v) amino acid sequence SEQ ID NO: 118 or an amino acid sequence encoded by nucleic acid sequence SEQ ID NO: 148, or
   (vi) amino acid sequence SEQ ID NO: 122 or an amino acid sequence encoded by nucleic acid sequence SEQ ID NO: 152;
wherein each of the one or more polypeptide probes is attached to a substrate.

8. The method of claim 2, wherein the detecting the level is by an immunoassay.

9. The method of claim 7, wherein the first panel further comprises one or more polypeptide probes comprising a polypeptide or epitope fragment of amino acid sequence SEQ ID NO: 5, 11, 12, 14, 56, 58, 60, 62, 64, 67, 69, 115, 116, 123 or 140.

10. The method of claim 7, wherein the first panel further comprises one or more polypeptide probes comprising a polypeptide or epitope fragment of an amino acid sequence encoded by nucleic acid sequence SEQ ID NO: 19, 25, 26, 28, 70, 73, 75, 77, 79, 82, 84, 145, 146, 153, or 170.

11. The method of claim 2, wherein the first panel comprises at least 3, 4, 5, 6, 7 or 8 polypeptide probes.

12. The method of claim 6, wherein the first or second biological fluid sample is serum, urine, or a previous tissue biopsy.

13. The method of claim 6, wherein the second panel is the same as the first panel.

14. The method of claim 2, wherein the symptom of prostate cancer is a PSA level greater than about 2.5 ng/mL.

15. The method of claim 2, wherein the detection of the binding of the autoantibodies to the polypeptide probes detects the presence of prostate cancer in the subject with a specificity of at least 30%.

16. The method of claim 2, wherein the detection of the binding of the autoantibodies to the polypeptide probes detects the presence of prostate cancer in the subject with a specificity of at least 45%.

17. The method of claim 7, wherein the first panel comprises the polypeptide probe comprising the polypeptide or epitope fragment of amino acid sequence SEQ ID NO: 2 or an amino acid sequence encoded by nucleic acid sequence SEQ ID NO: 16.

18. The method of claim 7, wherein the first panel comprises the polypeptide probe comprising the polypeptide or epitope fragment of amino acid sequence SEQ ID NO: 141 or an amino acid sequence encoded by nucleic acid sequence SEQ ID NO: 171.

19. The method of claim 7, wherein the first panel comprises the polypeptide probe comprising the polypeptide or epitope fragment of amino acid sequence SEQ ID NO: 129 or an amino acid sequence encoded by nucleic acid sequence SEQ ID NO: 159.

20. The method of claim 7, wherein the first panel comprises the polypeptide probe comprising the polypeptide or epitope fragment of amino acid sequence SEQ ID NO: 118 or an amino acid sequence encoded by nucleic acid sequence SEQ ID NO: 148.

21. The method of claim 7, wherein the first panel comprises the polypeptide probe comprising the polypeptide or epitope fragment of amino acid sequence SEQ ID NO: 122 or an amino acid sequence encoded by nucleic acid sequence SEQ ID NO: 152.

22. The method of claim 7, wherein the substrate is an array.

23. The method of claim 1, wherein the substrate is an array.

24. The method of claim 1, wherein the panel further comprises one or more polypeptide probes comprising a polypeptide or epitope fragment of amino acid sequence SEQ ID NO: 5, 11, 12, 14, 56, 58, 60, 62, 64, 67, 69, 115, 116, 123 or 140.

25. The method of claim 1, wherein the panel further comprises one or more polypeptide probes comprising a polypeptide or epitope fragment of an amino acid sequence encoded by nucleic acid sequence SEQ ID NO: 19, 25, 26, 28, 70, 73, 75, 77, 79, 82, 84, 145, 146, 153, or 170.

26. The method of claim 1, wherein the biological fluid sample comprises serum, urine, or a previous tissue biopsy.

27. The method of claim 1, wherein the biological fluid sample comprises serum.

28. The method of claim 2, wherein the first panel further comprises a polypeptide probe comprising a polypeptide or epitope fragment of an amino acid sequence selected from the group consisting of SEQ ID NO: 13, 2, 141, 129, 118, and 122.

29. The method of claim 2, wherein the first panel further comprises a polypeptide probe comprising a polypeptide or epitope fragment of an amino acid sequence encoded by a nucleic acid sequence selected from the group consisting of SEQ ID NO: 27, 16, 171, 159, 148, and 152.

* * * * *

```
                        SEQUENCE LISTING

<160> NUMBER OF SEQ ID NOS: 172

<210> SEQ ID NO 1
<211> LENGTH: 14
<212> TYPE: PRT
<213> ORGANISM: Artificial Sequence
<220> FEATURE:
<223> OTHER INFORMATION: Synthetic

<400> SEQUENCE: 1

Pro Gln Thr Thr Ala Pro Arg Arg Ala Arg Pro Arg Arg Ser
1               5                   10

<210> SEQ ID NO 2
<211> LENGTH: 25
<212> TYPE: PRT
<213> ORGANISM: Artificial Sequence
<220> FEATURE:
<223> OTHER INFORMATION: Synthetic

<400> SEQUENCE: 2

Pro Val Ser Ser Ser Gly Ser Tyr Ser Thr Pro Ile Arg Lys Ser Leu
1               5                   10                  15

Arg Arg Ala Ala Pro Pro Phe Arg Ala
            20                  25

<210> SEQ ID NO 3
<211> LENGTH: 7
<212> TYPE: PRT
<213> ORGANISM: Artificial Sequence
<220> FEATURE:
<223> OTHER INFORMATION: Synthetic

<400> SEQUENCE: 3

Ser Ser Phe Ser Pro Leu Asn
1               5

<210> SEQ ID NO 4
<211> LENGTH: 55
<212> TYPE: PRT
<213> ORGANISM: Artificial Sequence
<220> FEATURE:
<223> OTHER INFORMATION: Synthetic
```

```
<220> FEATURE:
<221> NAME/KEY: misc_feature
<222> LOCATION: (21)..(21)
<223> OTHER INFORMATION: Xaa can be any naturally occurring amino acid

<400> SEQUENCE: 4
```

Ala Ala Arg Arg Pro His Asp Ala Trp Ser Tyr Cys Lys Arg Arg Glu
1               5                   10                  15

Pro Ala Gly Val Xaa Gln Ser Ser Gly Ser Leu Pro Gln Lys Val Arg
            20                  25                  30

Glu Ala Glu Ser Pro Arg Met Gly Gly Tyr Arg Gln Ala Gly Gln Ala
        35                  40                  45

Gln Arg Ala Cys Ser Leu Arg
    50                  55

```
<210> SEQ ID NO 5
<211> LENGTH: 64
<212> TYPE: PRT
<213> ORGANISM: Artificial Sequence
<220> FEATURE:
<223> OTHER INFORMATION: Synthetic

<400> SEQUENCE: 5
```

Gln Ala Arg Leu Phe Ile Phe Ile Thr Gln Lys Ser Phe Ile Phe Leu
1               5                   10                  15

Phe Ser Phe Leu Thr Leu Cys Leu Cys Leu Gln His Phe His Asn Asp
            20                  25                  30

Phe Leu Leu Leu Asp Lys Glu Ser Thr Leu Asp Pro Val Thr Asn Thr
        35                  40                  45

Phe Ser Thr His Gly Thr Lys Thr Leu Leu Leu Thr Ser Leu Phe Leu
    50                  55                  60

```
<210> SEQ ID NO 6
<211> LENGTH: 22
<212> TYPE: PRT
<213> ORGANISM: Artificial Sequence
<220> FEATURE:
<223> OTHER INFORMATION: Synthetic

<400> SEQUENCE: 6
```

Leu Arg Gly Ile Thr Lys Asn Asp Arg Asn Phe Asn Arg Lys Ile His
1               5                   10                  15

Leu Asn Trp Ile Ser Lys
            20

```
<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7
```

Arg Gly Cys Cys Ala Gly Ile Arg Cys Thr
1               5                   10

```
<210> SEQ ID NO 8
<211> LENGTH: 118
<212> TYPE: PRT
<213> ORGANISM: Artificial Sequence
<220> FEATURE:
<223> OTHER INFORMATION: Synthetic

<400> SEQUENCE: 8
```

-continued

```
Ile Arg Asp Pro Asn Gln Gly Gly Lys Asp Ile Thr Glu Glu Ile Met
1               5                   10                  15

Ser Gly Ala Arg Thr Ala Ser Thr Pro Thr Pro Pro Gln Thr Gly Gly
            20                  25                  30

Gly Leu Glu Pro Gln Ala Asn Gly Glu Thr Pro Gln Val Ala Val Ile
        35                  40                  45

Val Arg Pro Asp Asp Arg Ser Gln Gly Ala Ile Ile Ala Asp Arg Pro
50                  55                  60

Gly Leu Pro Gly Pro Glu His Ser Pro Ser Glu Ser Gln Pro Ser Ser
65                  70                  75                  80

Pro Ser Pro Thr Pro Ser Pro Ser Pro Val Leu Glu Pro Gly Ser Glu
                85                  90                  95

Pro Asn Leu Ala Val Leu Ser Ile Pro Gly Asp Thr Met Thr Thr Ile
            100                 105                 110

Gln Met Ser Val Glu Glu
        115
```

```
<210> SEQ ID NO 9
<211> LENGTH: 22
<212> TYPE: PRT
<213> ORGANISM: Artificial Sequence
<220> FEATURE:
<223> OTHER INFORMATION: Synthetic

<400> SEQUENCE: 9

Gly Gly Gly Arg Gly Ala Gly Gly Arg Gly Ala Gly Ala Gly Gly
1               5                   10                  15

Gly Arg Pro Glu Ala Ala
            20
```

```
<210> SEQ ID NO 10
<211> LENGTH: 89
<212> TYPE: PRT
<213> ORGANISM: Artificial Sequence
<220> FEATURE:
<223> OTHER INFORMATION: Synthetic

<400> SEQUENCE: 10

Glu Ser Arg Pro Met Ser Tyr Asp Glu Lys Arg Gln Leu Ser Leu Asp
1               5                   10                  15

Ile Asn Lys Leu Pro Gly Glu Lys Leu Gly Arg Val Val His Ile Ile
            20                  25                  30

Gln Ala Arg Glu Pro Ser Leu Arg Asp Ser Asn Pro Glu Glu Ile Glu
        35                  40                  45

Ile Asp Phe Glu Thr Leu Lys Pro Ser Thr Leu Arg Glu Leu Glu Arg
50                  55                  60

Tyr Val Leu Ser Cys Leu Arg Lys Lys Pro Arg Lys Pro Tyr Ser Thr
65                  70                  75                  80

Tyr Glu Met Arg Phe Ile Ser Trp Phe
                85
```

```
<210> SEQ ID NO 11
<211> LENGTH: 11
<212> TYPE: PRT
<213> ORGANISM: Artificial Sequence
<220> FEATURE:
<223> OTHER INFORMATION: Synthetic

<400> SEQUENCE: 11
```

```
Leu Val Ser Ile Leu Leu Thr Lys Thr Ile Tyr
1               5                   10
```

<210> SEQ ID NO 12
<211> LENGTH: 84
<212> TYPE: PRT
<213> ORGANISM: Artificial Sequence
<220> FEATURE:
<223> OTHER INFORMATION: Synthetic

<400> SEQUENCE: 12

```
Lys Ala Glu Cys Phe Lys Asn Leu Ile Val Lys Lys Gln Lys Ser Leu
1               5                   10                  15

Cys Ser Gly Phe Lys Glu His Leu Asn Glu Ala Ser Ile Leu Ala Gln
                20                  25                  30

Val Ser Val Ser Ser Lys Arg Val Trp Lys Ser Trp Glu Asn Leu
            35                  40                  45

Ile Ser Ser Phe Met Val Trp Asn Pro Ala His Leu Ile Ile Ser Ile
50                  55                  60

Pro Asn Leu Glu Lys Thr Ser Asp Leu Ser Met Met Ser Lys Leu Ala
65                  70                  75                  80

Ala Ala Leu Glu
```

<210> SEQ ID NO 13
<211> LENGTH: 92
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (41)..(41)
<223> OTHER INFORMATION: Xaa can be any naturally occurring amino acid

<400> SEQUENCE: 13

```
Gln Arg Ser Gly Arg Asp Asn Gly Asp Val Gly Ala Gly Ala Pro Phe
1               5                   10                  15

Arg Leu Ser Ser Thr Ser Gln Pro Arg Arg Ile Lys Pro Ile Ala Pro
                20                  25                  30

Pro Pro Arg Ala Pro Ser Pro Glu Xaa Gly Ala Gly Gly Gly Gly Gly
            35                  40                  45

Gly Arg Gly Gly Gly Gly Gly Pro Gly Gly Gly Val Gly Gly
    50                  55                  60

Arg Gly Gly Gly Gly Gly Gly Gly Arg Gly Ala Gly Gly Gly Arg
65                  70                  75                  80

Gly Ala Gly Ala Gly Gly Gly Arg Pro Glu Ala Ala
                85                  90
```

<210> SEQ ID NO 14
<211> LENGTH: 77
<212> TYPE: PRT
<213> ORGANISM: Artificial Sequence
<220> FEATURE:
<223> OTHER INFORMATION: Synthetic

<400> SEQUENCE: 14

```
Pro Ala Ser Ala Ser Ile Leu Ala Gly Val Pro Met Tyr Arg Asn Glu
1               5                   10                  15

Phe Thr Ala Trp Tyr Arg Arg Met Ser Val Val Tyr Gly Ile Gly Thr
                20                  25                  30

Trp Ser Val Leu Gly Ser Leu Leu Tyr Tyr Ser Arg Thr Met Ala Lys
```

```
                35                  40                  45
Ser Ser Val Asp Gln Lys Asp Gly Ser Ala Ser Glu Val Pro Ser Glu
        50                  55                  60

Leu Ser Glu Arg Pro Ser Leu Arg Pro His Ser Ser Asn
65                  70                  75
```

<210> SEQ ID NO 15
<211> LENGTH: 221
<212> TYPE: DNA
<213> ORGANISM: Artificial Sequence
<220> FEATURE:
<223> OTHER INFORMATION: Synthetic

<400> SEQUENCE: 15

```
agctttcgct agagacgcct ccataagtca cttgcccgtt ggcccccacg atcggggtcg    60
gttgctcgca gggctgagca gagatgtgcc aggagggttg ttctcacgca agaggacgct   120
gtactcctgc tgctggaaag taggcgcctc gtcgttgacg tcagcgacac tgacggtcag   180
gacctgcgtg gccgagcgcg gcggggagcc gtggtctgag g                      221
```

<210> SEQ ID NO 16
<211> LENGTH: 267
<212> TYPE: DNA
<213> ORGANISM: Artificial Sequence
<220> FEATURE:
<223> OTHER INFORMATION: Synthetic

<400> SEQUENCE: 16

```
tggaggagag gctgggctgc cccaagcccc tgctcagggc ctcagaagcc atacaccttc    60
actctgattg tgctcatcaa ggcccagcat gcaggaggct caaagtagct tttggcttgg   120
gtgttgacga agagaggt aacctgggt cattcttgac acgttccagc cacctccggt      180
tggcctcaat tatgccctga aggtggtgc tgcccgcctc agggacttgc gaatgggagt    240
gctgtaggag ccggagctgc tcactgg                                      267
```

<210> SEQ ID NO 17
<211> LENGTH: 168
<212> TYPE: DNA
<213> ORGANISM: Artificial Sequence
<220> FEATURE:
<223> OTHER INFORMATION: Synthetic

<400> SEQUENCE: 17

```
gaattcgtca ttctcacctt tgaattaaag cttagactaa atagtaatat atcgtgggaa    60 ggatttggt tttgtgatat ttctgtgaat taaggaatag atgttaacca ttattttgta   120
gaaaagtgat tgtatgtgg ttaattataa ataaaactgg taccagaa                168
```

<210> SEQ ID NO 18
<211> LENGTH: 481
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t

<400> SEQUENCE: 18

```
tttattaacc cagcatggtt tgttctaatg cttcttgttg gcagctgcca cctgtccggc    60
gattctgtcc agatctcttt gtccctgagg tgtcagtttg cggccgccat cttggtcctt   120
ttccaccatt ttcagcccct ccagggcttg gaggacccgg cgggccacac tcttggagcc   180
tcggctgaag tggctgggca tgacgccgtt tctctgacgt cccccataga tcttggtcat   240
ggagccaacc ccagcgccac cccggaggta caggtgccgc gctgtgnaag cagctcgcgt   300
gtagaaccag ttctcatcgt agggagcaag ctctttgtgc ttggccagct tgacggtatc   360
cacccattcg gggactttca gcttcccgga cttttgagg aaggctgcca gagctctgac    420
naactcctgc tggttcacgt cttttacagt aactccaggc atcgtgcggc ctccgcgctg   480
c                                                                   481
```

<210> SEQ ID NO 19
<211> LENGTH: 326
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (60)..(60)
<223> OTHER INFORMATION: n is a, c, g, or t

<400> SEQUENCE: 19

```
ttctcgagtg cggccgcagc ttgggtatgg agacatatca tataagtaat gctagggtcn   60
gtggtaggaa gtttttttcat aggaggtgta tgagttggtc gtagcggaat cgggggtatg  120
ctgttcgaat tcataagaac agggaggtta gaagtagggt cttggttcca tgtgtgctaa   180
atgtgttcgt gacaggatca agcgtgcttt ccttatcgag gagcagaaaa tcgttgtgaa   240
agtgttgaag gcacaagcac agagtcagaa agctaaataa aaaaatgaaa cttttttgag   300
taataaaaat gaaagacgc gcttga                                         326
```

<210> SEQ ID NO 20
<211> LENGTH: 453
<212> TYPE: DNA
<213> ORGANISM: Artificial Sequence
<220> FEATURE:
<223> OTHER INFORMATION: Synthetic

<400> SEQUENCE: 20

```
ctctgagggg catcaccaaa aatgacagga atttcaacag gaagatacat ctgaattgga    60
tctcgaaata aggagtttgt gtaagagaaa aggaggacac aagcaaggag acacaaaaga   120
caatttgtcc aagagagtag tagtagaaac tgacaaaggt aaggctgctt ggtggccggg    180
tgcagtgact cacgcctgta atcccagcac tttgggaggc caaggcgggt ggatcacctg   240
aggtcaggag ttcgagacca ccctgaccaa caggtgaaac ccctctctac taaaaataca   300
aacattagcc catagtccca gctactgggg aggctgaggc aggagaatcg cttgaacctg   360
ggaggcggag gttgcagtga gccaagatcg tgccattgca ctccagcctg gcgacagaa    420 tgagactgtc tcaaaacaaa aggaaaaaaa aaa                                 453
```

<210> SEQ ID NO 21
<211> LENGTH: 388
<212> TYPE: DNA
<213> ORGANISM: Artificial Sequence
<220> FEATURE:
<223> OTHER INFORMATION: Synthetic

<400> SEQUENCE: 21

```
cacttcttca agctccaaca caaatgctgc ctcctttagg atgcctgctc tgtgctctcc      60
ctgcctcccc tagcccatac ctctgctggc accttctgta ccatgccttc agaaaccttc    120
ttatcccct catctctggg gcccctgtg gatctggcat acccaagttc agtaaatgtc      180
tatcagtaag ctgatggtac atgcattttc tagaatagag ctgggacttc ccatgtggcc    240
cacatctgac ctggcagccc atgtattccg gtcattaggg atgggaagcc atgaggacct    300
ggccttctgc ccgacccagg cagccattca agttgagcaa tggccacttc gaagactcaa    360
gtgcacctga tccctgcgca acagccac                                      388
```

<210> SEQ ID NO 22
<211> LENGTH: 361
<212> TYPE: DNA
<213> ORGANISM: Artificial Sequence
<220> FEATURE:
<223> OTHER INFORMATION: Synthetic

<400> SEQUENCE: 22

```
ttcttctaca gacatttgta tagttgtcat agtgtcccca ggaatagaga ggactgcgag     60
attaggctca gaccccggtt ccaagactgg ggatggtgat ggggtcggag aaggcgacga   120
aggctgggat tctgaagggc tatgctctgg gccaggcagc cctggccggt cagcaatgat   180
tgctccctgt gaccggtcat ctggccgac aatgacagca acctggggcg tctccccatt    240
agcttgaggc tccagaccgc ctcccgtctg ggaggggtg ggtgtggagg cagtgcgggc    300
cccagacatg atctcctctg tgatatcctt tcctccttgg tttggatctc gaattcggat   360
c                                                                    361
```

<210> SEQ ID NO 23
<211> LENGTH: 499
<212> TYPE: DNA
<213> ORGANISM: Artificial Sequence
<220> FEATURE:
<223> OTHER INFORMATION: Synthetic

<400> SEQUENCE: 23

```
atcacaaata ggacaatact tgctggtctc caggtaacga acaatacacg ttttacagaa     60
ggaatgtaga cattctatta tggttgtggc atcaatgaag taccctccac aaagcacaca   120
catcaggtgg ggatttagct cagtgatctt gattctcgtt gttcgatgca tttctgcttg   180
ataaaaaatc ccggaaagag cagccggcgc gaggcgatcg aagcgggcgg aaaagacaat   240
gaaagttaaa agtcgttcag cagaaaatga atgcgagcca agcggccatc ttgaagcgag   300
ctgcagacgc cgctgtcaat gggcaaccag cgcggcccg agcagccgcg gccgccacgc     360
tcgtctcatg ccgcctccgg ccggcctcct cctgctccgg cgcctcggcc tcctccggcg   420
cctcggcctc ctcctcctcc gcctccgcct cgacctccaa cgcctcctcc tccggggcct   480
cctcctcctc ctcctcggc                                                499
```

<210> SEQ ID NO 24
<211> LENGTH: 235
<212> TYPE: DNA
<213> ORGANISM: Artificial Sequence
<220> FEATURE:
<223> OTHER INFORMATION: Synthetic

<400> SEQUENCE: 24

```
tgtagggctt ccggggtttc ttacgtaggc aggaaaggac atagcgctca agctctctaa     60
```

```
gtgtggatgg cttgagtgtt tcaaaatcaa tctcaatctc ttctgggttt gaatcacgta        120
aagagggctc cctggcttgg attatatgca caactcggcc cagcttctcc ccaggtaatt        180
tgttgatgtc caggctcagc tgccgcttct catcgtaact catgggcctg ctctc            235
```

<210> SEQ ID NO 25
<211> LENGTH: 373
<212> TYPE: DNA
<213> ORGANISM: Artificial Sequence
<220> FEATURE:
<223> OTHER INFORMATION: Synthetic

<400> SEQUENCE: 25

```
ttactgttac ctgatcaatg acagagcctt ctgaggacat tccaagacag tatacagtcc        60
tgtggtctcc ttggaaatcc gtctagttaa catttcaagg caataccgt gttggttttg         120 actggatatt catataaact ttttaaagag ttgagtgata gagctaaccc ttatctgtaa        180
gttttgaatt tatattgttt catcccatgt acaaaaccat ttttcctac aaatagtttg         240 ggttttgttg ttgtttcttt tttttgtttt gttttgttt tttttttttt tgcgttcgtg         300
gggttgtaaa agaaaagaaa gcagaatgtt ttatcatggt ttttgcttca gcggctttag        360
gacaaattaa aag                                                           373
```

<210> SEQ ID NO 26
<211> LENGTH: 235
<212> TYPE: DNA
<213> ORGANISM: Artificial Sequence
<220> FEATURE:
<223> OTHER INFORMATION: Synthetic

<400> SEQUENCE: 26

```
aagcagagtg ctttaaaaat ttgatagtaa aaaagcaaaa atctctgtgc tctggtttta        60
aggaacattt gaatgaggca agcattttag cacaggtttc tgtttcaagt tcaaagagag        120
tctggaaaag ttgggaaaat ttaatatcat cttttatggt gtggaatcct gcccatttga       180
ttatttctat cccaaatctt gaaaaaacat cagacttatc tatgatgtca aagct            235
```

<210> SEQ ID NO 27
<211> LENGTH: 761
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t
<220> FEATURE:
<221> NAME/KEY: misc_feature
<222> LOCATION: (757)..(757)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t

<400> SEQUENCE: 27

```
aagcttatta tctcatcatc agttataatt ctcttatctt catctgcaac ctctcctcta        60
tcttcattag agccattggc agcatcagca gaaggatgag ctgcataaaa atcccttctt       120
```

```
ctcttcattt cattttttgaa aagccctgga actaatttgt atacaatatc ttggagagtt    180
ttatctgacc ttatattcag tagtggtctg gtcttgtgaa cttggacatc acaaatagga    240
caatacttgc tggtctccag gtaacgaaca atacacgttt tacagaagga atgtagacat    300
tctattatgg ttgtggcatc aatgaagtac cctccacaaa gcacacacat caggngggga    360
tttagctcag tgatcttgat tctcgttgtt cgatgcattt ctgcttgata aaaaatcccg    420
gaaagagcag ccggcgcgag gcgatcgaag cgggcggaaa agacaatgaa agttaaaagt    480
cgttcagcag aaaatgaatg cgagccaagc ggccatcttg aagcgagctg cagacgccgc    540
tgtcaatggn caaccagcgc ggccccgagc agccgcggcc gccacgctcg tctcatgccg    600
cctccggccg gcctcctcct gctccggcgc ctcggcctcc tccggcgcct cggcctcctc    660
ctcctccgcc tccgcctcga cctccaacgc ctcctcctcc gcttgaattc ggatccccga    720
gcatcacacc tgactggaat acgaacagct ccacatncng t                       761

<210> SEQ ID NO 28
<211> LENGTH: 190
<212> TYPE: DNA
<213> ORGANISM: Artificial Sequence
<220> FEATURE:
<223> OTHER INFORMATION: Synthetic

<400> SEQUENCE: 28
ttgggcgttc agagagttca ctgggtactt cacttgctga gccatccttt tggtctactg     60
acgacttcgc cattgtccgg ctatagtaaa gcagtgagcc caacacagac caggtgccga    120
tcccgtagac caccgacatc cgccggtacc aggccgtgaa ctcatttcga tacatgggta    180
cgccagcgag                                                            190

<210> SEQ ID NO 29
<211> LENGTH: 9911
<212> TYPE: DNA
<213> ORGANISM: Homo sapiens

<400> SEQUENCE: 29
gcgatcgcca tgcagaagga gctgggcatt gtgccttcct gccctggcat gaagagcccc     60 aggcccccacc tcctgctacc attgctgctg ctgctgctgc tgctgctggg ggctggggtg    120
ccaggtgcct ggggtcaggc tgggagcctg acttgcagaa ttgatgagga gcagccagcg    180
ggtacactga ttggcgacat cagtgcgggg cttccggcag gcacggcagc tcctctcatg    240
tacttcatct ctgcccaaga gggcagcggc gtgggcacag acctggccat tgacgaacac    300
agtggggtcg tccgtacagc ccgtgtcttg gaccgtgagc agcgggaccg ctaccgcttc    360
actgcagtca ctcctgatgg tgccaccgta aagttacag tgcgagtggc tgacatcaac    420
gaccatgctc cagccttccc acaggctcgg gctgccctgc aggtacctga gcatacagct    480
tttggcaccc gctacccact ggagcctgct cgtgatgcag atgctgggcg tctgggaacc    540
cagggctatg cgctatctgg tgatggggct ggagagacct tccggctgga cacgcccccc    600
ggtccagatg ggactccagt acctgagctg gtagttactg gggaactgga ccgagagaac    660
cgctcacact atatgctaca gctggaggcc tatgatggtg gttcaccccc cggagggcc    720 caggccctgc tggacgtgac actgctggac atcaatgacc atgccccggc tttcaatcag    780
agccgctacc atgtcgtggt gtctgagagc tctggcccctg gcagtcctgt cttgcaggtg    840
ttcgcatctg atgccgatgc tggtgtcaat ggggctgtga cttacgagat caaccggagg    900
cagagcgagg gtgatggacc cttctccatc gacgcacaca cggggctgct gcagttagag    960
```

```
cggccactgg actttgagca gcggcgggtc catgaactgg tggtgcaagc acgagatggt    1020 gggctcacc ctgagctggg ctcggccttt gtgactgtgc atgtgcgaga tgccaatgac     1080
aatcagccct ccatgactgt catctttctc agtgcagatg ctcccccca agtgtctgag     1140 gccgccccac ctggacagct cgttgctcgc atctctgtgt cagacccaga tgatggtgac    1200
tttgcccatg tcaatgtgtc cctggaaggt ggagagggcc actttgccct aagcacccaa    1260
gacagcgtca tctatctggt gtgtgtggct cggcggctgg atcgagagga gagggatgcc    1320
tataacttga gggttacagc cacagactca ggctcacctc cactgcgggc tgaggctgcc    1380
tttgtgctgc acgtcactga tgtcaacgac aatgcacctg cctttgaccg ccagctctac    1440
cgacctgagc ccctgcctga ggttgcgctg cctggcagct ttgtagtgcg ggtgactgct    1500
cgggatcctg accaaggcac caatggtcag gtcacttata gcctagcccc tggcgcccac    1560
acccactggt tctccattga ccccacctca ggcattatca ctacggctgc tcactggac    1620 tatgagttgg aacctcagcc acagctgatt gtggtggcca cagatggtgg cctgccccct    1680
ctagcctcct ctgccacagt tagcgtggcc ctgcaagatg tgaatgataa tgagccccaa    1740
ttccagagga ctttctacaa tgcctcactg cctgagggca cccagcctgg aacttgcttc    1800
ctgcaggtga cagccacaga cgcggatagt ggcccatttg gcctcctctc ctattccttg    1860
ggtgctggac ttgggtcctc cggatctccc ccattccgca ttgatgccca tagcggtgat    1920
gtgtgcacaa cccggaccct ggaccgtgac caggggccct caagctttga cttcacagtg    1980
acagctgtgg atgggggagg cctcaagtcc atggtatatg tgaaggtgtt tctgtcagac    2040
gagaatgaca accctcctca gttttatcca cgggagtatg ctgccagtat aagtgcccag    2100
agtccaccag gcacagctgt gctgaggttg cgtgcccatg accctgacca gggatcccat    2160
gggcgactct cctaccatat cctggctggc aacagccccc cactttttac cttggatgag    2220
caatcagggc tgttgacagt agcctggccc ttggccagac gggccaattc tgtggtgcag    2280
ctggagatcg gggctgagga cggaggtggc ctacaggcag aacccagtgc cgagtggac    2340 atcagcattg tgcctggaac ccccacacca cccatatttg agcaactaca gtatgttttt    2400
tctgtgccag aggatgtggc accaggcacc agtgtgggca tagtccaggc acacaaccca    2460
ccaggtcgct tggcacctgt gacccttttcc ctatcaggtg gggatccccg aggactcttc    2520
tccctagatg cggtatcagg actgttgcaa acacttcgcc ctctggaccg ggagctactg    2580
ggaccagtgt tggagctgga ggtgcgagca ggcagtggag tgcccccagc tttcgctgta    2640
gctcgggtgc gtgtgctgct ggatgatgtg aatgacaact cccctgcctt tcctgcacct    2700
gaagacacgg tattgctacc accaaacact gccccaggga ctcccatcta tacactgcgg    2760
gctcttgacc ccgactcagg tgttaacagt cgagtcacct ttaccctgct tgctgggggt    2820
ggtggagcct tcaccgtgga ccccaccaca ggccatgtac ggcttatgag gcctctgggg    2880
ccctcaggag ggccagccca tgagctggag ctggaggccc gggatggggg ctccccacca    2940
cgcaccagcc actttcgact acgggtggtg gtacaggatg tgggaacccg tgggctggct    3000
ccccgattca acagccctac ctaccgtgtg gacctgccct caggcaccac tgctggaact    3060
caggtcctgc aagtgcaggc caagcacca gatgggggc ctatcaccta tcaccttgca    3120
gcagagggag caagtagccc ctttggcctg gagccacaga gtgggtggct atgggtgcgg    3180
gcagcactag accgtgaggc ccaggaattg tacatactga aggtaatggc agtgtctggg    3240
tccaaagctg agttggggca gcagacaggc acagccaccg tgagggtcag catcctcaac    3300
```

```
cagaatgaac acagtccccg cttgtctgag gatcccacct tcctggctgt ggctgagaac    3360
cagcccccag ggaccagcgt gggccgagtc tttgccactg accgagactc aggacccaat    3420
ggacgtctga cctacagcct gcaacagctg tctgaagaca gcaaggcctt ccgcatccac    3480
ccccagactg gagaagtgac cacactccaa accctggacc gtgagcagca gagcagctat    3540
cagctcctgg tgcaggtgca ggatggaggg agcccacccc gcagcaccac aggcactgtg    3600
catgttgcag tgcttgacct caacgacaac agcccacgt tcctgcaggc ttcaggagct    3660
gctggtgggg gcctccctat acaggtacca gaccgcgtgc ctccaggaac actggtgacg    3720
actctgcagg cgaaggatcc agatgagggg gagaatggga ccatcttgta cacgctaact    3780
ggtcctggct cagagctttt ctctctgcac cctcactcag gggagctgct cactgcagct    3840
cccctgatcc gagcagagcg gccccactat gtgctgacac tgagtgctca tgaccaaggc    3900
agccctcctc gaagtgccag cctccagctg ctggtgcagg tgcttccctc agctcgcttg    3960
gccgagccgc ccccagatct cgcagagcgg gacccagcgg caccagtgcc tgtcgtgctg    4020
acggtgacag cagctgaggg actgcggccc ggctctctgt tgggctcggt ggcagcgcca    4080
gagcccgcgg gtgtgggtgc actcacctac acactggtgg gcggtgccga tcccgagggc    4140
accttcgcgc tggatgcggc ctcagggcgc ttgtacctgg cgcggcccct ggacttcgaa    4200
gctggcccgc cgtggcgcgc gctcacggta cgcgctgagg ggccgggagg cgcgggcgcg    4260
cggctgctgc gagtgcaggt gcaagtgcag gacgagaatg agcatgcgcc cgcctttgcg    4320
cgcgacccgc tggcgctggc gctgccagag aacccggagc ccggcgcagc gctgtacact    4380
ttccgcgcgt cggacgccga cggccccggc cccaatagcg acgtgcgcta ccgcctgctg    4440
cgccaggagc cgcccgtgcc ggcgcttcgc ctggacgcgc gcaccggggc gctcagcgct    4500
ccgcgcggcc tggaccgaga gaccactccc gcgctgctgc tgctggtgga agccaccgac    4560
cggcccgcca acgccagccg ccgtcgtgca gcgcgcgttt cagcgcgcgt cttcgtcacg    4620
gatgagaatg acaacgcgcc tgtcttcgcc tcgccgtcac gcgtgcgcct cccagaggac    4680
cagccgcctg ggcccgcggc cctgcacgtg gtagcccggg accggatct gggcgaggct    4740 gcacgcgtgt cctatcggct ggcatctggc ggggacggcc acttccggct gcactcaagc    4800
actggagcgc tgtccgtggt gcggccgttg gaccgcgaac aacgagctga gcacgtactg    4860
acagtggtgg cctcagacca cggctccccg ccgcgctcgg ccacgcaggt cctgaccgtc    4920
agtgtcgctg acgtcaacga cgaggcgcct actttccagc agcaggagta cagcgtcctc    4980
ttgcgtgaga caaaccctcc tggcacatct ctgctcaccc tgcgagcaac cgaccccgac    5040
gtgggggcca acgggcaagt gacttatgga ggcgtctcta gcgaaagctt ttctctggat    5100
cctgacactg gtgttctcac gactcttcgg gccctggatc gagaggaaca ggaggagatc    5160
aacctgacag tgtatgccca ggacagggc tcacctcctc agttaacgca tgtcactgtt    5220
cgagtggctg tggaggatga gaatgaccat gcaccaacct ttgggagtgc ccatctctct    5280
ctggaggtgc ctgagggcca ggaccccag acccttacca tgcttcgggc ctctgatcca    5340
gatgtgggag ccaatgggca gttgcagtac cgcatcctag atggggaccc atcaggagcc    5400
tttgtcctag accttgcttc tggagagttt ggcaccatgc ggccactaga cagagaagtg    5460
gagccagctt tccagctgag gatagaggcc cgggatggag gccagccagc tctcagtgcc    5520
acgctgcttt tgacagtgac agtgctggat gccaatgacc atgctccagc ctttcctgtg    5580
cctgcctact cggtggaggt gccggaggat gtgcctgcag ggaccctgct gctgcagcta    5640
caggctcatg accctgatgc tggagctaat ggccatgtga cctactacct gggcgccggt    5700
```

```
acagcaggag ccttcctgct ggagcccagc tctggagaac tgcgcacagc tgcagccttg   5760
gacagagaac agtgtcccag ctacaccttt tctgtgagtg cagtggatgg tgcagctgct   5820
gggcccctaa gcaccacagt gtctgtcacc atcacggtgc gcgatgtcaa tgaccatgca   5880
cccaccttcc ccaccagtcc tctgcgccta cgtctgcccc gcccaggccc cagcttcagt   5940
accccaaccc tggctctggc cacactgaga gctgaagatc gtgatgctgg tgccaatgct   6000
tccattctgt accggctggc aggcacacca cctcctggca ctactgtgga ctcttacact   6060
ggtgaaatcc gcgtggcccg ctctcctgta gctctaggcc cccgagatcg tgtcctcttc   6120
attgtggcca ctgatcttgg ccgtccagct cgctctgcca ctggtgtgat cattgttgga   6180
ctgcaggggg aagctgagcg tggaccccgc tttccccggg ctagcagtga ggctacgatt   6240
cgtgagaatg cgcccccagg gactcctatt gtctccccca gggccgtcca tgcaggaggc   6300
acaaatggac ccatcaccta cagcattctc agtgggaatg agaaagggac attctccatc   6360
cagcctagta caggtgccat cacagttcgc tcagcagagg ggctagactt cgaggtgagt   6420
ccacggctgc gactggtgct gcaggcagag agtggaggag cctttgcctt cactgtgctg   6480
accctgaccc tgcaagatgc caacgacaat gctccccgtt tcctgcggcc ccattatgtg   6540
gccttccttc ctgagtcccg gcccttggag gggcccctgc tgcaggtgga ggcggatgac   6600
ctggatcaag gctctggagg acagatttcc tacagtctgg ctgcatccca gccggcacgt   6660
ggattgttcc acgtagaccc aaccacaggc actatcacta ccacagccat cctggaccgt   6720
gagatctggg ctgaaacacg gttggtgctg atggccacag acagagggag cccagccctg   6780
gtgggctcag ctaccttgac ggtgatggtc atcgacacca atgacaatcg ccccaccatc   6840
ccccaacccT gggagctccg agtgtcagaa gatgcgttat tgggctcaga gattgcacag   6900
gtaacaggga atgatgtgga ctcaggaccc gtgctgtggt atgtgctaag cccatctggg   6960
ccccaggatc ccttcagtgt tggccgctat ggaggccgtg tctccctcac ggggcccctg   7020
gactttgagc agtgtgaccg ctaccagctg cagctgctgg cacatgatgg gcctcatgag   7080
ggccgtgcca acctcacagt gcttgtggag gatgtcaatg acaatgcacc tgccttctca   7140
cagagcctct accaggtaat gctgcttgag cacacacccc caggcagtgc cattctctcc   7200
gtctctgcca ctgatcggga ctcaggtgcc aacggtcaca tttcctacca cctggcttcc   7260
cctgccgatg gcttcagtgt tgaccccaac aatgggaccc tgttcacaat agtgggaaca   7320
gtggccttgg ccatgacggg tcaggagca gtggatgtgg tgctggaagc acgagaccac   7380
ggggctccag gccgggcagc acgagccaca gtgcacgtgc agctgcagga ccagaacgac   7440
cacgccccga gcttcacatt gtcacactac cgtgtggctg tgactgaaga cctgcccccT   7500
ggctccactc tgctcaccct ggaggctaca gatgctgatg aagccgcag ccatgccgct   7560 gtggactaca gcatcatcag tggcaactgg ggccgagtct tccagctgga acccaggctg   7620
gctgaggctg gggagagtgc tggaccaggc ccccgggcac tgggctgcct ggtgttgctt   7680
gaacctctag actttgaaag cctgacacag tacaatctaa cagtggctgc agctgaccgt   7740
gggcagccac cccaaagctc agtcgtgcca gtcactgtca ctgtactaga tgtcaatgac   7800
aacccacctg tctttaccg agcatcctac cgtgtgacag tacctgagga cacacctgtt   7860
ggagctgagc tgctgcatgt agaggcctct gacgctgacc ctggccctca tggcctcgtg   7920
cgtttcactg tcagctcagg cgacccatca gggctctttg agctggatga gagctcaggc   7980
accttgcgac tggcccatgc cctggactgt gagacccagg ctcgacatca gcttgtagta   8040
```

```
caggctgctg accctgctgg tgcacacttt gctttggcac cagtgacaat tgaggtccag    8100
gatgtgaatg atcatggccc agccttccca ctgaacttac tcagcaccag cgtggccgag    8160
aatcagcctc caggcactct cgtgaccact ctgcatgcaa tcgacgggga tgctggggct    8220 tttggggaggc tccgttacag cctgttggag gctgggccag gacctgaggg ccgtgaggca    8280
tttgcactga acagctcaac aggggagttg cgtgcgcgag tgccctttga ctatgagcac    8340
acagaaagct tccggctgct ggtgggtgct gctgatgctg ggaatctctc agcctctgtc    8400
actgtgtcgg tgctagtgac tggagaggat gagtatgacc ctgtatttct ggcaccagct    8460
ttccacttcc aagtgcccga aggtgcccgg cgtggccaca gcttgggtca cgtgcaggcc    8520
acagatgagg atgggggtgc cgatggcctg gttctgtatt cccttgccac ctcttccccc    8580
tattttggta ttaaccagac tacaggagcc ctgtacctgc gggtggacag tcggcacca    8640 ggcagcggaa cagccacctc tggggtggg ggccggaccc ggcgggaagc accacgggag    8700
ctgaggctgg aggtgatagc acgggggcct ctgcctggtt cccggagtgc cacagtgcct    8760
gtgaccgtgg atatcaccca caccgcactg ggcctggcac ctgacctcaa cctgctatta    8820
gtaggggccg tggcagcctc cttgggagtt gtggtggtgc ttgcactggc agccctggtc    8880
ctaggacttg ttcgggcccg tagccgcaag gctgaggcag ccctggccc aatgtcacag    8940 gcagcacccc tagccagtga ctcactgcag aaactgggcc gggagccacc tagtccacca    9000
ccctctgagc acctctatca ccagactctt cccagctatg gtgggccagg agctggagga    9060 ccctacccc gtggtggctc cttggaccct tcacattcaa gtggccgagg atcagcagag    9120
gctgcagagg atgatgagat ccgcatgatc aatgagttcc ccgtgtggc cagtgtggcc    9180 tcctctctgg ctgcccgtgg ccctgactca ggcatccagc aggatgcaga tggtctgagt    9240
gacacatcct gcgaaccacc tgcccctgac acctggtata agggccgaaa ggcagggctg    9300
ctgctgccag gtgcaggagc cactctctac agagaggagg ggccccagc cactgccaca    9360 gccttcctgg ggggctgtgg cctgagccct gcacccactg ggactatgg cttcccagca    9420 gatggcaagc catgtgtggc aggtgcgctg acagccattg tggccggcga ggaggagctc    9480
cgtggcagct ataactggga ctacctgctg agctggtgcc ctcagttcca accactggcc    9540
agtgtcttca cagagatcgc tcggctcaag gatgaagctc ggccatgtcc cccagctccc    9600
cgtatcgacc caccacccct catcactgcc gtggcccacc caggagccaa gtctgtgccc    9660
cccaagccag caaacacagc tgcagcccgg gccatcttcc caccagcttc tcaccgctcc    9720
cccatcagcc atgaaggctc cctgtcctca gctgccatgt ccccccagctt ctcaccctct    9780 ctgtctcctc tggctgctcg ctcacccgtt gtctcaccat ttgggtggc ccagggtccc    9840 tcagcctcag cactcagcgc agagtctggc ctggagccac ctgatgacac ggagctgcac    9900
atcgtttaaa c                                                        9911

<210> SEQ ID NO 30
<211> LENGTH: 5634
<212> TYPE: DNA
<213> ORGANISM: Homo sapiens

<400> SEQUENCE: 30
ttgcgcgctg cagggcaaca ccccggcgtc cctggaagct gggggagcgg gagaaataac      60
tttatttgga ctgagagctg gagaatgaga ataggacctg agagtatatt gggctaagga     120
ggagaggtgt ttgagcccag atgagtcatg gctggacgac ccctccgcat aggagatcag     180
ctggttctgg aagaagatta tgatgagacc tacattccta gtgagcaaga aattcttgaa     240
```

```
tttgcccggg agattggtat tgatcccatc aaggaaccag aactgatgtg gctggcgcga    300
gagggcatcg tggccccact gcctggagag tggaaaccat gccaggacat cacaggtgac    360
atttactatt tcaacttcgc caacgggcag tctatgtggg accatccatg tgacgaacac    420
tatcggagct tggtgatcca agagcgggca aagctgtcaa cttctggggc cattaagaag    480
aagaaaaaaa aaaaggaaaa gaaagacaag aaggacagag acccccccaa aagttcgctg    540
gccttgggtt cctcattagc cccagttcat gttcctcttg ggggcctggc tcctttacga    600
ggtcttgtgg ataccccacc ctctgctctt cgtggatctc aaagcgtgag cctggggagc    660
tcagtggagt ctggacgtca gcttggagaa ctcatgctgc cttcacaggg tctcaagacc    720
tctgcttata caaagggtct cttgggctcc atatatgagg acaagactgc tctcagcctc    780
ttgggtttag gagaagaaac caatgaggag gatgaggagg aaagtgacaa ccagagtgtc    840
cacagctcaa gtgagcctct taggaaccta cacctggaca ttggggcact gggggggtgac   900 tttgagtatg aggagtctct gagaacaagc cagccagagg agaagaagga tgtttctctg    960
gattcagatg ctgccggtcc ccctactccc tgcaagccct ccagcccagg tgcagacagc   1020
agtctgagca gtgctgttgg caaagggcga cagggaagtg gagcaagacc tggtcttcca   1080
gaaaaagagg aaaatgagaa gagtgaacct aagatttgca ggaatctggt gacccccaag   1140
gcagacccta caggcagtga gcctgccaaa gcctctgaaa aggaagcacc agaggacaca   1200
gtagatgcag gagaggaggg ttccaggagg gaagaggcag ccaaggagcc aaagaagaag   1260
gcttctgctc tggaagaggg cagttcagac gccagccaag aactggaaat tagtgaacac   1320
atgaaggaac cacagctctc agactccata gcttctgacc ccaagtcctt ccatggcctg   1380
gacttcggtt ttcgcagccg gatctcggag cacctgctgg atgttgatgt gctttcccca   1440
gtcctgggtg gagcttgtcg gcaggcccag caaccactgg aatagaagaa caaggatgac   1500
agccagtcca gccaagatga gctgcagagc aagcagtcca aaggcctgga ggagaggtta   1560
tctcctccac ttccacacga ggagcgggcc cagagtcccc ctcgcagcct ggccactgaa   1620
gaagagcctc cccagggccc cgaggggcag cccgagtgga aggaggcaga ggagcttggg   1680
gaggactctg cagccagcct cagcctgcag ctgtccctcc agagggagca ggccccaagc   1740
ccacctgctg cctgtgagaa gggcaaggag cagcattccc aggccgagga gctgggccct   1800
gggcaggaag aggcagagga tcctgaggag aaggtggcgg tcagccccac cccgccagtc   1860
tctccagagg tgcgatccac agagcctgtg gctcccccag agcagctctc agaggctgca   1920
ctaaaggcca tggaagaggc agtggcccaa gtactcgagc aagaccagag gcacctgctg   1980
gaatccaagc aagagaagat gcagcaactg cgggagaagc tgtgccaaga ggaggaagag   2040
gagatcctcc ggcttcacca gcagaaagag caatctctca gttccttgag ggagcggctg   2100
cagaaagcca ttgaggagga ggaggcccgg atgagagagg aggaaagcca gaggctatcc   2160
tggctccgag ctcaggtcca gtccagcaca aagcagatgg accaaaat cagggctgag     2220 caagaggctt ccctgcagaa actgagagaa gagttggagt ctcaacagaa ggctgagagg   2280
gccagcttgg aacagaaaaa taggcaaatg ctggagcagc tcaaggaaga gatagaggct   2340
tcggagaaga gcgagcaggc tgccctgaat gctgcaaagg agaaggctct gcagcagctg   2400
agggagcagc tggaagggga gaggaaagaa gctgtggcaa cgctggagaa ggagcacagt   2460
gctgagctga gcggctctg ctcctcattg gaggccaagc accgggaggt ggtctccagc   2520
ctccagaaga agatacagga agctcaacag aaagaggagg cccagctgca gaagtgcctt   2580
```

-continued

```
gggcaagtgg agcacagagt tcaccagaag tcttatcacg tggctgggta tgagcacgag    2640
ctcagcagtc tcctgcgaga gaagcgccag gaagtggaag gggagcatga gaggaggttg    2700
gacaagatga aggaggagca ccagcaagtg atggctaagg ccagagagca gtatgaagct    2760
gaggagagga agcagcgggc tgagcttctg gggcacctga ccggagagct ggagcgcctg    2820
cagagggccc atgaacgaga actggagact gtgaggcagg agcaacacaa gcgtcttgag    2880
gacttgcggc gccggcacag ggagcaggaa aggaagctcc aggatttaga gttggacctt    2940
gaaaccagag ctaaagatgt caaggccaga ttggctctgc tggaggtcca ggaggagacc    3000
gcccggaggg agaagcagca gctgcttgat gtgcagaggc aggttgctct gaagagtgag    3060
gaagccacag ccacccatca gcagctggag gaggcacaga aggagcacac ccacctgttg    3120
cagtcaaacc agcagctccg agaaattctt gatgagctgc aggcccgcaa gctgaagctg    3180
gagtcccaag tggatctgct gcaggctcag agccagcaac tgcagaaaca cttcagcagc    3240
ctggaggctg aagctcaaaa gaagcagcac ctgttgagag aagtgacagt tgaggaaaat    3300
aatgcttccc cacattttga gccagatctc catattgagg acctgaggaa atcccttgga    3360
acaaaccaga ccaaagaggt gtcttcttct ctctcccaga gcaaggagga cttatacttg    3420
gacagcctgt cctcccacaa tgtctggcac ctcctctctg ctgagggggt agccctccgt    3480
agtgccaagg agttccttgt gcagcagaca cgctccatgc ggaggcggca gacagctctg    3540
aaagctgccc agcagcattg gcgccatgag ctggccagtg cgcaggaggt ggccaaagac    3600
ccaccaggca tcaaggccct ggaagatatg cgcaagaacc tggagaagga gaccaggcac    3660
ctggatgaga tgaagtcggc catgcggaaa ggccacaacc tgctgaagaa gaagaggag    3720 aagctgaatc agttggagtc ctctctctttgg gaagaggcct cagatgaggg cactctggga    3780
ggatccccca ccaagaaggc agtaaccttc gacctcagtg acatggacag cctgagcagt    3840
gaaagttctg aatcttttttc cccgcctcac cgtgagtggt ggcggcagca gaggatcgac    3900
tcaaccccga gtctcacctc ccgcaagatc cacgggctta gccactccct ccggcagatc    3960
agcagccagc tgagcagtgt cctcagcatc ctggacagcc tcaaccctca gtcgccgccg    4020
ccgctcctcg cctccatgcc agcccagctc cctccccggg accctaagag cacccccacc    4080
cccacctact atggctccct ggccaggttc tcagccttat catctgctac acccacgtcc    4140
acccaatggg cctgggattc agggcagggg cccaggctcc cctcctctgt ggctcaaacg    4200
gtggacgact tcctgttgga gaagtggcgc aagtattttc catctggcat cccgctgctc    4260
agcaacagcc ccaccccgct ggagagcagg ctggggttaca tgtctgccag tgagcagctc    4320
cggctcctac agcactccca ttcgcaagtc cctgaggcgg gcagcaccac ctttcagggc    4380
ataattgagg ccaaccggag gtggctggaa cgtgtcaaga atgacccag gttacctctc    4440 ttctcgtcaa cacccaagcc aaaagctact ttgagcctcc tgcagctggg ccttgatgag    4500
cacaacagag tgaaggtgta tcgcttctga ggccctgagc aggggcttgg ggcagcccag    4560
cctctcctcc acccagacca agtgcctgag gagctgcctg ccttcttcca tctgagaaag    4620
caccctcctt ccccctttga cttgcaggag ccaccaggga ccaggggtt gagtggaaca    4680 gtaaagccac acattctgtg actatataac ctatctcagg ctaaaatgtg tggactcgta    4740
cgagctcttg tcattgacat ggcaagctga tggcgtgcgg tggctgcggg gtatcagggc    4800 cgggagcct ttgggaggaa gggaggcgtt agaggagctg ccttcggagg ctcagggagt    4860 cccttggag ctggttgttt ccttggccct gcagcgcact gctcggggct cccaaggagg    4920
ttgtgtgtat ggttcttaat tcatcaggac aaagacccccc agcatgtgtg taccctggga    4980
```

| | | | |
|---|---|---|---|
| cccgatttct | ctgggcccac | atctatctcc | aatacctcag cctcagatca gacccttct | 5040 |
| tttttgtctt | tcttctctta | atttttaaat | gcctcttttc ttgagcattc catctctctt | 5100 |
| tttgaccctc | tcaggactgg | gcttagctgt | ccagagccct gccggagggt gctgggggct | 5160 |
| gtccctctgc | aggcactgtg | ttttcctcag | gggctgtcct cagaacaccc ctcctgctcc | 5220 |
| ctggggctcc | tcagggagcc | atttcagctg | gagtctcagg tctcaaaaac aacttctcca | 5280 |
| ggaggccaaa | aaaagactgg | gttggcttct | ggtcctcatg atggctttta tcctcctggg | 5340 |
| acactttggg | tatattcatg | ggcattgttt | ccatctgtct tttctacctg tgccacccct | 5400 |
| gccctgattc | cacggctgcc | tcaggcaggc | aggcaaggag ctaggccggt gcccggccct | 5460 |
| ggcagcaagg | ggtctttgtg | cagttggaga | tgctgccgtt gtggcagagc gtcctgcagc | 5520 |
| cccgcttcca | tcagcaggct | ctggggtggg | ggctttgcag gggatgctct ctgatgtttg | 5580 |
| ttccgttgtt | taaataaaat | gcacttattt | ttgttttttt ttttgcaaaa aaaa | 5634 |

<210> SEQ ID NO 31
<211> LENGTH: 5228
<212> TYPE: DNA
<213> ORGANISM: Homo sapiens

<400> SEQUENCE: 31

| | | | |
|---|---|---|---|
| cattgtcgcc | cacgctgcag | tagcggcttc | tgcggctcca agccagcggg tcctgtgaag | 60 |
| gcgagcagac | gcggagaaag | gacgcgggag | tgagagaggg tgagtcagcc actgtctaaa | 120 |
| cgataacggg | aggcggctct | gcggggtagg | gttgaattca gtaaatgggc tcgtgctgct | 180 |
| gtctcttcgg | agacgctgct | atcttagcgt | cagcgaggga aggttgagga ggagccagag | 240 |
| ccgggtcctg | cagcgtttct | cgccatcagc | gcccgtcgcc atctccacca tgcagtcccg | 300 |
| ggaagacgcc | ccgcgctctc | gccgcctagc | cagtccccgt ggtgggaagc ggcccaagaa | 360 |
| gattcacaaa | cccacagttt | cggcctttt | cacgggtcca gaggaattaa aggacacggc | 420 |
| ccattctgca | gccctgctgg | cacagctcaa | gtccttctac gatgcgcggc tgctgtgtga | 480 |
| tgtgaccatc | gaggtggtga | cgcctggcag | cgggcctggc acgggtcgcc tgttcccctg | 540 |
| caaccgcaat | gtgctggccg | cggcatgtcc | ctacttcaag agcatgttca caggtggcat | 600 |
| gtacagagagc | cagcaggcca | gcgtgaccat | gcacgatgtg gacgccgagt ccttcgaggt | 660 |
| gttggtcgac | tactgctaca | cgggtcgtgt | gtctctcagt gaggccaacg tggagcgcct | 720 |
| gtacgcggcc | tccgacatgc | tacagctgga | atatgtgcgg gaagcctgtg cctccttctt | 780 |
| agcccgacgt | cttgacctga | ccaactgcac | cgccatcctc aagtttgcag atgcctttgg | 840 |
| ccatcgcaag | ctgcgatccc | aggcccagtc | ctatatagct cagaacttca gcaactcag | 900 |
| ccacatgggt | tcaattcggg | aggagactct | agcagatctg accctggccc agctgctggc | 960 |
| tgtcctgcgc | ttggatagtc | tggacgtgga | gagtgagcag acagtgtgcc atgtggcagt | 1020 |
| gcagtggctg | gaggctgctc | ccaaagagcg | ggtcccagt gctgcagaag tcttcaagtg | 1080 |
| cgtgcgctgg | atgcacttca | ctgaagaaga | tcaggactac ttagaagggc tgctgaccaa | 1140 |
| gcccatcgtg | aagaagtact | gcctggacgt | tattgaaggg gccctgcaga tgcgctatgg | 1200 |
| tgacctgttg | tacaagtctc | tggtgccagt | gccaaacagc agcagcagca gtagcagcag | 1260 |
| caactctctt | gtatctgcag | cagaaaatcc | accccagaga ctgggtatgt gtgccaagga | 1320 |
| gatggtgatc | ttctttggac | accccagaga | tcccttctc tgctgtgatc catactcggg | 1380 |
| ggacctttac | aaagtgccgt | cacctttgac | ctgtctggct cacactagga ctgtcaccac | 1440 |

-continued

```
tctagctgtc tgtatctctc ctgaccatga catctatcta gctgctcagc ccaggacaga    1500
cctctgggtg tataaaccag ctcagaatag ttggcagcaa cttgcagatc gcttgctgtg    1560
tcgtgagggc atggatgtgg catatctcaa tggctatatc tacattttgg ggggcgaga    1620
ccctattact ggagttaagt tgaaggaagt ggaatgctac aatgttaaga gaaaccagtg    1680
ggcattggtg gctccactgc cccattcttt tttatccttt gacctaatgg taattcgaga    1740
ctatctctat gctctcaaca gtaagcgcat gttctgttat gatcctagcc acaatatgtg    1800
gctgaagtgc gtttctctga agcgcaatga cttcaggaa gcctgcgtct tcaatgagga    1860
gatctattgt atctgtgata tcccagtcat gaaggtctac aacccagtta gggcagaatg    1920
gaggcaaatg aataatattc ccttggtctc agagaccaac aactacagaa ttatcaagca    1980
tggccaaaaa ttgttgctca tcacctctcg caccccacag tggaaaaaga accgggtgac    2040
tgtgtatgaa tatgatatta ggggagacca atggattaat ataggtacca cattaggcct    2100
cttgcagttt gattctaact ttttttgcct ctctgctcgt gtttatcctt cctgccttga    2160
acctggtcag agtttcctca ctgaagaaga agaaatacca agtgagtcta gcactgaatg    2220
ggacttaggt ggattcagtg agccagactc tgagtcagga agttcaagtt ctctttctga    2280
tgatgatttt tgggtgcgtg tagcgcctca gtgaaatgca caggatcaac agggtttgtt    2340
gtaactagat tgaaacacta agttgttttt actgttttgg aaaatatctt aaatatcctt    2400
tttgttccta aaggagagga aaagttgatt aacttctggt ttggtttaga aaaagtaatg    2460
tttgaaatac gaaggtaatt taatgttaca aattttaaca ctcaaatcaa ccttttaata    2520
attttctgtg ctaagggtcc agtatttatt tgattattta gtatgtttat gtttcatgac    2580
actaatttag tcttttgata cattttacat tctgtttact gccacaagca ctgtggcaat    2640
aacttttgaa ttttaatttt tataatagaa aaatgattag gaattgctag atagtgtttt    2700
gaaagcatat ctttttcttc agaacaatgt agacttccaa aatggttaac ctaaggggtc    2760
tttacaaaat gtgttataag ttaaacataa tttgggaagt tttacttttg ttttcttcta    2820
tgaagaaaaa aatgcaggct gggcgcggtg gctcacgcct gtaatcctag cactttggga    2880
ggccgaggca ggtggatcac ctgaggtcag ttcaagacca gcctggccaa catggtgaaa    2940
ccccgtctct actaaaaata caaaaattag ctgggcgtgg tggcatgcgc ctgtaatccc    3000
agctacccag gaggctgagg caggagaatt gctgaaaccc gggagtcaga ggctgcagag    3060
agccgagact gggccactgc actccagcct ggatgacaga gtgagactcc gtctcaaaaa    3120
aaaaaaaaaa aaaaaagga aaaaaaaaaa agaaaaaaaa ccatatgtgt attagggtga    3180
ctgagtggtg acttcattta taataataca gagaatagct ataagctcat tgacagtaaa    3240
aacaacaaac caggattcta ctgtttgaaa agaagtttcg ttttaatttt ggaatttaga    3300
atgtgtattt gcaaagtcac caattttcat ctaaaaggtt atattctagt tgtgtcacca    3360
aatcatcaaa aaaccttaaa aaagaagtaa cttgctttgt aggtttgtat tgttgatcta    3420
aacctgatac atgcttcatt taatcaggaa taatcctttt ttttctgctg acatgtata    3480
aatttcactg gattgtataa attttttatct attgccttaa acatttacat gattctcaat    3540
atgttttagc tgtacagttt tggtgttcat cttagaggat tcttcagcag aagtgatatt    3600
tctttactgt tttgtgaggt aatactgatt ttgaaaatat atataagcta aaaacagtat    3660
ttcgttgata tcagtagtca ttgtgttaac tataaagtca agtgccagca aagaacttta    3720
aaactgtaaa gctgtgtata gaactgtttt gtgtagcatg gaaatattct gtcagctttt    3780
taaagtcact aaatgttctt gattatcagc ttgaaggtat ttttgtatta caagttgaca    3840
```

```
gttgctgggt gtagtggctc atgcctgtaa tcctagcaac tcgggctga ggtgggagga      3900
ttgcttcagc ccaggagttt gagaccagcc tgggcaacat agcaaaaccc catctctaca      3960
aaaataaaaa atatgtctgg gcatggtggc ccaagtctga gtcccagtta cttgggagga      4020
tcacttgaat gtaggatcac ttgagtctag gagttcgggg ctgcagctat catctgcagc      4080
tataatcata gctcactgca gctatgatca tgtctcagca ctccagcttt ggcaacagaa      4140
cgagatccca tctcttagaa aaacaaagtt gatagttaaa gaacataagt ggatgatggc      4200
atttgaggcc actagtgaaa gtatgttttc tctaaaatat ttctctaata gtgatataaa      4260
tggctatttt attatgatgt ttgtatgtgt tttgtatttc tctgtaaacc atgctccagt      4320
cttttgttttt ctgttaccat aatgtaagag aaggtcctgg aacagagact aaatcccacg      4380
aaactgacat tgttaaacac actaaaacag aagtacttac ctcttgaaga tttaatatat      4440
aatggttgac atgatacatg tacatgatga atgaccagat gcttatggtc tacatttttcc      4500
tttatcctgt tagtattacc ttccttaatc tttgttcatt aacatgctaa ttcctcttca      4560
gtgtttattt tctagtgaca gaatgctaac atttcttaca ccctggcaga agggagagaa      4620
atgtgttttg gggtgggtaa ctaaattttt gagtgaaata tcataagatg agaatggaaa      4680
gagggagaca caaagagtta taacaaaaaa acaatggttt ttttagccat ttgactggct      4740
ctttaaatag tctacaagac attcacgttt aacatcactt ttagtgaaat aaaatgtgcc      4800
atactagtat gtgcttcaaa agggcaaatg tgctttagtg ccctaaggct aaattttggt      4860
catttgacat cagagatgtt gtaagtattg cacttaatac gcacctattt ctcaatagtg      4920
ttatttttg gctagcattt tctttaccac tatcttgttg atagcttttt gttctctaag      4980
gttgaaacat gacagtgctt atctcaaaca gattacccat ctgcagaact aaggaaagca      5040
atttatgtat gaaagaaatt cttgaattcg tcattctcaa cctttgaatt aaagcttaga      5100
ctaaatagta atatatcgtg ggaaggattt tggttttgtg atatttctgt gaattaagga      5160
atagatgtta accattattt tgtagaaaag tgatttgtat gtggttaatt ataaataaaa      5220
ctggtacc                                                              5228
```

<210> SEQ ID NO 32
<211> LENGTH: 872
<212> TYPE: DNA
<213> ORGANISM: Homo sapiens

<400> SEQUENCE: 32

```
gtactttcgc catcatagta ttctccacca ctgttccttc cagccacgaa cgacgcaaac       60
gaagccaagt tcccccagct ccgaacagga gctctctatc ctctctctat tacactccgg      120
gagaaggaaa cgcgggagga aacccaggcc tccacgcgcg accccttggc cctccccttt      180
acctctccac ccctcactag acaccctccc ctctaggcgg ggacgaactt tcgccctgag      240
agaggcggag cctcagcgtc taccctcgct ctcgcgagct tcggaactc tcgcgagacc      300
ctacgcccga cttgtgcgcc cgggaaaccc cgtcgttccc ttccccctgg ctggcagcgc      360
ggaggccgca cgatgcctgg agttactgta aaagacgtga accagcagga gttcgtcaga      420
gctctggcag ccttcctcaa aaagtccggg aagctgaaag tccccgaatg ggtggatacc      480
gtcaagctgg ccaagcacaa agagcttgct ccctacgatg agaactggtt ctacacgcga      540
gctgcttcca cagcgcggca cctgtacctc cggggtggcg ctggggttgg ctccatgacc      600
aagatctatg ggggacgtca gagaaacggc gtcatgccca gccacttcag ccgaggctcc      660
```

| | |
|---|---|
| aagagtgtgg cccgccgggt cctccaagcc ctggaggggc tgaaaatggt ggaaaaggac | 720 |
| caagatggcg gccgcaaact gacacctcag ggacaaagag atctggacag aatcgccgga | 780 |
| caggtggcag ctgccaacaa gaagcattag aacaaaccat gctgggttaa taaattgcct | 840 |
| cattcgtaaa aaaaaaaaaa aaaaaaaaaa aa | 872 |

<210> SEQ ID NO 33
<211> LENGTH: 1003
<212> TYPE: DNA
<213> ORGANISM: Homo sapiens

<400> SEQUENCE: 33

| | |
|---|---|
| gtctgcaggt atggatgttg ttctcttttc cctgtcttta tttccttacc aatcggctgc | 60 |
| catccgagga gctgaggaag cctagagctc tcagaagcag tcctttgagc tggtgtaggg | 120 |
| gcactcagaa tggtccagcg tttgacatac cgacgtaggc tttcctacaa tacagcctct | 180 |
| aacaaaacta ggctgtcccg aaccctggt aatagaattg tttacccttta taccaagaag | 240 |
| gttgggaaag caccaaaatc tgcatgtggt gtgtgcccag gcagacttcg aggggttcgt | 300 |
| gctgtaagac ctaaagttct tatgagattg tccaaaacaa agaaacatgt cagcagggcc | 360 |
| tatggtggtt ccatgtgtgc taaatgtgtt cgtgacagga tcaagcgtgc tttccttatc | 420 |
| gaggagcaga aaatcgttgt gaaagtgttg aaggcacaag cacagagtca gaaagctaaa | 480 |
| taaaaaaatg aaacttttttt gagtaataaa aatgaaaaga cgctgtccaa tagaaaaagt | 540 |
| tggtgtgctg gagctacctc acctcagctt gagagagcca gttgtgtgca tctctttcca | 600 |
| gttttgcatc cagtgacgtc tgcttggcat cttgagattg ttatggtgag agtatttaca | 660 |
| cctcagcaaa tgctgcaaaa tcctgttttc ccccagagag ctggaggtta aatactacca | 720 |
| gcacatccct agatactact caagttacag tatatgatca ctaatatagt atgctcttgg | 780 |
| taccaggagc tctgatatat atctggtaca tgtttgataa tgacttgatt gttattataa | 840 |
| gtacttatta atacttcgat tctgtaaaga gtttagggtt tgattttata aaatccaaaa | 900 |
| tgagcctttt attgaatcca gttctctatg tgaccagttc tctgtatgaa tggaagggaa | 960 |
| aagaattaaa aatcttgcaa aggggaaaaa aaaaaaaaaa aaa | 1003 |

<210> SEQ ID NO 34
<211> LENGTH: 5862
<212> TYPE: DNA
<213> ORGANISM: Homo sapiens

<400> SEQUENCE: 34

| | |
|---|---|
| gcgtccgagg gagcgcgcga cgggccacgc acgtccgggc gtccagttcg ggcagcttc | 60 |
| tccggctggt gggtgggtgg ggcagccttt caggcagggt ggcaaccaac tatatctgag | 120 |
| gaccagagcc attttggggc accagagctt gtgacctctc catctccacc cagctgggtc | 180 |
| caggggccac tctcagcact cacctcagca gctgacatca taaagcagac ttgggaacct | 240 |
| ggaagcactc tggagaacct ttccctgaga catggagctt tggggccgaa tgctgtgggc | 300 |
| cctcctgtct ggcccaggga ggaggggaag tacccggggc tgggccttca gctcatggca | 360 |
| accccaacca cctctggctg ggttatccag tgccatagaa ctggtcagcc actgactggg | 420 |
| ggtctttgag aagaggggta tccctgaggc ccgggaatcc agtgagtaca tcgtggctca | 480 |
| tgtccttgga gccaaaacat ttcagagcct gaggccggca cttggaccc agcccttgac | 540 |
| ctctcagcaa ctacagtgta tccgggagct gagtagccgt cgattgcaga ggatgccggt | 600 |
| gcagtacatc cttggagagt gggacttcca ggggctcagc ctaaggatgg tgcccccagt | 660 |

```
gtttattcct cggccagaaa cagaggaact ggttgagtgg gtgctggaag aggtggccca    720
gaggtcccat gctgtgggat ccccaggcag cccctcatt ctggaggtgg gctgcggatc    780
aggagccatc tccctcagcc tgctgagcca gctcccccag agccgagtca ttgctgtgga    840
taagcgggaa gctgctatct ctctgaccca tgagaatgct cagaggcttc ggttgcagga    900
caggatttgg atcatccacc tcgacatgac ctcagaaagg agctggacac acctgccctg    960
gggccccatg gacctgattg tcagcaaccc tccctacgtc ttccaccagg acatggagca    1020
gctggcccct gagatccgca gctatgaaga ccccgcggcc ctggatggtg gggaggaggg    1080
catggacatc attacccaca ttctggcctt ggcaccccgg ctcctgaaag actctggtag    1140
tatcttctta aagtggacc caaggcaccc ggagcttgtc agcagctggc ttcagagccg    1200
gcctgacctg taccttaatc ttgtggctgt gcgcagggac ttctgtggga ggccccggtt    1260
cctgcatatc cggaggtctg gccatagca tggctgccct gtggatgcct tgtcagtgcc    1320
gccagcctga ccagagggga ggtggatggc actttccaga gcccaggttc ttatggcatt    1380
tcccagggtt ctgtgatttc cccatgctct gcatttctag gatatttcta ggacacctgg    1440
attggctcca tcacatcaga gtggctgagg gcagttgctc tgtgttggtg aaattgctgt    1500
gggggtatcg ggggatatgg ccagtaaagt attgagagac taacaaatgg tgacctaatg    1560
ttttgtccat gacttgcagg tcccctgacc cccttactcc caggtagcac tggggcaagg    1620
gtttccttct gccccagcag ggctggccgt cagtccctg cttggtagtg gtgtggggt    1680 gcagtgtgga ggaaggcacg tgagtcctca ctcctggcct tggataccat gggtcctggc    1740
atagagcagc tcactcccag ggattgatta gtcctccact gccctgggtg catgcgtaca    1800
caattccctg gccaagcctg gctcgagcac aggaagctca tctgcgtttt ggctcaagga    1860
tgactgcctg ctttctggag gggagggtct ggaggtcttt gctgcacagt tcctgggtcg    1920
cacatccacg ttcatttaac tgaaggcttg agccagtgag gggtgtttcc tttttatccc    1980
catagctttt agctaaaaca tccctcccga gttgaccccc tggggtttca ataacccat    2040 gtgtccctgg ttgggggctgg ggagagtgag aagctgagat actgggcaca gggttgtggc    2100
ctccacccca gctctggtct gtgcagactc atggccacca ggaggcctgc agatccagcc    2160
ttcctgtcaa cagcgacagg aaatctctag gttggtgagt gctggtgatg tgagcctaca    2220
tcagggtggg tcctaagaaa catggcaaac caggctgtct cattccacta gactgccccc    2280
tgccaccctg gcacttccca gggcctggca gtatggtctg atgggcagta tggtccaata    2340
ggcagcatcc tctgctgcag ctgggagagc tgagttccag ggctgtgtcc tgcagtggga    2400
ccttgggcaa ctcctttccc tatgagaagc tggctcttct gagtccaggg ccaacgccaa    2460
ctggcaacct ctttactctt agtcaagtgg aatgtgcatg ctggcatctg aatgtccatt    2520
cgccaggcat ggagagcaag agaaggtatg tactgcctga ggtcacatga cagtgaccaa    2580
gtggagacag taagttagat ccctcccttt ggggagccta tattgctgga gtcatacccca    2640 gcctaagtgt tgccctgcac tatggctgga ggacacattt ggtagaggtc acactgcagc    2700
tcccagtgcc ccagtgtcct gcctgtgcc cagccccagc tgcatggact ctgagctgcc    2760
cctggcttcc tttaaggagg ctgctccaga aggaacctgg gtggggaggg cgaaggggt    2820 gcacaaccag ggcaaggctc cccacttcct tagtccccca tgctcacaga cctttgcctg    2880
ctaaggtcct caccagtatt gccctttctg tctttctcct tgtgcccttt ggctcttgct    2940
gtcttcagca gcatctcagg gtagctgccc tgacctcgga gcagtctgtc gccccctac    3000
```

```
acctcagcca gtcctggctt ccctgatggt ctctccctcc tggcctcagg cccattcctg    3060
aggaagggcc ttggcgagct tgtggatgtt gcaccagaag agagtgcagt gttggagagt    3120
gacactgtcg gggcagctgg ggccacaagc aggagccggc ctcgggcaca actttctgcc    3180
cagaaaaatg tgcagcttga ctctgctgag gaaaaggtcc aagccaagag gactggcagg    3240
cggggcctca agcctgcagc cactggcttg attgggccct ggacgttgag cccagatgtt    3300
ggagccacac cagcctggat ttcaatccca gaatctgccc ctcaccagga tgtgaccttg    3360
ggcagatgac ttcacctcac tcagccttgg cttctaaggc tgagaaatgg gacttaatgc    3420
tttattttat aggatgcatg tgaggagccc atggaatgtg cctggcttgg cacattgtgg    3480 cattttcct tgccttcctc ggagggcaga cacagggagg aaggacccag tgccctcagg    3540
cgtccatctg atgcatggga ccaacataag gcaggcaggg atacaaggca gtctggaaag    3600
aagggaaggc aggagtttca gtcttgggct cttgactcct cactgttgtc tagagatgga    3660
gccagcaggc tggtagcctg gcagcctaca tctcccctca gcctctcctc actatggccc    3720
cagtgccttg aggcccaggc cagggcagcc agtggctcta gctcagggaa agccaggccc    3780
acctgcccta tccctcccct tgctcctgag gccaaagcca gagactcgaa cagcctcccc    3840
accaccacca gcatatgtca aggagcactt gcaggcagaa tgggaggagg acatggagct    3900
gatggagtcc aggctgtgca agccctgag gtcttgagag atgtgcccac tgcccgtgca    3960
gcctccttca gccagagccc agagcataga caggagtgta ggagtccctg tttgatgtac    4020
tctgggagag taattctatc tcctccttctg atagttgggg aaactgaggc cttgtctcac    4080
agttggatgc ttttcccagt tgtcagtggg tttctccatg ggtctcatac agctgcctta    4140
ttgaaatagg ccccgaaccc cctaaatgca aaaaatactc ttttttgctc ctttacccccc    4200 acctggaccc tgggctattg gctgctccca atccttgccc caaacactta gctggctccc    4260
catgacttaa gtgtgttctc ttgtgtccta tggaatccag ttctgaagag gtggggagg    4320 acaactgtgg gaaaagccct gggggcccct cccaaggccc catcagtgct ctgagtaggc    4380
tgtcatcaga acaaagggct ccactgctga caaggtttga gaactgctgg cttgaggtga    4440
gaaccccttt aacctctgcg ggacagcatg tcttccccta tccaccttcg attcttttct    4500
cttttttttc ttcattggct ccttcttagt ggattctctt ctctactgcc ctgggcttca    4560
gcctttgtgc agtactctcg atgccctgaa cacacacctt ccctttgccc aggcggtgca    4620
aacaatccac ttcttcaagc tccaacacaa atgctgcctc ctttaggatg cctgctctgt    4680
gctctccctg cctcccctag cccataccct gctggcacc ttctgtacca tgccttcaga    4740
aaccttctta tcccctcat ctctggggcc ccctgtggat ctggcatacc caagttcagt    4800
aaatgtctat cagtaagctg atggtacatg cattttctag aatagagctg ggacttccca    4860
tgtggcccac atctgacctg gcagcccatg tattccggtc attagggatg ggaagccatg    4920
aggacctggc cttctgcccg acccaggcag ccattcaagt tgagcaatgg ccacttcgaa    4980
gactcaagtg cacctgatcc ctgcgcaaca gccacaccag gagaacaggc tgtccttggc    5040
ggcagtagga gcaggcgcca ggtttcctgg agctcttggc ttcagccagc cccagccag    5100 agtcctggct aggacagtga cctgatctcc tcctcatgac cttctgccct ggacaagccc    5160
cctgaactgg atttgggact gtcaaagcaa ctctacccct gctctggtag gctgaacagt    5220 gacccccaa aatggcagtg tcttaatcac ctaaaccta acatgtgact atattccttt    5280
cacatagcaa aatggacttt gcagatgtga ttaaggatct tgagatggaa ggagtatcct    5340 ggattttca ggtaaactga gtataatcac aagggcctct gtaaaggagg caggagtgtc    5400
```

```
agagtgacgg aagaaaatgt atgtaacaat ggaagcagag gtcagagtga tgcaattgct    5460
ggaggaagag ccatgagccg aggaatgcag acagcctctt ctcctctggg gcctcaagaa    5520
gaatgcagtc ctgccaatac cttgatttta agccctgtga aactgatttc agattgctga    5580
cctccagaac agtaagatca taaatttgtg ttgttttcac atgtgtgaaa acacatgtgt    5640
gataatttgt tacagcagcc acgggaaacg aatatagatt gtggtgccca aattagagtg    5700
ctgctgtaac acacgcctac tgattgaagt ggctttggaa ttgcaacgtg gaaatgggca    5760
gaggctggaa gaattttgag agtcatgata aattgcctta accacctctc ttctgatagg    5820
tgatgtggcc aggggaactc ttcctcaacc ttcagaccta aa                       5862
```

<210> SEQ ID NO 35
<211> LENGTH: 5662
<212> TYPE: DNA
<213> ORGANISM: Homo sapiens

<400> SEQUENCE: 35

```
tcctcgacgg ccgccgcccg cctggccttt tagggcctga ctcccgccct tcctggccta      60
cactcctggg cggcggcagg cctagcttct ggcccagtgc gggttcccg gcggcaggcg     120 tatcctgtgt gccctgggc caggcccgaa cccggtgtcc ccgggtgggg ggtggggacg      180
ccacggccga agcagctagc tccgttcgtg atccgggagc ctggtgccag cgagacctgg    240
aatttccggt ctggttggtc tggggccccg cggagccagg ttgataccct cacctcccaa     300
ccccaggccc tcggatgccc agaacctgta ggccgcaccg tggacttgtt cttaatcgag     360
ggggtgctgg ggggaccctg atgtggcacc aaatgaaatg aacaaagctc cacagtccac    420
aggcccccca cccgccccat cccccggact cccacagcca gcgtttcccc cggggcagac     480
agcgccggtg gtgttcagta cgccacaagc gacacaaatg aacacgcctt ctcagccccg    540
ccagcacttc tacccctagcc gggcccagcc ccgagcagt gcagcctccc gagtgcagag     600
tgcagcccct gcccgccctg gcccagctgc ccatgtctac cctgctggat ccaagtaat     660 gatgatccct tcccagatct cctacccagc ctcccagggg gcctactaca tccctggaca    720
ggggcgttcc acatacgttg tcccgacaca gcagtaccct gtgcagccag gagccccagg    780
cttctatcca ggtgcaagcc ctacagaatt tgggacctac gctggcgcct actatccagc    840
ccaaggggtg cagcagtttc ccactggcgt ggccccgcc ccagttttga tgaaccagcc    900
accccagatt gctcccaaga gggagcgtaa gacgatccga attcgagatc caaaccaagg    960
aggaaaggat atcacagagg agatcatgtc tggggcccgc actgcctcca cacccacccc    1020
tccccagacg ggaggcggtc tggagcctca agctaatggg gagacgcccc aggttgctgt    1080
cattgtccgg ccagatgacc ggtcacaggg agcaatcatt gctgaccggc cagggctgcc    1140
tggcccagag catagccctt cagaatccca gccttcgtcg ccttctccga ccccatcacc    1200
atccccagtc ttggaaccgg ggtctgagcc taatctcgca gtcctctcta ttcctgggga    1260
cactatgaca actatacaaa tgtctgtaga agaatcaacc cccatctccc gtgaaactgg    1320
ggagccatat cgcctctctc cagaacccac tcctctcgcc gaacccatac tggaagtaga    1380
agtgacactt agcaaccgg ttccagaatc tgagttttct tccagtcctc tccaggctcc     1440 caccccttg gcatctcaca cagtggaaat tcatgagcct aatggcatgg tcccatctga    1500
agatctggaa ccagaggtgg agtcaagccc agagcttgct cctcccccag cttgcccctc    1560
cgaatcccct gtgcccattg ctccaactgc ccaacctgag gaactgctca acggagcccc    1620
```

```
ctcgccacca gctgtggact taagcccagt cagtgagcca gaggagcagg ccaaggaggt    1680
gacagcatca atggcgcccc ccaccatccc ctctgctact ccagctacgg ctccttcagc    1740
tacttcccca gctcaggagg aggaaatgga agaagaagaa gaagaggaag aaggagaagc    1800
aggagaagca ggagaagctg agagtgagaa aggaggagag gaactgctcc ccccagagag    1860
taccccctatt ccagccaact tgtctcagaa tttggaggca gcagcagcca ctcaagtggc    1920
agtatctgtg ccaaagagga gacggaaaat taaggagcta aataagaagg aggctgttgg    1980
agaccttctg gatgccttca aggaggcgaa cccggcagta ccagaggtgg aaaatcagcc    2040
tcctgcaggc agcaatccag gcccagagtc tgagggcagt ggtgtgcccc cacgtcctga    2100
ggaagcagat gagacctggg actcaaagga agacaaaatt cacaatgctg agaacatcca    2160
gcccggggaa cagaagtatg aatataagtc agatcagtgg aagcctctaa acctagagga    2220
gaaaaaacgt tacgaccgtg agttcctgct tggttttcag ttcatctttg ccagtatgca    2280
gaagccagag ggattgccac atatcagtga cgtggtgctg acaaggcca ataaaacacc    2340
actgcggcca ctggatccca ctagactaca aggcataaat tgtggcccag acttcactcc    2400
atcctttgcc aaccttggcc ggacaaccct tagcacccgt gggcccccaa ggggtgggcc    2460
aggtggggag ctgccccgtg gccggctgg cctgggaccc cggcgctctc agcagggacc    2520
ccgaaaagaa ccacgcaaga tcattgccac agtgttaatg accgaagata taaaactgaa    2580
caaagcagag aaagcctgga acccagcag caagcggacg cgggctgata aggatcgagg    2640
ggaagaagat gctgatggca gcaaaaccca ggacctattc cgcagggtgc gctccatcct    2700
gaataaactg acaccccaga tgttccagca gctgatgaag caagtgacgc agctggccat    2760
cgacaccgag gaacgcctca aggggtcat tgacctcatt tttgagaagg ccatttcaga    2820
gcccaacttc tctgtggcct atgccaacat gtgccgctgc ctcatggcgc tgaaagtgcc    2880
cactacggaa aagccaacag tgactgtgaa cttccgaaag ctgttgttga atcgatgtca    2940
gaaggagttt gagaaagaca agatgatga tgaggttttt gagaagaagc aaaaagagat    3000
ggatgaagct gctacggcag aggaacgagg acgcctgaag aagagctgg aagaggctcg    3060
ggacatagcc cggcggcgct ctttagggaa tatcaagttt attggagagt tgttcaaact    3120
gaagatgta acagaggcaa taatgcatga ctgtgtggtc aaactgctta agaaccatga    3180
tgaagagtcc cttgagtgcc tttgtcgtct gctcaccacc attggcaaag acctggactt    3240
tgaaaaagcc aagccccgaa tggatcagta tttcaaccag atggaaaaaa tcattaaaga    3300
aaagaagacg tcatcccgca tccgctttat gctgcaggac gtgctggatc tgcgagggag    3360
caattgggtg ccacgccgag gggatcaggg tcccaagacc attgaccaga tccataagga    3420
ggctgagatg gaagaacatc gagagcacat caaagtgcag cagctcatgg ccaagggcag    3480
tgacaagcgt cggggcggtc ctccaggccc tcccatcagc cgtggacttc cccttgtgga    3540
tgatggtggc tggaacacag ttcccatcag caaaggtagc cgcccattg acacctcacg    3600
actcaccaag atcaccaagc ctggctccat cgattctaac aaccagctct ttgcacctgg    3660
agggcgactg agctggggca agggcagcag cggaggctca ggagccaagc cctcagacgc    3720
agcatcagaa gctgctcgcc cagctactag tactttgaat cgcttctcag cccttcaaca    3780
agcggtaccc acagaaagca cagataatag acgtgtggtg cagaggagta gcttgagccg    3840
agaacgaggc gagaaagctg gagaccgagg agaccgccta gagcggagtg aacggggagg    3900
ggaccgtggg gaccggcttg atcgtgcgcg gacacctgct accaagcgga gcttcagcaa    3960
ggaagtggag gagcggagta gagaacggcc ctcccagcct gagggctgc gcaaggcagc    4020
```

```
tagcctcacg gaggatcggg accgtgggcg ggatgccgtg aagcgagaag ctgccctacc      4080
cccagtgagc cccctgaagg cggctctctc tgaggaggag ttagagaaga aatccaaggc      4140
tatcattgag gaatatctcc atctcaatga catgaaagag gcagtccagt gcgtgcagga      4200
gctggcctca ccctccttgc tcttcatctt tgtacggcat ggtgtcgagt ctacgctgga      4260
gcgcagtgcc attgctcgtg agcatatggg gcagctgctg caccagctgc tctgtgctgg      4320
gcatctgtct actgctcagt actaccaagg gttgtatgaa atcttggaat tggctgagga      4380
catggaaatt gacatccccc acgtgtggct ctacctagcg gaactggtaa cacccattct      4440
gcaggaaggt ggggtgccca tgggggagct gttcagggga attacaaagc ctctgagacc      4500
gttgggcaaa gctgcttccc tgttgctgga gatcctgggc ctcctgtgca aaagcatggg      4560
tcctaaaaag gtggggacgc tgtggcgaga agccgggctt agctggaagg aatttctacc      4620
tgaaggccag gacattggtg cattcgtcgc tgaacagaag gtggagtata ccctgggaga      4680
ggagtcggaa gccctggcc agagggcact ccctccgag gagctgaaca ggcagctgga      4740
gaagctgctg aaggagggca gcagtaacca gcgggtgttc gactggatag aggccaacct      4800
gagtgagcag cagatagtat ccaacacgtt agttcgagcc ctcatgacgg ctgtctgcta      4860
ttctgcaatt attttttgaga ctcccctccg agtggacgtt gcagtgctga aagcgcgagc      4920
gaagctgctg cagaaatacc tgtgtgacga gcagaaggag ctacaggcgc tctacgccct      4980
ccaggccctt gtagtgacct agaacagcc tcccaacctg ctgcggatgt tctttgacgc      5040
actgtatgac gaggacgtgg tgaaggagga tgccttctac agttgggaga gtagcaagga      5100
ccccgctgag cagcagggca agggtgtggc ccttaaatct gtcacagcct tcttcaagtg      5160
gctccgtgaa gcagaggagg agtctgacca caactgaggg ctggtggggc cggggacctg      5220
gagccccatg gacacacaga tggcccggct agccgcctgg actgcagggg ggcggcagca      5280
gcggcggtgg cagtgggtgc ctgtagtgtg atgtgtctga actaataaag tggctgaaga      5340
ggcaggatgg cttgggctg cctgggcccc cctccaggat gccgccaggt gtccctctcc      5400
tcccctgggg gcacagagat atattatata taaagtcttg aaatttggtg tgtcttgggg      5460
tggggagggg caccaacgcc tgccctggg gtccttttt ttattttctg aaaatcactc      5520
tcgggactgc cgtcctcgct gctgggggca tatgccccag ccctgtacc acccctgctg      5580 ttgcctgggc aggggaagg gggggcacgg tgcctgtaat tattaaacat gaattcaatt      5640
aagctcaaaa aaaaaaaaaa aa                                              5662
```

<210> SEQ ID NO 36
<211> LENGTH: 3251
<212> TYPE: DNA
<213> ORGANISM: Homo sapiens

<400> SEQUENCE: 36

```
cagcaactat gaaataatcg tagtatgaga ggcagagatc ggggcgagac aatgggatg        60 tgggcgcggg agcccgttc cggcttagca gcacctccca gccccgcaga ataaaaccga      120
tcgcgccccc tccgcgcgcg ccctcccccg agtgcggagc gggaggaggc ggcggcggcc      180
gaggaggagg aggaggaggc cccggaggag gaggcgttgg aggtcgaggc ggaggcggag      240
gaggaggagg ccgaggcgcc ggaggaggcc gaggcgccgg agcaggagga ggccggccgg      300
aggcggcatg agacgagcgt ggcggccgcg gctgctcggg gccgcgctgg ttgcccattg      360
acagcggcgt ctgcagctcg cttcaagatg gccgcttggc tcgcattcat tttctgctga      420
```

```
acgactttta actttcattg tcttttccgc ccgcttcgat cgcctcgcgc cggctgctct    480
ttccgggatt ttttatcaag cagaaatgca tcgaacaacg agaatcaaga tcactgagct    540
aaatccccac ctgatgtgtg tgctttgtgg agggtacttc attgatgcca caaccataat    600
agaatgtcta cattccttct gtaaaacgtg tattgttcgt tacctggaga ccagcaagta    660
ttgtcctatt tgtgatgtcc aagttcacaa gaccagacca ctactgaata taaggtcaga    720
taaaactctc caagatattg tatacaaatt agttccaggg cttttcaaaa atgaaatgaa    780
gagaagaagg gattttttatg cagctcatcc ttctgctgat gctgccaatg gctctaatga    840
agatagagga gaggttgcag atgaagataa gagaattata actgatgatg agataataag    900
cttatccatt gaattctttg accagaacag attggatcgg aaagtaaaca aagacaaaga    960
gaaatctaag gaggaggtga atgataaaag atacttacga tgcccagcag caatgactgt   1020
gatgcactta agaaagtttc tcagaagtaa aatggacata cctaatactt tccagattga   1080
tgtcatgtat gaggaggaac ctttaaagga ttattataca ctaatggata ttgcctacat   1140
ttatacctgg agaaggaatg gtccacttcc attgaaatac agagttcgac ctacttgtaa   1200
aagaatgaag atcagtcacc agagagatgg actgacaaat gctggagaac tggaaagtga   1260
ctctgggagt gacaaggcca acagcccagc aggaggtatt ccctccacct cttcttgttt   1320
gcctagcccc agtactccag tgcagtctcc tcatccacag tttcctcaca tttccagtac   1380
tatgaatgga accagcaaca gccccagcgg taaccaccaa tcttcttttg ccaatagacc   1440
tcgaaaatca tcagtaaatg ggtcatcagc aacttcttct ggttgatacc tgagactgtt   1500
aaggaaaaaa attttaaacc cctgatttat atagatatct tcatgccatt acagctttct   1560
agatgctaat acatgtgact atcgtccaat ttgctttctt ttgtagtgac attaaatttg   1620
gctataaaag atggactaca tgtgatactc ctatggacgt taattgaaaa gaaagattgt   1680
tgttataaag aattggtttc ttggaaagca ggcaagactt tttctctgtg ttaggaaaga   1740
tgggaaatgg tttctgtaac cattgtttgg atttggaagt actctgcagt ggacataagc   1800
attgggccat agtttgttaa tctcaactaa cgcctacatt acattctcct tgatcgttct   1860
tgttattacg ctgttttgtg aacctgtaga aaacaagtgc tttttatctt gaaattcaac   1920
caacggaaag aatatgcata gaataatgca ttctatgtag ccatgtcact gtgaataacg   1980
atttcttgca tatttagcca ttttgattcc tgtttgattt atacttctct gttgctacgc   2040
aaaaccgatc aaagaaaagt gaacttcagt tttacaatct gtatgcctaa aagcgggtac   2100
taccgttttat tttactgact tgtttaaatg attcgctttt gtaagaatca gatggcatta   2160
tgcttgttgt acaatgccat attggtatat gacataacag gaaacagtat tgtatgatat   2220
atttataaat gctataaaga aatattgtgt ttcatgcatt cagaaatgat tgttaaaatt   2280
ctcccaactg gttcgacctt tgcagatacc cataacctat gttgagcctt gcttaccagc   2340
aaagaatatt tttaatgtgg atatctaatt ctaaagtctg ttccattaga agcaattggc   2400
acatctttct atactttata tacttttctc cagtaataca tgtttacttt aaaaattgtt   2460
gcagtgaaga aaaacccttta actgagaaat atggaaaccg tcttaatttt ccattggcta   2520
tgatggaatt aatattgtat tttaaaaatg catattgatc actataattc taaaacaatt   2580
ttttaaataa accagcaggt tgctaaaaga aggcatttta tctaaagtta ttttaatagg   2640
tggtatagca gtaattttaa atttaagagt tgcttttaca gttaacaatg gaatatgcct   2700
tctctgctat gtctgaaaat agaagctatt tattatgagc ttctacaggt atttttaaat   2760
agagcaagca tgttgaattt aaaatatgaa taaccccacc caacaatttt cagtttattt   2820
```

```
tttgctttgg tcgaacttgg tgtgtgttca tcacccatca gttatttgtg agggtgttta    2880
ttctatatga atattgtttc atgtttgtat gggaaaattg tagctaaaca tttcattgtc    2940
cccagtctgc aaaagaagca caattctatt gctttgtctt gcttatagtc attaaatcat    3000 tactttaca tatattgctg ttacttctgc tttctttaaa aatatagtaa aggatgtttt    3060
atgaagtcac aagatacata tattttatt ttgacctaaa tttgtacagt cccattgtaa    3120
gtgttgtttc taattataga tgtaaaatga aatttcattt gtaattggaa aaatccaat    3180 aaaaaggata ttcatttaga aaaaaaaaaa aaaaaaaaaa aaaaaaaaaa aaaaaaaaaa    3240
aaaaaaaaaa a                                                        3251

<210> SEQ ID NO 37
<211> LENGTH: 36230
<212> TYPE: DNA
<213> ORGANISM: Homo sapiens

<400> SEQUENCE: 37
accatatcct cctacactct gagcaatctc acggggtaga ccgcaggtta acacctctca     60
gactccttga aaatagctg gtgacgggtc agtgcccaga gctcacctgc ctttcgccaa    120
actctaaaca cccctgtgtg tttcccctac tatacccctgt tccctggggg caggtccctg    180
cattatgaag ccactaggaa aatgagataa agctttccta cttttcttcc cctgaaaaga    240
cagattttgt tttttatttt ttgagaatac caagtaagat tttattttt atttatttta    300 aattattttta acctttgttt taggttcaag ggtacacatg caggtttgtt atataggtaa    360
attgtgtgtc atcgggattt ggcgtaaaaa tttatttcat cacccaggta ataagtatag    420
tatctgatag gtagtgtttt gatcctctcc ctcctcccat cctccaccct caagtagggc    480
ccagtgtcta ttattcccctt ttttgtgtcc atgtgtactc aatgtttagc tcccacttat    540
aaaagtgaga acatgcagta tttcattttc tgctcctgtg ttagtttgcc taggataaca    600
gcccccagct ccatccatga tgctgcaaaa gacgtgatct cgtcctttt tgtctgtgga    660 gtattccatg gtgtatatgt accacatttt ctttatacag tctactgttg gtgggcattt    720
aggctgattc catgtctttg ctattatgaa tactgctgca gtgagcattc atgtgcatgt    780
gtccttatgg tagaacaatg tatactcctt tgggtatatg cctaataatg ggattcctgg    840
gacgaatggt agctctgttt taaggttctt gagaaattgc caaactgctt tcctcaatgg    900
ctgaactaat ttatgttccc accagcagtg tataagcctt ccgttttctc tgcaacctct    960
ccaacatttg ttatttttg acttttaat aatagccatt ctgactggtg tgagacggta   1020
tctcattatg attttgattt gcattttct aatcattagt aatgttgaac attgttcat   1080 atgcttcttg gtcacgtgtg tgtcttgaaa ggcagattt tatgtatttg cgtatttatt   1140
tttttcacag gttttttttt tgaaagtctc actctgtcgc ctaggctgga gtacagtggg   1200
ataatctcgg ctcactgcaa tcttcgcctc ctgggttcaa atgactctca tgcctcagcc   1260
acttgagtag ctggggttac agtcatgtgc caccactcct ggttagtttt tgtcttttt   1320 ttttttttgg tagagacagg gtttcatcat gttggccagg ctgttcttga actcctgacc   1380
tcaagtgatc cacccacctc agcctcctaa agtgctagga ttacaggcat gagccatcgt   1440
gcctggcctg aaaagcaga ttttaaacgg caattcattc ttctatccca ttgtgaacta   1500
tacagttgat ggattttcca tcactaactt gaaactctaa attggcttcc ttctgctccc   1560
cagtaggttt cagggctgcc tcttcacatc ttagtttctg agaactcttg gatttttatta  1620
```

```
aatagtgagc taaacaaaac aggattgtgg aaggggcccc ttgacaccac acttacctgc   1680
cctccctcaa agtccctgat ctcaggaaaa tctaacacct atgaagaaaa tggggataaa   1740
aaatgcatac aaagattatt accaaaaacg aaagattcgt tgtgtaacta attgagatta   1800
actgaagctc tgccatagct cccagccact gcccccactc accttgctta tatactctaa   1860
ctctgctaac gaactgtcaa gtgtgttgga atgggcagaa tatggggtgg ggagtgcata   1920
atctgtagag cttctacaga tacagtgcta ggtaggtcct ttctataata tctcatctca   1980
tcttaaaaga cttgttggcc gggcatggtg gctcacgctt gtaatcccag cactttggga   2040
ggctgaggaa ggcatatcac ctgaggtcag gagtttgaga ccagcctggc aaacatggtg   2100 aaacccccgtc tctacaaaaa atacaaaaat tagctgggtg tggtggcgcg tgcctgtaat   2160
cccagctact ctggaggctg aggcaggaga atcgattgaa cctgggaggt ggaggttgca   2220
gtgagccgag atcgtgccac tgcactccag cctgggtgac agaatgagac tgtctcaaaa   2280
aaaaaaaaaa aaaaaaaaaa cttgttaatt gtcctcatt  cccaggttgg aaaacaggtc   2340
caaagattca cacccaaggt ctaaaggctg taactcctct tcttatacag ctgttacaca   2400
tgcacgtgtg tacacacaca cacacataca cactctcttg agcatgccca cacactcact   2460
acatcttgga actgggatgg ctcaaataaa gggagttagt gaggcctccg ctgagaaaga   2520
gagaaagaga agagtcacaa tccataaccc aattcaccca agtcttatct ttcctgtcct   2580
cagagttcct tctgctctga gaaccaccgt cccttccact ttctcttttg acaagtttca   2640
aaactgaatt ttcccccaca cccccccaat acatttcccc ctcacattcc tccccatcct   2700
gcccaggtaa gctgttagcc taaccttata ggaaccaagt cctgggatcc ttttcaatgt   2760
ctacaaagcc tagccctggc aagggagcac tggctgtgtg gtcctgtgcc agcactgaac   2820
atggccctag ccagtaacag tggggctgaa tgtagttccc tcttatgtct agatctctgc   2880
tccggcagtc aaaggagatg tgaaaccttc tgtgaggcca aacaggaaa tggtaggaga   2940 ggatttcact tctctattaa ttcaaacact gagggagctc tttagaataa agaaggacag   3000
aaaacccaga cacctgtgct cagcagtgtt ttccttcctc tcctcctccc aacccttcca   3060
tttttacaga tatagctctg tcttttccacc tctagccaat tcaaaataac atttcagttg   3120
ctctgtccat tgttacttat tgttaatta ttgatatagc accgggaccg aagaggtatg   3180 gagcccaac caggttccca catgttgcct ttctttatt gcctacacac aaccacccaa   3240
agagtgagtc ctctccttt ccattgcctc tgcccttagc ctgaccacca catgcctgca   3300
gtaaactagt cccagggttt gtgtgcaaag cattactggg aaaatacaga gtgagaagat   3360
atggattctg cccccatatc gctttgcttg tacgtcaatt ggggagtgag aacaaacact   3420
ttaaatagtt tatattaaag taagtaagca ataaggccag tggtcttaaa agagaagaga   3480
gaaatcacca tggacatggt agacagggag tactctcagt cgagagggcc tggaatgagc   3540
cttgaatact gggctggatt tgtgttggag aggaggaagg cagttggcat tgtaggtctg   3600
gtgtatagct ccacaagctt gacaatgctg tgaggtgcca tcaggaggaa ggtgtcctac   3660
gagagcctgg gttagctaaa acaaagacaa gctacaataa cgtcactggc actgcacgtt   3720
ggaggaagtc acaaatgtga tttcttgttt ttttctgaga gtatggccat aataataaat   3780
ctcttctagg cacttcctaa agttgctcca tgtcagttcg caggttcttg gggcagacgg   3840
ttttaactga agtctccatt ttataaacac aaaattgctc aaccagttaa tcacgcctca   3900
tagcataaga ccacattcgt gacttcagtg tcttttcaaa actacacaca cctacatcct   3960
gccaagatta tattacttgc ccaatctgtc caatcccac cccaccccctg ccatctaccc   4020
```

```
cttacctcac ctccgcccac acacacaccc tcctaccctg tcaggattca ctgctctaga    4080
ccctgacctt tggattatag tttctgtagt cagttcacca tccttccaac ctacagtcaa    4140
attatttgaa ctactaggga tagtctatct gatttgccac aactattttt cctttttaa     4200 ttttattttt tgccaccaca actattgaag aatgctatct tcatcttacc cacgagaaaa    4260
tggaggcaga gggaggttaa gtggttgccc agatttaccc agatactaag taataaaacc    4320
attacttgaa ctcaggattt attactttaa atcctgtatt gccaataatc aattggaaaa    4380
taactgaaaa ttgcctacta tttataataa caataaaaac catagcatat ttatgaatta    4440
acatatcaaa tataagaatt ttaagaaaaa agaaaacttt attgaagtgc acaaagacct    4500
gagaggtgta gagatatacc atattcatgg ataggccatg ctaacataat gacaacctct    4560
ccccacatct ctaacctaaa tgctacccca attaaagtaa cagtaggatt tcaggagaat    4620
ttaacaaact gattatagaa tgtacatgga aataaagtcc aagagtatct tagaatattt    4680
tgataaagaa aaggaaaata aattttttgg gaaggtggtg aaggaatgga gactagttct    4740
actaaatagt aacacatatt aaaaagccaa aataatcaaa caatatgata ctgattagta    4800
atgagagaaa agcaaattaa aacaacaaaa taccactcta cacccaccat gttgccaaca    4860
tttgaaagtc aaataattac aagcattagt gagcataaag ggaaatgtga actatcttgc    4920
tttgttgatg ggagtgtaaa ctgtttatga tccctgaatt atagaaatta taaactagtt    4980
gggcgaaaaa attaacatag gaaataaagc ggcatatccc aatccttagg ttgagtgctt    5040
taagtcttgg aagatttcaa taaagagaaa ttagggggcag gttcatggaa taagttgaac    5100
tggagttgga cctatggagt gggttaagac aggaacaaga tgagcagaat aaagaaagca    5160
ttcttgtgag aggaaagagc ctgggcaaat gccctaaacc aaaatcagat ataataacctc   5220 aaggaagagt gaggaaaaaa gatttattca agaatagcat tcctgctggg aatagtgagt    5280
aatatttttt attagaaaag gggcaccaga ctagagagga tactgagtgc ttctagagta    5340
cttaagtaac agtatcatag aaggtttcat cagagagcat ctaatctaag cccatcattt    5400
tacagatgaa gactttgagg cccagagagg ggaagtgact tgtctaaagt cacacagcat    5460
aataaagcac ttttaagtct tgcctgacag gaaatatcta gataagttgg aaaacagaga    5520
gacagagaaa ttaggaagaa ctagaaagca ccacatctag aattactaac atgagaataa    5580
aaagaaaaac atctaaaatg gagaaaatac aatacttgaa gctagtattg aggtatattt    5640
cagaaaagag aaagaagtct acgaggcaac taagttctcc tctgaagatc aagaccaata    5700
atgataaggt taggttattc agcacatttt ctatgtgcca aacactattt taagcattct    5760
gtaggtatta acttatttaa gcttcacagc atgaggatat gctgccttat ttcctatatt    5820 aacttttttca ctcaactagt tcataatttc tgtaattcgg gcatcataaa cagtttacat    5880
tcccaccaac agaccaagat attacagttc acattttcct ttatcctcgc taatacttat    5940
ttgactttca aatgttggca acatggtggg tgtagagtgg taagggggac accattgtta    6000
tcatcatcct tttacagaaa atgacaccaa agcacaagtt aagtaacttg cccaagggct    6060
cacagctaaa cgctgacagt tacgattgaa tccccagcag tcaggttcca gagcccatgc    6120
ttcttaaccg gtacacatga tgctgttaga aatgagatgg ttcagacaca gtgcaacttc    6180
tcttagggag aatttaatat tttcttttag attagactct agtacaatgc caagaacaga    6240
aactccctca ccaaataatt gccctctcaa ctttattgcc accctgtcat ccaaagcaac    6300
tcccagaccc taaggaatgc aagaaagaaa gcatatgcaa agcaatttac caccagtggt    6360
```

-continued

```
catgtgctgc cacctttcgt tatcttccca ggacagcacc tgtgcagttc tccttggaca    6420
gttcactcag gccaaggaac agattgtcag gaaagacatg tgaattcttt gcccttccag    6480
gctgttttca cttcatgtta ggggcttcat gatactgttt tcccagaact gacataactg    6540
attggtatag cacttgggag cttattcttc ccatccctga gcttctgttt ctcagttacg    6600
gtgagggttg aagggagtta tatgttcctc agggcagcct atacgagaca taaacatttt    6660
cacaaacagt aaaatacaca acacacacac acacgcacaa aacacacaag cagcttcctt    6720
aaccattttg taagcagatt attagaaaat aactctgcct tcgtttctca catattttgc    6780
acaaaccgat agatggaaaa acatcatgta ccgccaagac cagggaataa gagctcagct    6840
ggcaaattag gggttttccc tatttccctc cctaacgagg tcaagctgtg ttcaggttaa    6900
ggcatgctga atttgaaacg acaacccact caagttgaga tatccagaaa caaataccat    6960
gagttaagaa agaagccaca ctgatataaa gaaatgagat ttattgcctt gtgggggaa    7020 gggatgtggt tgtgataggc aggccactct gggatccctg ggatgcaagc ccagggacag    7080
cagagtcccc aggtgggaaa tctacacaca cacccaggg atgtcccaga gacttcttct    7140
accctaagag gagatcctgg gcaggatgtg agaaatctga gcatcctctg tttggatggc    7200
cgaagctgct ggcatcaaac tctggtctgg aagaatcagt ctgggggaga gacagggatg    7260
gaggaaaggc atcagggat ccatcctcct cctccttctc ctcctcctcc tcccccacaa    7320
aggccttgct cgccctgcct gcaccacacc ctgcagaagt tgatctctcc ttgttcccaa    7380
atcatctcca agcacccttc ctacagcacc ccatgattcc tttttcact caaagcaatt    7440 cttgtgaccc ataactgtgt gtgtgtaact gggtccccaa ctgggaagat gtgcccccat    7500
ggtgctggat acaggccccc acacccaagg gcctgaggat cgctatatgt cccccatgc    7560 cacaaaataa tcctgacaca tgcacgcatg caccactgta tctggctccc acaggctcac    7620 ccgcccccte cagatgacat accacctgag caaggcttcc ggaagtagat gatgagaaca    7680
atgcccacga tgatgcccag cacacccagg ccaaaggcca cgccacacag cacattctcc    7740
agcagatctg agggcagtgc gttccgggt actggaggaa atgagtggct cagcctgggg    7800
acctagttag ggagcctccc acccagggaa atgacgtggg tgtctgggat gacatggag    7860 actgggatgg gcttagggta ggaatggact aaacaaggta ccagtggaga aagaagcctc    7920
ctcccatgga tctatccctt tttgccccca aaaggaccag aattccaggg agaaagcctc    7980 acccaatag gcaattgctg tgtagcggtc aatttcgtga gtcacaatgc aggagaaaat    8040
gtcagaaggt tctggtgtga agtttaagta agaaaaggcc tggaagctga gtccatcgac    8100
agctgagaca aaagtaggcc caaatccttc cacagggacg gaatgatgct gccagttcac    8160
tgtcagcatg ggtgggaaga gattactgac aaaacagacc aaagtgttgg gcttgccaaa    8220
ctccaggggc ttcagcgtga acacttcagc gataggaaac cctggtgggg ggattgaagt    8280 gtaggggaa aaagagacta gtttagatgg tatctctgtg tttggagggg ccatggcata    8340
tggaggggag ggcagagaag aacacagtgg gtcaggcttt gggagacaga gatgagcgag    8400
gagctgggct ctgaagggag gtcttcttcc aggcaaggac tgcagctaga cgtagaagca    8460
gagccagatc caggctactc tggacccctc caccatgact tccttcagca cttcctgtct    8520
agagctcaca ttgatgtcta accatgcact gtcttctcac taagacatag tcacgtcatc    8580
agatatttcc actcttccca tccatcttgc tgggcatagt agcacaagtg ttaatattca    8640
gtaggtatca gttggtacct gttgaattca tcacattcaa tacatagttc tgaatgccta    8700
ctacatgcta ggtacttcgg cccaccaaaa gaacacaggg tgcagaccaa ggctggtgga    8760
```

```
aaaattaagg tgatgaagag aaccagaaag tatttgagat ggggagctgg tatcaagggg   8820
aattattcag tgtacagatc aatgaggtta atgcagccct cctcccttca ctccccagaa   8880
aactcctgac ctctggacac cgggattttc ccatcaagtt ttggccctat ttgctggatc   8940
atccactcgc agaactcttt gtcaaataaa atggcaggag catctccctg ttcctgagcc   9000
cagtcagcaa attcgggcag gcgaggcacc cgagtgttct gggaaaagtc gaagaagaaa   9060
agctggtcct cgtcgtaggc ctcagagagt cccacactgg gactcccatc ctggcagtac   9120
actgtgtgca ggaatgtgtg gttttgcagg tcatctggcc acattggagt aggagctgca   9180
aaggacacag ggtgaggttc agggaggtgg gagccttctc ctccaactta aaaaacagca   9240
aggtggggct aggcgcagtg gctcatgcct gtaatcccag cactttggga ggccaaggtg   9300
ggtggatcat gaggtcagga gtttgagacc agcctggcca gcatggtgaa actccatctc   9360
tactaaaaat acaaaaaagt agctgggcat gttggcatgc cctgtagct actcgggagg   9420 ctgagggagg agaattgctt gaaccaggga ggcagaggtt gccggagct aagattaagc   9480 cactgcactc cagcctgggt gacagagtga gactctgtct caaaacaaaa caacaaaaac   9540
aagcaaggcc tgcttaagga gcgtgggctg aggtgagacc cttcctgtg tctgttattt   9600 agactccccc tcccaagggg ggtgaagaac aaattatggc atctctccaa gcttcccctg   9660
cctataaaaa ggccagttgg caaaagtaaa gagttctact ttctaaagtg acagattcag   9720
gccaggcatg gtggctcatg cctgtaatcc cagcactttg ggaggctgag gcaggcagat   9780
tgcttgagcc caggagttca agaccaacct gggcaacaca gcgagaccgt ctctacaaaa   9840
aatacaaaaa cttagccagg tgtggtggca acacctgtg gtctcagcta ctctggaggc   9900
tgaggcagga ggattgcttg tgcctaggaa gttggggctg cagtgagcca tgattgtgcc   9960
actggactcc agcccaggtg acagaatgag cccgtctcaa aaatatata tataaaggcc  10020 gggcgcggtg gctcaagctt gtaatcccag cactttggga ggccaaggcg ggtggatcac  10080
ctgaggtcag gagtttgaga ccagcctggc aaacataatg aaaccccatc tctactaaaa  10140
atacaaaaat cagctgggtg tggtggcatg cgcctgtaat cccagctact tgggaggctg  10200
aggcaggaga gtctcttgaa ccccagaggc aggggttgca gggagccgag atcacgtcac  10260
tgcactctag cctgggtgac agagcgagat gccgtgtcaa aaaaaataaa ttaaatcaaa  10320
taaaaatttt aaaaatgtat atatataaaa taaagtgaca gattcagagt cactgttcat  10380
tgtgtgtttg ggggctgcac aaagacacct agccaaagaa gcaagtgaaa gcctgcattc  10440
tgctcaccat gccatacatc ctggcatagg gctgtatcct cccaaagggg attcctttgt  10500
ctaattcata ccaggccact gtattgacta gagaaggcca tggatgggtt tctcactctt  10560
agaagggaaa gaggaggaat ggctacagcc tccccaagcc atagatggga ctgcctccca  10620
ctatccccag acacaaatgg taaattggaa aacctgtatc cagacatttc ttcagccact  10680
tcattggcac caagcgtctc tcaaaatgtc ttctgttcct taacctacca ggcctcccaa  10740
agacagcaat gggagaagtg acccccataac tgcataaaat aatccctctt ctttgaagct  10800
cttggcagga atcgctcagc cagcaggaaa cctttaaccc aatacccaga aaaacagaca  10860
tttggaggaa gagggatctt ccagattatt cttccattct gccccatcct ctacagagaa  10920
ggaaactaag acactttca agaatcacaa gataagttaa tgatagaaag cagagtagaa  10980
tcttgagtgg aggagtgaaa ataacattca ctttgttcaa atcccagctc taccactttc  11040
caatggtgtg aacttgcaca aataactctg agtctcattt tcttcatttg taaaatggag  11100
```

```
agaacaatct ccgcttcaag agattgtctt aaatggaaca tgcaaagcat cactgatatc   11160
gtttaccaac cacacatagc agctgtcttt ccccactccc ctgttgtttc cactgcctca   11220
taagacttcc caccactcac aaagcacagc gcttttcctc acaaagctga gtgggctccc   11280
taggttcagg atggaagtaa ataggagtac catcttacct tcagggacgg cccaggagtg   11340
gggtagcagc cacagaagtg gtaacatctg tagcagcgca gctccttggt tctgttcatg   11400
acccatacct tcttgccaca cagtaggtag gagctaccaa cccagccaac ccagcttccc   11460
caactccctc cccgagaggg tggccttaga tcatgttttg ccagatcatt tccaataggt   11520
gcccttgtca ttttgtctaa accaatcaga gaagcgtagg gtttaacatc atcagtcact   11580
ggggagacgc ctggggccag taacctcctg aagacttggc tgtttgacca gggcagagta   11640
tggcatgtaa ctgggctggg aagcccagtg gaggaatgtt gcttcctggt ggagttccct   11700

ctttggtttc aagctgtcag cctcagtctg taagcgacca gctggctctt cagagcagtg   11760
ccacctcctg gcagaatgct gcaatgggga accgcatctt ccccaagtaa acccccaggg   11820
ctcttcggac cctgccttct cctccctcct ggctcttcct ctttctcaaa aaaacttatt   11880
ctccttcagg cattagctct aattcatttg gcagacatat attgaaaata caagaaattc   11940

tgggtgttgg gcccagggct agaaatacaa agatgaatag gcatagtctg ccttcaaaga   12000
gcttagagtc tagtgctggg ggaggggggсс aagggataat tacacaacaa tgtaatgtat   12060
tcaaataaga atgtgccaag tgтттттggaa gtcgcagtaa ttttatgagg atgcggaata   12120
ggaggaacat aatcaggcag gctcctaaga cttgaaggaa aaacaatttg gccagcagaa   12180
catgaaggaa gagaaaaaca cgccagggca agggtaggc agaagtacaa agatcacagg   12240
catccagagg tcctctttgg agaccctgtg tactagttga tatgaatgtt gtgaaggtcg   12300
cttgggtgtt cctgtataat aggaggtaat gggggtaga aggatgttgt gataagctac   12360
aaattcgggc aagggccaga tcacgtgggc cctgctacgc cacaaggagg agcttgcttt   12420
tacttagcag atgatagaga tattaaaact ggggaatgac aatcatttta gcatttt gga   12480 aaaaatgttc tgattgatat tccaaacaat gaactggagc ttttaaagaa ttgaggcaaa   12540
actgctgggc aagagtctat agcataccaa gatgaacagt tgcacatata cacaccactc   12600
ctgtagcaat acagcaataa tttaaatgac agataataag agcctgaatt aagtcataat   12660
tagaggaggc agaggagata gaatatcaag ataattagga agtagaatct aaagggtttg   12720
gctactgatt agctgtggga gtgggaaggt ggaggagtca agatatctc agattccag   12780 catgggtggc tgggtgggtg tcagggatg gactgaattg aagcagaaaa gaatgccatg   12840
ggagcaggtt tacagagaga aagagcttga ttttgtacat gttgaattg aaatgccagt   12900 ggaacagcca gctgaaactg catgggagcg cagtgaggcg tgтggгатg accccaggt   12960 atggtctgaa gaccctgatt tgagagtcat cagcacaaat gtcgaagcag aggccatgaa   13020
taagatcacc caagtaaact gtgcagaagg agtgggaagt gaaacaagga caaaagcatg   13080
catgggctca accccaaac ctcataccag ttatccagga tccagtcagg agcatttaac   13140 tacttatgt gcttcagact gaaagaattt аататаgага attggttaca aaggtgttaa   13200
aagggcaaga agtacaaaaa aaaaaaaaaa ggagagtcct agaaatgtac attttaaaaa   13260
aagattgcta tctggaaatc agaagctgcc atcatccctg agctggaatc tgtaaatcta   13320
ctcattgcct tgtgagagac actgtcatag tcagttccaa tctactagaa aggtgccacc   13380
tccttcaagg ctagaatcct tgagaaggta cttctgctca ggaggctgga gtcctgagtc   13440
tcccattctt cctgctgcta cagctacagc caatagctac cagctattgc cagccaccgc   13500
```

```
cactgtttag aggctgaagc aggatgcttc tcagtttctc ttgccttctg atctcccatc    13560
agtgcctcct actggcagaa tcaaaaagga agccagatgt ccaggaaggc tgggaaatac    13620
acacctggct gactcctaag ctaagcagtt caaaacacag tagaggaggg tgtgtgtgtc    13680
actgagacaa agataataac gagtacactg aaatacctg gtttgtaaga atctggtggc     13740
acgaggacca tccagagcac taagaaaaga ccaaggtaga agcagatcag agaaataaaa    13800
aagaggtgtg ccatgaagga gggcaaggtc agcattttta aatgctactc aaaagtcaag    13860
aaaggattga aaagtgtcct tagatttggt gattatgaga tggctgacaa atttattgag    13920
agcagtttca gtgttgtagt gggagtcaac tccagattgt ggtgggctga agtaagtg      13980 ggaggtgagg aagaaactgt cagtgtacat gcttcaagtt tgttagacaa agaaagaga    14040 aagacagaag gggtggggga agaggcagtg agaaagctct aatgtggcaa tcaagtaatc    14100
tgagaaatta atatatgtga atattgtcca acagtgtttc tgaggctttc aaaattcata    14160
ccttccacct ttttttttt ttttttaag acaaagtttc ccctgttgcc cagactggag      14220
tgcagtggct acttacaggt gcaatcataa ctcactccag tcttgaaccc ccgagttcaa    14280
gcgatcctcc cgcctcagta gctggggact ataggcacat gccactgtgc ctggcttcat    14340
atcctctttt gataaacaag taatagcagc agtaatagcc aaaacaaaa acaactctat    14400 gacctcctag atattctgga acagcaatgt gtatatatgt gtgtgtgtct gtgtggtgga    14460
ggcagggtgc cagggaagga ctagggtttg gaaatcatgg taaccctcca gaaaacaaaa    14520
gaacatttcc cagtatccca acatttatgc actaacccat cagcggttct ggcagtgggg    14580
agattcaggc ccctggacag tagaaaagaa gtttatgaga ctaccagtgg ggagacatat    14640
gggacacagc cacctagagt cctaaaccag gggttagcaa acttttttctg taaagggcca   14700 gatggcaaat attttagaca ttgtgggcta tcagatctct gtcatgagta ctcaactgtg    14760
gcacgaaagc ctccatgcac aatatgtaaa tgaaggagag tggctgtgtt cctagtttcc    14820
tcctagcttt tcctcccact tcttgagcat ctccttctca gtctccttca tagactcctt    14880
cctttcagct actctttaaa tactggtgtt ccctggagtt tttgtcctca accctctttt    14940
tatttatgga cactaaaatt caaatttcat gtaattttca tgtgtcacga aatattcttc    15000
atttgctttt ttttcccta accatttaaa aatgtgaaga ccattcttag cttttaggcc    15060
atttaaaaac aggtggtagg caagattgtg ctcacagccc atagtgtgct gaatgatgct    15120
ctacacgtgg tcagaattgg tacgaaagcc ccaaattaaa cccacccttc aaagaggaac    15180
ctcagtcccc ttattattgg attggcaatc agttaacaaa cactttgtgc cagttacacc    15240
agtctatttg gaaggagatc tggggaagaa caggagaaac tagactgggt ggaagggcat    15300
aggaataggg acagcagaca ctgcaatttc tctgggtgag aggaacaagg cagagggtc     15360 caagttctcc atagggagca cagtgtagac aagaccaagg tgaggacaaa cataaccatc    15420
cctcaccaag actgtggtga ggggtggtta actccattct cccccttctat aatctcagtt   15480 taaatggtaa caagttcaaa cacttataac tactcttccc tccatgtaat ccttccccac    15540
caggacctcc caactacctc catcataagt atctccaggaa tagtctctca tcagtttgga   15600
aagtaataat tgtgggcaag agatgagcaa ggcagccagt tctgctttgc agtagttcac    15660
tgtctacttt gtcattagct atgaatgcct ctgaaaataa tggcacagca ccggtaaatc    15720
caggaggctc tggctttcta acactcagct ctgccatccc tttctagcat ttaaaaatgg    15780
actctatttg gccaggcgca gtgattcacg cctgtaatcc cagcactttg ggaggccgag    15840
```

```
gggggtggat cacgaggtca ggagatcaag gccatcctgg ttaatggtaa aatcccatct   15900
ctactaaaaa tacaaaaaaa aaaaaaaatt agccaggcgt gatggcgggt gcctgtaatc   15960
caagctactc aggaggctga ggcaggagaa tcacttgaat tcgggaggtg gaggttgcag   16020
tgagctgaga tcgtgccatt gcactccagc ctgggtgaca gagcaagact ccatctcaaa   16080
aaataaataa ataaatatat aaaaaggact ctattttttt tcccctagca gagtcagatt   16140
tcttggaaaa gtcatgggca actgtggccc cgctcccatt cttaccattt aatcttttaa   16200
ctctcaacaa tgcaattgtt caccaatact tttgtgttgc caaatcaaat gaactagtct   16260
ctgcaacatc tgacactgtt ggccataccc tatctcctaa attggtcaaa tttctggcat   16320
ccctgatggc actctctcct agttttccct cctacttttc tggcgtcccc ttttcagtcc   16380
ctttgggact cctttctttc agcaaccctt aagtattgg tgttccctgg agttttgtcc     16440
tcaaccttta ctcttcttag actatacact tgccctggat ggtcctctca tttactccca   16500
catgccttct gttaccaccc atttgctaat gtcttccaag cttacctctt cagctcagat   16560
cttgctctga gttccacact acccatatct gaaccacttc tggtcaaatc cacttggatg   16620
ctatgcaata gcagtttttt gtttttgttt ttttttttaaa tatggaacgc ttcatgaatt   16680
tgcatgttct taaactgtat tcttcacaat agcgttcctc aagaaataaa aaagtaagt    16740
ttgatgatag caatcattta tttttgaatt tatttccaca tagacataat gcaacatcaa   16800
acacatttat ataatatttt ttattatgta acaattatt atatttaata agtctattta    16860
ttgcaagcaa tagaaaccaa ttctggctaa cttacatttt aaaaatgagg atttattgga   16920
aagatactga tctaactcat gaaatgaaag taatagttga ataagctagc ctcaggtaga   16980
atagccacag ggaccttaga agcaggggtt gagttgccat taatatgctc acctgcaaag   17040
gcctcctgcc tctttatctt tcaagttttg ctttgctggg agagcctctc tcactggctc   17100
agcttgtatt aggtgtgtac cactggattc attggttgtg gccaggtaca gtattacctc   17160
tatggattag agctattcct agagaaggga gaatcatatg aaaagtaacc acctcaaatac  17220
agctattttc aacatatggc atctcagaca attgtatgag atcatctgag gcataaacat   17280
aaggttaaat ctgtgtatta atgctcaaac agcatttcct aactactcag gtgacatatg   17340
tcatctgctt gatgatctct ggtcggtcac ttgtcttatc acatattcaa attacattta   17400
tcatgtgatt caatattgat ttattaattt aaaattatat attccacgaa tttcctttga   17460
atctctgact aaaaaggttt ttttaatttt actttgaaaa gctccaagca cacacagaag   17520
agaagaatct aataaactcc aatgtactct catgaatgtc aacaattttc aacatttaac   17580
attcttccat tcttgtttca tctattgttc tgcattttt ggagtatttt aaacaaattc     17640
tgtcattaca tttcaccagt aaatactttt aggcatatct ataatagata taacctttc    17700
ccttaacata actataatgc catcaccaca accaacaaaa ttaaaaatta cttaacttca   17760
tttgacccaa tctgttcatt tctcctagtt atctcaaaaa tgtgtaagag aatgaagttt   17820
taaatgaaaa gcagtgtctt ataattttca aaccgtgcca ttagtttaaa aaaattggtg   17880
agttttctat tttatgtttc ataagctatt gatggttcaa taatgaattc taattaggta   17940
ttccataggc aaataaagtt agcaattgtt actctgaatg tatctccatc tcaagattac   18000
aagagtacac tcatcacttt cccttcccaa tatattccaa ctcctctctt atatttaaga   18060
cttcagtgaa taacaagatg tccacccgag ctacaaatgt gggtcatcgt tgatgacccc   18120
atcttcctca aaccttccca ttcaattgtc ctaacaattc tacctttcta atagctcttg   18180
aatcttcctt tcttttcctt ccattcctac tggtccaggc cttcaatggt tggttttcac   18240
```

```
tgattattgc aactttcttt ataattggtc tctctctctc caatcttatt attttccaca    18300
gtgctgccag aaggatattt ttattatgct tagttgatca tattatactt ctgcatgaaa    18360
accttccatg attgttaatg atctactttc cttgtcatga cccataatga cctgaagtct    18420
acttacctac ttctatatgt cttttcaggt gaaatctcac tcctctcagg aagccttcct    18480
tgaacccaga gttgagatta atagcctctt cagtacgttt ccaaagcacc ctgtgttggc    18540
cattatcact gttttaattg tattattctc ttccatttat atgtctgttt catagtcacc    18600
tcatctctac tgcaaggtcc ttaggggagg gtgtactata tatatatata tctccaccaa    18660
gaggcccact aagtgacctt tcactcgatg aacaaatggg ctaccagtct ctgaaggtgc    18720
tgaactgaga atggaagagc cttcaggtat tagatgatga tggattgtcc cttctaacag    18780
atgtttcaaa ggtaaatctt atcaggttta tctataagcc attcttttt tttttttttt     18840 gagatggagt ttcactctgt tgccaaggct ggagtgcagt ggtacggtgt ccgctcactg    18900
caacctccac ctcccaggtt caagtgattc tcctgcctca gcctctggag tatctgggac    18960
tacgggcacg tgccaccata cccggctaat ttttttttttt tttttttgta tttttagtag   19020
agatggggtt tcactgtgtt agccaggata atcttgatct cctgacctcg tgatccacct    19080
ggctcggcct ccctaagtgc tttgattaca ggcatgagca accacaccca gtctctatga    19140
gccattttac acctccacag ccttccctat atactctact acccttccaa ttccattcta    19200
ggcccttccc aagctccttg ccaactacca ttttcttcct actccctgcc acctcctgtt    19260
tcagagagca aacctagcca tccagctccc acatttactc ttatttctac ctcagtacat    19320
ttctccatac ccatattcat cctccctttt agtgacatta ctatgatgca gcaatcctta    19380
caactactct acaaggttat aatttattat ccccattata taaacaagaa aactgggact    19440
cagaaaggtt catttattta gcaaatattt attggccacc ttctgtgtct agcagtatgc    19500
tctgtatcag atacctgcca tcatcacact taaagtctaa tgaaaataaa gagacattaa    19560
acaagaaaac atacaaattt ataaactaaa aggtccacac acacacacac acaaaatctc    19620
ttagaattga taaattcagt acagttgcag gatacaaaat tatcatataa aaattaatgg    19680
tgcttctgga tacaaacagt aaactagtgg gaaaagaaat caaagaaagt aatcccattt    19740
acaatagcta caaccctcc ccccaccaaa aaaacaaaat agaataccta gaataaacca    19800
aggaggtgaa agatctctac aaggaaaact atgagacact gaggaaaaaa actgaagagg    19860
tcacaaaaaa atagaaagac atcctatgtc ttcggaagaa ttcgtatcgt gaaaatgact    19920
gtactaccaa aagcaatcta cagatttgtt gcaattccta tcaaaataca aagatattcc    19980
ttgcagaaac agaaaaaaca aacctaaaat taatatggaa ccacagaaaa cacaaatagt    20040
caaggtaatt ctgaacaaaa agaacaaagc tgtagacatc ataccaccca acttcaaaat    20100
atactacaaa gctacagtaa ctaaaagagc acggtactgg cataaaaaca gatacacaga    20160
ccaatagaac cgaataaagg acccagaaat aatagatcca catcttaaca gccaactgat    20220
tttcaacaaa ggtaccaaga tattcaatgg gaaaaggaca cactcttcat taaatggtgc    20280
tgggaacact gaataacaat atgcagaaaa atacaactac acccccatct ctcatcaaat    20340
acaaaaatta aatcaaaatg gattaaaaac ttaaatgtaa gacctgaaac tataaaagtt    20400
actgtaagaa aatactgggg aaatgctcaa gactttgagc aaacattttt tggtttaaga    20460
cttcaaaagg agaggcaatg aaagcaaaaa tacacaaatg ggattacatc aagctaaaag    20520
gcttctgcca cagcaaagga aacaatcaac agagtgaaga gacaaccttc agaatgggaa    20580
```

```
aaaatatgtg caaactatcc atctgataag ggattaataa ccagaatata taaggaactc  20640
aaactcaaca gcaaaaatcc tccaaataat cccatttgaa aatgggcaaa tgatctgaat  20700
agacatttct caaaagacat acaaatggcc aacaggcata tgaaaaaatt ctcaacgtta  20760
ctaaccatca gggatatgca aatcaaaacc acaatgagat atcatctgaa tctaattaaa  20820
atggctatta tcaaaaagac acagataaga gatactggtg aggatgcaaa gaaaggggaa  20880
tgctcatata ctgatggtag aaatgtaaat taacatagcc actatggaaa acagcataaa  20940
ggttcctcaa acaactaaaa atagatctac tagatgattc agcaatccca ctgctgggta  21000
tatatccaaa agaaaggaaa tcagtgtatc aaagagatgt gtacatgccc atgtttattt  21060
cagcactacc cacagtagcc aagacatgga atcaatctaa gtgtctatca agtgactgga  21120
taaagaaaat gtggtgtata tatatacaat ggatactagt cagccataaa aaagaatgaa  21180
atcctgtcat ttccagcaac atggatggaa ctggaagtca ttatgttaat gaaataagtc  21240
agacacagaa aaaaaaatat cacgttctca taagtgggag ctaaaaaagt tgatcttatg  21300
gaggtagagg gtagaatgat ggttaccaga gactgggaaa gggaggggt ggagggggga  21360 tgaagagaga ttcattaatg gttacaaaaa tatagttaaa ttgaaggaat aaattctata  21420
gtgtttgata gcacagctgg gtgactacag ttaacattaa tttactgtat attccaaaat  21480
agctagtaga tttgaagtgc tcccaacaga aggaaataat aaatgtttga ggtgatggat  21540
atcctaatta tcctgatttg atcattacac atcgtatgca tgtatcaaaa tatcatatgt  21600
accccataaa tatgtacaat tattatgtat caataaaaaa taaaaaaaaa caattcagaa  21660
gtccataaac ttggatggaa taaaaaaaag tcaactttat tttcaaaaaa ctctcactga  21720
aatctaattt tatgaatgta gaaaataaat cttttgtagta ccagccagca gctgtaacac  21780
tgtcatcaat agaaaacacc atcaattaat attttcatat cacattatag ttgttacaga  21840
catcttaaaa tatcacttac aattatggga gctgttaaac ttgccaaaaa atcatgcttt  21900
ttaatgtatt agtaaagaaa cactgtattg tattaataca gaaacacata ctactagatc  21960
atcacacgtt tctttgaata tagtagtgtc ccccacacag caccaaatgt gattatacag  22020
tttattccta tccatagata tacctatgat aaagtttaat ttataaattt gcacaggaag  22080
agattaacaa caaaatagga caattatatt gtaataaaag ttatgtgaat atggtccttc  22140
tgtctcatac acaaagtatc ttattgtact tattttcaga ccaggttgac cttgggtaac  22200
tgaaatcaca gaaattgaaa ctgcagttaa ggggggacca ctgtattttg ataactatag  22260
tttatatttt attttatgca tttacaaata ttatcagaca agatccaaag gcttcaccaa  22320
actgccaaaa aagctaatgg cacataaaaa gcttaaggag tcctgattta atcagtcatt  22380
caatgaacat gacatccttc ctggaaccat ctcctgttct agcttcctca cattatgttg  22440
ctctgcttct ccttgagatc ttccattggt tccacttcct attcttgctt cctgtatgaa  22500
gatgtaaccc aaagctcaat ccttcaccct aaattgtttt tatacccct cttttacaaa  22560 cctcagctac cttcgtggct gattcaaaca tcacctcaaa ggtgactctc aaatctgctt  22620
ttcctaatct tttttctcta acttcaatct tggatcttaa actccctgct gtgcctagta  22680
aacagaataa tatgccaccc agagtcagct gggttcaaat cccagttctg ctacttacta  22740
aaggtgtgac attaggtaaa tattacctgc tatggtttga atctctcctc caaaactctt  22800
gttgaaaata attgccattt tgacagtttt aagaagtggg acctttaaga gttaattagg  22860
tcatgagggc tctgctctca tgaatggatt aatgctacta atgtaggtat gggttcccat  22920
ttaaaagggg acattctgag gccgggcaca gtggctcaca cctgtaatcc cagcactttg  22980
```

```
ggaggccgag gcaggtggat catgaggtca ggagatggag accatcctgg ctaacacggt   23040
gaaaccccgt ccctactaaa aatacaaaaa attagccagg cttggtggcg ggcacctgta   23100
gtcctagcta cttgggaggc tgaggcagga gaatggtgtg aacccgggag gaggagcttg   23160
cagtgagtca agattgcact actgcactcc agtctgggcg acagagcgag actccgcctc   23220
aaaacaaaca aacaaacaaa caaacaaagg gtacattctg gcctctattc tctctccatc   23280
tcatgtgctt gtttgccttt ctgccgtggg atgatgcagc acaaggctct caccagatgc   23340
caatgccatg ctcttggact tccaagcaac tggaactgag ccaaataaac tactgtttat   23400
aaattaccca gtctgtggta ttctgtgata gcatcagaaa acagactaag acgtcctttg   23460
cttctgttgt ttcatttgaa aactgagggt gataatatta gtattgactt tatagggtta   23520
taaggattaa aagagttact acatgtactc attgcagtac ctgacacatt ttaactactc   23580
aataaatgtt ttgtatcacc aatcacatct ccttccaacc ccgacatttt aatttgatgt   23640
ttattaacat ggacggtgcc agccactgga agacagagtt tctatctaac aacataattc   23700
tgatcaagtc attagtcaaa aaatttcagt ggttccccac tgattccaaa cttaacagca   23760
ctggaaacct tctataatgt gttctctaat ataaatttac ctcccatttt ctcttctcct   23820
gctctacttc ttgtagctta tgttctggcc agactggact agactactct ctgtgacaat   23880
aacctgtgct gttctatgtc tgtctttcct cacataattc taatgtctca ggtttgaagg   23940
caataatttt gtctatgatt attccctat acatggcacc ccataaaaca tacacatttc     24000
aatcttacct aagtcacata cttacttaca catcaattca cctccatatt tgctcaattt   24060
gtgagaacct aatattggcc agatactgtg ctaggaccta gggatattaa aaaaaaaaa    24120
aaagcaaagc aagaaaaaga atgcataatg gccctgctct caaaatcaag gtctagtact   24180
agagagaaac atgtaatcac ataaatgcca ttcactgtgg aaagtaaaat cataagggga   24240
agggacacca aagaatgagc agttagctca acttgaacag taacattaag cttttcagag   24300
atgttatttg ggcgtacata gattggggaa aagtctactc catatagaaa gtgcacatgt   24360
gtaaaacaca gaggcatgaa acaaaatgat gtgtctggga aacagttcaa tacagctgga   24420
atatagggcc caagaggaag tggttagaca tgaggctgga aagctaggca gactgttttg   24480
gcaaacatag gaatttggac tttatcacat agccaataag gaataacaca gagtttttaaa  24540
aagagctatg gccagggcta tattttggaa agctctctcc tggcagtatt gtggcagagg   24600
cagagaggaa agtctaaagc agcactgtcc aacagaactt cttgtaatga ggccgcgcgc   24660
agtggctcac gcctgtaatc ccagcacttt gggaggctga ggcgggcgga tcacgaggtc   24720
aggaattcga gactaatttg gccaacatgg tgaaaccccg tgtctactaa aaatacagac   24780
actagccggg tgtggtggca ggcgcctgta atcccagcta ctcggaggc tgaggcagaa     24840
ttgcttgaac ccgggaggca gaggttgcag taagccaaga ctgcgccact gcactccatc   24900
ctaggccaca gagcaagact ccgtatcagg gaaagaaaaa aacaacttct tgcaatgaca   24960
caaatgttca ataatctgtg ctttcccata tgacagccac tagtcacatg tggctattga   25020
gaacttaaaa tgtggctagt gtattgaggc actaaattta aaattgtatt aatttaaatc   25080
caaatagcca tgtgtctagc aaataattta ggagactgtt ggtatagctc aggtgataga   25140
attaggacag aagggtgagt tgatggatag ttaagaggca aaattatgag tctgtaaggg   25200
tgtgagaaaa ggaaatcaag aacaggctcc cagattacag actttgtggt taaacagcca   25260
ccattactca ggacaacaga agagaaagag caggtctaga gtgtatagtg atttcatcaa   25320
```

```
ttttgaacat actggtgtct gagagttatc ccagtgggaa tatttagtag aaagtttagc    25380
ttagagagct gtctgaacta aagattcaga cttcagaggc tttgagccat ggagtcagat    25440
tacctagaga agttgaacaa aattagaagc aaacaagaat cacagcaaat atcaacacat    25500
aaaaaggggc taaggaagaa aaatctactg agactggaga ggaacagtta cacaaatagg    25560
aaaagaaaca agtgagagtg gtatagaagt caagggtaga gagaatgtca ggaaggaaac    25620
atgatcaaat gtcgaatgcc tcagaggtca aataaagtga gaactgtaaa gtgcttcctg    25680
actttgccag ttaggaggtt cttggtgaca tctgccagaa aagttttggt ggtagcagcc    25740
tgacagaggt agcttgaaga gtggggatgg ggaaagagaa tgtgaccaag aattgagata    25800
gtaaggataa tttcaatttc aggtcttggc tgtgcaagga agccgagaga catgagtctc    25860
taagagggca cgatattgag agggttgtta tctttctgtc agcggggaaa ccaagagaaa    25920
agtttaaaaa ggtcaaaagg gggagaaggg aagacagctt ccgggtaaca gagaaggttg    25980
accaggtcaa tagtaaagga tttcctcaaa ccgaagggag gacctctagt gaaatgagaa    26040
aggaatacac aattgaccca gtttgcaggt gggaaatggg aagccagttc tgcaaattgg    26100
cctttctgtt ctgtgaagtg ccatctgtcg gtgaggagag attagggtct gcagcgtgaa    26160
aatctggacc atactctggg taatcaaggg agaggttatc ggctaatgac aaattaaagg    26220
cttacttttt agctggcaac tgaatcacca taacatttta tgttaccagt tccaaaattt    26280 tgggggggaat tcactcaagc ttgggagagg agagatcata actttaagag tataagaggt    26340
ttaaacggtc cactacgaaa taaatagaga aggaaaagtt atcagctggt aaatatcgta    26400
gaaggtagag cggtccaggg actcacaggt ctcactaaag aaaagtctag cgtaggttca    26460
cggcacggag agattttaag gctgcctaag actaaagcca aatacgaagt ccacatctgc    26520
ggtccgcacc ttatctctcc gcgcggcagg cgcgacgagg gcgagaaact ccctctccag    26580
tggtcgcacc acacgacacc agggaagggg cccctctctc cagaccctca tatctccagg    26640
tccaggcccc attttcctcc gctgacagct cagcagcgtg cgcttccgct ggattcaggc    26700
caggaccagc gaagccgcac cttacaccca ccgaggagga aacaagcctg ccacccgag    26760 gctacccgc taggccgcgg gtagtggggg aggggcgct gaggcaggag gtcagcaccc    26820
gggcgcgggc tcccgcccca cgaaatgcgc gcgctccaag ccccgccgcc ggagatgcgg    26880
ttccggtccg gacgcctgcg cactacggct ctccccgcag cctctggccc tcttcccccc    26940
tcccccagtc agggcgcacc cttgcgcctg cgctgtgtgt gttcctggtc tgcggcagcc    27000
atgctgaact cgtatggaga ggcgagtggg ggggacagag tccaggactg cgggatagga    27060
agctggggat atggacaagc agcagcgtta tagcgctctg ggtttcggga cataggcctg    27120
ggccatgcgg cccccttggc cccttggcgc gaccccagg aacgttcgga aagctggtcc    27180
tcgtggctgg gggaaaggcg gggggtgggg gggaagcggg cacgtgaccc cggtcagcca    27240
atctgggtgc tgctgacgtg gccgcgcggc cccgatgctc tccccacccc cccagcccgt    27300
tcgggaaggg aggggctggg ggctacgccc cctcccccag cacggcttcg ttttctgggg    27360
gggggttgac accccggatt acatacccc taccaagccg agggcaactt ggaggcccc    27420 ctggaaggct ttaggatcca ggtgagaagg ggccttgtg gggcggagat gtcagtcaag    27480
tgcttaacca atggtgggga gtccgggagg gggattcttg gggttcagga aagaatcctg    27540
agagtgggaa gatttgtcct tcaaaccttt tacagccaat gggagcgtgg aggggggcg    27600 agcgggagag ggccatgggg ggggagggga atggccagcc tcatgcctcc gtacccattg    27660
gagggcaaag gggttagggg gcggtgtggc cccccctatt ccattcgtcc cctggggta    27720
```

```
cagcagccgg gagccaggtg agaagggatc catcggcggc cgagggaggg gtgacctggc   27780
ggtgggctga ggagtggtgg ctgtggcccc tacccgtgga tgtgaatgct ttaggagtta   27840
gccacccatg ttgtgaactg aggttgttcc caggcgccaa cttcctttct ccccagagcc   27900
tctggaggga gcattgctgt gcgcccttgt gtccgcggt agggagctc cagtcgtcac    27960 accgcaggct ggaggttacg cttcgagtcg cttaccgaat ttgtgtgcat tcacgtggac   28020
acggcctgtg gggccttttg cccctgtagg gtctttactg agcacgtgtc tactccaggc   28080
tggggtgctt acaagctgaa agcttgaggt ctgcttagga acagaaacca ggcccaaggt   28140
gggtgctggc agtaggggt ctagacagca tggtctgaga tgcgagggag gctcgggacc    28200
tggaatgatt tcacagctcc caaggtttcg ggtttctcca gggtggcctc ttccatcgcc   28260
tccctcatcc cctcccccag tcctgaacag ttctctcctt gtgtactgcg ggggagggaa   28320
cggaaaggag gaaagagtta ctttcccaaa ttactgagta gcagtagcct ccctggtgac   28380
tcatgtgggg gaagggagga taggatcg ggaggcagtg attttccgga atgcaggaa      28440 taaacgagag caatgtctgg ctgccctttt cctaaggcct agtattttct cagcctccta   28500 agttttact ccatggccgg cccctgatg ggctctgtc ctggcctgca gagcccggt       28560 ggagaaaagc agatttggga ggttgggccg ctaggggag gggaaaaggc ctctgcaaag    28620
ttgctgtgtc attgccctcc atgctgcagc cacccaaacg gggccgcttg tacttttggg   28680
ggccagggcc tgatccctgg ctggggggaag gggactctgc tctcctgacg ctcattttcc  28740
cccgccctcc cggggtttgc cctactcggg gggtcagaag acaggagatt ggcggccatt   28800
ttagacgcag taaccgaggt tggagttgaa gggctactgc agaggaggga gggtggcgtg   28860
gttgcagctc aaggacctag gcccttacga gcccttcccg ggcgaggggg aatcttaccg   28920
tatatttgtt cacctacgtt gattattttt cccagatacg tacacaagtt tgttttctcc   28980
ctggtagcga agaaagggga aacggggag gggacgcccc accaaagccc aggttttctc    29040
gggtggggga gatcctttca ctctcttgta agggggcggg gacggcccca gagatgctct   29100
ggagatcctg actctgggct ctggttgatt cacagagtct gcacccttat ttagataacc   29160
aagttaggag gaagacttaa gagtaagttg ggggagggg gcgaaactga gctcccaaaa    29220
tggctcctgc ccctcctcgg aggcggacgg ccgggggag gggaggaggg gaggaggggg    29280
agggctagtc tgagccgcag ccgccgcctc ctccgctcgc cctcctccct ggcgctgacc   29340
gatggaccag ccgctccgtg gggaggactc cggaccctgg tgggggggcg ggggggttct   29400
ttcgcccccg tggcggaggg cccctgagag gcggatacgg tgtgcctt ggggtgatg      29460 tggcgtgtgg ggggaaaggt ccgagctcgc ctggaggggg agggttttc ccttaagtca    29520 tccctcccag gacttgcttt ttctgctctg agccggacgc cggaatggag tttgaggaag   29580
aggtgaggtg tgttgcattg tatagggtag atggatgcgt ttggagattt taatcccact   29640 tttaggttg ccgaggattt ttcgaacgag cagaaatgta ttggtaactg taggtgtgag    29700
tggggaggga ttagaaaggt gcttggacgt gcaaatttgg gagacgtatt ttagcttttg   29760
tggtctttgg gactaaacag tagtaaataa tgttttgctc gtctttccat cgtttggctt   29820
gagggaggga gtggagtatt ataagactct ggcaacactg ttttagactg tggggcatgg   29880
gaacgttaga tcccctcatc gccgttctga agcccgtagc tgttcgccat agaggagcag   29940
gccgcggctt ctaagatggc gtctttttcc tcgtttcaga ttcttcgctg ctgctgcctt   30000
accgccgaga accaccaccc gccaggcgtc ttgcggccac acccctggcg ggttcaggca   30060
```

```
ggctacgccc acgcgacccc tcccgtttcc ctgctttggc caatggagga gctacgaatg   30120
gcacgacctg ctcgagcttg gcagtctcca gttgggctgt gcatggaagc ttgggaagac   30180
tttgttggaa ggggaggcgg ggagagagtg ctggaggctc tggggcgatg gcttccgcac   30240
ctcttccaac caccctcttt ccctggagtc ggcggaccac agctcagcca attggcttgg   30300
agatgtggcg ggttgccact tccctgtggg tctctgcggc actcttctgc ctggtgactg   30360
acaccttgga aatgaagttt atgacgtcat cgttgcggct ggccaataga aaagctccc    30420 gcggagaggt gttccttccc cttcgactca gcttcttcac ccgcgtgagc gagcgcgcgc   30480
gcgcggaggg ggtggggaaa atctcaagca gggtggcgcg catgagcggc gaagctcctc   30540
ctccccgcct atatataaag ggctggcgcg gggctcggcg gcgccatttc gtgctggagt   30600
ggagcagcct ctagaacgag ctggaggatt ctgcctaccg atacagagcc ttcgagtcgt   30660
ccggggccgc cattacaatc cacctccatc cgcttggaaa tggccttcgt cccggcctat   30720
gactggtccc agcgggcagt acagaccccc tagaagcccc tggagctccc cttttcggg    30780 ccccgcccaa tcctcggagt ctgtccaccc cctctactcc gccctcaaga ggatttcaaa   30840
gatggaggcg gcggctccct aaaccacttt tcgtgttcat ccgcctccat ccgagatcga   30900
aacgggacct cgtcggcccc gtaggggccc gacaagaaga gggaatccct gcagaccaac   30960
agcgggctat attgacgacg gtgtctgaga tcggggaccg tcttttgaag agtcagtccc   31020
tccttagttg cccgcctcag ctgaggccgc cgccattttc ttgctgtccg ccgtctgcag   31080
agcgcgccaa gctgcccgga gctctccgag aggccccaaa gagactgctt tcgtgccggc   31140
caggcagggg gtttgtcgcc tggaggccca agaggaacgg cctcccccca acttagcggg   31200
ttatgctgga ccgggcggtg aggggaaccg aggccacccg gactttccgc ggctgagggc   31260
agcgccggtt ccttgcggtc aagatgctgc aaaacgtgac tccccacaat aagtacgttt   31320
ccgcgagccg cgtgtgggaa ggggatgttg cagggcggcg gcacaggggt gtgggcgcc    31380 gtgttgggag tactgagcgg ccccggcgcg ctgctgttgc ggcgcagctg tcgactcggt   31440
cgcgcggagg gaattgagcg acggttttgg aacggtggtg gcggctcggc tactgctcgt   31500 ggagggggaat acaggttgtc aatttatacg ctattaatgc cgccgtggcc cagtcttaac   31560
cgagtcaggc agagctagtt tgacggtgga gtggagtgag gttgaacagc aggtttggcg   31620
tttggtgggt ctggtatcta gcggcggtct gttagccttt taggggggat tcacggacac   31680
ctctagcgcc ctgtagggtt gccatggtga cggagcgctt aagggactgg caacggggat   31740
tcccagagaa gggtaaaggg atcactctcc cgtgtgtgca ggttcctaat gcccagggca   31800
tgtcattaaa tcttttgctt tctttgggtg ggtgggttgt gtgtggtgtt tgttggtgca   31860
gggattgttt tttcctaaca ttaaaagttt gattcagggc aggagggtag agctaaggtt   31920
cctagttcag ctctgcgatg taaacaatga gattcccata tgatgtttta attcttaggt   31980
ggtaggaaag actgatcgga ggagcaccag agggactgta aatgaaccac tgttagcgtt   32040
tggtgtccgg agttggtgct acaggggaa ctggtagtgg aatcgtgttg tgtagtgggt    32100
gggtggaagg gggctatcac ttggtgacct tgactgtttt gtacggcttt ttgacttcct   32160
tggagtgagg agactctgat ttggtgcgaa taatttgag ggcctggaag ttacgggctg    32220
tgaagtctga caaattcttc cttgtctgaa tttgtttta agttgatatg gttcttcctc    32280
tgggtttcta gtcatgttc tgttgtggcg tgaactaccc agaccttgtg gaagatggtg    32340
ctctctcttc tatctaggtg gattattctg tgtcttatca gcattttatg gaatttttta   32400
tagccataat ttgttctttt cctccttacc ggcgctcaac caccatggca accaccaaac   32460
```

```
ccctagtgag gaggaagctt ggggtttgag tttcttaact ccacccattt tgcttaatcc   32520
ccatccccat agggctgtag ttctgagatg tcgtgccttg tcagaaacaa tttgggagtt   32580
ttttaaaata tgaaaaagaa cagatagagc ctatcagact taagaaggtg ggatctagat   32640
agtatactaa aaatattaat aaaaggaagg cggggccagc aataaaagct ccacagattg   32700
tttggatatt gtttctgctt aagaagcact tggcataagc ttaaccacct cactagggcc   32760
agcacctgga ttcatcagac tattgtgcag atgcactttt tcctcatttg gacgatattg   32820
ccctaatttt gttcccatct ttacaggctc cctggggaag ggaatgcagg gttgctgggg   32880
ctgggcccag aagcagcagc accagggaaa aggattcgaa accctctct cttgtatgag    32940 ggctttgaga gccccacaat ggcttcggtg cctgctttgc aacttacccc tgccaaccca   33000 ccaccccgg aggtgtccaa tcccaaaaag ccaggacgag ttaccaacca gctgcaatac    33060
ctacacaagg tagtgatgaa ggctctgtgg aaacatcagt tcgcatggcc attccggcag   33120
cctgtggatg ctgtcaaact gggtctaccg gtgagtagag acattggagc cggggaggtg   33180
tgggatgagc aagaatgcgt gtgaatgggg gtggtctgcc tagtgtagat gctgcggccc   33240
ctagggagtt cccatttctc ccctgtaggg cagttagcta ccagattcct gggtatcttg   33300
gtcctttgtg attgatccga ccgcttgctg taactatctt ggcatctttc cttgtgccct   33360
ccatgtgtcc ttccttaact tttgtgccct ggctccattt tacagattcc cacctcgggt   33420
tgggagagga ccacggtggc caaaattctt agcttcttcc tttccctcat gcagcccatg   33480
gatagccagc cccagaggta atgtcacagg atgggaagtt tccagagtgg gtgggaggtg   33540
ggtggttaga gaaaggcagc aggggcctcc ctgtggatgt caagaatctt ttttatttat   33600
ttatttattt tgtcccacag tttaattggg gccgcagttt aactgttcct ttgatgcata   33660
gggggtgtgt gtgtgtgtgt gtgtgtgtgt gagagtcggg gatcggtagt ctccctataa   33720
gcatttattt ttctgtggtt ctgacctaac atttctttat ttaggattat cacaaaatta   33780
taaaacagcc tatggacatg ggtactatta agaggagact tgaaaacaat tattattggg   33840
ctgcttcaga gtgtatgcaa gattttaata ccatgttcac caactgttac atttacaaca   33900
aggtgagttt ttctgtgtgt tcatttagta ggtggggaga aacagtaatt tctattattg   33960
ctggatatgt tgtctacata aagtttaaat cctttgctac tgaaggtgtt atccaggtag   34020
ggtagtcgga gtcttaaaaa cctgactcta gatggtacta ttgaacacag tgatgtgact   34080
tcagagctct agttgaaggt tatttagaac acttcatact tgggggtggt ggtcctgttt   34140
cttagaaatc accagagacc tgagtagacc agggatctgt tttcttgtca gctctcaagt   34200 ttttcttct ttcgaatttt gggagacagt taggagaaag tggaaattag tagtggcctg    34260
gagtagaaat tttctttaag atttgatgac aagatgactg gtgggggtat ggtaatggcc   34320
tagggcctga atgcctctga gaaagatggt gtgtatctat cttctgttgg catttttaa    34380 cttttctttat tgctgtctgt gttctcatag cccactgatg atattgtcct aatggcacaa   34440
acgctggaaa agatattcct acagaaggtt gcatcaatgc cacaagaaga acaagagctg   34500
gtagtgacca tccctaagaa cagccacaag aaggggggcca agttggcagg taggaagagt   34560
gggagttttg caaatggaca acttaaagat ggggaagaga atcaaactac acttttttcc   34620 tttttctag cgctccaggg cagtgttacc agtgcccatc aggtgcctgc cgtctcttct    34680
gtgtcacaca cagccctgta tactcctcca cctgagatac ctaccactgt cttcaacatt   34740
ccccacccat cagtcatttc ctctccactt ctcaagtcct tgcactctgc tggaccccg    34800
```

| | |
|---|---|
| ctccttgctg ttactgcagc tcctccagcc cagcccttg ccaaggtatg atctgtggat | 34860 |
| ttcctctggg cagcagggag gcaagggtct taagtaaagt gggcttggag tgacaggttc | 34920 |
| cctatcttgt ttctttctgc agaaaaaagg cgtaaagcgg aaagcagata ctaccacccc | 34980 |
| tacacctaca gccatcttgg ctcctggttc tccagctagc cctcctggga gtcttgagcc | 35040 |
| taaggcagca cggcttcccc ctatgcgtag agagagtggt cgccccatca gcccccacg | 35100 |
| caaagacttg cctgactctc agcaacaaca ccagagctct aagaaaggaa gctttcaga | 35160 |
| acagttaaaa cattgcaatg gcattttgaa ggagttactc tctaagaagc atgctgccta | 35220 |
| tgcttggcct ttctataaac cagtggatgc ttctgcactt ggcctgcatg actaccatga | 35280 |
| catcattaag cacccatgg acctcagcac tgtcaaggta cccactgcat ggggcagatg | 35340 |
| ggatgctcaa gcagtgatgg gagcctaggt gcaaaacaat aagtctcctt atgtgggcac | 35400 |
| acagcagtct ttggttcttg gcattttact tttataaaat aatagtggaa cagaaggtct | 35460 |
| ggtgttttga gaatttgtat ttcttggagt ttgaaacagt agggtggggt ttctttgtct | 35520 |
| tgagaaaaat actgtctata attaagtact aatgtggcag tgttgggtta aggaagttat | 35580 |
| agggtggaaa gacaggcata ggccacctct ctgtcactta gaaatgattt cttttctag | 35640 |
| acataaatat ttcttcaacc cacccaaatt cctttgactt caaacttgaa ccccaggca | 35700 |
| cagatcctta aggtcatccc cactgtgctc tcaagagagg ctcttcttg tggtgtctgg | 35760 |
| ggttggcagg gaaaggtgag tcttcctgcc tgtgcagctt ctgatgctgc ctccttctgc | 35820 |
| agcggaagat ggagaaccgt gattaccggg atgcacagga gtttgctgct gatgtacggc | 35880 |
| ttatgttctc caactgctat aagtacaatc cccagatca cgatgttgtg gcaatggcac | 35940 |
| gaaagctaca ggtgagtgga aaggttggag tttgaaaaat aaatggtatg gggagttatt | 36000 |
| ttgtcatgtg tgctgcatag cctcaacgtg agggtctcac tgttctgtac agttgtaaat | 36060 |
| tggagctata tcacttggtg gctgggtatg tagggcactg tttatcagca tagttttgag | 36120 |
| tttgtgcctc tttctaggat gtatttgagt tccgttatgc caagatgcca gatgaaccac | 36180 |
| tagaaccagg gcctttacca gtctctactg ccatgccccc tggcttggcc | 36230 |

<210> SEQ ID NO 38
<211> LENGTH: 2732
<212> TYPE: DNA
<213> ORGANISM: Homo sapiens

<400> SEQUENCE: 38

| | |
|---|---|
| ctttcgcctc agtctcgagc tctcgctggc cttcgggtgt acgtgctccg ggatcttcag | 60 |
| cacccgcggc cgccatcgcc gtcgcttggc ttcttctgga ctcatctgcg ccacttgtcc | 120 |
| gcttcacact ccgccgccat catggtgaag ctcgcgaagg caggtaaaaa tcaaggtgac | 180 |
| cccaagaaaa tggctcctcc tccaaaggag gtagaagaag atagtgaaga tgaggaaatg | 240 |
| tcagaagatg aagaagatga tagcagtgga gaagaggtcg tcatacctca gaagaaaggc | 300 |
| aagaaggctg ctgcaacctc agcaaagaag gtggtcgttt ccccaacaaa aaaggttgca | 360 |
| gttgccacac cagccaagaa agcagctgtc actccaggca aaaaggcagc agcaacacct | 420 |
| gccaagaaga cagttacacc agccaaagca gttaccacac ctggcaagaa gggagccaca | 480 |
| ccaggcaaag cattggtagc aactcctggt aagaagggtg ctgccatccc agccaagggg | 540 |
| gcaaagaatg caagaatgc caagaaggaa gacagtgatg aagaggagga tgatgacagt | 600 |
| gaggaggatg aggaggatga cgaggacgag gatgaggatg aagatgaaat tgaaccagca | 660 |
| gcgatgaaag cagcagctgc tgcccctgcc tcagaggatg aggacgatga ggatgacgaa | 720 |

```
gatgatgagg atgacgatga cgatgaggaa gatgactctg aagaagaagc tatggagact    780
acaccagcca aaggaaagaa agctgcaaaa gttgttcctg tgaaagccaa gaacgtggct    840
gaggatgaag atgaagaaga ggatgatgag gacgaggatg acgacgacga cgaagatgat    900
gaagatgatg atgatgaaga tgatgaggag gaggaagaag aggaggagga agagcctgtc    960
aaagaagcac ctggaaaacg aaagaaggaa atggccaaac agaaagcagc tcctgaagcc   1020
aagaaacaga agtggaagg cacagaaccg actacggctt tcaatctctt tgttggaaac   1080
ctaaacttta caaatctgc tcctgaatta aaaactggta tcagcgatgt ttttgctaaa   1140
aatgatcttg ctgttgtgga tgtcagaatt ggtatgacta ggaaatttgg ttatgtggat   1200
tttgaatctg ctgaagacct ggagaaagcg ttggaactca ctggtttgaa agtctttggc   1260
aatgaaatta aactagagaa accaaaagga aagacagta agaaagagcg agatgcgaga   1320
acacttttgg ctaaaaatct cccttacaaa gtcactcagg atgaattgaa agaagtgttt   1380
gaagatgctg cggagatcag attagtcagc aaggatggga aaagtaaagg gattgcttat   1440
attgaattta agacagaagc tgatgcagag aaaacctttg aagaaagca gggaacagag   1500 atcgatgggc gatctatttc cctgtactat actggagaga aaggtcaaaa tcaagactat   1560
agaggtggaa agaatagcac ttggagtggt gaatcaaaaa ctctggtttt aagcaacctc   1620
tcctacagtg caacagaaga aactcttcag gaagtatttg agaaagcaac ttttatcaaa   1680
gtaccccaga accaaaatgg caaatctaaa gggtatgcat ttatagagtt tgcttcattc   1740
gaagacgcta aagaagcttt aaattcctgt aataaaaggg aaattgaggg cagagcaatc   1800
aggctggagt tgcaaggacc caggggatca cctaatgcca gaagccagcc atccaaaact   1860
ctgtttgtca aaggcctgtc tgaggatacc actgaagaga cattaaagga gtcatttgac   1920
ggctccgttc gggcaaggat agttactgac cgggaaactg gtcctccaa agggtttggt   1980 tttgtagact tcaacagtga ggaggatgcc aaagctgcca aggaggccat ggaagacggt   2040
gaaattgatg gaaataaagt taccttggac tgggccaaac ctaagggtga aggtggcttc   2100
gggggtcgtg gtggaggcag aggcggcttt ggaggacgag gtggtggtag aggaggccga   2160
ggaggatttg gtgcagagg ccggggaggc tttggagggc gaggaggctt ccgaggaggc   2220
agaggaggag gaggtgacca caagccacaa ggaaagaaga cgaagtttga atagcttctg   2280
tccctctgct ttccctttc catttgaaag aaaggactct ggggttttta ctgttacctg   2340
atcaatgaca gagccttctg aggacattcc aagacagtat acagtcctgt ggtctccttg   2400
gaaatccgtc tagttaacat ttcaagggca ataccgtgtt ggttttgact ggatattcat   2460
ataaactttt taagagttg agtgatagag ctaacccta tctgtaagtt ttgaatttat   2520
attgtttcat cccatgtaca aaaccatttt ttcctacaaa tagtttgggt tttgttgttg   2580
tttctttttt ttgttttgtt tttgtttttt tttttttgc gttcgtgggg ttgtaaaaga   2640
aaagaaagca gaatgtttta tcatggtttt tgcttcagcg ctttaggac aaattaaaag   2700 tcaactctgg tgccagaaaa aaaaaaaaaa aa                                 2732
```

<210> SEQ ID NO 39
<211> LENGTH: 4768
<212> TYPE: DNA
<213> ORGANISM: Homo sapiens

<400> SEQUENCE: 39

```
ggcggcttgc gcctgcgcgg cgcggcgctg cggagaccgt tggttcattt gcatgtcccc     60
```

```
gcctcgcgcg gcggcggcgg cgggtgagga gcctgaggcg gcggcggggg tggctccgcg    120
cgcggtggtc tcgggggcaa ataacatgg cagccagacg aattacacag gagacttttg     180
atgctgtatt acaagaaaaa gccaaacgat atcacatgga tgccagtggt gaggctgtaa    240
gcgaaactct tcagtttaaa gctcaagatc tcttaagggc agtcccaaga tccagagcag    300
agatgtatga tgacgtccac agcgatggca gatactccct cagtggatct gtagctcact    360
ctagagatgc cggaagagaa ggcctgagaa gtgacgtatt tccagggcct tccttcagat    420
caagcaaccc ttccatcagt gatgacagct actttcgcaa agaatgtggc cgggatctgg    480
aattttctca ctctgattct cgggaccagg tcattggcca ccggaaattg gggcatttcc    540
gttctcagga ctggaaattt gcgctccgtg gttcttggga acaagacttt ggccatccag    600
tttctcaaga gtcctcttgg tcacaggagt atagttttgg tccctctgca gttttggggg    660
actttggatc ttccaggctg attgagaaag agtgtttgga aaggagagt cgggattatg     720
acgtggacca tcctggggag gctgactctg tgcttagggg cggcagtcaa gtccaggcca    780
gaggtcgagc tctaaacatc gttgaccagg aaggttccct cctaggaaag ggggagactc    840
agggcctgct cacagctaag gggggtgttg ggaaacttgt cacattgaga aatgtgagca    900
caaaaaaat acccaccgtg aatcgtatta ctcccaaaac tcagggcact aaccaaatcc     960
agaaaaacac tccaagtcct gatgtgaccc tggggacaaa cccagggaca gaagatatcc   1020
agttccccat tcagaagatc cctctggggc tggatctgaa gaatcttcgg ctccccagaa   1080
gaaagatgag ctttgacatc atagataagt ctgatgtttt ttcaagattt gggatagaaa   1140
taatcaaatg ggcaggattc cacaccataa aagatgatat taaattttcc caactttttcc  1200
agactctctt tgaacttgaa acagaaacct gtgctaaaat gcttgcctca ttcaaatgtt   1260
ccttaaaacc agagcacaga gattttttgct ttttactat caaattttta aagcactctg   1320
ctttgaaaac acccagagtt gataatgagt ttttaaacat gcttttagac aaaggtgctg   1380
tgaagaccaa aaattgcttt tttgaaatca taaagccttt tgacaagtac ataatgagac   1440
ttcaagaccg gcttctgaag agtgtcacac ctttgcttat ggcctgcaat gcctacgagc   1500
taagtgtcaa gatgaagacc ctcagtaacc ccctggactt ggctcttgcc ctagaaacca   1560
ccaactctct ctgccggaag tctttggccc tttttgggaca gacattttcc ttggcctctt   1620
ctttccggca ggagaaaatc ttagaagctg tcggcctgca agatatagct ccctcacctg   1680
ctgcgtttcc aaacttcgaa gactccactt tgtttgggcg agagtacata gaccacctga   1740
aggcctggct agtcagcagc ggatgtcccc tccaggttaa gaaagccgaa ccagagccga   1800
tgcgagagga ggagaaaatg attcctccta cgaaacctga aattcaggcc aaggctccaa   1860
gtagtctgag tgatgctgtc ccccagcgag cagatcacag ggtagtgggc accatcgacc   1920
agcttgtgaa acgtgtcatc gaaggcagcc tgtctcccaa agagagaact cttctcaaag   1980
aggaccctgc ttactggttt tgtctgatg aaaatagtct ggagtataaa tattacaagc    2040
tgaagttggc agaaatgcag cggatgagcg agaacttgcg aggagccgac cagaagccga   2100
cctcagcaga ctgtgcagtg agggccatgc tgtactcccg ggctgtccgc aacctcaaga   2160
agaaactcct tccgtggcag cggcgggggc tcctccgtgc tcaagggctc cggggctgga   2220
aggcgaggag agcgaccacc gggacccaga ccctcctatc ctcaggcacc aggctgaaac   2280
accacgccg gcaggctcca ggcctctcac aggcaaaacc atccctgcca gacagaaatg    2340
atgctgccaa ggactgcccg ccagacccag ttggaccttc tcctcaggac ccagcttag    2400
aagcctcagg cccatccccc aagccagcag gagtggacat ctctgaagca cctcagacct   2460
```

```
cttctccctg cccatctgct gacattgaca tgaagacaat ggagactgca gagaaactgg   2520
ctagatttgt tgctcaggtg ggaccagaga tcgaacaatt cagcatagaa aacagcaccg   2580
ataaccctga cctgtggttt ctacatgacc aaaatagttc tgctttcaaa ttctatcgaa   2640
agaaagtgtt tgaactatgt ccatcaattt gtttcacgtc atctccgcac aaccttcaca   2700
ctggtggtgg tgacaccacg ggttctcagg agagccccgt ggacctcatg aaggggaag    2760 cagagtttga agacgagccc cctccgcggg aggctgagct ggagagccca gaggtgatgc   2820
ctgaggagga ggacgaggac gatgaggatg ggggagagga ggcccccgct cctggagggg   2880
cgggcaagtc tgagggcagc acccctgccg acggccttcc cggcgaggct gccgaggacg   2940
acctggctgg agcacctgcc ttgtcacagg cctcctcagg tacctgcttc cctcggaaga   3000
ggatcagcag caagtcattg aaggttggca tgattccagc tcccaagaga gtgtgtctca   3060
tccaggagcc aaaagtccat gaaccagttc gaattgccta tgacaggcct cggggtcgtc   3120
ccatgtccaa aaagaagaaa cccaaggact tggacttcgc ccagcagaag ctgaccgata   3180
agaacctggg cttccagatg ctgcagaaga tgggctggaa ggagggccat ggcctgggct   3240
ccctcggaaa gggcatcagg gagccggtca gcgtgggaac cccctcggaa ggggaagggt   3300
tgggtgctga cgggcaggag cacaaagaag acacattcga tgtgttccga cagaggatga   3360
tgcagatgta cagacacaag cgggccaaca atagatcaa aaccactgat gtgaaagata   3420
agccttgaag cagcaattgc ccttaaaaca tcatccctgc cctggatcgg cctggagcca   3480
gtgcccaagt acggtttggt gtgtacatga aaacaaacgt ctctgcagtc tctggggcgg   3540
aggtttcgct ggcttttctt tctctcaaag aaaaaaacat gcaccatttt caatgtgctt   3600
ttgcctctcc tctctgttca catgctttta gcagcaagtc ccctccaaat ctgtcttggt   3660
tccccttcag aaggtggcgc tgcccccgaa aggcacctca gcctgtgagt gctgaggaac   3720
cagctcctct ggctgatttt ccagttggac tggccattgc tctccagaag tgctctgtta   3780
gcaaacgtga tgtggaaacg atcacagatg gtgttttctc gttgttcgcc agaatttata   3840
cgggggagac aaattcccgg taattaccaa gtctgcactc gggtaccaaa gctctgaagc   3900
tctctgaaca gttgccatac ttgagttgat gaatgtgtta ttcatggtgt ctcatctcat   3960
caatgcatct tgagagactt aatgaaattt tagcaacagt atagaatagc tctatcgggt   4020
ggggagtaat cattaaacag atgaaatcgg ccccagattt acatgtctct ttagaatcca   4080
cagtgtaagc aaactacagt tacaagggga tgggggttgt aaaccctctg agactctgca   4140
cttttcgcac gtatggcatc gtcaagtgct gtcttattac agcctttgta aggagaggca   4200
ggctcctcct ggggtgggct ctgcagctgc tctatttcca ggcatgtgat cgcccccgct   4260
ctccagattc cccagcactc tgctgcgtgt aactccactc aattctccac tcatccttcc   4320
ttgtgaagca ggatcgttga agtttttaagt atgggcaaaa atctggaaaa cttaggatcc   4380
ctctgacacc ccaggattag gggacacagc agtggctagg gcatcagcca cagaactgag   4440
cgggaaatgc cacttgtatt ggctgtaaag aaatcctggc tttgggccag gcacagtggc   4500
tcaagcctgt aatcccagca ctttaggagg ttgaggcgga tggatcacct gaggtcagga   4560
gtttgagacc agcctggcca acatggtgta accccgtctc tactaaaaat acaaaaaaat   4620
tagccaggcg tggtagcggg cacctgtaat cccagctact caggaggctg aggcaggaga   4680
atcacttgaa ccggggaggc agaggttgca gtgagctgag atcatgccac tccactccag   4740
cctgggcgac agagcaagac tccatctc                                     4768
```

<210> SEQ ID NO 40
<211> LENGTH: 395
<212> TYPE: DNA
<213> ORGANISM: Homo sapiens

<400> SEQUENCE: 40

| | | | | | | |
|---|---|---|---|---|---|---|
| ctgcgagaat | cgaggcactc | gctggcgtac | ccatgtatcg | aaatgagttc | acggcctggt | 60 |
| accggcggat | gtcggtggtc | tacgggatcg | gcacctggtc | tgtgttgggc | tcactgcttt | 120 |
| actatagccg | acaatggcg | aagtcgtcag | tagaccaaaa | ggatggctca | gcaagtgaag | 180 |
| tacccagtga | actctctgaa | cgcccaaaag | gattttatgt | ggaaacagtt | gtcacatata | 240 |
| aagaagattt | tgttccaaat | acagaaaaga | tcctcaacta | ttggaaatca | tggactggtg | 300 |
| gccctggtac | agaaccatga | ctggctgctg | aattctgaaa | accaggactt | ggttcaacat | 360 |
| ttaaatttga | tagttgccct | gattcccatt | ttggt | | | 395 |

<210> SEQ ID NO 41
<211> LENGTH: 137091
<212> TYPE: DNA
<213> ORGANISM: Homo sapiens

<400> SEQUENCE: 41

| | | | | | | |
|---|---|---|---|---|---|---|
| cgcggcgctg | ggtcggtggc | ggaggctgag | gagaaggagg | agcgggccgt | ggaggcttcg | 60 |
| ccgcctaggt | aagggcccgg | gactggaggg | gaggcgtgcc | agagcctgcc | agggaatagc | 120 |
| cagcagacag | gcccgctcta | gacatcgcag | gcccgcgcag | cctgaaagct | gtggcttcag | 180 |
| tgtcgcgggg | cggctgcggc | ctcgctcggg | aagaagacca | agcaacggtg | agatgaggga | 240 |
| ggcgccgccc | gtggcaggaa | cgccccggaa | ccgtcgcggg | cctggggcgg | ggcccggcgc | 300 |
| ggcagtagat | taccggtccc | gccgcggagc | ggccagctgt | gaggctgggg | ccggcgcgtg | 360 |
| gttgcggctc | tgtgctccta | ctcttcggag | ctgtaagcgg | gctgttcttg | cggttttcct | 420 |
| gtttcagatc | caattctgtg | gcatcactag | gaagggagct | cttgtgctta | gcacgtagcc | 480 |
| tcgtcctcag | acttggacag | acacaaggga | ggctccgctg | gaccggaggg | cacaagagct | 540 |
| ccgagcccgg | tcgtcggggc | ggtagaacct | ggaagcggga | gagtggtctg | gtgggttctg | 600 |
| cgcccgttag | gcaatgaagg | agaaggatgt | tttatcgtat | tcacgcttta | gattccatta | 660 |
| gcggtgtaaa | tagatgtttt | tctctttatt | ttagaattga | cgttaggcga | atgggttcaa | 720 |
| ctttgggaat | gccttttttt | tttttttttt | tttgaaggaa | gggccctgtt | tcgtagggta | 780 |
| cataaaccgt | gagcgtaatt | gtattttttg | catattccag | gtttgcttgt | gaaggtcaga | 840 |
| gtagccggat | ttaagtgaag | gagttcagta | gacatgcaga | catggtcacc | tggttcattt | 900 |
| tctgaaccct | ggattgtgcc | ctcggcttgc | tagtttccac | cttcctattg | agaaatgcca | 960 |
| ccagcgtgaa | tgatttaaat | atgtcaccat | tactgaattt | gtgaggtctc | taacgagagg | 1020 |
| tgtcaagagc | tggtgcgtga | tggtaggact | ggcagtgaag | aaagtaacta | aataatatgt | 1080 |
| taccattttg | gtgaaacaca | aaagttgaat | ttgaaccttg | tctcagaaac | tagcatctaa | 1140 |
| ctagatacct | aacctgcagg | acaggtccca | ggtctctctg | gatagttgta | gcacctttcc | 1200 |
| ttatagaatt | ctattaccag | gccgagcctg | gtggctcaca | cctgtaatcc | cagcactttg | 1260 |
| ggaggctgag | gtgggagtt | cgagaccagc | ctgactaaca | tggagaaacc | gcgtctctac | 1320 |
| taaaagtaca | aaattagccg | ggcatggtgg | cacatgcctg | taatcccagc | tacttgggag | 1380 |
| gctgaggcag | gagaatcgct | tgaacctggg | aggcggaggt | tgcggtgagc | tgagattgct | 1440 |
| ccattgcact | ccagcctggg | ccacaagagt | gaaactctgt | ctcaaaaaaa | aaaaaaaaa | 1500 |

```
aaaaaaaaaa aaacccgcaa aactcaacaa aaaccaacat agtagaggca gcgtttcgcc    1560
ttatgcccag ctaattttt gtatttttt agtagaggcg gagtttcgct atgttggcca      1620
ggctggtctt gaactactga cctcaggtga tccacctgcc ttggcctccc aaagtgctgg    1680
gattacaggc gtgagccacc gtgcccggcc ctgttatagt atttctaaaa caaattgtga    1740
gcctgggcaa catcgcaaaa ccctgtctct acaaaaaata caaaaaaaaa aaattagcca    1800
ggcgtggtgg catgctcctg ttagccctaa ctactcagga ggctgagatg gaaaaatcgc    1860
ttgagccggg gaggtagagg ttgtagtaag gggagatagt gccactgcac tccaacctgg    1920
gccacagaac aagactgtct caaaaaaaaa aaatcaatt aaataaattg tggtaaatat     1980
atatttttat gtatgtttat gtatatttta acaaaatttg ctctttaaac cattgttaag    2040
tatacaattc agccaggcac ggtggctcac gcctgtaatc ccagcacttt gggacgccga    2100
ggtgggcgga tcacgaggtc aggagatcga gaccatcctg gctaacacgg tgaaacccca    2160
tctctactaa aaatacaaaa aatgagccgt gcgtggtggt gggcgcctgt agtcccaggt    2220
actcaggagg ctgaggcagg agaatggtgt gaacccgaga ggcggagctt gcagtgagcc    2280
gagattgcgc cactgcactc cagcctgggc aacagagcga gactccgaga ctccatctca    2340 aaaaaaaaa aaaaagtat acaattcaat ggtattaatt acattcacaa tgtagtacaa      2400
gcaataccac tatttctgaa actttagtat ctcaaacaga aactctgtaa ccagggaggg    2460
catggtggct cacgcctgta atcccagcac tttgggaggt caacgtgggc agatcacttg    2520
agttcaggag ttcaagaaca gcctggccaa catggtgaaa ccccgtatct actaaaaata    2580
caaaaattag ccatgcatgg tggcatgcat ctgtaacacc agctactaag gaggcagagg    2640
ttgcagtgag ctgaggtcat gccattgcac ttcagcctgg gctgcacagc cagactccat    2700
ctcaaaaaaa aagaaaaaaa gaaactgtaa ccattaaaca agttaacttc ccatttcctc    2760
ctcttaatct ctaatctact ttgtgtctgt ctgtgagtgt gcttgttcta ggtactgcaa    2820
atactaaatg gaatcataca gtattgtcct ttttgtgtc tggtttattt cacttagtgt     2880
aatggtttca aggttgatcc atgttgtact gtgtatcaga atttcattcc tttttaaggc    2940
ttaatccgtt gtgtgtgtac actacatttt gtttattaat tcatttgtag cagacacttg    3000
ggttgcttct gccttttgac tattgtaaat aatgatgctg tgatcattgg tgtacaaata    3060
tctctttgag tccctgcttt gaattctttt gggtatatac ccagaaggga aattgctata    3120
tggtaattat tattattatt aattatttta tttatttttt tttgagacag ggtcttgctc    3180
tgttgcccag gctggagttc agtggcacag tcatggctca ctgcagcctc gaactcgagc    3240
tcaagcagtc atcccgcctc agcttcctga gtagctggga ctacaggcat gggctgccac    3300
aaccagctaa tttttttgtt taattttat tttttgtgat gaagtcttgc cttgttgtct     3360
agggtggtct cgaactcctg agttcaagtg atcctcctgt cttggcctcc gaagtgctg     3420 gcattacagg catgagccac cacatctggc ccataatttt tttatttaa ttttttgtg      3480 gagacagggt ctccctatgt tgcctatgct ggtctcaaac tcctggcctc aagccatttt    3540
ccctccttgg cctctcaagg tactggtatt acaggcatga gccactgcac ccagttgata    3600
cttggttatt atatgtttag cttttgagg acccaccata ctgttttcct caatggctgc     3660
atcgttttac attcccacca gtaatacaca agggttccaa ttttcccaca tcctccccaa    3720
cacttatttt ctgttttcc ttttttgata aatttgtgtg tgtatatgtg gttttttatt     3780 tgtgtgttt gatgatagcc accctaatgg gtgtgaagtg gtatctcgtt gtgttttctt     3840
```

```
ggtttttgct tgtttgtacc tttttaccca tttttaagtg tgctacttag tagtagtaag    3900
tacattcttc tttttgtgca accataataa aaatccagct tcagaactttt tttcatcttc   3960
ccaaactgag tttctgtacc cattgaatag taactcccta ttctctcctc ccctgacaat    4020
caccattctg ctttctgtct ctatgaattt gactactcta ggtatctcat gtaagtggaa    4080
tcatataata tttgatcttt tgtgtatggc ttattttact tagcataata tcttcaggat    4140
tcatccatct tgtagtatgt atcagaattt tattccttttt taaggctgag taatattcca   4200
ttatacatat ataccacatt ttgtttatcc atttatctat tgatggacat ttgggttgtt    4260
tccaccttttt tgctcttgtg aatataatgg tgctatgaat atcagtgtac aaatatcttt   4320
tttttttttt tttttgtgag acagtatcgc tcttgtcacc caggctggag tgcagtggcg    4380
cgaccttggc tcactgcaac ctctgcctcc tgggttcaag gcattctcct gcctcagcct    4440
cccgagtagc tgggattaca gatgtgcgcc accatgccta gctaattttt ttattttttag   4500
tagagaagga gtttcgccat gttgggcagg ctggtcttga acttctgacc tcaggtgatc    4560
aacctgcctc ggcctcccaa agtggtgaaa ttacaggtgt cagccaccgc gcccagccac    4620
aaatatcaag tctttacttt catttctttt gggaatatat atactcagaa atggaatcga    4680
caattgacag agcaaatggt aattctatgt gtaattttttt tttaaatttt ttttttttgag  4740
acggattctt gctctgtcgc ccaggctgga gtgcagtggc gtgatctcgg ctcactccaa    4800
gctccgcctc ctgggttctt gccattctcc tgcctcagcc tcccgagtag ctgggactac    4860
agcatccgcc accacgcccg gctaatttttt tgtattttta gtagagacgg gtttcaccg    4920
tgttagccag gatagtctcc atctcctgac ctcatgatct gcccgccttg gcctcccaaa    4980
gtgctgggat tacaggcgtg agccaccgcg cccggccaat tttttttttt tttttttta    5040
gacagggtct tgctctgttg tccaggctgg agtgcagtgg tgcagtcaca gttctctgca    5100
gccctgacct tctcagttca agctatcctc tcacctcacc ctcttaagta gctgagacta    5160
caggtgcatg ccaccatgcc taactaattt ttttattttt ttgtagctgt gggatttcgc    5220
taggttgccc aggctttatg tatcattttt tgaggaactg ccttactgtt ttccacactg    5280
gttgcaccat tttacattct gttagcagtg tacaaaggtt tgttataga ctgaattgtg     5340
tccccctgaa aattcacgtg ttgaagccct aagccccagt gtgactgtat ttggaaatag    5400
gacctttaca gagaaattaa aaagttagaa gatatcataa ggggctgggc gcggtggct    5460
catgcctgta atcccagcac tttgggaggc tgaggcaggc ggatcacaag gtcaggagat    5520
cgagaccatc ctggccaaca cggtgaaacc ccgtctctac taaaaataca aaacattaac    5580
cgggcgtggc ggcatgcacc tgtagtccca gctgctgggg aggctggggc aggagaatgg    5640
cgtgaacccg ggaggcacag cttgcagtga gccaaaatcg cgccactgca ctccagcctg    5700
ggcgacagag cgagactcca tctcaaaaaa aaaaaaaaa aaaaaaaag aagatataag     5760
gatgagacct taatccagca ggactgctgt cttcgtaaga aaaggactgg ataccaggag    5820
tgcgtgtaca gagagaaaaa gctgcatgag gacagaggta aaggggggct gcctgcaagc    5880
caaggagaga gacctcacct aaaacaaacc ttgctgacac cttgatcttg gactcccagc    5940
ctccagagct gtgagaataa tttctgtggc ttaagcctttc cactccatgg tattttgtta   6000
tggcagtcct agcatactgt gtaatatagg tttcaattca gtttctctgc atcctccaca    6060
tcctggccaa cacttgttat tttctttctt ttttttttttt ggagacagat tctcgctctg   6120
tcacgcaggc tggagtgcag tggcacaatc ttggctcact gcaacctcca cctcccgggt    6180
tcaagcgatt ctcctgcctc agcctcccga gtaactggga ttacaggcag ccgccaccgt    6240
```

```
gcccagctaa ttttttgcatt ttagttgaga tggtgtttct ccatgttggc caggctggtc   6300
ttgaactcct gacgtcaggt gacccgccag ccttggcctc ccaaagtgtt gggattataa   6360
gcatgagcca ccgcgcctgg cattttcttt tttttttgaga cagagtctca ctctgttgcc   6420
caggccggag tgaagtggca tgatctcggc tcactgcaac ctctgcctcc cagattgaag   6480
caattcttgt gcctcagcct cccgggtagc tgggattaca ggcgtgtgcc accacgcctg   6540
gctaatttttt gtatttttagt agagacaggg tttcaccata ttagccaggc tggtcttgaa   6600
ctcctgacct caagtgatct gtccaccttg gcctcccaag tgctgggat tacaggtgtg   6660
agccatctca cccggcctat tttctgtttc gtttttttttt ttttcattag tagctatcct   6720
agtggatgtg aagtggtatc ttattgtggt ttctgatttg catttccctg atgataagtg   6780
atgttgagcg tctgttcatg ttcttattgg ctatttgcat attctctttt ggagaagtat   6840
ctattcatgt cttttgttga ccatttttaaa atggggtttt tcatcctggc taacacggtg   6900
aaaccctgtc tctactaaaa atacaaaaaa aaaaaaaaaa aaaaattagc cgggcgcagt   6960
ggcaggcgcc tgtagtccca gctactcggg aggctgaggc agaaggatgg tgtgaacctg   7020
ggaggcagag ctcgcagtga gcagagattg agccactgca ctccagcctg ggcgacagag   7080
cgagactccg tctcaaaaaa aaaaggggg gggggggggg ttttgagctg ggtgtgcagg   7140
tgcacacctg tattcccagc tgctcaggag gctgaggtag gtggatctct tgagcccagg   7200
tgtttgaggg tgcagtgagc tgtgattgca ccactggact ctaccctggg tgacagagtg   7260
gcccagtctc taaaaataaa ataaaattag gttttttgtct gtgttgttga gttttaggag   7320
tcctttatac actctagata ttaattcctt gtcagatatt tgacttacaa atattttctc   7380
tctgtggttg tctttatact ctgttgatag tgtcttttga tgcacagagg ttttcatttt   7440
gatgaagtcc aatttatctt cttttttttaa aatctgtgcc tcatctgcaa atattaccaa   7500
tcgaaagtca tgaaatttttt cccctaagat tttatagttt tagcgcttac gtttgggtct   7560
ttgatccaat ttgagttaat tttttatata tttttgttgt gtaagagtcc cactttattg   7620
ttatgcatgt ggatattcag ttttcggagt accattttcc atttgggaaa aagattgtac   7680
tttccccatt ggatggtctt gacacctttg ttgaaaatca gttgactaaa gttcaagact   7740
agccttgcca acatggcaat atcccgtctg tactaaaaat accacaatta gctgggcatg   7800
gtggtgcctg gctgtaatcc cagctactcg ggaggctgag gcaggagaat cgcttgaact   7860
gggaggtgga ggctgcagtg agctgagatt gcgccactgc cctccagcct gggcgacaga   7920
gcgagacatg agaatctgtc ttaaaaaaaa aagaaaattg accatatatg tgaggattta   7980
tttctggtct ctccattcag ttgattggtc tttatgtcta tctttatgtc cttactgcac   8040
tgttgtgatg gctgtagcta aatggtacac ttaaaaatgg ttaaaatagg ccaggcacgg   8100
tggctcacgc ctataatctt agcactttag gaggctgagg tgggcagatt gcctgtgctc   8160
aggggttcga gaccagccta ggcaacatag tgaaacccccg attttactaa aatacaaaaa   8220
ttagctgggt gtggtgtgtg cctgtaattc cagctactca ggaggctaag gcacaagaat   8280
tgcttgaggc ctggtgctgt ggctcacgcc tgtaatccca gcactttggg aggccgaggc   8340
aggtcaagag atcgagacca tcctggccaa tgtcatgaaa cctagtctct actaaaaata   8400
caaaaaatta gctgggtgtg gtggcgcgca cctagtccca gctacttggg aggctgaggc   8460
aggaggatca cttgaaccca ggaggtggag gttgcagtga gccaagattg cgccactgca   8520
ctctagattg gcagcagagt gagactctgt ctcaaaaaag aaaaaaaaaa aaagaattg   8580
```

| | |
|---|---|
| cttgaaccca ggaggtagag gttgcagtga gctgagattg caccctgcac tccagcctgg | 8640 |
| gcaacagagt gagactattt acatacccaa tttttttttt tttttttttt tgggatggtg | 8700 |
| tcttgcactg tcgcccaggc tggagtgctg tggcgtgatc ttggctcact gcaacctctg | 8760 |
| cctcctgggt tcaagcaatt ctcctgcctc aggctctcaa gtagctgggt tacaggtacc | 8820 |
| tgccaccacg cctggctaat ttcttgtatt tttagtagag atggagtttc actatattgg | 8880 |
| ccaggctggt ctcaaatttc tgaccttgtg atccgctggc ctcagcctcc caaagtgctg | 8940 |
| ggactacagg tgtgagccac cacgcctggt catacccaaa tattttacca taattataca | 9000 |
| agaatttatt attttatttt ttttcttttt aaattcttta atcttcttca tttgttaatg | 9060 |
| ctttgctgaa tcataaaaaa ttatgaaata aaagaatag gtcttgttga ttcttctttt | 9120 |
| tacttacctc cccctactta cccctctta ctttatcaaa gaaacactt catttgaaac | 9180 |
| ttaacggaag tacattctcc cagagaggaa aatccttcag gacaacattt ttttttgttt | 9240 |
| gcttgttttt tttgagacgg agtctcactc tgtccccgag gctggagtgc agtggtgtga | 9300 |
| tcgcagctca ttgcaacctc tgcctcccgg gttcaagcga ttctcctgcc tcagcctccc | 9360 |
| gagtagctgg gactacaggc gcctgtcacc atgccctgct aatttctgta ttttttagtag | 9420 |
| aaacagttgg ccaggatggt ttcaatctta tgactttgtg atctgaccac tttggcctcc | 9480 |
| caaagtgctg ggaatacagg cgtgagccac agtgctcagc caattttttg tattttagt | 9540 |
| ggagaaaagg tttcaccgtc tttgccagga tggtcttgat ctcctgacct cgtgatccgc | 9600 |
| ccgcctccca agtgctggg attacaggcc tgagctacca cgcccagcct ttttattttt | 9660 |
| ttattttatt tattttattc tcagccttct gggtaactgg gactacaggt gtataccacc | 9720 |
| acgctcagct aatttatgta tttttagtag aaatggggtt tcgccatatt ggccaggctg | 9780 |
| gttttgaatt cctggtctca agtgatctgc ctgcctccgc ctcctaaagt gctgagatta | 9840 |
| caggcatgag ccactggccc agactacact taaaattttc aaatcgagat attttggggg | 9900 |
| gcaagggtgc ttctagcagc cactaattcc agttcttgag tgcatattaa agttgctact | 9960 |
| gtttaaaagc ttgtagttgg atccagggag tgggtaggcg gtcagagtaa cccttgcttc | 10020 |
| ttggtgtctc cttgatgctc ttagctgaat gtcctgtgta gcccacaaca tttactttgg | 10080 |
| gaaaaaatta agagtgttta aagcaggatc aagctgctgc ataccacagc taaaactact | 10140 |
| agaataagac ccctggttct gtttcattgt tttttggagc taaagtcatg attaagaagg | 10200 |
| atggcctggg atattggtac tgtgctgcta gaggtgcaat tcctggttct ttgcaagata | 10260 |
| gaccagagtg aaagcatttg ttaggaatgt ttttattaat caagagtgaa aggcaaggcc | 10320 |
| aggcgtggtg actcaggctt gtaatcccag cactttggga ggccaaggtg tgggatcatt | 10380 |
| tgaggtcagg agttcaagac cagcctggcc aacatggtga aaccccgtct ctactaaaaa | 10440 |
| tacaaaaatt ggctgggtgt ggtggtgcat gcctgtaatc ccagctactc gggagactga | 10500 |
| ggcaggagaa tcgcttgaat ccgggagacg gaggttgcag taagctgaga tcatgtcact | 10560 |
| gtggtacagt ctgggtgaca gagggagact gtttcaaaaa aaaaaaacag aaagaatgaa | 10620 |
| aggcaaaaca ttaaaaatag aattaccatg tgatctaaca attttacttc tggatatata | 10680 |
| tccaaaataa ttgaaaacaa agaaaaagaa aaacagagtc tcgatgagat atttgtaccc | 10740 |
| atgttcataa cagcgttatt cacattagct aaaatgtgga agcaacccaa ctattcattg | 10800 |
| atggatgaat agataaggaa aatgtggtat gtacatataa ctgaaaaatt attcagtgtt | 10860 |
| aggaaggaag gtaattctga catatgctac aacatggatg aaccttgagg atattatgct | 10920 |
| aagtgaaata agccagtcat gtaaaagaca aataccatat aatttcactt agacactttg | 10980 |

```
agtagtgaaa atcatagaaa cagaaaatag ttgtcaggga tggtgtgagg gatgaatcag   11040
cagttactat ttcttttttgt ttgtttgttt tttgagatgg ggtcttgctc tgttgcccag   11100
gctggagtac agtggtgtga tcttggctca ctgcaacctc tgcctcccag gcacaagcca   11160
tcttcccacc tcagcgtcct cagtagctgg gactacagat gtgttccacc ttgtccggct   11220
gatttgtgtg tgtgtatatg tgtgtgtgtg tgtggagaca aggttttgcc atgttgccca   11280
ggctggtctc gaactcctga gctcaagcat caagcaatct accttttca gctttccaaa    11340 gtgctggcat tacagacaag ggccactgtg cctggccttt actatatttt attttattta   11400
ttatttattt atttatttat ttatgtattt tgagatgaag tctcactctg ttgcccaggc   11460
tggagtgcag tggcacgatc ttggctcact gcatcctctg cctcccaagt tcaagtgatt   11520
ctcctgcctc agcctccagt tattattatt attattatta tttttttgtt gttctgtttt   11580
tttgaggtgg agtctcgccc tgtcgcccag gctggagtgc agtggcacaa actcggctca   11640
ctgcaacctc catctcccag gttcaagtga ttcttctgcc tcaacctccc aagtagctgg   11700
gaatacaggt gcccgccacc acgcctggct aattttgta ttttttagtag agacgggggtt   11760 tcaccacatt ggtcaggctg gtcttgatct cctgatcttg tggtccacct gcctcggcct   11820
cccaaagtgc tgggattata ggtgtgagcc cccatgccct gccttgttat tattattatt   11880
tttatttttt tgtctgagac ggagtcttgc tctgtcaccc aggctagaat gcagtggcac   11940
gatcttggct tagtacaacc tctgcctccc gagttcaagt gattctcctg cctcagcctc   12000
ccgagtatat aggactacag gtgtgtgcca ccatggctaa ttttgtatt tttagtagag    12060 atggggtttc accatgttgg tcaggatggt ctagatctct tgacctcgtg atctacccgc   12120
cttggcctcc caaagtgctg ggattacagg catgagccac tgcgcctggc ccagttttt    12180 gtattttaa tagagacagg gttttggcat gttggccagg ctggtctcag actcctgacc    12240
tcaagtgatc tgcccacttc agccttctga agtgctggga ttaaagacat gagcactgtg   12300
cccagccact tttactatat tttaaattag gttacttatc ctttgttttt ttttttttt    12360 gagacgaagt tttgctcttg ttgcccaggc tggtgtgcaa tggtgcatct cgactcaacg   12420
caacctctgt ctcccgggtt caagtgattc tcctgcctca gcctcccgag tagctgggat   12480
tacaggcatg catcaccacg ccagctaatt ttgtattttt agtagagaca gggtttctcc   12540
atgttggtca ggctggtctc aaactcccga cctcaggtga tccacctgcc ttggcctccc   12600
aaagtgttgg gattacaggc gtgtgccact gctcctggct tattttcctt tttgttactg   12660
agttgaaatc attttttata tatttttagat acaagtcact taccaaatat gtaatttgca   12720
caaattttct cccattctgt gggatgtctt ttcatttaaa ccaaaaaatt gtagagatgg   12780
gggttttgct gtgttgccca ggttggtctt gaactcctgg tcttaagtga tcctctgacc   12840
ttggcctcaa aaagtgctgc gattataggc atgagccaat gtgcgcagct tacctttct    12900 tcttttcttt tttttgagg caggggtcttg ctctgttgcc caggctggag tgcagtggtg   12960
caatcatggc ttactgcagg ctgaaactcc catgctcaag tgatcctccc actttagcct   13020
cctaggtaac tgggacctta ggggcgtgcc atcacacctt gctaattttt ttttttttt    13080 gagatggagt cttgccctgt cgcccaggtt ggagtgcagt ggagcgatct tggctcactg   13140
caaattccac ctcccggatt caagtgattc tcctccctca gcctcctgag tagctgggac   13200
tacaggcgtg tgccaccacg cccagctaat tttgtattc tgagtagaga cgggatttca    13260
ccacattggc caggctggtc tcgatctctt gacctcgtga tctgcccgcc ttggcctccc   13320
```

-continued

```
aaagtgctgg gattacaggt gtgagtgtga gccaccgaac ctggccttt ttttttttt     13380 tgagaccgtc tctgtcaccc aggctggagt gcagtaacat gacacaatct ccgctcactg     13440
caacctctgc cttctgggtt caagtgatcc ttctgccaca gcctcctgag tagctgggat     13500
tgcaggcatg tgctaccacg cctggctaat ttttgtattt ttagtagaga cggggtttca     13560
ccatgttggc ctacctggtc ttgaattcct gacctcagat gatctgcccg catcagcctc     13620
ccaaagtgct ggggttacaa gcgtgagcca ccacgcctag ctggacctga ctaattaaaa     13680
aaaaaatttt gtaggctggg cagggtggct cacacctgta atcccagtac tttgagaggt     13740
ggaggcgggg taatcgcctg aatcaggagt tgagaccag cccgggcaac ataacgaaac      13800
cctaggtcta ccagaaatac acaaaaaaat tagccgagca tggtagtgca catttgtagt     13860
cccagctact caggaggctg aggtgggagg atggctggag ccagggaagc agtggttaca     13920
gtgagccgag aatgtgccac tgcactcccg cttgggtgac agagtgagat aaggtctcag     13980
aaaaaaaaaa aaaatttata ggccgggcgc aatggctcac gcctgtaatc ccagcacttt     14040
gggaggacca ggcgggcgga tcacaaggtc aggagatcga gaccacctg gccaacatgg      14100 tgaaaccccg tctccactaa aaaaatacaa aaattagctg ggcgtggtgg cacgtgcctg     14160
tagtcccagc tacttggcag gctgaggcag aagaattgct tgaaccctgg aggcggaggt     14220
tgcagtgagc cgagattgca ccattgcact ccagcctggg cgacagagcg agactccatc     14280
tcaaaaaaaa aaaaaaaaaa aatttgtgaa gacaaggtct caatatttgc ccaggatggt     14340
ctgaaacttc tgggctcaag ccatccttct gcctcagcct cccaaagtat tggaattaca     14400
ggtgtgagcc actgtgtctg gcctatttat agactcttaa ttctgtttcc ttggtctgta     14460
tgtctatact atgtcagtgc cacactgtct tgattactgt agctttgtgg tgagttttgg     14520
aattgggaag tgtcagtcct ctaactttgt tgtatatatt cttttctgtt ttgcacagat     14580
atcaggttac aaatatttg cacactttt ttttttttg aaatggagtc ttactctgtc       14640
acccaggctg gagtgcagtg gcgcgatctc agcccactgc aagctccgcc tcccaggttc     14700
acaccattct cctgcctcag cctccccagc agctgggact gcaggcgcac actgccatgc     14760
ccagctaatt ttttgtatt ttaagtagag acagggtttc actgtgttag ccaggatggc      14820
ctcgatctcc tgacctcgtg atccgcctgc ctaggcctcc caaagtgctg ggattacagg     14880
cgtgagccac cgcacccggc cttgcacatg ttttttaaaac ttaatacata atagcttatc    14940
ctgtatcaat taacatagct actttattta ttcttagggc cgcatagtat ttttttttct    15000 ttctttttt tttttttttt tttttttgag actgagtctc gctctgttgc ccaggctgga     15060
gtgcagtggt gtgatcttgg cttaagcaac ctctgcctcc tgggatcaag cctcgggatc     15120
ctcctacctc aacctctgca gtatttggga ctacagacac ctgctaccac acccagttaa     15180
ttttcgtatt tttttgtaga gatagggtct ctattgatgt gcatttaggc tttataatat     15240
ttatatatat attttttgaa acaaagtttt gctcttgttg cccaggctgg agtgcagtgg     15300
catgatcttg gctcactgca accttcgcct cccaggttca agtgattctc ctgccttaga     15360
ctcccgagta gctgggatta cagttttaa aaaatgtatc ctaggctggg cgcagtggct     15420
cacgcctgta atcccagccc tttgggaggc tgaggcgggt ggatcacctg aggtttggag     15480
tttgagacca gcctggccaa catggtgaaa cctcgtctgt actaaaaata caaaaattag     15540
ctgggtgtac tggcgggcac ctgtaatctc agcttcttgg gaggctgaga caggagaatc     15600
tcttgaactt gagaggcggt ggttgcagtg agccattgca ctccagcctg ggtgtcaagc     15660
aaaactctgt ctctctctct ctctgtgtct ctctctctct ctctgtgtgt gtgtgtgtgt    15720
```

```
gtgtgtgtat atgtatatat attctgccaa tattttgtga ttagagagtt taaagtattt   15780
acatttaaag taattactga taaggacttt tgccattttg ctactacttt tatgtttagc   15840
tgattttttt tttttttggta gtgaaaaaaa attttttttt tttgagagca tgagactgtt   15900
gcctaggctt tggtgagcaa aatagtgcag tgccacaatc tcagctcact gcaactttgg   15960
gctcaagtga tcctcctgtc ccagtctcct gagtagctgg tagtataggt gtgccaccac   16020
catgcctggc taattttgt atttttttgta gagatagggt tttgccatgt tgcccaggct   16080
ggtctcaaac tgggttcaaa caatctacct gccttagcct tccaaagtgt tgggattaca   16140
ggcattagcc actttctgcc ccctccccg cttttttttt tttttttttt ttttttgagac   16200 ggagtttcac tcttgttgcc caggctggag tgcagtggca tgatttcagc tcactgcaac   16260
ctccgcctcc cgggttcagg cattttcctg cctctgcctc ccaagtagct gggattacag   16320
gcttgccacc atgcctggct aattttgtat ttttaataga gatgggttt ctctatgttg   16380 gtcaggctgg tctcgaactc ctgacctcag gtgatcctcc tgccttggct tcccaaagtg   16440
ctgggattat aggcgtaagc catcacgcct ggcccacgct ttatttttt atttttattt   16500 tttattattt atttatttat ttttttgagac ggagtttcgt tcttgttgcc caggctggag   16560
tgcaatggca taatctcagc tcaccgcagc ctccgcctcc tgggttcaag tgattctcct   16620
gcctcagcct cctgagtagc tgaatttaca ggcatgcgcc accatgccca gctaattttg   16680
tatttttagt agagacgggg tttctccatg ttggtcaggc tggtctcgaa ctccagacct   16740
caggtgatcc tcccgcctcg gcctcccaaa gtgctgggat tacaggcgta agccaccagg   16800
cctggcctgc ttttttaatt tttattatt ttttctttt aagagggag gtcttgctg   16860 tgttgtccag attggagaac agtgatgaga tcatagctca ctgcagactt ggattcctgg   16920
actcaagcaa tcctcccgct tcattctttg caagtaactg gaagtgcaga catgtgccac   16980
ctgccttttt tgttttttaa attttttcata gagatggggt cttgctatat tgcctaggct   17040
ggtctcaaac tcctggcctc aagcaatcgg cttcctgaag tgctgggatt acagatgtta   17100
gccactggcc tgttgtgaaa atgttttgac tttcttctca tttctttct ttcttttttt   17160 tttttttga agtagagaga gtctcactat atggccaatg gtggtttcaa acccctgagc   17220
ccaaggaatc ctcctgcctc agcctcccag tgcttgtcgt gctaggacaa caagcatgag   17280
ccactgtgcc tagccccttc tcattttctt tttctttcta gtgcataagc aggcaaccttt   17340 attttcttat gtgtatattc taaagatatg ttctttgcag ttaccatggg aattacacttt   17400 aacatctcac agtataatc taatttgaat ttatactaac ttaagttcca tagtatacaa   17460
atctctgctc ctatccagct cctttctctt cccttttctg ttaagtcatg gattacatct   17520
ttgtaaatcg tatctcagga acctagatta ataattttt atgcatctgt cttttagatc   17580
acattgaaag tgaaaagtag gagttacaaa gcaaaattgc aataatgcta gttttttacag   17640 ttgcccctgt atttgccttt accagagatc tttctttctt tttttttttt ttgggatgga   17700
gtctcgctct ttcgcccagg ctggagtgca atggcgcaat ctcagctgac tgtaacctct   17760
gcctcccggg ttcaaaagat tttcttgcct caggctcctg agtagctggg actgtagttg   17820
tacgccacca cacgtggctg attttgtat ttttagtaga gatgggggtt tgccatgttg   17880
gccaggctgg tcttgaactc ctgacctcag gtgtgagcca ccgcacctgg ccgagatctt   17940
tatttcttca catggcttca cgtctagctt ttaaaaattc attctgggcc gggcgcagtg   18000
gctcacgcct gtaatcccga cactttggga ggctaaggcg ggcggatcac gaggtcagga   18060
```

```
gatcgagacc atcctggtta acacagtgaa accccgtctc tactaaaaac acaaaaggcc   18120
gggtgcggtg gctcacgcct gtaatcccag cactttggga ggctgaggtg ggtggatcac   18180
gaggtcagga gatcgagacc atcctggcta acatggtgaa accccgtctc cactaaaaat   18240
acaaaaaaca aaacaaaaca aaaaaaacta ttagctggca ttgcggtggg cacctgtagt   18300
cccagctact cgggaggctg aggcaggaga atggcgtcaa cccaggaggc ggagcttgca   18360
gtgagccaag atcacgccac tgcactccag cctgggagac agcaagactc tgtctcaaaa   18420
acaaaaaaca aaaaccaca aaaattagcc gggcgtggtg gcgggcgcct gtagtcccag   18480
ttactcggga agctgaggca ggagaatggc atgaacccag gaggtggagc ttgcagtgag   18540
ccgagatcgc tcaactgcat tccagccttg gcaacagagc gagactccat ttcaaaaaaa   18600
aaaaaaattc attctgaaga attccttttt tttttttttt ttttgtaaaa atggagtctc   18660
actctgttgc cctggctgga gtgctgagtg ccatggcatg atctcagctc actgcaacca   18720
accccccactc caagttgaag cgatactcct gcctcagcct cctgactagc tgggattagg   18780
ggtgcctgct actgcacctg gctaatttt gtatttttag tagagacggg tttcaccatc   18840
ttggccaggc tggtgtcgaa ctcctgacct cgtgaccaac ccacttcggc ctcccaaagt   18900
gctgggatta caggcgtgag ccactgtgcc cggactgaag aattccctt tagcatttct   18960
tacaaggtct gtatagtggt aatgagcctc cctcagcttt tgtttatctg agaatgtctt   19020
gattttttc ctttttttt ttttttttg agatggagtc tcgctctgtc gcccaggctg   19080
gagtgcagtg gcgtgatctc agctcactgc aagctccgcc tcctgggttc acaccattct   19140
cctgcctcag cctcgtgagt agctgggact acaggtgccc gccaccacgc ctggctaatt   19200
ttttttttt ttttgtatt tttagtagag acggggtttc actgtgttag ccaggatggt   19260
ctcaatctcc tgaccttgtg atccgcccgc ctcggcctcc caaagtgctg ggattacagg   19320
tgtgagccgc ctcgcccggc caatgttttt ccctatttt tgaaagacag tgttgccatt   19380
tacagaattc ttggttggca atttatattt agggttttt ttttttttt tgagacagag   19440
tcttgctctg ttgcccaggc tggagtgcag tggtgtgacc tcggctcact gcaacctccg   19500
cctccagggt tcaagtcatt ctcctgcctc agcctcccaa gtagctggga ctacaggtgc   19560
ccgccactac gcctggctaa ttttttgtat ttttagtaga cgggggtgt caccatgttg   19620
gccaggctgg tctcgaactc ctgacctcaa gtgatccaca cgcctcagcc tcccaaagtg   19680
cagggattac agacatgagc ccccacgccc ggcctaggtc ttgtatgatc atacattttg   19740
ccttggcatt catatggctt tctaaatttc accatataca tgttgctttg gaatgtccta   19800
atttgccaaa gagtttcacc tcaacttctg tgggcatcta tctgtaatct cttgcccaa   19860
gtgcctgtta gtctgtagtc tgcttttgcag ctttcattag caatacctgc tgctttctct   19920
gcctgagttt tgtattaggt tgaaatagaa acatgcacct tatgtctgtc cttcaaatac   19980
ccccgcagac agggtagaac agatatgtac gataatttgc aaataaggtc tgctttgctc   20040
tttgagggag ggagctggga attgggcttc tactgcttta agacaaaaaa cactgccatg   20100
ctggagaggg ggtagggcaa ggttgagtaa acaccacag aactttcctt ctgttttgaa   20160
gatggctttt tcttcattgg atatttgctt gtaaaccttt gactcttttc taaaactgtc   20220
aaatttggtt cagacagtta ctacttgttt ttctgatgtt tctatgaagg aatgagacct   20280
tgaaacttcc tagtctgcca ttttgatgac ctatgggctg tctttgtact ctcttgatag   20340
tgtcctttga tacacagaag ttttaatt tggtgaagtc cctttatcta ctttttcttt   20400
taaagttcct tgtgctgtag gggtcatatt taagaaatca ttgccaaatc caaggtcatg   20460
```

```
aagatttgcc tcttttttcag tagctataac aaaggtcctg gaaataactt cttatcttga   20520
cttgagttac atgtctgtct tcaaagcaat gactgtggtg agggtaatag attattccga   20580
ttgctcatgc tggatggtgt ccgatcaggt ctgagacagt ggggttgata ctacagtgct   20640
gtttccaaaa aggaagggct agtgagcgct agaaaaatca gtaaatactt acttcatgta   20700
gtaaatgtga agcattcata gcacattgaa aagtttatgg tgcccagagt acctttttt    20760
tttttttttt ttgagacagc ctcactctgt ttcctgaact ggaatgcagt ggtgcgatct   20820
tggctcactg cagcctcaac ctcctgggtt caagcgatcc tcccccactt cagccttcca   20880
agaagctgag actacacata gtcatcatgc ctgactaatt tttgtatata tattttttaa   20940
gatggagtct cgctctgtca cccaggctgg agtgcagtgg catgatcttg gctgactgta   21000
gcctccgcct cccggtttca agcgtttctc ctgcctcagc ctcctgcata gctgggatta   21060
caggtgcctg ccaccacacc tggctaattt ttgtattttt agtagagatg agatttcacc   21120
atgttgccta ggctggtctc gaactcctga cctcaggtga tccacctgcc tagcctccca   21180
aagttctggt aattttttgta ttttttgtag agatggcatt ttgctatgtt gcccaggctg   21240
gtctcaaact ccttggctca agcggtctgc ctgccttggc ctcccaaagt gttgaggtta   21300
caggtatgag ccaccgtgcc cgaccccaga gtacacattt taattaaaaa cttatttttc   21360
tggccgggca cggtggctca cgcctgtaat cccagcactt tgggaggccg aggtgggtgg   21420
atcacaatgt taggagttcg agaccagcct ggccaatatg gtgaaacccc atctctacta   21480
aaaatacaaa aattagccgg gcatggtgac gcgtgcctgt agtcccagct actcgggagg   21540
ctgaggcaga agaatcgctc gaaccgggga ggcagaggtt gtggtgggct gagatagtgc   21600
cactggactc cagcctgggc gacagagaga gattctgtct ttaaaaaaaa aaaaaaagta   21660
ttttcttat tataaattta atatgtaagt gatgtaagtg tttgaaagtg acttccagct    21720
ggatgcggtg gctcatgcct gtaatcctag cactttggga ggccgaggcg gcggactgc    21780
ttgagctcag gagtttgaga ccagcctggg taacacagtg aaaacccgtc tctactaaaa   21840
tacaaaaaaa ttagctgggc ggccggcgtg cgcctgtagt tctagctact tgggaggctg   21900
aggcaggaga attgcttgaa cccggaggtt gcagtgggct gagatcgtgc ctttgcactt   21960
cagcctgggc aacaaagcaa gactccatct cttaaaaaaa aaaaaaaaaa agaaggccgg   22020
gtgcagtggc tcacgcctgt aatctcacac tttgggaggc ctaggtgggc ggatcatgag   22080
gtcaggagat ctagaccaca gtaaaccccg tctctactaa aaatacaaaa aattagctag   22140
gcgtggtggc gggcgcctgt agtcctagct actcggagg ctgaggcagg agaattgctt    22200
gaacccggag gttgcaatgg gctgagatca tgcctttgca ctccagcctg gcgacagag    22260
cgagactcca tctcaaaaaa aaaaagaaa agaaagaaaa gaaagacctt caaaattatt    22320
gctgctgatg tggtccctca taaccaagc agtgggaaac tggtttagct tttagttcac    22380
attctaaagt actaatttttt gtggtttatt ttgtacaggt actgctataa ccagaatttg   22440
gtagaaaaag gatttacttg ttggggccct cttgataaaa agagatgtgg ggggattctc   22500
gacctgctaa cagaactgga ccttttcggt aagttctcaa atttgaatat tgaaattgcc   22560
agtattttaa ttataaatgt gtaacatttt cgcctactat aaatgaagat attttctctg   22620
tggagaaata gtttctgatt ttttaaaaat agaaatttgg ctgggcgcgg tggctcacgc   22680
ctgtaatccc agcactttgg gaggctgagg cgggcagatc atgaggtcag gagatcgaga   22740
ccatcctggc tatcacggtg aaaccccgtc tctactaaaa aatacaaaaa aaactagccg   22800
```

```
ggcgtggtgg cggctgcctg tagtcccagc tactcgggag gctgaagcag gagaatggtg   22860
tgaacctggg aggcggagct tgcagtgagc cgagatcgtg ccactgcact ccagcttggg   22920
cgacagagga agactctgtc tcaaaaacaa aacaaaaaa aaaaaagaa aaaaaagaa     22980 aaatagaaac tcaatttgga aaataatttc gaaaatgatt gtgagcctga atcccagca   23040 tgccaaatgt tttgtcacat agcattttaa aattttattt atttgtttgt tttttgagac   23100
aagtctctct ctgtctccca ggctggagtg cagtggtgcg atcttgactt actgcaacat   23160
ccgcctcccg tgttcaagtg attctcctgc ctcagccttc tgagtagctg ggattacagg   23220
cgcgtgccac tatgcctggc taatttcatt attttaatat taaaaaatac ccaaatattt   23280
tatttctttt tgtctcttag cgaaggaata catatttggc tagtaaggaa agctagcaaa   23340
atttacataa atgtttataa aagttgtatt gagttcacta atttatgtct agaattcaga   23400
gctgtgcctt gtctgtggca tgttgacgca gtttgctaag ccacctctca attttagggg   23460
ttacttggta ccaagaagag tggagaaagt ggtagcattt agttgtaaat agattgtatt   23520
ttaaatttgt agggaattaa ttttttttata gctagtatca tacacactgt attttaacta   23580
gtatttaaac attttttcgta ttgtgtttac aattaatgag atgctatatg aatgtgactt   23640
ttttggtttt acttggtaca tagcaaataa atctgacctt taaatgtatg cattcataag   23700
tattgttgct ccagttgaaa cttctattaa ctagtacatt ttcctttttt tacctttttt   23760
caaaatggag tctcactctg ttgcccatgc tggagtgcag gggtatgatc tcagctcact   23820
gcagcctttg cctcctaggt tcaagtgatt ctcctccctt agcctcctga gtagctggga   23880
ctacaggtgt atgccaccat gcctggctaa ttattgtatt ttttttttta gtagagatgg   23940
cgtttcacca tgttggccag gctgatctca aactcctgac ctcaagtgat ccacctacct   24000
cagcctccca aagtgctggg actataagtg tgagccaccg cacctgccat ttggattggc   24060
aatctgcaag attttattac ttaaatgcaa cagatgttct cattcattgt tctgaagctt   24120
ggagttccaa tgaaaaattt aggtggagaa ctgagtttag aaaatccata taatgtttag   24180
taaaactagt attttcataaa tgctgaatga cagagattgg tctttaaatt aaaacaacag   24240
tgtgatgttg ggtattttttt ttcttttcaaa atactaagga ttagatcagt ggtcagcaaa   24300
ctacagctga tagcctgttt ttgtaaataa agttttactg gaaaacagcc actcttactc   24360
atttgcagat tgtgtatggc tgcttttcatg ctatgatggc agagttgaat agttgtaaca   24420
gagattgtat aacccacaaa atccgatatg tttacgaact ggctcttcat ggaaaaagtt   24480
tcctgacctc tcatctagat caatgggggtt gtacgttacc attaaaaat atttaggttg   24540 taatctatcc tcttattact tgtatttatg ggtaactatt ttgtaagtaa ggctgtttcg   24600
tatagaatta acgtggttta ggtaagcatt cagaaatgtt aggttaattt agctttattg   24660 tctaacttttt ttcaaattta gaacatttgt ctttgactcg tttaaactta tttaaaatta   24720
tattttccca ccttaattttt agtttaaatg taagtcatta tatgctgttt tttaacatct   24780
ttgactagga gggagacagt ttttgggaac taatttgaac caaaacagat ataggaaaat   24840
gattttgtta catttccttt gaacttttct tttaaaattt gttttttattt ggttgaaaat   24900 aattttcata actactgata ttttatatta gtagaatggt ttcttgattc gtctgtataa   24960
aatacaaatc taagaaccct gctacagtaa gttactctaa atctatttga tcttaattta   25020
gaagagtaag ataatcttta ggccatgttg gatgtgttct ggtcagaaaa catgtagatt   25080
tcatacctca gtcctcatcc catgagtgtc tgatgaagct taaatcttcc tgcaagaaag   25140
acttgaatga ttttaaacat gagagacact gtatttagtg gtaacatctt aattttagtg   25200
```

```
ttaaattgta ttgcctaaga agaacatcta gggcgggcgt ggcggctcac gcctgtaatc   25260
ccagcacttt gggaggccga ggcgggtgga tcacgaggtc aggagatcaa gaccatcctg   25320
gctaacacgg tgaaacccccg cctctacaaa aaatacaaaa aaattagctg ggcgtggtag   25380
cgggcgcctg tagtcccagc cccttgggaa gctgaggcag gagaatggcg tgaacccggg   25440
aggcggagct tgcagtgagc caatatcgcg ccactgcact ccagcctggg cgacagagcg   25500
agactccgtc tcaaaaaaaa aaaaagaag aacatctaaa cttgctcctc ttatgatgaa   25560
ccacatagac ataactagtg ttaatggggg tcagtggaag tcatcatgtt ctgaaaatcc   25620
attaaatgta catcattcta gtgtttaggt taatgctgtt aaattcctgt tactttaaga   25680
aagggttggc cgggcatggt ggctcacgcc tgtaaccccta accttgggga dacagagatg   25740
ggtggctcac ctgaggtcaa gagttcaaga ccagcctggg cagcatggta aaacccccatc   25800 tctgctaaaa ataaaaaaat tagctgggca tggtggcgca tgcctgtaat cccagctact   25860
ctggaggctg aggcatgaga attgcttgaa cccaggaggc agaggctgca gtgaaccgag   25920
atcatgccat tgcactccag cctgggcaac agagcgagac tccgtctcaa aaaaaagaa   25980 aaagagaaag aaaaggtttg gcattgcaac tatttctctt gaactgagtg acccagaatc   26040
agttgtcctt tgaattttag tatagtagca tagtctgagc tcagaagggc ttatgatag   26100 accctgtatg ttctgggagg caagaattga gttggtatta atatcttaat gcttttgttt   26160
tactgctgaa taacagatga cccttcaggt cttttcatgt tttccttttt catgtctccc   26220
tgcctaggat cctaggtgcc taattgccta cttaaactag tttagggaat cttggactga   26280
agccaaaaca tgtaaaatgc cctgaaggtt aggcaaaggg aagaagttgg gtagtatgaa   26340
agattaggtc acatcttgtt tatctcttga gttctataaa ttgagaatgt aaatttaata   26400
ctatgtctat ttttaaaatg tatttttattg ccatgaaaaa gtagcatgag acattggaat   26460
atggaatatc agcttcttca tttgggtcat ggggatcatg cttgaagacc taatgctctc   26520
tctaggtcta tctcagcatt gagcccctgg atgctgttgc gtggcttaga tgacttatac   26580 atgcttgtg gcatgattca tactaccttc taccttctgt gatacccttg ggtagttata   26640
ataggaccca ggttagagtg cttcttggtg gagccactgt agaactggga tttagatgca   26700
gccagggctg atgctcagct ggtgaacact ggtgtgcttg ttcctactgg tgatttacaa   26760
ccagtgtttc ttcttttttgg gcctgcatcc attttgattg ggtggtgtcc atgctgtatc   26820
tgtaataaaa tatttttgaa tgttaccgct ggatgcagcg tgagaaagat acctcctgaa   26880
acttactgta agaaatttac agtgcattga tttttctgat atataggaat cgtcatgttg   26940
accttggaat tcttaagttc cctggctgta ggaaatggaa attttgtag tatgtcacca   27000 ttgttagctt atttggtatt gcggattttc cctgttgcag gactgggtga agctttttc   27060 tgcagcagtc atgttgaaaa ccttgtgttg actttcctcg tgttctgaaa tgggagcata   27120
aaagtttact ccgccacttc gtcttaaaat agcaaaactt tgctgttttc tgcagatcta   27180
ggaccttgtt acagaactct gccaaaaaaa aaatgtttac agaagaatgt gctgtgatta   27240
gagaagaata tgctggtgtg tagatttcaa actctctgga caatatgaat aacactgtct   27300
ttgtttctac agtgggagcc aagaagaaag gtttgctccc gggtggaaca gggattatcc   27360
tcctcctccc cttaagagtc atgctcaaga gagacactct ggcaactttc ctggcagaga   27420
ttcacttccc tttgatttcc aggggcattc ggggcctcct tttgcaaatg tagaggagca   27480
ttctttcagc tatggagcta gagacggacc gcatggtgac tatcgaggag gggagggacc   27540
```

```
tggacatgat ttcaggggqq gagattttc gtcttctgat ttccagagca gagattcatc    27600
acagttggac ttcaggggta gggacataca ttctggggat tttcgggata gagaaggacc    27660
acctatggac tatagggggtg gagatggtac ttctatggat tatagaggta gggaggcacc   27720
tcatatgaac tacagagaca gggatgctca cgctgttgac ttcagaggta gggatgctcc    27780
tccatctgac ttcaggggcc ggggcactta tgatttagat tttagaggcc gggatggatc    27840
ccatgcagat tttaggggaa gggatttatc agatttggat tttagggcca gagaacagtc    27900
ccgttctgat tttaggaata gagatgtatc tgatttggac tttagagaca aagacggaac    27960
acaagtagac tttagaggcc gaggttcagg tactactgat ctagacttta gggacaggga    28020
tacgccacat tcagatttca gaggtagaca ccgatctagg actgatcagg attttagggg    28080
cagagagatg ggatcttgta tggaatttaa agatagggag atgcccctg tggatccaaa     28140 tatttggat tacattcagc cctctacaca agatagagaa cattctggta tgaatgtgaa      28200
caggagagaa gaatccacac atgaccatac gatagaaagg cctgcttttg gcattcagaa    28260
gggagaattt gagcattcag aaacaagaga aggagaaaca caaggtgtag cctttgaaca    28320
tgagtctcca gcagactttc agaacagcca aagtccagtt caagaccaag ataagtcaca    28380
gctttctgga cgtgaagagc agagttcaga tgctggtctg tttaaagaag aaggcggtct    28440
ggactttctt gggcggcaag acaccgatta cagaagcatg gagtaccgtg atgtggatca    28500
taggctgcca ggaagccaga tgtttggcta tggccagagc aagtcttttc cagagggcaa    28560
aactgcccga gatgcccaac gggaccttca ggtatgttga tggggtggat tgcttttttt    28620
tttttttttt ttttttttttt tgagacggag tctcgctctg ttgcccagcc tggagtgcag    28680
tggtgcgatc tctgctcatg caagctccgc ctcctgggtt catgccattc tcctgcctca    28740
gcctcctgag tagctgggac tgactacagg cgcccaccac cacgcctggt gtgagccacc    28800
gcgcccggcc tgctttttt tttttctttt aaataagact tttgtgaagg atgacattta     28860
tttatttatt tatttattta tttttgaaac ggagtcttgc tctgtcaccc aggctagagt    28920
gcagtgacat aatctcagct cactgcaacc tccgcctccc agggtcaagc aattttcctg    28980
cctcaacctc ctgagtagca gggattgcag gcatgtgcca ccatgcccag ttaattttg     29040 tatttttagt gcagatgggg tttcaccatg ttggccaggc tggtctcgaa ctcctgacct    29100
cgtgatccgc ccacctcggc ctcccaaagt gctggaatta caggcatgag ccaccgtgcc    29160
tggccagttt ttttttttt ttttcatttt attttatct ttgcataacc attagaaagc      29220
aaaatttgta ttcaggagtg gaatgtagga atgtaaatct ctagagaaaa ggtcctcagc    29280
tcagatcata tatgtgtg tgtgtgtgta tatatatata tgaatatata tgtatatata      29340
tgaatatata tttatatata tatatttctt ttttcttttta ttcttttctt cctgcttcac   29400
tttccatttg tgtatatatg tgtgtgtata tatgaaggaa ctatatatat atatatttga    29460
gacacggtct tgctctgtca ctcgggctga agtgcggtgg tgtaattatg gctccttgca    29520
gccttgacct cccaggctca agcgatcctc ccacctcagc cttctgagta gctggaacta    29580
cagatgtgcg ccagccacta tgcctggcta gttttttttt ttttcctttg agaatgagtc    29640
ttgctctgtc gctcaggctg aagtgcagtt gtgcgatctc agctcactgc aacctctacc    29700
tcctgggttc aaggggttcc cccgcctcag ccttccagga agctgggact acaggtatat    29760
ttcaccattc ctagttagtt gtgttttttt ttttctttt tgagatggag cctcaccgtg     29820
ttgcctaggc tggagtgcag tggcacgatc ttggctcaca gcaacctccg cctcccgtgt    29880
tcaagcagtc ttcctgcctc agcctcctga gtagttggga ctgtagttgt gcaccaccaa    29940
```

```
atctgactaa ttttttgtatt ttttgtagag atgaagttta ggcatgttac ctaggctggg    30000
ctggaacccc tgatctcaaa tgatccaccc ttctcagctt cccaaagagc tgggatttca    30060
ggcatgcacc accatgcctg gccagcaatt tttgtatttt tttgtagaca gaaggttgca    30120
acatatttcc caggctggtt tcaaattcct gggttcaagc agtcccccca ccttagcttc    30180
ccaaagtgct gggattacag caatgagcca ctgcccctac cctttttgatg tgtgtttatt    30240
cattattttg ttttatgatg ctgatttaca tgccttggga taatttagtt tgaaagtata    30300
tgtctttggg agttgactct tgcaactctc gcttagttag acctgtgatt gtttagggat    30360
catttttctta tttaaattca ttgagagaat acttaggagt ctccctagtt gtgaagagct    30420
gatattaatg ttgcaactat cctcttgcag ctaacgtaat taacttaaat gttaaacttc    30480
ttgaatatat gatttaagca aggagggtta tatttgtaat tttacaatga aggtattctc    30540
ttttaaagta gatttggctg ggtacagtgg cctatgcttg taatttcagt gctttaggag    30600
gctgaggtgg gaggatcact tgaggccagg aacttgagac cagtgtggtg caacctcagg    30660
agagaatgtg agggtgggga agaaaaataa ggccaggcac agtggctcat gcctgtaatc    30720
ccaacacttt gggaggcaaa ggtgggcaga tcatttgagg tcaggatttc aagaccagcc    30780
tggtcaacat ggtgaaaccc catctctact aaaaataaca aaaattaggc caggcgtggt    30840
ggttcttgcc tgtaatccca cactttggg aagctgaggc aggtggatca tttgaggtcg    30900
tgggtttgag accagcctga ccaacacgga gaaacccccat ttctactaaa aatacaaaat    30960
tagctgggcg tagtgatgca tgtgtgtaat cccagctact cgggaggctg aggcaggaga    31020
atcccttgaa cctgggaggc agaggttgcg gggaggcaga ggttgcacta ttacactcca    31080
gcctgggcag caagagcgaa actccatctg aaaaaaaaaa aaaaaacgaa aaccaaaacc    31140
agccaggtgt ggaggtgggc gcctgtaatc ccaactactt ggggaggctga ggcaggagaa    31200
ttgcttgaac ctgggggggcg gaggctgcag tgggctgaga ttgtgccact gcactccagc    31260
ctgggcgaca gagcgacact ctgtctcaaa aaaaaaaga cattatctag tcatcttctc    31320
tcaccagagg tatgaagtac tgctagttta cagcccattc tccagctctc agaccaggga    31380
aattttctt tttttttgag acggggggtct cgctctgtca cccaggctgg agtgcagtgg    31440
cacaatcttg gctcactgaa acctctgcct cccaggttca agtgattctt ccgcctcagc    31500
ctcctgagta gctgggacca caggcgtgca cagcacagtt ggctaatttt tgtatttttta    31560
gtagagacgg ttttaccatg ttggctaggc tgagaaaatt actgttttga gactatgtta    31620
gtgtgtctttt ctggttatta aagtcttact cagtcttgtc tctcgtaatg ttttgcttta    31680
ctttgaagac tcttttcagtg agacttggtc ttagcacatt tacattctta tgatttgaag    31740
tcacattctg gcactcagaa caatagagaa aattgtaatt ttttatatct tcacgtgaca    31800
tgtcattatc attttttgatc ctgagtggct aaatttcatg ttgatttgtg ttttgtgcag    31860
taaagtatat ttgtgaaata atttttcatt ctcaatttaa ggatcaagat tataggaccg    31920
gcccaagtga ggagaaaccc agcaggctta ttcgattaag tggggtaccct gaagatgcca    31980
caaagaaga ggtaaggcat gtcttctctc ctgtttctct gtgtcaatta aaaattaaaa    32040
aaacctttta atttgaaaaa ttgtagattc acaagaaggt gcaaagaaat gcacagaaa    32100
gtccttgtgta ttttttttccc atcttccctc agtgttaata ttttgcacaa ctgtggtata    32160
gtatctaaac caggaaattg accctggtat aatacataaa gttattcag atttcaccat    32220
ttatacatgc actcactgag gtgaggttaa aaaaaattat gacaaatgat tgctctcttt    32280
```

```
agacctgatc acatccttta gagcatatta tttctggagt atgtacataa ggatgcagtt    32340
tatttacaat agtaaaaact agaaactgcc taactgccct gtatcaaagg attggctgac    32400
taaattaagt ctgaacttat ggcagtgctc gctctgtgcc aggcattgtg tgatacttac    32460
aagcattagt tcatttaatt atcacatatt taatataatc actctaaata ttaagcatta    32520
ctgtatgtaa ttgttctaga tactgagtga cacagcagtg tatattatca agtcactgcc    32580
tccatggata atgaaaaagc aagcaaaagg attacacaat tttagtcagc aaataaatac    32640
tctgaagaaa actaaagtac aggcggggca tggtagctcg gcctgtaact cggagacaga    32700
gtcttgcttt gtcgcccagg ctggagtgtg tggcgcgacc ttggtgcact gcaacctcca    32760
cctccccagt tcaagcagtt ctcctgccgc agcctcccga gtagctggga ctacaggcac    32820
acaccaccac gcccagctaa ttttttgtact tttagtagag acggagtttc accacattgg    32880
tcaggctggt cttgaactcc tgacctcagg ttatctccct gcttctgcct cccaaagtac    32940
tgccattaca ggcatgagcc accaagccca gcccattttt gattttttttg aggcagcgtc    33000 tcactttgtt gcccaggctg gagtgcagtg gcacaatcac ggctcactgc agcttctacc    33060
tcttgggctc aatcgatcct accacctcag cctcctgagt agctgggacc acgggcatgc    33120
atgctaatgg ggctgttttt tgtattgtgt agttagggag acatcactga ggaagaggca    33180
ttcgagccca ggcttgaatg ccgtgagaga acagtttata tgaatatggg gaaatgaact    33240
gcccaggcag ttcatgctga ggaagtgctg tggccctgga ctgtaatgaa cccagtacat    33300
cattttatat ttaacacatg agaaactgga cactaaaagg ttacacagca agtgagcaga    33360
gagcttggaa tgcacacagt atgatttcag agcttaagcc tttgaaggtt atgctcttct    33420
gcttttcttt ttttttttttt tttttgaga cagagtctca ctctgtcacc caggctggag    33480
tgcagtggcg cgatctcggc tcactgcaac ctctgccgcc agggttcaag agattctcct    33540
gcctcagcct cccaagtagc tgggattaca agcacctgcc actgcaccca gctgattttt    33600 gtattttttag tagagatggg gtttcaccat cttggtcagg ctgatcttga actcctgacc    33660
tcaagtgatc cacccgcctc ggcctctcaa agtgctgaga ttacacgcat gagccaccgc    33720
gcccagcatt ttgtttgttt gttttgtttgt ttgttttttga cagagtctt tgctctgtca    33780 cccaggctgg agtgcagtgg cacaatcttg gtcactgca acctccgcct ctcgggttca    33840
aatggttctc ctgcctcagc ctcctgagta gctgggacta caggcatgtg ccaccacgcc    33900
cggctaagtt tttgtatttt tagtagagac ggggtttcac cgtgttagct aggatggtct    33960
cgatcccctg acgtcatgat ccgcctgtct cggcctccca aagtgctagg attacagatg    34020
tgagccaccg cttctggccc tgcttttcct atgtacctga gaatttttaa atatttattt    34080 atttatttttt gagacagggt actccagact ggagtgcaat ggcccaatca aggctcacta    34140
cagcctcaaa ctcctgggct caaactatcc tcccgagtag ctgggattat aggtgtgagc    34200
cagtactcct ggctaatttt tttttttttt ttgagatgga gtctcgctct gttgcccagg    34260
ctggaatgca gtggtgcgat cttggctcac tgcaagctcc ttctcccggg ttcacgccat    34320
tcttctgcct cagcctccca agtagctggg actacaggtg cccgccacca cgcctggcta    34380
atttcttgta ttttttagta gaaacggggt ttaccgtgt tagccaggat ggtctcaatc    34440
tcctgacctt gtgatctgcc cacctcggcc tcccaaagtg ctgggattac aggcgtgagc    34500
caccgtgccc ggccaattttt ttttttttt tttttttttt tttttaaag atagtgtctc    34560 gctctgttgc ccaggctgga gtgcagtgtc atgatctcag ctcactgcag cctcagcctt    34620
ccaggttcaa gtgattctcc tgcctcagcc ttccaagtag ctgggattac aggtgtgtgc    34680
```

```
caccacacca ggctaatttt tgtattttta gtagaaatgg ggtttcacca tgttagccag    34740
gctggtctcg aactcctgac ctcaggttat ccacccgcct tggattccca aagtgctggg    34800
attacatgtg tgagccacca cgcccggtct ctcctggcta attaagaatt tttttttttt    34860
ttttagagat agggtctcac tatgttgccc aggcttgtct caaacatgtg ctttaagca     34920 atcctctcac cttggcctcc caaagtgctg ggattatagg caggagccac tgcatcccac    34980 caattttttga ataattatgt tctactcatt caatatgtga atgccttgag tgttcatagt   35040
ttaactttgc ttttccaaag taatcatggc tttaaattat gtatgataaa aactgttagg    35100
gaaaatctga tattcagtgt ttgattatga tttgtatcat ttgtataaat gccatatttt    35160
tgcagattct taatgctttt cggactcctg atggcatgcc tgtaaagaac ttgcagttga    35220
aggagtataa cacaggtgag tttcttgact tgcatatggc cttgggttag aagggtctt    35280 tgtcagatct ctgcatcatg tgctacttaa aatttgtttc aagaaaccac aattaaaatt   35340
tccagaagcc tcccgttggt gcctccaaat aacaaccagc tttagtttta gctgtggttc    35400
tttgtggatg tttgtccaca catgggtgat gaggatgcat gttccagttc ttctgaatgc    35460
ctgtgatata tagagtgttg cagcaattgc cttgaatata ttttatataa ttattaaact    35520
tgctatgcat gttcttcatg gtggtggaat gtttatgctt gagcctaata ggatttaata    35580
agcttgttgt atgtaaaatt ttacattcat tgcttcagta aaatttatga cttcccagag    35640
aaattgtaca aattagtggt ttaattttca gttttgcttt gagaatggag tcctgttaca    35700
gttattttgt tgaaatccat gaatagaccc agaagagctt tcccttttgac atctgttctg   35760 tggtctgaat ggtagattaa acttttcaga atatcctcct agttgtattt cacagtacca    35820
atttcagtca tttcctttaa atcttactac agtaaaagta ggcaaaggtg aaatgccaag    35880
aactcaaggt ttttgaccaa tatttttaga actatgtata ataataagtt tatttattta    35940
aaaataaagg taatctttag gtgacctatt ttgcagaatt ttaaatggaa gggaatagag    36000
catgagtctt cacagaactt agaatttcag taattcagtt aaagacatct tcaagtaaga    36060
acatgtcata ttttgaggat ataatttact attagcagtt tatcatggga taaaaatttt    36120
gcattaacta gataacttct tcagaatgct tctgcagagg aaaattatcc acaaaataaa    36180
ttttggtgct tgaaagaata tggtgttaag ttcagaaata atttgttctg taatttgaga    36240
acaagctcag aagtattatt tctcagagag ccaattattt atttgtttta aaaacatcaa    36300
ccctgaattt gtggaagcat gagtaagagt agatatatta ttattcttgg tatctcactt    36360
atgttggtta tatttatttt ttgcatatgc cttatacatg ctttctttgg gaactcaagg    36420
tagaatttac aggctggaga tgcttttttaa ctctcaggat aataacctca gtctggtttc    36480
atgaactgtg ctttcattaa gtattgatat gtttaggaaa ggagatgtct taatatttaa    36540
atagcagttc aaactccagt ttctttagta ttcattgact ttctaattgt caaatttgtc    36600
aggacagtaa aaattgtatt aacatatagt gtctagagag gaagttctta aatttgccga    36660
ttgtggtagc tgttagaatt ggcagactga agacattgat acacatggga aatcattcag    36720
ggcagtgctt aaaaataaaa cgaaaaatac ctttcagcaa atacaatctt ttcttggcat    36780
tctgttaagt tgtgtttttt attttttgttt tttagtgaaa gaattggatt gctagtttca    36840
tgttatttat attacatctc tatgtgacaa ataggatgaa cttttgacaa tatcagccag    36900
atcatgttac tccatgtctc aaaccctct tagggccttc atcttcactt ggaagaaatt     36960
cccagcttct tcttttgtct tacaaaccca tgcgtgagct gacccttggc tgtttgatct    37020
```

```
cattcagtac tgccctccac ctaccctatt ttgctgtagc cacactgagc tttttctcttg    37080 tctttgacca atacaaactt ctttctgtgt cagggtcttt gcactactct tctctctgat    37140
ctttacttgt cttctggggt ttagttcttg gcttcagttt cacgtctctg aggccttgtg    37200
tcactctcaa atctaaaatc atcgggcagt tgttttccat catatccttg tttggatcta    37260
tcactgattg gatatttcta tcactggtat ttttcagttg gatctatcac tgatctatca    37320
ctggtcactg attggattga atctgtcagt ggtattggat ctatcactga tattttctc     37380 cgtggttttg tgtatcttat ttctctcact agagaggaat gtcagcagga gccttattcc    37440
ttcttgtttc caccagtgct tgacactcgg taggttccct atatgcatgg aatagattat    37500
tatttatggt gtatgtgaag agcagctgtg atttcccctc aggtgaggaa cataaaaggg    37560
tagtgtaggt tcacagcag tgcagcttag gtcttacata tctgttgaag aatatgtctt    37620
ggaacaatca gatgttctaa gaactatagt gtttactgtt aaaagatcat atgtggtagt    37680
caggcatggt gttgcacacc tgtagtccta gctacttggg agtctgagat gggagaattt    37740
tttgagcctg agaatttgag atcagcctga gcaacatagc aagaccttgt ctcttaaaaa    37800 gaaaagaaa aaaaaatgtg aatcttagta gtaacagtga cttaaaaatt tttttttata    37860
agagaaaggg tcttactctg ttgcccaggt tggagtgcat tggtacgatc atagcttact    37920
gtaacctcaa acccctcggc tcaagtgatc cttctgtctc aacctccaga gtatttggga    37980
ctacaggtgc gtaccaccat ggcaggctaa ttttttaaact ttttgtagag gcgcggtctc    38040
actatgtttc ccaggctggt cttgaactcc tgggttcaag tgattctcct gcctcatcct    38100
cccacagtgc tgggattaca gatgtgaacc agtatgcaca gacaaaaagg tgacattcat    38160
aggtgaaaac tggtaataaa tattttaggc tgagtgatga cctgcagaga ccatgcagga    38220
tggatattgc tcataagagg ggaattgtgg agtacagtct gtcctgttag ttgatgtaat    38280
ggagggctga tctataacac aggagagaag attaacgcct cttcgttgac tctagtaatg    38340
tattagtgta atttttgtct cctctagagc tgtataagta cagggtcaca atttttatcta    38400 gaacctgtga ggttaaatga gcttatgaat ttttcaagtt atagaaatgt agtttacata    38460
gatcatatgg gaattatatc tcccaggga atgtgtactc agacataata cttacgctgc    38520
aaaattatta atattctcac taacaggagt aaataaagtc tcacagtata ggccaggatt    38580
tgcctcaaaa tgagtttgtt gaattttacc aaaaaacttg acatttatgg gattttggaa    38640
ttgtagataa gagattttgg acctatatat gttgtgtata tttgaatttt tcatttgcca    38700
tttacaaata cattataacc ccatgaattg taaattatct tgaattatat gattatttct    38760 ggaaaagta ccaggagtaa aatgtctttt ggtgactaga caaactctag tatatatata     38820
aaatggaata cttctcagca atgaagaaga aactactcat gcacctaaca acatggatga    38880
atctcaatgg caatatgctg agtgaaagaa actagactca taaggatata tacactacca    38940
taaggaggaa tgaaatactg atgtatgcta caagttggat gaaccttgaa aacattataa    39000
aagaagccag acacaaaaga ccaaatattg tgcaattcag tttatatgaa atatctagag    39060
aaggcacacc cgtagagata gaaagcagat tggtggttgc caggggctaa gcgggaatgg    39120
ggaacgactc cctaatggtt atggtacttc ttttgggctg atagaagtgt tctggaacta    39180
ggtagtagtg atggttgcat gacattgtga atgtacttaa tgctcctgaa ttgtacactt    39240
taaaatgatg cattttattt gatgtgtatt tgcttacttt gttttttttt tttttttttg    39300
agatgaaatc ttgctcccgt tgtgtaggca ggagtgcagt ggcatgacct cggctcactg    39360
caacctccat ctcccgggtt caaacgattc tccttcctca gcctcccaag taactgggat    39420
```

```
tacaggtgtg tgccaccaca cctggctaat tttttgtatt tttagtagag acggggtttc    39480
gccatgttgg ccaggctggt cttgaactcc cgacctcagg ttatctacct gcctgggcct    39540
cccaaagagc tagcattaca ggagtgagcc actgtgccca gccagcttac aattttttaa    39600
aaaggctaca tactatatgt gtatgtgtga tttcacttat gtgacattct ggaagggaca    39660
aaattttagg gattggaaat agtggtggcc agggtattgg gggaggagtt aactataaag    39720
cggaagcatg agggaatttt tgggtataat ggaattgttc tatatcttga ttgtggtgat    39780
gatgtatcaa tgttaaattc cccgagttga taactactgt ggttatgtta gagaacatct    39840 ttttctttt cttttttttt ttaaacggag tctcgtttgg tcacccaagc tggagcgtaa    39900
tggcgcgatc tcagcttact gcaacctctg cctcctggat tcaagcaatt ctgcctgcct    39960
taacttcctg agtagctggg attacaggcg cctgccccta ctcctagcta attttgtat    40020 tttttttagt agcgacaggg ttgcgccatg ttgaccaggc tggtcttgaa cacctgacct    40080
caggtgatct gcccaccttg gcctcccaaa gtgctggaat tacagacgtg agccaccatg    40140
cccggctgag agtatcttta ttcttagaaa atacataatg aagtttttag aagtaaagta    40200
ctgtgatgta tgcagctttc tctcatggtt tcgaaaataa tacttgctat aaatggagaa    40260
ggaaggaaga gagtattgat aaagtagatg gatcacaatg ttattaatag ttgaatctgg    40320
ggccacacgc ggtggctcac gcctgtaatc ccagcacttt gggaggccaa ggcaggtaga    40380
tcatctgagg tcaggagttt gagaccagcc tggccaacat ggcgaacgaa acctgtctac    40440
taaaaaatac aaaaattagc cgggcgtggt ggcgggtgcc tgtaatccca gctactcggg    40500
aggctaaggc aggagaatca cttgaactcg ggaggcggag gttgcagtga gccaagatca    40560
cgccattgca ctccagcctg ggcgacagag caagaattca tcttaaaaaa aaaaaaaaa    40620 aaagttgaac ctgggtaaag catatatgaa tcttttccct gtactattat tattgcaatt    40680
tttttgtaac ttggaaatta tttccaataa aaagttgaaa aactgacaaa actgatttat    40740 tttatttttat tttttatttt tttgagacgg agtcttgcac tgtcaccagt gctggagtgc    40800
agtggcgcga tatcggctca ctgcaacctc cgcctcctgg gttcaagcga ttctcctgcc    40860
tcagccatcg gagtagctgg gattataggc gcctgccacc atgcccagct aatttttgt    40920 attttttagt agagacgggg tttcaccatg ttggccagcc tggtctcaaa ctgacctcat    40980
gattcgtcca cctctgcctc ccaaagtgct gggattacag gcatgagcca ctgcgtccgg    41040
cctatatttt atctttaaat gatcagcaga aaccttgtaa gctgaagact gcaatcaaca    41100
gcttatgtca agtaaactat agagcagtgg ttctcagagt ggatcctgga ccatcatcat    41160
ctctttaccc cttgggaact tgttggaatc caaattctta agccccatcc taaacctact    41220
gaatcagaaa ctctggggtg gggcccagta gcctgtgctt ttaagaagtc ctccagatat    41280
ttttaatgta ccctgaggac cactggcagt agataaagtg tttgtttaga ttctttattc    41340
tagaactttt gtatagttta aaagtgactt aataataagc aagtggacct tttgtaagta    41400
gacaaagcta atgcttatgt gctttaggag ccagtgctga tcacatgcct tgcctaccta    41460
atatcagttc tcctgctctg catagcagga gaaggagctg gagtagtgtt ggtactatct    41520
tatgacttta gttatatgta actaaggaca tataacttag ttgttttttc tgtttatata    41580
tagtatactt cctccagaga tcttggaatg gttgtagatc ttctcattca cacagtgttt    41640
ctgtgacata tgaatgcagg cagaattgct tttgattttt aggtttgttt gcatactacg    41700
tagtatataa gcttgctgtg atattttcc aaaagggatt tatatcattt aagcaaaaat    41760
```

```
gatacagctt ctggattatg tttcctaata aggctcaaac atagaaagta attatagtaa   41820
ctgaagtgct acagaattac tttagtactg gtttattaac taatgtcaca aagttagagg   41880
attactaagg tggtgttagt aggaagaagc aatatcttgc tttagcccgt cagtgttcat   41940
gtggtgaatg gacagtctct gtattcttgg gaaggaaaat tcttcttgga aagtgagtat   42000
ttgcaatgac taggtcagtc acttggtctg ttgcctggca ttttgggtct actgaaagtg   42060
acgttgtagc aaaggccctg taccttctgc atttcttttc ttttcttttt tttttttttt   42120
tttttttttt tttggtagaa acaaggtctt gctttgttgc ccaggctgcc cttgacctcc   42180
tgtcaagcag tcctcccacc ttagcttcct gagtagctgg gactacaggc gtgtgccacc   42240
atgcctggtt aatgtaaatt tgtttggttt ttttgagaca gagtttcact cttgttgccc   42300
aggttggagt gcagtgacgt gatctcagct cactacagtc tctgcctcct gggttcaagc   42360
gattctcctg cctcagtctc ccaagtagct gggcttacag gcacccgcca ccacgcccag   42420 ctaattttt gtattttttt agtagagacg gggtttcatc atgttggcca ggctggtctt   42480
gaactcccga gctcaggtga tccacccacc tcggcctccc aaagtgctgg gattacaggt   42540
gtgagccacc gtgtctggcc tattttaaaa ttttttttga cagagtctc ctctcagtca   42600 cccaggctgg agtgcagtgg tgcaatctca gctcactgca gtctctgcct cctgagttca   42660
attctcctgc ctcagcctcc ctagtagctg ggattacagg cctgccatcg tgcccagcta   42720
atttttgtat tttagtaga cagggttt caccatgttg gccaggctgg tttcaatctc   42780
ctgacttcaa gcaatccacc tgcctcggcc tcccaaagtg ctgggattac aggcatgaac   42840
caccacgcct ggcctaaatt tttttttgt agagacaggg tctcacgctg ttgctcaggc   42900
tggtcttaca ctccaaggct caagcaatcc tcctgccttg actcccaaa atgctgagat   42960 tacaagtgta agacactgag gccagctgcc ctttacatt cttaagggta acaggctcat   43020
gtcctttcat tattcacaat ttaaatattt tgagtctttta cttctgtgtc aatataacag   43080
aagtaacttc cttacgaaga aaattccaga gggaatcttt caatgtaggg atagaaatcc   43140
attgtgaaac tcgagaattg acactgatga tataaaacat gcacagtagc cgagtgtggt   43200
gatgtgtgcg tgtagtctta gctactcaac agtccgagac atgagctcag gagttttgtga   43260 ccagcatggg caatatagtg agactctgtc tcaaaaaaag gaaaaaaaaa agtgcatagt   43320
ttatggtatc ccaactggag gagctaaaga cagaatagct taacatcatt tagaaaaaa   43380 attataattg aaaagtgcaa atacacattt tgcagtgttt ttggcatttta caaaatatgt   43440 aaacactttt agtttcttag ggaaaagatg acgataggct gattgaaaaa tatcattttt   43500
acttgtcaca tctctaaaac agcagaagtt cttgttttta accaggagtc ctatcaggtt   43560
tgatacaacc ttcggggagg atgtggcagt tgaaatttaa ggaaacttag tttccttaag   43620
gtggctgagc ttaaaaaatc aaaatgttta ggaaggcagg agacactaat agggctgggc   43680
tagtcttgtg gaggcagtgg atggacgctt tggctggcct agggaagaat ctgtgattca   43740
gtgctgcagg gatcaggtga tcctggtgag agaggtcctg gaacaagggt taatttggtc   43800 attttggaa tgacctggga tttggcttat ttattttatt tttaaaattt cccgctgggc   43860
acagtggctc aaacctgtaa ttccagcact ttggaacgcc aaggccagtg gatcactcga   43920
gctcaggagt tcgagaccac cctgggcaac atggtgaaac tctatctctc caaaaaaat   43980 acaaaaaaaa ttagctggat gtggtggtgc atgcttgtag tcccagctac ttaggaggct   44040
aaagcaggaa gatcacttga gctagggagg tgagggtgga ggttgcagtg agccaagatc   44100
atgccactgc actccagcat gggcaacaga gagagacctt gtctcaaaaa aataaaatgg   44160
```

```
tgaatgtaaa ataaaatggt agctcacgcc tataatcctg gtactttggg aggccgagat    44220
gggtggatca cttgaggcca ggagttacag accagcctgg tcaatatggc aaaactccca    44280
tctctactaa aaatacaaaa actagctggg ctggtggtgt atgcctataa tcccagttac    44340
tcaggaggct gaggcagagg tcacagtgag ctgagatcac accactgcac tccaggctgg    44400
atgacagagt gagaccctgt ctaacgtgac atcacatcac atcacatcac atcacatcgc    44460
atcgcatcgc atcgcatcgc atcgcatcgc atcgcatcgc atcgcattgc atcacatcac    44520
atcacaacat aacataaatt ttcaaggcag aaatcttgta gtcagcctta ctgtttgttg    44580
acaaggcacg ggccctgagc acagaaatct cggcagttga taaagccaag aagaaggata    44640
ctaattaaag aaattttcag attttgcatc ttctggcatc tcagctaaat agctctgagg    44700
aggaggatgc cacttaccag ttttgagaca caggcaggtt atattatttt cctgaaaacc    44760
atttagctga gatggaattt gcctctctga ggttgtgggaa ggtgtttgaa ctctgtttac    44820
agccctctgt cagttccact gccttgctga gttccctcac ccttctttag atagaattgc    44880
tgttggcttc tatagtcctc acttacctct tttgccaaat gctcaggtag ccttggctga    44940
gtcttccagg tttgataagg ctgtatgggg cttcctatgc cttttggtag ttagaagtca    45000
ctgaagaggt acttctgcta cagtgacaag aagaaaaggg cattactcag cttgtatagt    45060
gcaagggctg cttgactccc agcttcagtc taggcagggg aatttattta tacaattacc    45120
ttaaatgagc accagataga ggccatctat aaaaactgtt tacaggattt aaaaatacgt    45180
tgacattggc ttcttccttt aactttctgc ttgcaacaga acatctgatg cgacctatgc    45240
tgctcactgt ttctaggtta cattctctac ccttgcagtg taaattaatt tttgcctggt    45300
tccatgtttc ttgcttaggt tatctcttag gtcttttgtc tgatttaaat ataagccttc    45360
ttaggactag atagtggtga tggttgcact actttgtcaa tataccactg aattgtatgt    45420
attcactctt ttaagaatga gtttattttt atttttattt ttattttgag atagagcctc    45480
actctgtcgc ccaggctgga gtgcagtggc gtgatctcag ctcactgcaa cctccacctc    45540
ccgggttcac gccattctcc tgcctcagcc tcccgagtag ctgggactac aggcgcctgc    45600
caccacgccc ggctaatttt ttgtattttt agcagagacg gggtttcact gtgttagcca    45660
ggatggtctc gatctcctga ccttgtgatc cgcccacctc ggcctcccaa agtgctgggt    45720
ttacaggcgt gagccaccat gcctggcctt aagaatgagt tgattgttct tagtctcagt    45780
tgagtacatt tgttatgta tagaaaatgt tatattttca tttttaaaaa ttattattat    45840
tattttgaga tggggtctca ctttgtcacc caggctggag tgcagtggca cggtcttggt    45900
tcactggcaa cctccacctc ccaggtacaa gtgattcttc tgcatcagcc tcctgaatag    45960
cgggaattac aggcgcctgc caccaagcct aagtaatttt tgtatttttt ttttttagta    46020 gagacgggt ttcaccatgt tagccaggct gatcttaaac tcctgacctc aagtgatcca    46080
ttcgtctcag actcccaaag tgctgggatt acagatgtga gccattgcgc ccagcccatt    46140
ttaaaaaatt aaactggcct ggtgcggtgg ctcacgcgtg tgatcccagc actttgggag    46200
gccgaggcaa gcggatcatg aggtcaggag attgagacca tcctggctaa catggtgaaa    46260
ccccatctgt actaaaaaat acaaaaaatt agccgggcat ggtggcgggc tcctgtagtc    46320
ccagctaatt gggaggctga gacaggagaa tggcatgaac ccgggaggca gagcttgcag    46380
tgagccgaga tagcgccaat gcactccagc ctgggcaaca gagcaagact ccgtctcaaa    46440
aaaaaaaaaa aacaaaacaa aaaaaaacca aaacattaaa ccatactctc taactgtgaa    46500
```

```
gaagttgtga tttattctttt agtgttacct gccattctttt ttgtctcttt ctctctcttc  46560
tcttctcctc tcttctcttc tctcttcttc cctcccttcc cctcccctcc cctcccctcc cctccccttc  46620
tcttttcttc tcttctcttt tcttttcttt cagagttttg ctctgttgcc caggatggag  46680
tgcattggca tgctcacggc tcactgcagt gtcaacctcc caggttcaag ctgtcctcct  46740
acctcaccct ccctagtagc tgggactata gacatgcacc accatgccta attattttgt  46800
attttttgta gagacgaggt tttgccatgt tgcccaggct ggtcttgaac tcctgagctc  46860
aagtgagcta cctgcctcag cctcccaaaa tgctgtgatt acaggtgtga gccttatttt  46920
attattttttt tttgggacag agtctctctc tgtcctccag gctggagtgc agtggcacga  46980
tcttggctca ctgcaacctc tgcttctcgg gttcaagcaa ttctcctgcc tcagcctccc  47040
aagtagcctc ccaaagtgct gggattacag gcatgagcca ccatgccagg cctctgatgc  47100
atatattttt taaaaatagt attttccacc ttacagtgta tttaagagtt tgtaaatttc  47160
ctttttttgtt ttcttttttgg aacagtgttg ctctgttgcc caggctggag tgcagtgaca  47220
tgatcttggc tcattgcaac ctccacctcc cagattcaag tgattctcct gcctcagctt  47280
cccgagtagc tgggattaca ggtgcccgcc actacgccca gctaaatttt ttgtaatttt  47340
agtagagaca ggtttcacca tgttggccag gcaggtcttg atctcctgac ctcaagtgat  47400
ccgcccacct cgacctccca aagtcctggg attacggaca taagatactg tgcctggctg  47460
agtttgtaaa ttctctttctt tctttttttct ttttttttttg agacagagtc ttactctgtc  47520
acctgggcta gaatgcaata atgcgatctc tgctcactgc aacctctgcc tcctgggttc  47580
aaacaattcc cctgcctcag cctcctgagt agctgggatt acagccgcct gccactatgc  47640
ccagctaatt tttgtattttt ttgtagagat ggggttttgc cgtgtaggcc aggctggtct  47700
agaactcctg acttcaggtg atccacccac cttggcctcc caagcgtggg gattacaggt  47760
atgagccacc acgcccggtc atcaaagata atgttttttaa tgatcaggag cactttgaga  47820
tgtttagaac aatctgaaac ctgatttcca agccatctca aaatatactt tggtaatcaa  47880
gacagggaaa tgatggtgtt atatcatttg tgggactcaa ctgattttgt tgagtattga  47940
ttttgctgtg ggattccttg ttctcttggt tgtgttgggc ctactgctttt ttaaaaaagt  48000
attttgagac agggtcttac tctgttgctc aggctggagt gtagtggcgc agtctcttgt  48060
ctctgcaacc tcaatctcct gggctcaagg gatcctccca cctcagcctc ccaagtagct  48120
gggaccacag gtacccacca tcacacctgg ctaattttttg tatttttttgt agacatgggg  48180
gtcactgtct tgcccaggca ggtcttgaac tcctaagctc aaacaaccgt cctgccttgc  48240
cctcccaaat tgctggaatt acaggtgtga gccagtgcgc ctggccttct ttttttttttt  48300
taaccactat ttttttagaac tagatttggc ctggaaagag aaaaaagata ttcctcgact  48360
tgatctatat attttatggt tcattcattt gctttagagg tagaaggagc aggaaaaagt  48420
acaacaaaac aaaatcttac ctttggtgtt taatttgaat gcccacagat gcttttgcat  48480
ttattagtag tgagttttca taattatcaa atatgtagta gaaaaatctg gctgtgcatg  48540
gtggctaatg cctgtaaatc cctatatgct gggaggctga ggcaggtgga ttttctgagc  48600
tcaggagttc aagaccagcc tgggcaacat ggcaaacccc catctctgcc aaaaataagc  48660
tgggtgtggt ggcacacgcc tgtggtacca ggtactccgg aggctgagct gagaagattg  48720
tggaggtttc agtgagccaa gattgcacca ctgcactcca acctgggtga cagagtgaga  48780
ctccatctca aaaaaaagaa aaaaaatct ccttgtccag gagctgtgtt gagtgggctg  48840
tggactagca ggaattcata gctctggtga aagatgacta gataatgtca ttttttttttt  48900
```

```
aaaagtccct gaatgattgt gacagggtag gaaaatcatc acatagcaaa atcttcatta   48960
gattttccct aatgacttat caactgggtt tgtgcaccaa acgaaacaac ttcctgcctt   49020
tgtttgtctg aaagtcaaag aaaatattat tcaggtatat tatattgtac tccatgctac   49080
agaagtttct ggcagcaata taggttatat gccaatcggt taaataatat ttgtgggcca   49140
ggcccggtgg ctcatgcctg taatgccagc actttgggag gccgaggcgg gtggatcact   49200
tgaggtcagg agttcaagac cagccagggc aacatggtga acccccatct ctactaataa   49260
aacaaaaatt agcctagtgt ggtggcacac gcctgtaatc ccagctactc aggaggctga   49320
ggtaggagaa tcgcttgaac ccggaaggtg gaggttgcag ctgagattgt gccattgcac   49380
tctagcctgg ggccacaaga gtgaaactgt ctcaaaataa ataaataaat aaataaaata   49440
ataataatat ttgtgtaagt acagggatat gtttcttcaa ctccaaagta tgagttaatg   49500
tgcatatgcc aactctagaa ataaagtatt aagtcaaaac tcccaagaaa atttccccaa   49560
aaagttgcta acagacgtta ttttatttta tttatttatt ttgatacaga gtctctccca   49620
ctgtcaccca ggctggagtg gtgcagtggc atcatctcga ttcactgtag cctccgcctc   49680
ccagattcaa gccattctcg tgcctcagcc tcccttgtag ctgggattac agttgccac    49740 caccacgcct ggctgatttt tgtattttta gtagagatga ggtttcacca tgttggccac   49800
gctggtctcg aactcctgac ctcaagtgat ctgcccgcct tggcttccca aagtgctggg   49860
attacagttg tgagccactg cacctggcct ttaatttaa   tttctaaaac tatggagtaa   49920
tactacattg agggaacaga attttctatt ccttcatttg tattattatt aaatacagtc   49980
atgcattgca taatgacagg aatacatttt gagaaatgga tcaagtgatt ttttcattgt   50040
gtaaacatca tagggtatat ttacacaaac tagatgttat agcctactat acagctaggc   50100
tatattgtat agcctgttac tcttcggcca caaaactgta cagtgtgtta ctgtattgaa   50160
caccataggc aattgagaca caacggcatt tgtgtatcta aatatagaaa aggtaatgca   50220
ttgtgccacc aaatcaacaa cagctatgat gtcactgggt gataggaatt tttcagtgcc   50280
attataatct tatggaacca ttgtttcata tgcatgcagt ttgctgttga tcaaaatgta   50340
gttaagcagc acatggctgt aattaaaaca ctattgtttg ttataataga aaataaaatt   50400
tttcttttta gcctctgtat taataaagag cactagaaag tactttgttt atcagataat   50460
gaatatgttt gacagatgta catacgtatt tatcaaatga atcttttttt gtgggggaaa   50520
ccttaactaa gaataggcct gtgttttaaa atggctgcct ggaggacaag tgctataagg   50580
aaatttcagt ggtatttgct tgacctggca ttaagtgggg ggaaaaacaa gccccaggtg   50640
aattgataga tggatgtctg aacatgttca ggaatgatgt tttgaacaat gtttgcctcc   50700
tgtgtcatgt aggcagagag atgataaaag ttttttttccc ctcttgatac caggtaattc   50760
tgataccgac taccagaagt tagcttcaga ctccgcaggt tgaagggctt tgtcccataa   50820
gaccattctt acttcagaca ccaattgcaa tgatcagtta tcaggtccca aggttaccta   50880
cacttatgtc tgatttggct acaaaattgg aggttcccac agtctacccc ttcagatttg   50940
ataactttct aatatggctg caaaaaactc agagaaatac ttatgtttat cagttttta    51000 taaggatac  aattagccag atgaggagat agatagggca aagtccagga gggtcctgag   51060
tgttgagtgt aggagtctct gtcctgtgga atatgccacc gtcccagcat gtagatgtat   51120
tcaccaatca ggaagctctc tgagcccttt tgtgtagttg ttttttatgga ggtctcatta   51180 tgtaggcagg attgattaaa tcattgacag tgggtgattt gctcaagccc ctctcccctc   51240
```

```
atcagaagtt ggtgggtggt actgaaagtt ctgaacttct ggtcaaggct ttgtctttct    51300
aggtagccct catcctgaag ctatctaggg gctttccaag agttgtctta ttagaacaaa    51360
gaacactcct atcaccctta tcactcagga aattccaagg gttttaggag ctgtatgcca    51420
ggaacctggg acagaccaag tatctttctg tgataccaca gaatgggacc ccaaaagcca    51480
gctccagctg gtgtctagtg cctttagttg ggcactggat atcggttaca gggcataagt    51540
ggcccagtgg ggttgccgtt taacccatct ctgctgtatt aacctcatgt acctcagctc    51600
atggctaggt cgtttcaagt ctcacctaat gtcagttgtt tcatccttct ctggatgcat    51660
gttcacttct ggaataggtg aatatctggg ccactatgtt tgctgtcatc ctgagcaaac    51720
ttccagctta gaaaccagct ttatggaatc atcccagagc ctttatttta ttttatttta    51780
ttttatttta tttatttatt tatttatttt ttgaggcaga gtcttgctct gtagcccagg    51840
ctgaaatgca gtggcaaagt catggctcac tgcagcttca acctcccagg ctcaagcaat    51900
ccttccgttt cagcctccca gtagctgagg attacaggtg tgtaccacga cacctggctg    51960
atttaaaacc ttttgtagag atagtgtccc agtgtgtttg cccaggctgg tctcagactc    52020
ctggggttaa gcgatcctct tgcctcagcc tcccaaaatg ttgggattac gggcgtgagc    52080
cactgaactt ggtcccagag cctttttagaa cagtgttgag ttgcccttta tttgcaccag    52140
ggctaaggca gtagaaaaaa aatgtttatg ggccatgttt ttcttcctag tcaaaataaa    52200
aatagccatg taatctatgg aggcagcaga tatgttgtta gtatacacta gaagtcagga    52260
aattcgtact gccttttcagc tgctaaagta ctgggacata tttgagaagc agtaatgcag    52320
aggcagctgt ctgatctttg atctctgata atgcttattt cattgcatcc ctgaaaccac    52380
cctgcaaagg atttatcatc tttgctgctt tgcatatgga ataagcatagg cccagagaga    52440 cgtagcttga ctgcaatcac atggtgagtt agttgtagct tctgcaaatg tacagaacta    52500
agaagctact tttcttgtgt gttattctag tgatgatggt cattataatt gatgtacctg    52560
atattatgct aggtttaggg atacagaaat gaaagaagat cacagtccct catctgggac    52620
ctctgttttt ttggtgtcac ctctctgcat agacagttct gcagtattga tgctgctgtt    52680
ctggttgatc cttctgtcat gcctgcacca tcttttctgc cagactgaag tgttcttgct    52740
tggggaaaag cagatttgca aaggttctct tttttcctgat tgttgctttg cagattgagt    52800
atatttgttt gtttgttttt aagtgaacaa aagttgaatg agattgatta ctggctcttt    52860
aaagaataat tactccccct tttgacttat gtagcatctt gaggtgatct atgaccgttt    52920
gtacttgtca tgacttccat tagattaaac tctggggcaa agacgttgct cttcattgtg    52980
ctcatatgac accattactg ccagtggaat tgaaataaat tgagtaaggg cgagtgtttc    53040
ctaacaaatg ttatcctggg cctgaggaac catcatcaag atggagtggc cctgcgatta    53100
attttggact taaagcaaaa aacaaacaaa ttttttttctt taaataacca gttggcacag    53160
atacagaata aaataagata gatccacgtg tagtttttga aaatttaggt caggtggctc    53220
actcctataa tcccagcact ttgggaggcc aaggcgtgtg gataactcga ggttaggagt    53280
ttaagaccag tctggccatc atgatgaaac cccatctcta ctaaaagtac aaaaattagc    53340
tgggcatggt ggcgcatgcc tgtaaaccta gctactcagg aggctaaggc aggagaattg    53400
cttgaacctg gtaggcggta gttgcaatga gccgagattg cgccactgca ctccagcctg    53460
ggtgacagag tgagactctg tctcaaaaga aaaaaaaatt taagaaataa tcatcagtgt    53520
atatcttcct tttttcattt ttctttaaaa aaaaaaacaa cccttgtatg catagctgaa    53580
ggagaaataa ttgaaagtgt ttataagatt tcaaggtgat gggctggaca cagttgctca    53640
```

| | |
|---|---|
| tgcctaataa tctgcacgcc tgtaatccca gctattcggg agcctgaggc aggagaatca | 53700 |
| cttgaaccca ggaggcagag gttgcagtgg gccgagatat tgccattgca ctctagcctg | 53760 |
| ggcgacaaag gtgaaactcc atctcaaata aaaaaaaaga tttcaaggtg atgggtttca | 53820 |
| tgtggaccaa ttttatcctt ccctgatgat aatttgacat atgagtcaga tattttccta | 53880 |
| attttcgtaa ttcgagtggg attgtgtgtt tgtttgtttg ttttgagaca gggtctcact | 53940 |
| ctgttgttca ggctggagtg cagtaggcca gtcatggctc actgtagcct ggcttctca | 54000 |
| ggctcaagtg agcctcccac ctcagcctct taagtagctg ggactatagg tgcgtgctcc | 54060 |
| cacacctggc taatttttc tgtttttttt tgtagagaca aggtctcatt atattgccga | 54120 |
| ggctgggact cctgagctca agtaatcctc ctaccttggt ctcctaaagt gctgggatta | 54180 |
| tatccacgag ccaccacacc cagcctcgca tgagatttta acagagcaaa gtacctgttg | 54240 |
| gaaatcttgc gcacaaagcc tcctttattc tgttattccc actgacagga attcagatac | 54300 |
| ctggatcaat tctgtttcgg ttttgctaaa atctctaact tgatatttta cttttctaaa | 54360 |
| aacctgtatt atcaatgaaa tggaattagg aaaacaggac ctatagaagt taagacctct | 54420 |
| tcaatctatt gatgtttcat ggtgcctttt atattcaaaa tgctttgttc tcacaaaaat | 54480 |
| aatactttt gtttggagaa aaaggctgtg gggtgtgtgt gtgtgtgtgt gtgtgtgttt | 54540 |
| tcctctcaaa gatagcagta aaataaactc cttctgacaa aggcttctta aagaaagga | 54600 |
| gaaaaaaaa ccttcctgct aattgtgttc tttaaaatcc tgattccccg ttttactttc | 54660 |
| tggatgtgta ttctgggctt tttcaatgtc aaccaatact ctcttgatgg gaaattcagc | 54720 |
| tggatttggg tatgttcatt gggttttcct agaacagttt gaagatccat ctcatttacc | 54780 |
| taaacaaata ttccttataa ttattatgaa aattgggcct gttatagact aataattgac | 54840 |
| ttaaaccata cagggttatg tttgtcagta tctcgtgagt cagcttttct aggggcagag | 54900 |
| attgaagagt tagttctgag attgaatact atttatcagg gttttgtttt gtgtaccta | 54960 |
| ttctcctgta accacctggt tggcttttat catagataca ttttgggaa acaggcaacc | 55020 |
| acatggttaa tgaagataga gaagacgtga aatttgttac ctttatagat tttttcccct | 55080 |
| tgccctgttc tcattcttct catttgccta aaaaaaaata taaggaggcc gggtgcggtg | 55140 |
| gctcacgcct gtaatcccag cactgaggca ggcagatcac ctgagctcag gagttcgaga | 55200 |
| ccagcctggc caacgtggcg aaactccgtc tctactgaaa atacaaaaat tagccgggcg | 55260 |
| tggtagtccc agctactgca ggtacctgag gcaggagaat tgcttgagcc tgagaggcag | 55320 |
| aggttgcaat gagccgagat tgtgtgccat tgcattccag cctgggtgac aaagcaagac | 55380 |
| tctgtctcaa aaaaaaaaa aaaagtataa ggagtattca catttctatg agatctgtaa | 55440 |
| atttaggtta gaaaatttag ttaactgtgt tttgtaatag tcatataaat aagcacaaag | 55500 |
| accctccaga cttcttccca gcatgtgaca gtggaagaaa ggggtaataa agtagatttt | 55560 |
| tttgttactc tcattggtaa aaataagtct gtccatggga aggttaacac tgagtttacc | 55620 |
| atcttgatga ttccatatgg ttcctagcaa ttctaatctc aaagttggtt ggcagaatgt | 55680 |
| ttaggtcttt gggtagaata tcttctgtgc cttttctgtg aattgtaaaa ttacatttgg | 55740 |
| gaaataaaga aaaaatccc tgattatccc actatagcaa tacaaccact gtaaacattt | 55800 |
| tggtatacag ttgtgttgca ttatatgcat tttctgattt ttgtatgtcc acctgtgctt | 55860 |
| atttgaactg tatcccccctc cccacttccc acaccctgtt ttctcactcc tggagtgagc | 55920 |
| atgggcagtg gggatgagac tcgcctgtgg cttcagtttg tctccttttc taagtttctc | 55980 |

```
tgagtgggca ttcactgtgc tggctgtgat tctgttatttt aaagcaatat attttcatac   56040
cttatggccc ttaaatgcaa gccaacctct tcatctggtg tcaaccaaag gaaaagtgat   56100
ctgttgcagc gctggaggaa aaactggcaa tgttggactt acctaaattg aaagatggta   56160
tgttgttctt caccttgggg tcttcaagta tgattttga cagtgcatgg tttttatctt   56220
acatgctgac ttttgtctct aacccttgag ttagatgcaa tttaattcca gccctttttc   56280
cctatataca ttttacataa ttatccataa gggtatattc attttaagg ctcttaaaat    56340 atactatatc aagtatcttt ccatattgct atacaattt tgtagctgtc atttataata    56400 agacattta gttttcgtct tttcagaaga attttgggag ctagtataat cagctcctta    56460
gaatgctttc taatttgcat actcaggtct actcacaata gttctgccat agatatttaa   56520
aatagaagca actgttatgc tgctaaattg aatatttctt aactaggctt atttcttaac   56580
aggggcatag atgtatgttt tcaggcatat gggacccttt ctgtaactag gcttctagag   56640
tttagaatta agattattta aattggtcta tgatcttatt gaagagtgag aggctagagt   56700
gtagtggtta aaaacatcaa cttgaatctg gactgcttgc atttaaagct cagtattggt   56760
acttacttgg ttactttgat cagtttacct atcctttctt tgccgccttc tacatggcta   56820
aaatcaggtt aataatattt acctcttaag atagtattgt gaatattaaa tcagtatata   56880
caaagtattt agaataaaat cttgaaccaa caagtttat gtaaatatta cttactttca    56940
taggctagtt tgctaattgc tgaaaatcct tatggcacaa ccatgagtct tgaacacaca   57000 gaatacctttt tttttttta acgttttagg cagtatagtt aaaccttaaa tttctgttct    57060
tgtttgatag ctaaagtttc agtcagaata aatttagtgt tgggcttgtg aatataatat   57120
taaatctgaa gtatgttgtc aacatatagt attgcagggt tgatgtctag aaatgctata   57180
ttagatgctc ataatgtttt ctgtatcttt ttcttcccaa tgtctacttg tccttttagca  57240 aagtatgaac gttgtcatga atcttttctc tctgtccaca gattctgtgt gctcctctgg   57300
gccacagtag ttacttcttt aagcacagaa aggaaactta gggctttgcc agttttagta   57360
ttagttctct atgtttttca tccgggcagc tatggagagg gttgctttcc acacacctgg   57420
gtactccatt gatatgttct gtagaggtaa tcaacacact agagagtaca cctgtttgtt   57480
ccatggctaa ccctttctga ttgtagacat gcatttgagt gtttgcagtg gatatttggt   57540
gctaacaggt gtcttagttc cttctgttat tctgtaatgt ttcccaagaa tattcagagc   57600
tgtttataaa atgcagagtg atttatgtat taggtgttca atgagtttga tcaagaagat   57660
tcacttgaaa ggaattaact aacaaagcag tttccattgt taataggata tgcatgctgt   57720
ttctctaaag tattttatt tcttcaaaga gttattaagc agaggagact gattttgtgg    57780
taagtttgga ggggttagtt ttaatccacg ttggtcaaaa ctaaaagtag attagaaaat   57840
ctatttctca tcctacagta gtgctgaggt ttctagtaga ttgttttct tcttcctagt    57900 cattttctga aactcaaaac aagaatcaac ctataccatt gtaatgtttc acagttaact   57960
tggagtattt aacaagtcta aaatcaaagt ttattgttat tagtaaaaca ttttgaagcc   58020
attcatttca tgtgacaagg aatcttattt caccaaatgt ggtatgtttt taaacttata   58080
ctttctattg ttctagtttt gttgatcttt gatattgatg cagtgatatc agtttcctat   58140
tgttatatat actttgtggt caaaattatc ataggggtttt gtgttttct ttgcctgagt    58200 tttgcttctc atctgaacat cacatctttt tcttgcggtt ccatttacac agtgtgattc   58260
ctagagatga gcttctttat cctctgaggc agtggaggaa gcatggaagc cacttgggga   58320
gcactgcatt gacaagtgta ttttgtagt cacatggtgg cagtgtcagg gaaattatag    58380
```

```
gactggttag attctagttc agcaacctat aaatcccagg acttcccagt ctcgtgagtc   58440
atacaactct caggcctgtg ctgcaaatga cacttgctta ggagtaaggt gaagggtatt   58500
ttatagctct aatggtttgt acagttctta aacatgtatt gattgctaac aactgctgtc   58560
tttctcccag cttgccccac caccagtctt tgtgcataag cacaatttg gacatagtta   58620 tttgtactta tttatgcttt tacaccttct tccttttata aagattttag ctggtttatg   58680
acttgagttg aaacaaggaa aaaagagga gacctgaaat ggtctgtccc ctgccaacca   58740
gaagcctcct gtggtatcca aacagaatag ttgcctcagt ctgtcagcac ttctgtcttt   58800
gaaggtggtt tctgcttgaa aagtggtgac tattagcata gcctggggat aattgctttt   58860
ttttcttctc tcgggatacc ttttttttt tttttttcca gatactttct tgctcttgtc   58920
gactttgttt ttccagaaga tttagcctgt ggttaaaatg tttcgggtcc ccacgtgaac   58980
tctctgtggg attacccaat tctggggtac cttcaccaga tcaccagtgc taaagagggc   59040
aaaggatctc cttggttaat agaaaaggct gttttggaat gaatctcaaa gtccagaaac   59100
atcgagactt tcttcaata cttttttcta tttggggtag caactttacc tagtgtaggg   59160
gagggagggg ttagttggga gggcttgtgt ttaaggggtt cagaaacagg ggatttaagt   59220
gtgtcttttg tgtttgcaag gcactaacac cactcccgtc tgtatttaaa tgctgtcccc   59280
aggttacgac tatggctatg tctgcgtgga gttttcactc ttggaagatg ccatcggatg   59340
catggaggcc aaccaggttg ctttatactt cggtcaaatg atgctggaag gatatatttt   59400
tttatatatg gggagggagg gtttcaaatg atttttacttt ggaaaggtac aagaagtcta   59460
tctgtggagc atactgtatt ccaaccatcg gttgtgagga aaatctttaa aaaggctgga   59520 aagcttctc tacaaaactt aatgggcaca gagtgcattt taaaagctag agcccagttg   59580
cttttggact agattccaaa gacaatagtt ggaaaaaaaa aaaaagaca catctggagt   59640 gtttcctttt ggagtgtgac tgagatggta atcctgatgc aaagaatgat ccttgattgt   59700
ctgtgacccc aaggatctgc ctagcacaga aattctaggt caatagttac acccagacct   59760
agggtgaaga cctctgatgg tgacttctgt ggcatcagat cctgcctgca ggggctactt   59820
ccaaaagaga gctatcaggg aagagagagg agtggattgt tggtgtctat tgcattcatc   59880 attgttttt gccaattgga gttgcatact caagtccttg gctgcgtata gtcagagctg   59940
gtgaatcaga atctgtactc accttacgtt tgaactatct ggagttactc agcttgccac   60000
ctagattttt catctatgtc tttaatagaa ccctacctgg tagttttgag aggaattaat   60060
aaataggtag aatccttctt gttatggtgc ttccttgggg aaagttgttt tctttgggtt   60120
gtttcagttc ctccatctgt aaagtaggaa aagaaactta ggaatatagt ttgatgtgtt   60180
ttttttttct ttttttttt ttttaatgta cccactgcct atacttaaca gtgtgaatac   60240
agtgggccca gaatctttct ttctttcttt tttttttt gagacggagt tttgctcttg   60300
ttgcccaggc tggattgcaa tggtgcgatc tcggctcact gctacctcca cctcccggt    60360 tcaagcgatt ctcctgtctc agcccctga gtagctggga ttacaggcat gcgccaccac   60420
gccggctaat tttgtatttt tagtagagat ggggtttctc catgttggtc aggctgctct   60480
cgaactccag acctcaggtg atctgcctgc ctcggcctcc caaagtcctg ggattacagg   60540
catgagccac cgtgcccagc caggcccaga atcttaaaag aaggctctgc cagagaagag   60600
tagttattag atgagaactc ttcttcttct gtagcctgat gctttgttca gctttgttta   60660
actcagtgtg gctcattata cgtacttttc tcttcttggc caagttctcc tcttatgggt   60720
```

```
atggagatga catgctctaa atgctttggg agcaagcact cattagagaa gacttttgat   60780
gtatccttat cttgttagta gtttaagctt gtcagatcct taaagaatga caggcttagg   60840
accatatccc ctagacttaa gaggattctc attgaccatt tgttcagtgt ccatcactga   60900
atcacttacc aaatacagtt gacactctgt atccacaggt tccacaccca tagattcaac   60960
caaatgctga ttggacatat tcaggaaaaa aatgcattaa cactgcaaca ataaaaaata   61020
atacaggcca ggagtggtgg cttactctgt aatcccaaca ttttgggagg cccgggtggg   61080
aggattgctt gaggccagga gtttgagacc agcctgggca acacagggag accccatctc   61140
tacaaaaaat aaaagtgaaa aaattagcca agtgtggtgg ctatcaactt gggaggctaa   61200
gatgagagga ttacttgagt ctggattgag actgcagtga gctgtgatca ctctgctgca   61260
ctctagcctg gggtgacaga gtgagacccc gtctcaaaaa acaaaaaagt acagttaact   61320
atttatatag tctttattag gtattagata taagtaatct agagatggtt taaagtatgt   61380
tggaggatgt gtgtaggttg tatgcaaata ccatgtgatt ttatataagg gacttgagca   61440
tcctgagatt tttgtgtcct tgtgggtcct ggaaccaatc ccctgtggac accaagggac   61500
aactgtacta accatgtgtc agaaactgct acatgccaat tttggagaga agaaaaaagc   61560
ttccaatctg tgtgctttcg gtggatccta ttctgacagt ctgtccaatt ttgagaacac   61620
tcattaattc ataagcagtg aatgtgatta agtcgttcgc ctctgtgcta aatactcaat   61680
gtaatagctg atagctgagt gctataaaga aaatgaagca gggtattggg agaatgcatc   61740
atggtggcaa ttttagaggg gtggtcaggg aaacttcttg aggagtgaca tacatttaag   61800
ttgtgactct tggcgaataa tgtatccaga acacttacta tagtacctag cacttggtag   61860
catttgaatt aatttgaaat tcagtgtcct tctttctctc tcttacccte ctccacatgt   61920 caagtaattt ccaattataa attttgtgtg tgtgtgtgag acggagtcca gccaggctgg   61980
agtgcagtgg cgtaatcttg gctcactgca acctccgcca cccgggttcc agagatcctc   62040
ctgtctcagc ctcccaggta gctgggacta cagatatgcg ccaccatgct tgggtaaatt   62100 tttttttcttt ttttttttttt ttgagatgga gtctcgctct gttgcccagg ctggagtgcg   62160
gtggcacgat ctcagctcat tgcaacctct acctcctggg ttcaagtgat tctcctgcct   62220
cagcctccca aatagctggg attacaggtg cccgccacca cacctggcta attttttgtat   62280 ttttagtaga gatggggttt caccatgttt gccaggctgg tctggaactc ctgacctcag   62340
gtgatccgac tgccttggcc tcccaaagtg ctgggactgc aggcgtgagc caccatgtcc   62400
tgccaatttt tgtattatta gtagagatgg ggtttcacta tgttggccag gctggtcttg   62460
aactgcagac cttaggtgat ctgcccacct tggcctccca aagtgctggg atgacacgca   62520
cgagtcaccg tgcctggcct tcaattataa ttataagaaa ataaatttat ttttatatct   62580
gaagtttaat aaaactaatt ctttaaggaa atggatgtgg attaaactcc ttatgacata   62640
gtaaacaatc ttatgagaga cataagaatg tgagggaaga agtcctgtct cctcagggtg   62700
aataaagtaa atattttggg aggctgaggc gagcggatca tgaggtcagg agagcaagac   62760
catcctgacc aacaaggtga aaccccgtct ctactaaaat acaaaaaaat tagccaggtg   62820
tggtggcgca cgcctgtagt cccagctact gggaggctg gggcaggata attgcttgaa   62880
cccaggaggt ggaggttgca gtgagccaag attgcaccac tgcactccag cctgctgaca   62940
gagcaagact ctgtctcaag aaaacaataa aattgaataa ataataaat aaataaata   63000 aatatttgtg gaagataaaa tgtgtttgta ggccgggcac tatggctcaa gcttataatc   63060
ccaccacttt gggagaccaa ggctggagga tcacttgagc ccaggagttt gaaatgagca   63120
```

```
tggggtaaat agtgagaccc tgtctaaatt taaaaaaaaa aaaaaaaaaa aaaaagtctt   63180
tgtctatcct ttcccccagt tttacttaca gaccaaattg gtatggattc tgagtcacca   63240
cgatctgctt ggcaactctt agtagagcct gagtgtgtgt gtgcctctga aaggttact    63300 ccgaagtact ttgagttttt ttgtaactct ttgctattcc gactcttgat gtgaaatgtc   63360
ttttatttat cattggctgg tacttgtagg cctaggggat ggaaataaag gaattttctg   63420
ctagcttgct ttgtcaaata ttgttgggta tgtgtgcctt cgtgaagttg ctcaagatga   63480
taaccaaggt ccctctagcc ttttcctggt gcctagatca agctgttaaa cagtaggatg   63540
ctctgcagca gtactgagct ttgtggctgt ggtgaccgat cagggtatca cttaggcagc   63600
agctgtctat ctggagaaat aatttccaac aggtatgaag gtatgaatct gttagtctgt   63660
accatcacca tttctgtcta ggagaagggg gcagccagca agcactgtca ggcagagcct   63720
ttcgttccac ccttcctgca aagtgtattt ctagccctgt catatgccct tggctttctt   63780
tgttgtcaag tctctgggag attgaggta catattattt ccttctgctt tgtgtgccct   63840
tgcactggga cttggggagg ggagtaagaa gtattgtgtt aaaatgttaa tcctttcat    63900 tggttgccca gttgtgagta ctagccctct cagactgttg gcatttggta tgcagggatt   63960
agcattttat gttctcaagt atgctggtgt gatgcttatt gtctattatt tggccaaatt   64020
agtcactaaa gtgcccttat agaagataac tctgggagag gtatttattt ctctgaaatt   64080
tttattctcc ttccccttt cctttccttt ccttttcctt ttctttttt tctttcttt     64140 ttctcccctc ccccccctcc cctctcctct tattggagac aaggtctccc tctgtcacct   64200
acgctggagt gtagtggtac aatcatggct cactgcggcc tcgatctctt gtgccgaagt   64260
gatcctccca actcagttct ctttagtagc tggaactacc accaccacag ctggctattt   64320
tttttttttt ttttttgtag aggcagggtt ttgcaacatt ccccaggctg gtcttgaact   64380
cctggactca agcaatttac ctatctcggc ctcccaaagc actgggattc caggtgtgag   64440
ccactatgcc tggcctattt ttaaattttt atttttttga gacttagggt tctgttctgt   64500
tgctcaggct ggagtacagt ggtacgatga gagctcattg cagctttgaa ctcctgggct   64560
taagcaatcc tctcacctca gccttctgag tagctggact acaggcacct gccaccatgt   64620
tcggctaatt aaaaaaataa caaactctgt tcgtaaagat ggggtcttgc tgtgttgctc   64680
aggctgctct tgaactcctt gcctcaagtg agcctcccac ctggacctgc caaattgctg   64740
ggattataag catgagccac tgcgcccagc cttactcacc ttttgtatg acactatcag    64800 tctttctaaa gtgcaaagaa aaagggttct gttatcatct gatgtgaaaa ttcctttaaa   64860
cattgacttt ttctggtgtg aggaatgaaa gctgtggaat acgtgaagtt ttatgaaata   64920
gtgttttttt gtgtgtgtgt caacaaaatt aagagagttt gggttattga agatacaaga   64980 gtgttttga aggtatatat aggaaaccaa atctcaaatg tggtctgtcc ttgtgattaa     65040
aattagagca ataggggaagc caggtgtgat ggctcacacc tgtaattcca gcactttgc   65100 aggctgtgac aggaggatca cttgagccca ggagttgagt ccagcctggg taacatagca   65160
agacctcatc tctacaaaac attgttaaaa attagctggg tgtagtggca catgcctatt   65220
gtcccagcta tttggaaggc taagtggga ggattgcttg agcctgggag gtcaaagcta    65280
cagtgagccg tgattgtgcc actgcactgc aacctgggcg acagagagat cctgcctcaa   65340
aaaaaaaaaa aaaagcaaca gagaaagctt atgtttttag tgatgagaat gctatttgtg   65400
aggccatgat ggaaaaaatt gaagaaccta gtttgttgga aacttaaatt ggtagtaaag   65460
```

```
acataatact atctgaaaca ctttagtact taaattgtgt gcattccaag caacaaaacc   65520
aataatctgt aggttgaagg ttgtagtgtt acctaaacaa ctatcacccc aaaaacactt   65580
cattgaggag tatccagcat cctagccaga gctcaactgt ataacttatg gctggaatca   65640
tgccattctt gctggaaact tcaatttcag tactttttcc ttatcaccct cagaagggta   65700
gtagtagaaa catggggaac tgcattctaa aatgagtgta taggttcata acctagctag   65760
aaaaaaaaat taaacaatt aatgagtaca aaccaagggt tattgaagag tctcgctctc    65820
aagagagttg gggtattcaa gaaaattgaa agtgagttta aggatcgatg acttgattac   65880
acattttggc tatttatcca ctgattgaga ctttttttt tgagatggag tctcactggt    65940
tcgcccaggc tgtagcgcag gggtgcgatt tatccactga ttgagacttt tttttttttt   66000
tttttcagat ggagtctcgc tgtgtcgccc aggctgtagc acagaggtgc tcactgcaac   66060
ctccgcctcc tgggttcaag tgattctcct gccttagcct cccgagtaac tgggattaca   66120
agcatgtgcc accacgcctg gctaattttt gtattttcag tagaaatggg gtttcaccat   66180
gttggccagg ctggtcttga actcctcacc tcaggtgatc cgcccgcctc ggcctcccag   66240
agtgctggga ttacacatgt gagccactgt gcccagccca gtgattgaga ctcgactgga   66300
catgaagcag tataatgtag cagtataaca tagtattctg gaagcagact accgggggtt   66360
gcatttcggc tccatcactt tctaaggtgt acttgaacaa gtggcttaac ctctctgtgt   66420
tttaacgtac tctcacacac atctagggat taaataagtt aatgcatgta aggtgattag   66480
aactggggct ggtggccggg tgcggtggct catgcctgta atcctagcaa gttgggaggc   66540
caagacgggc ggatcacgag gtcaggagat ggagaccatc ctggctaaca tggtgaaacc   66600
ccgtctctac taaaaataca aaaaattag ctgggcgtgg tggcgggcgc ctgtagtccc    66660
agctacttgg gaggctgagg caggagaatg gcgtgaactg ggaggcggag cttgcagtga   66720
gccgagatcg caccactgca ctccagcctg ggcgacagag tgagactcca tctcaaaaaa   66780
aaaaaaaag aactggggct ggcacaaagt gaatgttgag tgcatctttg ttgttttcac    66840
acaacttctc atctgaaaca aagtcttaag ttacagcagc tctggtcttg gcttaatgga   66900
gtatatggca aaaagaggat ttggtggcag tgcctaggag gattttttt tttcccatca    66960
acaatacttc tcatttagcc tgttgattga tacggattat caggggactc cttccagctt   67020
ccctagttgg agttttttt ttttttttc cttttttgag acagggtctc attctgtctc     67080
ctaggctgga gtgcagtggt gcgatctcgg ctcactgcaa cctccgtttt tggggctcaa   67140
gccactctca tgcctcagcc tcccaagtag ctgtggctac agacacgtgc ctggctaatt   67200
ttgtattttt gtagagacgg ggttttgcca tattgcccag gctgatctcg aactcctgag   67260
gtcaaagcga tctgcctacc tcagcctccc aaagtgctgg attacaggag tgagctacca   67320
tgtccggccc ttagtaggag tttctgctgc cttagccttc aagagagaat cttaaatttt   67380
cttttttttt tttgagacag agtctggctc tgtcgcccag gttggagtgc ggtggcgtga   67440
tctcggctca ctgcatgctc cgcctccgg gttcacacca ttctctcgcc tcagcctcct    67500
gagtagctgg gactacaggc gcctgccacc acacccggct aattttttg tattttagt     67560
agagacgggg tttcaccatg ttagccagga tggtctcgat ctcctgacct cgtgatccac   67620
ccgcctcggc ctcccaaagt gctgggatta caggcgtgag ccacctctcc cggccataag   67680
aatcttaaat tttctaaaga gaaagagcag gagacagaca gtaccacatg gagtatgttt   67740
aggccatgta ggaaatctag cctgtggctt taaaaccgta agttctaaat tagctgggta   67800
tggtggtgca cacctgtagt cctagctact ctggaggctg aggtaggagg atcacttgtg   67860
```

```
cccaggagtt caaggttgca gtgagctgtg atggtgtcac cgcactccag cctgggcaac   67920
agaatgagat gctgtctctc aaagcaaaac accctaagct ctgataacca gcccattatt   67980
tgccacatct caggctcttt aattatgaga ggtgctctaa acgactcatt ttaattctct   68040
cgaatttgaa aaataaacat ttatcatttg gcagttttaa gggaaccttc tgatatgtgt   68100
cctacaatgg gtttataatt attttttgtca caaatcatgg tttatttcta tggattaaag   68160
tagtttagtt cttaatttgt tctaaattgg aaatatacct atatgtttta acctcgtgct   68220
tcagtgttgt cacatctcat tagttcaggg gtcgtacaaa ggcatagttc agttagccat   68280
cttgattata actttggttt atgacccttat gtatgttcag atggtatagg gttcgtagca   68340
cagaaagatt tagaattcca gcttcattac ctcctggctc ttttgtaact tttttttttt   68400
tttttttttt ttttttgagac ggatcttgct ctgttgtcca agctggagtg cagtggtgtg   68460
atctgggctc aatgcaacct ccacctcccg ggttaaagcg attctcctgc cttggcctcc   68520
cgagtagctg ggattacggg catacaccac cacgcccagc taatgtttat tttagtagag   68580
atggggtttc accatgttgg ccaggctgga cttgaactcc tgacctcagg tgatccaccc   68640
accttggcct ttcaaagtgt tgggattata ggcgtgagcc accgtgcctg gcctctcttt   68700
tgtaacttct gaacctcagt tttctcatct gtaaaatgag aggatgatca taataccacc   68760
catagtgcag ttgtgaggtt agagtatgta gtatatgtaa agtgatcagc atgataactg   68820
gcatgtggta agtgctctgt agtaaagggt gattcataac actggactct gcttggttgt   68880
accaacttct cattttccct ggctccttat ccacctcttg ggattcagag ttggctgaaa   68940
gtggcaggca gtgctgcttt gggtggcagc ttgattttag acagccagtt cacatagtgc   69000
ttttgttcag gacctctcgg gatttctaga cagacagcaa gagagttggg ctaacacctg   69060
tcatgaagtg tctaaggaat gagtgcacaa gcattcaggc atgtgagggc agaagaccat   69120
gaccatacct gccttcctac agtaaacagc ctgttgtttc tgcaggtagc attgcaggta   69180
gttcttttat cagaaaattc ttgtaggctg caggtgacat tgagtgttat taggtatctt   69240
cttcattcaa gttgaacttg gaggttacag tatatcttta tgtcccctc tccacaggtg   69300 tttaagtgtt gtcattcatc ctctagtgca tagattatgt gtgcacattt cttgttaagg   69360
atattgatga actgatagtt tatctagaat aatgttatt ttatatttta ttttattgag   69420
acagggtctt gctctatcac ccaagctgga gtgcagcggc atgatcatgg ctcactgcag   69480
cctcaacctc ctgggttcaa gccatcctcc ctacctcagc cttctgaata gttgggacta   69540
caggtgtgcg ccaccacacc tggctaattt tgaggggta gaggggaggt acagatgaga   69600
tctcactgtg ttgtccaggc tggccttttg ctcctggact caagcagtcc tgcctcagac   69660
tcacaaagtt ctgaattac agatgtgagc cactgtaccc agcctagaat aattattatt   69720 tattttatt tttatttatt tatttttga acagagtttt tgctcttgtt acccaggctg   69780
gagtgcgatg gcacagtctt ggctcactgc aacctctgcc tcccgggttc cagtgattct   69840
cctgcctcag cctcccatgt agctggaatt acaggcacac caccacacct ggctaatttt   69900 tgtatttta gtagagacag ggtttcacca tgttggccag gctgctctcg aactcctgac   69960
ctcaggcaat ccacccgtct cggcctccca agtgctggg attacaggcg tgagtgatgg   70020
cacccagcca gaataattag ttttaatctc acagggtgag atttgtgagg ttaattttgt   70080
atattaatga tgtatatatt accaaaatct gtggtcaagt gaaatttgtg cttaatcttt   70140
gcaaatgcta tttccaaagg aaaatatgta ggagaaaagg tggtgtatca caggatgtag   70200
```

```
agtagtggtt actgggcaca agggtggccg gggagtcggg gggtggcagg agaggataga    70260
gaatgataac tgattgatac agggtctctt ttttgggatg aggaaaatat tttagaatta    70320
aatagtgagg atggttgacc aagcttgtgc atgtactaaa agccattaaa ttgtatatac    70380
tttaaaacag tggattttat ggtatgtgaa ttttatctca atttttaaaaa aagtctttaa   70440
atgtagtatg aaactttttt taaggccagg cagggtggct cacacctgta atcccagcac    70500
tttgggaggc tgaggcgggc agatcacctg aggtcaggag ttctagacta gcctggccaa    70560
catgatgaaa ccctgtctct accaaaaata cgaaaattag cccagcatgg tggtgtgttc    70620
ctgtagtccc agctactcgg gaggctgagg caggagaatt gcttgaactc aggaggcaga    70680
ggttgcagtg agctgagatt gtaccactgc actccagcct gggcgacaga gcaagactgt    70740
ctcaaaaaaa aaaaaaaaaa aaaaaagtt ttttagggt tccagcacaa tgggaatgag      70800
tccagatcta aaataaagta cagattcatt taccaccctc caccctaccc caaccccca    70860
aaaagattgt ctatcagttt gtcaggaagt tagagtaaaa tggtcttaaa atgcatcaag    70920
agggctgggc acagtggctg atgcctgtag tttcagctac tcaggaggct gagataggag    70980
gatcacttga gcccaggaat tcgagtgagc catgattaga tcactgcact ctagcctgaa    71040
tgacagagca ataccttgtc tcttaaaaaa aaaaaggcat gaagaatttt tttgctaatg    71100
gtatctactt accacagagg aacatttaag ctaaacatct gaaagattat ggatggagtt    71160
ggtaacaggc tccatttgaa ctggttatgt agtttatgct cagtaaggtt gaacggactt    71220
tctgctttga gttattcaca gttaaaaata aaggactatt ttgaagtaga ccgaaaatga    71280
aaataacatt aagaaatcct tggactaatt tttaggggag attcctgtaa tcggatggtt    71340
tgtagttgtc aatgtagacc tttcctggtt tcctgaaatt gctaatcaaa gctcaaagcc    71400
atgggaaaag actggattgc agctagaatg tgtgctctcc acatatgtct tcttagagg    71460
cctctttcaa gcagcattga cactatggct atcatctttg accctcttag tatacagaga   71520
gttgtaggtt ttcttttttt aaggggaaa acattattga cataaattat atatcataaa    71580
agtcactcat tttaactgta caattcaatg attttttagt aaatttacca agttgtaaca    71640
tttattatta taattagttt tacaacattt ttcttttctt tctttttttt ttttttttt    71700
tctttttttc tgggacacag gatcttgctc tgttgcccaa gctgagtgca gtggcatgac   71760
catggctcac tgcagcctcc acctcccggg ctcaagcaat tctcccacct caacctcctg    71820
agtagctgga actataagtt ggaaccatcg tgcccagcta attttttatt ttttgtagag    71880
agaaggtctt gctatattgt ccaggttggt cttgaacttc taaactcaag caatccttcc    71940
tgcctcacct tcccaaagtg ctgggattac aggtgtgaac catcatgcct ggtctagaac    72000
attttcatta cctcaatcgg atccccgttt ggggatacat ttacatttt aattttttaa    72060
tttttatttt ttttagagac gaggtctcaa tctattgcca aggtggtctt gaactcctgg    72120
tttcaagtga tcctcccacc ttggtttccc gaagtgctgg gattacaggc atgaaccacc    72180
atgcccagtc cattccaatt ttttttttct tttttttga gatagagcct cactctgtcg     72240
cccaggctgg agtgcagtgg cgtgatctca gctcactgca acctccacct cccgggttca    72300
cgccattctc ctgcctcagc ctcccgagta gctgggacta caggtgcctg ccaccacgcc    72360
cggctaagtt tttgtatttg tagtagagac ggggtttcac cgtgttagcc aggatggtct    72420
caatctcctg accctgtgat ccgcccgtct cagcctccca aagtgctgag attacaggcg    72480
tgagccaccg tgcctggccc attccaattt tttacaaaag tgatttcaga cttataaaaa    72540
agctgcaaaa attcctgtgt tcttttcacc tagattctac cttttttttt ttttttttt    72600
```

```
ttgaggcgga gttttgctct tgtttcccag gctggagtgc aatggcgcaa tctcggctca   72660
ccacaacctc cccgtcccgg gttcaagcaa ttctcctgcc tcagcctccc aagtaattgg   72720
gattacagcc atgcgccacc acgcctggct aatttatat ttttagtgg agaccaggtt    72780 cctccatgtt ggtcaggctg gtattgaact cccgacctca ggtgatctga ccacctgggc   72840
ctcctaaagt gctgggatta caggcgtgag ccaccgtgcc aggcccaccc agattcttct   72900
tagcacattt gaatgcagat ttttgaatag ttatgatcta ttctcattga aaagggaca    72960 tcatttgact tgacctccca ccagactctt cctttgaggt tggatggagg tgcttaatgg   73020
atgctgtgga tggtgtgtga atttccattg ggttgagtgg atgatgtatg tggaaggcga   73080
ttgggattta ctttgtcggt gtctccaaga ggtcccccac tgggctttgt caggtgctgg   73140
ggttggaggt caagaagtag ggcaacatct aaagcttcta ctcctgggca ctgtgaggtt   73200
tttataggtc ttttaaaaaa aacagtgaat aggccgaacg cggtggctca cacctgtaat   73260
cccagcactt tcagaggccg agggaggcgg atcacgaggt caagagatca agaccatcct   73320
ggcctcgtgg tgaaacccca tctctactaa aaatacaaaa attagctggg catggtggca   73380
catgtctgta gtcccagcta ctcgggaggc tggagcagga taatcgcttg aaccctggag   73440
gtggaggttg cagtgagccc agatttcacc actgcactcc agcctggcga cagcgaggct   73500
ctgtctcaaa aatatgttct tccatgagac agcgggcatt tggatgcctg atacaaaaag   73560
aggagggact atgtgctagt cagctttaga ctgagaagca gcagcaacca tggcaaaggg   73620
gaagcaaact ttcctgagtg gccttaataa tgttattcgt caggcagtgg ctcttaaaca   73680
ggggcttcaa gcagtgattt ttgacatgct cttctcctcc ccaaccactg gacatttggc   73740
aatgtctgga gacattttg gttgtcacca ctgggagagg gtgctactgg tatctagtga    73800
atagagccag ggatgctgct aaacatccta cagtgcaaag ggcagctctc cacacaaaga   73860
atcatctggc ccaaaaatct ctattgctga ggttgaaaaa tactggtgta aggagacaag   73920
agttgtggtt agtcagaaag gatgacctgg cttgccgtgg attgtcttat aataatcagt   73980
tatctctttc cttgccttat tcctggtccc aacagagtga ggattggcaa gggggtttgg   74040
gaatatagtg ggaatgctgt gtagtgagag tgcaggcacg gcactccaga ctaccagtca   74100
cgagcttagc ctgtgtcctt ggggtaggag ctgtagaata agacctattt tgatatgtgg   74160
accagaataa gttctttaaa taatcaaagg taataaacat tcttaaaata tactatcact   74220
aaggtagtct gtcatccagc agaatgaggg agtagtcaga agattacaca tatttggcag   74280
caattactag aaaaaacaaa caagttgaga gttttcaaaa tagatgttac ttcatatttc   74340
agatagtttt ccagggaata ttgaaaatgc aagtgcagat tttcacatcc ttctttatac   74400
tgattaaaac atttgaatct attggatcat cttttcatta ggctttactt cacagggcca   74460
tctactggat cctgtatgct gatatagtta aggggactga cctcaaagta aagatgcat    74520 atatttatc ttaatacaat atcactttgc tgtgaagggg agctgctgtg tatatagaat    74580
gctgtgtaat agtgattggg ctgttgggaa tcacattgga aatatcagta agcaactcat   74640
tttaactttt gttaacacag ttaagtgctg agcacctctt gtgtttgaag ctctgtgcta   74700
ggtaatatgt gttcattaat gaatgaaaaa acaatacaaa aattagccag gcatggtggc   74760
gtacacctgc agtcccagct actcaggagg ctgaggcaca agaattgctt gaacccagaa   74820
ggtggaggtt gcggtgagcc gagatcacgc cactgtactc cagcctggcc aacagagtga   74880
gactgtctca aaaaaaaaaa aaaaaaaaa aaaagttttt tattttaaa tttttgttt     74940
```

```
tatttcttttt ttactttttt ttcttttgag acagagtcac gctctgtcac ccaagctgga    75000
gtgcagtagc accatcttgg ctcactgcaa ccccccgcct gccaggttca agtggttgtc    75060
ctgcttcagc ctcccaagta gctgggacta caggtaccca ccaccacgcc cggctaattt    75120 ttgtatttt agcagaggcg gggtttcacc atattggcca ggctggtctc aaactcctga    75180
ccttatggtc tgcccgcctc agcctcccaa agtgctggga ttacaagcat gagccactgt    75240
gcctggcaaa attttatt tattattatt attatttt ttttttttt tgagatggag    75300 cctcgctctg ttgcccaggc tggagtgcag tggcgcgatc tcggatcact gcaagctccg    75360
cctcctgggt tcatgccatt ctcctgcctc agcctcctga gtagctggga ctacaggcgc    75420
gtgccaccac gcccggctaa tttttgaat ttttagta gaggcgggt ttcaccatgt    75480 tagccaggat ggtctccatc tcctgacctc gtgatccacc tgcctcagcc tcccaaagtg    75540
ctgggattac aggcgtgagc caccgctccc ggccaattt tatttattt ttaattgata    75600 attgtacatg tttatggagt acccatgtta tgatacatgt gcacattgta gaataatttt    75660
taattgataa ttgtatacgt ttatggagta cccacgttat gatacatgtg tacattgtag    75720
aatgattgaa tcagactagt taacatatcc atcacctcat gtagttattt ctttgtagtg    75780
agaacattta aaatctcttt tagcaatttt gaaatagata caatacattg ttattaacta    75840
tagtcaccat gctgtgcaat agataactaa aacttcttcc tcctgtctga ctgaaacttt    75900
atactctttg actaacattc tcccgttctc ctccacccgc cttctccacc cacggcctct    75960
ggtaaaccac cattctgctc tctacttctg tctgaatatt tgattttttt agattgcaca    76020
tgtgagatca tgcagtattt gtctttctgt acctagttta taatacactt agctaagtgt    76080
ccttcatgtt tttccacatg tcgcaaatgg cagaatttcc ttcttttta aggccaaata    76140 gtatttcatt gtgcttacat accacatttt cattatccat tcattcattg atgggcaatg    76200
gatgaatgga tatcatggct attgtgaata gtactgcagt gaacatggga atgcaggtat    76260
ctctcagaca taatgatttc agtttcattg gatatatact gtacccaaaa gtgggactgc    76320
tagatcatat ggtgattctc gttttagttt tttttttt aagaacctcc atacagtttc    76380
caaaatatct gtactaattt acattcccac agtgtaaagg gttcccttt ctccatatcc    76440 tcactaacac ttgttaccgt tcatcttttt tatagtaacc atgctaacaa gtatgaggtg    76500
acatctcatt atggttttgt ttgtttgttt gagacagtgt cttgctgcat cacacaggct    76560
ggagttcagt ggcgtgatcc cagctcattt gcagccttaa cttcctgcac tcaagcagtc    76620
ctcccacctc agcctcccag gtagctggtg tgtcaccatg cctagcgttt tttttttt    76680 ttttttgaga cagagtctcg ctgtgttgcc caggctggag tgcagtggta tgacctcggc    76740
ttactgcaat ctctgcctcc cgggttcaag taattctcat gcctcagcct cctgagtagt    76800
tgagattaca ggcatgtgcc accacaccca gttaactttt gtattttag tagagatgag    76860 gtttcattat gttgtccggg ctggtcttga actcctaggc tcaagtgatc ctcccacctt    76920
ggtttctgaa agtgctggga ttaccagcat gaaccactat gcccagctcc ttatggtttt    76980
aatttgtaat tctctgataa ttattgatgt tgaacatttt gtcatatatt ttttggcaat    77040
ttttttcctt cttttaaaaa ttttgttttt agccataagg ccaggaatgc acgtatgtct    77100 tcttcaaga aatgtctggg ctgggcacag tggctcacgc ctgtaatccc aacactttgg    77160
gaggccgagg cgggtggatc acgaggtcag gagatcgaga ccatcctggc taacatggtg    77220 aaacccccgtt tctactaaaa atacaaaaaa attagctggg tgtggtggtg ggcgcctgaa    77280
gtcccagcta tgtgggaggc tgaggcagga gaatggcgtg aacccaggag gtggagcgtg    77340
```

```
cagtgagcca agatcgcgcc actgcactcc agcctgggcg acagagcaag actctgtctc    77400
aaaaaaaaaa aaaagaaaaa gaaaaaaaaa tgtctattca ggtcctttgc ccattttta     77460 atagggttat ttgttttcat tattgagtag tttgagttct tgtacatttt tggatattag    77520 cccttttatca gatggaagat ttgtaagtat tttctctcaa tctgtgcatt gtttcttcac   77580
tttgttaatt gtttccttgc tttgcagaag cttttagtt tgacgcaatt ccatttgtct     77640 gttttgctt ttgttgcctg gcctttgggg gtcatgcaca agaaatcatt gcctagacca     77700
gtgttgtgga gctttccaac tatagtttct tctagtagtt ttacaatttc tgttcttaca    77760
tgaagctatg aacagttcct gtatagttat ccctgccacc cttctcccaa cattacatac    77820
acagcctccc caactatcag catcctgcag tgtagtgtat atgttacaat cagtgaagca    77880
acattgatac atcattatca agggttcact ctgggtgttg taccttctat gggtttccac    77940
aaatgtatgt catatatcca ccattatagt atcatacaga atagtttcat tgccctagaa    78000
accctctttt ctccacctgt ttgttctttc ctcttgcaaa cccctgcaac cactgaactt    78060
tttattgtcc gtgtagtttt gccttttgca gaattttata tagttggaat tggacaatat    78120
gtagcctttt cagattggct tctttcattt agtagtacat ttctctatgt agtctcattc    78180
ctctatgtct ttttgtggtt tgatagctca tttcttttta gcactgaata atatcccatt    78240
gtatggatat atcacagttt attcattcac ctactaaatg acatttttggt tgcttccatg   78300 ttttgacagt tacgaataaa gctgcaataa atatccatat gcatgttttt gtacggacat    78360
acgttttcaa ctagtttggg taaatacaag gggcatgatt actggatcgt atggtaggag    78420 tgtgttttt tttttttttt tttttttttt ttttgacacg gagccttgct ctgtcaccag     78480
ctggagtgca gtggtgcgat ctcggttcat tgcaacctct gcctcccagg ttcaagtgat    78540
tcttctgcct cagcctccca gtagctggg actacaggtg catgaccatg cccagctaat     78600 ttttgtatt tttagtagag acagggtttc aacatgttgg ccaggatggt cttgatcttg     78660
tgacctcgtg attcgtccac ctcggcctcc caaagtgttg ggattacagg cgtaagccac    78720
tgcacccagc ctgtagagta tgtttaatt tgtaagaaac tgtcaaacag ttttccaaa      78780 gtagcgatta caatttgcat tgctaccagc aatgaattag agttctgttg ctctgtatcc    78840
ttgccagcat ttggatggta gccattttta tttttattta tttatttttt tttttgaga    78900 caaggtcttg ctctttcacc caggctggag tacagttgga cgatctcagc tcactgcagc    78960
ctccgcctcc caggttcaag ttattctcct gcctcagcgt tctgcatagc tgggattaca   79020
ggcacgcacc accacaccca gctaatttt gtattttag tttcaccatg ttggctaaga     79080
tggtcttgaa ctcctgacct taggtgatct gccccgcctt ggcctcctga attgctggga   79140
ttacaggcat gagccaccat gcctggcctc ctttgggtat ttctattgga cagtcatgtc   79200
attcatgaat aaagacaatt ttatttcttc ctttctaatc catatacctt ttatgtcctt   79260
ttcttggctt attgcactag ctaggatttc tagtacaatg ctgaaaggag ctgtcttct    79320 cttcttttct ctccttttcct tgccttttcc ttttcttctt tttctttctt tcttcctat   79380 agagataggg tctcgctatg ttgccaaaac tggtctccag ctcttgggcc caggtgatcc   79440
tcccacctca gcctcccaaa gtgctgggat tacaggtgtg agccaccaca cctagctgaa   79500
aaggagctgt tgagaataca tccttgtctt gttcctgatg ttagtgggaa gaaagcatct   79560
agtctctcac cataagtgtg atgttagcta taggtttatc aagttgagga ggttcccctc   79620
tgttcctagt ttgctgagag gtttttttttt ttaaatcatg aaaggggatt ggattttgt   79680
```

-continued

```
caaatgattt ttctgcatct attggtatgt tcatgttaat ttcttcttca gcatgtcgat    79740
gtgatggatt acattaattg attttttttt tttttttttag atgcagggtc tcactctgtt    79800
gcccaggcta gagtgcagtg gcacaatcac agctcactat aacctcaagt tcctcagctc    79860
aagcaacttt cccatctcag cttttccaagt agctaggact acaggcacat accaccatac    79920
ccatctagtt ttttaaaaca ttatttgtaa agatgaagtc tctctatttt gtccaggctg    79980
gtctggaact cctgggcggg ctcaagcagt cttcaccttg gcctcccaat ttgtttggat    80040
tacaggtgtg agccactatg cccagcctca ttttgttat tagtaatttg tatcttcttt    80100 cttttttct tagactggtt aaatgtttat caatttatt gatcttttca aagaaccaac    80160
ttttggtttc actgatttat ctctattgat ttactgtttt caatttcatt gacttcagct    80220
ctaattttta ttattttctt ctgcttactt ttgatttaat ttgctctttt actggtttcc    80280
taaagtggaa gctcagatta ttgatttta gattttctt ctcttttaat atatgcattc    80340
agtgctataa atttccctct cagcactgct ttttgtgtat cgcacaaatt ttgataagtt    80400 gtgttttca ttatcgttta cagttgtgtg ttaatcccca tacagttaat gatggggata    80460
aattctgaga aatgcactct taggcaattt tgtctttgtg caaataccat ggagtgtaca    80520
tacacaaacc taaatggtat agcctgctac ccacctaggc tatatcattt agcctattgc    80580
tccttaactg caaacctgta caacttgtta ccatattgta tatgataggc agttgtgaca    80640
cagtagtatc taaagataga aacggtacag tgaaaataca gtatttcagt attttgggac    80700
caccatcata tatgcaagcc cattgttgac tgagatgtca ttatacagca tctgaccata    80760
attcggaata ttttttaaatt cctcttgaga tttcttcttt agcttgtgtg ttatttagaa    80820
gtatgttttt aaatctccat atactttggg attttacaa ctatattact gttactgact    80880
tctagtttaa ttctattgtg atctgagagc atatattatt ttttctgtca ttttaaactg    80940
gaaaaggtat gttttatggc ccataatgtg ctgcgtgagc ttgaagagaa tatgtagttc    81000
gctgttgctg gatgaaatag tctacaaatg ttgattagat tgctgctgtt attttgatgc    81060
gtatccttcc agattttct atgcatgtat catctatctg tgtatctatc tgtaggatag    81120
gagagtcttg tacaaatggt tttataactc tttaacttca aatattgtgg acttacttcc    81180
ttgtcattaa atacatttaa ggctgggtgc agtggctcat acctgtaatc ctagcacttt    81240
gggaggccga acaggcaga tcacctgagg tcaggagttt gagaccagcc tagccaacat    81300
gttgaaaccc cgtctctact aaaaatacaa aaattagctg ggtgtggtgg cacacgcctg    81360
taatcccagc tgctcaagag gctgaggcac gaaaatcggt tgaacccaag gaggcggagg    81420
ttgcggtgaa ccaagattgc gccagtgcac tccagcctgg gtgacagagc aaaactttgt    81480
ctctaaataa ataaataaac aaataaaata catacctatg tacatacata cattttaaga    81540 atcatttga tatattcatc tccatactga ggaatttaag tgcttttttt ttttttttt    81600 tttttttt tttgagacag agtctcactt tgttgcccag gctggagtgt ggcggcacga    81660
tcttggctca ctgcaacctc tctacctcct gggttcagga aattctcctg cctagccggg    81720
tgagatttcc tctttagctt gtgtgttatt tagaagcatg ttttgtacc tatcgtagct    81780 tctctagaga agggaggtag gagaatcgct tgagcccggg aggtcaaggc tgcagtgact    81840
gacccatgac catgccactg cactgtagcc tgggtgacag agtgagcccc tgtctcaaaa    81900
aggaaaaaaa agaaatcagc atattttatg acttaataaa tgtattcaaa ttccatccag    81960
atatttccta atttattatt ttactaacag tgtttgagag cacttgtctc ccctgccttc    82020
caaccagtgt caagtgtatt ttaacaaaat acttgtattg ggtagtagta catggttggt    82080
```

```
tgttactctc taatcgcctg ttgtgtttga aatatttaat aattttttta atgttgctag    82140
tgtagtgaag aagataatga tttagttttt cttctttctt ttttttttt  gagatggagt    82200 ttcacccttg ttgcccaggc tagagtgcaa tggtgcgatc tcagctcacc aaaacctctg    82260
cctcccgggt tcaagtgatt ctcctgcctc agcttcccga gtagctggga ttataggctc    82320
atgtcaccac gcctggctaa ttttgtattt ttagtagaga cagggtttct ccatgttggt    82380
caggctggtc gcgaactccc gatcttaggt gatctgccta ctttggcctc ccaaagtgct    82440
gggattacag gcgtgagcca ccgcacctga caaatgatgt agttttctc  ccttaggtta    82500 ttagtaggca gaatagtttt acatttgatt attagttatt catatttctt ttgtgacttg    82560
ttggttctta atatatctat tcagccaaaa atgaaaaata ggatatctta gcctgtctag    82620
tcttaaggta aatatatgtg ggatataagg agtttgggg  gctgggcgca gtgactcaca    82680
cctgtaatcc cagcacgttg ggaagctgag gtgggctgat cacttgagcc caggagttca    82740
agaccagcct gggcaatgta gcaaaacccc atctctacca aaagtacaaa aattagccag    82800
gtacagtggc acatacctgt attcccagct actagggagg ctgagatgga aggatagctt    82860
gagcccaaga ggttgaggct gcagtgagct ataagcatgc cccactacat tccagcctgg    82920
gtgacagagc gagaccctgt ctcaaaaaaa agattttttt gaaaagttga aatgagtat     82980 attcgctgaa tacgagatga gttttcccaa gaatttatcc ctcagaatct ttcacgttct    83040
tcctcctcct tctcctcctc ctgctttctt cttcttcttt cttcttttc  tgtttcttct    83100 tcttgctttt ataaagtctt agctcctgtg gagttttctc tcagttactt cttatttatt    83160
tatttgagac agagtttcac tcttgttgcc caggctggag tacagtggcg cgatctcggc    83220
tgactgcaac ctccgcctcc tgggttcaag ctattctcct gtttcagcat cccaagtagc    83280
tgggattaca ggtgcctgcc accacacctg actaatttct gttacttctt tgagccaca    83340 aagtatttga aaaagatgca ttaagtagtg accgcagtcc gtgctagtat tgggtgctta    83400
cagaggtcta gtagaatacc gtgttttaaa aggaggtgaa tttaataatt gctgtgatta    83460
ctctggcatt atacgctcac aaataaaatg tttggtgatt ttttttttt  ttttttttgg    83520 agacagattc ttgctctgtc acccaggctg tgcaatgatg tgatctcagc ttactgcaac    83580
ctccgagttc aagtgattct cgtgcctcag cctctcgagt agctgggatt acaggcaccc    83640
gccatcatgc ctggctaatt tttgtatttt tgtagagatg gggtttcacc atgttggcca    83700
ggctggtctt gaactcctga cttcaggtga tccacccatc tcagcctccc aaagtgctgg    83760
gattacaggt gtgagccact gctcccagcc gggtgtgata ttttttaataa aacaagtatt    83820 caaattcact tacaggacca atgaaagaat cgtttgtcgt aattttatgc caaagggtac    83880
ttgtggctta agataaactt cccataatga cattatccac agattcaaaa agtagtttat    83940
cttaaacaac ttctgtgaca ttttaaaatg atgtggctta gaaaattgct aggttatcta    84000
aaatggctct attgatgatg taaatgtagc acatgaagag cttgaataaa atagacttt     84060 gaagtgtgca aatggaaaga acagtccttc taaataatta tttccctcc  cttttattga    84120 cgtatacata cagaaaagat atcatgtcgt aagtgtattg cttagtgaat tactccaaag    84180
ttggatatac ctggttaacc accacctgaa tgaaaaaaac agaacactgc ttcatatgga    84240
gaagcccctc ctgcccctcc tggtcattgt cctttcatc  cctcccacag gtagtcactg    84300
agttctaata ccacagagtc ttttgacttt cttttgagcc ttatgtaatt agaatcacaa    84360
aagatgtatt cttttgcctg acttttatac ttagtattgt ttttgaaatt catcttgtgt    84420
```

```
gtaactgcga tttgttcatt ttcattgctt agtgaattat tccaaagttg gatatacctg   84480
gttaaccacc acccgaatga aaaaaacagt ttttggccgg gcacgatggc tcacgcctgt   84540
tatcccagca ctttgggagg ctgaagcgtg cagattacga ggtcaggaga tcaagaccat   84600
cctggctaac acggtgaaac cccgtctcta ctaaaaatac aaaaaattag ctgggcgtgg   84660
tgacgggccc ctgtagtccc agctactcag gaggctgagg caggacacct gtaatcccag   84720
ctacttgaga tgctgaaaca ggagagtggc gtgaacttgg gagatggagc ttgcagtgag   84780
ccgagattgc gccactgcac tccagcctgg gcgacagagc aagactccgt ctcaaaaaac   84840
aaaaaacaaa aaacaagaaa acagttttcc agtctaagaa tgtattacaa tttattcaaa   84900
ttccactcta gatggactgt gggttttttt ttttccccca tttggagcta tggcaaatga   84960
tgttttttca aagttgttat ttctcagcca ggcgcggtgg ctcacgcctg taatcccagt   85020
actttgggag actgaggtgg gcagatcacc tgaggtcaga agcaagacca gcctggctaa   85080
catggcgaaa ccccgtcttt tctaaaaata caaaaattag ccaggtgtgg tgatgggcac   85140
ctgtaatccc agctacacag gaggctgagg caggataatc acttgaaccc aggaggtaga   85200
ggttgcagtg agctgagatc acaccactgc actccagcct gggtgacaga gcgagactct   85260
atctcaaaaa agaaaacaaa acaccacgga attgttattt ctcttggcga ataggtagat   85320
gcacttattc ctgttaatat atacctacct gtgaatgtgc ttgttggatt ttctatgtat   85380
cttctgtctg ccacctagaa atttaacctt ttatatatat acaactttaa ttttttttt   85440 ttttttttta agagacaggg tgtcactatg ttgcccaggc tggttgggaa ctcctggcct   85500
taagccgtcc tcctgcttca gtctcccaaa gtgttgggaa tataggcgtg agccactgtg   85560
ccccactgtt caagttttca ttgattgctg cctacatata gttgttcaac agctattgat   85620
tccccctgct ctgtatatat gtctcctagt gtaggtatca gggttacagc agtaattaag   85680
accacattat ttcattttat catttaaata tataagacta attgataaat taagtataga   85740
actttgacca acatggtgaa accccatctc tactagaaat acaaaaatta gctgggtgtg   85800
gtggcagacg cctgtaatcc cagctactca ggaggccgag gcagaactgc ttggagatgg   85860
aggttgcagt gaaccaatat cagaccacta tactccagct tggatgacag agggagactt   85920
tgtctctttt ttttttttctt ttttttgag acggaatctc gccgtcttcc aggctggagt   85980
gcagtggcac gatctcggct cactgcagcc tccgcctccc gggttcaagc gattcttcta   86040
cctcagcctt ccgagtagct gggattacag gcacccacca ccatgcccgg ctaattttg   86100 tatttttagt agacagggtt tcaccatgtt ggccaggctg gtctcaaacc cctgacctca   86160
agggatcaac ctgctttggt ctcccaaagt gctaggatta taggcgtgag ccactgtgcc   86220
cggccctttt ttttttttt ggagacagaa tttcgcccag ttgccagact ggagtgcagt   86280
ggcacgatct cagctcactg caacctctgc ttcatgggtt caagccattt tcctgcctca   86340
gcctcccaaa tagctgggac tacaggcatg caccaccacg tctggctaat tttttgtatt   86400
tttagtaaag ccagagtccc aaagtgctgg gactaggcag cgtgaaccca ccacgcctgg   86460
ccaagactct gtctctcaaa aaaaaaaaa agaaaaaaaa atataggact ttgggaggcc   86520
gaggcaggca gatcacctga ggtcaaaagt ttgagaccag cctgactaac atggtgaatc   86580
cccatatcta ccaaaaaata caaaaattag gcaggtgtgg tggcgtgcac ctgtagtccc   86640
agctattggg gaagccgagg tgggagattg tacctgggag gcagtgagca gagatcgcac   86700
cactgcactc cagcctgggt gacagagtga gaccttgtct caccaaaaaa aaaaaaaaa   86760 aaaaaatagc ataggtaggc atttgatgat ttgatgattt cattcgcatc cctaaaagtt   86820
```

```
tatttgttcc tgggtcgtca gatagctttt tggccatctt cctgttgaga aaattgatgt   86880
acccttctgg agtcctccaa tttttccatta taatatggta agtgggagct agagctttgg   86940
gtaagaattg ggatgtgata aggaggatga gttttgcagt ggtgtgcatg gttaggagga   87000
gaaaaagctg gaggcagagt gttcacttag aggcttgggg taggaggggt aggtttaagt   87060
ggtgctcatc tgggccagaa tagggcaaaa agggaagaat gaaataacca gatgtctttg   87120
ctttgtcagt agtcttgcag ccctgaaagc ttttttttgtt gtgttatatt tgttgtaatt   87180
gaggtataat ccacataaca taaaacttac ctctttcaag tgtacaattt agtagttttt   87240
agtatattca taaaattgtg caactatcac cactgatacc agaacatttc tgggaacaaa   87300
aagaaactat atatccatta agagtcactc tccattttct cctacttcct tctctacccc   87360
cagtcatctg ctagtcggct ttctgtctct atagatttgc ctgctctgga tatttcatat   87420
aaatggaatc atataccata tggtcttttg tgactggctt cttttactta gcctaatgtt   87480
tttaaggttc atccatgtta tatgaatcag tacttaaatc atttataggg ttgaataata   87540
ttccatcata tggatatacc acattgtctt tatctgctca ttaattggta gacatttagg   87600
ttgtttccac ttttgtttat tatgaataat actattcaca ttcatgtaca aggttttgtg   87660
tggacacatt ttcagttctc ttcgatatat accaaagagc cacaatgcta aaacttccag   87720 cttttttacca gctatcccca gatgcgtagc ctagtaagcc ccatgttgga gtggtgtagt   87780
gttgaaaaca tggcatactc atacattaga taaccaggtt tcaattctgg tttggaagcc   87840
tttggatatt tgcattaccc atttgaattc tctcttgggc tgtgtttggt ttggggtttt   87900
gtacttgttt ttttttttttt aactagatgt tttgaggcac ttggtactgt ggacatgtgt   87960
cagtcttaaa tatttgggtt ttgagcatat caagggcttg gtttgcagtt gacagttgaa   88020
tagcagtctt cttccttcca ttccttacag attctcctgt tcagagtcaa ccattgaata   88080
gcatatttat tgtttctgcc tgtgtgtctg ttagtgctca tatggtctag ttcctgagtt   88140
aagaagtata gggtagtggt catcttttttt ctttgacttg attcctgcgt actgtgaatg   88200
cagagcaatg caggatatgt tgggttttct acaaacagag catcagccca gagacatgtt   88260
tgcatttgtt tctgtcaggt ttcctggctc aactggcacc ctttaaggcc agagaacgtt   88320
agtttaggca ctttttcctag taaaatactt cttgtggctc ttcctgtgta cttggaataa   88380
aggaggcatt ccattgttag acatgcttgg gtagttcagg gtaatcttag agtcatgaga   88440
gatatgatat aaaggaataa ctagctaaac cagaaaaaat gcctgggtaa tgactagcaa   88500
ataggtggtc aacagatgtc ctcattagat tgaaaggtcc atgaaagcag ggactatttc   88560
ttttctttac tgcttaaaaa ggttagaact ggacctggca acatatgatg agctaaataa   88620
atacatattt gtgaatlggg ttaacacata ttgcataaag tggttttggc tctgttttat   88680
tcttcataag ccctagtgat ctttttaatt tctgtaaaat gtggtcttga cccccccaac   88740
ccaagtgacc tccttatttg ctaggctctg atatttctgt taggtttcta ctgtattttc   88800
tgagatagca attagtagat actatttctc ctttgatgga gctagccata tattcttgtt   88860
tgttcatttt agctttcaaa tttctgtctg attcttgttc ttttactctg gaatgtagtg   88920
aatgaaatga cttggaaggt acaaggtagg tcagttagg ttgtctaggg ccttgcattt   88980
aaaagtttaa tttgatgaca tggtggatta caagaatgta acagtatcaa aatgatacta   89040
tcttcttgtg gtggtatgta gacttaaaaa gagaaactgc agagaaaagg gtccccttagg   89100 atgtagagca gcagttgata tgtgagaagt tgatgccttg cattagggat taggagtaga   89160
```

```
tgtggaagga agagatcagg tttgaaagag tttaaacaaa gaatctctag gatttgataa    89220
cactggatat cagaggggaa ggtacaagag agagggcaga atcaaaggcc actcagaggt    89280
taaaggaatc ataccggttt ggcatggtgg ctcacgcctg tcatcccagc actttgggag    89340
gctgaggcgg gcagatcacg aggtcaggag ttcgagacca gcctagccaa tatggcgaaa    89400
ccccgtctct actaaaaata caaaaattag ctgggcgtgg tggcgtgtac ctgtaggccc    89460
agctactcag gagactgagg cagaagaatc acttgaaccc aggaggcaga ggttgcagtg    89520
agccgagatc gtgccactgc actccagcca gggcgacaga gcgagactct gtctcaaaaa    89580
ataataataa taataaataa ataaaggagt aattccaaca cttgggaggc cgaggcagga    89640
ggattgcttg agcccaggag ttcaagacca gcctgggcaa catagtaaaa cctcatcgct    89700
ataaaatttt tttaaaaaga aatttagcca ggcatggtgg tgtgcccctg tagttcccat    89760
tactagagag gttgaggtgg aaggatctct tgaacccaag aggtcgagag tacagtgagc    89820
catgatgcac cagggcactc cagcatgggc aacagagtga gactttggga ggccatggca    89880
gaaggattgc ttgagcccag gagttcgaga ccagcctggg caatgtagtg ggaccttgtc    89940
tctataaaaa ttttacaaat atatataaaa gctgggcatg ggggcacgtg cctgtagtcc    90000
cagtgactgg tgggtggggc ggggggtgagg tgggagaatc acttgggccc aggaagtcga    90060
gattgcagtg agccatgatc atgccactgc tctctagcct gggtgacaga gtgagactct    90120
ttttgtctta aaaaaaaaaa aaaaaaaaa aaaaatggt tgtaccttga acagatacaa    90180
agcatgtaga agaggaaagc atttgggagg gagaataatt ggttggatac attaagtgtc    90240
aagtgacagt aggacctcta gaaatacaca aacagagctc cacaggtttt ttcattgtca    90300
tttcttatac cttttgttcc actacctact ttttttcctac aactttctgt ttattttata    90360
gtttatgaat tttaagcaaa atacttcctt ctgcctctta ccagtaattt tcaaaagcgt    90420
ctgtattggt taggattaga tttggctggg aatgacagaa aactaaaaat aaaagcagtt    90480
taaacaagtt tatttctctc taatgcaaat gaagtttgag ctgtccaggc tttcttatgg    90540
tggtttggtc atgatcaggg acccaggttc tttcaaccat gtagccccat cttaacatgt    90600
gatttctatc ttattgttca agatggctat ttgagtgtca gttatcagtt ttatttagca    90660
accaatggga aggaagggg atgaaaatgg gccctgtctt taaggatact tcctggacat    90720
agtgagtaga aggatggtta ccagagtatg ggaagggtag ttagggggct ggggggaagg    90780
tgggaatggt aaaggggtat aaaaaaggta gaatgagtaa gaccatcaga gaaatgcaaa    90840
tcaaaaccac aatgatatag gtggctcacg cctatatgta tctcacacca gttagaatag    90900
tgatcagtaa aaagccagga aacaacaggt gctggagagg atgtggagaa acaggaacac    90960
ttttacactg ttggtgggac tgtaaactag ttcagccatt gtggaagaca gtgtggcgat    91020
tcctcaagga tctagaacta gaaataccat ttgacccagc catcccatta ctgggtatat    91080
acccaaagga ttataaatca tgctgctata aagacacatg cacatgtatg tttattgcgg    91140
cactattcac aatagcaaag acttggaacc aatccaaatg tccatcaatg atagactgga    91200
ttaagaaaat gtggcacata taccatggaa tactatgc agcaataaaa aaggatgagt    91260
tcatgtcctt tgtagggaca tggatgaagc tgtaaaccat cattctgagc aaactatcta    91320
agggcagaaa accggacacc acatgttctc acttatacgt gggaattgaa caatgagaac    91380
acttggacac agagcgggga acatcacaca ctggggcctg tcgtggggtg ggggagggg    91440 gagtgatagc attaggagat atacttaatg taaatgacga gttaatgggt gcagcacacc    91500
aacatggcac atgtatacat gtgtaacaaa cctgcacatt gtgcaccatg taccctagaa    91560
```

```
cttaaagtat aaaaaaaaag acctactatt tgataccaca ataggqtgag tatagtcaat   91620 aatgacttaa ttgtacattt taaaataaca taaaagaaaa aaaataaaat aatgcagagt   91680
ataatttgat tggttgtaac tcaaaagata aatgcatgag gggatggata ctctattccc   91740
catgatatgc ttatttcaca ttgcatgcct gtatcaaaac atctcctgta ctccataaat   91800
aaatacacct actatgtatc cacaaaaatt tcttaaaaaa ggatacttt gagcgtttca    91860 agcattactt ctagttatgt tcagttgatc agaatttagt catagccaca cttcagcttc   91920
aaggagggct gcagaacgtc tttattttag gcagctatgt gcccagttaa aaagcagatt   91980
ttctcccaag gtaaagagag cagataggca ttaggagact actagtagtc ttttaatttt   92040
ccaggccggg cacggtggct cacacctgta atcccagcac tttgggaggt cgaggcaggc   92100
ggatcatgag atcaagagat ggagaccatc ctggccaaca tggtgaaacc ccatctctac   92160 taaaaaaat acaaaaatta gctgggcgtg gtggtgcgtg cctgtagtcc aagctactca    92220
ggaggctgag gcaggagaat tggttgaacc caggaggtgg aggttgcagt gagcgaaggt   92280
cgtgccattg cgctccagcc tggcaacagg gcgagactcc atctcaaaaa aaaaaaaaaa   92340
aaagcaggga tttgctccca agtaagagag caaatagac attgggagac tattagtagt    92400
ctcttaattt cccagaatga gaaccagatt cttccggtt acagaactcg tttctccaaa    92460
cattaattat tcttataata attttaaaaa atactaaata tataattatc accagccaaa   92520
tgcttctttt aagaaataga gacaggggc cgggcacggt ggctcacgcc tataatccca    92580
gcactttggg aggccgaggc aggtggatca cctaaggtca gagttcgaga ctagcctggc   92640
caacatgggg aaaccctgtc tctactaaaa atacaaaatt agccgggcat ggtggtgcat   92700
gcctgtaatt ccagctattc gggaggctga ggcaggagaa ccgcttgaaa caaggaggca   92760
gaggttgcag tgagccgaga tcgtgccatt gcactccaac ctgggcaaca agagcaaaac   92820
tccatctcaa aaaaaaaga aaagaaata gagaagagac agggaagcca agctcatgcc     92880
tgtaatcaca gcacttcggg aggccaaggt gggcagatca cctgaggtca ggagtttgag   92940
accagcctgg ccaacatgga gaaacccagt ctctactaaa aatacaaaaa ttagctgggc   93000
atggtggtgc ataccggtaa tcccagctac tcaggaggct cagacaggag aagtgcttga   93060
acccgggagg cagaggttgc agtgagccaa gactgtgcca ctgcactcca gcctgggtga   93120
cagagtgaga ctctgtctcg aaaagaaaaa aagaaaaag agacgggcc tcacatatgt     93180 acagtggtat gatccgtagt tcactataat cttgagctcc tgaaacctga tgctttaaaa   93240
caaaacagta caaaactact aaattatttaa ttaaatatat aaataaaata taataaaaat   93300
gttcacttct gttttttatat tctttaaaat gacccatagg ctggtgatta gtaactaaag   93360
catatgctgt ggaacatcca gcactgatgt aagtatatga agtttgaatg ccaggtcagt   93420
agattcagaa gctaagttac tgtatggtaa agaccatgtt ttgcctgagc agctttggat   93480
atggtttttt cttttttttc ttttttgag atggagtctc gctctgtcac caggtggagt    93540
gcagtggcgt aatctcagct cactgcaagc tctgcctccc aggttcaagt aattctgcct   93600
cagcctcccg agtagctggg gctacaggtg cataccacca cgcccagcta atttttgtat   93660
ttttagtaga gatggggttt taccatgtag gccaggatgg tctcaatctc ccgacctcgt   93720
gatccccctg ccttggcctc ccaaagtggt aggattacag gactgagcca cagcacttgg   93780
ccggatatag ttttctctatg tgtgttttcc ctaaacctta ttatacataa acatacaagg   93840
acagagatca aatgcccct gtctagaaac accatttctg ccaggcccat cttaataaga    93900
```

```
ctatgtcttc tttttatttg tttctatact tccttttttt tttttttttt tctgagacag   93960
ggtttcactc ttgttgccac cacactcagc taatttttgt gttttagta gagacaaggt    94020
ttcatcatgt tagccaggct ggtctggaac tcctgacctg aagtgatccc cccacctcgg   94080
catcccgaag tgctgggatt acaagcgtga gccatcacgc tcagcctaga cttcttagtg   94140
tggtgtttca ttttctttc tctggttccc atccagcttt gttcattgta catgctcacg    94200
gtgcacttta tatgacctgt tggcatattt tctcactctc tttttgtctc tcttcacttc   94260
cagcagtgtt aaataactct ttccattctg cagttttcct gataagaatt tcagatggtg   94320
gtggccaggt gcggtggctc acgcctgtaa tcccagcact tgggaggcc aaggcggcag    94380
atcacttgag gtcaggagtt tgagaccagc ctggccaaca tggcgaaacc ccatctctac   94440
taaaaataca aaagctagcc gggtgtagta gcgcatgctt gtaatcccag ctactaggga   94500
ggctgagtca ggagaattgc ttgaacccgg gaggcggaag ttgcagtgag ccgagatcac   94560
aacactgcac tccagcctgg gcgacagagc gagactccgt ctccaaaaaa aaaggcaatg   94620
aataattgga caaggaacca aaactttat tctgaaaaga gaaaattcca gtctatagca    94680
agggcagttt tccttctaag gaacagtact gatatatcat ggctaaagaa gcaggctcag   94740
cttctttgtc cctttcacta atttgctatg gcttctaaca taggctagga aaagaaaaaa   94800
atctgtttct ctttctccte tcctcttccc tcctcttccc tcctctcc tctcctctca    94860
tcttccctcc cctcccctcc cctctcctcc cctactcccc tctcctcccc tcccctctct   94920
ttatctgtct atctgctaag ggcagcaaat ctgtatccat acaggtctgc agcaacttca   94980
attcttgcct cctcagaaga aacaatttga ctgagggtca taaggcagaa ggagagacca   95040
aggcaagttt tacaacagga gagagtttat ttaaaagctt tagaacagga atgaaaggaa   95100
ggaaagtaca cttggaagag ggccaagcag gtgacctgaa agacaagtgc accaacacat   95160
agcctttcaa caggatagag agcagttaaa actgccctgg aaaagccaga cttacaggct   95220
actctgtata atagaaactt caggacaggg tgcggtggct cacacctgta atctcagcac   95280
tttgggaggc cgaggtgggc ggatcacgag gtcagaagat cgagaccatc ctggctaata   95340
cggtgaaacc ccgtctctac taaaaataca aaaaattagc cgggcatggt ggcgggtgcc   95400
tgtagtccca gctacttggg aggctgaggc aggagaatgg tgtgaacctg ggaagcggag   95460
cttgcagtga gctgagatca tgccattgca ctccagcctg gtcgacagag ccagactccg   95520
tctcaaaaaa aaataaataa aaaagaaact tcagcatgct tcctaatact gttcaaaggt   95580
ctccctttt atgatttat ttaaaaaaat tttttttttt tgagacagag tctcactctg    95640
ttgcccaggc tggaacgcag tggcgtgatt tcggctcact gcaacctccc ctcccaggtt   95700
caagcaattc tcgtgcctca gcctcctgag tagctgggat tacaggtgcc caccaccatg   95760
tctggctaat ttttttgtat ttttaataga cagggtttt caccatcttg gccaggctag    95820
tcttgaactc cacaccttgt gatccaccca ccttggcctc ccaaagtgct gggattacag   95880
acgtgagcca ctgcgcccag ctcaattttt atattttgg tacagaccag gtttcactat    95940
attggccagg ctgttctcaa actcctgacc tcagttgatt cgcccacctc agctcccaaa   96000
gtgctgggat tacaggcatg agccactgcg cccagcaggg tctccctttt taaacgtatt   96060
ttcttttat agcctacaaa ctacaagaga tgccttttaa taaactggat ggtatgtctt    96120
aacgtctgat ggagttaaa ggcatccaag ggttacgtct gtgatagatt gccaaggcat    96180
acaggtctga tcaggagagt ttcttgatga ctagctatgg gctatgcctt tgtagcacat   96240
gatcccaact ccagcaggga tatagttagt gacatgctgg cttgtcttc tccctaactc    96300
```

```
ctggattact acaaatttct tcttcgtgca ggaatcattc cctcactcta tacatatctg   96360
ctgttaaaaa aaaaaaagtt aagatattat agccattata ttgtagcagc catgatatta   96420
tagctcagta aatgctgctt tccaaatatt ggctaattta accatagcat gtcttcaatg   96480
ttagaagcca gccctcattt ttatcaaggg ctgaagtttg ataattcttt gtgttatttg   96540
cttgtgaaaa taagtagaac aaaaaggatt agggacctaa ccttgtatcc catgtatccc   96600
agtgaacctt ttctgactta aagcttcctt tcttttttt tggagatggg agtcttgctc   96660
tgtcgcgagg ctagagtgca gtggcgcgat cttggctcac tgcagcctcc gcctcctggg   96720
ttcaagtgat tctcctgcct cagcctccca gtaattggg actacaggct catgccacca   96780
tgcccagcta attttttttt taattttag tagagacggg gcttcaccat gttggccagt   96840
atggtctcga tctcttgacc tcgtgatcca tccaccttgg cctcccaaaa agcttccatt   96900
cttagtcttg gtacttctaa gtggcattgg gtcaatagct ttctgcctaa gagagaatt    96960 ggctgggcat gatggctaac acctgtaatt ccagcccttt gggaggctgt ggcaggagga   97020
tcatttgagc ccaggagttc aagaccagcc ggggcatcat aggaagaccc catgtctgca   97080
taaaataaaa taaattagcc agacttggtg acatgcacgt attgtcccag cttgtcagga   97140
agctgaggtg ggatgattgc ttgagctcag gagatcaagg ctacaatgag ctatgatcat   97200
acaacaccag tgcactctag cctgagtgac agagcaagac cctgtctcaa aaaaagcagg   97260
ggggcatagt cacctcccta aaatattagt tgaacagtat gtattcagaa gtccagaggc   97320
tctgtatttt attaatattt tcaaggcact atttctgcag aaatcaagtc agcaagactc   97380
tttgaggacg ttacaggcag aggggctaaa gatacctttg aggaagctca agtacttggg   97440
tgggaggtga tagataaagg gtcagtagaa ataatgtctc ttttattttt ttttcccatt   97500
aaaaaatttt gttttaatag caatggagat ggggtctcac tgtgttccct gagctggtct   97560
ggtctcgagc tcctgggttc aagcagttct cccaccttga ccttctaaag tgtagggatt   97620
atagacatga gccaccatgc gtggcaaatt tcttttcttt ccttttttt ttttttttt    97680 tgagacagag ttttgctctt gttgcccagg ctggagtgtg gtggcacgat cttggttcac   97740
tgcaccctcc acctcccagg ttcaggtgat tctcttgcct cagcctcctg agtagctggg   97800
attacaggcg cccgccacca tgcccgggta attttgtat ttttagtaga tgggatt     97860 caccatgttg gccaggctgg tcttgaactc ctgacctcag gtgatccacc cgcctcagcc   97920
tcccaaagtg ctgggattac aggtgtgagc caccgctgcc ggttccaatg tctcttttgg   97980
atggtggatc ctgaagaata gctgctggtt cttggggat gctgggaa tactgtgcag    98040 gctttgtgat gggctcagca gtgaggcctg tacagtatct taggtcttgt gggcctcagt   98100
ctgctctctt ggctgttctc taccacctcc tgccattaag ttttttaagaa aaaggaatag   98160 ttttattata ttctttggta aacaaagcaa attaagaagc tttatatttt ccacatttat   98220
ttaccaaact ccctatttgt ttttctctat agtgattcag tttagagacc tattcaatga   98280
agcatgcctt gatgttgaat ttagagtcta cttttttccag aagaaaagag ccagggagct   98340
ccaatagtag tcatctcaga atataaaagt gttatagaaa tgatgtaaat caggccgggt   98400
acaggggctc acgcctgtaa tcccagcact ttggaggcc gaggcgggcg gatcatgagg   98460
tccggagatc gagaacatcc tggctaacag ggtgaaaccc cgtctctact aaaaatacaa   98520
aaaaaatcag ccaggtgtgg tggccggcac ctgtagtccc aactactcag gaggctgaga   98580
caggagaatg gcgtgaaccc aggaggaaga gcttgcagtg agccgagatc gcgccactgc   98640
```

```
actccagcct aggcaacaga gcaagactcc gtccccaaaa aaagaagaaa aagaagaaaa  98700
gaaatgatgt aaatcagctg cccttcactc tgtgttgagg tggggatgt ccctaattgc    98760
agtaggagag agcctctctt ttatctggga ctaaaagccc ttgccctaca tacctcataa   98820
ttattttagg gttaactgat tcaattgtca gaaaagaaca agctgtatct tgtttctgta   98880
catattctac ttttgtgagta ttttatttc attgctatgt gattggaatc aactcaggaa   98940
agaggaaaaa aataagatag aggttataga attctgaatt ctgaagggaa ttctgagaat   99000
tatcagtaaa atatgtcaaa atgtgatatt ttacttccac caagaattag gccatatctt   99060
tgtgtgaaaa taaattatta ttatttattt atttattttg agatggagtc tcgctctttt   99120
cacccaggct ggagtgcaat cacacaatct cggctcgctg caacctccac ctcccaggtt   99180
caagcgatgc tcctgcctca gcctcccgag tagctgggat tagaagcgcc cattaccaca   99240
cccagctaat tttgtacttg tagtagagac agggtttcac catgttggcc aggctggtct   99300
cgaactcctg acctcaggtg atccaccccc cccccccca cccttggtct cccaaagtgc   99360
tgggattaca ggcatgggcc accgcaccca gcatacggaa ataaattatt aaccagaaa   99420
attttgacta aggttttat aaatgttagg tgaaccattg ctctaaaaga tacaaaatta   99480
taacaagctg aaaagttttt taaaaatctg cattttagtg gttcagtttt tcagttgttc   99540
tgagtgctaa tagttggagt ttataaattg taagaagcaa tctacggaga ttctgtgatg   99600
aaggaatttg ttgaatgccc tgtctgcctc acagtctcag tctttatgat agagtcttgt   99660
cttctcacaa ggagagaaaa gatttgaggc tcttttgatt acttacttac ttgcttattt   99720
atatattttg cctcttgtt tttgccgcaa atacaaatgt aatggaacct tagaatagga    99780
gagacgtgtg gatccctgg taggcactgt tcttctatg ttcctggagc caagttcatg     99840
gaattacctc caagactacg gatccctggt ttctttcat catgatagga ggcatttct     99900
agaacctgaa tcttactta aaatgcatgt aagacctgca aggagtggta gtgaagtggg     99960
tggaatatat tcttagcacc agacaccttt aaaatattta agttctcggc cgggtgccct  100020
ggctcacgcc tgtaatccca cactttggg aggccgaggt gggcagctca cgaggtcagg    100080
agaccgagac catcctggct aacacggtga accccatct ctactaaaaa tacaaaaaat   100140
tagccaggcg tggtgatggg tgcctgtagt cccagctact cgggaggctg aggcaggaaa  100200
attgcatgaa cccgggaggc agagcttgca gtgagctgag atcgcaccac tgcactccag  100260
cctgggtgac agagcaaggc tccttctcaa aaaaaaaaa aaaaaaaaa aaaatatat     100320
atatatat atatatatac acacacacac acacacacac gtgtgtatat atatacacac    100380
acacatgcat atatatatac acacacatgt atatctatag atatatacat atatatgtgt  100440
atatttacat tttcttatgt cagggtctgg cttggagtgt attgtgttcc cagagcagaa  100500
ttcttttttt ttttttgag attgggtctt actttgtcac ccaggctgga atgcaatggc   100560
gtgagcttgg ctcactgcag cctcgacctc acaggttcaa gcaaccctcc cacctcagcc  100620
cctggagtag ttaggataac aggcgcacac taccatttg tatttttgt agaggcgggg    100680
ttttatcaca ttgcccaggc tggtctcgaa ctcctgagct caagcaatcc acctgccttg  100740
acctccccaa atgctgggt tacaggcgtg agccactgtg cccagccgca gagttcatct   100800
tgagaccctg acttctgcca gctctgatcc tagtgggtgg ggctctgggg ctcagtgaaa  100860
cagtcagccg ttttgcttca gagaacacaa ataagatttt ggcttgatgc tggttgttgc  100920
tggcgtcata tagtctaaaa cgtttgctgt caagaacatt ttagtaaaag ttttgttgt    100980
gctttcatct agtcaagaaa agataggaag tggcagctga cagggcagtg tcttcatgcc  101040
```

```
cctcaacctt acattggaca ctgaagtagg attgtgtttt cactggaagt cccagtgggg    101100
ccttatctcc tggatgctca aagtgcagct cagatcctgt tgggtaaaaa gtctagtcaa    101160
aatggaggac atggagaagg ccaacaggca gagctataga gctgacatag ggcattcttt    101220
gtacttccct tagccactgt actttctttc ttcctccatc tcctccttcc ctcttctatc    101280
tcattttggt ttggcctttg ggaatagtgg gttttaaaaa atatttgaac tataacatat    101340
ccttgtacca taaagaatga gcctgactgc tttacaaagg atttctataa aaagtaatct    101400
tttatactaa gagaaatgac acatctgttt taaacctgtt acttttcttc cccgggcttt    101460
gctctttctg caggtccgtt tgacatggtt cttgaaactc ctggtagcag ccatttacta    101520
gtagcactct ttatcttaga cacagcacct aaagcaattg taggtgtttt aagaacagaa    101580
agcccatctt aagcagacca gtttgaggga ttggcagtgc tgtcaagaaa caagggcttt    101640
gtggcagtct ctctaaaaac tccctatgag tccatttctt gcaaacttct ttagactcta    101700
ctgtatcttt tcatcagaag ctacctcttt gatgtgggaa gtgtcatgaa tggactgact    101760
ctctggaatt taaaaacaaa gacaatatgg caaaagaaa acctgacttt tagtactgta    101820
tgtgttgcta attagctctg tattcttggg cagactactc catgtatccc agccatccat    101880
atgccctatt tgtaaggatc taatgagatg atattgtgaa gaatgccttt gtaaactgta    101940
aattgctttg tgaataaaga tactatctct gataaacagt accagttctc agccaccaat    102000
aacctgatac tcccatactg tgtttggaag aaacacaaaa caatgaagag taattgtgac    102060
ttttcaatgt gagttgtatt cacaaagctc atatacttt tccctgcctt ttgatactgt    102120
ttatcgcttt ctgtgttgta atgggaagat cacacagcaa tcattttctc agtacaaagt    102180
ataactacaa ctgagcttgc attgaagatc tttaacaaag atgcaaagct gctgtccaga    102240
aatgttttct ttccatttc tcttgtacct cccagtattt taagaatcct tgaggctggg    102300
caccataact cacgcctgta atctcaacac ttttgggaagc tgaggcagga ggatcacttg    102360
ggcccaggag tttgagacca gcctgggcaa catagtgaga ccccccatctc tacaaaaaaa    102420 tttaaaaatt agctgggcat ggtggtgtgc acctgtggtc tcagctactt agggaggctg    102480
aggtaggagg attgcttgag cctgggaggt caaggctgca gtcagtcatg attgcaccac    102540
tgtgctctat ctagcctcca acctgggcaa cagaagcgag accctgtctt ttttttaaaa    102600
aaaaaagact atccttgatg attggttttg agccaacgga atgggagcat atggtagagt    102660
ttcaacactc tgaccctagt ccttctgaca ggcagtcaca aaatgagatc atgaagtctc    102720
taagagcagc tgatgaaaaa ggaaatggga atgtagatgt tcaatcagca gccctccaga    102780
cccagagttt gctcctctgt ggtgtctcta ggtggagaat aaggacttga tttgccattc    102840
tggagtgcaa atatctagct ttttgcagct tcatattaag atttcttgaa atgtacttag    102900
taatatccat gtgtgacttt gccaagtgat ggctttgggc tggaaaggat tttagcaggt    102960
tttagtctaa tttaagccta atctaacact gctgagaaag gaggagatgt ctttggtttt    103020
actttctaat atatggtacc tcttagccgg gtgcagtggc tcatgcctgt aatcccagca    103080
cttcgggagg ccgaggcagg cgatcacttt aggccaggag ttcaagacca gcctggccaa    103140
catggtgaaa ccccatctct actaaaaata caaaaattat cccggtgtag tggcgcacac    103200
ctgtaatccc agctacttgg gaggcagaaa caggagaatc gcttgaacct gggaggcaga    103260
ggttgcagtg tgccaagatc atgccactgc atgccactcc agcctgggca acagagcaag    103320
accctgtctc aaaaaaaaaa aagagagatc tatctctctt ctttttatat acatatacat    103380
```

```
atacatacat acatacatat atgtatgtac acacatatat atatatggcc cctcttttt  103440
tatttgagtc ggaatctggc tctcttgcca ggctagagtg cagtggcatg atcttggctc  103500
actgcaacct ctgacttcct ggttcaaacg ttctcctgc ctcagcctcc cgagtagctg  103560
ggattacaag catgtgccac cacacccagc tcacttttgt attttagta gagacgggat  103620
ttcaccatgt tggcagggat ggtcttgatc tcctgacctt gtgatcctcc cacctcagcc  103680
tcccaaagtg ctgggattac aggcatgggc caccgtgccc agcctttttt ttttttttt  103740
taaagagacg gagtctcact ctgtcaccca ggctggagtg cagtggcgtg atcttggctc  103800
agtgcaacct ccacctcccg ggttctagca attctgcctc agtcttccga ctggctggga  103860
ctgcaggtgt atatcaccgc aaccagctaa tttttgtat tttagtagag acagggtttc  103920
actgtgttgc ccaggctggt ctcgaactga gctcaggcag tccacccgcc tcggcctccc  103980
aaagtgctag gattacaggc gtgagccacc gtgcctggcc tatatggtac ctctttagga  104040
gccagacctg gttaatcaga cacatggctt tcatgactcc tttgcttgag tagcttaata  104100
actcaataaa tcaaaagatg aataaatatt ctaatgtgtg aagatactct aatagataat  104160
aggcaattaa gaatggacat ccacggctgg gcgctggggc tcatgcctgt aatcccagca  104220
ctttgggagg ctgaggcggg tggatcatga ggtcaggagg tagagcccat cctggccaac  104280
atggtgaaac cccatctctg ctaaaataca agctactcga gaggccgagg caggagaatt  104340
gctcgaactt gggaggcgga ggttgcagtg agccaaaatc gcatcactgc actccagcct  104400
ggcgacagag cgagactccg tctcaaaaaa aaaaaaaaag aatggacatc tactgaaggt  104460
gattgcatca tcctacccat tcattaatct aactccctac aggatacttt cctaggagac  104520
actgacaggt ctgttttctg aaatccagag aaaggcagca atggggaggg gtgcagtgta  104580
tgtatgtcat acctgtgctt ggtatatctg agttgcctgt gtatgatagc agctgggaa  104640
tcaaatcata gataaattgt tctcatacag gtttgtccta tgactaccta ttcttattaa  104700
acaattggct atattgaccc ttttggttt tggaaaaata ataataattt ttttaagaga  104760
gaaaagaaa caattggcta cccttcaaca gtgatgttaa aaccatttca cattctttag  104820
cagtggtcac tgtcctatgt ctaactatgt gcaggttgag aaaaaggact gcccgagtta  104880
tagatgattc tgtgagaata agaaatcatt gcttttgtaa cacatgaggt aaaagtaatc  104940
tcaaagttga catgctgatg gggactcctg gcaagggag ttccctgccc tcaacaaaag  105000
gtcatccaca gctactggaa cattttttgtt gtctgagaag tataaagtgc cttagaaata  105060
cctgaatcca ttaatgcctc cagttggtga aatcagaatt tgcaggtgac tgaaattgac  105120
agtagtgcct tgttcttact cactgttcaa atgacaaccc acatgtttta tggattgggt  105180
atacagatgt atgctctaac agcagtatct ccctccagag ccactgtgta ccaagcacca  105240
ggtcctccag ggatagttgg ctctattcag tctttgattc attcaacaag agcttactaa  105300
gctccttttt ggtaccagat actcttgtt gctgaaaata aataaaaggc cagcaagatt  105360
aagtagactg tgagatctgg accagtaatt tgacaacaca agtactgtc gtaaagatac  105420
agtttctgat gtgtagtgac cattccgtat gaaagcttag tctttcagga gattaaaatg  105480
ggtggtggaa tattcctacc tagcaagcaa gcaaggtgaa atgagtggct gtttgactcc  105540
cacctgctga tgctggtctt ttttggttcc tagggcttat aatgatcaac atttcttgag  105600
ccctcactat attctatgct aagctctttta catgtatgaa tttacttaat cttcacaacc  105660
accctaagaa ataggtactg ttgtccttac tttacagatg aggaaatgga agcacaaaga  105720
agttaaggac cttgctgaag gtcatggagt agaggcagga ttcaaattta gggaactcag  105780
```

```
cctacagtcc atgctcttaa agatgttata tcctgtctct gggcttagaa ggggttcatc 105840
ttaggccgga cacagtggct cacgtctgta atcccagcac tttgggaggc caaagcgggc 105900
agatcacgag gtcaggagtt cgagaccagc ctgaccaaca tagtgaaacc ccatctctac 105960
taaaaataca aaaattagcc aggcatggtg gtgtgcgcct gtagtcccag ctactcggga 106020
ggctgaggca ggagaattgc ttgaacctgg gaggcggagg ttgtggtgag ccgagatcgt 106080
gccactgtac ttgagagtga gtgacagagc aagactctgt ctcaaaaaaa aaaaaaagac 106140
ggccaggcgc agtggcttac gcctgtaatc ccagcacttt gggaggccga ggtgggcgga 106200
ttacctaagg ttgggaattc gagaccagcc tgaccaacgt ggagaaaccc cgtctctact 106260
aaaaatacaa aattagccaa gcgtggtggc atatatctat aatcccagct actcgggagg 106320
ctgaggcagg agactcgctt gaacctggga ggcggaggtt gcagtgagcc gagatcacgc 106380
catagcactc cagcctgggc aacaagagcg aaactctgtc tcagggaaaa aaaaaaaaa 106440 aaaaggaggg ggcgcttcat cttgactaac ttcctgcatt ggtggagctt gatagagtgg 106500
tccttcccag atccttccct gcatacagag cctgtctctt ttctgattgg tccctaaggc 106560
cagattacct gtccctaata ctgagcagaa gctggtgaat gaaacaggag atccctcagt 106620
caaaacaaaa ggaaaagaa aaatgaaaca ggagatccct tctctacagc ccagatgtaa 106680
gtccagctgt gccttcacc acctgggtga ccccacctct gtgaacatag gtcctcatct 106740
gtaaagtgta gataatgtta tttcatcgga tcatttaggg gattaaataa gataatgtac 106800
ttcgtggttt ctggctctta gtaagtgctt aataaatgtt agcgattttt attatcattg 106860
tccttagcct tgagaacaag ccagggaata tgtgtctcaga ccagatgcta agacctaggt 106920
agatgggcaa ttttccttgg ttttgacaag acaataattt tatcctgtgt atttctcttg 106980
acttttttga tgtgaaaagc agagaggtaa agcattattt gacagatgta tggattcaag 107040
caagaaactg aggtccaatt gcaaagaaat ggcttgtata actcagagcc ctgtctgagg 107100
aaacacagag gaccctagag ggcggagaat gaacacagcg caggggctag ttccagagtc 107160
gcattctcgg ttagttcact ttcaagtgtg ggtgagggtc ccttgtcagt aggcagagaa 107220 ttttttttccc ctgcaccaac acatacctgc tgcctagtgt ttattaaaca aaactttatt 107280
ttaatgtgaa atagaattca tgacttgtcc aaaatggaga ggcaagggag ctctttaaca 107340
ggcttgttga gccccttttc ccacctgttc ctgtgccaga cttttcccaaa ggcttacttg 107400 ccaatggttg ctcctcagat ctcagggcta gctcactcta taggctccaa gccagagtga 107460
taccgccgcc gccgctgttg ctcccaccag ccaatcagtt tcctgctgta aggatgtaac 107520
ttgctgtgaa gctttcacct tcctcctttc ttcctgtctt caatgttgta tgtctttgtc 107580
ctggtgcttt tgccatacag ccagtgtttc aagaaaatt tcaggcact aaagttatag 107640 cccttactac ctttccaagg agatgtgaga tagctgtgga aaagaagagg gctcctctgc 107700
ctctgtgcag aaggaacagt ttacttcttg atagtgtgct agctcctgag ctaggtgggg 107760
gacttgctgg gattcaagag agtgcattac ctgacctctg gacaagtaga ctgggcatag 107820
cctgcccaag gacagcaccc taacctgcag gaaccaaggc cgaagactga tttcaccttc 107880
tcgtactccc ctttcctaag ctaaagcttg ctctgtaaca ctgccccagg tctgtggctt 107940
aaaacagcca tttcctttca ccagtgaatt aagctcactc tttataaaat gtttcagctt 108000
ggggattgga aaggctctct gtgcctttct gtctctgtct gtttctccaa gggttgatgt 108060
tgatggcttc tgtctttgtc tttacaggga actctaatga tccaggacaa agaagttacc 108120
```

```
ctggagtatg tatcaagcct ggattttggg tactgcaaac gagtaagtac caagaatccc    108180
tttctttaga agtaagtatc tggaataaca gctcctccat atctctagga aggctgcctg    108240
ctaacatgca ttcccaagga caaagctctt cttcctcagg tcacttcagt tgaacaggag    108300
gaggtcaaga caaggtcatt cataatttct ccttcccagc tgctacatgt ggccatagag    108360
agttctggac ctgcaattgg agacactttc ccaaggacat gtgccattat ttctatcagt    108420
tataaaaata acagttcctt gacatataat atcttctcac ctctcctggg ggtggtcata    108480
aaggaattct tggttggaaa agtaggtttg gagagactag ttctttggga gtcgtacatt    108540
ttttggatat tcttgggttt ccaagggtat agaacttcag acaccatggc attttacctc    108600
tattaaactc catattctct tagagtggga tatttaaaat tttaggctat actcttttt    108660 tttgaaacgg aatctcattc tgttgcccag gctagagtgc aatggcgtga tttccactca    108720
ctacaacctc tggctcctgg gttccagtga ttctgctgcc tcagcctccc gagtagctgg    108780
gattacaggc acttgccacc tcacctgcct gattttgta ttttagtag agatggggtt     108840 tcaccatgtt ggccaggctg gtcttgaact ccgacctcaa gtgatccacc tgcctcagcc    108900
tcccaaagtg ctgggattat aggcatgagc caccgcgctg gcctgtttat ttatttattt    108960
atttattttg agacagagtc ttgctctgtc gcccaggctg gagtgcagtg gcgcgatctc    109020
agctcactac aacctctgcc acccgggttc aaacgattct cctgcccag cctcccgagt     109080 agctaggatt acagttgtgt gccaccatgc tcagctaatt tttttgtagt ttttagtaga    109140
gatggggttt caccatcttg gccaggctgg tcttgaactc ctgacctcat tatccaccca    109200
cctcggcctc ccaaagtatt gagattacag gcttgagcca cggcacccag ccggctatac    109260 tcttttaaagg tccagtttga ttgcagtgag catgaaaata taatttgttt tcattgctac   109320
tacttagtat caaaaataat tatgaaaaat atataaagtt tctgagcccc gacacactaa    109380
aaatgttaca gtacttgaaa aaatttagta aagactttag cttgacattt gttagtctcg    109440
gtagaattga cattgtgtta gtctcggtag aatacaactt gaagagctat gattgttatt    109500
agccaaagta ctcatatttc atggatatac tcccttatgg tgtcattta ggaagatatt     109560 tcgtttcctt ttattgagat aaaatacatg taacattaca tttgccattt taaccatttt    109620
gaagcattaa ttcagtgaca ttaagtacct tcacaatgtt gtgcagctat caacactact    109680
tcctagaact tctttttttt ttttttttaa ataagagatg ggatctcact atgttgccca    109740
ggctggtctc acagtccctg gctcaagtca tcctctcacc tcaacctccc aaatagctgg    109800
gactataggt gccatcatgt ccaggttagt tccagaaatt tttttttct gtctttttt     109860 tgagacagga tctcactctt gtttctcaag ctggagtaca gtgatgtgat catggctcac    109920
tgtacccttg acctcctgtg ctcaagcgat cctctcacct tggcctcccg aagttctggg    109980
attacaggtg tgagctgcca tatctagcct cagatctttt ttaaaccctc aaaaggaaac    110040
ctcttatcat taatcagtaa cttcccactt cttcttcccc cagtcccag aaaccattaa     110100 tctttttct atctccatgg atttgcctat tccggatatt tcatataaat ggaatcaaaa    110160
tatgtaaact tttctgttgg cctttcacct agcatgtttt cagagttcat gtatgttgca    110220
gtatttatca gtacctcatt tctttttgtg gctaaataat atgaatatat cacatttgt    110280 tcatccattc ctcaattgat ggacatttgg gttgtttcta ccctgacttt ggtgaataat    110340 agaaccttg tgtgctagtt tttgtttgaa cagctgtttt cagttatttg ggggtatgta     110400
tccaggagtg gaattgctga gtcatatggt aatttatat ttaactcttt gaggaaccat     110460
caaactgtat ttcttttatt ttattagcaa accttttcat agaccacagc tgtaccattt    110520
```

-continued

```
tatattccag caatatgtaa gggcttcatt tctccacctg cttgccaaca tttgttcttt    110580
tcccttatt tgataatagc catcctaatg ggtatgaaat aatatctcat tgtggttttg    110640
atttgcattt tcctaatgac tttgagggtt ttttttcatg tgtttgttgg ccatttgtat    110700
acctcctttg gagaaatgtt caaccaagtc ctctgcccct tggaattgat ttgcatgtat    110760
ttttgttgtt gagttataag agtactttat attttctgga tattaatccc ttatcagata    110820
tatgatttat aaatattttc tatgtgttat ctttcacttt cttgagagta tccttctaa    110880
agaaaaaaaa agagagagag agagataagg tgtggctcat ggctgtaatc ccaacacttt    110940
gggaggctaa agtgggcaga tcacttgagc ccaggagttc gagaccagcc tgggcaacat    111000
ggcaaaaccc catctctaca aaaaatacaa aatttaactg ggtgtggtgg tgcatgccta    111060
tgatcgcggc tactaagcag gctgaggtgg gaggatcacc tgagcccagg aggtcgaggc    111120
atcagtgagc tatgatagtg ccactgtact tcagtactcc atcctgggtg acagagcaag    111180
accttgtctc aaaattttt ttagctgggt gtggtggctc acgcctataa tcccagcact    111240
tgggaggcc gaggcaggcg gatcatctga ggtcgggagt tggagatcag cctgaccaac    111300
atggagaaac cccatctcta ttaaaaatac aaagttagct gggcatggtg gcacatgcct    111360
gtaatcccag ctacttggga ggccgaggca ggagaatcac ttgaacctgg gaggcagagg    111420
ttgcggtgag ctgaaattgc actattgcac tccagcctgg acatcaagag tgaaactcca    111480
tctcaaaaac aaaaaagaaa aattttaagt ttattatgta cctattaaaa tttttttgta    111540
attaaaacaa atgctaatgg cggtattatt cataatagcc aaaaaatgga ataaccaaa    111600
atgtccattg gctgatggat ggatgaacaa gttggcatat ccatacaatg aaatgctatt    111660
tgacaatgaa aaggaatgaa gtactgatgc atgttacaac ctagatgaac cttgaaaata    111720
ctatgccaga cacagaagac catacattgc acaattccat gtccctaggg gtaagaatgg    111780
gggaggtaac tccactagat ttcttttggg gtgatgaaaa tgtttcagaa ttagattatg    111840
gtgatggttg cactatacat ttactaaaaa tcattgaatt gtacacataa aataggtaaa    111900
ctttatgggg tttgtttttg tttttaagag agagtcttgg tttgtcaccc aggctggatt    111960
gcagtggcac aatctcggct cacgacaacc tccacctccc aggttcaagt gattctcgtg    112020
cctcagcctc ccaagtagct gggattacag gcgtgtgcca ccatcccag ctaattttg    112080
tattttaat agagatgagg tttctccatg ttggctaggc tggtcttgaa ctcctggccc    112140
gaaatgatcc aacttcctcg gcctcccaaa gtactgggat tactggcatg agccatcatg    112200
ccaggcctgt tttatgctat ttaaattata cctactaagg ttaggatcct aactgccact    112260
cactaactga agtgtcacat actttattcg ttggcatgta tatactcagt tgtcccagca    112320
ccatttgttg aagagactat tctttcccca ttggcacttt ccccattgtt agaaatcagt    112380
tgaccataat ctataggttt attcctagat tctcagtttt attctgttga tctatatgtt    112440
tacaaatagc accagttacc acagcagctc tcctgtagta acaactctcc aatcccagta    112500
gcttaaaaca gcaagcatat tcttcactca cattacatgt cagggactat gggttgtttg    112560
ctacagttct gttccacgtg gcttctcatc ccaggaccca ggcggaagaa acagtctcaa    112620
tatgggcag tgtccctctg gctaagggag agagaggttc attcacgcaa gcagtggctc    112680
ctaaggcttc tcttagacct agtgtaggtc atgttcactc atgttttatt ggtgaaagca    112740
aggaaggcac atggccaagg ctgacaatgg agagaggaag tatactcacc ctgtgggaag    112800
gcataacagc catttggcag tgggcagggg tgtgtgtgtg tgtgtgtgtg tgtgtgtgtg    112860
```

-continued

```
tgtgtgtgtg tgtgtgtgtt tataatctgt ttatagggaa gggaacaatg aaataactga   112920
ctgtagtgat cttcctcaag tgagttaacc tctctaggcc tcagtttcct catctacaaa   112980
atgaggagat aagagtaccc atttcatgaa gtttattggg gttgtcagga tcaataagtg   113040
atgacatata cagtaggcca aatacatggt atgtactatt taagaattag ccggctgggc   113100
gcagtgactc acacctataa tcccagcaat ttgggaggcc gaggcgggca gatcacctga   113160
ggtcgggagt tcgagaccag cctgaccaac atggagaaac cctgcctcta ctaaaaatac   113220
aaaattagcc aggtgtagtg gcacatgcct gtaatcccgg ctactcggga ggctgaggca   113280
ggagaatcgc ttgaacccgg gaggtggagg ttgtggtaag ccgagatcat gccgttgcac   113340
tccagcctgg gcaacaagag tgaaactccg tctcaaaaga aaaaaaaaa aagaattagc   113400 cactgctact attgttattg ttttctcctc aactccatct ggcagacctt tactcgccct   113460
ataaggccct cctcaaatac catcctcttt atagttctta ctcttttatt tcctgccaac   113520
caagtttctg cccccatggc atttggaagc tcagtggcaa aagttcaggg atttcggggt   113580
tgggcagtgt gcttgacttt ttgttcacat gttcagacaa aaataattac attcacatta   113640
aaaatgtctc ttaccttatt ctgggctagt gaatgttccc tttcaatgtc ttttagatag   113700
ctgccagaga cactatctgt atctcttcct cctaccttgt acctcattat cagtgtttga   113760
gaaaggagtt gataactgaa ttctcagttc tagccaaatg tgaatgggga tctcatagtc   113820
agttcaggcc caagttttgg gtgcagactg taaatggctt tgggacaata atattctata   113880
aaccatgtaa cagtagtttt ctaggcatat ttcctatagg aatctttatc cagggcaaag   113940
gcatttgggc tgcaccaaag tcccagatgc cttgttataa ggtagctctc aaacagtagc   114000
tcatcagatc ccatctgcca gctctaatca gtggggaata tcagattctt tttttaagct   114060 ttgagggggat ctgggatatg gcttgtttct ttcattttttg ggggtttca ctttgttaga   114120 tatacataag attttttaaaa atgttttcag tcaaattgat ttccttcttc cttacagtgt   114180
aaggcaaaca ttggtgggca ccgatcttcc tgttcattct gcaagaaccc aagagaaggt   114240
gagtggcgaa agtggtagca gttttttatct cgtgcattga gcaaaacaaa tttcatgttt   114300
tccttggctt tgaagaatta tcatccctaa atccaagttg atctacaaac cttttttttt   114360 tttttttgaga tggagtctcg ctgtgttgcc caggctggag tgcagtggca ccatcttggc   114420
tcactgcaac ctccagctcc caggttcaag cgattcccct gcctagcct cctgattagc   114480 tgggattcca ggcatgtgcc accacgccct gtagcccggc taattttttt gtattttttag   114540 tagagacggg gtttcaccat gttggtcagg ctggccttga actcctgacc ttgtgacccg   114600
acccaccttg gcctcccata gtgctgggat tacaggtgtg aatcactgca caaggcctgc   114660 aaaccttttat ttatttattt attttttgaga cagagtctcg tactcaccca ggctggagtg   114720
cagtggcgca atctcggatc actgcaagct ccgcctccca ggttcacgct gttctcctgc   114780
ctcagcctct ctagtagctg ggactatagg cgcccaccac catgcccagc taattatttg   114840
tattttagta gagacggagt ttcaccgtgt tagccaggat ggtctcgatc tcctgacctc   114900
gtgatctgtc tgcctcagcc tcccaaagtg ctgcgattac aggcgtgaac caccacgacc   114960
ggcccaaacc tttcaaaagt gcaatttgag ctaggcatgg tggctaacgc ttgtaatccc   115020
agcactttgg gaggccaagg caggtggatc acctgtggtc aggagttcaa gaccagcctg   115080
accaacatgc cgaaaccctg tctctactaa aattacaaaa attagccaca ggtgtggtgg   115140
cacatgcttg gaatcccagc tcctgggag gctgagacac tagaatcgct tgaacccagg   115200
agtcagaggt tgcagtgagc tgagatctcg ccactgcact ccagcctagg caacagagtg   115260
```

```
agaaaaaaaa aattgcagtt tggtgcccaa cttaacgtaa cctgttagta aatgatttca    115320
gatcttattt tcaccagagg aaagagatag ggttgtgggc tcctaggcta aagtggctaa    115380
gtgggcagct gagcagaggt cagtatattg ttatttggaa tacatttaag gattaaggat    115440
gttaggttga aaaagagtct ttatgacatc agtctgtgtg gcaaaccttt ctcccactcc    115500
tacttctttg aagttattgg gaatcatttg ctctattgtt ttctctttta cattctgtaa    115560
gcatttcagg attttcaaga gaaaacatt tgttaaaata acagtaaaaa cataaatagg    115620
agaaaataat caggatgtgg ggaacatttt attattttag aggaataaaa ctaccagctt    115680
ctcaagcact tatctttaat gtaaatttct ttagagaaat ttcaggtagg caacttcgaa    115740
gagtcagaca catgcatcca taacaacagt cctgtagtca tcccttaagg aaagccacag    115800
catgaccata aaatatagtt cagtgcaggg attcaggtag ccttctgttt gttgcaaggt    115860
tagagtttaa tgtgcctaca aggagtttct taggtgggct tttgtcctct tgtggagatt    115920
ttactctggt gaagactgaa aggcaggtgt tctgaaaatc tttagggaa ggctgtgtat    115980 gttctagaaa ccaaaccaaa atgtgggaag gaggatgaac aactgagatt tttgcttgtt    116040
aggtcacttc aggttaggca aagttgtgtt ttttccccc cacaagaaac acttttttc     116100 aaagctattc cagcaaatga atagatagtt ttttgttttt tttctttttt tttttgagac    116160
ggagtcttgc tctgtcaccc aggctgaagt gcagtggcgc aatctcggct cactgcaagc    116220
tctgcctccc aggttcacgc cattctcctg cctcagcctc ccaagtagct gggattacag    116280
gcacccgcca ccgtgcccag ctaatttttt gtattttcag tagagacagg gtttcactgt    116340
gttagccagg atggtctcga tctcctgacc tcgtgatctg cccgcctcag tctcccaatg    116400
tgctgggatt acaggcgtga gccaccgctc ccggccatga atagatagtg tatgaaaacc    116460
actgggcacc ataccactaa gatgagacag ctttaatctg gaaacctgtc actgctatta    116520
tgtaatctct atattgctct catataatac ctcttttga gccacatgga ttccagtgaa     116580
ccctccaaga atgaattagt tacaagaatg tgcccctaat tataaaacaa actataaaga    116640
caaattatcc tgctgtagta ggacatttga aataaatcat ttatattttg aaggacgtct    116700
gcccattatg tttatttgca tataaaggag ctacgtgcag atagggtctg ttcctagctt    116760
cactggagga gggcctgtgg tcttacagga tatgagtagc tgtttgagca ctgtaacact    116820
ggaagaagca aggcttctag atgtgtgttt gggatatgtg tttctactaa accttaagta    116880
agggccatat cttcggtaat tttgtcccca gatgtgttgt tatcattgat tatgatagtc    116940 aggtcaagg tgtcatgaag gatttgttat atttaaatgt ttagtaggtg atatagagat     117000
ttcataagat tacatttttt aaatgcttgg atagtttctt ctgtgaacta tttcatgtcc    117060
tgtctcagct tcacttaaaa tattttgtca ggaactgtca gaggactttt tattagatat    117120
ttctgagata atattaaaag cattccaggc cgggcgtgtt tgctcacacc tgtaatccca    117180
gcactctggg aggccgaggc aagtggatca cctgaggtca ggagttcgag accagcctgg    117240
ccaacatggt gaaaccctcgt ttctactaaa aatacaaaaa attacctggg cgtggtggtg    117300
ggcacctgtg atcccagcta ctctgaaggc tgaggcagga gaatcgcttg aacccgggag    117360
gcagaggttg cagtgagcca agatcatgcc attgcacttc agctgggcaa caagagcaaa    117420
actccgtctc aaaaaaaaaa aaaaaaaaaa aaggcattcc agtatgagta tttgctggca    117480
ggtaaggaga aattacagta gcagtgtttt tctttttttt tttttttga taaagctttc    117540 tagagattct ctttgtttct gttccactag tgacagaggc caagcaagaa ttaataacct    117600
```

```
accctcagcc tcagaaaaca tccataccag caccattgga aaaacagccc aaccagcccc 117660
taagaccagc tgataaggaa cctgaaccca ggaagaggga agaaggccaa gagtcacgct 117720
taggacatca aaagagagaa gcagaaaggt atctgcctcc ttctcgaagg gaagggccaa 117780
ctttccgaag agaccgagag agggagtcat ggtctggaga gacacgccag gatggagaga 117840
gcaaaagtaa gtagtttgtc agggcacata ccagactgtg atcatcacaa tggagcatag 117900
atggccaatg ttatgtccgg gagctatctg ctttccagta ccctgagaga tctgtgcatg 117960
acctgatgac agaggccatt gctgtctgtg gaccttcctg tactgcttaa aggaatctat 118020
gcccttcaaa tagtaaattg ctatatgaat gcagtaaggc atgattttag atttctaagt 118080
attggtgaag aaaagtatgc agtatttatt tgtttagcat ttttttacag aaccagcctt 118140
gctagtagca tctatagtaa aaaatgacag tcagattctt gggacttcaa aaatttatct 118200
ttctctccct tgtgttgccc ttctcccatt tatggttgat tcagctatca tgctaaagcg 118260
tatctatcgt tccacaccac ctgaggtgat agtggaagtg ctggagccct atgtccgcct 118320
tactactgcc aacgtccgta tcatcaagaa cagaacaggc cctatggggc atacctatgg 118380
ctttattgac ctcgactccc atgcggtgag tttcctccac cttggattgg cctagagaca 118440
gatggctaaa gaaccttcaa gaaggtttga ctggggggccg ggcctggtgg cttacgcctg 118500
taatcccagc actttgggag gccgaggtgg gtggatcacg aggtcaggaa atcaagacca 118560
tcctggctaa cacggtgaaa ccctgtctct actaaaaaat acagaaaaat tagctgggcg 118620
tggtggcagg cgcctgtagt cgcagctact cgggaggctg aggcaggaga atggcgtgaa 118680
ctccggaggc ggagcttgca gtgagccgag atcgcgccac tgcacttcag cctgggtgac 118740
agagcgagac tctgtctcaa aaaaaaaaaa aaaaatttg agggacttct tgatcatttg 118800
aattcttgtg tgctacctga tatcataatc cctcttgctc tctcctttgg gtttattgtt 118860
cattcaggtc aggtgacagc cctcaaaagt taggatcccg tctggttttc taggttcatt 118920
tttttcttgt gtcatttact gtttccaact tactcgcttg tgaagaatct gagtactgaa 118980
tccttcatga ttttagtgaa ctttctgatt tattttgtcc agccacagat ggttttatat 119040
ttgatgataa acatttcct cttttttcctc aaagtattta tagattcctg tggcttaaat 119100
ttttagttgc ggggccttt tctatggaag taaggtgaag ataatgaaag tcattggtat 119160
ttcttagatt tttcatgctc aaaagtcaca agggactttg taaactgaat ctgattgatg 119220
ataattgcaa cctaaaagaa gaggatttga atttctgaag tttatgccag aactgacatc 119280
tattctgatt cctgttccaa tcagtccttc attaaaagtt gcctgtttct gccagtatgc 119340
tcttactgtt aaaattttga cagaatataa tgtagtaaat ttatcctctg agaaggaaaa 119400
tccacgttca cttctctttc aaaggagaat ttttctgtct ttgggttctg gcatttctg 119460
tctctgggtt caagtgtgtc tggttctata ggaagctctt cgtgtggtga agatcttaca 119520
gaaccttgat ccgccattta gcattgatgg gaagatggta gctgtaaacc tggccactgg 119580
aaaacgaagg taaggcagaa gggtgaggat ctcttgtgct gcccccactt gtgtttttga 119640
gaggaaactc cttttcctgg ctggaaaaac agtaaagcat gatgttttcc taacatggac 119700
tgcttcagat aggtgtttat tacagtttct ttctgaagcc tgacttgtcc tgactctcga 119760
attgttttct ttcttgaata atactaggta cttttgtcct ttcccttttg actgtctggt 119820
atctttgggt cccaaatggc ctggcgtggt agcacatatc tctattccaa gctactaaag 119880
aggctgaggc gagatgggga gcgggttaca tgagcccagg agttctaggc catagtgtgc 119940
aatgaagatg cctgtgaata accactgtac tctaccctgg gcaacacagc aagaccctat 120000
```

```
ctcttaacaa aaaaatgatg gtacagtttt ggatgtgcag acacatgtca atacattctt   120060
gccccttgca atcctaggaa aatgctgtcc tggcttttcc ttcccctgac cttgtgcata   120120
tttccatagc actgggaaat ctaatttctc tttcctcctt cactcatctt gacccaggag   120180
tggtaacttg gaaatggcca tgtcagagaa acaggcttac caatatgggg catatcttgc   120240
tctagcaccc tccacttaat ggctgttttg ctccaccact tggctttgta agagtcttac   120300
tgctcattgg gcaggcgtgg tggctcacgc ctgtaatctc agcacctggg gaggccgagg   120360
cgggcagatc atgaggtcag gagattgaga tcatcctggc taacacggta aaaccccgtc   120420
tctactaaaa atacaaaaaa aaaaaaatta gctgggcgtg gtggtgggca cctgtagtcc   120480
cagctacttg ggaggctgag gcaggagaat ggtgtgaacc caggaggcgg agcttgcagt   120540
gagctgagat cacgccaccg cactccagcc tgggcgacag agcaagactc cgtctcaaaa   120600 aaaaaaaaa aaaaaaaag agtcttactg ctcattcttt caggagtgtc tggaccaccc   120660
aacctgcttg ctgtctaggt tggttccttt ccctgcaaaa tgaggaacag aggatttctc   120720
gataggaact gtaggattaa gtactcgtca aatgccactt ggtagcagcc ttaagaattg   120780
ttgtgttatc tgttgcagaa atgattctgg ggaccattct gacccatgc attactatca    120840 ggtaggctgt aacaggtggg gagtgctcta ttaaaatcct caggtgacta aagggtgat    120900 cttgaatttt ctttagtggg tgactgttaa ggtgaatgac cattggatag ttctgtaatt   120960
ttaacttgcc tttctgtgat agggtaaaaa atatttccga gataggaggg gaggtggcag   121020
aaattcagac tggtcttcag atacaaatcg acaaggacaa cagtgtaagt aacctttgtt   121080
ttatttctgt tgctcttttt tgcttgactt gctactcatt acttgacatc tgtgtgatca   121140
cagttggcaa gatacactgt tgactgaggg tgctcatcca gagagaggca tctgtagatg   121200
cacctatttg tgttggtcac cctaattctt gggttcttga tgagtctcca gtaagggctt   121260
cattggacag agactaacat tggctctgat cttgttacct ttagcatcat ctgactgcta   121320
catatatgat tctgctactg gctactatta tgaccccttg gcaggaactt attatgaccc   121380
caatacccag gtgagtttgg ggctttttt tttttttttt tttttttacc tctgtcaatg    121440
attcttttga gaaaagcacc cataaatttgc tacttgagga ttttattccc tggattctct   121500
ggatgctcat tgcatgaaaa gtggaaaagt ttagatctat ggaaacagaa ctgttgccta   121560 tatgaaaat cagtgccttg tggcaataca ggtaagaaca gtgttgctct tgaaaaagtg    121620
gacagtgggt ggtctgaatg tgtcctggtc cctggagtgg gttttagat tgatgtggac    121680 tcttcttaga cttgtaagta aaaaagttgt ttcttcccct aaaagggaac tgtgcgcctt   121740
agacctggaa ttgctgggaa actgaaacat tctgtagact tacttgtttc caactgtatc   121800
gcagcaagaa gtctatgtgc cccaggatcc tggattacct gaggaagaag agatcaagga   121860 aaaaaaccc accagtcaag gaaagtcaag tagcaagaag gaaatgtcta aagagatgg     121920 caaggagaaa aaagacagag gagtgacgag ggtaagagga attgttaatt tgctgtcttt   121980
tgccacatag ttattaaaat gttggaggta cgaacagagg atatctatgt ttgcaagtgt   122040
aaagtaactt taaaaatact ctgtcagccg ggcgtggtgg ctaacgcctg taatcccagc   122100
actttgggag gccaaggcgg gcggatcatg aggtcaggag atcgagacca tcctggccaa   122160
catggtgaaa cccctgtctc tactaaaaat acaaaaatta gctgcgtgtg gtggtacacg   122220
cctgtagtcc cagctactca ggaggctgag gcaggagaat tgcttgaacc ctggaggcag   122280
aggttgcagt gagccgagat cgcgccacta cactccagcc tggcaacaga gcaagactct   122340
```

```
gtatcaaaaa aaaaaaaaaa acctctgtta atgagtattt ttacctggtg taggcaattc   122400
cctcacctct tatatcccaa ctctctcttt tacaaatggg aaaactatgg atggtagaac   122460
aaagtggccc agctcaaatc ccaacacctc agctccatac attttcactt ttctacattc   122520
cttttttagt gtttgacttt atacacattt ctctagttgt aattatagca ggagatactg   122580
tttagtcact ttttatccta agtatttttt ccatgtttct atatactcta ttattttttaa  122640 tgcccacatg gtaaaaattc acggtataac tgtaccttca ttttcttcat ctctcctaca   122700
ttatttgtct tctctttcta atcttttctt tttcctttttt tttttttttt ttctgagaca   122760
aagtcttcct ctgtctccca ggttggagtg cagtggcatg atcatagctc acttctacgt   122820
caaacccatg ggcttaagca gtcctcccac ctcagcctcc caagtagcgg ggactacagg   122880
catgagccac catgaccagc taatttttgc ttttttgtag agacaggatc ttgctagatt   122940
gaccaggctg atctcgaact tctggcctca agtaagcttc ctgtctcagt ctcccaaagt   123000
gcttcagtta caggcaagac ccaccttgct cgcctctttc taatcttata ctgtcataat   123060
atataacatt tagcattttg tttcttcttt taaattactc cctatgacac attttcagaa   123120
tcagagatga tgaacatttt tacatctaat acaaaatcaa attattaggc agggtgcagt   123180
ggctcacacc tgtaatccca gcacgttggg aggccaagac aggtggatgc ctgagtttag   123240
gagtttgaca ccagcaacat ggtgaaactc catctctacc aaaaatacaa aaaaattag    123300 cctactgtgg tgatgcatgc ctgtagtcca agctacttgg gagactgagt taagaggatc   123360
gcttgagccc aggagattgc agtgagctgt gattgcgcca ctgcactcca gcatggacaa   123420
cagagccaga cttgtctcaa aaaaaaaaaa aaagaaaat ctgccgggca tggtggctca    123480
tgcctgtaat cccagcactt tgagaggcca aggcaggcgg attactttag gtcaggagtt   123540
tgagaccgcc tagccaatat ggtgaaaccc ccatctctac taaaaagaca aaaattagct   123600
ggacgtggtg gcgcaagcct gtagtcccag ctactcagga ggctgaggca ggagaatctc   123660
ttgaacctga gaggcagagg ttgcagtgag ccaagatcac acctaccttg atatcagtta   123720
tgcattagtg aaaatggatg aatttgcttg tgattcaatt cataacacct ttttttccct   123780
tttttttctt ttgagacgga gccgctctgt cgcccaggct ggagtgcagt ggcgtgatct   123840
atctcggctc actgcaacct ccgccttcca ggctcaaggg attctcctgc ctcagcctcc   123900
tgagtagctg ggatatcagg cgctgccaca acgcccagct aattttttgta ttttttagtag  123960 agacgcggtt tcaccatgtt ggtcaagctg gtctcgaact cctgaccttg tgatccgccc   124020
acctcagcct accaaagtgc tgggattaca ggcatgagcc actgcgccca gccttttttt    124080 cccccttctaa cactgttagt tgtttagaga tacagaaaag aggagagaga gtgtgtgtgt    124140
gtgtttaaaa acttagagtc atactgatttt aatatttgga ctctgcttca gccacttaat   124200
ctgtcaaact atattcccaa tcatttgtaa aattaagata gtaaagctta cataggagga   124260
tcatagtaaa gtctgaagaa gacaatgttt atatatacat gcctcatctg gtctgacata   124320
cagtaatcat gcaatatata ctaacgtttt attttatttt attttatttt ttgagacaga   124380
gtctctctct gtcacccagg ctggaatgga gtggcacgat ctcggctcac tgcaacctct   124440
gcctcccagg ttccagcagt tcttctacct cagcctccca gtagctggg attacaggcc    124500 aaaaccacca cacccagcta attttttgtat ttttactaga gacggggttt caccatgttg   124560
gccaggctgg agcacagtgg cacaatcttg gctcactgca agctccgcct ctcgggttca   124620
ttctcctgcc tcagcctccc tactaactgg gactacaggt gccgccacc acgcccagct    124680 aattttttgt attttttagta gagatggagt ttcactgcat tagccagggt ggtctcgatc   124740
```

```
tcctgacgtt gtgatccacc tgccttgacc tcccagagtg ctgggattat aggcgtgagc  124800
caccgcaccc agcccagcct ttatcagtta ttatgagtga atatcatgtg agagttacct  124860
ctggtttgat cagtttcagg aaaatgccag tgaagggaag gcccctgcag aagacgtctt  124920
taagaagccc ctgcctccta ctgtgaagaa ggaagagagt cccctccag taagaccaac   124980
attgatcccc tggacctagg gctggggctg gggatggttc cgagtagaag aggaagcgca  125040
aaggctgatg ccttcctctg gtgttggtct tttacctcac tatgtctccc gaataaggat  125100
tcccatttct tttgagtaca agcatgagat aaagttttct gtctgctaat gggggtatta  125160
ctggagaacc agaggcagtt atctggactc tttctctctg ccctgtgcca ttcttaccag  125220
acgagatgcc tagcccttt tatcatcttg ttcttgtcag ttctctaaat caccaaggaa   125280
acccgttttc tcagcctcaa tctttcctgc cttttggcat cacacaagaa tctcttagat  125340
atggagtgca tgcgtggtca ttttttata gtttctgcct gttcagagtg aatgatgcta   125400
atattggtgc ccattttta gatgccttca agcagtagtc tcaacctaat caccagtgat   125460
tctgattgaa tgcaggtata taacaatagt gaccatgcat tatttattta ttttgagtga  125520
tcatagacca atgattatgc atcattattt aacagttctt ataaggtacc cttttcctgc  125580
tccgcattat taattcagct cattgtggca tctgtcttaa ccatgctttg ccttttaccttt 125640
acatgtgagc tggatctgtc tacccaagtg cctattaatg cagttgcttt tagtttactt  125700
cctaaatcct ctttgctaga gtcttaatga aagtcatctt ttcttccctc catgagttac  125760
agtaatttgg aggtatttat ctcttcctct ttgtaatttg taaccttta ctatttcta   125820
tgtttatttt cctttctctt ccttctcctc acattctgtt gctagagtca cttctaaagg   125880
aatctttctt gtttattctt aatgaacaag gagcaaagcc aagctctggc catgttgctt   125940
tcatctggga aatgagcagc atggctagtg agtttatttt gaacccaatt caatgaaatg   126000
agatgcccat atcagaatat caaaaaaaat ggaccccaaa atataggttg aatttggtat   126060
tgatccctgg ccttctcctt ccagcctaaa gtggtaaacc cactgatcgg cctcttgggt   126120
gaatatggag gagacagtga ctatgaggag gaagaagagg aggaacagac ccctccccca  126180
cagccccgca cagcacagcc ccagaagcga gaggagcaaa ccaagaagga gaatgaagaa   126240
gacaaactca ctgactggaa taaactggct tgtctgcttt gcagaaggca gtttcccaat  126300
aaagaagttc tgatcaaaca ccagcagctg tcagacctgc acaaggtatt aggggaagga   126360
gctatgccct ttcaaactgt tgactcttgg ccgggctttg tggctcatgc ctgtaatcct  126420
agcactttgg gaggccgagg cgggtggatt gcctgggctc agaagtacaa gaccagtctg  126480
ggcaacatgg tgaaacccc tttgtactaa aatacaaaaa attagccagg tgtggtgttg   126540
tgtgcctgta gtcccagcca ctcgggaggc tgaggcagga gaattgctag aacctgggag  126600
gcagaggttg cagtgagccg agatcgtgcc actgcactcc agcctgggta acagagcaag  126660
actccatctc ttaaaaaaca aaacaaaaca aaactgttga ctcatattat tgatgggat   126720
tatggggaat aaaaaagatt atttaggccg ggcctagtgg tttacacctg taatcccagc  126780
actttgggag gccaaggcac ctaggtagat cacttgagat caggagtttg agaccagctt  126840
ggccaacatg gtgaaactgt ctctactaaa aatacaaaaa ttacctggat gtggtggcgc   126900
atgcctgtaa tcccaactac ttgggaggtt gaggcaggag aatcgcttga acctgggagg   126960
caaaggttgc agtgaaccga gatcacacca ctgcactcca gcctgggtga cagaccaaga   127020
ctctatctca aaaaaaaaa aaaaaaaaa aaaaagccgc agcagcttat acaatccttc   127080
```

```
ctcagtgtat atcagcccca gttcctatca ttaaaacagt ccaattcaag aatgaattgc  127140
tctggattaa ggttatgcct accctcaaag aacttccatg tataggccga agccaagcat  127200
tatgactgtg gctagggtgc caaatatgga ggatgggtag gaagagaaag ggttgtggaa  127260
taggacatta cttgctgggt ttctcatctt agctgtgtca ttaacgttac agttggacct  127320
cagataagcc ccttttcttc tttggtcctt gtaacttcat ctgattctat ccagctctga  127380
cagtgtgcag ttttcaccat aggtgagtca aattctgcca tttcttcatg tagtgaatat  127440
tgttatgagc cacagcacaa catctatact tgggatgtta aaccgacata cattggtctt  127500
cccctgtagt attcccattt atatgaactg accaaggatc caaattatgg acaaataaag  127560
tccctaaatg gactcacatt ctcagagcaa tttgtttcac accccttctc tagtagatgt  127620
tgcaagagca ggtgatggaa ctagattcag actttctctg aatacagagc tcaaagtttt  127680
atttagctaa aagctgagaa gttctgcttt tggtaatagg tacactactt ttcccagcca  127740
tctctgtgga ggctttgcaa agataggact ctgaaaagct cctgataatc cctggaacag  127800
actacctccc atgtcctttg acctgaagtt gtgagttgtc agactgacac attgaaattt  127860
cacccatctg atgtaaatac taataaatgg ctaaagagat aaaaagtaat cgtcaggaaa  127920
gaggagccac aggtctggtg aattcacaaa ctgaactggt cataggacag tggaaagtag  127980
actgtagtac ttttccttc cttaaggtcg tctgctacaa agaaccacca cttcatgtaa  128040
gagctgcttt ggactcctta agtttcatac atatgtctga gggcttgtgt agtagagcca  128100
tgcgtgagga atttgcaact ctcagagcag tctcttggaa ccctgggct cctttccatg  128160
tttctctggg ggctgaaaga gtgactcatg tctgggaatg gtatgtatgg cagagtatgt  128220
gggcatttgg ttttcttcac tggtgtgccc acatcctctg tcccatgatt ttcaacttag  128280
ataaagagat agatatttgt ttcccacatc ttggagataa gtaaaatgat attcctctta  128340
tgccatacca cataactaat ctgcatgaca agaccagtta gggattgttg gttgcaggat  128400
acagtgatca tttagtagat ctgatcaatc aaaagagcta caatccaaaa gcaactattg  128460
ggaaaggcct agaagcatct ctaggaccat tgtttcttag acctatactc atagaattgc  128520
ctctcttctc agcaaaacct ggaaatccac cggaagataa aacagtctga gcaggagcta  128580
gcctatctgg aaaggagaga acgagaggta aactttggtg acctattact cccttgacct  128640
cagctctttt tgctttctga tatagacttc ataggctgtg ctgatccctc cttataagaa  128700
gatggagaac aaaagcagcc tcaaaagata gtgcatacat ttgccaaatt atataataca  128760
atcaaaatag gtgctttta ttatttgtaa gtttatactt caatgaagtt gatatctttt  128820
ttaaaaggtg gtgttagggt ctctaggtag ataacactcc tctttcctgc ttagctttta  128880
aattagttga gttaatgaac aagtgttgaa tagcgctgct gaaatagcat cttttactat  128940
taaaggctaa gctggaggaa gtagcttagt gtcagagtca aatggacttg ctacctcaac  129000
cacacagtta gggtgaatta cccagtcata ggcttcactg gcctctctca tgatggtaa  129060
gaacccacct atgggtcagg cacggtggct cacgcctata atcccagtac tttgggaggc  129120
tgagacgggc ggatcacttg agctcacaag tttgaaacca gcctgggcga catggcgaaa  129180
tcctatctct acaaaaaata taaaaattag gtggacatgg ggtgtgtgcc tgtagtccca  129240
gctacttgag aggctgaggg aggatcgcat gagctgggag gcagaggttg cagtgagctg  129300
agtttgtgcc actgcgctcc agcctgggtc atagagccag accttgtctc aaaaaaaaaa  129360
aaaaaaaagg aagccacctg tggagagcca ggcacagtgg cacatgcatg taatcccagc  129420
agtttaggag gctgaggtgg gagaattgct tgagcccaag agttccaggc tgcagtgagc  129480
```

```
tatgatcaca gccctgtact ccagcctggg tcacagagta agtccctgtc tcaaaaccaa    129540
acaaaagaat ccacctatgg aggactgtta gagatagtga attcacaaac tgaactggcc    129600
ataggacagt ggaaagtaga ttgtagtatt tttcctttcc ttagagttgt ctactacaaa    129660
gaaccacctc tccatgtaag agctgctttg gactccttaa gttttatatt atatgcccga    129720
gggcttgtat agtggagggc ttgtgtactt tcccctgctt ctcagaaggg gaaaagacag    129780
cggaaccaag cgtgccaact tattctttcc aaatgtttaa gttaggaagt cactgctttc    129840
tctagaagaa cgtgtaaagg agtgagagat tccaggagtt accaagtgag ctactttcac    129900
tttaaaagaa ataacaaggc cgggtgcggt ggctcacacc tgtaatccca gcactttggg    129960
aggccgaggc tggtggatca tgaggtcagg agttcgagac tagcctgact aacatagtga    130020
aaccccgtct ctactaaaaa tagaaaaatt agctgggcat tgtggcactc acctgtagtc    130080
ccagctactt gggaggctga ggcaggagaa tcgcttgaac ctgggaggcg gaggttgcag    130140
tgagctgaga tcacgccagt gtactccagc ctgggcaaca gagtgagact ctgtctcaag    130200
aaaaaaataa taataataac agcaatgggg tagaatttcc ccactcccca attccctcag    130260
gtggcaatct caggtctgct cttctgctta ccaacaggga aagtttaaag gaagaggaaa    130320
tgatcgcagg gaaaagctcc agtcttttga ctctccagaa aggaaacgga ttaagtactc    130380
cagggaaact gacaggtaag ccaggaactc ttcattcagc ctaggcctca agcctaatga    130440
taaaaccacc tcctccttca actgtactgc tgttttctgt ctcagggaga tgatattatg    130500
agtagattct gtctgaactg ctaaaacatg aggtctatgc cagccttttt actatctgtc    130560
tttatacggg gagtgtacat ggaaggttgg ctggcagctt cgccttccca aagccagggc    130620
tggagtagcc atgatcggga acccttctg tcttcatcag taatactgca ccctctttac    130680
gggcctgata agaatgtcac actcttgggc ttttctcta gggaacctcc attctcacac    130740
ataggtgcta aataaatggt tggctgctga tggagatgta tgatatctag cttcctatac    130800
ttgttttcag tcagctagtt cccaagttgt aagcccagag ttatatagaa tttgttgata    130860
acccactgtt tacaggtgtc aagtgcaaga aatactcagg tggacaagac atagattatc    130920
cttgactgaa cacagaatag acaagactta ggtgatggtg cgtctcatag ggcagacaca    130980
gaaatcagtg gggaagggaa gggcatttca gggaatttca tataccaggg atataagagc    131040
ttatgatgtg tttgaggagt tgcaaatagt ttgatggtcc tgaacactgc aggtatattg    131100
ttgagtgaca gtagataagc ctggtccaaa agatgcaggc cagttcatga agtttaaaca    131160
ccttgaacac cttgctaagg ctttatctta aaggcagtgg acggtcatgg aataattta    131220 agcagggtat tgacttagct ttgcattttg gagagattac taatcatgtg gaagatgagt    131280
ttgtagagag actaatgcat tatgcaaatt ctatagtaat tcaagtgaaa gatcatgatt    131340
gcctgagtga aggtgatgag tctagaaagg agagtggcct ataatcccaa cacagagagg    131400
ctgaggaagg aggatctctt gagcctagga gttccaggcc agcctaggca acataggag    131460 aagggagacc ctgcctctat ttaaaaaaag aaaagaaaag gagtgtggct tagagagagg    131520
tgtcagatct gccagtcttt gtgatcacct ggggaaaggg agaagtcact gatggtgttc    131580
aggtctctgg tctctggata gctaggagga gaagggacag taaagtcctt gaaaggaaa    131640 aatgggggcc aggcgtggtg gcttacgcct gtaatcccag cactttggga ggccgaggcg    131700
ggtggatcac aaggtcagga gttcgagacc agcctggcca agatggtgaa accccttctc    131760
tactaaaaat ataacaatta gctgggcgct gtggcaggcg cctgtaatcc cagctactca    131820
```

```
ggaggctggg gcagaagaat cgctcaaacc tgggaggcag aggttgcagt gagctgagat   131880
catgccactg cactctagcc tgggtgacag agcaagactc tgtctcaaaa aaaaaaaaaa   131940 aaaaaaaga aaggaaagg aaaaatgggg ccaggtgtgg tggctcacac ctgtaatccc     132000
agcactttgg gaggctgagg caggtggatc acttaaggtc aggagttcga accagcctg    132060 gccaacatgg tgaaaccctg tctctaccaa aaatataaaa aaattagcca ggcgtggtgg   132120
tgggtacctg taatcccagc tactcgggag actgggcag gagaatcgct tgaacatggg    132180
aggtggaggt tgcagtgagc caagattgca ccactgtact ctagcctggg taatagagcg   132240
agactccaaa tcaaaaaaaa aaagaaaag aaaagaaaag gaaagtgggg taacaagtgg    132300
atgcatgagc agaaggaaag ggagataatt gacagagcaa ggcccttgag gaggctggac   132360
aggttttggg gctctggcat tccagcttat ttgatccaac ccacaataag agaagtattt   132420
ttgtatcatg gcccaataat aaagtgtgtg tgtgcacaac tgaaaagtt ttcatctaaa    132480 atactttctt accaggtaca gtgaaccctg atatttttat tcaagtctag tctctcttca   132540
tttttatgag ttgttacagt gggaccattt agtgtgacat tccattgggt cattctctgc   132600
aatttgaaat acagtggatt aggactaggt gaaggagtca gccatcagga ggaaggacac   132660
cttggccttg agtcttctgg gacaaggctt aggtggggtg cggaaagaga cccttcttta   132720
ttctcagcac cctttatacc acattctcct ggctcttctc cttccagtc accttttctg    132780 ctcctcttcc ttttctggat aaatccaggt gttctctagg actcttctct cagtgcttct   132840
ttggtcttgc tgctctaccc tcttgacctg ggctttctaa ggtacccatg gcctcaacca   132900
ccaccacagt ctaacaagtc caaatctcct gtattattat ttcagagtag cagcatcata   132960
gcatcactgt ctacatggtc tgatccatcc tcctccttta tcccctgtgt ccaattagtg   133020
accaaatccc taattaagtc ttgcccctg tcttagtctg ttttatgata ccataactga    133080
ataccacaga ctgggtaatt tataatgaac agaaatttat ttggctcatg cttctggagg   133140
ctgggaggtc caagattgag gagctgcatc tggtgagggc cttcttgctg tgtcacctca   133200
tggtggaaag taaagaaca agagagctta ggcaaaagag ggggttggga gaaagaaacc    133260
agactaatca tttttatcagg agaacccact cctgcaataa cagcattaat ccatttgtga   133320
gggcagagct ctcatgacct aatcacttcc tgaagtttca cctctcaata ctgttgcatt   133380
ggggattatg tttccaacat atgtactttg agggacacat ttaaaccaca gcatctccca   133440
ttctattcca cctccacact ggactcctac tcccagtctt tgctcccact gttcttcagt   133500
ccattctcta ccctgccacc aaaatgactt ttgtaaagag aaatctactc ttataacttg   133560 tcttttaca aaccgtatac cttgcctaca gggaggcctg agctccaact tttgccagaa    133620
ggatgaggtt cagagacatg atttagctta ataagttcaa ggttttttac agtctgaccc   133680
catgcagcct ttttttttt tccttttgtt ttgagacagt ctcattctgt cgcccaggct    133740
ggagtgcaat ggcacgatct tggctcactg caacctccgc ctcccaggtt caagcgattc   133800
tcctgcctca gcctcccag tagctgggac tatgggctaa tgtttgtatt tttagtagag    133860
aggggtttca cctgttggtc agggtggtct cgaactcctg acctcaggtg atccacccgc   133920
cttggcctcc caaagtgctg ggattacagg cgtgagtcac tgcacccggc caccaagcag   133980
ccttaccttt gtcagtttct actactactc tcttggacaa attgtctttt gtgtctcctt   134040
gcttgtgtcc tccttttctc ttacacaaac tccttatttc gagatccaat tcagatgtat   134100
cttcctgtta aaattcctgt cattttggt gatgcccctt cagagtttc gttccttcta     134160 ctgcatttct tttttttttt tgaaacagag tttcactctt gttgcccagg ctggagtgca   134220
```

```
atggcgcgat atcagctaac cacaacctcc acctcctggg ttcaagcgat tctcctgcct   134280
cagcctcccg agtagctagg attacaggca tgcgccacca cacccggcta attttgtatt   134340
tttagtagag acagggtttc tccatgttgg tcaggctggt cacgaactcc caacctcagg   134400
tgatctgccc acctcagcct cccaaagtga ttccttctac tgtatttcta tagcagacat   134460
ctactgttgc tacatccatg gttgagctct cttcaatgtt ctataagcat ctcttgacat   134520
aatgtttgag acctttcttg tgaacagggc catatcttag tagtctgtgt acccagcaac   134580
aaaacatagc tatcaggcac tcagaggtac tgttaaatat acttacttaa taagaggcag   134640
atatgaatca agaggacaga gattttatat taggcttata agcaggtctt catcaaaatg   134700
atggtgtcag gttgggcatg gtggctcatg cctgtaatcc agcactttgg gaggccaagg   134760
catgcggatt acctgaggtc aggagtttga gagcagcctg gccaacacag tgaaactctg   134820
tctctactga aaaaaaaaaa aattaaaaat tagccaggtg tggtggcggg cacctgcaat   134880
cccagctaat cgggaggctg aggcaggaga atcgccgtga cccaggaggc agaggttgca   134940
gtaagctgag ttcgagccat tgcactccag cctgggcaaa aagagtgaaa ctccgtctca   135000
aaaaaaaaaa aaaaggaagt gatggtgtct gcttcttttg cagtgatcgt aaacttgttg   135060
ataaagaaga tatcgacact agcagcaaag gaggctgtgt ccaacaggct actggctgga   135120
ggaaagggac aggcctggga tatggccatc ctggattggc ttcatcagag gaggtaaaat   135180
ggtttccatc ttttggggg tgacatgaac ctggaatgta attaactttc actttctggc    135240
ctagagtgat gtctttgcca ttttgctggg ctttctctac tgctgggata ggacatgaga   135300
gttgaacact ttagccttga atactgggtt atagcttggc aggctgggcc cttttgcagtt  135360
tggagttagg aagagaagga aggagttgga atggatttca tcatactttt acatggagta   135420
aatagtagag cagtatctga ggcagtttga gactgaagaa tcatttgggc aaaagaacca   135480
gggaatcagc aatgaaaggt acagaggcat ctctgagagg gactgtcagc ggaagtcttt   135540
ggtggctaaa atttaaggag catgttgttc tggttcccat gaaggacttt gcccctcata   135600
tttcaagagc ctctagaaaa ggtgataaga ggaaacatta cccatttgt gttggcttgc     135660
ttctcctctg aaaatgccaa ccataagaga ttggcttatt tctctcctac cgagtttctc   135720
atatctctgg tattaaagcc tgtatcttgc aatcatagca tcaccaccca ccttaattca    135780
tcttgggtat ttgtttaata atgaaagatt cttttcttt tttttttttg agacagagtc    135840
ttgctctgtc gcccaggctg gaatgcagtg gtgcgatctc agctcactgc aacctcctcc   135900
tcccaggttc aagcaattct cccaccccaa cctcctgagt agctgggatt acaggtgcat   135960
accaccatac ccagctaatt tttgtgtttt tagtagagac agagttttgc catgttggcc   136020
aggctggtct cgaactcctg gcctcaagtg atccgcccac ctcagcctcc caaagtgttg   136080
ggattacagg cgtgagccac tgtgcccggc caaaagattc tttaaaaaaa ttatcctgcc   136140
agggtccggg cgcagtggct tatgcttgta atcccagcac tttgggaggc cgaggtgggt   136200
ggatcacaag gtcaggagtt cgagaccagc ctgaccaata tgatgaaacc cctgtctcta   136260
ctaaaaatac aaaaattagc tgggtgcagt ggcgcgcgcc tgtaatcaca gctactcagg   136320
aggctgaggc agaagaatcg cttgtaccgg ggaggcagag gttgcagtga ccaagatcct   136380
tgatcgtgcc actgcactcc agcctgggtg acagagcgag actctgtctc aaaaaaaaaa   136440
ttattctgcc aggtgtggtg gctcacatct gtaatcccaa cactttggga ggccaaggtg   136500
ggcggatcac ttgaggccag gagttcgaga ccagcctggc caacatggcg aaaccctgtc   136560
```

```
tctactaaaa atacaaaaat tagccgggcg tggtggcagg cgcctgtagt cccagctact    136620
cagaggctga ggcacaagaa ttgcttgaac cggggaggca gacttgcagt gagcccagat    136680
cgcaccactg cactctagcc cgggcgacag agcatgactc catctaaaaa aaaaaaaaaa    136740
attatcctat atactgcttc ttactagtcc agaaatgcct gtggtcaaag accagcgctg    136800
aggctaatta atctataggg cccacttcat agtttgtctt tgttttacag gctgaaggcc    136860
ggatgagggg ccccagtgtt ggagcctcag gaagaaccag caaaagacag tccaacgaga    136920
cttaccgaga tgctgttcga agagtcatgt ttgctcgata taaagaactc gattaagaaa    136980
ggagacaagt tccatgggat acaacctccc tcttgttttg tttgtctctc cttttctttt    137040
gttactgttc ttgctgctag aacttttttta aataaacttt ttttcaatgt g            137091

<210> SEQ ID NO 42
<211> LENGTH: 2604
<212> TYPE: DNA
<213> ORGANISM: Homo sapiens

<400> SEQUENCE: 42
ggggaggagc caaggggggcg agcaagctcg gtggctgggt gggttggggc gttccgcgcg      60
cccttcattg aagcggcggt ggccgggctg gcgccggta gtggaaagcg acggcgcggc      120
tggaaaatgc cagtccattc ccgagggat aagaaggaga ccaaccatca cgatgagatg      180
gaggtggact acgccgaaaa tgaggggagc agctccgagg acgaggacac tgagagctcg      240
tcggtctccg aggatggaga tagctcagaa atggatgatg aagactgtga agaagaaga      300 atggaatgtt tggatgaaat gtccaatctt gaaaaacagt ttaccgatct caaagatcaa      360
ctttataaag aacgattaag tcaggtggat gcaaaactac aagaagtcat agctggaaaa      420
gcaccagaat acttggaacc gctggcaact ttacaggaaa atatgcaaat tcgtacaaag      480
gtagcaggaa tctatagaga gctctgctta gaatctgtaa agaacaaata tgaatgtgaa      540
attcaagctt ctcgccagca ttgtgagagc gaaaagctgt tgctatatga tacagtccag      600
agtgaactag aggagaagat aagaaggctt gaagaggata ggcacagcat tgatattacc      660
tcagagctgt ggaatgatga gcttcagtca agaaaaaaga ggaaggatcc tttcagtcct      720
gacaaaaaga agccagttgt tgtttcaggt ccatatatag tttatatgct acaagatctt      780
gatattcttg aagactggac aacaattagg aaggcaatgg ctacattggg gccacacaga      840
gtgaaaacgg aaccacctgt gaaactggaa aaacatctgc acagtgctag atctgaagag      900
ggaagactat attatgatgg tgaatggtat atacgtggac aaacaatatg tattgataaa      960
aaagatgaat gtcctacaag tgctgtaatt acaacaatta accatgatga agtttggttt      1020
aagaggcctg atggaagcaa atctaagctt tacatttcac agctacagaa aggaaaaatat     1080 tcaattaaac attcataatc atgatttaag tgttatctaa atttacctta ttagtgttac     1140
caaatgtaag tgccatgaga gtaaaaaaat gtattcaata acttaatatt ctcactgaat     1200
catgagagaa tgtgtatttg taggtagtac tctaaataga tctcattgat atgttattaa     1260
aagaaacagt aataaaaatt ttatcacgat ccttacgttg atttgcctct taggtccgat     1320
gaccaatagg tattctgtat atggtagggg tttcttccta aacattttc tttggtttta      1380 aaaaagtta tgcaaatttg tcttatcttt agtaaactat gactacattt atctgcaatt     1440
tttaaaattt tccatatctt tgtcattcat tgtgtgtttg taaataaggc cgatagaatg     1500
tttcctataa atggtttgta ctagtacatt agtgttaaac cagaactgaa atttaaacat     1560
atatatatat gaggatgtat atatggcatc atcagcttat ttagaactga tggccatacc     1620
```

```
ttacaatctt gttttaccca aaattaagct attggggttg aaagctaaaa ggagcacttt      1680
tgtagaatag caacttttct tttcctcttt cttgattgta tggtggggtg gtgacctatt      1740
tttacaaatt atacctaatg agtaaaatta gtgtaaagtg ataacatgct tctacctgta      1800
tttctagtga cccctttagcg gcaggtattt atacctggta tttatgatgc agtatataag      1860
tggtgaacaa taactgacag tattgtgctt gctgtacatg tctggtcttt tgaaacagat      1920
tttagtaagc attttccaga ggtaaaactg tgtccttatt ctaattttat cctagggca      1980 aagtagacag ggattatttc cttgaatcta tttccaaatt aatattttt tctttggtat      2040 ttctacactt taaggccatt tggtgcaatt tagaaagtgt tggcctccct tccgctagcc      2100
acattcaaaa ttaacttcca aaacctcagg aacagtacaa agaattgaaa ccctcaatat      2160
ggcagcacac ccggctgtag tgtatattta gggtacacca aatcaggtat tcctggtggt      2220
cttgtgcact ttaatttctg ttacaatgag ttaagaggat gaggaagaaa tctacttatt      2280
aacacttact gcagaaatgt ctgcattatt ccgtttgttt tcttattatt ttacctctcc      2340
aaacatcttc ctgtgcagat cactacttca tagttgccaa attttaaaac acttaactgc      2400
tgaaattcag tgtcagcaaa gtgatattac gttgttctgt ttctaattaa ccttagcaaa      2460
tgtacataat gtcaaaaccc aatagtattt gacagtactt atgtatacaa tgtttgataa      2520 gcattttaa taagatttgt atttttaaat ttagtatata ataaaagat gtgtttcagt      2580 gtgaaaaaaa aaaaaaaaa aaaa                                            2604

<210> SEQ ID NO 43
<211> LENGTH: 3281
<212> TYPE: DNA
<213> ORGANISM: Homo sapiens

<400> SEQUENCE: 43
gcggtgcggg ccgggcgggt gcattcaggc caaggcgggg ccgccgggat gctcaggggtt       60 ccggagccgc ggcccgggga ggcgaaagcg gaggggccg cgccgccgac cccgtccaag      120
ccgctcacgt ccttcctcat ccaggacatc ctgcgggacg gcgcgcagcg gcaaggcggc      180
cgcacgagca gccagagaca gcgcgacccg gagccggagc cagagccaga gccagaggga      240
ggacgcagcc gcgccggggc gcagaacgac cagctgagca ccgggccccg cgccgcgccg      300
gaggaggccg agacgctggc agagaccgag ccagaaaggc acttggggtc ttatctgttg      360
gactctgaaa acacttcagg cgcccttcca aggcttcccc aaaccctaa gcagccgcag      420 aagcgctccc gagctgcctt ctcccacact caggtgatcg agttggagag gaagttcagc      480
catcagaagt acctgtcggc ccctgaacgg gcccacctgg ccaagaacct caagctcacg      540
gagacccaag tgaagatatg gttccagaac agacgctata agactaagcg aaagcagctc      600
tcctcggagc tgggagactt ggagaagcac tcctctttgc cggccctgaa agaggaggcc      660
ttctcccggg cctccctggt ctccgtgtat aacagctatc cttactaccc ataccctgtac      720 tgcgtgggca gctggagccc agcttttttgg taatgccagc tcaggtgaca accattatga      780
tcaaaaactg ccttccccag ggtgtctcta tgaaaagcac aaggggccaa ggtcagggag      840
caagaggtgt gcacaccaaa gctattggag atttgcgtgg aaatctcaga ttcttcactg      900
gtgagacaat gaaacaacag agacagtgaa agtttaaata cctaagtcat tcctccagtg      960
catactgtag gtcattttt ttgcttctgg ctacctgttt gaaggggaga gagggaaaat     1020
caagtggtat tttccagcac tttgtatgat tttggatgag ttgtacaccc aaggattctg     1080
```

```
ttctgcaact ccatcctcct gtgtcactga atatcaactc tgaaagagca aacctaacag    1140
gagaaaggac aaccaggatg aggatgtcac caactgaatt aaacttaagt ccagaagcct    1200
cctgttggcc ttggaatatg gccaaggctc tctctgtccc tgtaaaagag aggggcaaat    1260
agagagtctc caagagaacg ccctcatgct cagcacatat ttgcatggga gggggagatg    1320
ggtgggagga gatgaaaata tcagcttttc ttattccttt ttattccttt taaaatggta    1380
tgccaactta agtatttaca gggtggccca aatagaacaa gatgcactcg ctgtgatttt    1440
aagacaagct gtataaacag aactccactg caagaggggg ggccgggcca ggagaatctc    1500
cgcttgtcca agacaggggc ctaaggaggg tctccacact gctgctaggg gctgttgcat    1560
ttttttatta gtagaaagtg gaaaggcctc ttctcaactt ttttcccttg ggctggagaa    1620
tttagaatca gaagtttcct ggagttttca ggctatcata tatactgtat cctgaaaggc    1680
aacataattc ttccttccct cctttttaaaa ttttgtgttc cttttttgcag caattactca    1740
ctaaagggct tcattttagt ccagatttttt agtctggctg cacctaactt atgcctcgct    1800
tatttagccc gagatctggt cttttttttt tttttttttt ttttttttcc gtctccccaa    1860
agctttatct gtcttgactt tttaaaaaag tttggggggca gattctgaat tggctaaaag    1920
acatgcattt ttaaaactag caactcttat ttctttcctt taaaaataca tagcattaaa    1980
tcccaaatcc tatttaaaga cctgacagct tgagaaggtc actactgcat ttataggacc    2040
ttctggtggt tctgctgtta cgtttgaagt ctgacaatcc ttgagaatct ttgcatgcag    2100
aggaggtaag aggtattgga ttttcacaga ggaagaacac agcgcagaat gaagggccag    2160
gcttactgag ctgtccagtg gagggctcat gggtgggaca tggaaaagaa ggcagcctag    2220
gccctgggga gcccagtcca ctgagcaagc aagggactga gtgagccttt tgcaggaaaa    2280
ggctaagaaa aaggaaaacc attctaaaac acaacaagaa actgtccaaa tgctttggga    2340
actgtgttta ttgcctataa tgggtcccca aaatgggtaa cctagacttc agagagaatg    2400
agcagagagc aaaggagaaa tctggctgtc cttccatttt cattctgtta tctcaggtga    2460
gctggtagag gggagacatt agaaaaaaat gaaacaacaa acaattact aatgaggtac     2520
gctgaggcct gggagtctct tgactccact acttaattcc gtttagtgag aaacctttca    2580
atttctttt attagaaggg ccagcttact gttggtggca aaattgccaa cataagttaa     2640
tagaaagttg gccaatttca ccccattttc tgtggtttgg gctccacatt gcaatgttca    2700
atgccacgtg ctgctgacac cgaccggagt actagccagc acaaaaggca gggtagcctg    2760
aattgctttc tgctctttac atttctttta aaataagcat ttagtgctca gtccctactg    2820
agtactcttt ctctccccctc ctctgaattt aattctttca acttgcaatt tgcaaggatt    2880
acacatttca ctgtgatgta tattgtgttg caaaaaaaaa aaaaaagtgt ctttgtttaa    2940
aattacttgg tttgtgaatc catcttgctt ttttccccatt ggaactagtc attaacccat    3000
ctctgaactg gtagaaaaac atctgaagag ctagtctatc agcatctgac aggtgaattg    3060
gatggttctc agaaccattt cacccagaca gcctgtttct atcctgttta ataaattagt    3120
ttgggttctc tacatgcata acaaaccctg ctccaatctg tcacataaaa gtctgtgact    3180
tgaagtttag tcagcacccc caccaaactt tatttttcta tgtgtttttt gcaacatatg    3240
agtgttttga aaataaagta cccatgtctt tattagattt a                       3281
```

<210> SEQ ID NO 44
<211> LENGTH: 1155
<212> TYPE: DNA
<213> ORGANISM: Homo sapiens

<400> SEQUENCE: 44

```
cgcctgtctt ttccgtgcta cctgcagagg ggtccatacg gcgttgttct ggattcccgt    60
cgtaacttaa agggaaattt tcacaatgtc cggagcccct gatgtcctgc aaatgaagga   120
ggaggatgtc cttaagttcc ttgcagcagg aacccactta ggtggcacca atcttgactt   180
ccagatggaa cagtacatct ataaaaggaa aagtgatggc atctatatca taaatctcaa   240
gaggacctgg gagaagcttc tgctggcagc tcgtgcaatt gttgccattg aaaaccctgc   300
tgatgtcagt gttatatcct ccaggaatac tggccagagg gctgtgctga gtttgctgc    360
tgccactgga gccactccaa ttgctggccg cttcactcct ggaaccttca ctaaccagat   420
ccaggcagcc ttccgggagc cacggcttct tgtggttact gaccccaggg ctgaccacca   480
gcctctcacg gaggcatctt atgttaacct acctaccatt gcgctgtgta acacagattc   540
tcctctgcgc tatgtggaca ttgccatccc atgcaacaac aagggagctc actcagtggg   600
tttgatgtgg tggatgctgg ctcgggaagt tctgcgcatg cgtggcacca tttcccgtga   660
acacccatgg gaggtcatgc ctgatctgta cttctacaga gatcctgaag agattgaaaa   720
agaagagcag gctgctgctg agaaggcagt gaccaaggag gaatttcagg gtgaatggac   780
tgctcccgct cctgagttca ctgctactca gcctgaggtt gcagactggt ctgaaggtgt   840
acaggtgccc tctgtgccta ttcagcaatt ccctactgaa gactggagcg ctcagcctgc   900
cacggaagac tggtctgcag ctcccactgc tcaggccact gaatgggtag gagcaaccac   960
tgactggtct taagctgttc ttgcataggc tcttaagcag catggaaaaa tggttgatgg  1020
aaaataaaca tcagtttcta aaagttgtct tcatttagtt tgcttttac tccagatcag  1080
aatacctggg attgcatatc aaagcataat aataaataca tgtctcgaca tgagttgtac  1140
ttctaaaaaa aaaaa                                                    1155
```

<210> SEQ ID NO 45
<211> LENGTH: 784
<212> TYPE: DNA
<213> ORGANISM: Homo sapiens

<400> SEQUENCE: 45

```
gcccacgcgc cagagtcgca gtgggcgggc ctacgtgctc cgcccgctgt gagcctgtcc    60
ggcccccgcc cgctccggag caacccgcga gcttacaccg gcttctctct gtcctcagcc   120
cgcgcgccgc catcgccgtc atgctgggcg ccgctctccg ccgctgcgct gtggccgcaa   180
ccacccgggc cgaccctcga ggcctcctgc actccgcccg gaccccgggc ccgcgtgg    240
ctatccagtc agttcgctgc tattcccatg ggtcacagga gacagatgag gagtttgatg   300
ctcgctgggt aacatacttc aacaagccag atatagatgc ctgggaattg cgtaaaggga   360
taaacacact tgttacctat gatatggttc cagagcccaa aatcattgat gctgctttgc   420
gggcatgcag acggttaaat gattttgcta gtacagttcg tatcctagag gttgttaagg   480
acaaagcagg acctcataag gaaatctacc cctatgtcat ccaggaactt agaccaactt   540
taaatgaact gggaatctcc actccggagg aactgggcct tgacaaagtg taaaccgcat   600
ggatgggctt cccaaggat ttattgacat tgctacttga gtgtgaacag ttacctggaa   660
atactgatga taacatatta ccttatttga acaagtttct ctttattgag taccaagcca   720
tgtaatggta acttggactt taataaaagg gaaatgagtt tgaactgaaa aaaaaaaaa   780
aaaa                                                                784
```

<210> SEQ ID NO 46
<211> LENGTH: 5740
<212> TYPE: DNA
<213> ORGANISM: Homo sapiens

<400> SEQUENCE: 46

```
cgccgccgcc gcacgccgcc tgcctcctgc acgccgccgc cgcgcctagc gcccgggccc      60
gcgacaccgc ccgctaagcg ccgggccgag ttcacgcagc cgcggtctgg cggctccgcg     120
gcggcggcgg gtgcgggcgg cctggccggt gccggttaaa gggacgagtt gcaaacactt     180
caggaagtga caagtcgatt tcctcctccc cgggagtcgc tcgtacaaag cgctcggcgc     240
cggcaggcga gcgtgcgcgc ggcggacgcg cggcgggcac cccggacgac ttggcgagcg     300
ctggcggtga cggcgcgggg tccgcgcccg gagcgccccg ccgcgcacag gagttgacca     360
catttggcca tttcccagaa gggccccacc ccaagggtga gtggccaatg gggagctgtt     420
tctgctgaca tcaattcccc aggaggtact caccccaagt ctgccaagt gaagatggct      480
gatacccacc ctgggatgga gcccagcgcc tgaggcccct tatcatggtga tggtcctaag    540
tgaaagcctc agcacccggg gagctgactc cattgcatgt gggaccttca gccgtgaact     600
gcacacgcca agaagatga gtcaaggacc tacactttc tcttgtggaa ttatggaaaa       660
tgacagatgg cgagacctgg acaggaaatg ccctcttcag attgaccaac cgagcaccag    720
catctgggaa tgcctgcctg aaaaggacag ctcactatgg caccgggagg cagtgaccgc    780
ctgcgctgtg accagtctga tcaaagacct cagcatcagc gaccacaacg ggaacccctc    840
agcacccct agcaagcgcc agtgccgctc actgtccttc tccgatgaga tgtccagttg     900
ccggacatca tggaggccct tgggctccaa agtctggact cccgtggaaa agagacgctg    960
ctacagcggg gcagcgtcc agcgctattc aacggcttc agcaccatgc agaggagttc     1020
cagcttcagc ctcccttccc gggccaacgt gctctcctca ccctgcgacc aggcaggact    1080
ccaccaccga tttggagggc agccctgcca aggggtgcca ggctcagccc cgtgtgtgaca   1140
ggcaggtgac acctggagcc ctgacctgca ccccgtggga ggaggccggc tggacctgca    1200
gcggtcccctc tcttgctcac atgagcagtt ttcctttgtg gaatactgtc ctccctcagc   1260
caacagcaca cctgcctcaa caccagagct ggcgagacgc tccagcggcc tttcccgcag    1320
ccgctcccag ccgtgtgtcc ttaacgacaa gaaggtcggt gttaaaaggc ggcgccctga    1380
agaagtgcaa gagcagaggc cttctctaga ccttgccaag atggcacaga actgtcagac    1440
cttcagcagc ctcagctgcc tgagcgcagg gacagaggac tgcggtcccc agagcccctt   1500
cgcccgccac gtcagcaaca ccagggcctg gaccgccctg ctctcagcct ccggcccagg    1560
gggcaggacc cccgctggga ccccggtccc tgagcctctt ccccttcct tcgacgacca     1620
cctcgcctgc caggaggacc tgtcctgtga ggagtcagac agctgcgccc tggacgagga    1680
ttgtggcagg agagcggagc cggctgcagc ctggcgggac cgcggggccc ctgggaacag    1740
cctctgctcc ctggacggcg agttggacat tgagcagata gagaagaact gaggggtgt    1800
gggcccaggc agggctgggg tgtgctggca tcgacagccc ccactctggg cactaggtgg    1860
gccccttgaag gggagcccaa ctcgtgggcc tgatgaaagc ttcctgagtg gtgtcgggtc   1920
ccagagaggg agcccacctg ctgcctgggg gagagcctgg cctggccgcg tcatacagcg    1980
ggtgtgtcag cctctcaccg gctccccgag cgtggcagcc accaggtcca cagaactact    2040
gcagcccaga ggacagcttt gaagtttgcg tcttttctgc ctctttccct gtgggatgtt    2100
gggcagtctc tgttgtcccc ggcagagctg ggcaccgctc tgtatccccc tggtggtggg    2160
```

```
ggctgtcagg gagggcctgg ggtgggggcc aggggccatc tgctatgtca gggcccttct    2220
tggcctcact caggttcact tctggggagt cggccccgca gcttctttca ctcagtttta    2280
ctccgtgcct tctctcccag gtctccctgc ttcaggcttg ggaaggttcg ggagatgctt    2340
ccttctgtaa caccagaacc atttggcctt aattccaatg tgagagacag aatccctggg    2400
gtgctggact ggccctccag agggtaagcc atgtccggag tctcgggccc aaggaacgat    2460
ttggagggtg cttgttaggg cctcccgtgt tgggtagaaa tttggtggat ctgttggctg    2520
aaaagacgga cttgcttgcc tctcctacag catggagagg ctgaccccat ggctctgcca    2580
ccgttggggc agggttagca gatggcagcc cttctctgtg gctgacaggt cactgagtga    2640
taagcatggt tggttccggt gagtgtaggg atggcacgat accagggcag cctcttgaaa    2700
acggcctcgg gagacgggag ctgcgagcag gtgggcagat gagggcccta tgcgcactca    2760
ggggtgaagg gcgtccgctg gccactctgc aggggcccct gcaggattcc aggcacctcc    2820
cgtttgtcct tgaggactgc tggctgtaac caggcacat  cacccacctc aagacaagcc    2880
cacgcccttg tcagcttagg gggagcccag tcctgagggc tgcatctctg ttgtaggccc    2940
agccaccggc acaaagctgg attcatgctc cctgcccta  ccccaccctg gctcctcacc    3000
ctggggcatc cgaggagcct agccccctga gggtttgctc tcctctcaag gtttgtagct    3060
cctctccggt tgccttgcag acaccaccac atgggtctg  ctctatggga atctggcttt    3120
tagcgaatgt ggcgtcttct gcaaacaata gcaattgggc tggcttagga gcaagtggct    3180
cattttccca taaggctaaa aataactggt gcgctccctt tgtgttggctg acacgcgcgt   3240
tcaaagcact tttgtagtca ctttgctttt gctcgtcttc atggacgagt gaacgcctcg    3300
cttctgcagg ttgagtccag atgcttctca ccttctttct cctcaagaaa gatgcttttt    3360
gggaaacgtt gtttaaatct tatttttta  ctacatcaaa aggatggtgg ttcaagttcc    3420
caatatgtgg gtggcacttc ttaaaaatca gctttaagga gctggcagaa agcccccagc    3480
cccacagccc tgagagatgg tgttgctagc tcaggtggct gacacatggg gtatgccggg    3540
cactgggcag gtcccagagc cggggaacca gctcacctct ggttgctgta gctcctgccg    3600
gaggcatgtc tacttgtgat cccggacagc cgaacccaag agctggtggc tctgagcaga    3660
cagagacatc ttggcctgtc cctgcctggg ggtcatggag accatgtctt cttagagcaa    3720
atgtggaggc ggccagggca gttgttgggt gaatgtggag agcacatggc catgtcttgc    3780
ccccggagta ccactgggcg tgggggtcc  tggcaccaca tgcccggtgt ggccgagggc    3840
acacagcctc tatagcaggc cttcctgtgg aaggcagagg cagtgaggga ggtggacggt    3900
gccagctgag gctgaggcat gcagcagccc ccagctacct ttgcttaggg ctggggtggg    3960
aggcacatgg tgacaggtat atgtcgtggg actgggtgt  gggtgacctg ccctcaaacc    4020
ttgcctgcca cctccccatt caggcctggt ggcaggaagg acaagctgt  ggagctggct    4080
gagtcacagc cacctcccca cctccccgca agctggtccc atcgaccagc aagcccagcc    4140
ccagggcgct tagggagaaa tgacccagcc tcctcagacc ccgcctgcct gtcctgtgcc    4200
caccacgcag cagtcagggg agaaaatggt ggctatccct tctgcttaga gaaagaaatg    4260
gcctttagct ggtttcatgt ttgtgttttg actggaggga gtagaccct  tctataaggt    4320
gccaccccat catccaagct gccacactgc ccggagcagc ctgttcctgc actccaccct    4380
gctgccccca ggacttctga tctcagtcct ctgggaggga ggttcgccta ggaggtgccc    4440
cccacattgg tgtccccatg ggcagcaggc agacagctca cccccaccag catgatggcc    4500
```

-continued

```
ccagctgggg gcagtggcag gagccttact tttgtcacag ccttgcccac aaaccctgcc      4560
tctgagggga gactgaggaa gggcagagcc agaagcaagc cgtgccaggc catctgcctg      4620
ctcatggggt cctaaagcgc gggctaagcc tgcaggaaag ccggggcggt ggggggggct      4680
tagtgccaca tgcaccccac tcattccaaa gccaccaaac tgccagggc tgccgtccac      4740 ccgtggggcc caggggctgg ggccacagcc ttgccatttt cgttgccata ccctcttgcc      4800
ttactcgcgg tggaggccgg atttgcacgg gcagacgtgc acctgggccc gtggggagct      4860
tgttctgacc agacgtacag attttcattc tcagaaagcc ttacttttca accaaatttt      4920
tgtagccagt tttgtgaatt tgtacactga agaaaattt aaataaaggg gaagtccaca      4980
ttaaaaagaa aacaaaacaa accctaacta acttccaaat gggtctcctg gtgcgggggc      5040
gtgagtggcc gtgccctggg tgtgctgcct gtctgagcaa gcttccctag ctgtggaacc      5100
ccgggccccc tgctgcgggc tctgccttgg tgtcatgcct gctgcacccc cgtttccact      5160
gacgtgccgt ctgtggctat gggggtggtc actggaatga cggtcactcc agacgtcagc      5220
cggcagggat gcagcaggct ggccgcgcac cggggctcgg gcaccctctg gccccacact      5280
ggcaatgatg ccacaccttg ccatgtccac gctgttggtc aaacccctct gtcatgcctc      5340
tttaaagaga aagaagaga aagatttttt tttttttaa tggcagaccg aagtggagat      5400
cttgtagcct agataggata gtctgacctt ctagcatagt cttttttggca aatgatttgt      5460 gttttcagtg tgtggggaag ctgtcctggg ggctggggcg acagatagca cataggctgt      5520
ttctggggct gcaggggctt ccctgagctg gatgttgtgg gtgttgccgt gcttcaggaa      5580
gtgtggcgac cagaaagcgt agacccgggg cccagggtct gcccgcccct gcagcctggc      5640
ctccccgcac aggctgtggc ttgcactcca gccgctctag tctctcagga atttgcttgt      5700
tacttgtact gtgtaaataa agcttcctgg ttcaataccc                           5740
```

<210> SEQ ID NO 47
<211> LENGTH: 1980
<212> TYPE: DNA
<213> ORGANISM: Homo sapiens

<400> SEQUENCE: 47

```
gcaatggaca agtcttggtt aaatgtgctt tggaggaact tcctgaaatg gggaagagga       60
tcatctgaaa atgagataga gatccacatc tgatttgtaa ttttgaacct aatagtttat      120
tatttatatt tgagagtatc ctaaatctgc tattagcagc caaaaatgaa tacaagaaag      180
tacaatcgtt atttaaaaga agcaagttat agttgacaaa gattaaaatg ttaaaagttg      240
tttgaagttt aggcaactga caataacaga acaacttatt aataacagta atgaagttaa      300
aaattataga gcatttgcta taacctaagt atgtccgttt aaacttcacc actttcttag      360
attaggaagc tgaccttcag ataagtaaaa ttatatcgga aaggtcctct taattcacag      420
tgccaaatcc agattttccc tgacttcccc aaatgccact tataagataa tttaattatt      480
attcatcccc tgatgactgc aggaaaacct ctgtgggtaa gtagagataa atgtgaagag      540
cagaagcaaa gaaaagagct agcagtagtg aatgttgaac ttcatgtgct aattggtgtg      600
tgtccatttc tgatacagcc actttgagac aagggctata tcatccatga attggatctt      660
aatgtccatt gctgtatttt tacttctcta gtttttaaga aatttaggct gtggttcaca      720
ttgtgtattc gaaagataga atacctcgct aactagacaa acaaaagctt tgttctaaaa      780
atgtactttc cttaaagcag aagtaacctg cagagaagca ggatgcctga agagagatgg      840
atctctgctt actgtgtctt tagaacagaa atagtggttt tcaacttcac aactctgcat      900
```

```
tgagccctcc tttcacatct tccctgtatc attgcagaat tgatctgaat aattctcatt      960
ttatcttaga caattttttg tgtggcttga aaaataaat ttgcaataga ggtgaaatgg      1020
aaaaaattat ccttcatttc ctactccaaa ctgaggataa acaattattc ttggaaattc    1080
caccatagaa ttgaattcat tgtacgtgtg aattgcacct tttaagcttt taaatgatgt    1140 ggcatttta tttagcagca ttccaaaagg gaccacgaaa taaatgagct ccctggtttt     1200
gcagcatttt ataattccaa tatgaaagtt ttagcattat tactaactga agaatcagaa    1260
aggaaattca tagactatca cttctgggtt ttcaagtatt tttaatccat gcaactcttc    1320
ctccaaactt tttcttcaac ttctcatgag aaagtcagca tataaagttc ttaaaagctg    1380
tgctcccctg accgaaatgg agatgagtac catggtggga aatgcatct ttccccctcg     1440 agagtcctct agcacctgcg gtggtctctg gaagaactca gcagaactcc caagtgccaa    1500
ggaacacata ttacagaaca acggactgca gaaattcaga tagatgaaaa ctatagatca    1560
ttctaggtac tttgttccca gacttataat actcccaata gcttctctaa tgtatgatca    1620
agtggctgtc tgctgtaata ttttcagagc tataatgttt atatctaacc tcttatattt    1680
atgtccaaat cagctggtat attttggctt attctgagca gtagctgcta gatctatctt    1740
gtggtacaca ttaagcctat tccttcttcc acagttcttc ttgacattat gctacttaaa    1800
aagtcatccc ttatcaaaat caaatttcat tattttagtt atatcacatc caatatttaa    1860
ttgtgtaaac cactctttac tctagctatt cgtcctcaga attgcttctg ttataaatgc    1920 tcttttttgaa cagacttcct agagtagaag agaaagctcc agatatgatc tgatgggggt   1980
```

<210> SEQ ID NO 48
<211> LENGTH: 5602
<212> TYPE: DNA
<213> ORGANISM: Homo sapiens

<400> SEQUENCE: 48

```
atggagccct ccagagcgct tctcggctgc ctagcgagcg ccgccgctgc cgccccgccg      60
ggggaggatg agcaggggc cggggccgag gaggaggagg aggaggagga ggaggcggcg      120
gcggcggtgg gccccgggga gctggctgc gacgcgccgc tgccctactg gacggccgtg      180
ttcgagtacg aggcggcggg cgaggacgag ctgaccctgc ggctgggcga cgtggtggag    240
gtgctgtcca aggactcgca ggtgtccggc gacgagggct ggtggaccgg gcagctgaac    300
cagcgggtgg gcatcttccc cagcaactac gtgaccccgc gcagcgcctt ctccagccgc    360
tgccagcccg gcggcgagga ccccagttgc tacccgccca ttcagttgtt agaaattgat    420
tttgcggagc tcaccttgga agagattatt ggcatcgggg ctttgggaa ggtctatcgt    480 gctttctgga taggggatga ggttgctgtg aaagcagctc gccacgaccc tgatgaggac   540
atcagccaga ccatagagaa tgttcgccaa gaggccaagc tcttcgccat gctgaagcac   600
cccaacatca ttgccctaag agggggtatgt ctgaaggagc ccaacctctg cttggtcatg   660
gagtttgctc gtggaggacc tttgaataga gtgttatctg ggaaaaggat tcccccagac   720
atcctggtga attgggctgt gcagattgcc agagggatga actacttaca tgatgaggca   780
attgttccca tcatccaccg cgaccttaag tccagcaaca tattgatcct ccagaaggtg   840
gagaatggag acctgagcaa caagattctg aagatcactg attttggcct ggctcgggaa    900
tggcaccgaa ccaccaagat gagtgcggca gggacgtatg cttggatggc acccgaagtc    960
atccgggcct ccatgttttc caaaggcagt gatgtgtgga gctatgggt gctactttgg   1020
```

| | |
|---|---|
| gagttgctga ctggtgaggt gcccttcga ggcattgatg gcttagcagt cgcttatgga | 1080 |
| gtggccatga acaaactcgc ccttcctatt ccttctacgt gcccagaacc ttttgccaaa | 1140 |
| ctcatggaag actgctggaa tcctgatccc cactcacgac catcttcac gaatatcctg | 1200 |
| gaccagctaa ccaccataga ggagtctggt ttctttgaaa tgcccaagga ctccttccac | 1260 |
| tgcctgcagg acaactggaa acacgagatt caggagatgt tgaccaact cagggccaaa | 1320 |
| gaaaaggaac ttcgcacctg ggaggaggag ctgacgcggg ctgcactgca gcagaagaac | 1380 |
| caggaggaac tgctgcggcg tcgggagcag gagctggccg agcgggagat tgacatcctg | 1440 |
| gaacgggagc tcaacatcat catccaccag ctgtgccagg agaagccccg ggtgaagaaa | 1500 |
| cgcaagggca agttcaggaa gagccggctg aagctcaagg atggcaaccg catcagcctc | 1560 |
| ccttctgatt tccagcacaa gttcacggtg caggcctccc ctaccatgga taaaaggaag | 1620 |
| agtcttatca acagccgctc cagtcctcct gcaagcccca ccatcattcc tcgccttcga | 1680 |
| gccatccagt tgacaccagg tgaaagcagc aaaacctggg gcaggagctc agtcgtccca | 1740 |
| aaggaggaag gggaggagga ggagaagagg gccccaaaga agaagggacg gacgtggggg | 1800 |
| ccagggacgc ttggtcagaa ggagcttgcc tcgggagatg aaggatcccc tcagagacgt | 1860 |
| gagaaagcta atggtttaag tacccccatca gaatctccac atttccactt gggcctcaag | 1920 |
| tccctggtag atggatataa gcagtggtcg tccagtgccc ccaacctggt gaagggccca | 1980 |
| aggagtagcc cggccctgcc agggttcacc agccttatgg agatggcctt gctggcagcc | 2040 |
| agttgggtgg tgcccatcga cattgaagag gatgaggaca gtgaaggccc agggagtgga | 2100 |
| gagagtcgcc tacagcattc acccagccag tcctacctct gtatcccatt ccctcgtgga | 2160 |
| gaggatggcg atggcccctc cagtgatgga atccatgagg agcccacccc agtcaactcg | 2220 |
| gccacgagta cccctcagct gacgccaacc aacagcctca gcggggcgg tgcccaccac | 2280 |
| cgccgctgcg aggtggctct gctcggctgt ggggctgttc tggcagccac aggcctaggg | 2340 |
| tttgacttgc tggaagctgg caagtgccag ctgcttcccc tggaggagcc tgagccacca | 2400 |
| gcccgggagg agaagaaaag acgggagggt cttttcaga ggtccagccg tcctcgtcgg | 2460 |
| agcaccagcc ccccatcccg aaagcttttc aagaaggagg agcccatgct gttgctagga | 2520 |
| gaccctctg cctccctgac gctgctctcc ctctcctcca tctccgagtg caactccaca | 2580 |
| cgctccctgc tgcgctccga cagcgatgaa attgtcgtgt atgagatgcc agtcagccca | 2640 |
| gtcgaggccc ctcccctgag tccatgtacc cacaacccc tggtcaatgt ccgagtagag | 2700 |
| cgcttcaaac gagatcctaa ccaatctctg actcccaccc atgtcaccct caccaccccc | 2760 |
| tcgcagccca gcagtcaccg gcggactcct tctgatgggg cccttaagcc agagactctc | 2820 |
| ctagccagca ggagccctc cagcaatggg ttgagcccca gtcctggagc aggaatgttg | 2880 |
| aaaaccccca gtcccagccg agacccaggt gaattccccc gtctccctga ccccaatgtg | 2940 |
| gtcttccccc caaccccaag gcgctggaac actcagcagg actctacctt ggagagaccc | 3000 |
| aagactctgg agtttctgcc tcggccgcgt ccttctgcca accggcaacg gctggaccct | 3060 |
| tggtggtttg tgtccccag ccatgcccgc agcacctccc cagccaacag ctccagcaca | 3120 |
| gagacgccca gcaacctgga ctcctgcttt gctagcagta gcagcactgt agaggagcgg | 3180 |
| cctggacttc cagccctgct cccgttccag gcagggccgc tgccccgac tgagcggacg | 3240 |
| ctcctggacc tggatgcaga ggggcagagt caggacagca ccgtgccgct gtgcagagcg | 3300 |
| gaactgaaca cacacaggcc tgcccttat gagatccagc aggagttctg gtcttagcac | 3360 |
| gaaaaggatt ggggcgggca aggggacag ccagcggaga tgagggagc tggcgggcac | 3420 |

```
agcccttcct cagggttgga cccctgaga tccagcccta cttcttgcac tgataatgca   3480
cttgaagat   ggaagggatg gaaacagggc cacttcagag gtctcctgc   cctgcagggc   3540
ctttctaccc gtgtccactg gaggggctgt ggccatcagc tctggctgtg taggggagga   3600
aggggtgcat gcatgtcccc caccctccac agtcttcctt gcctttagag tgaccctgca   3660
gagtcactca gccaaatctg tctgctgctc cctctcctca gccagttggg tgtgcgcaga   3720
gctgtcatag ggtccctttg tcagcccga  gttcagcttc ccaaacacca gtgttggata   3780
ttctgtgatt gattttggtc ctcctccgct gtccccaac  acccaggaat gggaatctgg   3840
cttggttcga gataggagct tttctgtgtc ctaagccctt tcatgctagc aggaagactg   3900
aaagcaaggt ggcccagtgt ggggtcatag ggcttgatag acctggcact gcctatctgc   3960
acttccaggt gccccaccta tttatctgag cccacaggtg gaaaggggaa ctgcctcagt   4020
gagaacgggg ggacggggat gttaggaaaa atacagtaaa gttgcaatga agaggttcat   4080
gaagtatgtc cttgttcttt ttggaaactc tcggcaaagg gcaaaccagc aagtattgag   4140
ggtacccatc tagctacttg gggtcaggac ctcgtcagac caggttcgga tacaatcatc   4200
tgctcatccc aggaatagtt tcttggggga ctcactcact ggtgccagtt ctaagtcaga   4260
gacaaaattc cactgtctgt tccttttgct gtctgaactt tatgtgttac tcccttcctt   4320
tggtcttcac tctaatccct ggagtttgtg ggcttttggt tatgtttggt tagtagatat   4380
caccgcaatg ccctagaaca gctatgaagc agaataccat atggccacct ggacattggg   4440
acttgggaat tcactctcaa ctgggccatc catgttgtga tgcccttgaa gtaaaatgga   4500
gccagcagga gtaccttctg taaatgcatg tggcaaagtg ctatttatag ggtgcccagg   4560
gagccgctga tgtacaataa ccttgaggtc ccccatactg aaaactgacc aaggcctgtg   4620
cacaggtagc ccctcatgct gggctctgga ccatgagctg agtaggaagg atagcagagg   4680
ccaaccctga ccttcctgga agttgtttcc ttaacttgaa tgttgagctt cctctaaagc   4740
tttctcgtgt atgtcttctc catgccacta ctctgaggcc tcctgtgtta tgtgtgaaca   4800
gttgtcttta tgtgggaatg acgacttgat tgggagtaga gtctcaaggt cattcccctc   4860
ttccctcaag actctctgaa tgctgctcca ctgtcttttg tcttggaggt cactcagcag   4920
gttccttgca tttgctgcct ggatgtgcag ctggcaacag tgatgaattg gtcactgctc   4980
tttctctata actgggatag atgtcctgcc ttggggtcac taaaggggtg accttgttcc   5040
ttgcttatg  agcccattag cactttggtt caagggccc   accaagtctt ggacgggaag   5100
gcgctactgg ttttattgcc caaggttttg ttattgcttc tcttctgtgt ccttctcttt   5160
gttcagtgaa gccaatatgt aagatactgt ttttgtcccc attcccctac tcctgagcta   5220
ggaggaaaaa atgtgaatct taccagcagt tccagccaac caagtgattc ttcttcattc   5280
ttgatgggga gaagtacata caaagtttgt tctgacaggg cgcggtggct cacgcctgta   5340
atcccagcgc tttgggaggc agaggcaggt ggatcacctg aggtcgggag ttcgagacca   5400
gcctgaccaa catggagata tcctgtctct actaaaaata caaaaaaatt agccaggcat   5460
ggtggcacgt gcctgtaatc ccagctactc gcaaggctga ggcaggagaa tcgcttgaac   5520
ctgggaggcg gaggttgcag tgagccaaga ttgcgccatt gcactccagc ctgggcaaca   5580
agagagaaac tctgtctcaa aa                                              5602
```

<210> SEQ ID NO 49
<211> LENGTH: 824
<212> TYPE: DNA

<213> ORGANISM: Homo sapiens

<400> SEQUENCE: 49

```
ccgggccccg ccgcgccgcc tccttcccag ctcgcccgcc caggcctggc ctcctgcttt      60
tccatttgat tccctgcctc tttctattcg gactggaatg ccgggccagg ctccggggcg     120
cgccgctgcg gcagccgcac ctcgcaggtc ccccggccga ccccgacgcg gaagcggcgg     180
ccctcctcgc cgtcggggag ccagggagcc ggggacgatc agtcacataa ggcttagagg     240
atcaaggatc ctgcccagat gacttaccga aatgttacag attaagttgg tgtggtaacc     300
tgggctgagc actctgggag aggaagagaa gagagaagac aggaaacaac tgaactatga     360
ccaatcccag cacggaggcc cagaaaactt taagatttga gtattaatgt ctcaaggtca     420
ggagcaacct caaggctaaa actcagatct caggactcaa tttcacagaa gttccactat     480
aaaggcaata atctaaagct ttaaatgata tgaaaatttt gtaataagag ttcagtattt     540
ctgccaacat tggcgcatgg attgcaaagt tcacaggatt gaaaacacca tcgacataat     600
ggaaattgaa cagcatctga ttactgagtg ctatatcagc aagttaaaag gatcttttgc     660
atacctttta atggtatata tcctaaaact gaagtgttca atatagacat ccagattgaa     720
actcaggcag tgaattacat acacaacaaa tcagttgaac atggcagagc ttgtcagact     780
tatgaaagat taaatacatt ttacatttcc acaagtgtgg tatt                      824
```

<210> SEQ ID NO 50
<211> LENGTH: 7130
<212> TYPE: DNA
<213> ORGANISM: Homo sapiens

<400> SEQUENCE: 50

```
gaattccaca ttgtttgctg cacgttggat tttgaaatgc tagggaactt tgggagactc      60
atatttctgg gctagaggat ctgtggacca caagatcttt ttatgatgac agtagcaatg     120
tatctgtgga gctggattct gggttgggag tgcaaggaaa agaatgtact aaatgccaag     180
acatctattt caggagcatg aggaataaaa gttctagttt ctggtctcag agtggtgcag     240
ggatcaggga gtctcacaat ctcctgagtg ctggtgtctt agggcacact gggtcttgga     300
gtgcaaagga tctaggcacg tgaggctttg tatgaagaat cggggatcgt acccaccccc     360
tgttctgtt tcatcctggg catgtctcct ctgcctttgt ccctagatg aagtctccat       420
gagctacaag ggcctggtgc atccagggtg atctagtaat tgcagaacag caagtgctag     480
ctctccctcc ccttccacag ctctgggtgt gggagggggt tgtccagcct ccagcagcat     540
ggggagggcc ttggtcagcc tctgggtgcc agcagggcag gggcggagtc ctggggaatg     600
aaggttttat agggctcctg ggggaggctc cccagcccca agcttaccac ctgcacccgg     660
agagctgtgt caccatgtgg gtcccggttg tcttcctcac cctgtccgtg acgtggattg     720
gtgagagggg ccatggttgg ggggatgcag gagagggagc cagccctgac tgtcaagctg     780
aggctctttc ccccccaacc cagcaccccca gcccagacag ggagctgggc tcttttctgt     840
ctctcccagc cccacttcaa gcccataccc ccagcccctc catattgcaa cagtcctcac     900
tcccacacca ggtccccgct ccctcccact taccccagaa cttttctcccc attgccagc     960
cagctccctg ctcccagctg ctttactaaa ggggaagttc ctgggcatct ccgtgtttct    1020
cttttgtgggg ctcaaaacct ccaaggacct ctctcaatgc cattggttcc ttggaccgta    1080
tcactggtcc atctcctgag cccctcaatc ctatcacagt ctactgactt tcccattca     1140
gctgtgagtg tccaacccta tcccagagac cttgatgctt ggcctcccaa tcttgcccta    1200
```

```
ggatacccag atgccaacca gacacctcct tcttcctagc caggctatct ggcctgagac    1260
aacaaatggg tccctcagtc tggcaatggg actctgagaa ctcctcattc cctgactctt    1320
agccccagac tcttcattca gtggcccaca ttttccttag gaaaaacatg agcatcccca    1380
gccacaactg ccagctctct gattcoccaa atctgcatcc ttttcaaaac ctaaaaacaa    1440
aaagaaaaac aaataaaaca aaaccaactc agaccagaac tgttttctca acctgggact    1500
tcctaaactt tccaaaacct tcctcttcca gcaactgaac ctggccataa ggcacttatc    1560
cctggttcct agcaccccctt atccctcag aatccacaac ttgtaccaag tttcccttct    1620
cccagtccaa gaccccaaat caccacaaag gacccaatcc ccagactcaa gatatggtct    1680
gggcgctgtc ttgtgtctcc taccctgatc cctgggttca actctgctcc cagagcatga    1740
agcctctcca ccagcaccag ccaccaacct gcaaacctag gaagattga cagaattccc    1800
agcctttccc agctccccct gcccatgtcc caggactccc agccttggtt ctctgccccc    1860
gtgtcttttc aaacccacat cctaaatcca tctcctatcc gagtccccca gttcccctg     1920
tcaaccctga ttcccctgat ctagcacccc ctctgcaggc gctgcgcccc tcatcctgtc    1980
tcggattgtg ggaggctggg agtgcgagaa gcattcccaa ccctggcagg tgcttgtggc    2040
ctctcgtggc agggcagtct gcggcggtgt tctggtgcac ccccagtggg tcctcacagc    2100
tgcccactgc atcaggaagt gagtaggggc ctggggtctg gggagcaggt gtctgtgtcc    2160
cagaggaata acagctgggc attttcccca ggataacctc taaggccagc cttgggactg    2220
ggggagagag ggaaagttct ggttcaggtc acatggggag gcagggttgg ggctggacca    2280
ccctccccat ggctgcctgg gtctccatct gtgtccctct atgtctcttt gtgtcgcttt    2340
cattatgtct cttggtaact ggcttcggtt gtgtctctcc gtgtgactat tttgttctct    2400
ctctccctct cttctctgtc ttcagtctcc atatctcccc ctctctctgt ccttctctgg    2460
tccctctcta gccagtgtgt ctcacccctgt atctctctgc caggctctgt ctctcggtct    2520
ctgtctcacc tgtgccttct ccctactgaa cacacgcacg ggatgggcct ggggggaccc    2580
tgagaaaagg aagggctttg gctgggcgcg gtggctcaca cctgtaatcc cagcactttg    2640
ggaggccaag gcaggtagat cacctgaggt caggagttcg agaccagcct ggccaactgg    2700
tgaaacccca tctctactaa aaatacaaaa aattagccag gcgtggtggc gcatgcctgt    2760
agtcccagct actcaggagg ctgagggagg agaattgctt gaacctggga ggttgaggtt    2820
gcagtgagcc gagaccgtgc cactgcactc cagcctgggt gacagagtga gactccgcct    2880
caaaaaaaaa aaaaaaaaa aaaaaaaaa agaaaagaaa agaaagaaa aggaatcttt       2940
tatccctgat gtgtgtgggt atgagggtat gagagggccc ctctcactcc attccttctc    3000
caggacatcc ctccactctt gggagacaca gagaagggct ggttccagct ggagctggga    3060
ggggcaattg agggaggagg aaggagaagg gggaaggaaa acagggtatg ggggaaagga    3120
ccctggggag cgaagtggag gatacaacct tgggcctgca ggccaggcta cctacccact    3180
tggaaaccca cgccaaagcc gcatctacag ctgagccact ctgaggcctc ccctccccgg    3240
cggtccccac tcagctccaa agtctctctc ccttttctct cccacacttt atcatccccc    3300
ggattcctct ctacttggtt ctcattcttc ctttgacttc ctgcttccct ttctcattca    3360
tctgtttctc actttctgcc tggttttgtt cttctctctc tctttctctg gcccatgtct    3420
gtttctctat gtttctgtct tttctttctc atcctgtgta ttttcggctc acctgtttg     3480
tcactgttct cccctctgcc ctttcattct ctctgtcctt ttaccctctt ccttttcccc    3540
```

```
ttggtttctc tcagtttctg tatctgccct tcaccctctc acactgctgt ttcccaactc    3600
gttgtctgta tttttggcct gaactgtgtc ttccccaacc ctgtgttttt ctcactgttt    3660
cttttttctct tttggagcct cctccttgct cctctgtccc ttctctcttt ccttatcatc   3720
ctcgctcctc attcctgcgt ctgcttcctc cccagcaaaa gcgtgatctt gctgggtcgg    3780
cacagcctgt ttcatcctga agacacaggc caggtatttc aggtcagcca cagcttccca    3840
cacccgctct acgatatgag cctcctgaag aatcgattcc tcaggccagg tgatgactcc    3900
agccacgacc tcatgctgct ccgcctgtca gagcctgccg agctcacgga tgctgtgaag    3960
gtcatggacc tgcccaccca ggagccagca ctggggacca cctgctacgc ctcaggctgg    4020
ggcagcattg aaccagagga gtgtacgcct gggccagatg gtgcagccgg gagcccagat    4080
gcctgggtct gagggaggag gggacaggac tcctgggtct gagggaggag ggccaaggaa    4140
ccaggtgggg tccagcccac aacagtgttt ttgcctggcc cgtagtcttg accccaaaga    4200
aacttcagtg tgtggacctc catgttattt ccaatgacgt gtgtgcgcaa gttcaccctc    4260
agaaggtgac caagttcatg ctgtgtgctg gacgctggac agggggcaaa agcacctgct    4320
cggtgagtca tccctactcc caagatcttg aggggaaagg tgagtgggga ccttaattct    4380
gggctggggt ctagaagcca acaaggcgtc tgcctcccct gctccccagc tgtagccatg    4440
ccacctcccc gtgtctcatc tcattccctc cttccctctt ctttgactcc ctcaaggcaa    4500
taggttattc ttacagcaca actcatctgt tcctgcgttc agcacacggt tactaggcac    4560
ctgctatgca cccagcactg ccctagagcc tgggacatag cagtgaacag acagagagca    4620
gcccctccct tctgtagccc ccaagccagt gaggggcaca gcaggaaca gggaccacaa     4680
cacagaaaag ctggagggtg tcaggaggtg atcaggctct cggggaggga aaggggtgg     4740
ggagtgtgac tgggaggaga catcctgcag aaggtgggag tgagcaaaca cctgccgcag    4800
gggagggag ggccctgcgg cacctggggg agcagaggga acagcatctg gccaggcctg      4860
ggaggagggg cctagagggc gtcaggagca gagaggaggt tgcctggctg gagtgaagga    4920
tcggggcagg gtgcgagagg gaagaaagga cccctcctgc agggcctcac ctgggccaca    4980
ggaggacact gcttttcctc tgaggagtca ggaactgtgg atggtgctgg acagaagcag    5040
gacagggcct ggctcaggtg tccagaggct gccgctggcc tccctatggg atcagactgc    5100
agggagggag ggcagcaggg atgtggaggg agtgatgatg gggctgacct gggggtggct    5160
ccaggcattg tccccacctg ggcccttacc cagcctccct cacaggctcc tggccctcag    5220
tctctcccct ccactccatt ctccacctac ccacagtggg tcattctgat caccgaactg    5280
accatgccag ccctgccgat ggtcctccat ggctccctag tgccctggag aggaggtgtc    5340
tagtcagaga gtagtcctgg aaggtggcct ctgtgaggag ccacggggac agcatcctgc    5400
agatggtcct ggcccttgtc ccaccgacct gtctacaagg actgtcctcg tggaccctcc    5460
cctctgcaca ggagctggac cctgaagtcc cttccctacc ggccaggact ggagccccta    5520
cccctctgtt ggaatccctg cccaccttct tctggaagtc ggctctggag acatttctct    5580
cttcttccaa agctgggaac tgctatctgt tatctgcctg tccaggtctg aaagatagga    5640
ttgcccaggc agaaactggg actgacctat ctcactctct ccctgctttt acccttaggg    5700
tgattctggg ggcccacttg tctgtaatgg tgtgcttcaa ggtatcacgt catggggcag    5760
tgaaccatgt gccctgcccg aaaggccttc cctgtacacc aaggtggtgc attaccggaa    5820
gtggatcaag gacaccatcg tggccaaccc ctgagcaccc ctatcaactc cctattgtag    5880
taaacttgga accttggaaa tgaccaggcc aagactcaag cctccccagt tctactgacc    5940
```

```
tttgtcctta ggtgtgaggt ccagggttgc taggaaaaga aatcagcaga cacaggtgta    6000
gaccagagtg tttcttaaat ggtgtaattt tgtcctctct gtgtcctggg gaatactggc    6060
catgcctgga gacatatcac tcaatttctc tgaggacaca gataggatgg ggtgtctgtg    6120
ttatttgtgg gatacagaga tgaaagaggg gtgggatcca cactgagaga gtggagagtg    6180
acatgtgctg gacactgtcc atgaagcact gagcagaagc tggaggcaca acgcaccaga    6240
cactcacagc aaggatggag ctgaaaacat aacccactct gtcctggagg cactgggaag    6300
cctagagaag gctgtgagcc aaggagggag ggtcttcctt tggcatggga tggggatgaa    6360
gtaaggagag ggactggacc ccctggaagc tgattcacta tgggggggagg tgtattgaag   6420 tcctccagac aaccctcaga tttgatgatt cctagtaga actcacagaa ataaagagct    6480
cttatactgt ggtttattct ggtttgttac attgacagga gacacactga aatcagcaaa    6540
ggaaacaggc atctaagtgg ggatgtgaag aaaacaggga aaatctttca gttgttttct    6600
cccagtgggg tgttgtggac agcacttaaa tcacacagaa gtgatgtgtg accttgtgta    6660
tgaagtattt ccaactaagg aagctcacct gagccttagt gtccagagtt cttattgggg    6720
gtctgtagga taggcatggg gtactggaat agctgacctt aacttctcag acctgaggtt    6780
cccaagagtt caagcagata cagcatggcc tagagcctca gatgtacaaa acaggcatt    6840 catcatgaat cgcactgtta gcatgaatca tctggcacgg cccaaggccc caggtatacc    6900
aaggcacttg ggccgaatgt tccaagggat taaatgtcat ctcccaggag ttattcaagg    6960
gtgagccctg tacttggaac gttcaggctt tgagcagtgc agggctgctg agtcaacctt    7020
ttactgtaca gggggggtgag ggaaagggag aagatgagga aaccgcctag ggatctggtt   7080
ctgtcttgtg gccgagtgga ccatggggct atcccaagaa ggaggaattc               7130

<210> SEQ ID NO 51
<211> LENGTH: 534
<212> TYPE: DNA
<213> ORGANISM: Homo sapiens

<400> SEQUENCE: 51
cgactttccc gatcgccagg caggagtttc tctcggtgac tactatcgct gtcatgtctg      60
gtcgtggcaa gcaaggaggc aaggcccgcg ccaaggccaa gtcgcgctcg tcccgcgctg     120
gccttcagtt cccggtaggg cgagtgcatc gcttgctgcg caaaggcaac tacgcggagc     180
gagtgggggc cggcgcgccc gtctacatgg ctgcggtcct cgagtatctg accgccgaga     240
tcctggagct ggcgggcaac gcggctcggg acaacaagaa gacgcgcatc atccctcgtc     300
acctccagct ggccatccgc aacgacgagg aactgaacaa gctgctgggc aaagtcacca     360
tcgcccaggg cggcgtcttg cctaacatcc aggccgtact gctccctaag aagacggaga     420
gtcaccacaa ggcaaagggc aagtgaggct gacgtccggc ccaagtgggc ccagcccggc     480
ccgcgtctcg aagggcacc tgtgaactca aaaggctctt ttcagagcca ccca            534

<210> SEQ ID NO 52
<211> LENGTH: 1478
<212> TYPE: DNA
<213> ORGANISM: Homo sapiens

<400> SEQUENCE: 52
gggtcctcgg agctgctctg gctgcgcgcg gagcgggctc cggagggaag tcccgagaca      60
aagggaagcg ccgccgccgc cgccccgctc ggtcctccac ctgtccgcta cgctcgccgg     120
```

```
ggctgcggcc gcccgaggct gccctgagga tctgtgtttg gtgaaaagga gccaaattca      180
cctgcagggc aggcggctct agcagcttca gaagcctggt gccctggcga cactggacct      240
gccttggctt ctttgatccc aaccccaccc ccgatttctg ctctgctgac tggggaagtc      300
atcgtgccac ccagaacctg agtgcgggcc tctcagagct ccttcgtccg tgggtctgcc      360
ggggactggg ccttgtctcc ctaacgagtg ccagggactt tgaacatgtc ggggatcgcc      420
ctcagcagac tcgcccagga gaggaaagca tggaggaaag accacccatt tggtttcgtg      480
gctgtcccaa caaaaaatcc cgatggcacg atgaacctca tgaactggga gtgcgccatt      540
ccaggaaaga aagggactcc gtgggaagga ggcttgttta aactacggat gcttttcaaa      600
gatgattatc catcttcgcc accaaaatgt aaattcgaac caccattatt tcacccgaat      660
gtgtacccct cggggacagt gtgcctgtcc atcttagagg aggacaagga ctggaggcca      720
gccatcacaa tcaaacagat cctattagga atacaggaac ttctaaatga accaaatatc      780
caagacccag ctcaagcaga ggcctacacg atttactgcc aaaacagagt ggagtacgag      840
aaaagggtcc gagcacaagc caagaagttt gcgccctcat aagcagcgac cttgtggcat      900
cgtcaaaagg aagggattgg tttggcaaga acttgtttac aacattttg caaatctaaa      960 gttgctccat acaatgacta gtcacctggg ggggttgggc gggcgccatc ttccattgcc     1020
gccgcgggtg tgcggtctcg attcgctgaa ttgcccgttt ccatacaggg tctcttcctt     1080
cggtcttttg tatttttgat tgttatgtaa aactcgcttt tattttaata ttgatgtcag     1140
tatttcaact gctgtaaaat tataaacttt tatacttggg taagtccccc aggggcgagt     1200
tcctcgctct gggatgcagg catgcttctc accgtgcaga gctgcacttg gcctcagctg     1260
gctgtatgga aatgcaccct ccctcctgcc gctcctctct agaaccttct agaacctggg     1320
ctgtgctgct tttgagcctc agaccccagg tcagcatctc ggttctgcgc cacttccttt     1380
gtgtttatat ggcgttttgt ctgtgttgct gtttagagta aataaactgt ttatataaag     1440
gttttggttg cattattatc attgaaagtg agaggagg                             1478
```

<210> SEQ ID NO 53
<211> LENGTH: 3670
<212> TYPE: DNA
<213> ORGANISM: Homo sapiens

<400> SEQUENCE: 53

```
cgcagcaaac acatccgtag aaggcagcgc ggccgccgag aaccgcagcg ccgctcgccc       60 gccgccccc accccgccgc ccccgccggc gaattgcgcc ccgcgcccct cccctcgcgc      120
ccccgagaca aagaggagag aaagtttgcg cggccgagcg gggcaggtga ggagggtgag      180
ccgcgcggga ggggccccgcc tcggcccccgg ctcagccccc gcccgcgccc ccagcccgcc      240
gccgcgagca gcgcccggac ccccagcgg cggcccccgc ccgcccagcc cccggcccg      300 ccatgggcgc cgcggcccgc accctgcggc tggcgctcgg cctcctgctg ctggcgacgc      360
tgcttcgccc ggccgacgcc tgcagctgct ccccggtgca cccgcaacag gcgttttgca      420
atgcagatgt agtgatcagg gccaaagcgg tcagtgagaa ggaagtggac tctggaaacg      480
acatttatgg caaccctatc aagaggatcc agtatgagat caagcagata aagatgttca      540
aagggcctga gaaggatata gagtttatct acacggcccc ctcctcggca gtgtgtgggg      600
tctcgctgga cgttggagga aagaaggaat atctcattgc aggaaaggcc gaggggacg      660 gcaagatgca catcaccctc tgtgacttca tcgtgcccg ggacaccctg agcaccaccc      720
agaagaagag cctgaaccac aggtaccaga tgggctgcga gtgcaagatc acgcgctgcc      780
```

```
ccatgatccc gtgctacatc tcctccccgg acgagtgcct ctggatggac tgggtcacag    840
agaagaacat caacgggcac caggccaagt tcttcgcctg catcaagaga agtgacggct    900
cctgtgcgtg gtaccgcggc gcggcgcccc ccaagcagga gtttctcgac atcgaggacc    960
cataagcagg cctccaacgc ccctgtggcc aactgcaaaa aaagcctcca agggtttcga    1020
ctggtccagc tctgacatcc cttcctggaa acagcatgaa taaacactc atcccatggg     1080
tccaaattaa tatgattctg ctccccccctt ctccttttag acatggttgt gggtctggag   1140
ggagacgtgg gtccaaggtc ctcatcccat cctccctctg ccaggcacta tgtgtctggg    1200
gcttcgatcc ttgggtgcag gcagggctgg gacacgcggc ttccctccca gtccctgcct    1260
tggcaccgtc acagatgcca agcaggcagc acttagggat ctcccagctg ggttagggca    1320
gggcctggaa atgtgcattt tgcagaaact tttgagggtc gttgcaagac tgtgtagcag    1380
gcctaccagg tccctttcat cttgagaggg acatggccct tgttttctgc agcttccacg    1440
cctctgcact ccctgcccct ggcaagtgct cccatcgccc cggtgcccac catgagctcc    1500
cagcacctga ctcccccccac atccaagggc agcctggaac cagtggctag ttcttgaagg    1560
agccccatca atcctattaa tcctcagaat tccagtggga gcctccctct gagccttgta    1620
gaaatgggag cgagaaaccc cagctgagct gcgttccagc ctcagctgag tcttttttggt   1680
ctgcacccac cccccacccc cccccccccc gcccacatgc tccccagctt gcaggaggaa    1740
tcggtgaggt cctgtcctga ggctgctgtc cggggccggt ggctgccctc aaggtccctt    1800
ccctagctgc tgcggttgcc attgcttctt gcctgttctg gcatcaggca cctggattga    1860
gttgcacagc tttgctttat ccgggcttgt gtgcagggcc cggctgggct ccccatctgc    1920
acatcctgag gacagaaaaa gctgggtctt gctgtgccct cccaggctta gtgttccctc    1980
cctcaaagac tgacagccat cgttctgcac ggggctttct gcatgtgacg ccagctaagc    2040
atagtaagaa gtccagccta ggaagggaag gattttggag gtaggtggct ttggtgacac    2100
actcacttct ttctcagcct ccaggacact atggcctgtt ttaagagaca tcttattttt    2160
ctaaaggtga attctcagat gataggtgaa cctgagttgc agatatacca acttctgctt    2220
gtatttctta aatgacaaag attacctagc taagaaactt cctagggaac tagggaacct    2280
atgtgttccc tcagtgtggt ttcctgaagc cagtgatatg ggggttagga taggaagaac    2340
tttctcggta atgataagga gaatctcttg tttcctccca cctgtgttgt aaagataaac    2400
tgacgatata caggcacatt atgtaaacat acacacgcaa tgaaaccgaa gcttggcggc    2460
ctgggcgtgg tcttgcaaaa tgcttccaaa gccaccttag cctgttctat tcagcggcaa    2520
ccccaaagca cctgttaaga ctcctgaccc ccaagtggca tgcagccccc atgcccaccg    2580
ggacctggtc agcacagatc ttgatgactt ccctttctag ggcagactgg gagggtatcc    2640
aggaatcggc ccctgcccca cgggcgtttt catgctgtac agtgacctaa agttggtaag    2700
atgtcataat ggaccagtcc atgtgatttc agtatataca actccaccag acccctccaa    2760
cccatataac accccacccc tgttcgcttc ctgtatggtg atatcatatg taacatttac    2820
tcctgttctt gctgattgtt tttttaatgt tttggtttgt ttttgacatc agctgtaatc    2880
attcctgtgc tgtgtttttt attacccttg gtaggtatta gacttgcact ttttttaaaaa   2940
aaggtttctg catcgtggaa gcatttgacc cagagtggaa cgcgtggcct atgcaggtgg    3000
attccttcag gtctttcctt tggttctttg agcatctttg ctttcattcg tctcccgtct    3060
ttggttctcc agttcaaatt attgcaaagt aaaggatctt tgagtaggtt cggtctgaaa    3120
```

| | |
|---|---:|
| ggtgtggcct ttatatttga tccacacacg ttggtctttt aaccgtgctg agcagaaaac | 3180 |
| aaaacaggtt aagaagagcc gggtggcagc tgacagagga agccgctcaa ataccttcac | 3240 |
| aataaatagt ggcaatatat atatagttta agaaggctct ccatttggca tcgtttaatt | 3300 |
| tatatgttat gttctaagca cagctctctt ctcctatttt catcctgcaa gcaactcaaa | 3360 |
| atatttaaaa taaagtttac attgtagtta ttttcaaatc tttgcttgat aagtattaag | 3420 |
| aaatattgga cttgctgccg taatttaaag ctctgttgat tttgtttccg tttggatttt | 3480 |
| tgggggaggg gagcactgtg tttatgctgg aatatgaagt ctgagacctt ccggtgctgg | 3540 |
| gaacacacaa gagttgttga aagttgacaa gcagactgcg catgtctctg atgctttgta | 3600 |
| tcattcttga gcaatcgctc ggtccgtgga caataaacag tattatcaaa gagaaaaaaa | 3660 |
| aaaaaaaaaa | 3670 |

<210> SEQ ID NO 54
<211> LENGTH: 2428
<212> TYPE: DNA
<213> ORGANISM: Homo sapiens

<400> SEQUENCE: 54

| | |
|---|---:|
| cgtccagttt gagtctaggt tggagttgga accgtggaga tgcggaagga aaccccaccc | 60 |
| cccctagtgc ccccggcggc ccgggagtgg aatcttcccc caaatgcgcc cgcctgcatg | 120 |
| gaacggcagt tggaggctgc gcggtaccgg tccgatgggg cgcttctcct cggggcctcc | 180 |
| agcctgagtg ggcgctgctg ggccggctcc ctctggcttt ttaaggaccc ctgtgccgcc | 240 |
| cccaacgaag gcttctgctc cgccggagtc caaacggagg ctggagtggc tgacctcact | 300 |
| tgggttgggg agagaggtat tctagtggcc tccgattcag gtgctgttga attgtgggaa | 360 |
| ctagatgaga atgagacact tattgtcagc aagttctgca agtatgagca tgatgacatt | 420 |
| gtgtctacag tcagtgtctt gagctctggc acacaagctg tcagtggtag caaagacatc | 480 |
| tgcatcaagg tttgggacct tgctcagcag gtggtactga gttcataccg agctcatgct | 540 |
| gctcaggtca cttgtgttgc tgcctctcct cacaaggact ctgtgtttct ttcatgcagc | 600 |
| gaggacaata gaattttact ctgggatacc cgctgtccca agccagcatc acagattggc | 660 |
| tgcagtgcgc ctggctacct tcctacctcg ctggcttggc atcctcagca aagtgaagtc | 720 |
| tttgtctttg gtgatgagaa tgggacagtc tcccttgtgg acaccaagag tacaagctgt | 780 |
| gtcctgagct cagctgtaca ctcccagtgt gtcactgggc tggtgttctc cccacacagt | 840 |
| gttcccttcc tggcctctct cagtgaagac tgctcacttg ctgtgctgga ctcaagcctt | 900 |
| tctgagttgt ttagaagcca agcccacaga gactttgtga gagatgcgac ttggtccccg | 960 |
| ctcaatcact ccctgcttac cacagtgggc tgggaccatc aggtcgtcca ccacgttgtg | 1020 |
| cccacagaac ctctcccagc ccctggacct gcaagtgtta ctgagtagat tggatttaag | 1080 |
| acaaaaagca gtcccccat gagtgtccac ttctttgccc tgccctctca gcttgtgaga | 1140 |
| caacacagga gccttctata gtatgttgat atgctagatc tgtgccgtta ataggcatcg | 1200 |
| tctctcagcc tgagggaggc tggattctgg gttcctgtag tcacagggag gaaaagcttt | 1260 |
| cttaaaaatg gacatgtatg tgcgtgtgag tgtgtgtgta gatttatagt ttttggtagt | 1320 |
| ggcaggaata aaaaaaatcc atcctacatc ttccctaagc actgcctctc tctcaccccc | 1380 |
| caaaacaagt tgacgaaagg gtttatgta gctgtctatg aggaattggc cgtgtctggg | 1440 |
| tgggttatgg gatgtgggca tccctgggtt cttggaagca gctcttatgc tactcataga | 1500 |
| gatgggattg actttatttt tttatagtgc ttaattcacc attatgagaa atgcttccag | 1560 |

| | |
|---|---|
| tcacaaaaat gcagcccagc tcactctgag gaagaagcag gacttggtac ggttttacac | 1620 |
| aactccttac cattaaactg aatcagaaat ccatttctg gctgaataaa agtttggct | 1680 |
| tgcctgtgta atgcccactc ccttccccct ggctccctag tgatgggaca tatatgagag | 1740 |
| agaagtgttt ttctatcata gacaccatag gggaaagttt ggggatgaag gagagcttaa | 1800 |
| aggtgtttca attaagttag aaaactgaca caggctgttg agaattcttt gccacttttc | 1860 |
| ccaccccaaa acagcatggg gcctgacatc ttctgccctg gtcccctttc tcttgatgtg | 1920 |
| gaaagtctga atgcagtatt tatagacttc taaggtttta aaatccagta tcaagaagaa | 1980 |
| aatcagaaat actggttggt gaaataaaga gtttaggcat tgttggcctg tcttttttga | 2040 |
| agcatgtgtg ttatgtgtag ttagatatat ttcacttatg tgagtcatca tggtgttggt | 2100 |
| cttgtagccc attattttc ctgtgcttcc ccagcttccc aaagtagcta gttagaactt | 2160 |
| aaggtaaata tttattcttg ggttggtgga gtggatattg ccagttagga gtcatggatc | 2220 |
| aattactgat tatattgaaa gtaaatataa tcaattatgt acttttgagc tttgcaggtt | 2280 |
| caatttaggt aaaaatcaca ttatgaaact gggaaagtct gaaggaatat gggcaaaata | 2340 |
| tttctcagta aagcttccat gcttcaccct tgacatgatt acccttgagt aaaacatggg | 2400 |
| aatttgtaaa aaaaaaaaa aaaaaaaa | 2428 |

<210> SEQ ID NO 55
<211> LENGTH: 1980
<212> TYPE: DNA
<213> ORGANISM: Homo sapiens

<400> SEQUENCE: 55

| | |
|---|---|
| ttcgattttg gtgctgtgaa aagaatagaa aagaaaaaga aaatgaagag gtaagctcat | 60 |
| agcagattct ctttgtatgg atttaaggga aggacattat ccacaacaga aaactgacca | 120 |
| tttggatttt cttgtttgta gaaggtctttt aacatttcca ctgcttcctc agcccgatat | 180 |
| ccagggatac actgatggaa tgagaaagtt gagaataaac ataggcctat gaaaatgtgt | 240 |
| gctgtatccc ataaaaacaa catatatata catgattatg taaacagatt tcagatgtta | 300 |
| ataaactttg gggatattag taacatgggt aaggaggtac acttccaaaa gatgtttgat | 360 |
| atatcatctt tttcattact cccaatcaac tgttattagg catcactccc aatcaactgt | 420 |
| tattcatcca ttaactatta tagaagttac cagcttgtg atcttgggtt aggcacttaa | 480 |
| actctccatg ccttatttat acaatgctgg caataatagc acttacttca ggggattttg | 540 |
| tgaggattaa gtgagataat acctgttaaa taccaggcac atcataagtg ctcattaagc | 600 |
| attagttatt tttatctgct cctatttact agtggtccat taagcattcc atgctataga | 660 |
| gctagggttg gcaaattata cttggtggac caaatctgtt ccatagctga gaactgtgag | 720 |
| ctaagaatgg tttttatatc ttaaaagctt tgttaaagaa aaaaaagac taggtgacag | 780 |
| agatgtaagc ggctcacaaa gggtgaaata tttactagtt aacccctttgc agaaaaagtt | 840 |
| tatcaaccct tgctacagag gatttttaaaa aataaaatac agcttgttct atctttagca | 900 |
| tctaactggg gaaagaaat cataacatgt gaaagaataa ataagaaatt gtgctaacag | 960 |
| taaggagtgt tatatgaaat attacctgaa gaacatgaaa cttgaacttg ccttagagat | 1020 |
| agagaatatt taagaggct aagcagagca tttcagggaa agggcaagaa gaagcctggg | 1080 |
| ttgtgtgtga ggaaatcagc tgacagagga ggagactatt aaggaagcat aaggaaagaa | 1140 |
| agacaaaaaa ttggggtaaa aatatgtacg gctttgaaag cttgtcagaa gagtttggac | 1200 |

```
ttaaaaccaa gcacccttct gaagtgcatg aagtgacaca atgagcatct ggaaggaagg    1260
agccagaaag cataggcaca gaggacagga ggaccagcta ctgtgagatg ctgttcagaa    1320
cgaacctccc attctcctgt gtcttcagtc tgcccttgcc tgggcctccg acacctgcat    1380
aaaccttcgc cataacaaat aaccttccat ccaccctgtc ccgtcaaagg ctgacaccct    1440
gctcctgcct tcactcctca gtggcctcat cttcactggc ttgagttccc agcacttcac    1500
tgagtctgcc ctctcagaaa tccccaggtc cctactgacc aaaacacttg cctcctttca    1560
gattcctcaa ctctgcagtc ctggaggcaa ctggccacac ctgctctgtc tgaccgctct    1620
tgcctccctt ggcttctcag cattttacca tcctaaccac tgccagccag tcccgtcaca    1680
gctgccccct gcttcctgct gtgttaagtg ctggagctcc ccagaggtcc ccctccactc    1740
cactcgcaca ctcagagccc tctcctctta cgtgggatga gagcagtggt tctcaaccat    1800
tgctgctcag gagaaccagt tggaactctc tggaaacaca gcactgttgg ccccctgcct    1860
tctgattcag atggtctggg gcagggactg agcagagtca ggcacagaag cctccaggtg    1920
attctaacgg gcagtccggg atgagaactg ctgagttaca ggcctcgaag gaaactgcac    1980
```

<210> SEQ ID NO 56
<211> LENGTH: 55
<212> TYPE: PRT
<213> ORGANISM: Artificial Sequence
<220> FEATURE:
<223> OTHER INFORMATION: Synthetic

<400> SEQUENCE: 56

Ala Pro Arg Thr Arg Thr Leu Arg Ala Arg Arg Ser Pro Arg Met Glu
1               5                   10                  15

Ile Ala Gln Lys Trp Met Met Lys Thr Val Lys Glu Glu Trp Asn
            20                  25                  30

Val Trp Met Lys Cys Pro Ile Leu Lys Asn Ser Leu Pro Ile Ser Lys
        35                  40                  45

Ile Asn Phe Ile Lys Asn Asp
    50                  55

<210> SEQ ID NO 57
<211> LENGTH: 18
<212> TYPE: PRT
<213> ORGANISM: Artificial Sequence
<220> FEATURE:
<223> OTHER INFORMATION: Synthetic

<400> SEQUENCE: 57

Gly Thr Asn Gln Arg Arg Glu Gly Lys Ser Ser Gly Ile Phe Gln His
1               5                   10                  15

Phe Val

<210> SEQ ID NO 58
<211> LENGTH: 47
<212> TYPE: PRT
<213> ORGANISM: Artificial Sequence
<220> FEATURE:
<223> OTHER INFORMATION: Synthetic

<400> SEQUENCE: 58

Gly Lys Trp Cys His Ala Cys Ala Glu Leu Pro Glu Pro Ala Ser Thr
1               5                   10                  15

Thr Ser Asn Pro Leu Ser Glu Leu Pro Cys Cys Met Gly Trp Gln
            20                  25                  30

```
Cys Pro His Ser Ala Glu Glu Asn Leu Cys Tyr Thr Ala Gln Trp
         35                  40                  45
```

<210> SEQ ID NO 59
<211> LENGTH: 77
<212> TYPE: PRT
<213> ORGANISM: Artificial Sequence
<220> FEATURE:
<223> OTHER INFORMATION: Synthetic

<400> SEQUENCE: 59

```
Ile Asn Thr Leu Val Thr Tyr Asp Met Val Pro Glu Pro Lys Ile Ile
1               5                  10                  15

Asp Ala Ala Leu Arg Ala Cys Arg Arg Leu Asn Asp Phe Ala Ser Thr
            20                  25                  30

Val Arg Ile Leu Glu Val Val Lys Asp Lys Ala Gly Pro His Lys Glu
        35                  40                  45

Ile Tyr Pro Tyr Val Ile Gln Glu Leu Arg Pro Thr Leu Asn Glu Leu
    50                  55                  60

Gly Ile Ser Thr Pro Glu Glu Leu Gly Leu Asp Lys Val
65                  70                  75
```

<210> SEQ ID NO 60
<211> LENGTH: 39
<212> TYPE: PRT
<213> ORGANISM: Artificial Sequence
<220> FEATURE:
<223> OTHER INFORMATION: Synthetic

<400> SEQUENCE: 60

```
Glu Val His Ile Lys Lys Lys Thr Lys Gln Thr Leu Thr Asn Phe Gln
1               5                  10                  15

Met Gly Leu Leu Val Arg Gly Arg Glu Trp Pro Cys Pro Gly Cys Ala
            20                  25                  30

Ala Cys Leu Ser Lys Leu Pro
        35
```

<210> SEQ ID NO 61
<211> LENGTH: 22
<212> TYPE: PRT
<213> ORGANISM: Artificial Sequence
<220> FEATURE:
<223> OTHER INFORMATION: Synthetic

<400> SEQUENCE: 61

```
Asp His Ser Met Val Glu Phe Pro Arg Ile Ile Val Tyr Pro Gln Phe
1               5                  10                  15

Gly Val Gly Asn Glu Gly
            20
```

<210> SEQ ID NO 62
<211> LENGTH: 150
<212> TYPE: PRT
<213> ORGANISM: Artificial Sequence
<220> FEATURE:
<223> OTHER INFORMATION: Synthetic

<400> SEQUENCE: 62

```
Ser Ser Gly Ser Gly Glu Ser Arg Leu Gln His Ser Pro Ser Gln Ser
1               5                  10                  15

Tyr Leu Cys Ile Pro Phe Pro Arg Gly Glu Asp Gly Asp Gly Pro Ser
            20                  25                  30
```

Ser Asp Gly Ile His Glu Glu Pro Thr Pro Val Asn Ser Ala Thr Ser
            35                  40                  45

Thr Pro Gln Leu Thr Pro Thr Asn Ser Leu Lys Arg Gly Gly Ala His
    50                  55                  60

His Arg Arg Cys Glu Val Ala Leu Leu Gly Cys Gly Ala Val Leu Ala
65                  70                  75                  80

Ala Thr Gly Leu Gly Phe Asp Leu Leu Glu Ala Gly Lys Cys Gln Leu
                85                  90                  95

Leu Pro Leu Glu Glu Pro Glu Pro Pro Ala Arg Glu Lys Lys Arg
            100                 105                 110

Arg Glu Gly Leu Phe Gln Arg Ser Ser Arg Pro Arg Arg Ser Thr Ser
            115                 120                 125

Pro Pro Ser Arg Lys Leu Phe Lys Lys Glu Glu His Gln Ala Cys Gly
        130                 135                 140

Arg Thr Arg Val Thr Ser
145                 150

<210> SEQ ID NO 63
<211> LENGTH: 30
<212> TYPE: PRT
<213> ORGANISM: Artificial Sequence
<220> FEATURE:
<223> OTHER INFORMATION: Synthetic

<400> SEQUENCE: 63

Gln Lys Leu Cys Gln Ala Lys Glu Lys Gly Met Cys Met Lys Lys Leu
1               5                   10                  15

Arg Met Leu Trp Glu Cys Gln Lys Leu Tyr Ser Leu Gly Phe
            20                  25                  30

<210> SEQ ID NO 64
<211> LENGTH: 16
<212> TYPE: PRT
<213> ORGANISM: Artificial Sequence
<220> FEATURE:
<223> OTHER INFORMATION: Synthetic

<400> SEQUENCE: 64

Ser Glu Gly Arg Thr Val Thr Asn Lys Val Ser Arg Lys Tyr Thr Gly
1               5                   10                  15

<210> SEQ ID NO 65
<211> LENGTH: 42
<212> TYPE: PRT
<213> ORGANISM: Artificial Sequence
<220> FEATURE:
<223> OTHER INFORMATION: Synthetic

<400> SEQUENCE: 65

Gln Arg Gly Ser Gly Gln Gln Glu Asp Ala His His Pro Ser Ser Pro
1               5                   10                  15

Pro Ala Gly His Pro Gln Arg Arg Gly Thr Glu Gln Ala Ala Gly Gln
            20                  25                  30

Ser His His Arg Pro Gly Arg Arg Leu Ala
        35                  40

<210> SEQ ID NO 66
<211> LENGTH: 44
<212> TYPE: PRT
<213> ORGANISM: Artificial Sequence
<220> FEATURE:
<223> OTHER INFORMATION: Synthetic -continued

<400> SEQUENCE: 66

Ile Leu Tyr Pro Glu Thr Leu Leu Lys Leu Leu Ile Ser Leu Arg Arg
1               5                   10                  15

Phe Trp Ala Glu Met Met Glu Phe Ser Arg Tyr Thr Ile Met Ser Ser
            20                  25                  30

Glu Asn Arg Asp Asn Leu Thr Ser Ser Phe Pro Asn
        35                  40

<210> SEQ ID NO 67
<211> LENGTH: 25
<212> TYPE: PRT
<213> ORGANISM: Artificial Sequence
<220> FEATURE:
<223> OTHER INFORMATION: Synthetic

<400> SEQUENCE: 67

Cys Ser Lys His Ser Ser Leu Leu Phe Ser Ser Cys Lys Gln Leu
1               5                   10                  15

Lys Ile Phe Lys Ile Lys Phe Thr Leu
            20                  25

<210> SEQ ID NO 68
<211> LENGTH: 36
<212> TYPE: PRT
<213> ORGANISM: Artificial Sequence
<220> FEATURE:
<223> OTHER INFORMATION: Synthetic

<400> SEQUENCE: 68

Asn Ser Leu Pro Leu Phe Pro Pro Gln Asn Ser Met Gly Pro Asp Ile
1               5                   10                  15

Phe Cys Pro Gly Pro Leu Ser Leu Asp Val Glu Ser Leu Asn Ala Val
            20                  25                  30

Phe Ile Asp Phe
        35

<210> SEQ ID NO 69
<211> LENGTH: 27
<212> TYPE: PRT
<213> ORGANISM: Artificial Sequence
<220> FEATURE:
<223> OTHER INFORMATION: Synthetic

<400> SEQUENCE: 69

Val Ser Gly Ser Gln Arg Val Lys Tyr Leu Leu Val Asn Pro Leu Gln
1               5                   10                  15

Lys Lys Phe Ile Asn Pro Cys Tyr Arg Gly Phe
            20                  25

<210> SEQ ID NO 70
<211> LENGTH: 343
<212> TYPE: DNA
<213> ORGANISM: Artificial Sequence
<220> FEATURE:
<223> OTHER INFORMATION: Synthetic

<400> SEQUENCE: 70
tcgtcgaggc tcctgctcct gtgactctcg agcagccaga ggctcctacc tctatcgagt      60
ctttacctac tacttctgac actttcttct tcttacctta caaacctact ttacaggtta     120 gaacttttg tcaaatggct agagtttcta gttgaaatat ttcttgctaa ttcagtccac      180

```
ctacgttttg atgttcttca gtatcgacct tttcgtggtc ttatgaacct tggcgaccgt    240
tgaaatgtcc ttttatacgt ttaagcatgt ttccatcgtc cttagatatc tctcgagacg    300
aatcttagac atttcttgtt tatacttaca ctttaagttc gaa                      343
```

<210> SEQ ID NO 71
<211> LENGTH: 711
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t

<400> SEQUENCE: 71

```
ggaggtcgag gcggaggcgg aggaggagga ggccgaggcg ccggaggagg ccgaggcgcc     60
ggagcaggag gaggccggcc ggaggcggca tgagacgagc gtggcggccg cggctgctcg    120
gggccgcgct ggttgnccat tgacagcggc gtctgcagct cgcttcaaga tggccgcttg    180
gctcgcattc attttctgct gaacgacttt taactttcat tgtcttttcc gcccgcttcg    240
atcgcctcgc gccggctgct ctttccggga ttttttatca agcagaaatg catcgaacaa    300
cgagaatcaa gatcactgag ctaaatcccc ncctgatgtg tgtgctttgt ggagggtact    360
tcattgatgc cacaaccata atagaatgtc tacattcctt ctgtaaaacg tgtattgttc    420
gttacctgga gaccagcaag tattgtccta tttgtgatgt ccaagttcac aagaccagac    480
cactactgaa tataaggtca gataaaaactc tccaagatat tgtatacaaa ttagttccag    540
ggcttttcaa aaatgaaatg aagagaagaa gggatttta tgcagctcat ccttctgctg    600
atgctgccaa tggctctaat gaagatagag gaggacggtt gcagatgaag ataagagaat    660
tataanctga tgatgagata ataaggcttg cggccgcact cgagaaacag t             711
```

<210> SEQ ID NO 72
<211> LENGTH: 126
<212> TYPE: DNA
<213> ORGANISM: Artificial Sequence
<220> FEATURE:
<223> OTHER INFORMATION: Synthetic

<400> SEQUENCE: 72

```
ggagagaggg aaaatcaagt ggtattttcc agcactttgt atgattttgg atgagttgta     60
cacccaagga ttctgttctg caactccatc ctcctgtgtc actgaatatc aactctgaaa    120
gagcaa                                                               126
```

<210> SEQ ID NO 73
<211> LENGTH: 404
<212> TYPE: DNA
<213> ORGANISM: Artificial Sequence
<220> FEATURE:
<223> OTHER INFORMATION: Synthetic

<400> SEQUENCE: 73

```
cgggaaatgg tgccacgcat gcgcagaact tcccgagcca gcatccacca catcaaaccc     60
```

```
actgagtgag ctcccttgtt gttgcatggg atggcaatgt ccacatagcg cagaggagaa    120
tctgtgttac acagcgcaat ggtaggtagg ttaacataag atgcctccgt gagaggctgg    180
tggtcagccc tggggtcagt aaccacaaga agccgtggct cccggaaggc tgcctggatc    240
tggttagtga aggttccagg agtgaagcgg ccagcaattg gagtggctcc agtggcagca    300
gcaaacttca gcacagccct ctggccagta ttcctggagg atataacact gacatcagca    360
gggttttcaa tggcaacaat tgcacgagct gccagcagaa gctt                    404
```

<210> SEQ ID NO 74
<211> LENGTH: 412
<212> TYPE: DNA
<213> ORGANISM: Artificial Sequence
<220> FEATURE:
<223> OTHER INFORMATION: Synthetic

<400> SEQUENCE: 74

```
gataaacaca cttgttacct atgatatggt tccagagccc aaaatcattg atgctgcttt     60
gcgggcatgc agacggttaa atgattttgc tagtacagtt cgtatcctag aggttgttaa    120
ggacaaagca ggacctcata aggaaatcta cccctatgtc atccaggaac ttagaccaac    180
tttaaatgaa ctgggaatct ccactccgga ggaactgggc cttgacaaag tgtaaaccgc    240
atggatgggc ttccccaagg atttattgac attgctactt gagtgtgaac agttacctgg    300
aaatactgat gataacatat taccttattt gaacaagttt tcctttattg agtaccaagc    360
catgtaatgg taacttggac tttaataaaa gggaaatgag tttgaactga aa           412
```

<210> SEQ ID NO 75
<211> LENGTH: 281
<212> TYPE: DNA
<213> ORGANISM: Artificial Sequence
<220> FEATURE:
<223> OTHER INFORMATION: Synthetic

<400> SEQUENCE: 75

```
gggaagtcca cattaaaaag aaaacaaaac aaaccctaac taacttccaa atgggtctcc     60
tggtgcgggg gcgtgagtgg ccgtgccctg ggtgtgctgc ctgtctgagc aagcttccct    120
agctgtggaa ccccgggccc cctgctgcgg gctctgcctt ggtgtcatgc ctgctgcacc    180 cccgttttcca ctgacgtgcc gtctgtggct atggggtgg tcactggaat gacggtcact    240
ccagacgtca gccggcaggg atgcagcagg ctggccgcgc a                        281
```

<210> SEQ ID NO 76
<211> LENGTH: 327
<212> TYPE: DNA
<213> ORGANISM: Artificial Sequence
<220> FEATURE:
<223> OTHER INFORMATION: Synthetic

<400> SEQUENCE: 76

```
attctatggt ggaatttcca agaataattg tttatcctca gtttggagta ggaaatgaag     60
gataattttt tccatttcac ctctattgca aatttatttt ttcaagccac acaaaaaatt    120
gtctaagata aatgagaat tattcagatc aattctgcaa tgatacaggg aagatgtgaa    180
aggagggctc aatgcagagt tgtgaagttg aaaaccacta tttctgttct aaagacacag    240
taagcagaga tccatctctc ttcaggcatc ctgcttctct gcaggttact tctgctttaa    300
ggaaagtaca ttttttagaac aaagctt                                       327
```

```
<210> SEQ ID NO 77
<211> LENGTH: 532
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (493)..(493)
<223> OTHER INFORMATION: n is a, c, g, or t
<220> FEATURE:
<221> NAME/KEY: misc_feature
<222> LOCATION: (502)..(502)
<223> OTHER INFORMATION: n is a, c, g, or t
<220> FEATURE:
<221> NAME/KEY: misc_feature
<222> LOCATION: (513)..(514)
<223> OTHER INFORMATION: n is a, c, g, or t
<220> FEATURE:
<221> NAME/KEY: misc_feature
<222> LOCATION: (526)..(527)
<223> OTHER INFORMATION: n is a, c, g, or t
<220> FEATURE:
<221> NAME/KEY: misc_feature
<222> LOCATION: (529)..(529)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t

<400> SEQUENCE: 77
tcaagcggga gtggagagag tcgcctacag cattcaccca gccagtccta cctctgtatc      60
ccattccctc gtgagagga tggcgatggc ccctccagtg atggaatcca tgaggagccc     120
accccagtca actcggccac gagtacccct cagctgacgc caaccaacag cctcaagcgg     180
ggcggtgccc accaccgccg ctgcgaggtg gctctgctcg gctgtggggc tgttctggca     240
gccacaggcc tagggtttga cttgctggaa gctggcaagt gccagctgct tcccctggag     300
gagcctgagc caccagcccg ggaggagaag aaaagacggg agggtctttt tcagaggtcc     360
agccgtcctc gtcggagcac cagccccca tcccgaaagc ttttcaagaa ggaggagcac     420
caagcttgcg gccgcactcg agtaactagt taacccttg gggcctctaa acgggtcttg     480
agggggttan ctngttactc gngtgcggcc gcnngcttgg tgctcnncnt tn            532

<210> SEQ ID NO 78
<211> LENGTH: 358
<212> TYPE: DNA
<213> ORGANISM: Artificial Sequence
<220> FEATURE:
<223> OTHER INFORMATION: Synthetic

<400> SEQUENCE: 78
atcccagcac ggaggcccag aaaactttaa gatttgagta ttaatgtctc aaggtcagga      60
gcaacctcaa ggctaaaact cagatctcag gactcaattt cacagaagtt ccactataaa     120
ggcaataatc taaagcttta aatgatatga aaatttgta ataagagttc agtatttctg      180
ccaacattgg cgcatggatt gcaaagttca caggattgaa aacaccatcg acataatgga     240
aattgaacag catctgatta ctgagtgcta tatcagcaag ttaaaggat cttttgcata      300 cctttttaatg gtatatatcc taaaactgaa gtgttcaata tagacatcca gattgaaa      358
```

<210> SEQ ID NO 79
<211> LENGTH: 439
<212> TYPE: DNA
<213> ORGANISM: Artificial Sequence
<220> FEATURE:
<223> OTHER INFORMATION: Synthetic

<400> SEQUENCE: 79

```
tgtgtgggta tgagggtatg agagggcccc tctcactcca ttccttctcc aggacatccc    60
tccactcttg ggagacacag agaagggctg gttccagctg gagctgggag ggcaattga    120 gggaggagga aggagaaggg ggaaggaaaa cagggtatgg gggaaaggac cctggggagc    180
gaagtggagg atacaacctt gggcctgcag gccaggctac ctacccactt ggaaacccac    240
gccaaagccg catctacagc tgagccactc tgaggcctcc cctccccggc ggtccccact    300
cagctccaaa gtctctctcc cttttctctc ccacactcta tcatccccg gattcctctc    360 tacttggttc tcattcttcc tttgacttcc tgatcctgtg tattttcggc tcaccttgat    420
ttgtcactgt tctcccctc                                                   439
```

<210> SEQ ID NO 80
<211> LENGTH: 236
<212> TYPE: DNA
<213> ORGANISM: Artificial Sequence
<220> FEATURE:
<223> OTHER INFORMATION: Synthetic

<400> SEQUENCE: 80

```
acgcggctcg gggacaacaa gaagacgcgc atcatccctc gtcacctcca gctggccatc    60
cgcaacgacg aggaactgaa caagctgctg ggcaaagtca ccatcgccca gggcggcgtc   120
ttgcctaaca tccaggccgt actgctccct aagaagacgg agagtcacca caaggcaaag   180
ggcaagtgag gctgacgtcc ggcccaagtg ggcccagccc ggcccgcgtc tcgaag        236
```

<210> SEQ ID NO 81
<211> LENGTH: 380
<212> TYPE: DNA
<213> ORGANISM: Artificial Sequence
<220> FEATURE:
<223> OTHER INFORMATION: Synthetic

<400> SEQUENCE: 81

```
tgtggcatcg tcaaaaggaa gggattggtt tggcaagaac ttgtttacaa cattttttgca    60 aatctaaagt tgctccatac aatgactagt cacctggggg ggttgggcgg cgccatctt    120 ccattgccgc cgcgggtgtg cggtctcgat tcgctgaatt gcccgtttcc atacagggtc    180
tcttccttcg gtcttttgta tttttgattg ttatgtaaaa ctcgctttta ttttaatatt    240
gatgtcagta tttcaactgc tgtaaaatta taaactttta tacttgggta agtccccag    300 gggcgagttc ctcgctctgg gatgcaggca tgcttctcac cgtgcagagc tgcacttggc    360
ctcagctggc tgtatggaaa                                                 380
```

<210> SEQ ID NO 82
<211> LENGTH: 352
<212> TYPE: DNA
<213> ORGANISM: Artificial Sequence
<220> FEATURE:
<223> OTHER INFORMATION: Synthetic

<400> SEQUENCE: 82

```
atgttctaag cacagctctc ttctcctatt ttcatcctgc aagcaactca aaatatttaa    60
```

```
aataaagttt acattgtagt tattttcaaa tctttgcttg ataagtatta agaaatattg    120
gacttgctgc cgtaatttaa agctctgttg attttgtttc cgtttggatt tttgggggag    180
gggagcactg tgtttatgct ggaatatgaa gtctgagacc ttcggtgctg ggaacacaca    240
agagttgttg aaagttgaca agcagactgc gcatgtctct gatgctttgt atcattcttg    300
agcaatcgct cggtccgtgg acaataaaca gtattatcaa agagaaaaaa aa            352
```

<210> SEQ ID NO 83
<211> LENGTH: 506
<212> TYPE: DNA
<213> ORGANISM: Artificial Sequence
<220> FEATURE:
<223> OTHER INFORMATION: Synthetic

<400> SEQUENCE: 83

```
gccactttc ccaccccaaa acagcatggg gcctgacatc ttctgccctg gtcccctttc     60
tcttgatgtg gaaagtctga atgcagtatt tatagacttc taaggtttta aaatccagta   120
tcaagaagaa aatcagaaat actggttggt gaaataaaga gtttaggcat tgttggcctg   180 tctttttga agcatgtgtg ttatgtgtag ttagatatat ttcacttatg tgagtcatca    240
tggtgttggt cttgtagccc attatttttc ctgtgcttcc ccagcttccc aaagtagcta   300
gttagaactt aaggtaaata tttattcttg ggttggtgga gtggatattg ccagttagga   360
gtcatggatc aattactgat tatattgaaa gtaaatataa tcaattatgt acttttgagc   420
tttgcaggtt caatttaggt aaaaatcaca ttatgaaact gggaaagtct gaaggaatat   480
gggcaaaata tttctcagta aagctt                                        506
```

<210> SEQ ID NO 84
<211> LENGTH: 401
<212> TYPE: DNA
<213> ORGANISM: Artificial Sequence
<220> FEATURE:
<223> OTHER INFORMATION: Synthetic

<400> SEQUENCE: 84

```
gagatgtaag cggctcacaa agggtgaaat atttactagt taaccccctt gcagaaaaag    60
ttatcaaccc ttgctacaga ggattttaaa aaataaaata cagcttgttc tatctttagc   120
atctaactgg ggaaaagaat cataacatgt gaaagaataa ataagaaatt gtgctaacag   180
taaggagtgt tatatgaaat attacctgaa gaacatgaaa cttgaacttg ctagagatag   240
agaatattta aagaggctaa gcagagcatt tcagggaaag gcaagaaga agcctgggtt   300 gtgtgtgagg aaatcagctg acagaggagg agactattaa ggaagcataa ggaaagaaag   360
acaaaaaatt ggggtaaaaa tatgtacggc tttgaaagct t                       401
```

<210> SEQ ID NO 85
<211> LENGTH: 2407
<212> TYPE: DNA
<213> ORGANISM: Homo sapiens

<400> SEQUENCE: 85

```
gagcgccgca cctacaccag ccaacccaga tcccgaggtc cgacagcgcc cggcccagat    60
ccccacgcct gccaggagca agccgagagc cagccggccg gcgcactccg actccgagca   120
gtctctgtcc ttcgacccga gcccgcgcgc ctttccggga cccctgcccc gcgggcagcg   180
ctgccaacct gccggccatg gagacccgt cccagcggcg cgccacccgc agcggggcgc    240
aggccagctc cactccgctg tcgcccaccc gcatcacccg gctgcaggag aaggaggacc   300
```

```
tgcaggagct caatgatcgc ttggcggtct acatcgaccg tgtgcgctcg ctggaaacgg      360
agaacgcagg gctgcgcctt cgcatcaccg agtctgaaga ggtggtcagc cgcgaggtgt      420
ccggcatcaa ggccgcctac gaggccgagc tcggggatgc ccgcaagacc cttgactcag      480
tagccaagga gcgcgcccgc ctgcagctgg agctgagcaa agtgcgtgag gagtttaagg      540
agctgaaagc gcgcaatacc aagaaggagg gtgacctgat agctgctcag gctcggctga      600
aggacctgga ggctctgctg aactccaagg aggccgcact gagcactgct ctcagtgaga      660
agcgcacgct ggagggcgag ctgcatgatc tgcggggcca ggtggccaag cttgaggcag      720
ccctaggtga ggccaagaag caacttcagg atgagatgct gcggcgggtg gatgctgaga      780
acaggctgca gaccatgaag gaggaactgg acttccagaa gaacatctac agtgaggagc      840
tgcgtgagac caagcgccgt catgagaccc gactggtgga gattgacaat gggaagcagc      900
gtgagtttga gagccggctg gcggatgcgc tgcaggaact gcgggcccag catgaggacc      960
aggtggagca gtataagaag gagctggaga agacttattc tgccaagctg gacaatgcca     1020
ggcagtctgc tgagaggaac agcaacctgg tgggggctgc ccacgaggag ctgcagcagt     1080
cgcgcatccg catcgacagc ctctctgccc agctcagcca gctccagaag cagctggcag     1140
ccaaggaggc gaagcttcga gacctggagg actcactggc ccgtgagcgg acaccagcc      1200 ggcggctgct ggcggaaaag gagcgggaga tggccgagat gcgggcaagg atgcagcagc     1260
agctggacga gtaccaggag cttctggaca tcaagctggc cctggacatg gagatccacg     1320
cctaccgcaa gctcttggag ggcgaggagg agaggctacg cctgtccccc agccctacct     1380
cgcagcgcag ccgtggccgt gcttcctctc actcatccca gacacaggt gggggcagcg     1440 tcaccaaaaa gcgcaaactg gagtccactg agagccgcag cagcttctca cagcacgcac     1500
gcactagcgg gcgcgtggcc gtggaggagg tggatgagga gggcaagttt gtccggctgc     1560
gcaacaagtc caatgaggac cagtccatgg gcaattggca gatcaagcgc cagaatggag     1620 atgatcctt gctgacttac cggttcccac caaagttcac cctgaaggct gggcaggtgg     1680
tgacgatctg ggctgcagga gctgggggca cccacagccc ccctaccgac ctggtgtgga     1740
aggcacagaa cacctgggc tgcgggaaca gcctgcgtac ggctctcatc aactccactg     1800
gggaagaagt ggccatgcgc aagctggtgc gctcagtgac tgtggttgag gacgacgagg     1860
atgaggatgg agatgacctg ctccatcacc accacggctc ccactgcagc agctcggggg     1920
accccgctga gtacaacctg cgctcgcgca ccgtgctgtg cgggacctgc gggcagcctg     1980
ccgacaaggc atctgccagc ggctcaggag cccaggtggg cggaccccatc tcctctggct     2040 cttctgcctc cagtgtcacg gtcactcgca gctaccgcag tgtgggggc agtggggtg      2100 gcagcttcgg ggacaatctg gtcacccgct cctacctcct gggcaactcc agcccccgaa     2160
cccagagccc ccagaactgc agcatcatgt aatctgggac ctgccaggca ggggtggggg     2220
tggaggcttc ctgcgtcctc ctcacctcat gccacccc tgccctgcac gtcatggag      2280 ggggcttgaa gccaaagaaa aataacccctt tggttttttt cttctgtatt ttttttcta     2340 agagaagtta ttttctacag tggttttata ctgaaggaaa aacacaagca aaaaaaaaa      2400 aaaaaaa                                                              2407
```

<210> SEQ ID NO 86
<211> LENGTH: 567
<212> TYPE: DNA
<213> ORGANISM: Homo sapiens

<400> SEQUENCE: 86

```
gcgcagggtt tgaaacatgg cggacgacgt agaccagcaa caaactacca acactgtaga      60
ggagcccctg gatcttatca ggctcagcct agatgagcga atttatgtga aaatgagaaa     120
tgaccgagag cttcgaggca gattacatgc ttatgatcaa catttaaata tgatcttggg     180
agatgtggaa gaaactgtga ctactataga aattgatgaa gaaacatatg aagagatata     240
taaatcaacg aaacggaata ttccaatgct ctttgtccgg ggagatggcg ttgtcctggt     300
tgcccctcca ctgagagttg gctgaaacaa agaatttgtc ctgtatggaa aacgggagac     360
tttgtacagt ggcctctcta aaagtacaaa acattcataa gagaaacctg catacatttt     420
gatattaaga aataattccg gggattcttc cactcctgaa atgagttgat ttgcagataa     480
ctcacaactt cttaagctaa atggtatttt catttttctc aagctctcca ataaatatga     540
ccaccaagaa aaaaaaaaaa aaaaaaa                                          567
```

<210> SEQ ID NO 87
<211> LENGTH: 1980
<212> TYPE: DNA
<213> ORGANISM: Homo sapiens

<400> SEQUENCE: 87

```
tttaagggtg tacaagctct aattgttttt tttttttttt tgagatggag tttcactctg      60
tagcccaggc tggagtgcag tggcgcaatc gcggctcact gcaagctccg cctcctgggt     120
tcacaccatt ctcctgcctc agtctcccga gtagctggga ctacaggcgc tcgccaccac     180
gcccggctaa ttttttttgta ttttttagtag agacgggggtt tcaccatgtt agccaggtg     240
gtctcgatct cctgaccttg tgatccgcct gcctcggcct cccaaagtgc tgggattaca     300
ggcgtgagtg actgcgccca gcctcacagg ctctaattct tgactaattt tcctgtacac     360
gtcacttgta attgaaaagc tgagtgtaag atcagccgac acacccagag ttttattta      420
ttttattat ttatttatgg ttttttttg agatggagtc tcactctgtc gcccaggcta      480
gagtgcagtg gcgccatctc ggcttactgc aagctccacc tcctgggttc acgccattct     540
cctacctcag tctcctgagt agctgggact acaggcgccc accaccacgc ctggctaatt     600
ttttttgtatt tttagtagag acagggtttc accgtgttag gcaggatggt ctcgatctcc     660
tgacctcgtg attcgcccgc ctcggcctcc caaagcgctg ggattagaag cgtgagccac     720
cgcgcccgga ctattttatt tatttttttg agatggagtt tcacttttgt tgcccaggat     780
tgagtgcagt gccccgatct tggctcacta caacctctgc ctcctgggtt caagcgactc     840
tcctgcctca gtgtcctgag tagctgggat tacaggcgtc tgccaccacg cccggctaat     900
tttgtatttt tagtagagaa caggtttcac tatgttggtc aggctggtct tgaactcctg     960
acctcagcgc atccagaatt ttagacgggg ccccagggt gaggtcttgg caccctccag   1020
tagagaagaa gggacatggg ccatacgtgg ggtgtccttt ctgggagcct tgcgtccctt   1080
acctgcctag ccagggattg cacctcacag cacgcagcca gcaggaacgg caccgtgatc   1140
tgatttcacc tgcgggccct gggccctggg ggtgtttgac aattggggca tatcacagtg   1200
tgagctagtc ccgtctcggg ggtttggagg ctccacgtgg ccgtggtaca ggagcaggca   1260
gttccatcct ctggcctgga tcaggctctg cacacggagg cctgtgggcc agatgactga   1320
caggagggga gttgggtgga acctcggcct gcctgatatc cagcaacaga gggcaagggc   1380
ggcagcacct ccagcatgac agtcccttcc aagcacgtca ggatgctccc ttgcctgtgc   1440
tggcagcttc ctaaacatgg ggactgggca tggtggcagg ttttttgtcct tctgaaagag   1500
```

```
caattttgct gtgaggttac ttgctccttg agttcttgtc tgaggcccac ctggcggctg    1560
ctccgtgagg aacgaggtgg ccctgctgca gctcagcatc ccgccacgct cccaggagtg    1620
tgtgtttcct gggggagcg gcccgggacc gtggctctgt ggtccattct gtggatgtcc    1680
acaaggcctg ggcgttctgt gggtttgggt ggcagtcccg tctgggcagc tcctgctggg    1740
ctgggtgtgg gtctcctgct ggtctgcccc cagctgcaca acgtgtcttg tgccttgccc    1800
tcttgtacct ctgcaggttt tggctacggg cctccacctc caccgccaga tcagtttgcc    1860
cctccggggg ttcctcctcc accagccact cccggggcag cacctctggc tttcccaccg    1920
cctccgtctc aggctgcccc ggacatgagc aagcccccga cagctcagcc agacttcccc    1980

<210> SEQ ID NO 88
<211> LENGTH: 4005
<212> TYPE: DNA
<213> ORGANISM: Homo sapiens

<400> SEQUENCE: 88
cggcagggtt ggaaaatgat ggaagaggcg gaggtggagg cgaccgagtg ctgagaggaa      60
cctgcggaat cggccgagat ggggtctggc gcgcgctttc cctcggggac ccttcgtgtc     120
cggtggttgc tgttgcttgg cctggtgggc ccagtcctcg gtgcggcgcg gccaggcttt     180
caacagacct cacatctttc ttcttatgaa attataactc cttggagatt aactagagaa     240
agaagagaag cccctaggcc ctattcaaaa caagtatctt atgttattca ggctgaagga     300
aaagagcata ttattcactt ggaaaggaac aaagaccttt tgcctgaaga ttttgtggtt     360
tatacttaca caaggaagg gactttaatc actgaccatc ccaatataca gaatcattgt     420
cattatcggg gctatgtgga gggagttcat aattcatcca ttgctcttag cgactgtttt     480
ggactcagag gattgctgca tttagagaat gcgagttatg ggattgaacc cctgcagaac     540
agctctcatt ttgagcacat catttatcga atggatgatg tctacaaaga gcctctgaaa     600
tgtggagttt ccaacaagga tatagagaaa gaaactgcaa aggatgaaga ggaagagcct     660
cccagcatga ctcagctact tcgaagaaga gagctgtctt gccacagac ccggtatgtg     720 gagctgttca ttgtcgtaga caaggaaagg tatgacatga tgggaagaaa tcagactgct     780
gtgagagaag atgattgtct cctggcaaac tacttggata gtatgtatat tatgttaaat     840
attcgaattg tgctagttgg actggagatt tggaccaatg aaacctgat caacatagtt     900 gggggtgctg gtgatgtgct ggggaacttc gtgcagtggc gggaaaagtt tcttatcaca     960
cgtcggagac atgacagtgc acagctagtt ctaaagaaag gttttggtgg aactgcagga    1020
atggcatttg tgggaacagt gtgttcaagg agccacgcag gcgggattaa tgtgtttgga    1080
caaatcactg tggagacatt tgcttccatt gttgctcatg aattgggtca taatcttgga    1140
atgaatcacg atgatgggag agattgttcc tgtggagcaa agagctgcat catgaattca    1200
ggagcatcgg gttccagaaa ctttagcagt gcagtgcag aggactttga agttaact      1260 ttaaataaag gaggaaactg ccttcttaat attccaaagc ctgatgaagc ctatagtgct    1320
ccctcctgtg gtaataagtt ggtggacgct gggaagagt gtgactgtgg tactccaaag    1380
gaatgtgaat tggacccttg ctgcgaagga agtacctgta gcttaaatc atttgctgag    1440 tgtgcatatg gtgactgttg taaagactgt cggttccttc caggaggtac tttatgccga    1500
ggaaaaacca gtgagtgtga tgttccagag tactgcaatg gttcttctca gttcgtcag    1560 ccagatgttt ttattcagaa tggatatcct tgccagaata caaagccta ttgctacaac    1620
```

-continued

```
ggcatgtgcc agtattatga tgctcaatgt caagtcatct ttggctcaaa agccaaggct      1680
gcccccaaag attgtttcat tgaagtgaat tctaaaggtg acagatttgg caattgtggt      1740
ttctctggca atgaatacaa gaagtgtgcc actgggaatg ctttgtgtgg aaagcttcag      1800
tgtgagaatg tacaagagat acctgtattt ggaattgtgc ctgctattat tcaaacgcct      1860
agtcgaggca ccaaatgttg gggtgtggat ttccagctag gatcagatgt tccagatcct      1920
gggatggtta acgaaggcac aaaatgtggt gctggaaaga tctgtagaaa cttccagtgt      1980
gtagatgctt ctgttctgaa ttatgactgt gatgttcaga aaaagtgtca tggacatggg      2040
aaatgaatac tgcattgagg gacggacttc tggtcttctt cttcctaatt gttcccctta      2100
ttgtctgtgc tattttttatc ttcatcaaga gggatcaact gtggagaagc tacttcagaa      2160
agaagagatc acaaacatat gagtcagatg gcaaaaatca agcaaaccct tctagacagc      2220
cggggagtgt tcctcgacat gtttctccag tgacacctcc cagagaagtt cctatatatg      2280
caaacagatt tgcagtacca acctatgcag ccaagcaacc tcagcagttc ccatcaaggc      2340
cacctccacc acaaccgaaa gtatcatctc agggaaactt aattcctgcc cgtcctgctc      2400
ctgcacctcc tttatatagt tccctcactt gattttttta accttctttt tgcaaatgtc      2460
ttcagggaac tgagctaata cttttttttt ttcttgatgt tttcttgaaa agcctttctg      2520
ttgcaactat gaatgaaaac aaaacaccac aaaacagact tcactaacac agaaaaacag      2580
aaactgagtg tgagagttgt gaaatacaag gaaatgcagt aaagccaggg aatttacaat      2640
aacatttccg tttccatcat tgaataagtc ttattcagtc atcggtgagg ttaatgcact      2700
aatcatggat ttttgaaca tgttattgca gtgattctca aattaactgt attggtgtaa      2760 gattttgtc attaagtgtt taagtgttat tctgaatttt ctaccttagt tatcattaat      2820
gtagttcctc attgaacatg tgataatcta atacctgtga aaactgacta atcagctgcc      2880
aataatatct aatatttttc atcatgcacg aattaataat catcatactc tagaatcttg      2940
tctgtcactc actacatgaa taagcaaata ttgtcttcaa aagaatgcac aagaaccaca      3000
attaagatgt catattattt tgaaagtaca aaatatacta aaagagtgtg tgtgtattca      3060
cgcagttact cgcttccatt tttatgacct ttcaactata ggtaataact cttagagaaa      3120
ttaatttaat attagaattt ctattatgaa tcatgtgaaa gcatgacatt cgttcacaat      3180
agcactattt taaataaatt ataagcttta aggtacgaag tatttaatag atctaatcaa      3240
atatgttgat tcatggctat aataaagcag gagcaattat aaaatcttca atcaattgaa      3300
cttttacaaa accacttgag aatttcatga gcactttaaa atctgaactt tcaaagcttg      3360
ctattaaatc atttagaatg tttacattta ctaaggtgtg ctgggtcatg taaaatatta      3420
gacactaata ttttcataga aattaggctg gagaaagaag gaagaaatgg ttttcttaaa      3480
tacctacaaa aaagttactg tggtatctat gagttatcat cttagctgtg ttaaaaatga      3540
atttttacta tggcagatat ggtatggatc gtaaaatttt aagcactaaa aatttttca      3600 taacctttca taataaagtt taataatagg tttattaact gaatttcatt agttttttaa      3660
aagtgttttt ggtttgtgta tatatacata tacaaataca acatttacaa taaataaaat      3720
acttgaaatt ctcttttgtg tctcctagta gcttcctact caactattta taatctcatt      3780
aattaaaaag ttataatttt agataaaaat tctagtcaaa tttttacaga tattatctca      3840
ctaattttca gacttttgcc aaagtgtgca caatggcttt tgttaataa agaacagatt      3900 agttttgaag aaggcaaaaa tttcagtttt ctgaagacag catgttattt taacaatcaa      3960
gtatacatat taaaaattgt gagcaatctc aaaaaaaaaa aaaaa                    4005
```

<210> SEQ ID NO 89
<211> LENGTH: 1278
<212> TYPE: DNA
<213> ORGANISM: Homo sapiens

<400> SEQUENCE: 89

| | | | | | |
|---|---|---|---|---|---|
| ccattggcct | gtagattcac | ctcccctggg | cagggcccca | ggacccagga | taatatctgt | 60 |
| gcctcctgcc | cagaaccctc | caagcagaca | caatggtaag | aatggtgcct | gtcctgctgt | 120 |
| ctctgctgct | gcttctgggt | cctgctgtcc | cccaggagaa | ccaagatggt | cgttactctc | 180 |
| tgacctatat | ctacactggg | ctgtccaagc | atgttgaaga | cgtccccgcg | tttcaggccc | 240 |
| ttggctcact | caatgacctc | cagttcttta | gatacaacag | taaagacagg | aagtctcagc | 300 |
| ccatgggact | ctggagacag | gtggaaggaa | tggaggattg | gaagcaggac | agccaacttc | 360 |
| agaaggccag | ggaggacatc | tttatggaga | ccctgaaaga | catcgtggag | tattacaacg | 420 |
| acagtaacgg | gtctcacgta | ttgcaggaag | ggtttggttg | tgagatcgag | aataacagaa | 480 |
| gcagcggagc | attctggaaa | tattactatg | atggaaagga | ctacattgaa | ttcaacaaag | 540 |
| aaatcccagc | ctgggtcccc | ttcgacccag | cagcccagat | aaccaagcag | aagtgggagg | 600 |
| cagaaccagt | ctacgtgcag | cgggccaagg | cttacctgga | ggaggagtgc | cctgcgactc | 660 |
| tgcggaaata | cctgaaatac | agcaaaaata | tcctggaccg | gcaagatcct | ccctctgtgg | 720 |
| tggtcaccag | ccaccaggcc | ccaggagaaa | agaagaaact | gaagtgcctg | gcctacgact | 780 |
| tctacccagg | gaaaattgat | gtgcactgga | ctcgggccgg | cgaggtgcag | gagcctgagt | 840 |
| tacggggaga | tgttcttcac | aatggaaatg | gcacttacca | gtcctgggtg | gtggtggcag | 900 |
| tgccccccgca | ggacacagcc | ccctactcct | gccacgtgca | gcacagcagc | ctggcccagc | 960 |
| ccctcgtggt | gccctgggag | gccagctagg | aagcaagggt | tggaggcaat | gtgggatctc | 1020 |
| agacccagta | gctgcccttc | ctgcctgatg | tgggagctga | accacagaaa | tcacagtcaa | 1080 |
| tggatccaca | aggcctgagg | agcagtgtgg | ggggacagac | aggaggtgga | tttggagacc | 1140 |
| gaagactggg | atgcctgtct | tgagtagact | tggacccaaa | aaatcatctc | accttgagcc | 1200 |
| caccccccacc | ccattgtcta | atctgtagaa | gctaataaat | aatcatccct | ccttgcctag | 1260 |
| cataaaaaaa | aaaaaaaa | | | | | 1278 |

<210> SEQ ID NO 90
<211> LENGTH: 1980
<212> TYPE: DNA
<213> ORGANISM: Homo sapiens

<400> SEQUENCE: 90

| | | | | | |
|---|---|---|---|---|---|
| tcatttcaaa | atttaggagt | taatttatat | ttttaattga | atcagatttc | ataggcatag | 60 |
| atattgtctg | tcaatattca | tatgtttata | tagtggtaat | ttattaaact | tcttaatcca | 120 |
| gatgtattat | tttagttatc | tttttttccac | tctagtgtca | tagtttaaac | ttgttctttg | 180 |
| atgttgagta | tttattataa | caatagtttt | ttttgcctgc | actctacaat | gtatatttcc | 240 |
| agatataatt | tgtttatgta | acttgttgac | catttataat | ggggaaaaaa | gcttgctaaa | 300 |
| agttctcaag | atagctagga | aaatatcaat | gagatatatc | taaagaaag | ggagaggggt | 360 |
| ttggaagatt | actgccactc | tctttcctta | tatatttctt | aggacttctg | aggtgctttt | 420 |
| atgcttcttg | ttttgtgtaa | agtatatata | tatatatata | tatatacaca | cacacaaagt | 480 |
| atatataaac | acaaagtata | tatatacaca | cacatataca | caaagtatat | atatatacac | 540 |

| | |
|---|---|
| acaaagtata tatatatgta cacaaaatat atatatatac acaaaagtac ttacaaggca | 600 |
| tgttcttacc tcaaaaagat gccaacttat ttatgagaaa tagatcctac tttatggaaa | 660 |
| agcaaaatag gaacatgaca ataaaccaat atgataaagc actgtcagag ttcaaaaaca | 720 |
| cctatgatac ctaaatgtac tcatgtagtt tggatcaacc agaaaggctg gtgacaagag | 780 |
| gtacagctta cttggtaact taaagaataa gaagggtttg aaagtgaaga dacggtgaga | 840 |
| atagctaaag aagaggaaaa cagcatagcc tacaagacag gagatgataa agttagggg | 900 |
| ctatttagca ataataaat aaattgattt agaatagaag aaatcatgtg ttggaaaaga | 960 |
| ggcttgaaac aagttcggtg ttagagaaga gaatattaag aaacaagtgg gagataggac | 1020 |
| ttctaaatgc tgcactaagg atttcggatt tattctcatg gtaaaggaga gccagccaag | 1080 |
| gcttttctac aggagagagg tataatcaag cagcgtgaag ctgagtcagt aggggatca | 1140 |
| gtgagaatag gaagacatca gggttgggga agatgaaagc ttagtttaag catgagttaa | 1200 |
| ttctaccagg atgatggtaa ttgttatatt aagataggga tgaataagaa atatttcaaa | 1260 |
| ggtataaagg ataagcttgt tgactgactg aacttaagga acaaagtaaa aagcagagtc | 1320 |
| aaagtggcag aggctatagc cagggacaac gactacatat ccagcctttt ctatgtctcg | 1380 |
| gggtgaagat gcctttctta ttcactattt ctctcttcaa ctcctccaca ccaccatgca | 1440 |
| aaatcatagc ccatctatgc ttgacgtgcc tacatgtaga aacctgtgat gatctctcca | 1500 |
| gcgagaaagc aggtttaatc ccttgacagt ccttgactca tagtaagttc ttatttatt | 1560 |
| tttaagaccg gcatggatga ctttactta atatctgttc tttgccattt aatgctagag | 1620 |
| ctgatgatat tgagtggcca tttcacaata tgtacctgtt ctgtgttagg aacacttcta | 1680 |
| aaagggctt ggaattatta atttatacaa aaacataaaa tttcatcttg aatctataaa | 1740 |
| cttgctttaa tacaatgagt aaaagtgatc attttagctt tggatctgaa tttcacttga | 1800 |
| aggcatgcac atgggattag gagttgggtg aataatcagg actggaaaag taaacctaga | 1860 |
| aattattgac atggataaag agttgttgat accctgtgag aaggaacttt gggaaatgtg | 1920 |
| gatggaggag gacagaaagg agcagagaat aaaagtatga aagctagccc tgtaggctca | 1980 |

<210> SEQ ID NO 91
<211> LENGTH: 4319
<212> TYPE: DNA
<213> ORGANISM: Homo sapiens

<400> SEQUENCE: 91

| | |
|---|---|
| ctctgagtca ccggaatcta ggtggggccg cccggagcgg cgtcctcggg agccgcctcc | 60 |
| ccgcggcctc ttcgcttttg tggcggcgcc cgcgctcgca ggccactctc tgctgtcgcc | 120 |
| cgtcccgcgc gctcctccga cccgctccgc tccgctccgc tcggcccgc gccgcccgtc | 180 |
| aacatgatcc gctgcggcct ggcctgcgag cgctgccgct ggatcctgcc cctgctccta | 240 |
| ctcagcgcca tcgccttcga catcatcgcg ctggccggcc gcggctggtt gcagtctagc | 300 |
| gaccacggcc agacgtcctc gctgtggtgg aaatgctccc aagagggcgg cggcagcggg | 360 |
| tcctacgagg agggctgtca gagcctcatg gagtacgcgt ggggtagagc agcggctgcc | 420 |
| atgctcttct gtggcttcat catcctggtg atctgtttca tcctctcctt cttcgccctc | 480 |
| tgtggacccc agatgcttgt cttcctgaga gtgattggag gtctccttgc cttggctgct | 540 |
| gtgttccaga tcatctccct ggtaatttac cccgtgaagt acacccgac cttcacccttt | 600 |
| catgccaacc ctgctgtcac ttacatctat aactgggcct acggctttgg gtgggcagcc | 660 |
| acgattatcc tgattggctg tgccttcttc ttctgctgcc tccccaacta cgaagatgac | 720 |

```
cttctgggca atgccaagcc caggtacttc tacacatctg cctaacttgg gaatgaatgt    780
gggagaaaat cgctgctgct gagatggact ccagaagaag aaactgtttc tccaggcgac    840
tttgaaccca ttttttggca gtgttcatat tattaaacta gtcaaaaatg ctaaataat    900
ttgggagaaa atattttta agtagtgtta tagtttcatg tttatctttt attatgtttt    960
gtgaagttgt gtcttttcac taattaccta tactatgcca atatttcctt atatctatcc   1020
ataacattta tactacattt gtaagagaat atgcacgtga aacttaacac tttataaggt   1080
aaaaatgagg tttccaagat ttaataatct gatcaagttc ttgttatttc caaatagaat   1140
ggactcggtc tgttaagggc taaggagaag aggaagataa ggttaaaagt tgttaatgac   1200
caaacattct aaaagaaatg caaaaaaaaa gtttattttc aagccttcga actatttaag   1260
gaaagcaaaa tcatttccta aatgcatatc atttgtgaga atttctcatt aatatcctga   1320
atcattcatt ttagctaagg cttcatgttg actcgatatg tcatctagga aagtactatt   1380
tcatggtcca aacctgttgc catagttggt aaggctttcc tttaagtgtg aaatatttag   1440
atgaaatttt ctcttttaaa gttctttata gggttagggt gtgggaaaat gctatattaa   1500
taaatctgta gtgttttgtg tttatatgtt cagaaccaga gtagactgga ttgaaagatg   1560
gactgggtct aatttatcat gactgataga tctggttaag ttgtgtagta aagcattagg   1620
agggtcattc ttgtcacaaa agtgccacta aaacagcctc aggagaataa atgacttgct   1680
tttctaaatc tcaggtttat ctgggctcta tcatatagac aggcttctga tagtttgcaa   1740
ctgtaagcag aaacctacat atagttaaaa tcctggtctt tcttggtaaa cagatttaa    1800
atgtctgata taaaacatgc cacaggagaa ttcggggatt tgagtttctc tgaatagcat   1860
atatatgatg catcggatag gtcattatga ttttttacca tttcgactta cataatgaaa   1920
accaattcat tttaaatatc agattattat tttgtaagtt gtggaaaaag ctaattgtag   1980
ttttcattat gaagttttcc caataaacca ggtattctaa acttgtttcc agtttgtagt   2040
ttttccattt ttcaaatctg gggaaaggaa ttaaaaaaaa aatgggtaat aagaacatgg   2100
gatataatga aaagtggttt ttgtttgttt ttttgtttga agttttaagg gccttgctca   2160
ttttaggtgt ccaaaaccaa ttttgagtg gagattaatg aattctaata gtctattccc   2220
tgaacttttc ctcaatgaac aatacctag acacacatta aacaatttct ctgcagtgct   2280
atcaaccaga ggaaaatgga ctaagagatt tctggcaggt tcagacaccc ggggacatg   2340
tgtgcagtgt agctgaagcc tcctccttgt gctggggtcc ccttccattc aggtggtggg   2400
gtagcagtct ctctattttc cccttgccct ccttcccatt ttatcatttg ttattttttt   2460
tcccaccata agtcatatgt tacttccact atggtgtatg tcattgtgag gatgggtgca   2520
gagaggctgg gtgggagaac ggaaatatat ctccctaggg ctactgttgg ccagctagtc   2580
cttggcagtg aattttttcta tgcttttcaa aatgcgaggt gaatgtttct catagagaaa   2640
tgtaatctgg gtgattatac caaaattgaa aagaaaaacc cacacaacta tgccgtggct   2700
ggtggagaat ttgaagtggt cattaaaaat gttaaaaatc ccatcttta aagtgatacc    2760
acagctcatt caagaagata ctggatatct agagattaag aaacgtggtc tcctgttaaa   2820
catgaaaatg actccgtta taagcttctc taccacatgc acttgtcttt gcatgatttc    2880
ccatccagcc ttcttcccct cctcaatcac acaatacctt aacggcgcac atttaggaaa   2940
aatgcaacct cctgggacca acgagcctga tataatagaa ccatgtcaac ctaaagtatt   3000
tatgacaaag ataaactctt attttgcaga aatggtctgc ttccttcagc cttgttctag   3060
```

```
tatagagatc tgccattcct tgttgatcca gattcaccaa gacagatacc tttatgtcat    3120
aacagaaggg aagttccaga ggattctgga gagtaatgaa gaattgggct gagaaaccac    3180
ctgaaggcta acagtgcatt gcatgagatt tcccacagta aagctgaggt gcttttggt     3240 tcagtaatta aatattgagt tcccacccct taaataagca gttctaggtt cctaagcaat    3300
tatttcactc tgtaagtagc cagacatgct aagtggcact tactgctgat tgtaacaaag    3360
aagtaatata tcaaggtctt tccatgttca cacaaggtag cttgtgtgta ataacttagc    3420
ttcaaaacca tagactgcag aactcacaag ttcaacagcc tttcctttt  taaggaaatg    3480 aaaacaatgg aaaatatagt catcataact taattcggtt tatttttttt ttctgtaaac    3540 tcccctgaa agacattcct attaatacag taaatgtgaa cactgacttg tttttataag    3600
cacatctgaa agggcatatt tgagtctcat cccaactttg gtccttgcta tctgtgcagg    3660
cttgggcagg tcatctccct gctggtctca atatcctcac ctgtaaaatg attgtaaatg    3720 atcccctac cttcaagatt ctctgattga tagaattttt tctttaatta aaaaatttta    3780
aatattcctt gagttggaag cactgatcaa taagtggatt gctagggag  gttggaacga    3840 atagattcag tcccaacttc ctcttttaaa ttccctcttc ctcactcttc ctgcaacact    3900
tatttttaca gttgagtttt aaaaataagt aatatataaa ataatttctg tagtgtggtt    3960
tcagatttaa aaattcctgc agacaggctg ggcttgcaac cccatcagtc gatggtcaga    4020 gcccttgct ttttgagacc atttttaggt gagcttggct tgcctggata cagtgtgcag    4080
tgcattcttc ctgaattttg caattctggt atctgggtgt attttctagg tgtgtcaggg    4140
tgagtgtaat ccacctaggg tgtggaaaaa gccaagaaag ggaaattaaa agaggttcct    4200
atccagtcat gttaatgatc ttccacttgt actatcctgt gcttcgttgt taacctcgaa    4260
aacatacttt gttggctgca aaataaaca  aagggaaact caaaaaaaaa aaaaaaaa     4319
```

<210> SEQ ID NO 92
<211> LENGTH: 1980
<212> TYPE: DNA
<213> ORGANISM: Homo sapiens

<400> SEQUENCE: 92

```
ggcaccgtgg gagtttgcag ctctggttgc tccaagagca caaatattaa tgtagcacag      60
atattaatat tattaattag cacagacatt aatgtagtca cagaaagaaa aagagatgaa     120
aaagagacag gttcttcact gcatgagagg ctccgtttgg gatctctcag aaatgtggaa    180
gcagaggcta cagcacaagc ctgggttatt gctagtagca agacagaaaa taaggcttgg    240
gtaagctgta gttatagtta caatggaaat gactggccca agagagtgct acagattaca    300
tagcagctac taagaaaaag gacaggcaga aggggtaggc aagacatgtt ctctggctgt    360
tgcagccacc aaaaagccag gatacaaagg cagggagtta tctgaactgc cttcctggag    420
ggtcatgcat ttaggatccg actcattgac tcttttcctt aatttgctc  tgtacatttc    480 tctaagaggg ctaaccagtg tcaaggtttg ataaatatctg aaatggtatt ctggtgccaa    540
agtatcatct cacaaattat ttagaaattg caaagagaaa atatatttta taatccagat    600
atctggcagt taaccacatg accaaattta gcatcactaa cagtaggaca actagatatt    660
atatacctct tgctgtgata tactatgaag tacacatcat caactatgaa gtattatttt    720
ttttttcttt gagataggt  catgctctgt cgcccaattt agagtgcagc gatgcaatca    780
tagctcactg cagctttgac ctcccagtct caagtgatcc tcccacctca gcctccctag    840
tagctgggac tacagatgtg ttccaccaca cctggctaat ttttatatat tttttgtagt    900
```

-continued

```
gatgggttt caccatgttg cacaggctgg tcttgaactc ctgggcttaa gcaatctgcc    960
tgaaagttct gggattatag gcatgagcca ctgtgtccag actatgaagt attcttgcca   1020
aaactgatca acctaaatct aatcaagctt ctgggccaga actgtccaat agcaatgtaa   1080
tgtcagctac atgtaattta aaattttcta gttgccacca aaagcacaga aaagaaaaaa   1140
tagataaatt gtgctacatc aagattaaat acttctttgc atcaaggac ataatcaaca    1200 cagagaaaag gcaaaccact gaatgggaga aaatatttgc aaattgatat tcataatatg   1260
taaagaatct ttacaactca acacccacaa aataaaaaaa aagattaaaa aatgggaaa    1320 ggacttgaat agacatttct ccaaagaaga tgtacaactt gccaataagc acagaaaag    1380 actaattatg agggaaatgc aaattaaaac cacaatgaga tcaaacacat tatgttggct   1440
atcataaaaa gaaagtgcca ggcgcaatga tcacagctac tcacaggct gggtggaaga    1500 atcccttgag accaggagtt agaggctgca gtgtgttatg atcatgcctg tgaatagcca   1560
ctgcactcca acataggtaa catagcaagc cccatccata aaataaaata aaataaaata   1620
aaataaaggc aacaaaaaat aacaagtatt ggtaaggatg tggagaaatt ggaaccctcg   1680
tgcattgctg gtgggtgtgt aaaaaggtat ggctgctgtg aaaaatggga tggctattct   1740
tcaaaaaatt aaccacagaa ttactatatg atccagcaat cccacttctg catacacatc   1800
caaaagaagt ggactcaagg actcagacag atatttgtac cccctgttc atagcagcat    1860 tatttacaat agccaaaaag tagaagcaac cacagattca tcaatgtatg aatggataaa   1920
caaaatgtgg catatacaca tagtgggata tcattcagct ttaaaaggg aggaaattct    1980
```

<210> SEQ ID NO 93
<211> LENGTH: 784
<212> TYPE: DNA
<213> ORGANISM: Homo sapiens

<400> SEQUENCE: 93

```
gcccacgcgc cagagtcgca gtgggcgggc ctacgtgctc cgcccgctgt gagcctgtcc     60 ggccccgcc cgctccggag caacccgcga gcttacaccg gcttctctct gtcctcagcc    120
cgcgcgccgc catcgccgtc atgctgggcg ccgctctccg ccgctgcgct gtggccgcaa    180
ccacccgggc cgaccctcga ggcctcctgc actccgcccg dacccccggc ccgccgtgg    240 ctatccagtc agttcgctgc tattcccatg ggtcacagga gacagatgag gagtttgatg    300
ctcgctgggt aacatacttc aacaagccag atatagatgc ctgggaattg cgtaaaggga    360
taaacacact tgttacctat gatatggttc cagagcccaa aatcattgat gctgctttgc    420
gggcatgcag acggttaaat gattttgcta gtacagttcg tatcctagag gttgttaagg    480
acaaagcagg acctcataag gaaatctacc cctatgtcat ccaggaactt agaccaactt    540
taaatgaact gggaatctcc actccggagg aactgggcct tgacaaagtg taaaccgcat    600
ggatgggctt ccccaaggat ttattgacat tgctacttga gtgtgaacag ttacctggaa    660
atactgatga taacatatta ccttatttga acaagttttc ctttattgag taccaagcca    720
tgtaatggta acttggactt taataaaagg gaaatgagtt tgaactgaaa aaaaaaaaa    780 aaaa                                                               784
```

<210> SEQ ID NO 94
<211> LENGTH: 1980
<212> TYPE: DNA
<213> ORGANISM: Homo sapiens

<400> SEQUENCE: 94

```
ttcacttctg agtcccagag gttacccaag gcacccctct gacatccggc ctgcttcttc    60
tcacatgaca aaaactagcc cccatctcaa tcatatacca aatctctccc tcactaaacg   120
taagccttct cctcactctc tcaatcttat ccatcatagc aggcagttga ggtggattaa   180
accaaaccca gctacgcaaa atcttagcat actcctcaat tacccacata ggatgaataa   240
tagcagttct accgtacaac cctaacataa ccattcttaa tttaactatt tatattatcc   300
taactactac cgcattccta ctactcaact aaaactccag caccacgacc ctactactat   360
ctcgcacctg aaacaagcta acatgactaa caccccttaat tccatccacc ctcctctccc   420
taggaggcct gcccccgcta accggctttt tgcccaaatg ggccattatc gaagaattca   480
caaaaaacaa tagcctcatc atccccacca tcatagccac catcccctc cttaacctct   540
acttctacct acgcctaatc tactccacct caatcacact actccccata tctaacaacg   600
taaaaataaa atgacagttt gaacatacaa aacccacccc attcctcccc acactcatca   660
cccttaccac gctactccta cctatctccc cttttatact aataatctta tagaaattta   720
ggttaaatac agaccaagag ccttcaaagc cctcagcaag ttgcaatact taatttctgt   780
aacagctaag gactgcaaaa ccccactctg catcaactga acgcaaatca gccactttaa   840
ttaagctaag cccttactag accaatggga cttaaaccca caaacactta gttaacagct   900
aagcacccta atcaactggc ttcaatctac ttctcccgcc gccggaaaaa aaggcgggag   960
aagccccggc aggtttgaag ctgcttcttc gaatttgcaa ttcaatatga aaatcacctc  1020
ggagctggta aaaagaggcc tagccccgt ctttagattt acagtccaat gcttcactca  1080
gccatttac ctcacccca ctgatgttcg ccgaccgttg actattctct acaaaccaca  1140
aagacattgg aacactatac ctattattcg gcgcatgagc tggagtccta ggcacagctc  1200
taagcctcct tattcgagcc gagctgggcc agccaggcaa ccttctaggt aacgaccaca  1260
tctacaacgt tatcgtcaca gcccatgcat ttgtaataat cttcttcata gtaatacccca  1320
tcataatcgg aggctttggc aactgactag ttcccctaat aatcggtgcc cccgatatgg  1380
cgtttccccg cataaacaac ataagcttct gactcttacc tccctctctc ctactcctgc  1440
tcgcatctgc tatagtggag gccggagcag gaacaggttg aacagtctac cctcccttag  1500
cagggaacta ctcccaccct ggagcctccg tagacctaac catcttctcc ttacacctag  1560
caggtgtctc ctctatctta ggggccatca atttcatcac aacaattatc aatataaaac  1620
cccctgccat aacccaatac caaacgcccc tcttcgtctg atccgtccta atcacagcag  1680
tcctacttct cctatctctc ccagtcctag ctgctggcat cactatacta ctaacagacc  1740
gcaacctcaa caccaccttc ttcgacccg ccggaggagg agaccccatt ctataccaac  1800
acctattctg attttcggt caccctgaag tttatattct tatcctacca ggcttcggaa  1860
taatctccca tattgtaact tactactccg gaaaaaaaga accatttgga tacataggta  1920
tggtctgagc tatgatatca attggcttcc tagggtttat cgtgtgagca caccatatat  1980
```

<210> SEQ ID NO 95
<211> LENGTH: 7505
<212> TYPE: DNA
<213> ORGANISM: Homo sapiens

<400> SEQUENCE: 95

```
gagggcgggg cgggaaggcg gcgaggagcc gagctgggtg cggtgaggcg cgcagatcac    60
cgcggttcct gggcagggca cggaaggcta agcaaggctg acctgctgca gctcccgcct   120
```

| | |
|---|---|
| cgtgcgctcg ccccacccgg ccgccgcccg agcgctcgag aaagtcctct cgggagaagc | 180 |
| agcgcctgtt cccggggcag atccaggttc aggtcctggc tataagtcac catggcacag | 240 |
| caagctgccg ataagtatct ctatgtggat aaaaacttca tcaacaatcc gctggcccag | 300 |
| gccgactggg ctgccaagaa gctggtatgg gtgccttccg acaagagtgg ctttgagcca | 360 |
| gccagcctca aggaggaggt gggcgaagag gccatcgtgg agctggtgga aatgggaag | 420 |
| aaggtgaagg tgaacaagga tgacatccag aagatgaacc cgcccaagtt ctccaaggtg | 480 |
| gaggacatgg cagagctcac gtgcctcaac gaagcctcgg tgctgcacaa cctcaaggag | 540 |
| cgttactact cagggctcat ctacacctat tcaggcctgt tctgtgtggt catcaatcct | 600 |
| tacaagaacc tgcccatcta ctctgaagag attgtggaaa tgtacaaggg caagaagagg | 660 |
| cacgagatgc cccctcacat ctatgccatc acagacaccg cctacaggag tatgatgcaa | 720 |
| gaccgagaag atcaatccat cttgtgcact ggtgaatctg gagctggcaa gacggagaac | 780 |
| accaagaagg tcatccagta tctggcgtac gtggcgtcct cgcacaagag caagaaggac | 840 |
| cagggcgagc tggagcggca gctgctgcag gccaaccccca tcctggaggc cttcgggaac | 900 |
| gccaagaccg tgaagaatga caactcctcc cgcttcggca aattcattcg catcaacttt | 960 |
| gatgtcaatg gctacattgt tggagccaac attgagactt atcttttgga gaaatctcgt | 1020 |
| gctatccgcc aagccaagga gaacggacc ttccacatct tctattatct cctgtctggg | 1080 |
| gctggagagc acctgaagac cgatctcctg ttggagccgt acaacaaata ccgcttcctg | 1140 |
| tccaatggac acgtcaccat ccccgggcag caggacaagg acatgttcca ggagaccatg | 1200 |
| gaggccatga ggattatggg catcccagaa gaggagcaaa tgggcctgct gcgggtcatc | 1260 |
| tcaggggttc ttcagctcgg caacatcgtc ttcaagaagg agcggaacac tgaccaggcg | 1320 |
| tccatgcccg acaacacagc tgcccaaaag gtgtcccatc tcttgggtat caatgtgacc | 1380 |
| gatttcacca gaggaatcct caccccgcgc atcaaggtgg acgggatta cgtccagaag | 1440 |
| gcgcagacta aagagcaggc tgactttgcc atcgaggcct tggccaaggc gacctatgag | 1500 |
| cggatgttcc gctggctggt gctgcgcatc aacaaggctc tggacaagac caagaggcag | 1560 |
| ggcgcctcct tcatcgggat cctggacatt gccggcttcg agatctttga tctgaactcg | 1620 |
| tttgagcagc tgtgcatcaa ttacaccaat gagaagctgc agcagctctt caaccacacc | 1680 |
| atgttcatcc tggagcagga ggagtaccag cgcgagggca tcgagtggaa cttcatcgac | 1740 |
| tttggcctcg acctgcagcc ctgcatcgac ctcattgaga agccagcagg ccccccgggc | 1800 |
| attctggccc tgctggacga ggagtgctgg ttccccaaag ccaccgacaa gagcttcgtg | 1860 |
| gagaaggtga tgcaggagca gggcacccac cccaagttcc agaagcccaa gcagctgaag | 1920 |
| gacaaagctg atttctgcat tatccactat gccggcaagg tggattacaa agctgacgag | 1980 |
| tggctgatga agaacatgga tccctgaat gacaacatcg ccacactgct ccaccagtcc | 2040 |
| tctgacaagt ttgtctcgga gctgtggaag gatgtggacc gcatcatcgg cctgaccagg | 2100 |
| gtggccggca tgtcggagac cgcactgccc ggggccttca gacgcggaa gggcatgttc | 2160 |
| cgcactgtgg ggcagcttta caaggagcag ctggccaagc tgatggctac gctgaggaac | 2220 |
| acgaacccca actttgtccg ctgcatcatc cccaaccacg agaagaaggc cggcaagctg | 2280 |
| gacccgcatc tcgtgctgga ccagctgcgc tgcaacggtg ttctcgaggg catccgtatc | 2340 |
| tgccgccagg gcttccccaa cagggtggtc ttccaggagt tcggcagag atatgagatc | 2400 |
| ctgactccaa actccattcc caagggtttc atggacggga agcaggcgtg cgtgctcatg | 2460 |

```
ataaaagccc tggagctcga cagcaatctg taccgcattg ccagagcaa agtcttcttc    2520
cgtgccggtg tgctggccca cctggaggag gagccgagacc tgaagatcac cgacgtcatc  2580
ataggggttcc aggcctgctg caggggctac ctggccagga aagcatttgc caagcggcag  2640
cagcagctta ccgccatgaa ggtcctccag cggaactgcg ctgcctacct gaagctgcgg   2700
aactggcagt ggtggcggct cttcaccaag gtcaagccgc tgctgcaggt gagccggcag   2760
gaggaggaga tgatggccaa ggaggaggag ctggtgaagg tcagagagaa gcagctggct   2820
gcggagaaca ggctcacgga gatggagacg ctgcagtctc agctcatggc agagaaattg   2880
cagctgcagg agcagctcca ggcagaaacc gagctgtgtg ccgaggctga ggagctccgg   2940
gcccgcctga ccgccaagaa gcaggaatta aagagagatct gccatgacct agaggccagg  3000
gtggaggagg aggaggagcg ctgccagcac ctgcaggcgg agaagaagaa gatgcagcag   3060
aacatccagg agcttgagga gcagctggag gaggaggaga gcgcccggca gaagctgcag   3120
ctggagaagg tgaccaccga ggcgaagctg aaaaagctgg aggaggagca gatcatcctg   3180
gaggaccaga actgcaagct ggccaaggaa agaaactgc tggaagacag aatagctgag    3240
ttcaccacca acctcacaga agaggaggag aaatctaaga gcctcgccaa gctcaagaac   3300
aagcatgagg caatgatcac tgacttggaa gagcgcctcc gcagggagga gaagcagcga   3360
caggagctgg agaagacccg ccggaagctg gagggagact ccacagacct cagcgaccag   3420
atcgccgagc tccaggccca gatcgcggag ctcaagatgc agctggccaa gaaagaggag   3480
gagctccagg ccgccctggc cagagtggaa gaggaagctg cccagaagaa catggccctc   3540
aagaagatcc gggagctgga atctcagatc tctgaactcc aggaagacct ggagtctgag   3600
cgtgcttcca ggaataaagc tgagaagcag aaacgggacc ttggggaaga gctagaggct   3660
ctgaaaacag agttggagga cacgctggat tccacagctg cccagcagga gctcaggtca   3720
aaacgtgagc aggaggtgaa catcctgaag aagaccctgg aggaggaggc caagacccac   3780
gaggcccaga tccaggagat gaggcagaag cactcacagg ccgtggagga gctggcggag   3840
cagctggagc agacgaagcg ggtgaaagca aacctcgaga aggcaaagca gactctggag   3900
aacgagcggg gggagctggc caacgaggtg aaggtgctgc tgcagggcaa aggggactcg   3960
gagcacaagc gcaagaaagt ggaggcgcag ctgcaggagc tgcaggtcaa gttcaacgag   4020
ggagagcgcg tgcgcacaga gctggccgac aaggtcacca gctgcaggt ggagctggac    4080
aacgtgaccg ggcttctcag ccagtccgac agcaagtcca gcaagctcac caaggacttc   4140
tccgcgctgg agtcccagct gcaggacact caggagctgc tgcaggagga gaaccggcag   4200
aagctgagcc tgagcaccaa gctcaagcag gtggaggacg agaagaattc cttccgggag   4260
cagctggagg aggaggagga ggccaagcac aacctggaga agcagatcgc caccctccat   4320
gcccaggtgg ccgacatgaa aaagaagatg gaggacagtg tggggtgcct ggaaactgct   4380
gaggaggtga gaggaagct ccagaaggac ctggagggcc tgagccagcg cacgaggag    4440
aaggtggccg cctacgacaa gctggagaag accaagacgc ggctgcagca ggagctggac   4500
gacctgctgg tggacctgga ccaccagcgc cagagcgcgt gcaacctgga gaagaagcag   4560
aagaagtttg accagctcct ggcggaggag aagaccatct ctgccaagta tgcagaggag   4620
cgcgaccggg ctgaggcgga ggcccgagag aaggagacca aggctctgtc gctggcccgg   4680
gccctggagg aagccatgga gcagaaggcg gagctggagc ggctcaacaa gcagttccgc   4740
acggagatgg aggaccttat gagctccaag gatgatgtgg gcaagagtgt ccacgagctg   4800
gagaagtcca gcgggcccct agagcagcag gtggaggaga tgaagacgca gctggaagag   4860
```

```
ctggaggacg agctgcaggc caccgaagat gccaagctgc ggttggaggt caacctgcag    4920
gccatgaagg cccagttcga gcgggacctg cagggccggg acgagcagag cgaggagaag    4980
aagaagcagc tggtcagaca ggtgcgggag atggaggcag agctggagga cgagaggaag    5040
cagcgctcga tggcagtggc cgcccggaag aagctggaga tggacctgaa ggacctggag    5100
gcgcacatcg actcggccaa caagaaccgg gacgaagcca tcaaacagct gcggaagctg    5160
caggcccaga tgaaggactg catgcgcgag ctggatgaca cccgcgcctc tcgtgaggag    5220
atcctggccc aggccaaaga gaacgagaag aagctgaaga gcatggaggc cgagatgatc    5280
cagttgcagg aggaactggc agccgcggag cgtgccaagc gccaggccca gcaggagcgg    5340
gatgagctgg ctgacgagat cgccaacagc agcggcaaag gagccctggc gttagaggag    5400
aagcggcgtc tggaggcccg catcgcccag ctggaggagg agctggagga ggagcagggc    5460
aacacggagc tgatcaacga ccggctgaag aaggccaacc tgcagatcga ccagatcaac    5520
accgacctga acctggagcg cagccacgcc cagaagaacg agaatgctcg gcagcagctg    5580
gaacgccaga acaaggagct taaggtcaag ctgcaggaga tggagggcac tgtcaagtcc    5640
aagtacaagg cctccatcac cgccctcgag gccaagattg cacagctgga ggagcagctg    5700
gacaacgaga ccaaggagcg ccaggcagcc tgcaaacagg tgcgtcggac cgagaagaag    5760
ctgaaggatg tgctgctgca ggtggatgac gagcggagga acgccgagca gtacaaggac    5820
caggccgaca aggcatctac ccgcctgaag cagctcaagc ggcagctgga ggaggccgaa    5880
gaggaggccc agcgggccaa cgcctcccgc cggaaactgc agcgcgagct ggaggacgcc    5940
actgagacgg ccgatgccat gaaccgcgaa gtcagctccc taaagaacaa gctcaggcgc    6000
ggggacctgc cgtttgtcgt gccccgccga atggcccgga aggcgccgg ggatggctcc    6060 gacgaagagg tagatggcaa agcggatggg gctgaggcca aacctgccga ataagcctct    6120
tctcctgcag cctgagatgg atggacagac agacaccaca gcctcccctt cccagacccc    6180
gcagcacgcc tctccccacc ttcttgggac tgctgtgaac atgcctcctc ctgccctccg    6240
ccccgtcccc ccatcccgtt tccctccagg tgttgttgag ggcatttggc ttcctctgct    6300
gcatccccct ccagctccct cccctgctca gaatctgata ccaaagagac agggcccggg    6360
cccaggcaga gagcgaccag caggctcctc agccctctct tgccaaaaag cacaagatgt    6420
tgaggcgagc agggcaggcc cccggggagg ggccagagtt ttctatgaat ctatttttct    6480
tcagactgag gccttttggt agtcggagcc cccgcagtcg tcagcctccc tgacgtctgc    6540
caccagcgcc cccactcctc ctcctttctt tgctgtttgc aatcacacgt ggtgacctca    6600
cacacctctg ccccttgggc ctcccactcc catggctctg ggcggtccag aaggagcagg    6660
ccctgggcct ccacctctgt gcagggcaca gaaggctggg gtgggggag gagtggattc    6720 ctccccaccc tgtcccaggc agcgccactg tccgctgtct ccctcctgat tctaaaatgt    6780
ctcaagtgca atgcccccctc ccctccttta ccgaggacag cctgcctctg ccacagcaag    6840
gctgtcgggg tcaagctgga aaggccagca gccttccagt ggcttctccc aacactcttg    6900
gggaccaaat atatttaatg gttaagggac ttgtcccaag tctgacagcc agagcgttag    6960
aggggccagc ggccctccca ggcgatcttg tgtctactct aggactgggc ccgagggtgg    7020
tttacctgca ccgttgactc agtatagttt aaaaatctgc cacctgcaca ggtatttttg    7080
aaagcaaaat aaggttttct tttttcccct ttcttgtaat aaatgataaa attccgagtc    7140
tttctcactg cctttgttta gaagagagta gctcgtcctc actggtctac actggttgcc    7200
```

-continued

| | |
|---|---|
| gaatttactt gtattcctaa ctgttttgta tatgctgcat tgagacttac ggcaagaagg | 7260 |
| cattttttt ttttaaagga aacaaactct caaatcatga agtgatataa aagctgcata | 7320 |
| tgcctacaaa gctctgaatt caggtcccag ttgctgtcac aaaggagtga gtgaaactcc | 7380 |
| caccctaccc ccttttttat ataataaaag tgccttagca tgtgttgcag ctgtcaccac | 7440 |
| tacagtaagc tggtttacag atgttttcca ctgagcatca caataaagag aaccatgtgc | 7500 |
| tacga | 7505 |

<210> SEQ ID NO 96
<211> LENGTH: 2487
<212> TYPE: DNA
<213> ORGANISM: Homo sapiens

<400> SEQUENCE: 96

| | |
|---|---|
| gctattggta agactcgcgg gaaaagaaag ggtgagcgcg gctggaagcg cgcatgcgct | 60 |
| gtggctaatg ccgtaggctc cttcagggct gagccatccc gcgtgtcttg cgctcggtgg | 120 |
| aaatgcccag ccgagggacg cgaccagagg acagctctgt gctgatcccc accgacaatt | 180 |
| cgaccccaca caaggaggat ctaagcagca agattaaaga acaaaaaatt gtggtggatg | 240 |
| aactttctaa ccttaagaag aataggaaag tatataggca acaacagaac agcaatatat | 300 |
| tctttcttgc agaccgaaca gaaatgctgt ctgagagcaa gaatatattg gatgaactga | 360 |
| aaaagaata ccaagaaata gaaaacttag acaagaccaa aatcaagaaa tagtcaacct | 420 |
| gatttcacat aacaatgtgt ggcatttgtt gttctgtaaa cttttctgct gagcatttca | 480 |
| gtcaagattt aaaagaggac ttactatata atcttaaaca gcggggaccc aatagtagta | 540 |
| aacaattgtt aaagtctgat gttaactacc agtgtttatt ttctgctcac gtcctacact | 600 |
| tgaggggtgt tttgactacc cagcctgtgg aagatgaaaa aggcaatgtg tttctatgga | 660 |
| atggagaaat ttttagtgga ataaaggttg aagctgaaga gaatgacact caaattttgt | 720 |
| ttaattatct ttcctcctgt aagaatgaat ctgagatttt gtcactcttc tcagaagtac | 780 |
| aaggtccctg gtcatttata tattatcaag catctagtca ttatttatgg tttggtaggg | 840 |
| attttttttgg tcgccgtagc ttgctttggc attttagtaa tttgggcaag agtttctgcc | 900 |
| tctcttcagt tggcacccaa acatctggat tggcaaatca gtggcaagaa gttccagcat | 960 |
| ctggactttt cagaattgat cttaagtcta ctgtcatttc cagatgcatt attttacaac | 1020 |
| tgtatccttg gaaatatatt tctagggaga atattattga agaaaatgtt aatagcctga | 1080 |
| gtcaaatttc agcagactta ccagcatttg tatcagtggt agcaaatgaa gccaaactgt | 1140 |
| atcttgaaaa acctgttgtt cctttaaata tgatgttgcc acaagctgca ttggagactc | 1200 |
| attgcagtaa tatttccaat gtgccaccta caagagagat acttcaagtc tttcttactg | 1260 |
| atgtacacat gaaggaagta attcagcagt tcattgatgt cctgagtgta gcagtcaaga | 1320 |
| aacgtgtctt gtgtttacct agggatgaaa acctgacagc aaatgaagtt ttgaaaacgt | 1380 |
| gtgataggaa agcaaatgtt gcaatcctgt tttctggggg cattgattcc atggttattg | 1440 |
| caacccttgc tgaccgtcat attccttttag atgaaccaat tgatcttctt aatgtagctt | 1500 |
| tcatagctga agaaaagacc atgccaacta cctttaacag agaagggaat aaacagaaaa | 1560 |
| ataaatgtga atacccttca gaagaattct ctaaagatgt tgctgctgct gctgctgaca | 1620 |
| gtcctaataa acatgtcagt gtaccagatc gaatcacagg aagggcggga ctaaaggaac | 1680 |
| tacaagctgt tagcccttcc cgaatttgga attttgttga aattaatgtt tctatggaag | 1740 |
| aactgcagaa attaagaaga actcgaatat gtcacttaat tcggccattg gatacagttt | 1800 |

```
tggatgatag cattggctgt gcagtctggt ttgcttctag aggaattggt tggttagtgg    1860
cccaggaagg agtgaaatcc tatcagagca atgcaaaggt agttctcact ggaattggtg    1920
cagatgagca acttgcaggt tattctcgtc atcgtgtccg ctttcagtcg catgggctgg    1980
aaggattgaa taaggaaata atgatggaac tgggtcgaat tcttctaga aatcttggtc    2040 gtgatgacag agttattggt gatcatggaa aagaagcaag atttcctttc ctggatgaaa    2100
atgttgtctc ctttctaaat tctctgccga tttgggaaaa agcaaacttg acttaccccc    2160
gaggaattgg tgaaaaatta cttttacgcc ttgcagctgt ggaacttggt cttacagcct    2220
ctgctcttct gcccaaacgg gccatgcagt ttggatcaag aattgcaaaa atggaaaaaa    2280
ttaatgaaaa ggcatctgat aaatgtggac ggctccaaat catgtcctta gaaaatcttt    2340
ctattgaaaa ggagactaaa ttgtaatgtg attcacaatg taacaatata aaaataagtt    2400
tttatataat tatataaaag taagatactc tgctgcttta ctattgtata atatagtagt    2460
tttaaagttc aaaaaaaaaa aaaaaaa                                        2487

<210> SEQ ID NO 97
<211> LENGTH: 2032
<212> TYPE: DNA
<213> ORGANISM: Homo sapiens

<400> SEQUENCE: 97
ggaggactca ggccccgctg gccgcgggct cggtacccgg tgggtcggtg gagcgtctgt     60
tgggtccggg ccgccggctt cgccctcgcc atggcgccct ggctgcagct cctgtcgctg    120
ctggggctgc tcccgggcgc agtggccgcc ccgcccagc cccgagccgc cagctttcag     180
gcctgggggc cgccgtcccc ggagctgctg cgcccaccc gcttcgcgct ggagatgttc     240
aaccgcggcc gggctgcggg gacgcgggcc gtgctgggcc ttgtgcgcgg ccgcgtccgc    300
cgggcgggtc aggggtcgct gtactccctg gaggccaccc tggaggagcc accctgcaac    360
gaccccatgg tgtgccggct cccgtgtcc aagaaaaccc tgctctgcag cttccaagtc    420
ctggatgagc tcggaagaca cgtgctgctg cggaaggact gtgggcccagt ggacaccaag    480 gttccaggtg ctggggagcc caagtcagcc ttcactcagg gctcagccat gatttcttct    540
ctgtcccaaa accatccaga caacagaaac gagactttca gctcagtcat ttccctgttg    600
aatgaggatc ccctgtccca ggacttgcct gtgaagatgg cttcaatctt caagaacttt    660
gtcattacct ataaccggac atatgagtca aaggaagaag cccggtggcg cctgtccgtc    720
tttgtcaata acatggtgcg agcacagaag atccaggccc tggaccgtgg cacagctcag    780
tatggagtca ccaagttcag tgatctcaca gaggaggagt tccgcactat ctacctgaat    840
actctcctga ggaagagcc tggcaacaag atgaagcaag ccaagtctgt gggtgacctc    900 gcccacctg aatgggactg gaggagtaag ggggctgtca caaaagtcaa agaccagggc    960
atgtgtggct cctgctgggc cttctcagtc acaggcaatg tggagggcca gtggtttctc    1020
aaccagggga ccctgctctc cctctctgaa caggagctct ggactgtga caagatggac    1080 aaggcctgca tgggcggctt gccctccaat gcctactcgg ccataaagaa tttgggaggg    1140
ctggagacag aggatgacta cagctaccag ggtcacatgc agtcctgcaa cttctcagca    1200
gagaaggcca aggtctacat caatgactcc gtggagctga ccagaacga gcagaagctg    1260 gcagcctggc tggccaagag aggcccaatc tccgtggcca tcaatgcctt tggcatgcag    1320
ttttaccgcc acgggatctc ccgccctctc cggcccctct gcagcccttg gctcattgac    1380
```

| | |
|---|---|
| catgcggtgt tgcttgtggg ctacggcaac cgctctgacg ttcccttttg ggccatcaag | 1440 |
| aacagctggg gcactgactg gggtgagaag ggttactact acttgcatcg tgggtccggg | 1500 |
| gcctgtggcg tgaacaccat ggccagctcg gcggtggtgg actgaagagg ggccccagc | 1560 |
| tcgggacctg gtgctgatca gagtggctgc tgccccagcc tgacatgtgt ccaggcccct | 1620 |
| ccccgggagg tacagctggc agagggaaag gcactgggta cctcagggtg agcagagggc | 1680 |
| actgggctgg ggcacagccc ctgcttccct gcaccccatt cccaccctga agttctgcac | 1740 |
| ctgcaccttt gttgaattgt ggtagcttag gaggatgtcg gggtgaaggg tggtatcttg | 1800 |
| gcagttgaag ctggggcaag aactctgggc ttgggtaatg agcaggaaga aaattttctg | 1860 |
| atcttaagcc cagctctgtt ctgccccgc tttcctctgt ttgatactat aaattttctg | 1920 |
| gttcccttgg atttagggat agtgtccctc tccatgtcca ggaaacttgt aaccaccctt | 1980 |
| ttctaacagc aataaagagg tgtccttgtc ccgaaaaaaa aaaaaaaaa aa | 2032 |

<210> SEQ ID NO 98
<211> LENGTH: 1980
<212> TYPE: DNA
<213> ORGANISM: Homo sapiens

<400> SEQUENCE: 98

| | |
|---|---|
| ttgagtaata gaaataaat ctgggtcact ttttgtagc tgtaaatcca gccttagtaa | 60 |
| tcctgacctc cattaacata gctagtattt caaattccac tgtaacagtt gctctgactc | 120 |
| tttgggggct gggaggcaat ccaagtagcc agagaagcaa ttgtttcaca tgcttcaatc | 180 |
| ctgccactcc agaaaaaata taggggggac tagggcaaaa gaaaatctct tatttgtttt | 240 |
| ccatttctca tttctcgtat ctttattgct tctctctcat ccttaacctg tatctcccctt | 300 |
| cagctgatgc ctgattacct tctaccatgt tcaacattat gatcagtcac ctactatgtg | 360 |
| ccaggaagtg tgcagtgtgt gaggatacca gaccctacct actgggagct tacagtctag | 420 |
| ctcaacaggc acatcattaa ataagcaatt gcagcaatta tattaagtgc tgggccaagg | 480 |
| gaggtaccag aagtcataag aatccctcct ctgagggat agaagtgaag acttcagagg | 540 |
| ggaagtaatg attctggatg tgtaggactc agccaggtga agtgtaaaag taaggatgga | 600 |
| ggagagtgtt ctaaagagg gaacaacata atcaaagttc tggacaggag agagatttga | 660 |
| catatttgag gaagtgaaaa ttttatctag aaacttgcaa tgagtaagta aacaccaggt | 720 |
| caagaggaac tgagagattg gcagacaatg gaaaaccatt gaaaaggatt aaactgggaa | 780 |
| gtgatatgtt ctcttttgca tttaaaaaga tcaccaatgg ggatatggag aatggtctgg | 840 |
| ataggtctta agactagagc caggaagaca tgttagaagg ctatcaattg accctaaaga | 900 |
| cactgcttca atcccttga tgacagtgag tttgcttcc ccagagatag cttattggac | 960 |
| ctcaggactg ctgtgagaaa cagaaaatgc tcctttacgt gttgcctgaa gttaggctca | 1020 |
| ccgatttggg gcatgttcta attctaccag ctaggaacac acagaatcgc ttgtcaaaca | 1080 |
| ttctgagtca gatatgtcct ccctatgtct tttctgagaa aggcatacag aaattcccag | 1140 |
| ctaaacatca ccagttccct catttgttcc tcagatgata tggtccattc aagttttgta | 1200 |
| atcatcatgg gggtagatgg agggtcccag tcctcacaac cattctggta atttactctt | 1260 |
| gaatttactg gttcacatgt atctattttg tagtgtggct cctgaaactg aaaaacctac | 1320 |
| cccaggtatt ctgtgaacag acagagtaga gagtctgtca ctgcccacgg agagatgatt | 1380 |
| aggcttccgg gaaaaggtga gaacactggc aaagttccgg aaggaggaac aatatcccctt | 1440 |
| cttcccttct tcatgagtcg taccatccct tactttggc tggtcacata accacccaaa | 1500 |

```
ataagggcta cattttccag ccactctagc agctaggggt gacagagtga ctaagattta    1560
cctggaagta tcgtgtgtga cttctgggaa gggtccttaa agagaggggt agtcctggct    1620
gggtgcggtg gctcacgtct gtaatcccag cactttggga ggccgaggca ggcggatcac    1680
aaggtcagga gttcaagacc agcctggcca agatgctgaa accccatctc taataaaaat    1740
acaaaaaaat tagccgggca tgctggcggg cgcctgtaat cccagctact taggaggctg    1800
agatggagaa ttgcttgaac ttgggaggca gagtttgcag tgggccaaaa tggcgccact    1860
gcactccagc ctgggcaaca gagcaagcct ccgtctcaaa aaaaaaaaa aaaaaaaaa     1920 aagagagggg tagtccttgt tgctgttgct gcaggtattt tctccttctt cccagctgga    1980

<210> SEQ ID NO 99
<211> LENGTH: 1674
<212> TYPE: DNA
<213> ORGANISM: Homo sapiens

<400> SEQUENCE: 99
gcggccgccc gccgccgcgc tcctcctcct cctcctccag cgcccggcgg cccgctgcct      60
cctccgcccg acgccccgcg tccccgcccg cgccgccgcc gccaccctct gcgccccgcg     120
ccgccccccg gtcccgcccg ccatgcccgg cccggccgcg ggcagcaggg cccgggtcta     180
cgccgaggtg aacagtctga ggagccgcga gtactgggac tacgaggctc acgtcccgag     240
ctggggtaat caagatgatt accaactggt tcgaaaactt ggtcggggaa aatatagtga     300
agtatttgag gccattaata tcaccaacaa tgagagagtg gttgtaaaaa tcctgaagcc     360
agtgaagaaa aagaagataa aacgagaggt taagattctg gagaaccttc gtggtggaac     420
aaatatcatt aagctgattg acactgtaaa ggaccccgtg tcaaagacac agctttggt     480 atttgaatat atcaataata cagattttaa gcaactctac cagatcctga cagactttga     540
tatccggttt tatatgtatg aactacttaa agctctggat tactgccaca gcaagggaat     600
catgcacagg gatgtgaaac ctcacaatgt catgatagat caccaacaga aaaagctgcg     660
actgatagat tggggtctgg cagaattcta tcatcctgct caggagtaca atgttcgtgt     720
agcctcaagg tacttcaagg gaccagagct cctcgtggac tatcagatgt atgattatag     780
cttggacatg tggagtttgg gctgtatgtt agcaagcatg atctttcgaa gggaaccatt     840
cttccatgga caggacaact atgaccagct tgttcgcatt gccaaggttc tgggtacaga     900
agaactgtat gggtatctga agaagtatca catagaccta gatccacact tcaacgatat    960
cctgggacaa cattcacgga aacgctggga aaacttatc catagtgaga acagacacct    1020
tgtcagccct gaggccctag atcttctgga caaacttctg cgatacgacc atcaacagag    1080
actgactgcc aaagaggcca tggagcaccc atacttctac cctgtggtga aggagcagtc    1140
ccagccttgt gcagacaatg ctgtgctttc cagtggtctc acggcagcac gatgaagact    1200
ggaaagcgac gggtctgttg cggttctccc acttttccat aagcagaaca gaaccaaat    1260 caaacgtctt aacgcgtata gagagatcac gttccgtgag cagacacaaa acggtggcag    1320
gtttggcgag cacgaactag accaagcgaa gggcagccca ccaccgtata tcaaacctca    1380
cttccgaatg taaaaggctc acttgccttt ggcttcctgt tgacttcttc ccgacccaga    1440
aagcatgggg aatgtgaagg gtatgcagaa tgttgttggt tactgttgct ccccgagccc    1500
ctcaactcgt cccgtggccg cctgtttttc cagcaaacca cgctaactag ctgaccacag    1560
actccacagt gggggggacgg gcgcagtatg tggcatggcg gcagttacat attattattt    1620
```
taaaagtata tattattgaa taaaaggttt taaaagaaaa aaaaaaaaaa aaaa      1674

<210> SEQ ID NO 100
<211> LENGTH: 1032
<212> TYPE: DNA
<213> ORGANISM: Homo sapiens

<400> SEQUENCE: 100 cccgcaccccc ctgggattgt gggaaatgta gttttttgcc tccgtaaggg accaggcgga    60
gctgaggaac cgcgcgagga ctgggaccgt gattccacta accggaaacc gtcgcctttc   120
gggcccggcg gggcctgagc caatgcagaa tcggggccg cgaggacgcc agcgggcgct    180
gtgcgtagga accgccgggt ggccgctgcc gatcggggcc gacttgggga cggaccggaa   240
gtgcccgagg gcggccgcag aacggtcaat ttgagccgcg tcgagctccc ctgggacctg   300
tggccgccgc ccacagacca tgctcctggg gcgcctgact tcccagctgt tgagggccgt   360
tccttgggca ggcggccgcc cgccttggcc cgtctctgga gtgctgggca gccgggtctg   420
cgggcccctt tacagcacat cgccggccgg cccaggtagg gcggcctctc tccctcgcaa   480
gggggcccag ctggagctgg aggagatgct ggtccccagg aagatgtccg tcagccccct   540
ggagagctgg ctcacggccc gctgcttcct gcccagactg gataccggga ccgcagggac   600
tgtggctcca ccgcaatcct accagtgtcc gcccagccag ataggggaag gggccgagca   660
ggggggatgaa ggcgtcgcgg atgcgcctca aattcagtgc aaaaacgtgc tgaagatccg   720
ccggcggaag atgaaccacc acaagtaccg gaagctggtg aagaagacgc ggttcctgcg   780
gaggaaggtc caggagggac gcctgagacg caagcagatc aagttcgaga agacctgag   840
gcgcatctgg ctgaaggcgg ggctaaagga agccccccgaa ggctggcaga cccccaagat   900
ctacctgcgg ggcaaatgag tctggcgccg cccttcccgc ccgttgctgc tgtgatccgt   960
agtaataaat tctcagagga ctcagccttt aaaaaaaaaa aaaaaaaaaa aaaaaaaaaa  1020
aaaaaaaaaa aa                                                      1032

<210> SEQ ID NO 101
<211> LENGTH: 1980
<212> TYPE: DNA
<213> ORGANISM: Homo sapiens

<400> SEQUENCE: 101
aagaaataag cttattcaag acctgtagga ccaattttag caagaatcct gctaaatcaa    60
tttatgattt ccccccccgct ccacacccctt gaaatctgat cacccttgat atatagctcc  120
tcatctccca cctttgatct gtaagtcctt ggcctgcctt tagcaagagt cctattaggt   180
cgggttagca agaatccccc tacacttgat gtctcctctt aataatttc ccctcttagt   240
gaattttcct ctcccctcac actctgccca ttggctataa atttccagct gtctttgctg   300
tattcagaat agagccctat ctctgcctcc tactgtaata ctctaatgca atatagtctt   360
caataaagct ttacttacca tctcaaccag catcagaata ttttttcctt taacatatcc   420
aagcttggtc agaattaggg tgtacctaca cctacctgca ctattaatac tccgcacagc   480
agggagaaag gaactaccta ccaggtgtca tgggcatgga aggatgtgag gaacgctagc   540
actggccaaa tacagtggcc tcacaagcca tcttcacctt caggaaaatg aatattgagc   600
tgccacagac actctgctgc cctcttaatt taccattacc atgaatctac aggatgctct   660
gttccaaaca cccagtacat tcttatacat cttgtcctga tagatgcctg tgaggtaggc   720
agggctgaga attatgaatt gttgtctatc aggctgaagt gactttccaa aaattgaagt   780

| | | | |
|---|---|---|---|
| tgacagcaat | aaggtcaaga atcagctctg tgctgttttg acggagtgag tcattgcctc | 840 |
| cttgaatctg | gcacatacca gccaactgtc aaggtttgtt cttccacatg gtctaactgc | 900 |
| taaatacaaa | gtatactagg tttgtcagct tagggcatgt ttgcttccac tctgaaaaca | 960 |
| tttcagctgc | cctaatatat tgctataaag aattctctta ttattactgt cttcctcctc | 1020 |
| atatttagct | ctgtcttcca tcacttcaaa agaagcattt gtagcttccc catcctcttt | 1080 |
| cttttctagtt | gactttgaag actatctata aagtatttc tggcataaaa ctgacaggta | 1140 |
| aatgacttca | aagctaattt ccgccccccc ccaccccttg ccctttttca gtctcaagat | 1200 |
| accatgtcag | tcctctattc actctcaaaa atgatggctt aactgcacag tgccgttctg | 1260 |
| ggtcaattct | taaatatact agaatatact agacatatct ggctcattta agtcattctt | 1320 |
| caccaatctt | tcttcttatt tacctccttc ctcaacttgg aaattttgcc ttttcacaat | 1380 |
| atgtggatag | ccatttctgc caagattgtg ccgacaagac tggttataaa tctacctact | 1440 |
| ttgtaaaagg | ggaatatttt tgtaaccatt gcatatctct attaaaacat gaaagaaaca | 1500 |
| ctgaaggcca | agtgttcaag tgacacgcag gaaaaaaaaa agctgatatt cagaaagcca | 1560 |
| agcatacaga | gaaataatga gaggttaatg aagtgagttc tgaatcacaa gtgctgttca | 1620 |
| gaaaacaaaa | aaagacatct gtgaaggctg accttggaac tagtcactgt tattcagtcc | 1680 |
| atatgtatgt | atgtttttat taaaataact gttcaaagtt aactttcatc caagttaact | 1740 |
| tctgaagaaa | taaaaaggca tcacgttaag gtttcaaaaa tttaaccatt ctacctttag | 1800 |
| caatggttag | tccaccttat tttcacacat ttccatctta atgaaagcaa gtacattaaa | 1860 |
| ggatactcag | aatagctgca aggcatacca caagatgtac cacaagatta gaaatttctt | 1920 |
| taaaagtaat | taagatcggc cgagtgcagt ggctgactcc agcaatccca gcattttggg | 1980 |

<210> SEQ ID NO 102
<211> LENGTH: 3939
<212> TYPE: DNA
<213> ORGANISM: Homo sapiens

<400> SEQUENCE: 102

| | | | |
|---|---|---|---|
| ggtcggcctc | tgctgcgcct gcgtggtcgg gaggggaagt gaggcggttt cctcggcgcc | 60 |
| ttttccggca | gcggcggcgg cagaactggg aggaggagtt ggaggccgga gggagcccgc | 120 |
| gctcggggcg | gcgctggag gcagcgcacc gagttcccgc gaggatccat gacctgacgg | 180 |
| ggccccggag | ccgcgctgcc tctcgggtgt cctgggtcgg tggggagccc agtgctcgca | 240 |
| ggccggcggg | cgggccggag ggctgcagtc tccctcgcgg tgagaggaag gcggaggagc | 300 |
| gggaaccgcg | gcggcgctcg cgcggcgcct gcgggggggaa gggcagttcc gggccgggcc | 360 |
| gcgcctcagc | agggcggcgg ctcccagcgc agtctcaggg cccgggtggc ggcggcgact | 420 |
| ggagaaatca | agttgtgcgg tcggtgatgc ccgagtgagc gggggggcctg ggcctctgcc | 480 |
| cttaggaggc | aactcccacg caggccgcaa aggcgctctc gcggccgaga ggcttcgttt | 540 |
| cggtttcgcg | gcggcggcgg cgttgttggc tgaggggacc cgggacacct gaatgccccc | 600 |
| ggccccggct | cctccgacgc gatggggaag gtgctatcca aaatcttcgg gaacaaggaa | 660 |
| atgcggatcc | tcatgttggg cctggacgcg gccggcaaga acaatcct gtacaagttg | 720 |
| aagctgggcc | agtcggtgac caccattccc actgtgggtt tcaacgtgga gacggtgact | 780 |
| tacaaaaatg | tcaagttcaa cgtatgggat gtgggcggcc aggacaagat ccggccgctc | 840 |
| tggcggcatt | actacactgg gacccaaggt ctcatcttcg tagtggactg cgccgaccgc | 900 |

```
gaccgcatcg atgaggctcg ccaggagctg caccgcatta tcaatgaccg ggagatgagg      960
gacgccataa tcctcatctt cgccaacaag caggacctgc ccgatgccat gaaaccccac     1020
gagatccagg agaaactggg cctgacccgg attcgggaca ggaactggta tgtgcagccc     1080
tcctgtgcca cctcagggga cggactctat gaggggctca catggttaac ctctaactac     1140
aaatcttaat gagcattctc cacccatccc ctggaaggag agaaatcaaa acccattca      1200
taggattatc gccaccatca cctctttcaa ttgccacttt ctcttctttt gaatttgaac     1260
tctggagtta ctgttctaca gtttggcggg gacggggctt gggggttttc tcttttgttt     1320
gtttcccttt cttttttcctt tttttttttt ttttttttttt gttggctttg cgttaggatg   1380
ctctgatctg acatttgaca tgaacacaaa gttgctagat gctcttgttg acttccagca     1440
gatgggatgg gggaaacaca gcagttcttg gtaaagtcct ttgtaataat agtttgattt     1500
ttttatttcg agagaatctt tcattttcct atgtatgctt ttttcctttt ttgcccagtt     1560
tccttatcac ttgctgtaga tggcttattt tgcattcatg cagactatgt tgcaagtctg     1620
tttcatctag taaactgaaa attattgctt aatcaaactg ccgtttgtct tttatattta     1680
aggccttccc ccccccttcct tatgagttct aacttagtaa tttcaaatgt gacctttat    1740
atctaagacc agtatagtaa acttagccca cagtggcaaa taatgagtaa tattgtaata    1800
tgttccagtt gcacctcagt atgttaaaca ggtaatgtaa aagttctctc gaaatgtcag    1860
caagtaagtt ctgaaacaca tcatgcatga gtaggaataa aacccaagtt ccccataacg    1920
tagataactt aatgctgcat aaaaatatga aagtgtaacc catgaaggac acttttttctt   1980
tccactgcaa agttagccac tttgctgttt ttcctcttttt ttaaactttg aaaatagact   2040
ctttccagaa attggagcaa taatggtgtt accacacaca gattaaataa tttgtagata    2100
ttttaagtga cttttgggca aaactggaat gtatactttt accttgtttc aaacacctaa    2160
gaccagtaat ttaaaaatta ctaaaaggtt tactttgttc attaataaaa catttaacaa    2220
ttcaaattat atgcaccttt tacctagttg aaaaaaatac acattcctgt tttcacatta    2280
tagcaactga ttaagctgaa gctgtaagtc attttttata gatgagtgat ccgcatctcc    2340
atcaattaga acactggaaa agatgtttta taaagaggt  attaattttt gtttgtagga    2400
ttaactcatg caaataataa aaaagatatc ctgttggttc aatagtacac tgtctccttt    2460
aaggaaggaa gcgtgatgaa tgaatgatgt gtagacttga gggatgacta ttaaagggga    2520
cgtaggatga agagaaagaa cctacagatg acaatgaatg taaacttatt tttcttcatg    2580
tgtaagcagt gtgctcgctg gtgatatcca gatcctaaca agattacttg gttagctggt    2640
taggaccagt aactggattg cgaccactat gataatattt tgaaccaaat gttaatgctt    2700
gatgcagaat tgtaaagcag catctggttc ctatatagcc ttaaggatta attttagtga    2760
tcctcaagga attaaatagg gaatttcaga aatgtagact gcaaaggcag tatacaggaa    2820
aaggtggagt gggttttgtt tatgagggtg tctgaaaact aaaattgagc gggatatcat    2880
ggtatagttg gacagtattg gtccttcaca cttttggccat attgtataat ggagctttta   2940
ccaaagatgt atgagaagtg taagactata aaaaaatgaa ctattcaaag taaaactctt    3000
aacaaacatt ttacttaaag cagatgcaaa agggtattct catgtaggct cctgttggtg    3060
cagagggatt ttttttgattt caggatacaa ctaaagtacg aagttctcag tttcactttta  3120
gtagaaagag ctctagaaat gaggctgata aacacatcta agaacactgg ttgctttcta    3180
aaatttccaa agctccacca taatgtaatt ttttagtgtt tcaaatgatt gcattttaaa    3240
gtatataaat atgggttatc caatatcaat gctatagtaa catcctgaaa caaaacaagc    3300
```

| | | |
|---|---|---|
| acaaaggtat aaatgcctaa actggaggaa acttgaaacc ctcatgttaa atcttaaatg | 3360 | |
| tagtatttct aacttgtgaa gacagattgg taggcagcca tttttttgtg tcttaaaata | 3420 | |
| actgggggca tagttaaaat tttatacatc aagtgattgc tattattgaa tgttgcaggt | 3480 | |
| gagatgtggt tattttagt ttatttgaaa tgtttgactg gaaagggggg aggggaagc | 3540 | |
| aaatatttga aatttggaaa accctaaacc ttttggtaag aaattgtaat tttcacttaa | 3600 | |
| aattttcttt aaggatataa gaggtttata attgatgtag ttaaattgaa caataaccat | 3660 | |
| tggtgactgg agcaggtaat tatagcctgc agaaaaaatt atctaagaat tttaaaaata | 3720 | |
| agatcctgaa gttgtttaat tgcatccatt tctgtattta tgtgaattta taaactgcag | 3780 | |
| taagttttga atgaggttaa tcttgtttaa tataagtaaa tgagtctgta gactgtgatc | 3840 | |
| tccccaaact aaaaagtaca gtacttggaa ttgtgttctt tatggttgta gtgttggtaa | 3900 | |
| agcactaata tgcagaaaat aaaggaatta cacagtgca | 3939 | |

<210> SEQ ID NO 103
<211> LENGTH: 1980
<212> TYPE: DNA
<213> ORGANISM: Homo sapiens

<400> SEQUENCE: 103

| | | |
|---|---|---|
| ttgtcactag aaggaggaag gaatgctgtg tggcaaggaa aggaattaat gtccacttga | 60 | |
| gatggatttg agaaggatgt ctgcaagcag aaataaaggg ttaaagggtg cttacattaa | 120 | |
| aaattttgat agctactgct ctcaaaattg tatcgcgatt tatattccca gtgccaacag | 180 | |
| tgtttgaaga gtctggctct ccagagcctg tagacactgg atattgtcag tgttttaaat | 240 | |
| ttcagcagat ctgatatcta aaaatggtat ctcactgttc taaactgttc tagtatggtg | 300 | |
| ttctacgtga acacccttc atgtgtttag ctggcctttg catttctttt ttttttttt | 360 | |
| tgaactgcct atgcatatct tttggtcaaa attcaattga attgcccttt tttattgtta | 420 | |
| gagctgctac aaacattact gaaaaggcaa ctcagttgtg tgtgtgtgta tgcacacaca | 480 | |
| tatatattta taatacatat gttacttagg gtttgtacca gctctatgag ctccttgagg | 540 | |
| gtggcacctt gctgtaatac agcctgacac ctaatacgaa gtagaaatca gtgattattt | 600 | |
| atcacgcaaa taagaaaaca aataagtgaa cgaatgaatg agtcaatagt gttgactgcc | 660 | |
| ttgtattgtc ctaggcccaa gagacagtga aatatccctg ttcttgtata cttttctgta | 720 | |
| agtttctgga agtttctctg taaagcatct cagtaagctt ttctataggc tgtgagaaac | 780 | |
| gcatgagtca ggctaatagg aggcatataa ttttgaattg cttttcagaa atggccttca | 840 | |
| tattccttta cactcactca tcctgttgat aagagcagat ggcctactgc atgtgactca | 900 | |
| gactcaaaca cacacctccg ctcccttgaa gtgccagccc tggagctttg ttgaggctcg | 960 | |
| catctgccac gggagtcagc tagtacgttg cccagttcaa catccatcca ggatttcata | 1020 | |
| ggaacttgag aatcattgtt tttggcttga atcctgggtt tgaggtttct tcgtgtagga | 1080 | |
| atctgaaaaa aggatttgga aacgttgttg tctctaatcc caagtatgt atctgggagg | 1140 | |
| ctgccttcgc catcacccac ctaataactc aggctcccgg ggccatttcg ctcaagtgca | 1200 | |
| ttcattcctt tggtagaatc aaaagaaact gatccaggtg acagagtacc tgggttctaa | 1260 | |
| tcccagtttt gatgagcaag ttatttaccc cttacagccc catttcccct attctaaaat | 1320 | |
| gatatggttg caactgacga tctccaagtc tccgtccaac tcaacaattc agagtggaat | 1380 | |
| tctgaattct gctctgccac caacagcatg tcctcggagc tttgcctatt actcatgaga | 1440 | |

| | |
|---|---|
| atgtcaacgt ctgggtaaat agatattttg gggtcagctc taaaaaaccc agaagtacgt | 1500 |
| attgtatgtt gattttggca cacggacaag cctgaacagg gctgtgtcaa gccttttacc | 1560 |
| atgatagctg ccggaagaaa ggccaggcga agcagtctgg gtgagctgct tggaatgaag | 1620 |
| aggaccagcc cacatcccat ggcacagatg accttcagga gaagtggagg ggagcagcta | 1680 |
| atgtaaagaa atcattagca tctgtgttgg aaatggctta tgacactgtc tcaaagccac | 1740 |
| gttctcagac aacagggaaa gctgtaaata gatgcacaca gttatccaag catagcagag | 1800 |
| taaaactaaa ggaaagccaa attaaacagg ctcaaccaaa gttttgagtg aaagtgttga | 1860 |
| atattgctca tgccttcaga acgggaagct ctgtttagaa tactcacaat ggtgggtcct | 1920 |
| cttgaggtga ctacaggctg gtaggtcggt tctatcctcc ccctaggagc catctcagca | 1980 |

<210> SEQ ID NO 104
<211> LENGTH: 1980
<212> TYPE: DNA
<213> ORGANISM: Homo sapiens

<400> SEQUENCE: 104

| | |
|---|---|
| gttcaacttt aaatttgccc acagaaccct ctaaatcccc ttgtaaattt aactgttagt | 60 |
| ccaaagagga acagctcttt ggacactagg aaaaaacctt gtagagagag taaaaaattt | 120 |
| aacacccata gtaggcctaa aagcagccac caattaagaa agcgttcaag ctcaacaccc | 180 |
| actacctaaa aaatcccaaa catataactg aactcctcac acccaattgg accaatctat | 240 |
| caccctatag aagaactaat gttagtataa gtaacatgaa acattctccc tccgcataag | 300 |
| cctgcgtcag attaaaacac tgaactgaca attaacagcc caatatctac aatcaaccaa | 360 |
| caagtcatta ttaccctcac tgtcaaccca acacaggcat gctcataagg aaaggttaaa | 420 |
| aaaagtaaaa ggaactcggc aaatcttacc ccgcctgttt accaaaaaca tcacctctag | 480 |
| catcaccagt attagaggca ccgcctgccc agtgacacat gtttaacggc cgcggtaccc | 540 |
| taaccgtgca aaggtagcat aatcacttgt tccttaaata gggacctgta tgaatggctc | 600 |
| cacgagggtt cagctgtctc ttacttttaa ccagtgaaat tgacctgccc gtgaagaggc | 660 |
| gggcatgaca cagcaagacg agaagaccct atggagcttt aatttattaa tgcaaacagt | 720 |
| acctaacaaa cccacaggtc ctaaactacc aaacctgcat taaaaatttc ggttggggcg | 780 |
| acctcggagc agaacccaac ctccgagcag tacatgctaa gacttcacca gtcaaagcga | 840 |
| actactatac tcaattgatc caataacttg accaacggaa caagttaccc tagggataac | 900 |
| agcgcaatcc tattctagag tccatatcaa cataggggtt tacgacctcg atgttggatc | 960 |
| aggacatccc gatggtgcag ccgctattaa aggttcgttt gttcaacgat taaagtccta | 1020 |
| cgtgatctga gttcagaccg gagtaatcca ggtcggtttc tatctacttc aaattcctcc | 1080 |
| ctgtacgaaa ggacaagaga ataaggcct acttcacaaa gcgccttccc ccgtaaatga | 1140 |
| tatcatctca acttagtatt atacccacac ccacccaaga acagggtttg ttaagatggc | 1200 |
| agagcccggt aatcgcataa aacttaaaac tttacagtca gaggttcaat tcctcttctt | 1260 |
| aacaacatac ccatggccaa cctcctactc ctcattgtac ccattctaat cgcaatggca | 1320 |
| ttcctaatgc ttaccgaacg aaaaattcta ggctatatac aactacgcaa aggccccaac | 1380 |
| gttgtaggcc cctacgggct actacaaccc ttcgctgacg ccataaaact cttcaccaaa | 1440 |
| gagcccctaa aaccgccac atctaccatc accctctaca tcaccgcccc gaccttagct | 1500 |
| ctcaccatcg ctcttctact atgaaccccc tcccccatac ccaaccccct ggtcaacctc | 1560 |
| aacctaggcc tcctatttat tctagccacc tctagcctag ccgtttactc aatcctctga | 1620 |

| | |
|---|---|
| tcagggtgag catcaaactc aaactacgcc ctgatcggcg cactgcgagc agtagcccaa | 1680 |
| acaatctcat atgaagtcac cctagccatc attctactat caacattact aataagtggc | 1740 |
| tcctttaacc tctccaccct tatcacaaca caagaacacc tctgattact cctgccatca | 1800 |
| tgacccttgg ccataatatg atttatctcc acactagcag agaccaaccg aaccccttc | 1860 |
| gaccttgccg aagggagtc cgaactagtc tcaggcttca acatcgaata cgccgcaggc | 1920 |
| cccttcgccc tattcttcat agccgaatac acaaacatta ttataataaa caccctcacc | 1980 |

<210> SEQ ID NO 105
<211> LENGTH: 1980
<212> TYPE: DNA
<213> ORGANISM: Homo sapiens

<400> SEQUENCE: 105

| | |
|---|---|
| ctggagaatc ccttgaaccc aggaggagga ggttgcagtg agcgatcctg ccacggcact | 60 |
| ccagcagggg tgacaagaat gaaactctat ttcaaaataa agaaaaaaaa gaaaaaaaaa | 120 |
| gaaaacccaa cctcaactag cttaagcaaa agcaaattta tgtggtgaaa gggtggatct | 180 |
| ggttttagaa tcagttacca agggctcaag aagtgtcaca gggactgatc cccccacccc | 240 |
| cccgtccccc atgtcgtgtc attctccagg tctttccttt tcattgccag gagctccagg | 300 |
| tttctacccct cagaactcca aggccattgg aaaacagagg gcagttttct tagttgccca | 360 |
| aggaaatgtt cccaaattgt atcaaaagcc cacctctagg ttaattattg tggctggagg | 420 |
| atgtaatcca ttcataggtc agggctggcc aggtgtagtg gctcatgcct gtaatcccag | 480 |
| cactttggga gactgagatg ggtgggtcac ttgaggtcag aagttcgaga ccagcctggc | 540 |
| caacaggatg aaacccccgtc tctactaaaa atacaaaaat tagccaggca tggtggcggg | 600 |
| cgcctgtaat cccagctgct cgggaggctg aggcaggaga atggattgaa cccaggaggt | 660 |
| ggaggttgca gtgagcagag atcacgccac tgcactcaag cccaggcaac gaagcgagac | 720 |
| tccttctcaa aaaaaaaaaa agagagaaac ataggctagg actaggcata tgccatgcct | 780 |
| tgtgacataa actggacatg gggaagggga gtgattcccc agtgttagtt agccttgctc | 840 |
| ttgtcactag aaggaggaag gaatgctgtg tggcaaggaa aggaattaat gtccacttga | 900 |
| gatggatttg agaaggatgt ctgcaagcag aaataaaggg ttaaagggtg cttacattaa | 960 |
| aaattttgat agctactgct ctcaaaattg tatcgcgatt tatattccca gtgccaacag | 1020 |
| tgtttgaaga gtctggctct ccagagcctg tagacactgg atattgtcag tgtttttaaat | 1080 |
| ttcagcagat ctgatatcta aaaatggtat ctcactgttc taaactgttc tagtatggtg | 1140 |
| ttctacgtga cacccttttc atgtgtttag ctggcctttg catttctttt ttttttttt | 1200 |
| tgaactgcct atgcatatct tttggtcaaa attcaattga attgcccttt tttattgtta | 1260 |
| gagctgctac aaacattact gaaaaggcaa ctcagttgtg tgtgtgtgta tgcacacaca | 1320 |
| tatatattta taatacatat gttacttagg gtttgtacca gctctatgag ctccttgagg | 1380 |
| gtggcacctt gctgtaatac agcctgacac ctaatacgaa gtagaaatca gtgattattt | 1440 |
| atcacgcaaa taagaaaca aataagtgaa cgaatgaatg agtcaatagt gttgactgcc | 1500 |
| ttgtattgtc ctaggcccaa gagacagtga aatatccctg ttcttgtata cttttctgta | 1560 |
| agtttctgga agtttctctg taaagcatct cagtaagctt ttctataggc tgtgagaaac | 1620 |
| gcatgagtca ggctaatagg aggcatataa ttttgaattg cttttcagaa atggccttca | 1680 |
| tattccttta cactcactca tcctgttgat aagagcagat ggcctactgc atgtgactca | 1740 |

```
gactcaaaca cacacctccg ctcccttgaa gtgccagccc tggagctttg ttgaggctcg    1800
catctgccac gggagtcagc tagtacgttg cccagttcaa catccatcca ggatttcata    1860
ggaacttgag aatcattgtt tttggcttga atcctgggtt tgaggtttct tcgtgtagga    1920
atctgaaaaa aggatttgga aacgttgttg tctctaatcc caaagtatgt atctgggagg    1980
```

<210> SEQ ID NO 106
<211> LENGTH: 1980
<212> TYPE: DNA
<213> ORGANISM: Homo sapiens

<400> SEQUENCE: 106

```
attcatctgt gttattggga aatgatgtga acttaatttc tctttccctt ctaaaacttt      60
gcttactgaa tggaaatgtt cctgagatct gtttatttgg ttctatattt atgtacctcc     120
cttttaaaat agagaataca tgttaatgtt tctttgatga ctcagtgtgt attatcggta     180
acagtccatt catgatgttg ccataccaca cagcataatt ttctatctgc ttctgattga     240
ttcttcattc tcccttgatc tcagtttgtc atttaataca tctaagtttt tcactcaaca     300
aatcaaatac tgatggagaa tctgctatac caggcact gtgctgctag gagctgagga      360
ttgaacgggg agaaacagga agctccctgc tctcatagtg cttcttagtt ggggagaaaa     420
gacattcatg atataatcac ataaatacct atttttatat gtaaaaaatg ttgtcaaaga     480
aaagaacggg gtgatgggaa cagttggaag aggtgtaaaa actccagaga agctgtggct     540
cctagaaaga aggtaggttt taggactaga atggtgatag tgggccggaa gagagagagt     600
gcattcgaaa gacactgagg agattgcatc agtaggactt ggtgacacat tagatgcaga     660
ggaagaggga cagaaatgct tcaaggagga cttttaggca tctgtcttgg gtaactagat     720
gatgccaatg gctgagatgg ggaattcttg gtagatgag gtttggtggg atggtgattg      780
ttataacttt gactttgaac gtgctgagtt caggtgacat tgtgataccc caaaggaggt     840
gcagagtagg tagctggaga cacaggcccg aagatgatga gaggtctggc ctagaaacat     900
ggatgcagga gtcatggatc catcaaggca ctgtgagttt ggatgagatc atctagcaga     960
acacttaagt ggagaagcaa agtggtctag agactaagcc atgaggaact ccaacactta    1020
gaggcgtaga aagcaggtag aaagggaaca cctgaagact taggaaggag gggccagaaa    1080
gggatgatgg cacccgaaga cagtggtgtt caggaagcca agggaggaag gtatttagac    1140
aggaggggga gagcagaatt ggcaaagctg tggagaaagt gagatgagaa ctcctattaa    1200
aaacacacaa ctggtccaat gacatgggat ggcatgaaaa tcactgatga ccaagcagga    1260 gacagggtg gaccgcaggg gaaaaagagc aagctgaagc cagctaagga atgtcctcgg     1320
gccatctcct agcggaggcg gtagagccgt ggttgaaggt acaggaagtg gactgttagg    1380
gcccaggttc cccttaacca tgagacctga agcaagttac tttatttctc tagggctcaa    1440
ttttctcacc tgtaaaacaa gagtaacagt gctcacctac taggttgctg tgaggttctt    1500 tttcttttc tttttttttt ggagacagag tctcactctg tcacccaggc tggagtgcag     1560
tggtgcaatc ttggctcact gcaatctcca cctcccgggt tccagctatt ctcctgcctt    1620
agcctcctga gtggctggga ctacaggcgc ctgccaccac aactggctaa ttttttgtatt   1680 tttagtagag atggggtttc accacgttgg ccagcctgga ctcaaactcc tgacctcagg    1740
tgatctgcct gcttcagcct cccaaagtgc tgggattaca ggcgtgagcc accacacctg    1800
gccttctgtg aggttcttaa catgtaagcc acttagccca gtggctgact catagtagtt    1860
gctgaataaa tgctaatttt atattaacac cctcataacc cattaaatca atatttattg    1920
```

```
agcatccatc tgccaggcac tgtactagat gctgacaaag acaccccccaa caacaaataa    1980
```

<210> SEQ ID NO 107
<211> LENGTH: 1980
<212> TYPE: DNA
<213> ORGANISM: Homo sapiens

<400> SEQUENCE: 107

```
tgagcctagg agtttgagat cacccaggc agtgtggcaa aaccgcatct ctacatgaaa      60
aatacaaaaa taagtcaggc atggcagcat gtgcctgtgg tcctggctac tagggaggct    120
gaggtgagag gatcaattga gcccaggagg tcaaggccac agtgagctga gattgcacca    180
ctgcactctg gcctggggga cagagtgaga ccctgtctca aaaaaaaaaa aaaaaaatag    240
tattgtatca atgttaattt cctggttttg ataatagtgc caaaggtata taaactgtta    300
aggcaagagc aagtggctga aggctataca ggaactctct gcactatttt tgcaacttct    360
ctgttatcct aaaattattt caaaataaaa agttaaaaaa aaagtgttta ggccgggcgc    420
ggtggctcac gcctataatc ccagcacttt gggaggccga ggcgggcgga tcacgaggtc    480
aggagatcaa gaccatcctg gctaacacag tgaaacccca tctctactaa agatacaaaa    540
aattagccgg gcgaggtagc gggcgcctgt agtcccagct acgtgggagg ctgaggcagg    600
agaatggcat gaaccccagg gggtggagcc tgcagtgagc cgagatcgtg ccactgcact    660
ccagcctggg tgaaagagcg agactccttc tcaaaaaaaa aaaaaaaaaa aaaagtgtt    720
taatctttttt tccaaaagga gcacacagaa cagagagtac agtacaagtc ccttaagaat    780
ttgttttttc tcagactatt ttctcacttg tcatcaagaa tcagcctta gattattggc    840
agcattagtc ctctagtaca gtctgcttgt gggtgaccag atggagtaat gctgagcaca    900
gagactatga tggccgtgct aaggtaagag tattgataat gtaagcatac ttcctctatc    960
aacaataatt gttaacagct gcttcaagca cttgatatta ccactagttg ttaactgaat   1020
caagcatgtg ctccaagttc acattaatgt gaattgaaca gcattgtgta cgtacgagga   1080
gcttcatgca agtgttatac actgcactca caagtattat gatcttacta agcattagaa   1140
atactctgtg ttaaagaagc ttggtctagg ccaagcgtgg tggctcatgc ctataatctc   1200
agcactttgg gaggccaagg caggcagatc acatgaggcc aggaatttga gaccagcctg   1260
gccaacatgg tgaaacccca tctctactaa aaatacaaat attagccagg tatgatggcg   1320
catgcctata atcctaacta ctcaggaggc cgaagcagaa gaatcacttg aacctgggag   1380
gcggaggttg cagtgagcca agatcatgcc actgcactcc agcctgggtg acagagtgag   1440
actctgtctc aaaaaaaaaa aaagaaaga aagaaaaag aaacttggtc tagttatttt    1500
ccttcctctg gggaagtaac catttgggtg ggaatagttt tgttgttgat ccatcttgc    1560
tggtttggaa acaatgcact ggctccactt ttccactcat gggctttaag gcccccttga   1620
gtcccagtct ttctcctgac acatggctgt ctcctgacag tccctctgc tttacattgt    1680
tctcagaggg tcctgggcca tcgtttgagc ttcattcttt caaatacact tccctctttc   1740
tctatcaagc caaggctccc ctcccccaga actctgcata ggcccttcag cctccatgaa   1800
tcccttagtg agtgagtaaa ctaccactgg attcagtcac tgcaaatgta ctttatttac   1860
cccttagcac tcttactaca tgtatgtgtt agggttcttc aaagaaacag aaccaatagg   1920
atacatagag atatataaga gaagatttat aatgggaatt ggctcatgtg attatggagg   1980
```

<210> SEQ ID NO 108

<211> LENGTH: 1063
<212> TYPE: DNA
<213> ORGANISM: Homo sapiens

<400> SEQUENCE: 108

| | | | | | |
|---|---|---|---|---|---|
| agaatacgag | gaggaagagg | tggccatacc | gttgaccgct | cctccaacta | accagtaagt | 60 |
| taagactgct | gttcaggaat | ttgggaagct | ggccccagaa | aagaagtgga | aatgaagggg | 120 |
| tggtatcacg | gaaaacttga | cagaacgata | gcagaagaac | gcctcaggca | ggcagggaag | 180 |
| tctggcagtt | atcttataag | agagagtgat | cggaggccag | ggtcctttgt | actttcattt | 240 |
| cttagccaga | tgaatgttgt | caaccatttt | aggattattg | ctatgtgtgg | agattactac | 300 |
| attggtggaa | gacgttttc | ttcactgtca | gacctaatag | gttattacag | tcatgtttct | 360 |
| tgtttgctta | aaggagaaaa | attactttac | ccagttgcac | caccagagcc | agtagaagat | 420 |
| agaaggcgtg | tacgagctat | tctaccttac | acaaaagtac | cagacactga | tgaaataagt | 480 |
| ttcttaaaag | gagatatgtt | cattgttcat | aatgaattag | aagatggatg | gatgtgggtt | 540 |
| acaaatttaa | gaacagatga | acaaggcctt | attgttgaag | acctagtaga | agaggtgggc | 600 |
| cgggaagaag | atccacatga | aggaaaaata | tggttccatg | ggaagatttc | caaacaggaa | 660 |
| gcttataatt | tactaatgac | agttggtcaa | gtctgcagtt | ttcttgtgag | gccctcagat | 720 |
| aatactcctg | gcgattattc | actttatttc | cggaccaatg | aaaatattca | gcgatttaaa | 780 |
| atatgtccaa | cgccaaacaa | tcagtttatg | atgggaggcc | ggtattataa | cagcattggg | 840 |
| gacatcatag | atcactatcg | aaaagaacag | attgttgaag | gatattatct | taaggaacct | 900 |
| gtaccaatgc | aggatcaaga | acaagtactc | aatgacacag | tggatggcaa | ggaaatctat | 960 |
| aataccatcc | gtcgtaaaac | aaaggatgcc | ttttataaaa | acattgttaa | gaaaggttat | 1020 |
| cttctgaaag | aggccaaaaa | aaaaaaaaaa | aaaaaaaaa | aaa | | 1063 |

<210> SEQ ID NO 109
<211> LENGTH: 2599
<212> TYPE: DNA
<213> ORGANISM: Homo sapiens

<400> SEQUENCE: 109

| | | | | | |
|---|---|---|---|---|---|
| agctctctcg | agtcactccg | gcgcagtgtt | gggactgtct | gggtatcgga | aagcaagcct | 60 |
| acgttgctca | ctattacgta | taatcctttt | cttttcaaga | ttttattttt | agatgcctga | 120 |
| ggaagtgcac | catggagagg | aggaggtgga | gactttgcc | tttcaggcag | aaattgccca | 180 |
| actcatgtcc | ctcatcatca | ataccttcta | ttccaacaag | gagattttcc | ttcgggagtt | 240 |
| gatctctaat | gcttctgatg | ccttggacaa | gattcgctat | gagagcctga | cagacccttc | 300 |
| gaagttggac | agtggtaaag | agctgaaaat | tgacatcatc | cccaaccctc | aggaacgtac | 360 |
| cctgactttg | gtagacacag | gcattggcat | gaccaaagct | gatctcataa | ataatttggg | 420 |
| aaccattgcc | aagtctggta | ctaaagcatt | catggaggct | cttcaggctg | gtgcagacat | 480 |
| ctccatgatt | gggcagtttg | gtgttggctt | ttattctgcc | tacttggtgg | cagagaaagt | 540 |
| ggttgtgatc | acaaagcaca | acgatgatga | acagtatgct | tgggagtctt | ctgctggagg | 600 |
| ttccttcact | gtgcgtgctg | accatggtga | gcccattggc | aggggtacca | agtgatcct | 660 |
| ccatcttaaa | gaagatcaga | cagagtacct | agaagagagg | cgggtcaaag | aagtagtgaa | 720 |
| gaagcattct | cagttcatag | gctatcccat | cacccttat | ttggagaagg | aacgagagaa | 780 |
| ggaaattagt | gatgatgagg | cagaggaaga | gaaaggtgag | aaagaagagg | aagataaaga | 840 |
| tgatgaagaa | aaacccaaga | tcgaagatgt | gggttcagat | gaggaggatg | acagcggtaa | 900 |

```
ggataagaag aagaaaacta agaagatcaa agagaaatac attgatcagg aagaactaaa      960
caagaccaag cctatttgga ccagaaaccc tgatgacatc acccaagagg agtatggaga     1020
attctacaag agcctcacta atgactggga agaccacttg gcagtcaagc acttttctgt     1080
agaaggtcag ttggaattca gggcattgct atttattcct cgtcgggctc cctttgacct     1140
ttttgagaac aagaagaaaa agaacaacat caaactctat gtccgccgtg tgttcatcat     1200
ggacagctgt gatgagttga taccagagta tctcaatttt atccgtggtg tggttgactc     1260
tgaggatctg cccctgaaca tctcccgaga aatgctccag cagagcaaaa tcttgaaagt     1320
cattcgcaaa aacattgtta agaagtgcct tgagctcttc tctgagctgg cagaagacaa     1380
ggagaattac aagaaattct atgaggcatt ctctaaaaat ctcaagcttg aatccacga      1440 agactccact aaccgccgcc gcctgtctga gctgctgcgc tatcatacct cccagtctgg     1500
agatgagatg acatctctgt cagagtatgt ttctcgcatg aaggagacac agaagtccat     1560
ctattacatc actggtgaga gcaaagagca ggtggccaac tcagcttttg tggagcgagt     1620
gcggaaacgg ggcttcgagg tggtatatat gaccgagccc attgacgagt actgtgtgca     1680
gcagctcaag gaatttgatg ggaagagcct ggtctcagtt accaaggagg gtctggagct     1740
gcctgaggat gaggaggaga agaagaagat ggaagagagc aaggcaaagt tgagaacct      1800 ctgcaagctc atgaaagaaa tcttagataa aaggttgag aaggtgacaa tctccaatag      1860
acttgtgtct tcaccttgct gcattgtgac cagcacctac ggctggacag ccaatatgga     1920
gcggatcatg aaagcccagg cacttcggga caactccacc atgggctata tgatggccaa     1980
aaagcacctg gagatcaacc ctgaccaccc cattgtggag acgctgcggc agaaggctga     2040
ggccgacaag aatgataagg cagttaagga cctggtggtg ctgctgtttg aaaccgccct     2100
gctatcttct ggcttttccc ttgaggatcc ccagacccac tccaaccgca tctatcgcat     2160
gatcaagcta ggtctaggta ttgatgaaga tgaagtggca gcagaggaac ccaatgctgc     2220
agttcctgat gagatccccc ctctcgaggg cgatgaggat gcgtctcgca tggaagaagt     2280
cgattaggtt aggagttcat agttggaaaa cttgtgccct tgtatagtgt ccccatgggc     2340
tcccactgca gcctcgagtg cccctgtccc acctggctcc cctgctggt  gtctagtgtt     2400 tttttccctc tcctgtcctt gtgttgaagg cagtaaacta agggtgtcaa gccccattcc     2460
ctctctactc ttgacagcag gattggatgt tgtgtattgt ggtttattttt attttcttca    2520 ttttgttctg aaattaaagt atgcaaaata agaatatgc cgttttata cgaaaaaaaa      2580 aaaaaaaaaa aaaaaaaa                                                    2599
```

<210> SEQ ID NO 110
<211> LENGTH: 829
<212> TYPE: DNA
<213> ORGANISM: Homo sapiens

<400> SEQUENCE: 110

```
cctctttcc gtggcgcctc ggaggcgttc agctgcttca agatgaagct gaacatctcc       60
ttcccagcca ctggctgcca gaaactcatt gaagtggacg atgaacgcaa acttcgtact     120
ttctatgaga gcgtatggc cacagaagtt gctgctgacg ctctgggtga agaatggaag     180
ggttatgtgg tccgaatcag tggtgggaac gacaaacaag gtttccccat gaagcagggt     240
gtcttgaccc atgccgtgt ccgcctgcta ctgagtaagg ggcattcctg ttacagacca     300
aggagaactg gagaaagaaa gagaaaatca gttcgtggtt gcattgtgga tgcaaatctg    360
```

| | |
|---|---|
| agcgttctca acttggttat tgtaaaaaaa ggagagaagg atattcctgg actgactgat | 420 |
| actacagtgc ctcgccgcct gggcccccaaa agagctagca gaatccgcaa acttttcaat | 480 |
| ctctctaaag aagatgatgt ccgccagtat gttgtaagaa agcccttaaa taaagaaggt | 540 |
| aagaaaccta ggaccaaagc acccaagatt cagcgtcttg ttactccacg tgtcctgcag | 600 |
| cacaaacggc ggcgtattgc tctgaagaag cagcgtacca agaaaaataa agaagaggct | 660 |
| gcagaatatg ctaaacttt tggccaagaga atgaaggagg ctaaggagaa cgccaggaa | 720 |
| caaattgcga agagacgcag actttcctct ctgcgagctt ctacttctaa gtctgaatcc | 780 |
| agtcagaaat aagattttt gagtaacaaa taaataagat cagactctg | 829 |

<210> SEQ ID NO 111
<211> LENGTH: 1980
<212> TYPE: DNA
<213> ORGANISM: Homo sapiens

<400> SEQUENCE: 111

| | |
|---|---|
| ttgatcttcc tgcctcagcc ttccaagtag ctgggactta aaggcgtgag ccaccacacc | 60 |
| tgactaattt tcgtattttt tgtagagatg gggtttcgcc atgttgcccg ggctgttctc | 120 |
| gaactcctga gctcaagcaa tctgcccacc tcagcctccc aaagcgctgg gattacaggc | 180 |
| atgagccacc atcccagcca aaactataaa actttagaa aagaacatag aagaaaatct | 240 |
| ttgggtcctg ggggcaaaga gctctgagac ttgacatcaa aagcatgccg cataatagga | 300 |
| aaatactaga cttatttag gggttaagag tttagactct ggactctctc agccttggtt | 360 |
| tcactagtta gctctatcac taactacatt gggcattgaa aattcctctg ttgtcccacg | 420 |
| tggtgcatgg atgattgtag acgaggacac tgagatcctg aaggcagaag taatttctct | 480 |
| aagcaacgtt gttggttggt ggcagagtct gggttacaac ccctggtttc ctgattccga | 540 |
| gtccaagtga atacttttg cccctgcagt agaccctgct acagaggata aaaaggcacg | 600 |
| tcataggcta ggagaaaaat tttgcctacc acatatgtaa ccaaggacta gcagctagga | 660 |
| catctgaaga attctcaaca ttcaacgggg tagaagaatg aacgattcaa tagaatatgg | 720 |
| gcaaaagaca tgaagaggca ttttaccaaa catagggtgc tatggtccga atgttttgcat | 780 |
| tctcctcaaa ttcctgtgtt gaaatcctaa cccccaaggt attggtatta ggaggcaggg | 840 |
| gccctgggaa gtgattaggt cataaaggtg gagtcctcat ggatgggatt agtgtctta | 900 |
| taaaagagac ctttgccatg tgaggttaca gtgagaagac atctgtctat gaagaaagtg | 960 |
| ggcccctcacc aaaacagtc tgctggcact ttgcacttca actccccagc ttccagaact | 1020 |
| gtaaggaata taagtctgtt gttggtaagc cacccggtct atgatatttt gttatagcag | 1080 |
| cccaaacaga ctaagacagg tgacaaataa acatgaaaag atgttcaaca tcattagcca | 1140 |
| ttagggaaat gcagattaaa accacagcga aatatcatga tacagttttc agcatggcta | 1200 |
| aactagaaaa tagtgacacc accaaatgcc gacaaggctg tggggaaact gggttgttca | 1260 |
| gacactgcca ctggggctgt agcgtactat agccactttc ataaacagtt tgtcagtttc | 1320 |
| ttaaaaaact aaacctgcaa ctaccatatg acccagcaat tacaccctg ggcacctacc | 1380 |
| caagagaaat gaaaactcaa cgtttgcgca aaacctgtg taggaatgtt caagcagctt | 1440 |
| tattcataat atgcccaaac aggaaacaac tcagctgtcc ttcagtaggt aaatagttaa | 1500 |
| gcaaattgtc atacccctgt gtcatggagc actacctagc aataacaagg agcaaattat | 1560 |
| tgatacataa caatctggat gaatctccag agaattatgt tgaatgaaaa aagccagccc | 1620 |
| ctgaaggata catactgtat gatgccattt acataacatt cttgaaattc taaaattaca | 1680 |

```
gagatgggga acagatttgt ggttaaagat ggagccgggt gggaagaaag taggtgtggc    1740
tataaacggg taacatgaag gatccttgtg gtgatggaaa tttctgtatt tttattgtat    1800
ccgtgtcagt atcctggttg tgatatggta atacagtttt gcaagatact acccttaggg    1860
gaaatgaggt aagacctggc atctctctgt attatttctt aattgcatgt gaatctacaa    1920
ttatttcaaa ataaaaagta tgattgaagt aactctcagg aagcttagcc tactgtggat    1980
```

<210> SEQ ID NO 112
<211> LENGTH: 79
<212> TYPE: PRT
<213> ORGANISM: Artificial Sequence
<220> FEATURE:
<223> OTHER INFORMATION: Synthetic

<400> SEQUENCE: 112

Ser Cys Gly Pro Ser Met Arg Thr Arg Trp Ser Ser Ile Arg Arg Ser
1               5                   10                  15

Trp Arg Arg Leu Ile Leu Pro Ser Trp Thr Met Pro Gly Ser Leu Leu
            20                  25                  30

Arg Gly Thr Ala Thr Trp Trp Gly Leu Pro Thr Arg Ser Cys Ser Ser
        35                  40                  45

Arg Ala Ser Ala Ser Thr Ala Ser Leu Pro Ser Ser Ala Ser Ser Arg
    50                  55                  60

Ser Ser Trp Gln Pro Arg Arg Ser Leu Arg Pro His Ser Ser
65                  70                  75

<210> SEQ ID NO 113
<211> LENGTH: 12
<212> TYPE: PRT
<213> ORGANISM: Artificial Sequence
<220> FEATURE:
<223> OTHER INFORMATION: Synthetic

<400> SEQUENCE: 113

Met Arg Asn Asp Arg Ala Ala Ser Arg Gln Ile Thr
1               5                   10

<210> SEQ ID NO 114
<211> LENGTH: 76
<212> TYPE: PRT
<213> ORGANISM: Artificial Sequence
<220> FEATURE:
<223> OTHER INFORMATION: Synthetic

<400> SEQUENCE: 114

Leu Ala His Arg Pro Pro Cys Ala Glu Pro Asp Pro Gly Gln Arg Met
1               5                   10                  15

Glu Leu Pro Ala Pro Val Pro Arg Pro Arg Gly Ala Ser Lys Pro Arg
            20                  25                  30

Asp Gly Thr Ser Ser His Cys Asp Met Pro Asn Cys Gln His Pro Gln
        35                  40                  45

Gly Pro Gly Pro Ala Gly Glu Ile Arg Ser Arg Cys Arg Ser Cys Trp
    50                  55                  60

Leu Arg Ala Val Arg Cys Asn Pro Trp Leu Gly Arg
65                  70                  75

<210> SEQ ID NO 115
<211> LENGTH: 20
<212> TYPE: PRT
<213> ORGANISM: Artificial Sequence
<220> FEATURE:
<223> OTHER INFORMATION: Synthetic

<400> SEQUENCE: 115

Asn Ser Gly Ala Ser Gly Ser Arg Asn Phe Ser Ser Cys Ser Ala Glu
1               5                   10                  15

Asp Phe Glu Lys
            20

<210> SEQ ID NO 116
<211> LENGTH: 31
<212> TYPE: PRT
<213> ORGANISM: Artificial Sequence
<220> FEATURE:
<223> OTHER INFORMATION: Synthetic

<400> SEQUENCE: 116

Ser Ser Val Pro Pro Gln Asp Thr Ala Pro Tyr Ser Cys His Val Gln
1               5                   10                  15

His Ser Ser Leu Ala Gln Pro Leu Val Val Pro Trp Glu Ala Ser
            20                  25                  30

<210> SEQ ID NO 117
<211> LENGTH: 37
<212> TYPE: PRT
<213> ORGANISM: Artificial Sequence
<220> FEATURE:
<223> OTHER INFORMATION: Synthetic

<400> SEQUENCE: 117

Val Ala Val Ala Gln Gly Ser Gly Ala Leu Glu Ser Ser Lys Trp Pro
1               5                   10                  15

Leu Leu Asn Leu Asn Gly Cys Leu Gly Arg Ala Glu Gly Gln Val Leu
            20                  25                  30

Met Ala Ser His Pro
        35

<210> SEQ ID NO 118
<211> LENGTH: 11
<212> TYPE: PRT
<213> ORGANISM: Artificial Sequence
<220> FEATURE:
<223> OTHER INFORMATION: Synthetic

<400> SEQUENCE: 118

Ser Ala Phe Arg Gly Tyr Leu Ala Asn Asn Lys
1               5                   10

<210> SEQ ID NO 119
<211> LENGTH: 36
<212> TYPE: PRT
<213> ORGANISM: Artificial Sequence
<220> FEATURE:
<223> OTHER INFORMATION: Synthetic

<400> SEQUENCE: 119

Ser Leu Ala His Arg Pro Pro Cys Ala Glu Pro Asp Pro Gly Gln Arg
1               5                   10                  15

Met Glu Leu Pro Ala Pro Val Pro Arg Pro Arg Gly Ala Ser Lys Pro
            20                  25                  30

Pro Arg Arg Asp
        35

```
<210> SEQ ID NO 120
<211> LENGTH: 51
<212> TYPE: PRT
<213> ORGANISM: Artificial Sequence
<220> FEATURE:
<223> OTHER INFORMATION: Synthetic

<400> SEQUENCE: 120

Leu Phe Ile Phe Ile Thr Gln Lys Ser Phe Ile Phe Leu Phe Ser Phe
1               5                   10                  15

Leu Thr Leu Cys Leu Cys Leu Gln His Phe His Asn Asp Phe Leu Leu
            20                  25                  30

Leu Asp Lys Glu Ser Thr Leu Asp Pro Val Thr Asn Thr Phe Ser Thr
        35                  40                  45

His Gly Thr
    50

<210> SEQ ID NO 121
<211> LENGTH: 10
<212> TYPE: PRT
<213> ORGANISM: Artificial Sequence
<220> FEATURE:
<223> OTHER INFORMATION: Synthetic

<400> SEQUENCE: 121

Pro Tyr Gln Ile Tyr Gln Val Met Ile Asn
1               5                   10

<210> SEQ ID NO 122
<211> LENGTH: 19
<212> TYPE: PRT
<213> ORGANISM: Artificial Sequence
<220> FEATURE:
<223> OTHER INFORMATION: Synthetic

<400> SEQUENCE: 122

Val Ser Thr Phe Leu Ser Arg Val Gly Arg Val Ser Leu Leu Asn Phe
1               5                   10                  15

Leu Pro Phe

<210> SEQ ID NO 123
<211> LENGTH: 76
<212> TYPE: PRT
<213> ORGANISM: Artificial Sequence
<220> FEATURE:
<223> OTHER INFORMATION: Synthetic

<400> SEQUENCE: 123

Asn Thr Leu Val Thr Tyr Asp Met Val Pro Glu Pro Lys Ile Ile Asp
1               5                   10                  15

Ala Ala Leu Arg Ala Cys Arg Arg Leu Asn Asp Phe Ala Ser Thr Val
            20                  25                  30

Arg Ile Leu Glu Val Val Lys Asp Lys Ala Gly Pro His Lys Glu Ile
        35                  40                  45

Tyr Pro Tyr Val Ile Gln Glu Leu Arg Pro Thr Leu Asn Glu Leu Gly
    50                  55                  60

Ile Ser Thr Pro Glu Glu Leu Gly Leu Asp Lys Val
65                  70                  75

<210> SEQ ID NO 124
<211> LENGTH: 61
<212> TYPE: PRT
<213> ORGANISM: Artificial Sequence
```

<220> FEATURE:
<223> OTHER INFORMATION: Synthetic

<400> SEQUENCE: 124

Pro Pro Ser His His Ile Pro Asn Leu Ser Leu Thr Lys Arg Lys Pro
1               5                   10                  15

Ser Pro His Ser Leu Asn Leu Ile His His Ser Arg Gln Leu Arg Trp
            20                  25                  30

Ile Lys Pro Asn Pro Ala Thr Gln Asn Leu Ser Ile Leu Leu Asn Tyr
        35                  40                  45

Pro His Arg Met Asn Asn Ser Ser Ser Thr Val Gln Pro
    50                  55                  60

<210> SEQ ID NO 125
<211> LENGTH: 8
<212> TYPE: PRT
<213> ORGANISM: Artificial Sequence
<220> FEATURE:
<223> OTHER INFORMATION: Synthetic

<400> SEQUENCE: 125

Ser Ala Gly Ser Cys Ser Ser Ala
1               5

<210> SEQ ID NO 126
<211> LENGTH: 51
<212> TYPE: PRT
<213> ORGANISM: Artificial Sequence
<220> FEATURE:
<223> OTHER INFORMATION: Synthetic

<400> SEQUENCE: 126

Lys Leu Leu Phe Ala Leu Gln Leu Trp Asn Leu Val Leu Gln Pro Leu
1               5                   10                  15

Leu Phe Cys Pro Asn Gly Pro Cys Ser Leu Asp Gln Glu Leu Gln Lys
            20                  25                  30

Trp Lys Lys Leu Met Lys Arg His Leu Ile Asn Val Asp Gly Ser Lys
        35                  40                  45

Ser Cys Pro
    50

<210> SEQ ID NO 127
<211> LENGTH: 131
<212> TYPE: PRT
<213> ORGANISM: Artificial Sequence
<220> FEATURE:
<223> OTHER INFORMATION: Synthetic

<400> SEQUENCE: 127

Glu Asp Asp Tyr Ser Tyr Gln Gly His Met Gln Ser Cys Asn Phe Ser
1               5                   10                  15

Ala Glu Lys Ala Lys Val Tyr Ile Asn Asp Ser Val Glu Leu Ser Gln
            20                  25                  30

Asn Glu Gln Lys Leu Ala Ala Trp Leu Ala Lys Arg Gly Pro Ile Ser
        35                  40                  45

Val Ala Ile Asn Ala Phe Gly Met Gln Phe Tyr Arg His Gly Ile Ser
    50                  55                  60

Arg Pro Leu Arg Pro Leu Cys Ser Pro Trp Leu Ile Asp His Ala Val
65                  70                  75                  80

Leu Leu Val Gly Tyr Gly Asn Arg Ser Asp Val Pro Phe Trp Ala Ile
                85                  90                  95

```
Lys Asn Ser Trp Gly Thr Asp Trp Gly Glu Lys Gly Tyr Tyr Tyr Leu
            100                 105                 110

His Arg Gly Ser Gly Ala Cys Gly Val Asn Thr Met Ala Ser Ser Ala
        115                 120                 125

Val Val Asp
    130

<210> SEQ ID NO 128
<211> LENGTH: 11
<212> TYPE: PRT
<213> ORGANISM: Artificial Sequence
<220> FEATURE:
<223> OTHER INFORMATION: Synthetic

<400> SEQUENCE: 128

Gly Thr Asn Gln Arg Gln Thr Met Glu Asn His
1               5                   10

<210> SEQ ID NO 129
<211> LENGTH: 115
<212> TYPE: PRT
<213> ORGANISM: Artificial Sequence
<220> FEATURE:
<223> OTHER INFORMATION: Synthetic

<400> SEQUENCE: 129

Ser Ser Cys Ser Glu Tyr Asn Val Arg Val Ala Ser Arg Tyr Phe Lys
1               5                   10                  15

Gly Pro Glu Leu Leu Val Asp Tyr Gln Met Tyr Asp Tyr Ser Leu Asp
            20                  25                  30

Met Trp Ser Leu Gly Cys Met Leu Ala Ser Met Ile Phe Arg Arg Glu
        35                  40                  45

Pro Phe His Gly Gln Asp Asn Tyr Asp Gln Leu Val Arg Ile Ala
    50                  55                  60

Lys Val Leu Gly Thr Glu Glu Leu Tyr Gly Tyr Leu Lys Lys Tyr His
65                  70                  75                  80

Ile Asp Leu Asp Pro His Phe Asn Asp Ile Leu Gly Gln His Ser Arg
                85                  90                  95

Lys Arg Trp Glu Asn Leu Ser Ile Val Arg Thr Asp Thr Leu Ser Ala
            100                 105                 110

Leu Arg Pro
        115

<210> SEQ ID NO 130
<211> LENGTH: 89
<212> TYPE: PRT
<213> ORGANISM: Artificial Sequence
<220> FEATURE:
<223> OTHER INFORMATION: Synthetic

<400> SEQUENCE: 130

Ala Ala Arg Leu Gly Pro Ser Leu Glu Cys Trp Ala Ala Gly Ser Ala
1               5                   10                  15

Gly Pro Phe Thr Ala His Arg Arg Pro Ala Gln Val Gly Arg Pro Leu
            20                  25                  30

Ser Leu Ala Arg Gly Pro Ser Trp Ser Trp Arg Arg Cys Trp Ser Pro
        35                  40                  45

Gly Arg Cys Pro Ser Ala Pro Trp Arg Ala Gly Ser Arg Pro Ala Ala
    50                  55                  60
```

```
Ser Cys Pro Asp Trp Ile Pro Gly Pro Gln Gly Leu Trp Leu His Arg
 65                  70                  75                  80

Asn Pro Thr Ser Val Arg Pro Ala Arg
                85

<210> SEQ ID NO 131
<211> LENGTH: 11
<212> TYPE: PRT
<213> ORGANISM: Artificial Sequence
<220> FEATURE:
<223> OTHER INFORMATION: Synthetic

<400> SEQUENCE: 131

Gly Lys Glu Arg Glu Asn Ile Arg Thr Asn Thr
 1               5                  10

<210> SEQ ID NO 132
<211> LENGTH: 22
<212> TYPE: PRT
<213> ORGANISM: Artificial Sequence
<220> FEATURE:
<223> OTHER INFORMATION: Synthetic

<400> SEQUENCE: 132

Pro Lys Cys Arg Leu Gln Arg Gln Tyr Thr Gly Lys Gly Gly Val Gly
 1               5                  10                  15

Phe Val Tyr Glu Gly Val
                20

<210> SEQ ID NO 133
<211> LENGTH: 40
<212> TYPE: PRT
<213> ORGANISM: Artificial Sequence
<220> FEATURE:
<223> OTHER INFORMATION: Synthetic

<400> SEQUENCE: 133

Gln Thr Gln Thr His Thr Ser Ala Pro Leu Lys Cys Gln Pro Trp Ser
 1               5                  10                  15

Phe Val Glu Ala Arg Ile Cys His Gly Ser Gln Leu Val Arg Cys Pro
                20                  25                  30

Val Gln His Pro Ser Arg Ile Ser
            35                  40

<210> SEQ ID NO 134
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 134

Pro Arg Leu His Gln Xaa Lys Ala Asn Tyr Ile Tyr Ser Ile Asp Pro
 1               5                  10                  15

Ile Thr

<210> SEQ ID NO 135
<211> LENGTH: 14
<212> TYPE: PRT
<213> ORGANISM: Artificial Sequence
<220> FEATURE:
```

<223> OTHER INFORMATION: Synthetic

<400> SEQUENCE: 135

Pro Gln Thr Thr Ala Pro Arg Arg Ala Arg Pro Arg Arg Ser
1               5                   10

<210> SEQ ID NO 136
<211> LENGTH: 47
<212> TYPE: PRT
<213> ORGANISM: Artificial Sequence
<220> FEATURE:
<223> OTHER INFORMATION: Synthetic

<400> SEQUENCE: 136

Gly Thr Ile Ser Ile Val Cys Cys Trp Gly Cys Leu Cys Gln His Leu
1               5                   10                  15

Val Gln Cys Leu Ala Asp Gly Cys Ser Ile Asn Ile Asp Leu Met Gly
            20                  25                  30

Tyr Glu Gly Val Asn Ile Lys Leu Ala Phe Ile Gln Gln Leu Leu
        35                  40                  45

<210> SEQ ID NO 137
<211> LENGTH: 18
<212> TYPE: PRT
<213> ORGANISM: Artificial Sequence
<220> FEATURE:
<223> OTHER INFORMATION: Synthetic

<400> SEQUENCE: 137

Gly Met Ser His His Ala Trp Pro Arg Pro Ser Phe Phe Asn Thr Glu
1               5                   10                  15

Tyr Phe

<210> SEQ ID NO 138
<211> LENGTH: 160
<212> TYPE: PRT
<213> ORGANISM: Artificial Sequence
<220> FEATURE:
<223> OTHER INFORMATION: Synthetic

<400> SEQUENCE: 138

Asp Arg Arg Pro Gly Ser Phe Val Leu Ser Phe Leu Ser Gln Met Glu
1               5                   10                  15

Thr Asn Val Val Thr His Phe Arg Ile Ile Ala Met Glu Thr Cys Gly
            20                  25                  30

Asp Tyr Tyr Ile Gly Gly Arg Arg Phe Ser Ser Leu Ser Asp Leu Ile
        35                  40                  45

Gly Tyr Tyr Ser His Val Ser Cys Leu Leu Lys Gly Glu Lys Leu Leu
    50                  55                  60

Tyr Pro Val Ala Pro Pro Glu Pro Val Glu Asp Arg Arg Val Arg
65                  70                  75                  80

Ala Ile Leu Pro Tyr Thr Lys Val Pro Asp Thr Asp Glu Ile Ser Phe
                85                  90                  95

Leu Lys Gly Asp Met Glu Thr Phe Ile Val His Asn Glu Leu Glu Asp
            100                 105                 110

Gly Trp Met Glu Thr Trp Val Thr Asn Leu Arg Thr Asp Glu Gln Gly
        115                 120                 125

Leu Ile Val Glu Asp Leu Val Glu Val Gly Arg Glu Glu Asp Pro
    130                 135                 140

His Glu Gly Lys Ile Trp Phe His Gly Lys Ile Ser Lys Gln Glu Ala

<210> SEQ ID NO 139
<211> LENGTH: 88
<212> TYPE: PRT
<213> ORGANISM: Artificial Sequence
<220> FEATURE:
<223> OTHER INFORMATION: Synthetic

<400> SEQUENCE: 139

```
Tyr Phe Ala Tyr Leu Ile Ser Glu Gln Asn Glu Asn Lys Ile Asn
1               5                   10                  15

His Asn Thr Gln His Pro Ile Leu Leu Ser Arg Val Arg Glu Gly Met
            20                  25                  30

Gly Leu Asp Thr Leu Ser Leu Leu Pro Ser Thr Gln Gly Gln Glu Arg
        35                  40                  45

Glu Lys Asn Thr Arg His Gln Gln Gly Glu Pro Gly Gly Thr Gly Ala
    50                  55                  60

Leu Glu Ala Ala Val Gly Ala His Gly Asp Thr Ile Gln Gly His Lys
65                  70                  75                  80

Phe Ser Asn Tyr Glu Leu Leu Thr
                85
```

<210> SEQ ID NO 140
<211> LENGTH: 152
<212> TYPE: PRT
<213> ORGANISM: Artificial Sequence
<220> FEATURE:
<223> OTHER INFORMATION: Synthetic

<400> SEQUENCE: 140

```
Cys Ile Val Asp Ala Asn Leu Ser Val Leu Asn Leu Val Ile Val Lys
1               5                   10                  15

Lys Gly Glu Lys Asp Ile Pro Gly Leu Thr Asp Thr Thr Val Pro Arg
            20                  25                  30

Arg Leu Gly Pro Lys Arg Ala Ser Arg Ile Arg Lys Leu Phe Asn Leu
        35                  40                  45

Ser Lys Glu Asp Asp Val Arg Gln Tyr Val Val Arg Lys Pro Leu Asn
    50                  55                  60

Lys Glu Gly Lys Lys Pro Arg Thr Lys Ala Pro Lys Ile Gln Arg Leu
65                  70                  75                  80

Val Thr Pro Arg Val Leu Gln His Lys Arg Arg Arg Ile Ala Leu Lys
                85                  90                  95

Lys Gln Arg Thr Lys Lys Asn Lys Glu Ala Ala Glu Tyr Ala Lys
            100                 105                 110

Leu Leu Ala Lys Arg Met Glu Thr Lys Glu Ala Lys Glu Lys Arg Gln
        115                 120                 125

Glu Gln Ile Ala Lys Arg Arg Arg Leu Ser Ser Leu Arg Ala Ser Thr
    130                 135                 140

Ser Lys Ser Glu Ser Ser Gln Lys
145                 150
```

<210> SEQ ID NO 141
<211> LENGTH: 22
<212> TYPE: PRT
<213> ORGANISM: Artificial Sequence
<220> FEATURE:
<223> OTHER INFORMATION: Synthetic

<400> SEQUENCE: 141

```
Leu Ile Cys Ile Ser Leu Met Ala Asn Asp Val Glu His Leu Phe Met
1               5                   10                  15

Phe Ile Cys His Leu Ser
            20
```

<210> SEQ ID NO 142
<211> LENGTH: 219
<212> TYPE: DNA
<213> ORGANISM: Artificial Sequence
<220> FEATURE:
<223> OTHER INFORMATION: Synthetic

<400> SEQUENCE: 142

```
aagcttcgcc tccttggctg ccagctgctt ctggagctgg ctgagctggg cagagaggct    60
gtcgatgcgg atgcgcgact gctgcagctc tcgtgggca gcccccacca ggttgctgtt   120
cctctcagca gactgcctgg cattgtccag cttggcagaa taagtcttct ccagctcctt   180
cttatactgc tccacctggt cctcatgctg ggcccgcag                          219
```

<210> SEQ ID NO 143
<211> LENGTH: 438
<212> TYPE: DNA
<213> ORGANISM: Artificial Sequence
<220> FEATURE:
<223> OTHER INFORMATION: Synthetic

<400> SEQUENCE: 143

```
aatgagaaat gaccgagcag cttcgaggca gattacatga cttatgatct acatttaaat    60
atgatcttgg gagatgtgga agaaactgtg actactatag aaattgatga agaaacatat   120
gaagagatat ataaatcaac gaaacggaat attccaatgc tctttgtccg gggagatggc   180
gttgtcctgg ttgcccctcc actgagagtt ggctgaaaca agaatttgt cctgtatgga    240 aaacgggaga ctttgtacag tggcctctct aaaagtacaa acattcata agagaaacct    300 gcatacattt tgatattaag aaataattcc ggggattctc cactcctgaa atgagttgat   360
ttgcagataa ctctacaact tcttaagcta aatggtattt tcattttct caagctctcc    420 aataaatatg accaccaa                                                  438
```

<210> SEQ ID NO 144
<211> LENGTH: 555
<212> TYPE: DNA
<213> ORGANISM: Artificial Sequence
<220> FEATURE:
<223> OTHER INFORMATION: Synthetic

<400> SEQUENCE: 144

```
ggagtttcac ttttgttgcc caggattgag tgcagtgccc cgatcttggc tcactacaac    60
ctctgcctcc tgggttcaag cgactctcct gcctcagtgt cctgagtagc tgggattaca   120
ggcgtctgcc accacgcccg gctaatttg tattttagt agagaacagg tttcactatg     180
ttggtcaggc tggtcttgaa ctcctgacct cagcgcatcc agaattttag acggggcccc   240
cagggtgagg tcttggcacc ctccagtaga gaagaaggga catgggccat acgtggggtg   300
tcctttctgg gagccttgcg tcccttacct gcctagccag ggattgcacc tcacagcacg   360
cagccagcag gaacggcacc gtgatctgat tcacctgcg ggccctgggc cctggggtg    420 ttgacaattg gcatatcac agtgtgagct agtcccgtct cggggtttgg aggctccacg   480
tggccgtggt acaggagcag gcagttccat cctctggcct ggatcaggct ctgcacacgg   540
```
aggcctgtgg gccag                                                      555

<210> SEQ ID NO 145
<211> LENGTH: 306
<212> TYPE: DNA
<213> ORGANISM: Artificial Sequence
<220> FEATURE:
<223> OTHER INFORMATION: Synthetic

<400> SEQUENCE: 145
tcggcataaa gtacctcctg gaaggaaccg acagtcttta caacagtcac catatgcaca     60
ctcagcaaat gatttaagct tacaggtact tccttcgcag caagggtcca attcacattc    120
ctttggagta ccacagtcac actcttcccc agcgtccacc aacttattac cacaggaggg    180
agcactatag gcttcatcag gctttggaat attaagaagg cagtttcctc ctttatttaa    240
agttacttct caaagtcctc tgcactgcaa ctgctaaagt ttctggaacc cgatgctcct    300
gaattc                                                               306

<210> SEQ ID NO 146
<211> LENGTH: 463
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (433)..(434)
<223> OTHER INFORMATION: n is a, c, g, or t
<220> FEATURE:
<221> NAME/KEY: misc_feature
<222> LOCATION: (448)..(448)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (457)..(457)
<223> OTHER INFORMATION: n is a, c, g, or t
<220> FEATURE:
<221> NAME/KEY: misc_feature
<222> LOCATION: (459)..(460)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t

<400> SEQUENCE: 146

```
tcaagcgtgc ccccgcagga cacagccccc tactcctgcc acgtgcagca cagcagcctg    60
gcccagcccc tcgtggtgcc ctgggaggcc agctaggaag caagggttgg aggcaatgtg   120
ggatctcaga cccagtagct gcccttcctg cctgatgtgg gagctgaacc acagaaatca   180
cagtcaatgg atccacaagg cctgaggagc agtgtggggg gacagacagg aggtggattt   240
ggagaccgaa gactgggatg cctgtcttga gtagacttgg acccaaaaaa tcatctcacc   300
ttgagcccac ccccacccca ttgtctaatc tgtagaagcc ggaagcttgc ggccgcactc   360
gagtaactag ttaaccccttt gggggcctcta aacgggtctt gagggggttan ctngttnctc   420
gngtgcggcc gcnngcttcc ggcttctncn gnttngncnn tgn                     463
```

<210> SEQ ID NO 147
<211> LENGTH: 388
<212> TYPE: DNA
<213> ORGANISM: Artificial Sequence
<220> FEATURE:
<223> OTHER INFORMATION: Synthetic

<400> SEQUENCE: 147

```
gtggctgttg cgcagggatc aggtgcactt gagtcttcga agtggccatt gctcaacttg    60
aatggctgcc tggtcgggc agaaggccag gtcctcatgg cttcccatcc ctaatgaccg   120
gaatacatgg gctgccaggt cagatgtggg ccacatggga agtcccagct ctattctaga   180
aaatgcatgt accatcagct tactgataga catttactga acttgggtat gccagatcca   240
caggggccc cagagatgag ggggataaga aggtttctga aggcatggta cagaaggtgc   300
cagcagaggt atgggctagg ggaggcaggg agagcacaga gcaggcatcc taaaggaggc   360
agcatttgtg ttggagcttg aagaagtg                                     388
```

<210> SEQ ID NO 148
<211> LENGTH: 292
<212> TYPE: DNA
<213> ORGANISM: Artificial Sequence
<220> FEATURE:
<223> OTHER INFORMATION: Synthetic

<400> SEQUENCE: 148

```
taagctttca tcttcccaa ccctgatgtc ttcctattct cactgatccc cctactgact    60
cagcttcacg cttcttgatt atacctctct cctgtagaaa agccttggct ggctctcctt   120
taggatgaga ataaatccga aatccttagt gtagcattta gaagtcctat ctcccacttg   180
tttcttaata ttctcttctc taacaccgaa cttgtttcaa gcctcttttc caacacatga   240
tttcttctat tctaaatcaa tttatttatt atttgctaaa tagcccctaa ac          292
```

<210> SEQ ID NO 149
<211> LENGTH: 419
<212> TYPE: DNA
<213> ORGANISM: Artificial Sequence
<220> FEATURE:
<223> OTHER INFORMATION: Synthetic

<400> SEQUENCE: 149

```
ggctaatttt gtattttag tagagaacag gtttcactat gttggtcagg ctggtcttga    60
actcctgacc tcagcgcatc cagaatttta gacggggccc ccagggtgag gtcttggcac   120
cctccagtag agaagaaggg acatgggcca tacgtggggt gtcctttctg ggagccttgc   180
```

```
gtcccttacc tgcctagcca gggattgcac ctcacagcac gcagccagca ggaacggcac    240
cgtgatctga tttcacctgc gggccctggg ccctggggggt gtttgacaat tggggcatat    300
cacagtgtga gctagtcccg tctcgggggt ttggaggctc cacgtggccg tggtacagga    360
gcaggcagtt ccatcctctg gcctggatca ggctctgcac acggaggcct gtgggccag     419

<210> SEQ ID NO 150
<211> LENGTH: 157
<212> TYPE: DNA
<213> ORGANISM: Artificial Sequence
<220> FEATURE:
<223> OTHER INFORMATION: Synthetic

<400> SEQUENCE: 150
gtcttttcat ttttattact caaaaaagtt tcattttttt atttagcttt ctgactctgt     60
gcttgtgcct tcaacacttt cacaacgatt ttctgctcct cgataaggaa agcacgcttg    120
atcctgtcac gaacacattt agcacacatg gaaccaa                             157

<210> SEQ ID NO 151
<211> LENGTH: 397
<212> TYPE: DNA
<213> ORGANISM: Artificial Sequence
<220> FEATURE:
<223> OTHER INFORMATION: Synthetic

<400> SEQUENCE: 151
cttaccagat ctatcaggtc atgataaatt agacccagtc catctttcaa tccagtctac     60
tctggttctg aacatataaa cacaaaacac tacagattta ttaatatagc attttcccac    120
accctaaccc tataaagaac tttaaagag aaaatttcat ctaaatattt cacacttaaa    180
ggaaagcctt accaactatg gcaacaggtt tggaccatga aatagtactt tcctagatga    240
catatcgagt caacatgaag ccttagctga aatgaatgat tcaggatatt aatgagaaat    300
tctcacaaat gatatgcatt taggaaatga ttttgctttc cttaaatagt tcgaaggctt    360
gaaaataaac ttttttttg catttctttt aaaagtt                             397

<210> SEQ ID NO 152
<211> LENGTH: 644
<212> TYPE: DNA
<213> ORGANISM: Artificial Sequence
<220> FEATURE:
<223> OTHER INFORMATION: Synthetic

<400> SEQUENCE: 152
gtttccacat tcttgtcaag ggttggtagg gtcagtcttt taaatttctt gccattttag     60
tgactgtgca ttggtatttc attgtggttt atttgcatga tgactaatgc tcaacaccaa    120
ctaatcatgt tgagtatttt taatgtgctt atttgccact catatatctt ctttgatgaa    180
gtgtctcttc aaatattttg cccatttaaa aactgtattg attcttatta ttgaattgca    240
ataattcttt ctatccggat atatatcctt tgccagatat gtgtattaca aatgttttct    300
cctagccttc cacctcagcc tcccaagtag ctgggaatgc aggtgtgcac caccactcca    360
gggttttttg ttgttgttgt tgttgttttt ctgtagagac agggtcttgc catgctgccg    420
aggctgctct caaactcctg ggatcaagaa atcctcctgc ctcggcctcc caaagtgctg    480
acattacaag catgagccac tgtgcctggc taacttttca tctttttaaag tagtgtcttg    540 caaagaacaa cattttaatg aagtccattt atcaactttt tgattcattg tccatgcttt    600
ttgcataata agaaatcttt gcctgcctca aaattgcaaa gctt                     644
```

<210> SEQ ID NO 153
<211> LENGTH: 263
<212> TYPE: DNA
<213> ORGANISM: Artificial Sequence
<220> FEATURE:
<223> OTHER INFORMATION: Synthetic

<400> SEQUENCE: 153

```
aacacacttg ttacctatga tatggttcca gagcccaaaa tcattgatgc tgctttgcgg    60
gcatgcagac ggttaaatga ttttgctagt acagttcgta tcctagaggt tgttaaggac   120
aaagcaggac ctcataagga aatctacccc tatgtcatcc aggaacttag accaacttta   180
aatgaactgg gaatctccac tccggaggaa ctgggccttg acaaagtgta accgcataat   240
aaaagggaaa tgagtttgaa ctg                                           263
```

<210> SEQ ID NO 154
<211> LENGTH: 236
<212> TYPE: DNA
<213> ORGANISM: Artificial Sequence
<220> FEATURE:
<223> OTHER INFORMATION: Synthetic

<400> SEQUENCE: 154

```
gcccccatct catcatatac caaatctctc cctcactaaa cgtaagcctt ctcctcactc    60
tctcaatctt atccatcata gcaggcagtt gaggtggatt aaaccaaacc cagctacgca   120
aaatcttagc atactcctca attacccaca taggatgaat aatagcagtt ctaccgtaca   180
accctaacat aaccattctt aatttaacta tttatattat cctaactact accgca       236
```

<210> SEQ ID NO 155
<211> LENGTH: 332
<212> TYPE: DNA
<213> ORGANISM: Artificial Sequence
<220> FEATURE:
<223> OTHER INFORMATION: Synthetic

<400> SEQUENCE: 155

```
gggttcgtgt tcctcagcgt agccatcagg cttggccagc tgctccttgt aaagctgccc    60
cacagtgcgg aacatgccct tccgcgtctt gaaggccccg ggcagtgcgg tctccgacat   120
gccggccacc tggtccaggc cgatgatgcg gtccacatcc ttccacagct ccagacaaa    180 cttgtcagag gactggtgga gcagtgtggc gatgttgtca ttcagggat ccatgttctt    240 catcagccac tcgtcagctt tgtaatccac cttgccggca tagtggataa tgcagaaatc   300
agctttgtcc ttcagctgct tgggcttctg ga                                 332
```

<210> SEQ ID NO 156
<211> LENGTH: 279
<212> TYPE: DNA
<213> ORGANISM: Artificial Sequence
<220> FEATURE:
<223> OTHER INFORMATION: Synthetic

<400> SEQUENCE: 156

```
aaattacttt tcgccttgca gctgtggaac ttggtcttac agcctctgct cttctgccca    60
aacgggccat gcagtttgga tcaagaattg caaaaatgga aaaaattaat gaaaaggcat   120
ctgataaatg tggacggctc caaatcatgt cctttagaaaa tctttctatt gaaaggaga   180 ctaaattgta atgtgattca caatgtaaca atataaaaat aagttttat ataattatat    240
```
aaaagtaaga tactctgctg ctttactatt gtataatat                                279

<210> SEQ ID NO 157
<211> LENGTH: 877
<212> TYPE: DNA
<213> ORGANISM: Artificial Sequence
<220> FEATURE:
<223> OTHER INFORMATION: Synthetic

<400> SEQUENCE: 157
cagaggatga ctacagctac cagggtcaca tgcagtcctg caacttctca gcagagaagg         60
ccaaggtcta catcaatgac tccgtggagc tgagccagaa cgagcagaag ctggcagcct        120
ggctggccaa gagaggccca atctccgtgg ccatcaatgc ctttggcatg cagttttacc        180
gccacgggat ctcccgccct ctccggcccc tctgcagccc ttggctcatt gaccatgcgg        240
tgttgcttgt gggctacggc aaccgctctg acgttcccct ttgggccatc aagaacagct        300
ggggcactga ctggggtgag aagggttact actacttgca tcgcgggtcc ggggcctgtg        360
gcgtgaacac catggccagc tcggcggtgg tggactgaag aggggccccc agctcgggac        420
ctggtgctga tcagagtggc tgctgcccca gcctgacatg tgtccaggcc cctccccggg        480
aggtacagct ggcagaggga aaggcactgg tacctcaggg tgagcagagg gcactgggct        540
ggggcacagc ccctgcttcc ctgcacccca ttcccaccct gaagttctgc acctgcacct        600
ttgttgaatt gtggtagctt aggaggatgt cagggtgaag ggtggtatct tggcagttga        660
agctggggca agaactctgg gcttgggtaa tgagcaggaa gaaaattttc tgatcttaag        720
cccagctgtg ttctgccccc gctttcctct gtttgatact ataaatttc tggttccctt         780
ggatttaggg atagtgtccc cctccatgtc caggaaactt gtaaccaccc ttttctaaca        840
gcaataaaga gggtccttgt cccgaaaaaa aaaaaaa                                 877

<210> SEQ ID NO 158
<211> LENGTH: 568
<212> TYPE: DNA
<213> ORGANISM: Artificial Sequence
<220> FEATURE:
<223> OTHER INFORMATION: Synthetic

<400> SEQUENCE: 158
ggcagacaat ggaaaaccat tgaaaaggat taaactggga agtgatatgt tctcttttgc         60
atttaaaaag atcaccaatg gggatatgga gaatggtctg gataggtctt aagactagag        120
ccaggaagac atgttagaag ctatcaatt gaccctaaag acactgcttc aatccctttg         180
atgacagtga gtttgctttc cccagagata gcttattgga cctcaggact gctgtgagaa        240
acagaaaatg ctcctttacg tgttgcctga agttaggctc accgatttgg ggcatgttct        300
aattctacca gctaggaaca cacagaatcg cttgtcaaac attctgagtc agatatgtcc        360
tccctatgtc ttttctgaga aaggcataca gaaattccca gctaaacatc accagttccc        420
tcatttgttc ctcagatgat atggtccatt caagttttgt aatcatcatg ggggtagatg        480
gagggtccca gtcctcacaa ccattctggt aatttactct tgaatttact ggttcacatg        540
tatctatttt gtagtgtggc tccagaaa                                          568

<210> SEQ ID NO 159
<211> LENGTH: 522
<212> TYPE: DNA
<213> ORGANISM: Artificial Sequence
<220> FEATURE:
<223> OTHER INFORMATION: Synthetic

<400> SEQUENCE: 159

```
tcatcctgct cggagtacaa tgttcgtgta gcctcaaggt acttcaaggg accagagctc    60
ctcgtggact atcagatgta tgattatagc ttggacatgt ggagtttggg ctgtatgtta   120
gcaagcatga tctttcgaag ggaaccattc ttccatggac aggacaacta tgaccagctt   180
gttcgcattg ccaaggttct gggtacagaa gaactgtatg ggtatctgaa gaagtatcac   240
atagacctag atccacactt caacgatatc ctgggacaac attacgaaa acgctgggaa    300
aacttatcca tagtgagaac agacaccttg tcagccctga ggcctagat cttctggaca    360
aacttctgcg atacgaccat caacagagac tgactgccaa agaggccatg gagcacccat   420
acttctaccc tgtggtgaag gagcagtccc agccttgtgc agacaatgct gtgctttcca   480
gtggtctcac ggcagcacga tgaagactgg aaagcgacgg gt                      522
```

<210> SEQ ID NO 160
<211> LENGTH: 363
<212> TYPE: DNA
<213> ORGANISM: Artificial Sequence
<220> FEATURE:
<223> OTHER INFORMATION: Synthetic

<400> SEQUENCE: 160

```
cggccgcccg ccttggcccg tctctggagt gctgggcagc cgggtctgcg ggcccctta    60
cagcacatcg ccggccggcc caggtagggc ggcctctctc cctcgcaagg gggcccagct   120
ggagctggag gagatgctgg tccccaggaa gatgtccgtc agcccctgg agagctggct    180
cacggcccgc tgcttcctgc ccagactgga taccgggacc gcagggactg tggctccacc   240
gcaatcctac cagtgtccgc ccagccagat aggggaaggg gccgagcagg gggatgaagg   300
cgtcgcggat gcgcctcaaa ttcagtgcaa aaacgtgctg aagatccgcc ggcggaagat   360
gaa                                                                 363
```

<210> SEQ ID NO 161
<211> LENGTH: 662
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (413)..(413)
<223> OTHER INFORMATION: n is a, c, g, or t

<400> SEQUENCE: 161

```
ggcagggaag ggagaacatt aggacaaata cctaatgcac gccaggccct antaatcgta    60
gatgatgggt tgatgggtgt agcaaaccac catggcacat gtatatctat gtaacaaacc   120
tgcacattct gtacatgtat cccagaactt caagtaaaat tttaaaaaat tcaaaaaaag   180
taataggaaa aggggaaaca tccacgtgag cagtccagtt tcccaatctg gaacttggag   240
ctgttcacct ggtgggtgtt tgtgactatt cagacacaga caacaaaggc tactccagat   300
tgaagtgcac tgcttacttt cagtgacctc atagaactac tcaacattgt ttttggtgat   360
tcctgtgcta tggtttgaat ggctccgctc caaaactcag gtgttgccaa tgngatggta   420
ttaagaagta gggcatttaa aaaacaacaa caggcctggc gcggtggccc acgcctgtaa   480
```

```
tcccagcact ttgggaggct aaggcgggcg gatcaccgga ggtcaggaat tcaaaaccag      540
cctggccaac atggcgaaac cctgtctcta ctaaaaatac aaaaattagc caggcatggt      600
tgcgggcgcc tgtaatcccg gctactcggg aggctgaggc aggggaatcc ttgaacccgg      660
ga                                                                    662
```

<210> SEQ ID NO 162
<211> LENGTH: 547
<212> TYPE: DNA
<213> ORGANISM: Artificial Sequence
<220> FEATURE:
<223> OTHER INFORMATION: Synthetic

<400> SEQUENCE: 162

```
gaaatgtaga ctgcaaaggc agtatacagg aaaaggtgga gtgggttttg tttatgaggg       60
tgtctgaaaa ctaaaattga gcgggatatc atggtatagt tggacagtat tggtccttca      120
cactttggcc atattgtata atggagcttt taccaaagat gtatgagaag tgtaagacta      180
taaaaaaatg aactattcaa agtaaaactc ttaacaaaca ttttacttaa agcagatgca      240
aaagggtatt ctcatgtagg ctcctgttgg tgcagaggga ttttttttgat ttcaggatac      300 aactaaagta cgaagttctc agtttcactt tagtagaaag agctctagaa atgaggctga      360
taaacacatc taagaacact ggttgctttc taaaatttcc aaagctccac cataaatgta      420
atttttagtg tttcaaatga ttgcatttta agtatataa atatgggtta tccaatatca      480
atgctatagt aacatcctga acaaaacaa gcacaaaggt ataaatgcct aaactggagg      540
aagcttg                                                               547
```

<210> SEQ ID NO 163
<211> LENGTH: 277
<212> TYPE: DNA
<213> ORGANISM: Artificial Sequence
<220> FEATURE:
<223> OTHER INFORMATION: Synthetic

<400> SEQUENCE: 163

```
ctcagactca aacacacacc tccgctccct tgaagtgcca gccctggagc tttgttgagg       60
ctcgcatctg ccacgggagt cagctagtac gttgcccagt tcaacatcca tccaggattt      120
cataggaact tgagaatcat tgttttttggc ttgaatcctg ggtttgaggt ttcttcgtgt      180
aggaatctga aaaaaggatt tggaaacgtt gttgtctcta atcccaaagt atgtatctgg      240
gaggctgcct tcgccatcac ccacctaata actcagg                              277
```

<210> SEQ ID NO 164
<211> LENGTH: 337
<212> TYPE: DNA
<213> ORGANISM: Artificial Sequence
<220> FEATURE:
<223> OTHER INFORMATION: Synthetic

<400> SEQUENCE: 164

```
agacttcacc agtcaaagcg aactacatat actcaattga tccaataact tgaccaacgg       60
aacaagttac cctagggata acagcgcaat cctattctag agtccatatc aacaataggg      120
tttacgacct cgatgttgga tcaggacatc ccgatggtgc agccgctatt aaaggttcgt      180
ttgttcaacg attaaagtcc tacgtgatct gagttcagac cggagtaatc caggtcggtt      240
tctatctact tcaattcct ccctgtacga aggacaaga gaaataaggc ctacttcaca      300
aagcgccttc ccccgtaaat gatatcatct caagctt                             337
```

<210> SEQ ID NO 165
<211> LENGTH: 276
<212> TYPE: DNA
<213> ORGANISM: Artificial Sequence
<220> FEATURE:
<223> OTHER INFORMATION: Synthetic

<400> SEQUENCE: 165

```
ctcgctcaaa cacacacctc cgctcccttg aagtgccagc cctggagctt tgttgaggct      60
cgcatctgcc acgggagtca gctagtacgt tgcccagttc aacatccatc caggatttca     120
taggaacttg agaatcattg tttttggctt gaatcctggg tttgaggttt cttcgtgtag     180
gaatctgaaa aaaggatttg gaaacgttgt tgtctctaat cccaaagtat gtatctggga     240
ggctgccttc gccatcaccc acctaataac tcaggc                                276
```

<210> SEQ ID NO 166
<211> LENGTH: 717
<212> TYPE: DNA
<213> ORGANISM: Artificial Sequence
<220> FEATURE:
<223> OTHER INFORMATION: Synthetic

<400> SEQUENCE: 166

```
attgtttgtt gttgggggtg tctttgtcag catctagtac agtgcctggc agatggatgc      60
tcaataaata ttgatttaat gggttatgag ggtgttaata taaaattagc atttattcag     120
caactactat gagtcagcca ctgggctaag tggcttacat gttaagaacc tcacagaagc     180
caggtgtggt ggctcacgcc tgtaatccca gcactttggg aggctgaagc gggcagatca     240
cctgaggtca ggagtttgag tccaggctgg ccaacgtggt gaaaccccat ctctactaaa     300
aatacaaaaa ttagccagtt gtggtggcag gcgcctgtag tcccagccac tcaggaggct     360
aaggcaggag aatagctgga acccgggagg tggagattgc agtgagccaa gattgcacca     420
ctgcactcca gcctgggtga cagagtgaga ctctgtctcc aaaaaaaaaa gaaaagaaa      480 aagaacctcc agcaacctag taggtgagcc cggttactct tgttttacag gtgagaaaat     540
tgagccctag agaaataaag taacttgctt caggtctcat ggttaagggg aacctgggcc     600
ctaacagtcc acttcctgta ccttcaacca cggttctacc gcctccgcta ggaaatggcc     660
cgaggacatt ccttagctgg cttcagcttg ctcttttttcc cctgcggtcc acccctg       717
```

<210> SEQ ID NO 167
<211> LENGTH: 316
<212> TYPE: DNA
<213> ORGANISM: Artificial Sequence
<220> FEATURE:
<223> OTHER INFORMATION: Synthetic

<400> SEQUENCE: 167

```
agagggagta tagggctgtg cacagagact atgatggccg tgctaaggta agagtattga      60
taatgtaagc atacttcctc tatcaacaat aattgttaac agctgcttca agcacttgat     120
attaccacta gttgttaact gaatcaagca tgtgctccaa gttcacatta atgtgaattg     180
aacagcattg tgtacgtacg aggagcttca tgcaagtgtt atacactgca ctcacaagta     240
ttatgatctt actaagcatt agaaatactc tgtgttaaag aagcttggtc taggccaagc     300
gtggtggctc atgcct                                                      316
```

<210> SEQ ID NO 168
<211> LENGTH: 457
<212> TYPE: DNA

<213> ORGANISM: Artificial Sequence
<220> FEATURE:
<223> OTHER INFORMATION: Synthetic

<400> SEQUENCE: 168

```
gatcggaggc cagggtcctt tgtactttca tttcttagcc agatgaatgt tgtcacccat      60
tttaggatta ttgctatgtg tggagattac tacattggtg gaagacgttt ttcttcactg     120
tcagacctaa taggttatta cagtcatgtt tcttgtttgc ttaaaggaga aaaattactt     180
tacccagttg caccaccaga gccagtagaa gatagaaggc gtgtacgagc tattctacct     240
tacacaaaag taccagacac tgatgaaata agtttcttaa aaggagatat gttcattgtt     300
cataatgaat tagaagatgg atggatgtgg gttacaaatt taagaacaga tgaacaaggc     360
cttattgttg aagacctagt agaagaggtg ggccgggaag aagatccaca tgaaggaaaa     420
atatggttcc atgggaagat ttccaaacag gaagctt                               457
```

<210> SEQ ID NO 169
<211> LENGTH: 361
<212> TYPE: DNA
<213> ORGANISM: Artificial Sequence
<220> FEATURE:
<223> OTHER INFORMATION: Synthetic

<400> SEQUENCE: 169

```
tgaagtggca gcagaggaac ccaatgctgc agttcctgat gagatccccc ctctcgaggg      60
cgatgaggat gcgtctcgca tggaagaagt cgattaggtt aggagttcat agttggaaaa     120
cttgtgccct tgtatagtgt ccccatgggc tccactgca gcctcgagtg cccctgtccc      180
acctggctcc ccctgctggt gtctagtgtt ttttccctc tcctgtcctt gtgttgaagg      240
cagtaaacta agggtgtcaa gccccattcc ctctctcact cttgacagca ggattggatg     300
ttgtgtattg tggtttattt tatttcttc attttgttct gaattaagt atgcaaaata      360
a                                                                     361
```

<210> SEQ ID NO 170
<211> LENGTH: 487
<212> TYPE: DNA
<213> ORGANISM: Artificial Sequence
<220> FEATURE:
<223> OTHER INFORMATION: Synthetic

<400> SEQUENCE: 170

```
gttgcattgt ggatgcaaat ctgagcgttc tcaacttggt tattgtaaaa aaaggagaga      60
aggatattcc tggactgact gatactacag tgcctcgccg cctgggcccc aaaagagcta     120
gcagaatccg caaacttttc aatctctcta aagaagatga tgtccgccag tatgttgtaa     180
gaaagcccct taaataagaa ggtaagaaac ctaggaccaa agcacccaag attcagcgtc     240
ttgttactcc acgtgtcctg cagcacaaac ggcggcgtat tgctctgaag aagcagcgta     300
ccaagaaaaa taagaagag gctgcagaat atgctaaact tttggccaag agaatgaagg     360
aggctaagga gaagcgccag gaacaaattg cgaagagacg cagactttcc tctctgcgag     420
cttctacttc taagtctgaa tccagtcaga aataagattt tttgagtaac aaataaataa     480
gatcaga                                                               487
```

<210> SEQ ID NO 171
<211> LENGTH: 319
<212> TYPE: DNA
<213> ORGANISM: Artificial Sequence

```
<220> FEATURE:
<223> OTHER INFORMATION: Synthetic

<400> SEQUENCE: 171
cctgggcagt gattaggtca taaaggtgga gtcctcatgg atgggattag tgtctttata      60
aaagagacct ttgccatgtg aggttacagt gagaagacat ctgtctatga agaaagtggg     120
ccctcaccaa acacagtctg ctggcacttt gcacttcaac tccccagctt ccagaactgt     180
aaggaatata agtctgttgt tggtaagcca cccggtctat gatattttgt tatagcagcc     240
caaacagact aagacaggtg acaaataaac atgaaaagat gttcaacatc attagccatt     300
agggaaatgc agattaaaa                                                  319

<210> SEQ ID NO 172
<211> LENGTH: 30
<212> TYPE: PRT
<213> ORGANISM: Artificial Sequence
<220> FEATURE:
<223> OTHER INFORMATION: Synthetic

<400> SEQUENCE: 172

Gly Gly Arg Gly Gly Gly Gly Gly Gly Gly Arg Gly Ala Gly Gly
1               5                   10                  15

Gly Arg Gly Ala Gly Ala Gly Gly Gly Arg Pro Glu Ala Ala
            20                  25                  30
```